(12) United States Patent
Petter et al.

(10) Patent No.: US 11,542,492 B2
(45) Date of Patent: Jan. 3, 2023

(54) LIGAND-DIRECTED COVALENT MODIFICATION OF PROTEIN

(71) Applicant: Celgene CAR LLC, Pembroke (BM)

(72) Inventors: Russell C. Petter, Stow, MA (US); Charles F. Jewell, Columbia, MD (US); Kwangho Lee, Waltham, MA (US); Aravind Prasad Medikonda, Arlington, MA (US); Deqiang Niu, Lexington, MA (US); Lixin Qiao, Andover, MA (US); Juswinder Singh, Ashland, MA (US); Zhendong Zhu, Westborough, MA (US)

(73) Assignee: Celgene CAR LLC, Pembroke (BM)

( * ) Notice: Subject to any disclaimer, the term of this patent is extended or adjusted under 35 U.S.C. 154(b) by 657 days.

(21) Appl. No.: 15/423,115

(22) Filed: Feb. 2, 2017

(65) Prior Publication Data

US 2017/0218353 A1 Aug. 3, 2017

Related U.S. Application Data

(62) Division of application No. 12/982,352, filed on Dec. 30, 2010, now abandoned.

(Continued)

(51) Int. Cl.
| | |
|---|---|
| C12N 9/96 | (2006.01) |
| G16B 15/00 | (2019.01) |
| C07D 405/14 | (2006.01) |
| C07D 491/08 | (2006.01) |
| C07D 487/04 | (2006.01) |
| C07D 495/04 | (2006.01) |
| G01N 33/68 | (2006.01) |
| C07D 519/00 | (2006.01) |
| C07D 401/04 | (2006.01) |
| C07D 403/12 | (2006.01) |
| C07D 405/12 | (2006.01) |
| C07D 417/14 | (2006.01) |
| C07D 207/16 | (2006.01) |
| C07D 417/06 | (2006.01) |
| C07D 493/04 | (2006.01) |
| C07D 409/12 | (2006.01) |
| C07D 401/14 | (2006.01) |
| C07D 239/49 | (2006.01) |
| C07D 513/04 | (2006.01) |
| G16C 20/50 | (2019.01) |
| G16B 15/30 | (2019.01) |
| C07D 403/14 | (2006.01) |
| C12N 9/12 | (2006.01) |
| C12N 9/50 | (2006.01) |
| C12N 9/00 | (2006.01) |

(Continued)

(52) U.S. Cl.
CPC ............. *C12N 9/96* (2013.01); *C07D 207/16* (2013.01); *C07D 239/49* (2013.01); *C07D 401/04* (2013.01); *C07D 401/14* (2013.01); *C07D 403/12* (2013.01); *C07D 403/14* (2013.01); *C07D 405/12* (2013.01); *C07D 405/14* (2013.01); *C07D 409/12* (2013.01); *C07D 417/06* (2013.01); *C07D 417/14* (2013.01); *C07D 487/04* (2013.01); *C07D 491/08* (2013.01); *C07D 493/04* (2013.01); *C07D 495/04* (2013.01); *C07D 513/04* (2013.01); *C07D 519/00* (2013.01); *C12N 9/12* (2013.01); *C12N 9/506* (2013.01); *C12N 9/93* (2013.01); *C12Q 1/25* (2013.01); *C12Q 1/37* (2013.01); *C12Q 1/485* (2013.01); *C12Y 207/11001* (2013.01); *C12Y 304/21098* (2013.01); *C12Y 603/02* (2013.01); *G01N 33/68* (2013.01); *G16B 15/00* (2019.02); *G16B 15/30* (2019.02); *G16C 20/50* (2019.02)

(58) Field of Classification Search
CPC . C12N 9/96; C12N 9/12; C12N 9/506; C12N 9/93; G01N 33/68; C07D 519/00; C07D 401/04; C07D 403/12; C07D 405/12; C07D 417/14; C07D 207/16; C07D 417/06; C07D 493/04; C07D 409/12; C07D 401/14; C07D 239/49; C07D 513/04; C07D 403/14; C07D 405/14; C07D 491/08; C07D 487/04; C07D 495/04; G16B 15/00; C12Y 207/11001; C12Y 304/21098; C12Y 603/02; A61P 43/00; A61P 31/14; G16C 20/50; C12Q 1/25; C12Q 1/27; C12Q 1/485
See application file for complete search history.

(56) References Cited

U.S. PATENT DOCUMENTS

| | | | |
|---|---|---|---|
| 3,710,795 A | 1/1973 | Higuchi et al. | |
| 4,650,750 A | 3/1987 | Giese | |

(Continued)

FOREIGN PATENT DOCUMENTS

| | | |
|---|---|---|
| CN | 1717396 A | 1/2006 |
| CN | 101054380 A | 10/2007 |

(Continued)

OTHER PUBLICATIONS

He et al, Molecules, 2019, 24, 1855, 1-34 (Year: 2019).*

(Continued)

*Primary Examiner* — Sudhakar Katakam
(74) *Attorney, Agent, or Firm* — Jones Day

(57) ABSTRACT

The present invention relates to enzyme inhibitors. More specifically, the present invention relates to ligand-directed covalent modification of proteins; method of designing same; pharmaceutical formulation of same; and method of use.

7 Claims, 23 Drawing Sheets

Specification includes a Sequence Listing.

Related U.S. Application Data

(60) Provisional application No. 61/335,043, filed on Dec. 30, 2009.

(51) Int. Cl.
*C12Q 1/25* (2006.01)
*C12Q 1/37* (2006.01)
*C12Q 1/48* (2006.01)

(56) References Cited

U.S. PATENT DOCUMENTS

| | | | |
|---|---|---|---|
| 4,709,016 | A | 11/1987 | Giese |
| 5,262,564 | A | 11/1993 | Kun et al. |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 5,756,466 | A | 5/1998 | Bemis et al. |
| 5,760,041 | A | 6/1998 | Wissner et al. |
| 5,856,116 | A | 1/1999 | Wilson et al. |
| 6,002,008 | A | 12/1999 | Wissner et al. |
| 6,025,147 | A | 2/2000 | Bemis et al. |
| 6,057,119 | A | 5/2000 | Wilson et al. |
| 6,162,613 | A | 12/2000 | Su et al. |
| 6,251,912 | B1 | 6/2001 | Wissner et al. |
| 6,288,082 | B1 | 9/2001 | Wissner et al. |
| 6,335,155 | B1 | 1/2002 | Wells et al. |
| 6,344,455 | B1 | 2/2002 | Bridges et al. |
| 6,384,051 | B1 | 5/2002 | Frost et al. |
| 6,552,216 | B1 | 4/2003 | Singh et al. |
| 6,569,876 | B1 | 5/2003 | Cheronis et al. |
| 6,602,863 | B1 | 8/2003 | Bridges et al. |
| 6,664,247 | B2 | 12/2003 | Bebbington et al. |
| 6,686,350 | B1 | 2/2004 | Zheng et al. |
| 6,849,267 | B2 | 2/2005 | Bemis et al. |
| 6,919,178 | B2 | 7/2005 | Erlanson et al. |
| 6,949,534 | B2 | 9/2005 | Zheng et al. |
| 6,974,809 | B2 | 12/2005 | Galee et al. |
| 7,202,033 | B2 | 4/2007 | Prescott et al. |
| 7,235,576 | B1 | 6/2007 | Riedl et al. |
| 7,383,135 | B1 | 6/2008 | Xie et al. |
| 7,407,939 | B2 | 8/2008 | Livnah et al. |
| 7,504,410 | B2 | 3/2009 | Bryant et al. |
| 7,528,143 | B2 | 5/2009 | Noronha et al. |
| 7,792,665 | B2 | 9/2010 | Alessi et al. |
| 7,982,036 | B2 | 7/2011 | Singh et al. |
| 7,989,465 | B2 | 8/2011 | Singh et al. |
| 8,188,137 | B2 | 5/2012 | Niu et al. |
| 8,242,271 | B2 | 8/2012 | Singh et al. |
| 8,293,705 | B2 | 10/2012 | Niu et al. |
| 8,309,685 | B2 | 11/2012 | Petter et al. |
| 8,329,901 | B2 | 12/2012 | Singh et al. |
| 8,338,439 | B2 | 12/2012 | Singh et al. |
| 8,445,498 | B2 | 5/2013 | Singh et al. |
| 8,450,335 | B2 | 5/2013 | Singh et al. |
| 8,524,760 | B2 | 9/2013 | Niu et al. |
| 8,563,568 | B2 | 10/2013 | Witowski et al. |
| 8,586,600 | B2 | 11/2013 | Singh et al. |
| 8,603,737 | B2 | 12/2013 | Hagel et al. |
| 8,609,679 | B2 | 12/2013 | Singh et al. |
| 8,710,222 | B2 | 4/2014 | Singh et al. |
| 8,741,837 | B2 | 6/2014 | Niu et al. |
| 8,748,606 | B2 | 6/2014 | Singh et al. |
| 8,778,877 | B2 | 7/2014 | Niu et al. |
| 8,980,935 | B2 | 3/2015 | Niu et al. |
| 9,040,541 | B2 | 5/2015 | Singh et al. |
| 9,067,929 | B2 | 6/2015 | Singh et al. |
| 9,163,061 | B2 | 10/2015 | Petter et al. |
| 9,556,426 | B2 | 1/2017 | Singh et al. |
| 2002/0058809 | A1 | 5/2002 | Emmanuel et al. |
| 2004/0009890 | A1 | 1/2004 | Erickson et al. |
| 2004/0023957 | A1 | 2/2004 | Wang et al. |
| 2004/0049032 | A1 | 3/2004 | Charrier et al. |
| 2004/0229937 | A1 | 11/2004 | Dumas et al. |
| 2004/0235829 | A1 | 11/2004 | Scott et al. |
| 2005/0026933 | A1 | 2/2005 | Greenberger et al. |
| 2005/0032798 | A1 | 2/2005 | Boyer et al. |
| 2005/0038031 | A1 | 2/2005 | Dumas et al. |
| 2005/0059703 | A1 | 3/2005 | Wilhelm et al. |
| 2005/0186630 | A1 | 8/2005 | Erlanson et al. |
| 2006/0003317 | A1 | 1/2006 | Perni et al. |
| 2006/0030553 | A1 | 2/2006 | Zheng et al. |
| 2006/0079494 | A1 | 4/2006 | Santi et al. |
| 2006/0174816 | A1 | 8/2006 | Acharya et al. |
| 2006/0235046 | A1 | 10/2006 | Zacharchuk et al. |
| 2006/0247262 | A1 | 11/2006 | Baenteli et al. |
| 2007/0020684 | A1 | 1/2007 | Bledsoe et al. |
| 2007/0020704 | A1 | 1/2007 | Wilhelm et al. |
| 2007/0082884 | A1 | 4/2007 | Taunton et al. |
| 2007/0179083 | A1 | 8/2007 | Paul et al. |
| 2007/0249031 | A1 | 10/2007 | Binch et al. |
| 2007/0259869 | A1 | 11/2007 | Binch et al. |
| 2007/0299092 | A1 | 12/2007 | Floyd et al. |
| 2008/0032963 | A1 | 2/2008 | Binch et al. |
| 2008/0108636 | A1 | 5/2008 | Honigberg et al. |
| 2008/0269140 | A1 | 10/2008 | Wang et al. |
| 2008/0300268 | A1 | 12/2008 | Singh et al. |
| 2009/0137588 | A1 | 5/2009 | Singh et al. |
| 2009/0306085 | A1 | 12/2009 | Petter et al. |
| 2010/0185419 | A1 | 7/2010 | Singh et al. |
| 2011/0117073 | A1 | 5/2011 | Singh et al. |
| 2011/0230476 | A1 | 9/2011 | Niu et al. |
| 2011/0269244 | A1 | 11/2011 | Petter et al. |
| 2013/0065879 | A1 | 3/2013 | Singh et al. |
| 2013/0072469 | A1 | 3/2013 | Singh et al. |
| 2013/0131105 | A1 | 5/2013 | Petter et al. |
| 2014/0057929 | A1 | 2/2014 | Witowski et al. |
| 2014/0213574 | A1 | 7/2014 | Singh et al. |
| 2014/0303165 | A1 | 10/2014 | Singh et al. |
| 2014/0323465 | A1 | 10/2014 | Niu et al. |
| 2015/0031106 | A1 | 1/2015 | Niu et al. |
| 2015/0175657 | A1 | 6/2015 | Niu et al. |
| 2015/0252019 | A1 | 9/2015 | Singh et al. |

FOREIGN PATENT DOCUMENTS

| | | |
|---|---|---|
| EP | 1939625 | 7/2008 |
| JP | 2000508657 | 7/2000 |
| JP | 2005534286 | 11/2005 |
| JP | 2006508997 | 3/2006 |
| JP | 2006517959 | 8/2006 |
| JP | 2007522116 | 8/2007 |
| JP | 2010504324 | 2/2010 |
| WO | WO 97/38983 | 10/1997 |
| WO | WO 99/06378 | 2/1999 |
| WO | WO 2000/18895 | 4/2000 |
| WO | WO 03/081210 | 10/2003 |
| WO | WO 2004/000833 | 12/2003 |
| WO | WO 2004/048343 | 6/2004 |
| WO | WO 2004/069791 | 8/2004 |
| WO | WO 2004/072261 | 8/2004 |
| WO | WO 2004/078128 | 9/2004 |
| WO | WO 2004/078746 | 9/2004 |
| WO | WO 2004/078747 | 9/2004 |
| WO | WO 2004/113274 | 12/2004 |
| WO | WO 2005/000197 A2 | 1/2005 |
| WO | WO 2005/000284 | 1/2005 |
| WO | WO 2005/026158 | 3/2005 |
| WO | WO 2005/034840 A2 | 4/2005 |
| WO | WO 2005/069894 | 8/2005 |
| WO | WO 2005/075425 | 8/2005 |
| WO | WO 2005/114219 A2 | 12/2005 |
| WO | WO 2006/021544 | 3/2006 |
| WO | WO 2006/040056 | 4/2006 |
| WO | WO 2006/084058 A2 | 8/2006 |
| WO | WO 2006/117567 A2 | 11/2006 |
| WO | WO 2006/117570 A1 | 11/2006 |
| WO | WO 2006/125539 | 11/2006 |
| WO | WO 2006/132739 A2 | 12/2006 |
| WO | WO 2006/132739 A3 | 12/2006 |
| WO | WO 2007/038613 A2 | 4/2007 |
| WO | WO 2007/062459 A1 | 6/2007 |

(56) References Cited

FOREIGN PATENT DOCUMENTS

| | | |
|---|---|---|
| WO | WO 2007/085833 | 8/2007 |
| WO | WO 2007/1203 3 9 | 10/2007 |
| WO | WO 2007/117215 A1 | 10/2007 |
| WO | WO 2007/133352 A2 | 11/2007 |
| WO | WO 2007/136790 A2 | 11/2007 |
| WO | WO 2008/039218 A2 | 4/2008 |
| WO | WO 2008/049123 | 4/2008 |
| WO | WO 2008/073687 | 6/2008 |
| WO | WO 2008/079719 | 7/2008 |
| WO | WO 2008/092199 A1 | 8/2008 |
| WO | WO 2008/144463 | 11/2008 |
| WO | WO 2008/144464 | 11/2008 |
| WO | WO 2008/151183 A1 | 12/2008 |
| WO | WO 2009/030890 | 3/2009 |
| WO | WO 2009/051822 | 4/2009 |
| WO | WO 2009/082697 | 7/2009 |
| WO | WO 2009/082701 | 7/2009 |
| WO | WO 2009/091550 A2 | 7/2009 |
| WO | WO 2009/091550 A8 | 7/2009 |
| WO | WO 2009/158571 | 12/2009 |
| WO | WO 2010/028236 | 3/2010 |
| WO | WO 2011/031896 | 9/2010 |
| WO | WO 2010/123870 | 10/2010 |
| WO | WO 2011/002807 | 1/2011 |
| WO | WO 2011/002808 | 1/2011 |
| WO | WO 2011/034907 | 3/2011 |
| WO | WO 2011/082285 | 7/2011 |
| WO | WO 2011/090760 | 7/2011 |
| WO | WO 2012/021444 | 2/2012 |

OTHER PUBLICATIONS

Lu et al, International Journal of Molecular Sciences, 2016, 17, 561, 1-22 (Year: 2016).*

Atwell et al., "A Novel Mode of Gleevec Binding is Revealed by the Structure of Spleen Tyrosine Kinase," The Journal of Biological Chemistry, 279:55827-55832 (2004).

Abdulhameed et al., "Microscopic Modes and Free Energies of 3-Phosphinoditide-Dependent Kinase-1 (PDK-1) Binding with Celecoxib and Other Inhibitors," J. Phys. Chem. B, 2006, 110:26365-26374.

Abdulhameed, "Computational Design of 3-Phosphoinositide-dependent Kinase-1 Inhibitors as Potential Anti-Cancer Agents," University of Kentucky Doctoral Dissertations, paper 757, Jul. 13, 2009.

Bain et al., "The Selectivity of Protein Kinase Inhibitors: a further update," Biochem. J. 2007, 408:297-315 & Supplementary Figures.

Baker, "Factors in Design of Active-Site Directed Irreversible Inhibitors", J. Pharmaceutical Sciences, 1964, 53(4), 347-364.

Bantscheff et al., "Quantitative chemical proteomics reveals mechanisms of action of clinical ABL kinase inhibitors", Nature Biotechnology, 25:1035-1044 (2007).

Barbas et al., "Immune Versus Natural Selection: Antibody Aldolases with Enzymic Rates But Broader Scope;" Science; vol. 278, Dec. 19, 1997; www.sciencemag.org; pp. 2085-2092.

Baskin et al., Copper-free click chemistry for dynamic in vivo imaging; PNAS: Proceedings of the National Academy of Sciences of the United States of America, The Geography of poverty, vol. 104, No. 43, Oct. 23, 2007; www.pnas.org/cgi/doi/10.1073/pnas.0707090104; pp. 16793-16797.

Bilodeau et al., "Potent N-(1,3-Thiazol-2-yl)pyridine-2-amine Vascular Endothelial Growth Factor Receptor Tyrosine Kinase Inhibitors with Excellent Pharmacokinetics and Low Affinity for the hERG Ion Channel", J. Med. Chem., 47:6363-6372 (2004).

Blight et al., "Molecular virology of hepatitis C virus: an update with respect to potential antiviral targets;" Antiveral Therapy 3 (Supplement 3); Second International Conference on Therapies for Viral Hepatitis; Copyright 1998 International Medical Press; pp. 71-81.

Boggon, 2005, "Crystal structure of the Jak3 kinase domain in complex with a staurosporine analog", Blood, 106(3):996-1002.

Braselmann et al., "R406, An Orally Available Spleen Tyrosine Kinase Inhibitor Blocks Fc Receptor Signaling and Reduces Immune Complex-Mediated Inflammation," J Pharmacol Exp Ther., 319:998-1008 (2006).

CAS Registry No. 1026864-16-3; STN entry date Jun. 10, 2008.

Choi et al., "Chemoselective small molecules that covalently modify one lysine in a non-enzyme protein in plasma;" Natural Chemical Biology; vol. 6, Feb. 2010; www.nature.com/naturechemicalbiology; pp. 133-139.

Cohen et al., 2005, "Structural bioinformatics-based design of selective, irreversible kinase inhibitors", Science; 308:1318-1321.

Dal Maso and Franceschi, "Epidemiology of non-Hodgkin lymphomas and other haemolymphopoietic neoplasms in people with AIDS;" The Lancet Oncology, vol. 4, Feb. 2003; hllp:l/oncology.thelancel.com; pp. 110-119.

De Biase et al., "Chemistry of the Inactivation of 4-Aminobutyrate Aminotransferase by the Antiepileptic Drug Vigabatrin;" The Journal of Biological Chemistry; Copyright 1991 by The American Society for Biochemistry and Molecular Biology, Inc.; vol. 266, No. 30, Oct. 25, 1991; pp. 20056-20061.

Del Rio et al., "A computational workflow for the design of irreversible inhibitors of protein kinases," J. Comput. Aided Mol. Des., 2010, 24:183-194.

Denny, 2002, "Irreversible inhibitors of the erbB family of protein tyrosine kinases", Pharmacol Ther; 93:253-261.

Dewitte et al. 1996, "SMoG: de novo design method based on simple, fast, and accurate free energy estimates. 1. Methology and supporting evidence", J Am Chem Soc; 118:11733-11744.

Doorn et al., "Inhibition of Human Mitochondrial Aldehyde Dehydrogenase by 4-Hydroxynon-2-enal and 4-Oxonon-2-enal," Chem. Res. Toxicol., 2006, 19:102-110.

Doppalapudi et al. "Chemically programmed antibodies: Endothelin receptor targeting CovX-Bodies;" Bioorganic & Medicinal Chemistry Letters 17, The Tetrahedron Journal for Research at the Interface of Chemistry and Biology; www.sciencedirect.com; Copyright 2006 Elsevier Ltd.; (2007); pp. 501-506.

Dragovich et al., "Structure-Based Design, Synthesis, and Biological Evaluation of Irreversible Human Rhinovirus 3C Protease Inhibitors. 6. Structure-Activity Studies of Orally Bioavailable, 2-Pyridone-Containing Peptidomimetics", J. Med. Chem., 45:1607-1623 (2002).

Ekicki et al., 2003, "Design, synthesis and evaluation of novel irreversible inhibitors for caspases", Ph.D. Thesis, Georgia Institute of Technology, Chapter 4.

European Search Opinion and Supplementary European Search Report dated Apr. 17, 2014, from European Application No. 10817748.6.

European Search Opinion and Supplementary European Search Report dated Feb. 6, 2014, from European Application No. 10841710.6.

Feldman et al., J. Biol. Chem., vol. 280, No. 20, pp. 19867-19874, 2005.

Fradera et al., "Unsupervised guided docking of covalently bound ligands", Journal of Computer-Aided Molecular Design, 18: 635-650 (2004).

Fretheim et al. Int. J. Protein Res. 14, pp. 451-456, 1979.

Fry et al. 1999, "Inhibition of the Epidermal Growth Factor Receptor Family of Tyrosine Kinases as an Approach to Cancer Chemotherapy: Progression from Reversible to Irreversible Inhibitors", Pharmacol. Ther.; 82(2-3):207-218.

Fry et al., "Specific, irreversible inactivation of the epidermal growth factor receptor and erbB2, by a new class of tyrosine kinase inhibitor", Proc. Natl. Acad. Sci. USA, 95:12022-12027 (1998).

Gaspar et al., "Cysteine 116 Participates in Intermolecular Bonding of the Human VEGF121 Homodimer," Archives of Biochemistry and Biophysics, 404:126-135 (2002).

Gordon and Ford, 1972, "The Chemist's Companion", John Wiley and Sons, Inc., p. 108.

Govindan et al., "New cycloartanol sulfates from the algo Tydemania expeditionis: inhibitors of the protein kinase pp60v-src," Journal of Natural Products, 1994, 57:74-78.

Graupera et al., "Angiogenesis selectively requires the p1 OOa isoform of P13K to control endothelial cell migration;" The Inter-

(56) References Cited

OTHER PUBLICATIONS national Weekly Journal of Science: Nature, A Gut Issue: Bacterial symbiosis shapes a healthy immune response, vol. 453, No. 7195, May 29, 2008; pp. 662-666.

Guillerm et al., "Inactivation of S-Adenosyi-Lhomocysteine Hydrolase by 6'-Cyano-5', 6'-didehydro-6'-deoxyhomoadenosine and 6'-Chloro-6'-cyano-5', 6'-didehydro-6'-deoxyhomoadenosine. Antiviral and Cytotoxic Effects;" Journal of Medicinal Chemistry, vol. 49, No. 4, Feb. 23, 2006; Copyright 2006 by The American Chemical Society; Published on the web Jan. 27, 2006; pp. 1223-1226.

Guo et al., "Breaking the one antibody-one target axiom;" Proceedings of the National Academy of Sciences of the United States of America; vol. 103, No. 29, Jul. 18, 2006; www.pnas.org/cgi/doi/10.1073/pnas.0603822103; pp. 11009-11014.

Hagel et al., 2011, "Selective irreversible inhibition of a protease by targeting a noncatalytic cysteine", Nat Chem Biol; 7(1):22-24.

Hansen et al., 2005, "Allosteric inhibition of PTP1B activity by selective modification of a non-active site cysteine residue", Biochemistry; 44(21):7704-7712.

Heredia et al., "In Situ Preparation of Protein—"Smart" Polymer Conjugates with Retention of Bioactivity," J. Am. Chem. Soc., 127:16955-16960 (2005).

Hermann and Niedobilek, "Epstein-Barr virus-associated carcinomas: facts and fiction;" Journal of Pathology, The Journal of the Pathological Society of Great Britain and Ireland, vol. 199, No. 2, Feb. 2003; Published online in Wiley InterScience (www.interscience.wiley.com); Copyright 2003 John Wiley & Sons, Ltd.; pp. 140-145.

Hernandez-Avila et al., "Human Papilloma Virus 16-18 Infection and Cervical Cancer in Mexico: A Case-Control Study;" Archives of Medical Research, vol. 28, No. 2; 1997; pp. 265-271.

Huang et al., The role of thyroid autoantibodies in the development of thyroid dysfunction in Taiwanese chronic hepatitis C patients with interferon-alpha and ribavirin combination therapy; Journal of Viral Hepatitis, vol. 13, No. 6, Jun. 2006; Copyright 2006 Blackwell Publishing Ltd; pp. 396-401.

Huang, "Fluorescence Polarization Competition Assay: The Range of Resolvable Inhibitor Potency Is Limited by the Affinity of the Fluorescent Ligand;" Biojournal of Biomolecular Screening, The Official Journal of The Society for Biomolecular Screening, vol. 8, No. 1, Feb. 2003; Copyright 2003 The Society for Biomolecular Screening; www.sbsonline.org; pp. 34-38.

Hung et al., "Long-term effect of interferon alpha-2b plus ribavirin therapy on incidence of hepatocellular carcinoma in patients with hepatitis C virus-related cirrhosis"; Journal of Viral Hepatitis, vol. 13, No. 6, Jun. 2006; Copyright 2006 Blackwell Publishing Ltd., pp. 409-414.

Hur et al., 2008, "Clinical stage EGFR inhibitors irreversibly alkylate Bmx kinase", Bioorg Med Chem Lett; 18(22):5916-5919.

Institute of Molecular Function, Docking Study with HyperChem (online), Sep. 4, 2007, ftp://ftp.molfunction.com/molfimcrelease/pamphletDS.pdf, Date of search: Mar. 11, 2015 (with partial English translation).

International Preliminary Report on Patentability of International Application No. PCT/US2009/056025, dated March 8, 2011.

International Preliminary Report on Patentability of International Application No. PCT/US2010/048916, dated Mar. 20, 2012.

International Preliminary Report on Patentability of International Application No. PCT/US2010/062473, dated Jul. 4, 2012.

International Search Report and Written Opinion from International Application No. PCT/US2010/048916, dated Mar. 15, 2011.

International Search Report and Written Opinion from International Application No. PCT/US2010/062473, dated May 24, 2011.

International Search Report and Written Opinion from International Application No. PCT/US2009/056025, dated Feb. 2, 2010.

Johnson et al., "Structure-Based Design of a Parallel Synthetic Array Directed Toward the Discovery of Irreversible Inhibitors of Human Rhinovirus 3C Protease", J. Med. Chem., 45:2016-2023 (2002).

Johnson et al., 2003, "Inhibitors tethered near the acetylcholinesterase active site serve as molecular rulers of the peripheral and acylation sites", J Biol Chem; 278:38948-38955.

Kitahara et al., "Synthesis of -tumeronol A, an inhibitor of soybean lipoxygenase, and -ar-turmerone," Bioscience Biotechnology & Biochemistry, 1993, 57:1137-1140.

Kwak et al., "Irreversible inhibitors of the EGF receptor may circumvent acquired resistance to Geftinib." Proc. Natl. Acad. Sci. 102:7665-7670 (2005).

Lawate et al., "Trifluoromethylacetylenic Alcohols as Affinity Labels: Inactivation of Estradiol Dehydrogenase by a Trifluoromethylacetylenic Secoestradiol;" Journal of Medicinal Chemistry; vol. 33, No. 9, Sep. 1990; Copyright 1990 American Chemical Society; pp. 2319-2321.

Lee et al., "Irreversible Inactivation of Trypanothione Reductase by Unsaturated Mannich Bases: A Divinyl Ketone as Key Intermediate," J. Med. Chem., 2005, 48:7400-7410.

Leite et al. 2007, "Frog: a FRee Online druG 3D conformation generator", Nucleic Acids Res; 35:W568-W572.

Levitsky et al., 2003, "Selective inhibition of engineered receptors via proximity-accelerate alkylation", Org Lett; 5(5):693-696.

Li et al. 2004, "Chemical Adaptor Immunotherapy: Design, Synthesis, and Evaluation of Novel Integrin-Targeting Devices;" Journal of Medicinal Chemistry, vol. 47, pp. 5630-5640.

Lima et al., 2005, "Bioisosterism: A Useful Strategy for Molecular Modification and Drug Design", Curr Med Chem; 12:23-49.

Lyne, 2002, "Structure-based virtual screening: anoverview", Drug Discovery Today; 7 (20):1047-1055.

Marone et al., "Targeting phosphoinosilide 3-kinase-Moving towards therapy;" Biochimica et Biophysica Acta (BBA), Proteins and Proteomics, vol. 1784, No. 1, Jan. 2008; Copyright 2007 Elsevier B.V.; pp. 159-185.

Marrano et al., 2001, "Evaluation of novel dipeptide-bound α,β-unsaturated amides and epoxides as irreversible inhibitors of guinea pig liver transglutaminase", Bioorganic & Medicinal Chemistry; 9:1923-1928.

Mitsuhashi et al., "Tautomycetin Is a Novel and Specific Inhibitor of Serine/Threonine Protein Phosphatase Type 1, PP1," Biochemical and Biophysical Research Communications, 2001, 287:328-331.

Moll et al., 2005, "BALLView: An object-oriented molecular visualization and modeling framework", Journal of Computer-Aided Molecular Design; 19:791-800.

Moradpour and Blum, "Current and evolving therapies for hepatitis C;" European Journal of Gastroenterology & Hepatology; Official Journal of the European Association for Gastroenterology and Endoscopy, vol. 11, No. 11; Copyright 1999 Lippincott Williams & Wilkins; pp. 1199-1202.

Mortreux et al., "Molecular and cellular aspects of HTLV-1 associated leukemogenesis in vivo;" Leukemia, Normal and Malignant Hemopoiesis, vol. 17, No. 1, Jan. 2003; www.nature.com/leu; Official Journal of the Leukaemia Research Fund, UK; Copyright 2003 Nature Publishing Group; pp. 26-38.

Nakamura, Pharmacia, 2005, 41(12): 1144-1148 (with partial English translation).

Nango et al., "Active Site Mapping of 2-Deoxy-scyllo-inosose Synthase, the Key Starter Enzyme for the Biosynthesis of 2-Deoxystreptamine. Mechanism-Based Inhibition and Identification of Lysine-141 as the Entrapped Nucleophile;" Journal of the American Chemical Society, JOC Articles published on the web Sep. 23, 2003; Copyright 2004 American Chemical Society; J. Org. Chem. 2004, vol. 69, No. 3, Feb. 6, 2004, pp. 593-600.

Nonaka et al., "FLAG-tag selective covalent protein labeling via a binding-induced acyl-transfer reaction;" Bioorganic & Medicinal Chemistry Letters 19, The Tetrahedron Journal for Research at the Interface of Chemistry and Biology; www.sciencedirect.com; Copyright 2009 Elsevier Ltd.; (2009); pp. 6696-6699.

Notice of Allowance dated Jul. 24, 2015 for U.S. Appl. No. 12/882,484, filed Sep. 15, 2010.

Notification of Transmittal of the International Search Report and the Written Opinion of the International Searching Authority, or the Declaration for International Application No. PCT/US2010/062473 dated May 24, 2011.

(56) References Cited

OTHER PUBLICATIONS

Nurtjahja-Tjendraputra et al., "Effective anti-platelet and COX-1 enzyme inhibitors from pungent constituents of ginger," Thrombosis Research, 2003, 111:259-265.
Office Action dated Apr. 27, 2015 for U.S. Appl. No. 12/554,433, filed Sep. 4, 2009.
Office Action dated Apr. 30, 2013 for U.S. Appl. No. 12/982,352, filed Dec. 30, 2010.
Office Action dated Dec. 10, 2012 for U.S. Appl. No. 12/982,352, filed Dec. 30, 2010.
Office Action dated Dec. 31, 2014 for U.S. Appl. No. 12/982,352, filed Dec. 30, 2011.
Office Action dated Jan. 20, 2015 for U.S. Appl. No. 12/882,484, filed Sep. 15, 2010.
Office Action dated Jun. 26, 2014 for U.S. Appl. No. 12/554,433, filed Sep. 4, 2009.
Office Action dated Jun. 5, 2014 for U.S. Appl. No. 12/882,484, filed Sep. 15, 2010.
Office Action dated Mar. 27, 2012 for U.S. Appl. No. 12/554,433, filed Sep. 4, 2009.
Office Action dated Nov. 21, 2014 for U.S. Appl. No. 12/554,433, filed Sep. 4, 2009.
Office Action dated Nov. 26, 2012 for U.S. Appl. No. 12/554,433, filed Sep. 4, 2009.
Office Action dated Oct. 22, 2015 for U.S. Appl. No. 12/982,352, filed Dec. 30, 2010.
Office Action dated Sep. 12, 2014 for U.S. Appl. No. 12/982,352, filed Dec. 30, 2010.
Pan et al., "Discovery of Selective Irreversible Inhibitors for Bruton's Tyrosine Kinase", ChemMedChem, 2:58-61 (2007).
Ploeman et al., 1996, "Irreversible inhibition of cytosolic glutathione-S-transferases", Glutathione S-Transferases Structure, Function and Clinical Implications, Taylor and Francis Ltd. London, Chapter 13:143-152.
Popkov et al., "Instant immunity through chemically programmable vaccination and covalent self-assembly;" Proceedings of the National Academy of Sciences of the United States of America, Signaling networks and body shape; vol. 106, No. 11, Mar. 17, 2009; www.pnas.org/cgi/doi/10.1073/pnas.09001471 06; pp. 4378-4383.
Powers et al., "SAR and Mode of Action of Novel Non-Nucleoside Inhibitors of Hepatitis C NS5b RNA Polymerase", J. Med. Chem., 49:1034-1046 (2006).
Rader et al., "Chemically programmed monoclonal antibodies for cancer therapy: Adaptor immunotherapy based on a covalent antibody catalyst;" Proceedings of the National Academy of Sciences of the United States of America, Fungal susceptibility caused by apoptosis inhibitors; vol. 100, No. 9, Apr. 29, 2003; www.pnas.org/cgi/doi/10.1073/pnas.0931308100; pp. 5396-5400.
Ray et al., "Design of Novel Synthetic MTS Conjugates of Bile Acids for Site-Directed Sulfhydryl Labeling of Cysteine Residues in Bile Acid Binding and Transporting Proteins," Bioorganic & Medicinal Chemistry Letters, 16:1473-1476 (2006).
Reynolds et al., "Phospholipase A2 Inhibition and Modification by Manoalogue;" Journal of the American Chemical Society; Copyright 1988 American Chemical Society; J. Am. Chem. Soc 1998, 110, pp. 5172-5177.
Rostovtsev et al., "A Stepwise Huisgen Cycloaddition Process: Copper(I)-Catalyzed Regioselective "Litigation" of Azides and Terminal Alkynes;" Angewandte Cheme, A Journal of the Gesellschaft Deutscher Chemiker; International Edition 2002, vol. 41, No. 14, Jul. 15, 2002; Copyright 2002 WILEY-VCH Verlag GmbH, 69451 Weinheim, Germany 2002; pp. 2596-2599.
Schirmer et al., "Targeted covalent inactivation of protein kinases by resorcylic acid lactone polyketides", Proc. Natl. Acad. Sci., 103:4234-4239 (2006).
Schulz, "Metabolism of 4-Pentenoic Acid and Inhibition of Thiolase by Metabolites of 4-Pentenoic Acid," Biochemistry, 1983, 22: 1827-1832.
Shimada et al., 2000, "Analysis of knowledge-based protein-ligand potentials using a self-consistent method", Protein Sci., 9(4)765-75.

Singh et al., "Structure-Based Design of a Potent, Selective, and Irreversible Inhibitor of the Catalytic Domain of the erbB Receptor Subfamily of Protein Tyrosine Kinases", J. Med. Chem., 40:1130-1135 (1997).
Singh et al., 2010, "Targeted covalent drugs of the kinase family", Curr Opin Chem Biol; 14:475-480.
Singh et al., 2011, "The resurgence of covalent drugs", Nat Rev Drug Discovery; 10:307-317.
Statsuk et al., "Tuning a Three-Component Reaction For Trapping Kinase Substrate Complexes;" Journal of the American Chemical Society, JACS Articles published on web Nov. 20, 2008; Copyright 2008 American Chemical Society; J. Am. Chem. Soc., vol. 130, No. 51,2008, 130, pp. 17568-17574.
Steindl et al., "Human Rhinovirus 3C Protease: Generation of Pharmacophore Models for Peptidic and Nonpeptidic Inhibitors and Their Application in Virtual Screening," J. Chem. Inf. Model., 2005, 45:716-724.
Sun et al., Structure-Based Design, Synthesis, Evaluation, and Crystallographic Studies of Confoimationally Constrained Smac Mimetics as Inhibitors of the X-linked Inhibitor of Apoptosis Protein (XIAP); Journal of Medicinal Chemistry, vol. 51, No. 22, Nov. 27, 2008; J. Med. Chem. 2008; Copyright 2008 American Chemical Society; Published on Web Oct. 28, 2008; pp. 7169-7180.
Sun et al., "Carbohydrate and Protein Immobilization onto Solid Surfaces by Sequential Diels-Aider and Azide-Aikyne Cycloadditons;" Bioconjugate Chemistry, vol. 17, No. 1, Jan./Feb. 2006; Bioconjugate Chem. 2006; Copyright 2006 American Chemical Society; Published on Web Dec. 21, 2005; pp. 52-57.
Sun et al., "Design, Synthesis, and Evaluation of Potent, Nonpeptidic Mimetics of Second Mitochondria-Derived Activator of Caspases;" Journal of Medicinal Chemistry, vol. 52, No. 3, Feb. 12, 2009; J. Med. Chem. 2009; Copyright 2009 American Chemical Society; Published on the web Jan. 12, 2009; pp. 593-596.
Thompson et al., "Mechamstic Studies on b-Ketoacyl Thiolase from Zoogloea ramigera: Identification of the Active-Site Nucleophile as Cys89, Its Mutation to Ser89 and Kinetic and Thermodynamic Characterization of Wild-Type and Mutant Enzymes," Biochemistry, 1989, 28:5735-5742.
Toth et al., "Computational Approach to Site-Directed Ligand Discovery", Proteins, 68:551-560 (2007).
Tsou et al., 2005, "Optimization of 6,7-disubstituted-4-(arylamino)quinoline-3-carbonitriles as orally active, irreversible inhibitors of human epideimal growth factor receptor-2 kinase activity", Journal of Medicinal Chemistry; 48:1107-1131.
Tsuji, "Development of the Structure-based Drug Design Systems, HMHC and DSHC," Molecular Science (online), 2007, 1(1), NP004, http://j-molsci.jp/np/NP004.pdf, Date of search: Mar. 11, 2015 (with partial English translation).
Walker, "Hepatitis C virus: an overview of current approaches and progress;" Drug Discovery Today, vol. 4, No. 11, Nov. 11, 1999; Copyright 1999 Elsevier Science Ltd.; pp. 518-529.
Wang et al., "Characterization of HKI-272 Covalent Binding to Human Serum Albumin;" Drug and Metabolism and Disposition, vol. 38, No. 7, Jul. 2010; Copyright 2010 by The American Society for Pharmacology and Experimental Therapeutics, pp. 1083-1093.
Weiland, "Interferon therapy in chronic hepatitis C virus infection;" FEMS Microbiology Reviews, Special Issue, Papers presented at the FEMS Symposium on The Hepatitis C Virus and its Infection; Istanbul, Turkey, Jun. 29-Jul. 1, 1993; Copyright 1994 Federation of European Microbiological Societies; pp. 279-288.
Wissner et al., "2-(Quinazolin-4-ylamino)-[1,4] benzoquinones as Covalent-Binding, Irreversible Inhibitors of the Kinase Domain of Vascular Endothelial Growth Factor Receptor-2", J. Med. Chem., 48:7560-7581(2005).
Wissner et al., 2003, "Synthesis and structure-activity relationships of 6,7-disubstituted 4-anilinoquinoline-3-carbonitriles. The design of an orally active, irreversible inhibitor of the tyrosine kinase activity of the epidermal growth factor receptor (EGFR) and the human epidermal growth factor receptor-2 (HER-2)", Journal of Medicinal Chemistry; 46:49-63.
Wood et al.. "6-Ethynylthieno[3,2-d]- and 6-ethynylthieno[2.3-d]pyrimidin-4-anilines as tunable covalent modifiers of ErbB kinases", Proc. Natl. Acad. Sci., 105:2773-2778 (2008).

(56) References Cited

OTHER PUBLICATIONS

Wymann et al., 1996, "Wortmannin inactivates phosphoinositide 3-kinase by covalent modification of Lys-802, a residue involved in the phosphate transfer reaction", Mol Cell Biol; 16(4):1722-1733.
Yang et al., "Importance of Ligand Reorganization Free Energy in Protein-Ligand Binding-Affinity Prediction:" National Institutes of Health; J. Am Chem. Soc. 2009; Sep. 30, 2009; 131(38): pp. 13709-13721.
Yang et al., 2009, "Importance of ligand reorganization free energy in protein-ligand binding-affinity prediction", J Am Chem Soc; 131:13709-13721.
Zhang et al., "Targeting cancer with small molecule kinase inhibitors", Nature Reviews Cancer; 9:28-39 (2009).
Blair et al., "Structure-guided development of affinity probes for tyrosine kinases using chemical genetics," Nature Chemical Biology; 3(4):229-238 (Apr. 2007).
Clayden et al., Organic Chemistry, Oxford University Press, 2001, 227-240, 424-426.
Communication pursuant to Rule 114(2) EPC dated Mar. 16, 2017 for EP Application No. 10817748,6, filed Mar. 24, 2011 (including Third Party Observations).
CSF1R—Macrophage colony-stimulating factor 1 receptor, *Homo sapiens*, http://www.uniprot.org/uniprot/P07333, accessed Jul. 12, 2016.
Hur et al., 2008, "Clinical stage EGFR inhibitors irreversibly alkylate Bmx kinase", Bioorg Med Chem Lett; 18(22):5916-5919; Supplemental Data.
Mast/stem cell growth factor receptor Kit, *Homo sapiens*, http://www.uniprot.org/blast/?about=P10721[546-976]&key=Topologicaldomein, accessed Jul. 12, 2016.
Notice of Grounds for Rejection regarding Japanese Patent Application No. 2015-174949 dispatched from the Japanese Patent Office dated Nov. 4, 2016 (with English Translation).
Notice of Grounds for Revocation (in connection with Opposition No. 2016-700411) against Japanese Patent No. 5806670 dated Sep. 1, 2016; Dispatching No. 078712 (with English Translation).
Office Action dated Nov. 18, 2016 for U.S. Appl. No. 12/554,433, filed Sep. 4, 2009.
Office Action dated Apr. 20, 2016 for U.S. Appl. No. 12/554,433, filed Sep. 4, 2009.
Office Action dated Nov. 3, 2016 for U.S. Appl. No. 12/982,352, filed Dec. 30, 2010.
Opposition No. 2016-700411 filed against Japanese Patent No. 5806670 on May 10, 2016; dated Jun. 24, 2016 (with English Translation).
Palmer et al., "Tyrosine Kinase Inhibitors. 11. Soluble Analogues of Pyrrolo- and Pyrazoloquinazolines as Epidermal Growth Factor Receptor Inhibitors: Synthesis, Biological Evaluation, and Modeling of the Mode of Binding," J. Med. Chem., 1997, 40:1519-1529.
Powers et al., "Irreversible Inhibitors of Serine, Cysteine, and Threonine Proteases," Chem. Rev.; 102:4639-4750 (2002).
Printout from the NCBI Protein website: https://www.ncbi.nlm.nih.gov/protein/P07333.2, accessed Apr. 17, 2017.
Response to Communication pursuant to Art. 94(3) EPC dated Dec. 6, 2013 for EP 08770044.9 based on PCT/US2008/065646 (WO 2008/151183), submitted Jun. 16, 2014.
Smaill et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J. Med. Chem., 2000, 43:1380-1397.
Soyaku kagaku (Drug-Production Chemistry), Approaches from Organic Synthesis (2004) Tokyo Kagaku Dojin, North Yasuyuki and Hiraoka Tetsuo, eds., p. 116 (with partial English Translation).
Third Party Observation regarding Japanese Patent Application No. 2015-174949 submitted to the Japanese Patent Office on Sep. 12, 2016 (with English Translation).
Zhang et al., "Targeting cancer with small molecule kinase inhibitors", Nature Reviews Cancer; 9:28-39 (2009), Supplementary Information S1.
Zhang et al., "Targeting cancer with small molecule kinase inhibitors", Nature Reviews Cancer; 9:28-39 (2009), Supplementary Information S2.
Zhang et al., "Targeting cancer with small molecule kinase inhibitors", Nature Reviews Cancer; 9:28-39 (2009), Supplementary Information S3.
Zhou et al., "A Structure-Guided Approach to Creating Covalent FGFR Inhibitors," Chemistry and Biology, 2010, 17(3):285-295.

\* cited by examiner

X-ray co-crystal structure (2JK7) shows key lysines in XIAP proximal to bound Smac-mimetic ligand

LIGAND-DIRECTED COVALENT MODIFICATION OF PROTEIN

PRIORITY CLAIM

This application is a divisional of U.S. patent application Ser. No. 12/982,352, filed on Dec. 30, 2010, which claims the benefit of U.S. Provisional Application No. 61/335,043, filed on Dec. 30, 2009, each of which is relied on and incorporated herein by reference into the present application in its entirety. All patents, patent applications and referenced articles are hereby incorporated by reference into this application in their entireties.

DESCRIPTION OF THE TEXT FILE SUBMITTED ELECTRONICALLY

The instant application contains a Sequence Listing which has been submitted electronically in ASCII format and is hereby incorporated by reference in its entirety. Said ASCII copy, created on Apr. 10, 2017, is named seq_listing_14247_146_999.txt and is 25,669 bytes in size.

FIELD OF THE INVENTION

The present invention relates to enzyme inhibitors. More specifically, the present invention relates to ligand-directed covalent modification of lysine-containing proteins.

BACKGROUND OF THE INVENTION

Compounds that inhibit the activity of proteins, such as enzymes, are important therapeutic agents. Most inhibitors reversibly bind to their target protein and therefore reversibly inhibit the activity of their target protein. Although reversible inhibitors have been developed that are efficacious therapeutic agents, reversible inhibitors have certain disadvantages. For example, many reversible inhibitors of kinases interact with the ATP-binding site. Because the structure of the ATP-binding site is highly conserved among kinases, it has been very challenging to develop reversible inhibitors that selectively inhibit one or more desired kinases. In addition, because reversible inhibitors dissociate from their target protein, the duration of inhibition may be shorter than desired. Thus, when reversible inhibitors are used as therapeutic agents higher quantities and/or more frequent dosing than is desired may be required in order to achieve the intended biological effect. This dosing requirement may produce toxicity or result in other undesirable effects.

Irreversible inhibitors that covalently bind to their target protein have been described in the art. Covalent irreversible inhibitors of drug targets have a number of important advantages over their reversible counterparts as therapeutics. Prolonged suppression of the drug targets may be necessary for maximum pharmacodynamic effect and an irreversible inhibitor can provide this advantage by permanently eliminating existing drug target activity, which will return only when new target protein is synthesized. When an irreversible inhibitor is administered, the therapeutic plasma concentration of the irreversible inhibitor would need to be attained only long enough to briefly expose the target protein to the inhibitor, which would irreversibly suppress activity of the target and plasma levels could then rapidly decline while the target protein would remain inactivated. This irreversible binding has the potential advantage of lowering the minimal blood plasma concentration at which therapeutic activity occurs, minimizing multiple dosing requirements and eliminating the requirement for long plasma half-lives without compromising efficacy. All of these considerations could reduce toxicity due to any nonspecific off-target interactions that may occur at high or prolonged blood plasma levels. Irreversible inhibitors also likely have advantages in overcoming drug resistance requirements in two ways. First, irreversible inhibitors eliminate the requirement for long blood plasma half-lives without compromising efficacy. Second, because resistance mutations may compromise non-covalent binding, but even in the face of reduced non-covalent affinity, the inactivation mechanism will often, nonetheless, lead to protein target modification and irreversible inhibition. All of these considerations could reduce toxicity due to any nonspecific off-target interactions that may occur at high or prolonged blood plasma levels. Another advantage of irreversible inhibitors is that the inactivation mechanism that drives potency will often lead to a selectivity profile that is "orthogonal" to those readily achieved using only non-covalent binding interactions—a profile that is both pharmacologically advantageous and difficult to achieve using non-covalent inhibition.

Many reversible inhibitors of proteins are presently known, as are many of their binding sites in the proteins to which the reversible inhibitors bind. The binding sites of these reversible inhibitors are sometimes populated with amino acids that are capable of covalent modification with suitably reactive ligands. In other instances, amino acids are located near the binding sites of reversible inhibitors that are capable of covalent modification with suitably reactive ligands. Amino acids capable of covalent modification are typically those which have a heteroatom such as O, S, or N in the side chain, such as threonine, cysteine, histidine, serine, tyrosine, and lysine. Sulfur is amenable to covalent modification due to the nucleophilicity of sulfur, and as such there are examples of ligands that modify cysteine in proteins of interest. However, amino acids such as lysine are usually sufficiently unreactive that ligands do not react in vivo with lysine. In fact, highly reactive indiscriminate reagents are usually employed for lysine modification. And, as such, ligand-directed modification of lysine has heretofore remained unrealized. For this reason and others, there is a need for irreversible inhibitors of proteins of medicinal interest, which inhibitors exert their biological influence through a ligand-directed modification of lysine.

I. SUMMARY OF INVENTION

In one aspect, the invention provides a method for designing a ligand that covalently binds a target protein. The method comprises (a) providing a structural model of a reversible ligand docked within, or in proximity to, a ligand-binding site in a target protein, (b) identifying a lysine residue of the target protein in, or in proximity to, the ligand-binding site that is less than about 15 Å from the reversible ligand when the reversible ligand is docked in, or in proximity to, the ligand-binding site, (c) producing at least a structural model of at least one ligand-warhead compound docked within, or in proximity to, the ligand-binding site wherein the ligand-warhead compound comprises the reversible ligand in step (b) or a portion thereof, a warhead comprising a reactive chemical moiety, and optionally a Tether, and (d) identifying a ligand-warhead compound whose structural model allows the lysine residue in step (b) to readily assume a conformation that brings the side chain primary amine group of the lysine residue within bond-forming proximity of the warhead electrophile.

In another aspect, the invention provides a method for designing a ligand that covalently binds a lysine residue of a target protein. The method comprises (a) providing a structural model of a reversible ligand docked in, or in proximity to, a ligand-binding site in a target protein, wherein the reversible ligand makes at least one non-covalent contact with the ligand-binding site; (b) identifying a lysine residue in, or in proximity to, the ligand-binding site of the target protein that is adjacent to the reversible ligand when the reversible ligand is docked in, or in proximity to, the ligand-binding site; (c) producing structural models of a plurality of ligand-warhead compounds docked in, or in proximity to, the ligand-binding site wherein each ligand-warhead compound comprises a warhead covalently attached to a substitutable position of the reversible ligand in step (b) the warhead comprising a reactive chemical moiety and optionally a linker; (d) identifying among the structural models in step (c) at least one ligand-warhead compound whose structural model allows the side chain primary amine group of the lysine residue in step (b) to be within bonding distance of the warhead electrophile; and (e) further identifying among the structural models identified in step (d) a hydrogen-bond donor-containing amino acid residue in, or in the proximity to, the ligand-binding site, wherein the hydrogen-bond donor amino acid residue is within hydrogen-bonding distance of the warhead.

In another aspect, the invention provides a method for identifying at least one lysine residue within at least one protein that can be modified covalently. The method comprises (a) identifying at least one protein having a ligand-binding site, (b) providing a three-dimensional structural model for the identified protein, (c) docking a reversible ligand in, or in proximity to, the identified protein's ligand-binding site in the structural model, wherein the reversible ligand makes at least one non-covalent contact with the ligand-binding site, thereby creating a structural model of a reversible ligand bound to, or in proximity to, an identified protein's ligand-binding site; and (d) identifying in the structural model of a reversible ligand bound to, or in proximity to, an identified protein's ligand-binding site one or more lysine residues in, or in proximity to, the ligand-binding site of the identified protein which is less than about 15 Å from the reversible ligand.

In yet another aspect, the invention provides a method of covalently modifying a lysine residue in, or in proximity to, a ligand-binding site of a protein, comprising contacting a compound of Formula I:

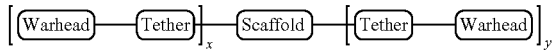

wherein Scaffold, Tether, Warhead, x and y are as defined herein;

with the protein containing a lysine residue in, or in proximity to, the ligand-binding site of the protein and forming a covalent bond between the side chain primary amine group of the lysine residue and the Warhead of the compound.

In another aspect, the invention provides compounds of Formula I:

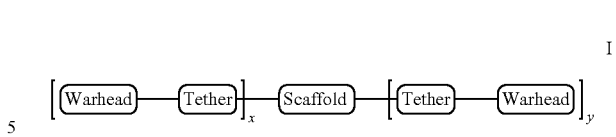

wherein Scaffold, Warhead, Tether, x and y are as defined herein.

In a further aspect, the invention provides protein-modifier-ligand conjugates of Formula XIII:

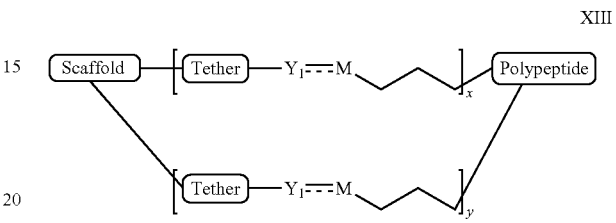

wherein Scaffold, Polypeptide, Tether, M, $Y_1$, x and y are as defined herein.

In yet another aspect of the disclosure, a method for selecting a warhead that binds to a target lysine within a ligand binding site of a protein is disclosed. The method comprises (a) identifying at least one protein having a ligand-binding site, (b) providing a three-dimensional structural model for the identified protein, (c) identifying the locations of at least one lysine in, or in proximity to, the ligand-binding site of step (a); (d) providing at least one warhead in proximity to the at least one identified lysine; (e) aligning the electrophilic atom of the warhead within bonding distance of the primary amine of the at least one identified lysine; (f) forming a covalent bond between the electrophilic atom of the warhead and the primary amine of the at least one lysine; (g) docking a reversible ligand in the identified protein's ligand-binding site within 15 Å of the covalently attached warhead of step (f), wherein the reversible ligand maintains most of its known noncovalent interactions with the ligand binding site; (h) aligning the closest atom of the ligand with the covalently bound warhead of step (f) and determining the geometric requirements for a Tether between the ligand and the covalently bound warhead of step (f).

II. BRIEF DESCRIPTION OF THE FIGURES

III. DETAILED DESCRIPTION OF INVENTION

A. Definitions

Figure 1:
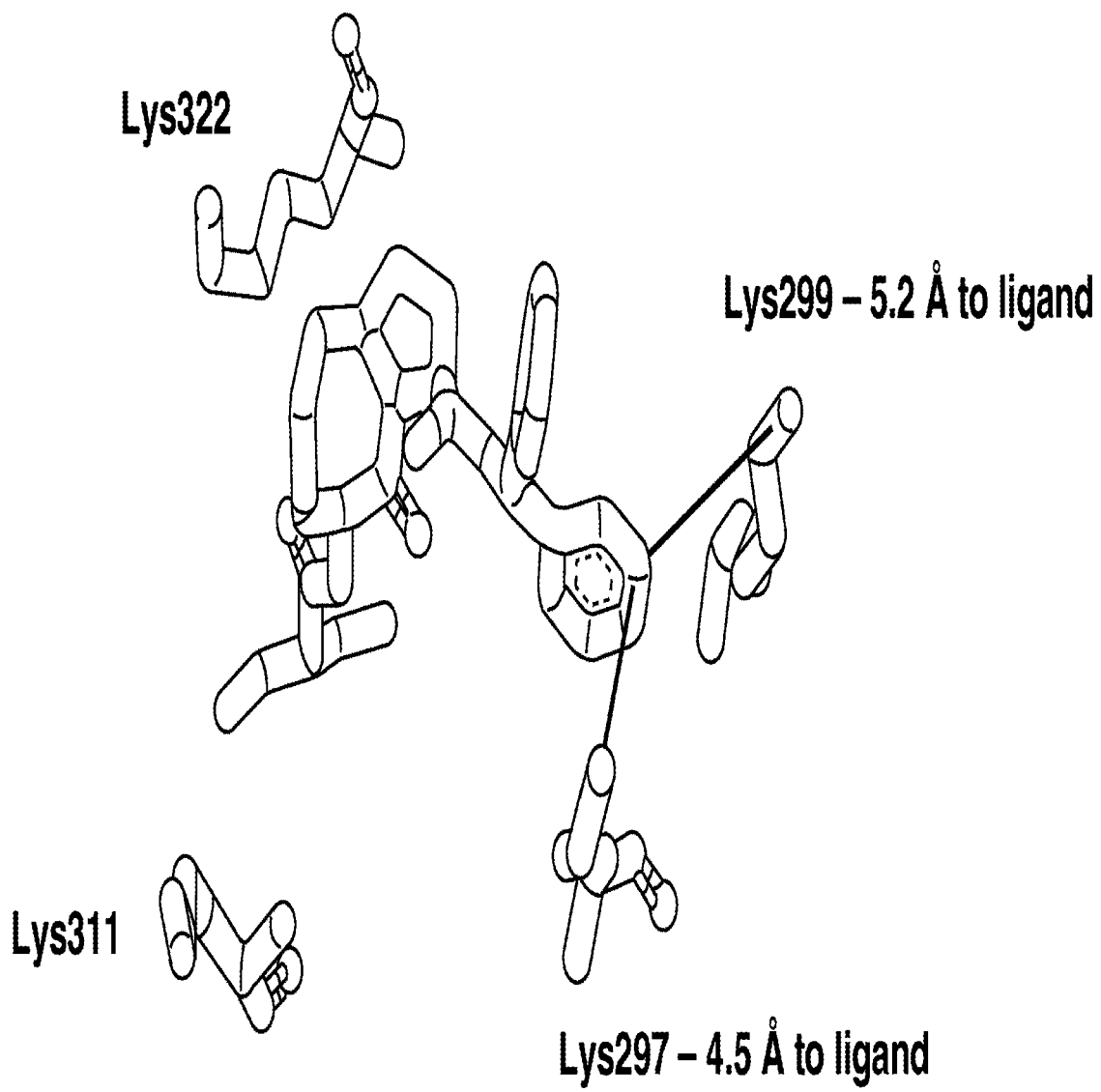
FIG. 1 shows the X-ray co-crystal structure (2JK7) with key lysines in XIAP proximal to bound Smac-mimetic ligand.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference. The biochemical definitions can be found in Structure and Mechanism in Protein Science: A Guide to Enzyme Catalysis and Protein Folding, Alan Fersht, W. H. Freeman, 1998, 1st Edition; Enzymatic Reaction Mechanisms, Perry A. Frey and Adrian D. Hegeman, Perry A. Frey (Author), Oxford University Press, 2007, 1st Edition; and Biochemistry, 6th Edition, Jeremy M. Berg, W. H. Freeman, 2007; the entire contents of which are hereby incorporated by reference.

As used herein the term "protein" means linear polymers made up of the 20 different naturally occurring L-α-amino acids, as well as other less common amino acids. The amino acids in a polymer are joined together by peptide bonds between the carboxyl and amino groups of adjacent amino acid residues. The term polypeptide can be used interchangeably herein with the term protein. Polypeptides can be full length proteins, as well as any portion of a protein. As used herein the terms protein and polypeptide are used to describe proteins containing ligand binding sites. Any protein or polypeptide contemplated herein will be large enough to fold and constitute a ligand binding site.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic," "cycloaliphatic" or "cycloalkyl"), that has a single point of attachment to the rest of the molecule. Unless otherwise specified, aliphatic groups contain 1-8 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e., carbocyclic or heterocyclic, saturated or partially unsaturated, having at least one bridge. As defined by IUPAC, a "bridge" is an optionally substituted chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7- to 12-ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group or the bridge is optionally substituted with one or more substituents as set forth for aliphatic groups. Additionally or alternatively, any substitutable nitrogen of a bridged bicyclic group is optionally substituted. Exemplary bridged bicyclics include:

-continued

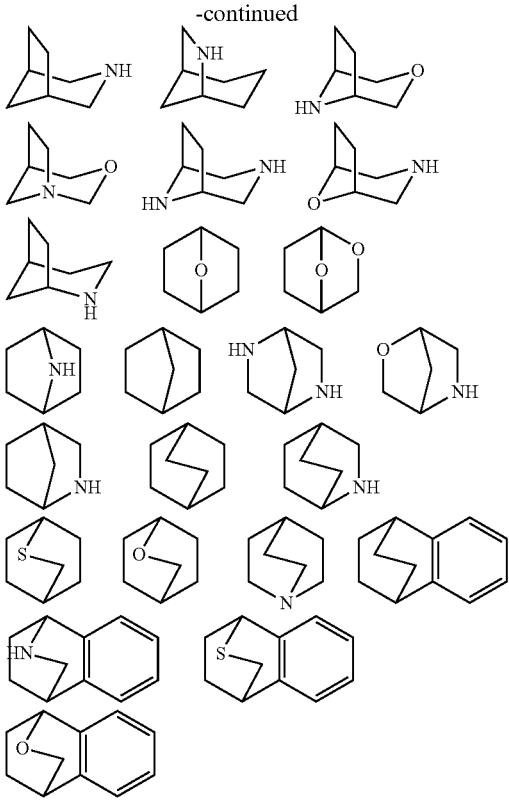

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure

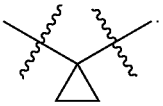

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" as used within this definition refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O$(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}$-pyridyl which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched)alkylene)O—$N(R°)_2$; or —$(C_{1-4}$ straight or branched alkylene)C(O)O)—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5- to 6-membered heteroaryl ring), or a 5- to 6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —$SSR^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R$^•$ include halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, $C_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of $R^*$ are independently halogen, —$R^*$, -(halo$R^*$), —OH, —O$R^*$, —O(halo$R^*$), —CN, —C(O)OH, —C(O)O$R^*$, —NH$_2$, —NH$R^*$, —N$R^*_2$, or —NO$_2$, wherein each $R^*$ is unsubstituted or where preceded by "halo" is substituted only with one or more halogens, and is independently $C_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 66, 1-19 (1977), incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

As used herein, the term "irreversible" or "irreversible inhibitor" refers to an inhibitor (i.e., a compound) that is able to covalently binds to an enzyme, or portion thereof in a substantially non-reversible manner. That is, whereas a reversible inhibitor is able to bind to (but is generally unable to form a covalent bond with) an enzyme, and therefore can become dissociated from the enzyme an irreversible inhibitor will remain substantially bound to an enzyme once covalent bond formation has occurred. Irreversible inhibitors usually display time dependency, whereby the degree of inhibition increases with the length of time with which the inhibitor is in contact with the enzyme. In certain embodiments, an irreversible inhibitor will remain substantially bound to an enzyme once covalent bond formation has occurred and will remain bound for a time period that is longer than the life of the enzyme.

Methods for identifying if a compound is acting as an irreversible inhibitor are known to one of ordinary skill in the art. Such methods include, but are not limited to, enzyme kinetic analysis of the inhibition profile of the compound with the enzyme, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to lysine, present in or near the binding pocket of a target protein, thereby irreversibly inhibiting the protein. It will be appreciated that in some embodiments the Tether-Warhead group, as defined and described herein, provides such warhead groups for covalently, and irreversibly, inhibiting the protein.

As used herein, the term "inhibitor" is defined as a compound that binds to and/or inhibits an enzyme with measurable affinity. In certain embodiments, an inhibitor has an $IC_{50}$ and/or binding constant of less about 10 less than about 1 µM, less than about 100 nM, or less than about 10 nM.

The terms "measurable affinity" and "measurably inhibit," as used herein, means a measurable change in any lysing-containing protein, such as, e.g., XIAP, PI3Kβ/γ, PDPK1 and HCV-NS3 protease activity between a sample comprising a compound of the present invention, or composition thereof, and at least one of XIAP, PI3Kβ/γ, PDPK1 and HCV-NS3 protease, and an equivalent sample comprising at least one of XIAP, PI3Kβ/γ, PDPK1 and HCV-NS3 protease, in the absence of said compound, or composition thereof.

The disclosure of U.S. application Ser. No. 12/554,433, filed Sep. 4, 2009, entitled "Design Algorithm", is hereby incorporated by reference into the subject application in its entirety. As described therein, the incorporated application describes design methods and algorithms for the modification of one or more cysteine residues in a protein target, which design methods and algorithms are equally applicable to the modification of one or more lysine residues in a protein target. Any structural and computational modeling, as well as the software used to generate that modeling described therein, are equally useful in the instant design of covalent inhibitors of lysine and, accordingly are herein incorporated by reference in their entireties into this application.

B. Protein Families Containing Targetable Lysine Residues

In general, lysine residues located in, or in proximity to, a ligand binding site in any targeted family of proteins can be targeted for ligand-directed lysine modification. For example, lysine residues of protein family members targeted for ligand-directed modification by irreversible inhibitors include, without limitation, those summarized in Table 1, below, where "Family" column refers to a family of proteins of interest; the "UniProtAC" column refers to the accession number identifier of a particular protein in accordance with UniProt Knowledgebase (UniProtKB) accession numbers (www.uniprot.org); the "Sequence" column refers to an identifying fragment of the Family member protein's amino acid sequence which includes the lysine of interest; and the "Residue Number" column refers to the lysine residue number as set forth in the sequence. However, antibodies, as a family of proteins, are not contemplated within the present invention and therefore are excluded. (See e.g., Carlos F. Barbas, III, et al., Science 278, 2085-2092 (1997); Popkov et al., Proc Natl Acad Sci USA, 106, 4378-4383, (2009); Doppalapudi et al., Bioorganic & Medicinal Chemistry Letters 17, 501-506, (2007); Li et al., J. Med. Chem., 47, 5630-5640, (2004); Guo et al., Proc. Natl. Acad. Sci. USA, 103, 11009-11014, (2006); Rader et al., Proc Natl Acad Sci USA, 100, 5396-5400, (2003).

1. TABLE OF PROTEIN FAMILIES

| Family | UniProt KB AC | Protein Name | Sequence | Residue Number |
|---|---|---|---|---|
| BCL-2 | Q9BXK5 | Bcl-2-lIKe protein 13 (BCL2L13 aka** MIL1) | 107-LGEKVSQ-113 (SEQ ID NO: 4) | K110 |
| | | | 118-PLHKALQ-124 (SEQ ID NO: 5) | K121 |
| | | | 149-GWNKILV-155 (SEQ ID NO: 6) | K152 |
| | Q16548 | Bcl-2-related protein A1 (BCL2A1 aka BCL2L5 aka BFL1 aka GRS aka HBPA1) | 043-SVQKEVE-049 (SEQ ID NO: 7) | K046 |
| | | | 047-EVEKNLK-053 (SEQ ID NO: 8) | K050 |
| | | | 074-VMEKEFE-080 (SEQ ID NO: 9) | K077 |
| | | | 144-FVKKFEP-150 (SEQ ID NO: 10) | K147 |
| | Q9UMX3 | Bcl-2-related ovarian killer protein (BOK aka BCL2L9) | 119-TWGKVVS-125 (SEQ ID NO: 11) | K122 |
| Calpains | P20807 | Calpain-3 (CAPN3 aka CANP3 aka CANPL3 aka NCL1) | 217-EALKGGN-223 (SEQ ID NO: 12) | K220 |
| | | | 417-HFTKLEI-413 (SEQ ID NO: 13) | K410 |
| | O15484 | Calpain-5 (ITIH2 aka IGHEP2) | 230-ASIKAVT-236 (SEQ ID NO: 14) | K233 |
| | Q9Y6Q1 | Calpain-6 (CAPN5 aka NCL3) | 078-LGHKPMV-084 (SEQ ID NO: 15) | K081 |
| | | | 333-NFHKLNV-339 (SEQ ID NO: 16) | K336 |
| | O14815 | Calpain-9 (CAPN9 aka NCL4) | 185-EALKGGS-191 (SEQ ID NO: 17) | K188 |
| | | | 327-HFDKVEI-333 (SEQ ID NO: 18) | K330 |
| Caspases | P42575 | Caspase-2 (CASP2 aka ICH1 aka NEDD2) | 378-RNTKRGS-384 (SEQ ID NO: 19) | K381 |
| | P42574 | Caspase-3 (CASP3 aka CPP32) | 207-RNSKDGS-213 (SEQ ID NO: 20) | K210 |
| | P55212 | Caspase-6 (CASP6 aka MCH2) | 262-DFCKDPS-268 (SEQ ID NO: 21) | K265 |
| | Q14790 | Caspase-8 (CASP8 aka MCH5) | 250-KVPKLHS-256 (SEQ ID NO: 22) | K253 |
| | | | 450-VSNKDDK-456 (SEQ ID NO: 23) | K453 |
| | | | 453-KDDKKNM-459 (SEQ ID NO: 24) | K456 |
| | | | 454-DDKKNMG-460 (SEQ ID NO: 25) | K457 |

1. TABLE OF PROTEIN FAMILIES

| Family | UniProt KB AC | Protein Name | Sequence | Residue Number |
|---|---|---|---|---|
| | P55211 | Caspase-9 (CASP9 aka MCH6) | 355-RDPKSGS-361 (SEQ ID NO: 26) | K358 |
| | | | 391-VSVKGIY-397 (SEQ ID NO: 27) | K394 |
| | Q92851 | Caspase-10 (CASP10 aka MCH4) | 295-TSLKDRQ-301 (SEQ ID NO: 28) | K298 |
| | P31944 | Caspase-14 (CASP14) | 093-GFLKGED-099 (SEQ ID NO: 29) | K096 |
| | Q9UDY8 | Mucosa-associated lymphoid tissue lymphoma translocation protein 1 (MALT1 aka MLT) | 355-EHPKLKA-361 (SEQ ID NO: 30) | K358 |
| | | | 357-PKLKAPL-363 (SEQ ID NO: 31) | K360 |
| | | | 463-MCRKRND-469 (SEQ ID NO: 32) | K466 |
| | | | 510-IFMKFLK-516 (SEQ ID NO: 33) | K513 |
| Cathepsins | Q9UBX1 | Cathepsin F (CTSF) | 325-DCDKMDK-331 (SEQ ID NO: 34) | K328 |
| | | | 328-KMDKACM-334 (SEQ ID NO: 35) | K331 |
| | | | 371-EKAKVYI-377 (SEQ ID NO: 36) | K374 |
| | P09668 | Cathepsin H (CTSH aka CPSB) | 275-TPDKVNH-281 (SEQ ID NO: 37) | K278 |
| | P56202 | Cathepsin W (CTSW) | 264-INMKPLQ-270 (SEQ ID NO: 38) | K267 |
| HCV | P26663 | Genome polyprotein (N53 Protease) | 1233-GSGKSTK-1239 (SEQ ID NO: 39) | K1236[1] |
| | P26663 | Genome polyprotein (NS5A aka p56) | 2013-RGYKGVW-2019 (SEQ ID NO: 40) | K2016 |
| | P26663 | Genome polyprotein (NS5B aka RNA-directed RNA polymerase aka p68) | 2557-IMAKNEV-2563 (SEQ ID NO: 41) | K2560 |
| HDAC | Q13547 | Histone deacetylase 1 (HDAC1 aka RPD3L1) | 028-HPMKPHR-034 (SEQ ID NO: 42) | K031 |
| | Q96DB2 | Histone deacetylase 11 (HDAC11) | 303-GYQKRTA-309 (SEQ ID NO: 43) | K306 |
| | Q92769 | Histone deacetylase 2 (HDAC2) | 029-HPMKPHR-035 (SEQ ID NO: 44) | K032 |
| | O15379 | Histone deacetylase 3 (HDAC3) | 022-HPMKPHR-028 (SEQ ID NO: 45) | K025 |
| | Q9UBN7 | Histone deacetylase 6 (HDAC6) | 350-GDPKGEM-356 (SEQ ID NO: 46) | K353 |
| | Q9BY41 | Histone deacetylase 8 (HDAC8 aka HDACL1) | 030-SLAKIPK-036 (SEQ ID NO: 47) | K033 |
| HSP70 | P17066 | Heat shock 70 kDa protein 6 (HSPA6 aka HSP70B') | 055-DAAKSQA-061 (SEQ ID NO: 48) | K058 |
| | | | 070-FDAKRLI-076 (SEQ ID NO: 49) | K073 |
| | | | 270-ERAKRTL-276 (SEQ ID NO: 50) | K273 |
| | P11142 | Heat shock cognate 71 kDa protein (HSPA8 aka HSC70 aka HSP73 aka HSPA10) | 058-DAAKNQV-064 (SEQ ID NO: 51) | K061 |
| | | | 068-FDAKRLI-074 (SEQ ID NO: 52) | K071 |
| | | | 268-ERAKRTL-274 (SEQ ID NO: 53) | K271 |
| HSP90 | P07900 | Heat shock protein HSP 90-alpha (HSP90AA1 aka HSP90A aka HSPC1 aka HSPCA) | 055-ALDKIRY-061 (SEQ ID NO: 54) | K058 |
| | P08238 | Heat shock protein HSP 90-beta (HSP90AB1 aka HSP90B aka HSPC2 aka HSPCB) | 050-ALDKIRY-056 (SEQ ID NO: 55) | K053 |

1. TABLE OF PROTEIN FAMILIES

| Family | UniProt KB AC | Protein Name | Sequence | Residue Number |
|---|---|---|---|---|
| IAP | Q13075 | Baculoviral IAP repeat-containing protein 1 (NAIP aka BIRC1) | 188-FTGKQDT-194 (SEQ ID NO: 56) | K191 |
| | | | 216-EHAKWFP-222 (SEQ ID NO: 57) | K199 |
| | Q13490 | Baculoviral IAP repeat-containing protein 2 (BIRC2 aka C-IAP1 aka API1 aka IAP2 aka MIHB) | 302-DDVKCFC-308 (SEQ ID NO: 58) | K305 |
| | Q13489 | Baculoviral IAP repeat-containing protein 3 (BIRC3 aka C-IAP2 aka API2 aka IAP1 aka MIHC) | 288-DDVKCFC-294 (SEQ ID NO: 59) | K291 |
| | P98170 | Baculoviral IAP repeat-containing protein 4 (XIAP aka ILP1 aka HILP aka API3 aka BIRC4 aka IAP3) (SEQ ID NO: 62) | 294-EGDKVKC-300 (SEQ ID NO: 60) | K297 |
| | | | 296-DKCKCFH-302 (SEQ ID NO: 61) | K299 |
| | | | 308-TDWKPSE-314 | K311 |
| | O15392 | Baculoviral IAP repeat-containing protein 5 (BIRC5 aka Survivin aka API4 aka IAP4) | 059-FCFKELE-065 (SEQ ID NO: 63) | K062 |
| | | | 076-EKHKKSS-082 (SEQ ID NO: 64) | K079 |
| | Q6R308 | Baculoviral IAP repeat-containing protein 7 (BIRC7 aka ML-IAP aka livin aka K-IAP) | 118-HQDKVRC-124 (SEQ ID NO: 65) | K121 |
| | | | 132-QSWKRGD-138 (SEQ ID NO: 66) | K135 |
| | | | 143-EHAKWPF-149 (SEQ ID NO: 67) | K146 |
| | Q96P09 | Baculoviral IAP repeat-containing protein 8 (BIRC8 aka ILP2 aka TsIAP) | 033-QEDKVQC-039 (SEQ ID NO: 68) | K036 |
| | | | 047-ANWKPKE-053 (SEQ ID NO: 69) | K050 |
| | | | 058-QHAKWYP-064 (SEQ ID NO: 70) | K061 |
| Kinase | P15056 | B-Raf proto-oncogene serine/threonine-protein kinase (BRAF aka BRAF1 aka RAFB1) | 480-VAVKMLN-486 (SEQ ID NO: 71) | K483 |
| | O96017 | Serine/threonine-protein kinase Chk2 (CHEK2 aka CHK2 aka RAD53) | 221-IMSKTLG-227 (SEQ ID NO: 72) | K224 |
| | | | 242-TCKKVAI-248 (SEQ ID NO: 73) | K245 |
| | | | 249-VAIKISK-256 (SEQ ID NO: 74) | K252 |
| | | | 346-RDLKPEN-352 (SEQ ID NO: 75) | K349 |
| | P00533 | Epidermal growth factor receptor (EGFR aka ERBB1) | 713-KKIKVLG-719 (SEQ ID NO: 76) | K716 |
| | | | 725-TVYKGLW-731 (SEQ ID NO: 77) | K728 |
| | | | 742-VAIKELR-748 (SEQ ID NO: 78) | K745 |
| | P08581 | Hepatocyte growth factor receptor (MET aka c-MET) | 1107-CAVKSLN-1113 (SEQ ID NO: 79) | K1110 |
| | | | 1158-PYMKHGD-1164 (SEQ ID NO: 80) | K1161 |
| | O15530 | 3-phosphoinositide-dependent protein kinase 1 (PDPK1 aka PDK-1) | 083-KFGKILG-089 (SEQ ID NO: 81) | K086 |
| | | | 160-SYAKNGE-166 (SEQ ID NO: 82) | K163 |
| | | | 166-ELLKYIR-172 (SEQ ID NO: 83) | K169 |
| | | | 170-YIRKIGS-176 (SEQ ID NO: 84) | K173 |
| | | | 204-RDLKPEN-210 (SEQ ID NO: 85) | K207 |

1. TABLE OF PROTEIN FAMILIES

| Family | UniProt KB AC | Protein Name | Sequence | Residue Number |
|---|---|---|---|---|
| | P11309 | Proto-oncogene serine/threonine-protein kinase Pim-1 (PIM1) | 257-RDIKDEN-263 (SEQ ID NO: 86) | K260 |
| | P11362 | Basic fibroblast growth factor receptor 1 (FGER1) | 511-VAVKMLK-517 (SEQ ID NO: 87) | K514 |
| | | | 563-YASKGNL-569 (SEQ ID NO: 88) | K566 |
| | P21802 | Fibroblast growth factor receptor 2 (FGFR2) | 514-VAVKMLK-520 (SEQ ID NO: 89) | K517 |
| | | | 566-YASKGNL-572 (SEQ ID NO: 90) | K569 |
| | P22607 | Fibroblast growth factor receptor 3 (FGFR3) | 557-YAAKGNL-563 (SEQ ID NO: 91) | K560 |
| | | | 505-VAVKMLK-511 (SEQ ID NO: 92) | K508 |
| | P22455 | Fibroblast growth factor receptor 4 (FGFR4) | 500-VAVKMLK-506 (SEQ ID NO: 93) | K503 |
| | | | 552-CAAKGNL-558 (SEQ ID NO: 94) | K555 |
| | P15056 | Serine/threonine-protein kinase B-raf (b-RAF) | 470-TVYKGKW-476 (SEQ ID NO: 95) | K473 |
| | P04049 | RAF proto-oncogene serine/threonine-protein kinase (RAF1 aka c-RAF) | 362-TVYKGKW-368 (SEQ ID NO: 96) | K365 |
| | | | 372-VAVKILK-378 (SEQ ID NO: 97) | K375 |
| | | | 428-SLYKHLH-434 (SEQ ID NO: 98) | K431 |
| | P43405 | Tyrosine-protein kinase SYK | 372-LEDKELG-378 (SEQ ID NO: 99) | K375 |
| | | | 384-TVKKGYY-390 (SEQ ID NO: 100) | K387 |
| | | | 455-PLNKYLQ-461 (SEQ ID NO: 101) | K458 |
| MDM2 | Q00987 | E3 ubiquitin-protein ligase Mdm2 (MDM2) | 048-YTMKEVL-064 (SEQ ID NO: 102) | K051 |
| | | | 091-FSVKEHR-097 (SEQ ID NO: 103) | K094 |
| | O15151 | Protein Mdm4 (MDM4 aka MDMX) | 047-FTVKEVM-053 (SEQ ID NO: 104) | K050 |
| | | | 090-FSVKDPS-096 (SEQ ID NO: 105) | K093 |
| | Q96GM5 | SWI/SNF-related matrix-associated actin-dependent regulator of chromatin subfamily D member 1 (SMARCD1 aka BAF60A) | 324-KTHKLQD-330 (SEQ ID NO: 106) | K327 |
| | Q92925 | SWI/SNF-related matrix-associated actin-dependent regulator of chromatin subfamily D member 2 (SMARCD2 aka BAF60B) | 298-IPMKLAG-304 (SEQ ID NO: 107) | K301 |
| | Q6STE5 | SWI/SNF-related matrix-associated actin-dependent regulator of chromatin subfamily D member 3 (SMARCD3 aka BAF60C) | 299-SHDKEYI-305 (SEQ ID NO: 108) | K302 |
| MMP | P39900 | Macrophage metalloelastase (MMP12 aka HME) | 230-SDPKAVM-236 (SEQ ID NO: 109) | P233 |
| | | | 238-PTYKYVD-244 (SEQ ID NO: 110) | P241 |
| | P45452 | Collagenase 3 (MMP13) | 147-AFKKAFK-153 (SEQ ID NO: 111) | K150 |
| | | | 246-YTGKSHF-252 (SEQ ID NO: 112) | K249 |
| | P50281 | Matrix metalloproteinase-14 (MMP14 aka MMP-X1) | 143-AIRKAFR-149 (SEQ ID NO: 113) | K146 |

1. TABLE OF PROTEIN FAMILIES

| Family | UniProt KB AC | Protein Name | Sequence | Residue Number |
|---|---|---|---|---|
| | P51511 | Matrix metalloproteinase-15 (MMP15 aka SMCP-2) | 281-YQWKDVD-287 (SEQ ID NO: 114) | K284 |
| | O60882 | Matrix metalloproteinase-20 (MMP20) | 248-YKYKNPY-254 (SEQ ID NO: 115) | K251 |
| NHR | P03372 | Estrogen receptor (ESR1 aka ESR aka NR3A1) | 526-YSMKCKN-532 (SEQ ID NO: 116) | K529 |
| | Q92731 | Estrogen receptor beta (ESR2 aka ESTRB aka NR3A2) | 311-SWAKKIP-317 (SEQ ID NO: 117) | K314 |
| | Q07869 | Peroxisome proliferator-activated receptor alpha (PPARA aka NR1C1 aka PPAR) | 249-MAEKTLV-264 (SEQ ID NO: 118) | K252 |
| | | | 355-MEPKFDF-361 (SEQ ID NO: 119) | K358 |
| | P06401 | Progesterone receptor (PGR aka NR3C3) | 916-QLPKILA-922 (SEQ ID NO: 120) | K919 |
| PI3K | P42336 | Phosphatidylinositol-4,5-bisphosphate 3-kinase catalytic subunit alpha isoform (PI3K-alpha aka PIK3CA) | 773-SSAKRPL-779 (SEQ ID NO: 121) | K776 |
| | | | 799-IIFKNGD-805 (SEQ ID NO: 122) | K802 |
| | P42338 | Phosphatidylinositol-4,5-bisphosphate 3-kinase catalytic subunit beta isoform (PI3K-beta aka PIK3CB aka PIK3C1) | 774-EKCKYMD-780 (SEQ ID NO: 123) | K777 |
| | | | 802-VIFKNGD-808 (SEQ ID NO: 124) | K805 |
| Phosphatase | P48736 | Phosphatidylinositol-4,5-bisphosphate 3-kinase catalytic subunit gamma isoform (PI3K gamma aka PIK3CG) | 799-EKCKVMA-805 (SEQ ID NO: 125) | K802 |
| | | | 804-MASKKKP-810 (SEQ ID NO: 126) | K807 |
| | | | 830-IIFKHGD-836 (SEQ ID NO: 127) | K833 |
| | | | 880-EIVKDAT-886 (SEQ ID NO: 128) | K883 |
| | | | 887-TIAKIQQ-893 (SEQ ID NO: 129) | K890 |
| | P08575 | Leukocyte common antigen (PTPRC aka CD45) | 620-DDEKQLM-626 (SEQ ID NO: 130) | K623 |
| | | | 756-NRNKCAE-762 (SEQ ID NO: 131) | K759 |
| | P18031 | Tyrosine-protein phosphatase non-receptor type 1 (PTPN1 aka PTP1B) | 117-GSLKCAQ-123 (SEQ ID NO: 132) | K120 |
| | Q06124 | Tyrosine-protein phosphatase non-receptor type 11 (PTPN11 aka PTP2C aka SHPTP2) | 257-QECKLLY-263 (SEQ ID NO: 133) | K260 |
| | | | 277-NRYKNIL-283 (SEQ ID NO: 134) | K280 |
| | | | 361-ERGKSKC-367 (SEQ ID NO: 135) | K364 |
| | | | 363-GKSKCVK-369 (SEQ ID NO: 136) | K366 |
| | Q12923 | Tyrosine-protein phosphatase non-receptor type 13 (PTPN13 aka PNP1 aka PTP1E aka PTPL1) | 2221-QELKPLD-2227 (SEQ ID NO: 137) | K2224 |
| | | | 2241-NRYKNIL-2247 (SEQ ID NO: 138) | K2244 |
| | | | 2313-EGEKIKC-2319 (SEQ ID NO: 139) | K2316 |
| | | | 2315-EKIKCQR-2321 (SEQ ID NO: 140) | K2318 |
| | Q15678 | Tyrosine-protein phosphatase non-receptor type 14 (PTPN14 aka PEZ) | 1015-GRTKSHR-1021 (SEQ ID NO: 141) | K1018 |
| | | | 915-QIPKKKA-921 (SEQ ID NO: 142) | K918 |
| | | | 916-IPKKKAN-922 (SEQ ID NO: 143) | K919 |
| | Q99952 | Tyrosine-protein phosphatase non-receptor type 18 (PTPN18 aka BDP1) | 038-AAWKADG-044 (SEQ ID NO: 144) | K041 |
| | | | 060-NRYKDVL-066 (SEQ ID NO: 145) | K063 |

1. TABLE OF PROTEIN FAMILIES

| Family | UniProt KB AC | Protein Name | Sequence | Residue Number |
|---|---|---|---|---|
| | P17706 | Tyrosine-protein phosphatase non-receptor type 2 (PTPN2 aka PTPT) | 035-RVAKFPE-041 (SEQ ID NO: 146) | K038 |
| | Q9Y2R2 | Tyrosine-protein phosphatase non-receptor type 22 (PTPN22 aka PTPN8) | 029-LKLKRQS-035 (SEQ ID NO: 147) | K032 |
| | | | 036-TKYKADK-042 (SEQ ID NO: 148) | K039 |
| | | | 133-EMGKKKC-139 (SEQ ID NO: 149) | K136 |
| | | | 135-GKKKCER-141 (SEQ ID NO: 150) | K138 |
| | P26045 | Tyrosine-protein phosphatase non-receptor type 3 (PTPN3 aka PTPH1) | 653-LYRKKPG-659 (SEQ ID NO: 151) | K656 |
| | | | 663-TFAKLPQ-669 (SEQ ID NO: 152) | K666 |
| | | | 674-NRYKDVL-680 (SEQ ID NO: 153) | K677 |
| | | | 750-GRTKCHQ-756 (SEQ ID NO: 154) | K753 |
| | P29074 | Tyrosine-protein phosphatase non-receptor type 4 (PTPN4 aka MEG) | 662-LYRKKPG-668 (SEQ ID NO: 155) | L665 |
| | | | 759-GRVKCHQ-765 (SEQ ID NO: 156) | K762 |
| | P54829 | Tyrosine-protein phosphatase non-receptor type 5 (PTPN5) | 326-NRYKTIL-332 (SEQ ID NO: 157) | K329 |
| | | | 404-MNEKCTE-410 (SEQ ID NO: 158) | K407 |
| | P29350 | Tyrosine-protein phosphatase non-receptor type 6 (PTPN6 aka HCP aka PTP1C) | 274-NRYKNIL-2280 (SEQ ID NO: 159) | K277 |
| | P35236 | Tyrosine-protein phosphatase non-receptor type 7 (PTPN7) | 123-DRYKTIL-129 (SEQ ID NO: 160) | K126 |
| | P43378 | Tyrosine-protein phosphatase non-receptor type 9 (PTPN9) | 408-GRRKCGQ-414 (SEQ ID NO: 161) | K411 |
| | P23467 | Receptor-type tyrosine-protein phosphatase beta (PTPRB aka PTPB) | 1808-GRVKCDH-1814 (SEQ ID NO: 162) | K1811 |
| Transthyretin | P02766 | Transthyretin (Prealbumin aka TBPA aka TTR aka ATTR aka PALB) | 032-LMVKVLD-038 (SEQ ID NO: 163) | K035 |
| PARP | P09874 | Poly [ADP-ribose] polymerase 1 (PARP1 aka ADPRT aka PPOL aka ADPRT) | 900-MVSKSAN-906 (SEQ ID NO: 164) | K903 |
| | Q9Y6F1 | Poly [ADP-ribose] polymerase 3 (PARP3 aka ADPRT3 aka ADPRTL3 aka IRT1) | 418-ENSKSAG-424 (SEQ ID NO: 165) | K421 |
| | Q53GL7 | Poly [ADP-ribose] polymerase 10 (PARP10) | 938-DGHKAVF-944 (SEQ ID NO: 166) | K941 |
| | Q9H0J9 | Poly [ADP-ribose] polymerase 12 (PARP12 aka ZC3HDC1) | 606-HYSKSDT-612 (SEQ ID NO: 167) | K609 |
| | Q460N3 | Poly [ADP-ribose] polymerase 15 (PARP15 aka BAL3) | 563-SYGKGTY-569 (SEQ ID NO: 168) | k566 |
| | | | 576-YSAKDTY-582 (SEQ ID NO: 169) | K579 |
| | | | 633-RSPKLFV-639 (SEQ ID NO: 170) | K636 |
| | O95271 | Tankyrase-1 (TNKS aka PARP5A, PARPL aka TIN1 aka TINF1 aka TNKS1) | 1217-NSSKSNQ-1223 (SEQ ID NO: 171) | K1220 |
| | | | 1264-STIKMAH-1270 (SEQ ID NO: 172) | K1269 |
| HIV Protease | P03369 | Gag-Pol polyprotein (HIV protease aka Retropepsin aka PR) | 532-WKPKMIG-538 (SEQ ID NO: 173) | K535 |

[1] In Protein Databank (PDB; www.pdb.org): alternatively numbered as K136.

In some embodiments, the family of proteins having targetable lysine residues according to the present invention is BCL-2. In other embodiments, the family of proteins is Calpains. In other embodiments, the family of proteins is Caspases. In other embodiments, the family of proteins is Cathepsins. In other embodiments, the family of proteins is HCV. In other embodiments, the family of proteins is HDAC. In other embodiments, the family of proteins is HSP70. In other embodiments, the family of proteins is HSP90. In other embodiments, the family of proteins is IAP. In other embodiments, the family of proteins is Kinase. In other embodiments, the family of proteins is MDM2. In other embodiments, the family of proteins is MMP. In other embodiments, the family of proteins is NHR. In other embodiments, the family of proteins is PI3K. In other embodiments, the family of proteins is Phosphatase. In other embodiments, the family of proteins is Transthyretin. In other embodiments, the family of proteins is PARP. In other embodiments, the family of proteins is HIV Protease.

In some embodiments, the members of the BCL-2 family of proteins comprise Bcl-2-like protein 13, Bcl-2-related protein A1, and Bcl-2-related ovarian killer protein. In these embodiments, the target lysines are K110, K121, and K152 in Bcl-2-like protein 13; K046, K050, K077, and K147 in Bcl-2-related protein A1; and K122 in Bcl-2-related ovarian killer protein.

In other embodiments, the members of the Calpains family of proteins comprise Calpain-3, Calpain-5, Calpain-6, and Calpain-9. In these embodiments, the target lysines are K220, and K410 in Calpain 3; K233 in Calpain-5; K081 and K336 in Calpain-6; and K188 and K330 in Calpain-9.

In some embodiments, the members of the Caspases family of proteins comprises Caspase-2, Caspase-3, Caspase-6, Caspase-8, Caspase-9, Caspase-10, Caspase-14, and Mucosa-associated lymphoid tissue lymphoma translocation protein 1. In these embodiments, the target lysines are K381 in Caspase-2; K210 in Caspase-3; K265 in Caspase-6; K253, K453, K456, and K457 in Caspase-8; K358 and K394 in Caspase-9; K298 in Caspase-10; K096 in Caspase-14, and K358, K360, K466, and K513 in Mucosa-associated lymphoid tissue lymphoma translocation protein 1.

In some embodiments, the members of the Cathepsin family of proteins comprise Cathepsin F, Cathepsin H, and Cathepsin W. In these embodiments, the target lysines are K238, K331, and K374 in Cathepsin F; K278 in Cathepsin H; and K267 in Cathepsin W.

In some embodiments, the members of the HCV family of proteins comprises Genome polyprotein (NS3), Genome polyprotein (NS5A), and Genome polyprotein (NS5B). In these embodiments, the target lysines are K1236 in Genome polyprotein (NS3); K2016 in Genome polyprotein (NS5A); and K2560 in Genome polyprotein (NS5B).

In some embodiments, the members of the HCV family of proteins comprises HCV-NS3, HCV-NS5A, and HCV-NS5B.

In some embodiments, the members of the HDAC family of proteins comprise Histone deacetylase 1, Histone deacetylase 11, Histone deacetylase 2, Histone deacetylase 3, Histone deacetylase 6, and Histone deacetylase 8. In these embodiments, the target lysines are K031 in Histone deacetylase 1; K306 in Histone deacetylase 11; K032 in Histone deacetylase 2; K025 in Histone deacetylase 3; K353 in Histone deacetylase 6; and K033 in Histone deacetylase 8.

In some embodiments, the members of the HSP70 family of proteins comprise Heat shock 70 kDa protein 6, and Heat shock cognate 71 kDa protein. In these embodiments, the target lysines are K058, K073, and K273 in Heat shock 70 kDa protein 6; and K061, K071, and K271 in Heat shock cognate 71 kDa protein.

In some embodiments, the members of the HSP90 family of proteins comprise Heat shock protein HSP 90-alpha, and Heat shock protein HSP 90-beta. In these embodiments, the target lysines are K058 in Heat shock protein HSP 90-alpha; and K053 in Heat shock protein HSP 90-beta.

In some embodiments, the members of the IAP family of proteins comprise Baculoviral IAP repeat-containing protein 1 (NAIP aka BIRC1), Baculoviral IAP repeat-containing protein 2 (BIRC2 aka C-IAP1 aka API1 aka IAP2 aka MIHB), Baculoviral IAP repeat-containing protein 3 (BIRC3 aka C-IAP2 aka API2 aka IAP1 aka MIHC), Baculoviral IAP repeat-containing protein 4 (XIAP aka ILP1 aka HILP aka API3 aka BIRC4 aka IAP3), Baculoviral IAP repeat-containing protein 5 (BIRC5 aka Survivin aka API4 aka IAP4), Baculoviral IAP repeat-containing protein 7 (BIRC7 aka ML-IAP aka livin aka K-IAP), and Baculoviral IAP repeat-containing protein 8 (BIRC8 aka ILP2 aka TsIAP). In these embodiments, the target lysines are K191 and K199 in Baculoviral IAP repeat-containing protein 1; K305 in Baculoviral IAP repeat-containing protein 2; K291 in Baculoviral IAP repeat-containing protein 3; K297, K299, and K311 in Baculoviral IAP repeat-containing protein 4; K062 and K079 in Baculoviral IAP repeat-containing protein 5; K121, K135, and K146 in Baculoviral IAP repeat-containing protein 7; and K036, K050, and K061 in Baculoviral IAP repeat-containing protein 8.

In some embodiments, the members of the IAP family of proteins comprises XIAP, cIAP1, cIAP2, and ML-IAP.

In some embodiments, the members of the Kinases family of proteins comprise B-Raf proto-oncogene serine/threonine-protein kinase, Serine/threonine-protein kinase Chk2, Epidermal growth factor receptor, Hepatocyte growth factor receptor, 3-phosphoinositide-dependent protein kinase 1 (PDPK1), Proto-oncogene serine/threonine-protein kinase Pim-1.Basic fibroblast growth factor receptor 1 (FGFR1), Fibroblast growth factor receptor 2 (FGFR2), Fibroblast growth factor receptor 3 (FGFR3), Fibroblast growth factor receptor 4 (FGFR4), 3-phosphoinositide-dependent protein kinase 1 (PDPK1), Serine/threonine-protein kinase B-raf (b-RAF), RAF proto-oncogene serine/threonine-protein kinase (RAF1 aka c-RAF), and Tyrosine-protein kinase SYK. In these embodiments, the target lysines are K483 in B-Raf proto-oncogene serine/threonine-protein kinase; K224, K245, K252, and K349 in Serine/threonine-protein kinase Chk2; K716, K728, and K745 in Epidermal growth factor receptor; K1110 and K1161 in Hepatocyte growth factor receptor; K086, K163, K169, and K207 in PDPK1; K260 in Proto-oncogene serine/threonine-protein kinase Pim-1; K514,
K566 in basic fibroblast growth factor receptor 1 (FGFR1), K517, K569 in basic fibroblast growth factor receptor 2 (FGFR2); K560, K508 in basic fibroblast growth factor receptor 3 (FGFR3); K503, K555 in basic fibroblast growth factor receptor 4 (FGFR4); K173 in 3-phosphoinositide-dependent protein kinase 1 (PDPK1); K473 in Serine/threonine-protein kinase B-raf (b-RAF); K365 in RAF proto-oncogene serine/threonine-protein kinase (RAF1 aka c-RAF); K375 and K431 in RAF proto-oncogene serine/threonine-protein kinase (RAF1 aka c-RAF); and K375, K387, and K458 in Tyrosine-protein kinase SYK.

In some embodiments, the members of the PDK family of proteins comprises PDPK1.

In some embodiments, the members of the MDM2 family of proteins comprise E3 ubiquitin-protein ligase Mdm2, Protein Mdm4, SWI/SNF-related matrix-associated actin-dependent regulator of chromatin subfamily D member 1, SWI/SNF-related matrix-associated actin-dependent regulator of chromatin subfamily D member 2, and SWI/SNF-related matrix-associated actin-dependent regulator of chromatin subfamily D member 3. In these embodiments, the target lysines are K051 and K094 in E3 ubiquitin-protein ligase Mdm2; K050 and K093 in Protein Mdm4; K327 in SWI/SNF-related matrix-associated actin-dependent regulator of chromatin subfamily D member 1; K301 in SWI/SNF-related matrix-associated actin-dependent regulator of chromatin subfamily D member 2; and K302 in SWI/SNF-related matrix-associated actin-dependent regulator of chromatin subfamily D member 3.

In some embodiments, the members of the MMP family of proteins comprise Macrophage metalloelastase, Collagenase 3, Matrix metalloproteinase-14, Matrix metalloproteinase-15, and Matrix metalloproteinase-20. In these embodiments, the target lysines are K233 and K241 in Macrophage metalloelastase; K150 and K249 in Collagenase 3; K146 in Matrix metalloproteinase-14; K284 in Matrix metalloproteinase-15; and K251 in Matrix metalloproteinase-20.

In some embodiments, the members of the NHR family of proteins comprise Estrogen receptor, Estrogen receptor beta, Peroxisome proliferator-activated receptor alpha, and Progesterone receptor. In these embodiments, the target lysines are K529 in Estrogen receptor; K314 in Estrogen receptor beta; K252 and K358 in Peroxisome proliferator-activated receptor alpha; and K919 in Progesterone receptor.

In some embodiments, the members of the PI3K protein family comprise Phosphatidylinositol-4,5-bisphosphate 3-kinase catalytic subunit alpha isoform (PI3K-alpha aka PIK3CA), Phosphatidylinositol-4,5-bisphosphate 3-kinase catalytic subunit beta isoform (PI3K-beta aka PIK3CB aka PIK3C1), and Phosphatidylinositol-4,5-bisphosphate 3-kinase catalytic subunit gamma isoform (PI3K gamma aka PIK3CG). In these embodiments, the target lysines are K776 and K802 in Phosphatidylinositol-4,5-bisphosphate 3-kinase catalytic subunit alpha isoform; K777 and K805 in Phosphatidylinositol-4,5-bisphosphate 3-kinase catalytic subunit beta isoform; and K802, K807, K833, K883, and K890 in Phosphatidylinositol-4,5-bisphosphate 3-kinase catalytic subunit gamma isoform.

In some embodiments, the members of the PI3K family of proteins comprises PI3Kα, PI3Kβ and PI3Kγ. The term P13K, as used herein, refers to PI3Kβ and PI3Kγ interchangeably as the ligand-directed warhead of the present invention, directed to P13K will modify both PI3Kβ as well as PI3Kγ.

In some embodiments, the members of the Phosphatase family of proteins comprise Leukocyte common antigen, Tyrosine-protein phosphatase non-receptor type 1, Tyrosine-protein phosphatase non-receptor type 11, Tyrosine-protein phosphatase non-receptor type 13, Tyrosine-protein phosphatase non-receptor type 14, Tyrosine-protein phosphatase non-receptor type 18, Tyrosine-protein phosphatase non-receptor type 2, Tyrosine-protein phosphatase non-receptor type 22, Tyrosine-protein phosphatase non-receptor type 3, Tyrosine-protein phosphatase non-receptor type 4, Tyrosine-protein phosphatase non-receptor type 5, Tyrosine-protein phosphatase non-receptor type 6, Tyrosine-protein phosphatase non-receptor type 7, Tyrosine-protein phosphatase non-receptor type 9, and Receptor-type tyrosine-protein phosphatase beta. In these embodiments, the target lysines are K623 and K759 in Leukocyte common antigen; K120 in Tyrosine-protein phosphatase non-receptor type 1; K260, K280, K364, K366 in Tyrosine-protein phosphatase non-receptor type 11; K2224, K2244, K2316, and K2318 in Tyrosine-protein phosphatase non-receptor type 13; K918, K919, and K1018 in Tyrosine-protein phosphatase non-receptor type 14; K041 and K063 in Tyrosine-protein phosphatase non-receptor type 18; K038 in Tyrosine-protein phosphatase non-receptor type 2; K032, K039, K136, and K138 in Tyrosine-protein phosphatase non-receptor type 22, K656, K666, K677, and K753 in Tyrosine-protein phosphatase non-receptor type 3; K665 and K762 in Tyrosine-protein phosphatase non-receptor type 4; K329 and K407 in Tyrosine-protein phosphatase non-receptor type 5; K277 in Tyrosine-protein phosphatase non-receptor type 6; K126 in Tyrosine-protein phosphatase non-receptor type 7; K411 in Tyrosine-protein phosphatase non-receptor type 9; and K1811 in Receptor-type tyrosine-protein phosphatase beta.

In some embodiments, the member of the Transthyretin family of proteins comprises Transthyretin (Prealbumin aka TBPA aka TTR aka ATTR aka PALB). In these embodiments, the target lysine is K035 in Transthyretin.

In some embodiments, the members of the PARP family of proteins comprise Poly [ADP-ribose] polymerase 1 (PARP1 aka ADPRT aka PPOL aka ADPRT), Poly [ADP-ribose] polymerase 3 (PARP3 aka ADPRT3 aka ADPRTL3 aka IRT1), Poly [ADP-ribose] polymerase 10 (PARP10), Poly [ADP-ribose] polymerase 12 (PARP12 aka ZC3HDC1), Poly [ADP-ribose] polymerase 15 (PARP15 aka BAL3), and Tankyrase-1 (TNKS aka PARP5A, PARPL aka TIN1 aka TINF1 aka TNKS1). In these embodiments, the target lysines are K903 in Poly [ADP-ribose] polymerase 1; K421 in Poly [ADP-ribose] polymerase 3; K941 in Poly [ADP-ribose] polymerase 10; K609 in Poly [ADP-ribose] polymerase 12; K566, K579 and K636 in Poly [ADP-ribose] polymerase 15; and K1220 and K1269 in Tankyrase-1.

In some embodiments, the member of the HIV Protease family of proteins comprises Gag-Pol polyprotein (HIV protease aka Retropepsin aka PR). In these embodiments, the target lysine is K535 in Gag-Pol polyprotein.

IV. METHODS FOR DESIGNING A LIGAND THAT COVALENTLY BINDS A TARGET PROTEIN

One aspect of the present disclosure is a method for designing a ligand that covalently binds a target protein. The method comprises (a) providing a structural model of a reversible ligand docked within, or in proximity to, a ligand-binding site in a target protein, (b) identifying a lysine residue of the target protein in, or in proximity to, the ligand-binding site that is less than about 15 Å from the reversible ligand when the reversible ligand is docked in, or in proximity to, the ligand-binding site, (c) producing at least a structural model of at least one ligand-warhead compound docked within, or in proximity to, the ligand-binding site wherein the ligand-warhead compound comprises the reversible ligand in step (b) or a portion thereof, a warhead comprising a reactive chemical moiety, and optionally a Tether, and (d) identifying a ligand-warhead compound whose structural model allows the lysine residue in step (b) to readily assume a conformation that brings the side chain primary amine group of the lysine residue within bond-forming proximity of the warhead electrophile.

Figure 2:
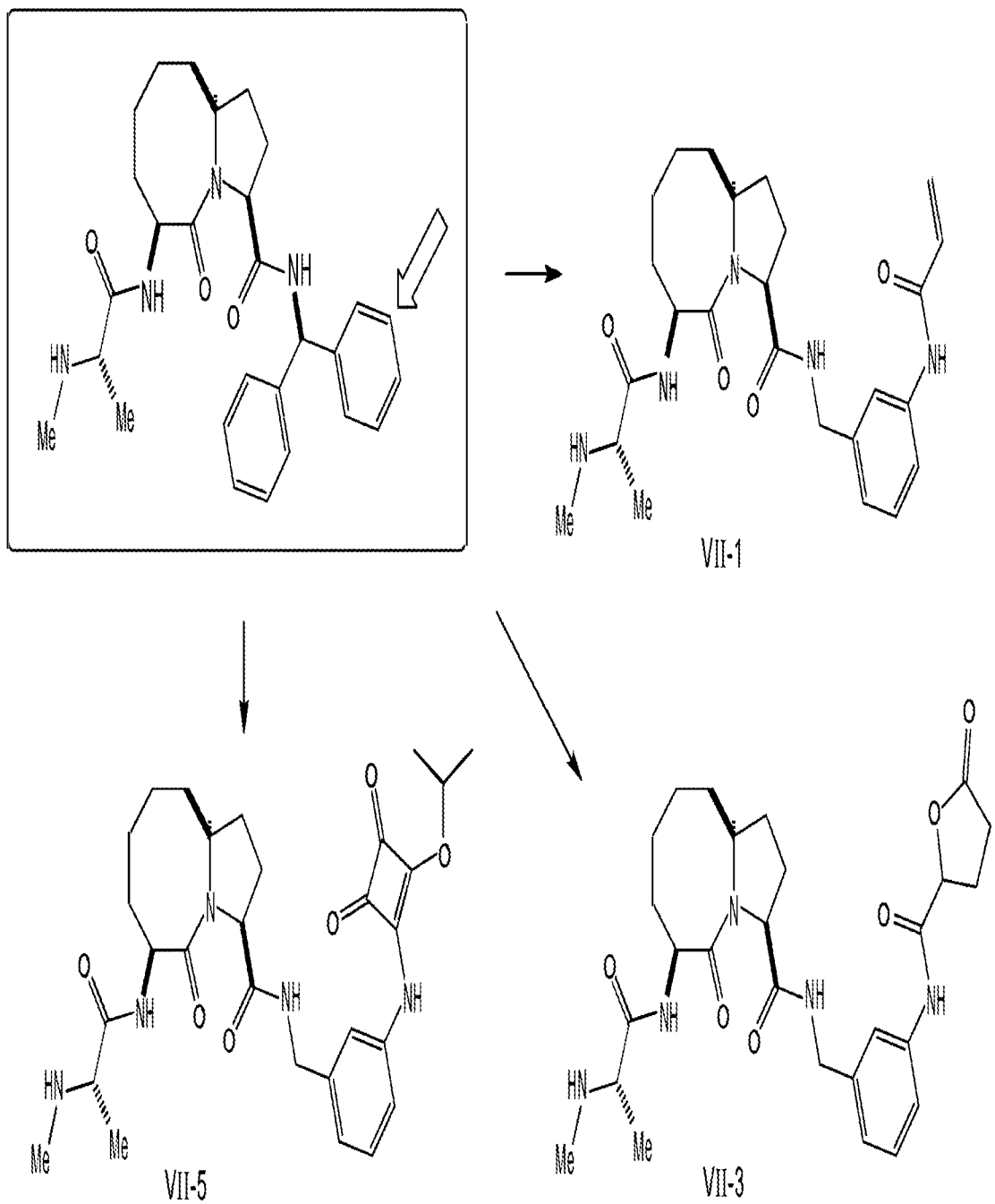
FIG. 2 depicts non-limiting examples of weaponizing the Smac-mimetic ligand.

A non-limiting example of steps (a) and (b) of the method described above is depicted in FIG. 1. FIG. 1 shows X-ray co-crystal structure (2JK7) showing key lysines in XIAP proximal to bound Smac-mimetic ligand. Review of the space occupied by Smac-mimetic ligand in relation to protein XIAP, allowed lysines 299 and 297 to be identified that were about 5.2 Å and 4.5 Å, respectively, from portions of the Smac-mimetic ligand. FIG. 2 depicts non-limiting lysine-targeted warheads installed on scaffolds such that they are directed toward the targeted lysines positioned strategically at portions of compounds based on the pharmacophore of the Smac-mimetic ligand which are in proximity to the identified lysines, above. The reactive warheads (along with a Tether when required) are positioned in silico such that docking of a modified pharmacophore of the ligand in the structural model of the protein binding site (provided in step (a) above), as described in step (c) above, allows for determination of the spatial arrangement of the reactive warhead vis a vis the identified lysine of step (b).

The disclosure of U.S. application Ser. No. 12/554,433, filed Sep. 4, 2009, entitled "Design Algorithm", is hereby incorporated by reference into the subject application in its entirety. As described therein, the incorporated application describes design methods and algorithms for the modification of one or more cysteine residues in a protein target, which design methods and algorithms are equally applicable to the modification of one or more lysine residues in a protein target. Any structural and computational modeling, as well as the software used to generate that modeling described therein, are equally useful in the instant design of covalent inhibitors of lysine and, accordingly are herein incorporated by reference in their entireties into this application.

In certain embodiments, the method further comprises step (e): forming, for the ligand-warhead compound identified in step (d), a ligand-protein, covalent adduct by forming a covalent bond between the side chain primary amine group of the lysine residue identified in step (b) and the warhead electrophile in ligand-warhead compound identified in step (d) while maintaining the binding elements of the pharmacophore required for non-covalent binding to the ligand's target protein.

In some embodiments, the method further comprises step (f): evaluating the conformation of the resulting ligand-protein covalent adduct formed in step (e) by analyzing the global energy of the resulting conformation, or by analyzing the energy of the conformation of the Tether. In other embodiments, the method comprises alternate step (f): determining whether the ligand-binding site is occluded when the covalent bond is formed between the side chain primary amine group of the lysine residue in, or in proximity to, the ligand-binding site and the warhead electrophile.

In other embodiments, the method comprising steps (a)-(f) is iterated with changes to the Tether and the global energy of the resulting conformation is less than the previous iteration.

In certain embodiments, the covalent bond formed in step (e) is formed using a computational method in which the warhead and the side chain of the lysine residue are flexible and the remainder of the structures of the ligand-warhead compound and the ligand-binding site are fixed.

In some embodiments, in step (b) of the method, each of the lysine residues in, or in proximity to, the ligand-binding site of the target protein, which is less than about 15 Å from the reversible ligand, when the reversible ligand is docked in, or in proximity to, the ligand-binding site, is identified.

In other embodiments, step (c) of the method further comprises providing a plurality of models of the ligand-warhead compound, wherein the warhead is bonded to a different substitutable position of the ligand or a portion of the ligand in each model of the ligand-warhead compound, optionally with the Tether in between the warhead and the substitutable position.

In certain embodiments of the method disclosed, the target protein, is an identified member of an identified protein family and the lysine residue is not conserved across the identified members of the protein family.

In other embodiments of the method, the target protein is an identified member of an identified protein family and the lysine residue is conserved among more than one identified member of the identified protein family.

In some embodiments, the lysine residue is conserved across identified members of the protein family.

In some embodiments of the method disclosed herein, the target protein has catalytic activity.

In other embodiments, the target protein family is selected from the group consisting of BCL-2, Calpains, Caspases, Cathepsins, HCV, HDAC, HSP70, HSP90, IAP, Kinase, MDM2, MMP, NHR, PI3Kβ/γ, Phosphatase, Transthyretin, PARP, and HIV Protease.

In some embodiments, the target family of proteins is selected from the group consisting of IAP, PI3K, PDPK1, and HCV.

In other embodiments, the target protein is selected from the group consisting of XIAP, PI3Kβ/γ, PDPK1, and HCV.

In certain embodiments of the method disclosed, the ligand-binding site is a ligand-binding site for a substrate or cofactor.

In other embodiments of the methods, the lysine residue for covalent modification is not a catalytic residue.

In another aspect, the disclosure provides a method for designing a ligand that covalently binds a lysine residue of a target protein. The method comprises (a) providing a structural model of a reversible ligand docked in, or in proximity to, a ligand-binding site in a target protein, wherein the reversible ligand makes at least one non-covalent contact with the ligand-binding site, (b) identifying a lysine residue in, or in proximity to, the ligand-binding site of the target protein that is adjacent to the reversible ligand when the reversible ligand is docked in, or in proximity to, the ligand-binding site, (c) producing one or more structural models of a plurality of ligand-warhead compounds docked in, or in proximity to, the ligand-binding site wherein each ligand-warhead compound comprises a warhead covalently attached to a substitutable position of the reversible ligand in step, (b) the warhead comprising a reactive chemical moiety and optionally a linker; (d) identifying among the structural models in step (c) at least one ligand-warhead compound whose structural model allows the side chain primary amine group of the lysine residue in step (b) to be within bonding distance of the warhead electrophile, and (e) further identifying among the structural models identified in step (d) a hydrogen-bond-donor-containing amino acid residue in, or in proximity to, the ligand-binding site, wherein the hydrogen-bond donor group is within hydrogen-bonding distance of the warhead.

In some embodiments, the hydrogen-bond donor amino acid can participate in the chemical reaction between the warhead of the ligand-warhead and the targeted lysine of the protein. For example, when the hydrogen bond donating amino acid is either lysine or arginine, the interaction between lysine and lysine or lysine and arginine are repulsive interactions that lower the pKa of the targeted lysine, thus enhancing its nucleophilicity. In other examples, hydrogen bond donation, either by a sidechain, or even a main-chain amide can, in many cases, enhance the electrophilicity of a warhead. When such a hydrogen bond donor is also positively charged, Coulombic attraction can accelerate the reaction, for example, by stabilizing the formation of an enolate. In a specific embodiment, when the warhead of the ligand-warhead comprises an acrylamide, the warhead requires a hydrogen bond donor amino acid residue in, or in proximity to, the ligand-binding site, wherein the hydrogen-bond donor group is within hydrogen-bonding distance of the warhead comprising acrylamide.

In certain embodiments, the method further comprises step (f) forming, for the ligand-warhead compound identified in step (e), a ligand-protein covalent adduct by forming a covalent bond between the side chain primary amine group of the lysine residue identified in step (b) and the warhead electrophile; and also forming a hydrogen bond between the hydrogen-bond donor moiety and the warhead electrophile; or a hydrogen bond between the hydrogen-bond donor moiety and the side chain primary amine group of the lysine residue identified in step (d) while substantially maintaining the non-covalent interactions between the pharmacophore of the ligand and the ligand-binding site.

In certain embodiments of the method of designing a ligand, the method further comprises step (g) evaluating a resulting conformation of the ligand-protein covalent adduct by analyzing the global energy of the resulting conformation.

In some embodiments of the method, steps (a) through (g) are iterated with changes to the linker and the global energy of the resulting conformation is less than the previous iteration.

In other embodiments of the method, the hydrogen-bond donor-containing amino acid residue is any amino acid residue that is capable of acting as a hydrogen bond donor. In yet other embodiments of the method, the hydrogen-bond donor-containing amino acid residue is selected from the group consisting of arginine, lysine, threonine, serine, histidine, and tyrosine.

In certain embodiments of the method, the target protein is selected from the group consisting of XIAP, PDPK1, PI3Kβ/γ, and HCV. In other embodiments, when the warhead comprises an acrylamide moiety, the warhead requires a hydrogen-bond donor-containing amino acid residue in, or in proximity to, the ligand-binding site, wherein the hydrogen-bond donor group is within hydrogen-bonding distance of the warhead comprising acrylamide in order for the warhead to covalently bind to the target lysine. In some embodiments, the hydrogen-bond donor-containing amino acid residue is lysine. methods for identifying at least one lysine residue within at least one protein that can be modified In yet another aspect, a method for identifying at least one lysine residue within at least one protein that can be modified covalently is disclosed. The method comprises (a) identifying at least one protein having a ligand-binding site, (b) providing a three-dimensional structural model for the identified protein, (c) docking a reversible ligand in, or in proximity to, the identified protein's ligand-binding site in the structural model, wherein the reversible ligand makes at least one non-covalent contact with the ligand-binding site, thereby creating a structural model of a reversible ligand bound to, or in proximity to, an identified protein's ligand-binding site; and (d) identifying in the structural model of the reversible ligand bound to, or in proximity to, an identified protein's ligand-binding site one or more lysine residues in, or in proximity to, the ligand-binding site of the identified protein which is less than about 15 Å from the reversible ligand.

In certain embodiments, the method further comprises identifying a plurality of proteins having ligand-binding sites that are structurally homologous. Herein, the method further comprises (a) providing a three-dimensional structural model for at least one of the identified proteins, (b) docking a reversible ligand in, or in proximity to, the structural model of the ligand-binding site of at least one of the identified proteins, wherein the reversible ligand makes at least one non-covalent interaction with the ligand-binding site, thereby creating a structural model of a reversible ligand bound to, or in proximity to, the identified protein's ligand-binding site; and (c) identifying in the structural model of a reversible ligand bound to, or in proximity to, the identified protein's ligand-binding site one or more lysine residues in, or in proximity to, the ligand-binding site of the identified protein which is less than about 15 Å from the reversible ligand.

In some embodiments of the method, the method comprises comparing the three-dimensionally equivalent amino acid positions of the homologous ligand-binding sites of more than one of the plurality of identified proteins and determining the prevalence of lysine residues in, or in proximity to, the ligand binding sites of the identified proteins.

In other embodiments of the method, the prevalence of lysine residues in, or in proximity to, the ligand binding sites of the identified proteins is in only one of the identified proteins.

In certain embodiments, the prevalence of lysine residues in, or in proximity to, the ligand binding sites of the identified proteins are in more than one of the identified proteins.

In some of these embodiments, the prevalence of lysine residues in, or in proximity to, the ligand binding sites of the identified proteins, is in less than 10% of the identified proteins of a family at the ligand binding site position. In other embodiments, the prevalence of lysine residues in, or in proximity to, the ligand binding sites of the identified proteins is in less than or greater than 50% of the identified proteins. More than 50%, in some embodiments, the prevalence of lysine residues in, or in proximity to, the ligand binding sites of the identified proteins is in more than 75% of the identified proteins, while in other embodiments, the prevalence of lysine residues in, or in proximity to, the ligand binding sites of the identified proteins is in all of the identified proteins.

In certain embodiments of the method, the protein is selected from the group consisting of BCL-2, Calpains, Caspases, Cathepsins, HCV, HDAC, HSP70, HSP90, IAP, Kinase, MDM2, MMP, NHR, PI3Kβ/γ, Phosphatase, Transthyretin, PARP, and HIV Protease.

In other embodiments, the protein is selected from the group consisting of XIAP, PI3Kβ/γ, PDPK1, and HCV.

V. METHODS FOR DESIGNING WARHEADS THAT BIND TO A TARGET LYSINE WITHIN A LIGAND BINDING SITE OF A PROTEIN

In yet another aspect of the disclosure, a method for selecting a warhead that binds to a target lysine within a ligand binding site of a protein is disclosed. The method comprises (a) identifying at least one protein having a ligand-binding site, (b) providing a three-dimensional structural model for the identified protein, (c) identifying the location of at least one lysine in, or in proximity to, the ligand-binding site of step (a); (d) providing at least one warhead in proximity to the at least one identified lysine; (e) aligning the electrophilic atom of the warhead within bonding distance of the primary amine of the at least one identified lysine; (f) forming a covalent bond between the electrophilic atom of the warhead and the primary amine of the at least one lysine; (g) docking a reversible ligand in the identified protein's ligand-binding site within 15 Å of the covalently attached warhead of step (f), wherein the reversible ligand maintains noncovalent interactions with the ligand binding site; and (h) aligning the closest atom of the ligand with the covalently bound warhead of step (f) and providing the spatial requirements necessary for designing a tether between the ligand and the covalently bound warhead of step (f). In step (h), it is advantageous when the area between the tether and the ligand is complementary with the protein surface in the region between the warhead and the ligand.

VI. METHODS OF COVALENTLY MODIFYING LYSINE

In another aspect, the method comprises contacting a compound of Formula I with a protein containing a lysine residue in, or in proximity to, a ligand-binding site of a protein and forming a covalent bond between the side chain primary amine group of the lysine residue and Warhead of the compound. The method encompasses compounds of Formula I:

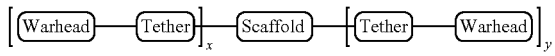

wherein

Scaffold is
a) a radical resulting from the removal of a hydrogen of a ligand capable of binding to, or in proximity to, the ligand-binding site; or
b) a portion of a pharmacophore of a ligand resulting from truncation of the pharmacophore, such that the Scaffold is capable of binding to, or in proximity to, the ligand-binding site;

Warhead is an organic moiety optionally containing one or more heteroatoms selected from O, N, and S, and has a molecular weight of about 14 daltons to about 200 daltons, the Warhead is capable of reacting with a side chain primary amine group of a lysine residue and attaches to the Scaffold through the Tether;

Tether is null, a bond, or a bivalent $C_1$-$C_{15}$ saturated, unsaturated, straight, branched, cyclic, bicyclic, tricyclic alkyl, alkenyl, alkynyl; bridged bicyclic, heterocycle, heteroaryl, or aryl moiety; wherein optionally one or more methylene units of the hydrocarbon chain are independently replaced by —$NR_1$—, —O—, —C(O)—, —S—, —SO—, —$SO_2$—, —C(=S)—, or C(=$NR_1$)—; optionally, one or more hydrogens are independently replaced by heteroatoms, and optionally, one or more methine groups of the $C_1$-$C_{15}$ alkyl, when present, are independently replaced by

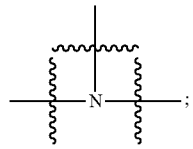 [SMILES: *N(*)*]

x is 0, 1, or 2;
y is 1, 2, or 3; and
$R_1$ is hydrogen or $C_1$-$C_8$ alkyl.

In some embodiments, the compound of Formula I is a compound of Formula I',

It is to be understood that naturally occurring compounds that exert their biological effects through an inherent ability to covalently modify lysine are not contemplated or claimed in this disclosure, nor are synthetically modified analogues of the same, where the inherent lysine covalent modifying mechanism has not been substantially altered. Furthermore, compounds which are based primarily on single amino acids, nucleoside/nucleotide derived drugs, anhydrides, compounds comprising an yne-one, are also not contemplated in the present invention. Further, compounds that are mechanism-based irreversible inhibitors, i.e. suicide inhibitors, such as, for example Vigabatrin, or carbaglucose-6-phosphate (pseudo-DL-glucose, C-6-P) are not contemplated in the present invention. (See *Structure and Mechanism in Protein Science: A Guide to Enzyme Catalysis and Protein Folding*, Alan Fersht, W. H. Freeman, 1998, 1st Edition; *Enzymatic Reaction Mechanisms*, Perry A. Frey and Adrian D. Hegeman, Perry A. Frey (Author), Oxford University Press, 2007, 1st Edition, for a definition of the term mechanism-based irreversible inhibitors.) Antibodies, as a family of proteins, are not contemplated within the present invention and therefore are excluded. (See e.g., Carlos F. Barbas, III, et al., Science 278, 2085-2092 (1997); Popkov et al., Proc Natl Acad Sci USA, 106, 4378-4383, (2009); Doppalapudi et al., Bioorganic & Medicinal Chemistry Letters 17, 501-506, (2007); Li et al., J. Med. Chem., 47, 5630-5640, (2004); Guo et al., Proc. Natl. Acad. Sci. USA, 103, 11009-11014, (2006); Rader et al., Proc Natl Acad Sci USA, 100, 5396-5400, (2003).

For example, the natural product wortmannin is known to covalently modify lysine in the protein phosphatidylinositol 3-kinase (PI3K). Thus, wortmannin is a naturally occurring compound known to covalently modify lysine and exert its biological effects through its inherent ability to covalently bind to lysine. Known analogues of wortmannin that covalently modify lysine through substantially the same mechanism as wortmannin, are also excluded from the present invention. Examples of such wortmannin analogues include, without limitation:

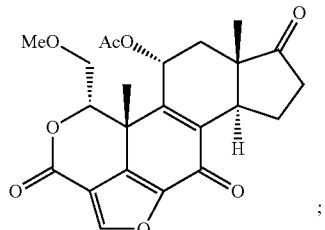

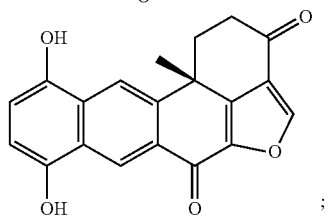

-continued

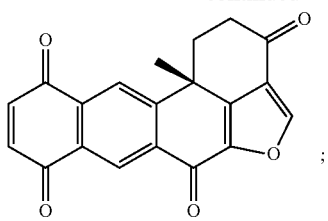

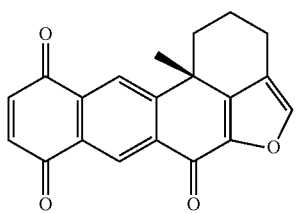

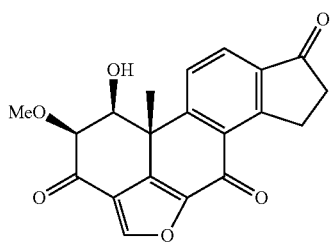

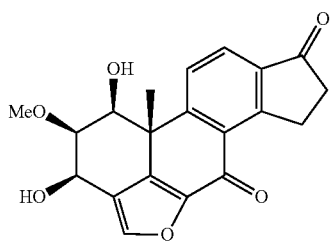

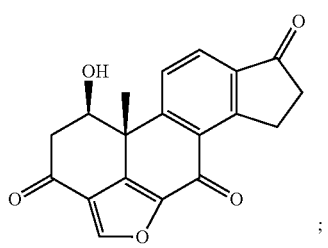

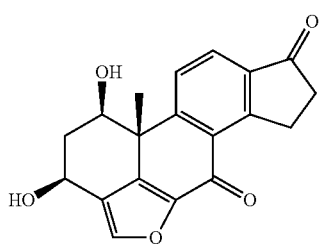

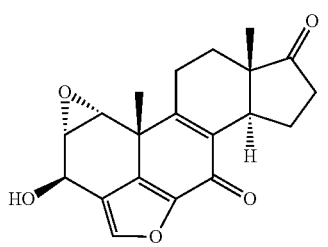

-continued

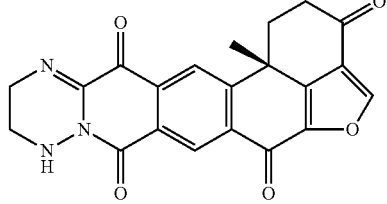

Another example of a naturally occurring compound that is believed to covalently modify lysine and is not encompassed within the present invention is Liphagal:

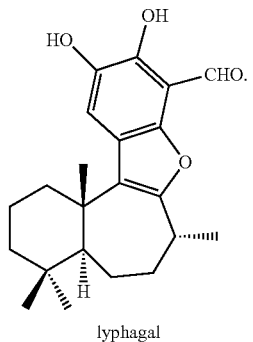

lyphagal

Other compounds not encompassed within the present invention are the following compounds disclosed in Choi et al., Nature Chemical Biology, advance online publication, Dec. 20, (2009):

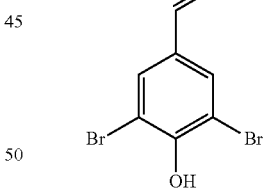
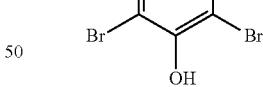

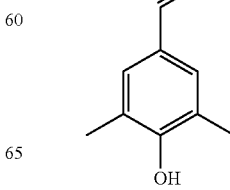

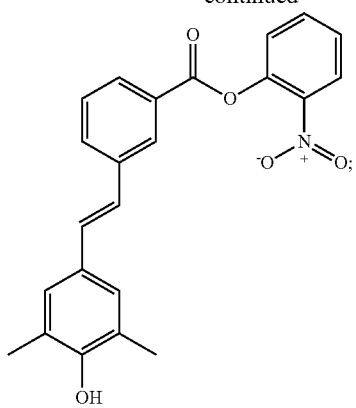

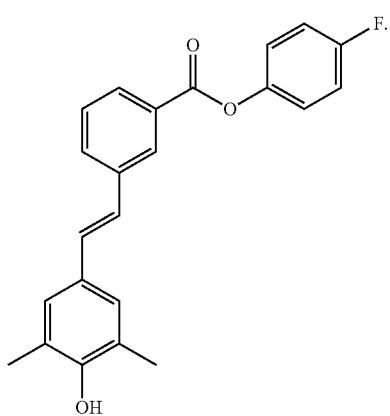

Additional compounds not encompassed within the present invention are the following compounds disclosed in Lawate et al., J. Med. Chem. 33, 2319, (1990):

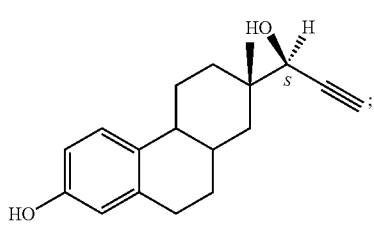

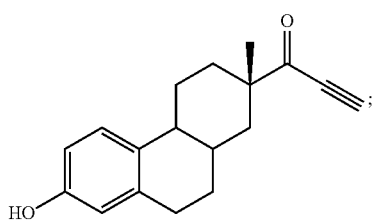

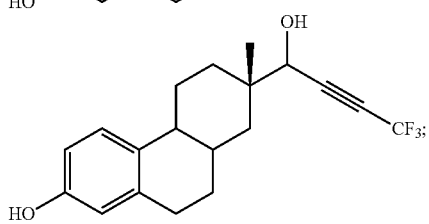

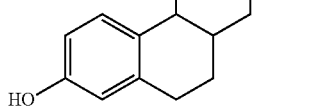

Other compound not encompassed within the present invention is the following compound disclosed in Nango et al., J. Org. Chem. 69, 593-600, (2004):

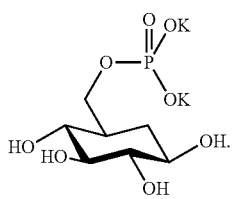

Compounds based primarily on amino acids such as tyrosine derived DpaTyr-Ni (II) complex that binds to FLAG (Bioorganic and Medicinal Chemistry Letters, 19, 6696, (2009) and Vigabatrin (also known as 4-aminohex-5-enoate or vinylGABA (Daniela De Biase, D., et al., J. Biol. Chem., 266, 20056, 1991)) are also not contemplated in the present invention.

Nucleoside/nucleotide derived drugs, such as, for example, those disclosed in Statsuk, A. V., et al., JACS, 130, 17568, (2008) and Guillerm, G., et al., J. Med. Chem., 49, 1223, (2006), and the like, are also not contemplated in the present invention.

Another example of a natural product and analogues thereof that are not encompassed in the present invention is manolide and its analogues which are believed to covalently modify lysine, such as manoalogue (Reynolds, L. J., et al., J. Am. Chem. Soc., 1988, 110, 5172-5177):

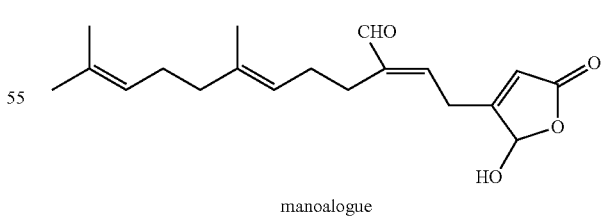

manoalogue

A further example of a compound and analogues thereof that are not encompassed in the present invention is neratinib (aka HKI-272) which covalently modify lysine in intact proteins (Wang, J., et al., Drug Metabolism and Disposition, 2010, 38, 1083-1093):

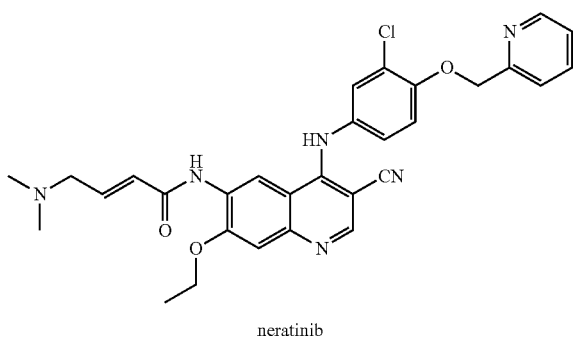 [SMILES: CCOc1cc2ncc(C#N)c(Nc3ccc(OCc4ccccn4)c(Cl)c3)c2cc1NC(=O)/C=C/CN(C)C]

neratinib

Another example of a natural product and analogues thereof that are not encompassed in the present invention is azaphilone and its analogues which are believed to covalently modify lysine. Non limiting illustrative examples of azaphilone cores are described below:

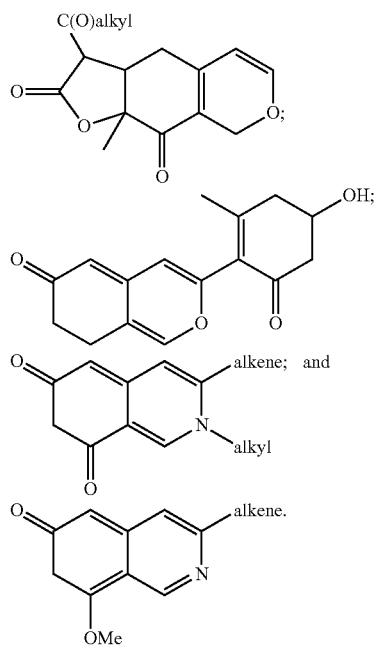

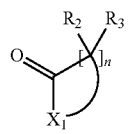

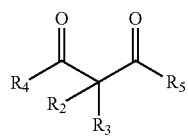

In certain embodiments, the Warhead of Formula I is a radical resulting from the removal of a hydrogen of a compound of Formula I-a, I-b, I-c, I-d, I-e, I-f, I-g, I-h, I-j, I-k, I-l, I-m, I-n, I-o, I-p, I-q, I-r, I-s, and I-t:

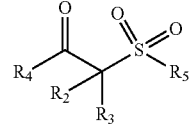

I-a

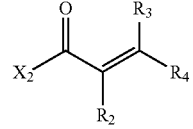

I-b

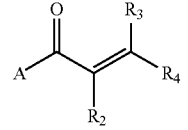

I-c

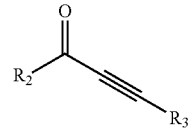

I-d

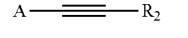

I-e

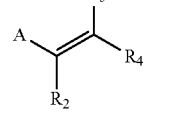

I-f

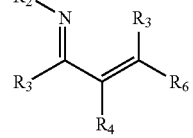

I-g

I-h

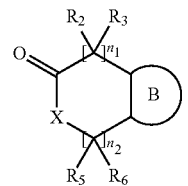

I-i

I-j

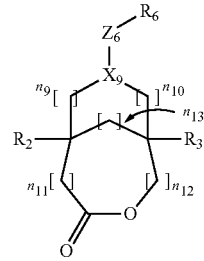

I-k

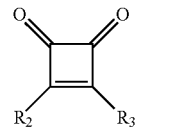

I-l

-continued

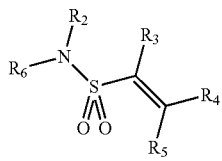

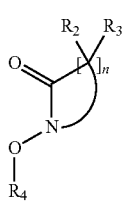

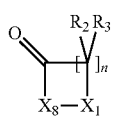

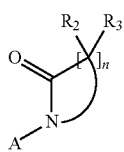

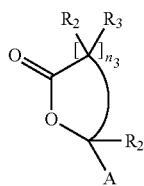

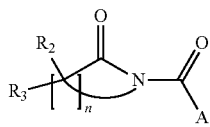

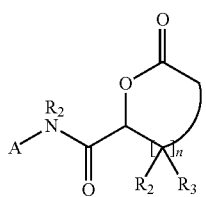

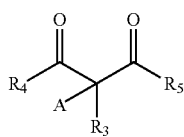

wherein each $X_1$ and $X_8$ is independently —O—, —S—, or —NR$_6$—;

each $X_2$ is independently —R$_6$, —OR$_6$, or —NR$_6$R$_7$;

each $X_9$ is independently

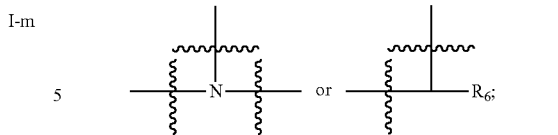

each $R_2$, $R_3$, $R_4$, $R_5$, $R_6$, $R_7$, and $R_8$ is independently hydrogen or $C_1$-$C_6$ alkyl; wherein one or more methylene groups of the $C_1$-$C_6$ alkyl can be replaced by —NR$_1$—, —O—, —C(O)—, —S—, —SO—, —SO$_2$-, or —C(=S)—; one or more methine groups of the $C_1$-$C_6$ alkyl, when present, can be independently replaced by

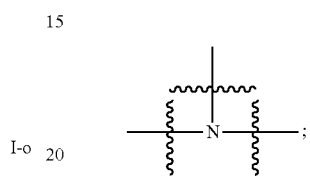

$R_1$ is hydrogen or $C_1$-$C_8$ alkyl;

wherein optionally when proper any two of $R_2$, $R_3$, $R_4$, $R_5$, $R_6$, $R_7$, and $R_8$ when taken together form a 3- to 8-membered carbocyclic or heterocyclic ring or an aryl or heteroaryl group; and optionally $X_2$ and any one of $R_2$, $R_3$, and $R_4$ when taken together form a 3- to 8-membered carbocyclic or heterocyclic ring or an aryl or heteroaryl group;

A and B are each independently an optionally substituted monocyclic, bicyclic, or tricyclic aryl or heteroaryl; and n is an integer from 2-4; each $n_1$ and $n_2$ is independently an integer from 0-2; $n_3$ is an integer from 1-2; $n_4$ is an integer from 1-3; and each one of $n_9$, $n_{10}$, $n_{11}$, and $n_{12}$ is an integer from 0-1; and $n_{13}$ is an integer from 0-2, wherein when any one of the foregoing n integers is more than 1, the adjacent carbons represented by the integer can form a single or double bond.

In some embodiments, at least one of $R_2$ and $R_3$ of the compounds of Formula I-b and I-c is hydrogen.

In other embodiments, the compound of Formula I-a, I-d, I-e, I-j, I-k, or I-l is a compound of Formula II-a, II-b, II-c, II-d, II-e, II-f, II-g, II-h, II-j, II-k, II-l, II-m, II-n, II-o, II-p, II-q, II-r, II-s, II-t, II-u, II-v, II-w, II-x, II-y, II-z, II-aa, II-bb, II-cc, II-dd, II-ee, II-ff, II-gg, II-hh, II-jj, II-kk, II-ll, II-mm, II-nn, II-oo, or II-pp:

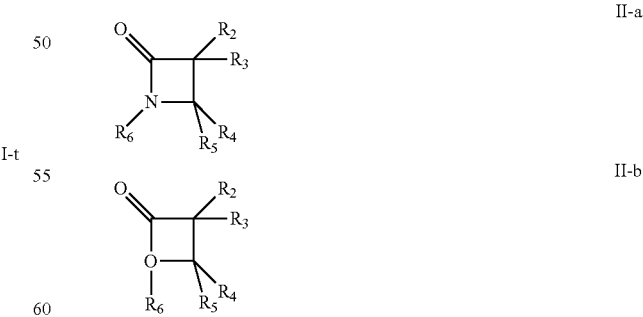

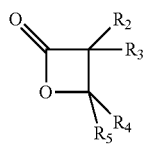

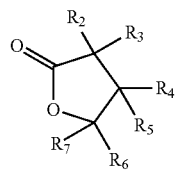
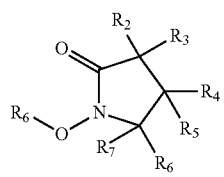
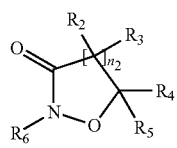
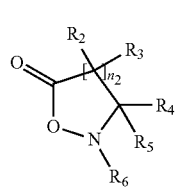
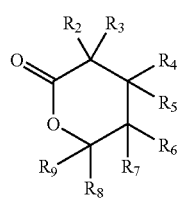
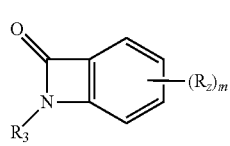
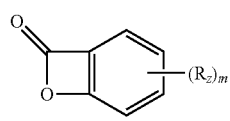
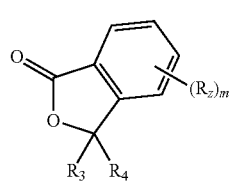
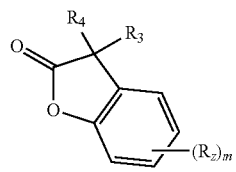
II-d
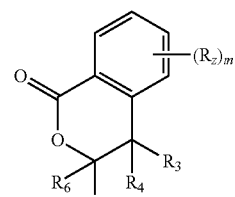
II-e
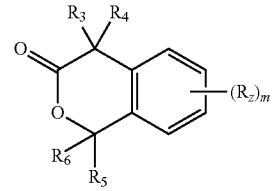
II-f
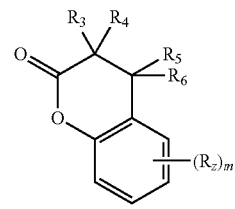
II-g
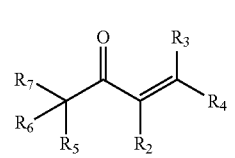
II-h
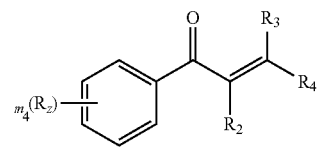
II-i
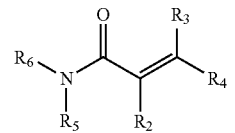
II-j
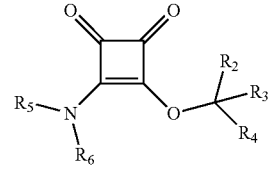
II-k
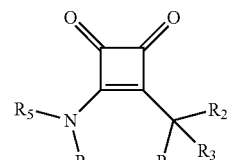
II-l
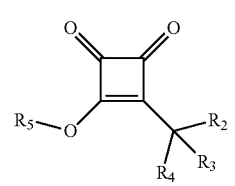
II-m
II-n
II-o
II-p
II-q
II-r
II-s
II-t
II-u

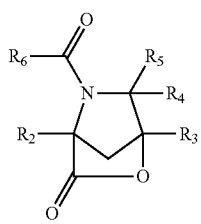 II-v
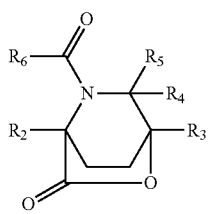 II-w
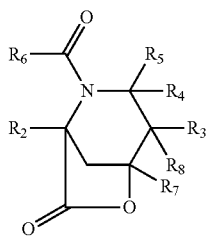 II-x
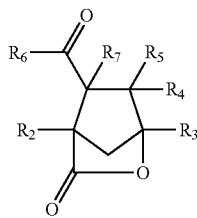 II-y
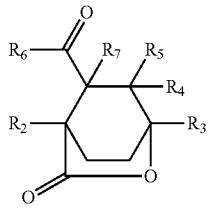 II-z
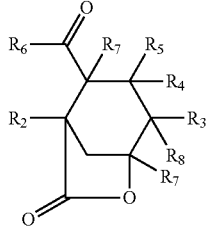 II-aa
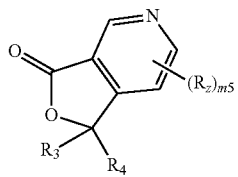 II-bb
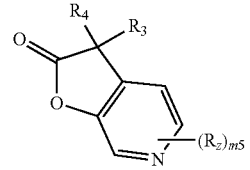 II-cc
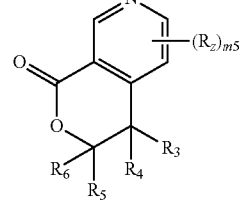 II-dd
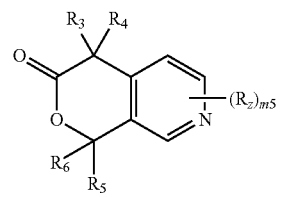 II-ee
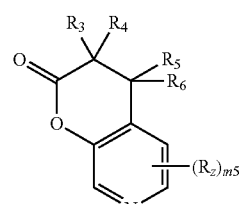 II-ff
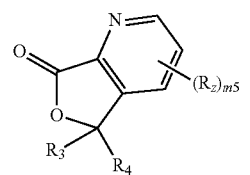 II-gg
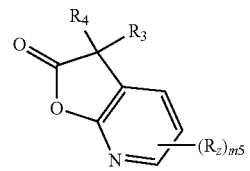 II-hh
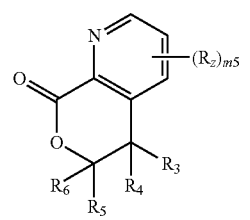 II-ii
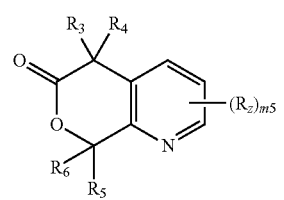 II-jj -continued

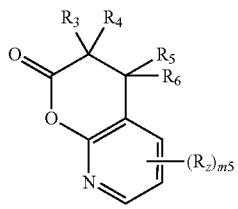
II-kk

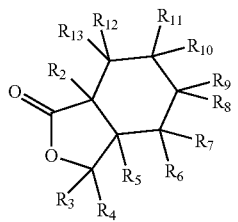
II-ll

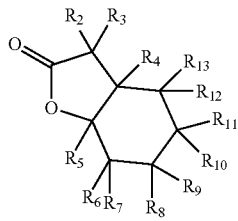
II-mm

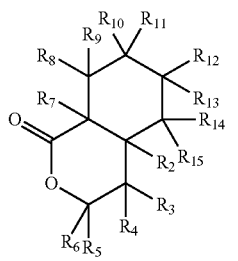
II-nn

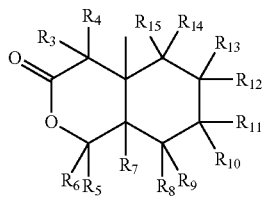
II-oo

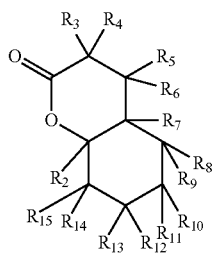
II-pp wherein
each m is independently an integer from 0-4;
each $m_5$ is independently an integer from 0-3;
each $m_4$ is independently an integer from 0-5;
each $n_2$ is independently an integer from 0-2;
each $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ is independently hydrogen or $C_1$-$C_6$ alkyl and $R_z$ is hydrogen, $C_1$-$C_6$ alkyl, halogen, $CF_3$, or nitro, wherein one or more methylene groups of the $C_1$-$C_6$ alkyl can be replaced by —$NR_1$—, —O—, —C(O)—, —S—, —SO—, —$SO_2$—, or —C(=S)—, one or more methine groups of the $C_1$-$C_6$ alkyl, when present, can be independently replaced by

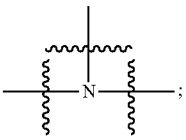 [SMILES: *N(*)*]

$R_1$ is hydrogen or $C_1$-$C_8$ alkyl; and, optionally, when proper any two of $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$, when taken together, form a 3- to 8-membered carbocyclic or heterocyclic ring or an aryl or heteroaryl group.

In yet another embodiment, the compound of Formula I-d, or I-h is a compound of Formula III-a, III-b, III-h, or III-i:

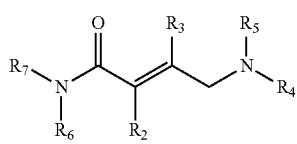
III-a

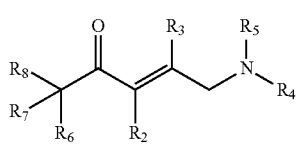
III-b

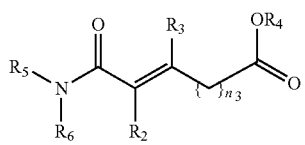
III-c

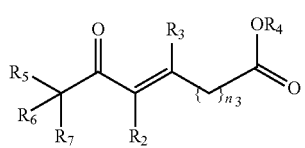
III-d

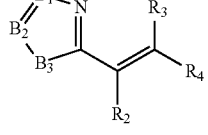
III-e

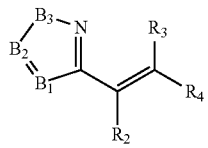
III-f

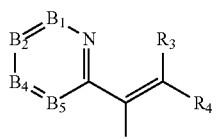
III-g

III-h

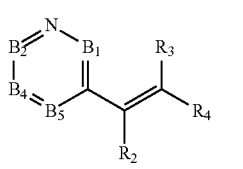

III-i

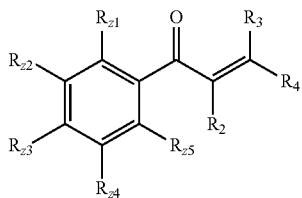

wherein
n₃ is an integer from 0-2;
each $R_2$, $R_3$, $R_4$, $R_5$, $R_6$, $R_7$, and $R_8$ is independently hydrogen or $C_1$-$C_6$ alkyl;
each $B_1$, $B_2$, $B_4$, and $B_5$ is independently $CR_7$ or N;
each $B_3$ is $NR_7$, O, or S;
each $R_{z1}$, $R_{z2}$, $R_{z3}$, $R_{z4}$, and $R_{z5}$ is hydrogen, $C_1$-$C_6$ alkyl, halogen, $CF_3$, or nitro, wherein one or more methylene groups of the $C_1$-$C_6$ alkyl can be optionally replaced by —$NR_1$—, —O—, —C(O)—, —S—, —SO—, —$SO_2$—, or —C(=S)—, one or more methine groups of the $C_1$-$C_6$ alkyl, when present, can be independently replaced by

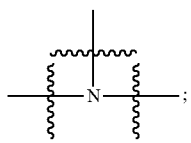 [SMILES: *N(*)*]

$R_1$ is hydrogen or $C_1$-$C_8$ alkyl; and,
optionally, when proper any two of $R_2$, $R_3$, $R_4$, $R_5$, $R_6$, $R_7$, and $R_8$ when taken together form a 3- to 8-membered carbocyclic or heterocyclic ring or an aryl or heteroaryl group.

In certain embodiments, the compound of Formula I-h is a compound of Formula IV-a, IV-b, IV-c, IV-d, IV-e, IV-f, IV-g, IV-h, or IV-i:

IV-a

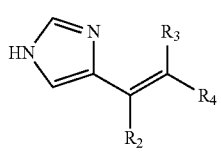

IV-b

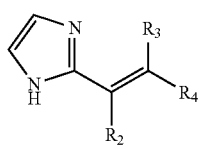

IV-c

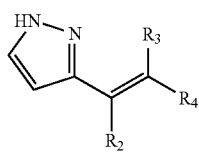

IV-d

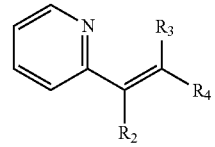

IV-e

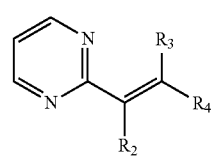

IV-f

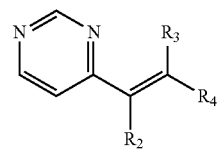

IV-g

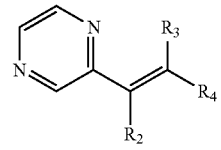

IV-h

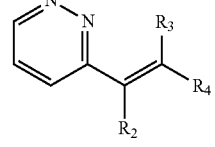

IV-i

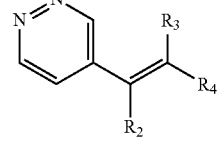

wherein
$R_1$, $R_2$, and $R_3$ are as defined above for Formula I-h; and
any of the substitutable hydrogens on the nitrogen heterocycle of the compound can be substituted with alkyl, alkoxy, amido, acyl, acyloxy, oxoacyl, or halogen.

In other embodiments, the radical resulting from the removal of a hydrogen of a compound of Formula I-a, I-d, I-k, or I-m is a radical of Formula V-a, V-b, V-c, V-d, V-e, V-f, V-g, V-h, V-i, or V-j:

V-a

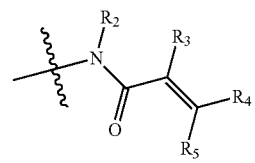

-continued

V-b 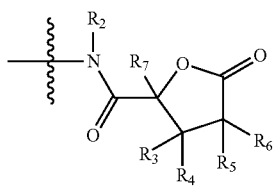

V-c 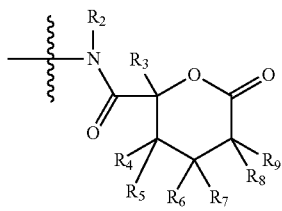

V-d 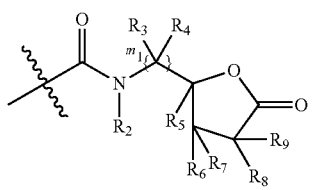

V-e 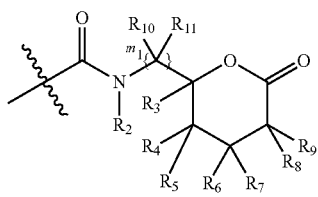

V-f 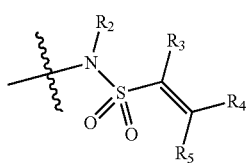

V-g 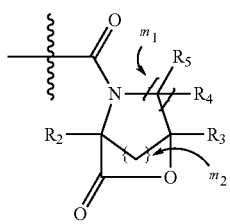

V-h 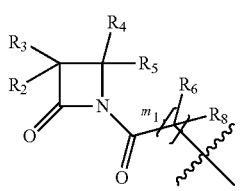

V-i 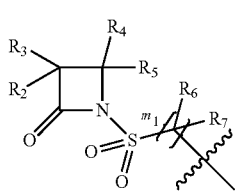

-continued

V-j 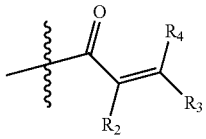

wherein
$m_1$ and $m_2$ are each independently an integer from 0 to 2;
each $R_2$, $R_3$, $R_4$, $R_5$, $R_6$, $R_7$, $R_8$, $R_9$, $R_{10}$, and $R_{11}$ is independently hydrogen or $C_1$-$C_6$ alkyl, wherein one or more methylene groups of the $C_1$-$C_6$ alkyl can be optionally replaced by —$NR_1$—, —O—, —C(O)—, —S—, —SO—, —$SO_2$—, or —C(=S)—; one or more methine groups of the $C_1$-$C_6$ alkyl, when present, can be independently replaced by

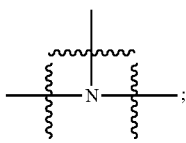 [SMILES: *N(*)*]

$R_1$ is hydrogen or $C_1$-$C_8$ alkyl; and
optionally when proper any two of $R_2$, $R_3$, $R_4$, $R_5$, $R_6$, $R_7$, $R_8$, $R_9$, $R_{10}$, and $R_{11}$, when taken together, form a 3- to 8-membered carbocyclic or heterocyclic ring or an aryl or heteroaryl group.

In some illustrative embodiments, the compounds of Formulae I-a, I-b, I-c, I-d, I-e, I-f, I-g, I-h, I-j, I-k, I-l, I-m, I-n, I-o, I-p, I-q, I-r, I-s, and I-t are described below:

aa 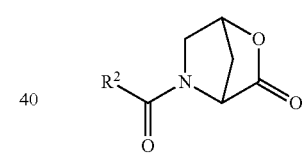

bb 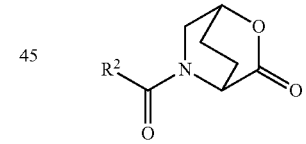

cc 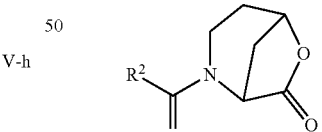

dd 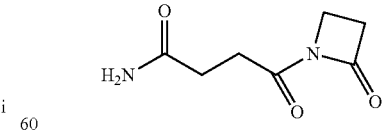

ee 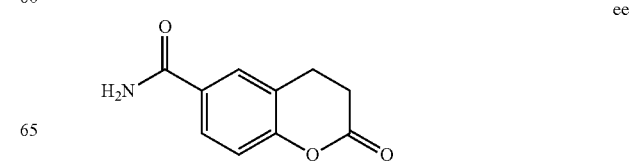

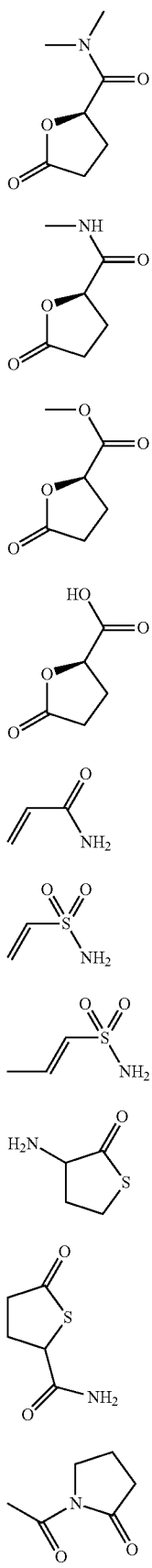
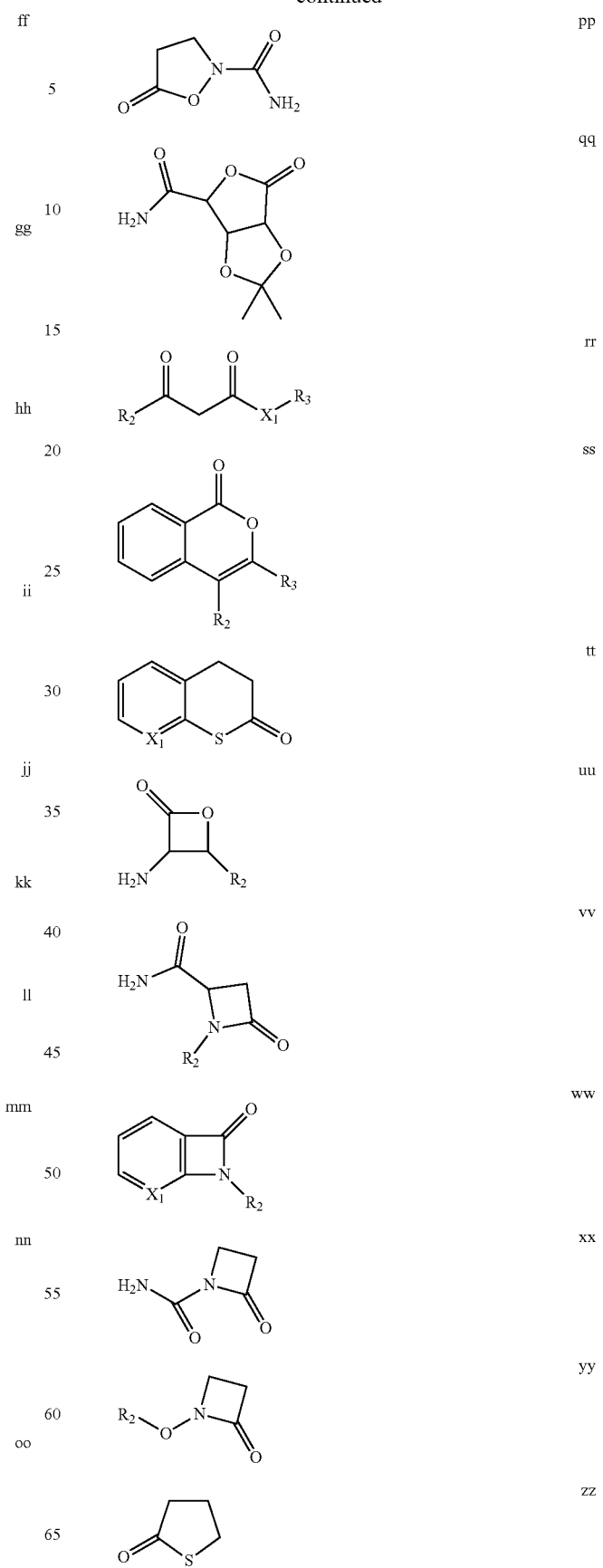

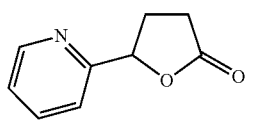
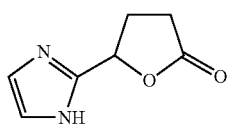
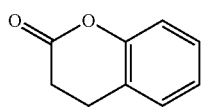
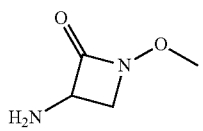
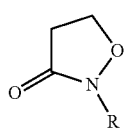
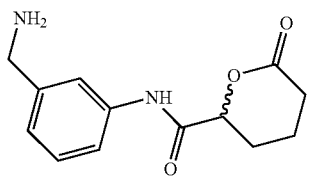
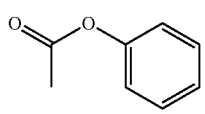
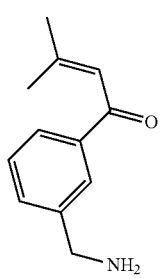
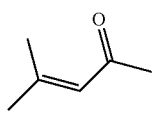
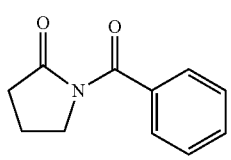

aaa
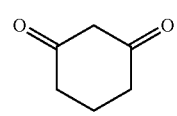

bbb
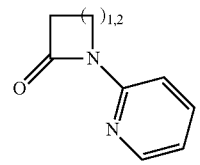

ccc ddd
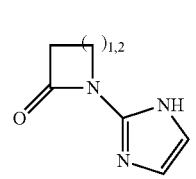

eee
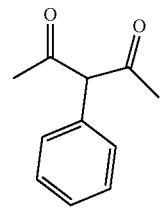

fff

In the foregoing compounds aa-ooo, any substitutable hydrogen may be substituted with the substituents as those defined by $R_2$-$R_8$.

In certain embodiments, the radical resulting from the removal of a hydrogen of a compound of Formula I-a, I-d, I-k, or I-m is a radical of Formula VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, or VI-t:

VI-a
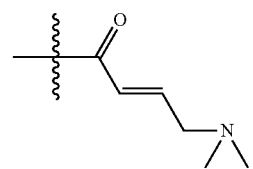

VI-b
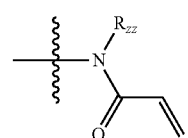

VI-c
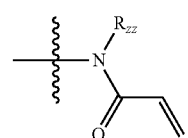

VI-d
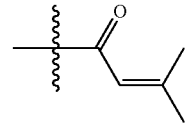

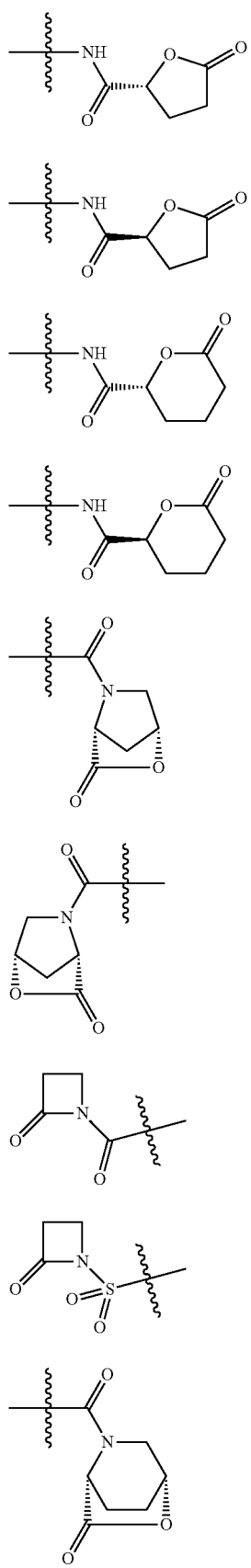

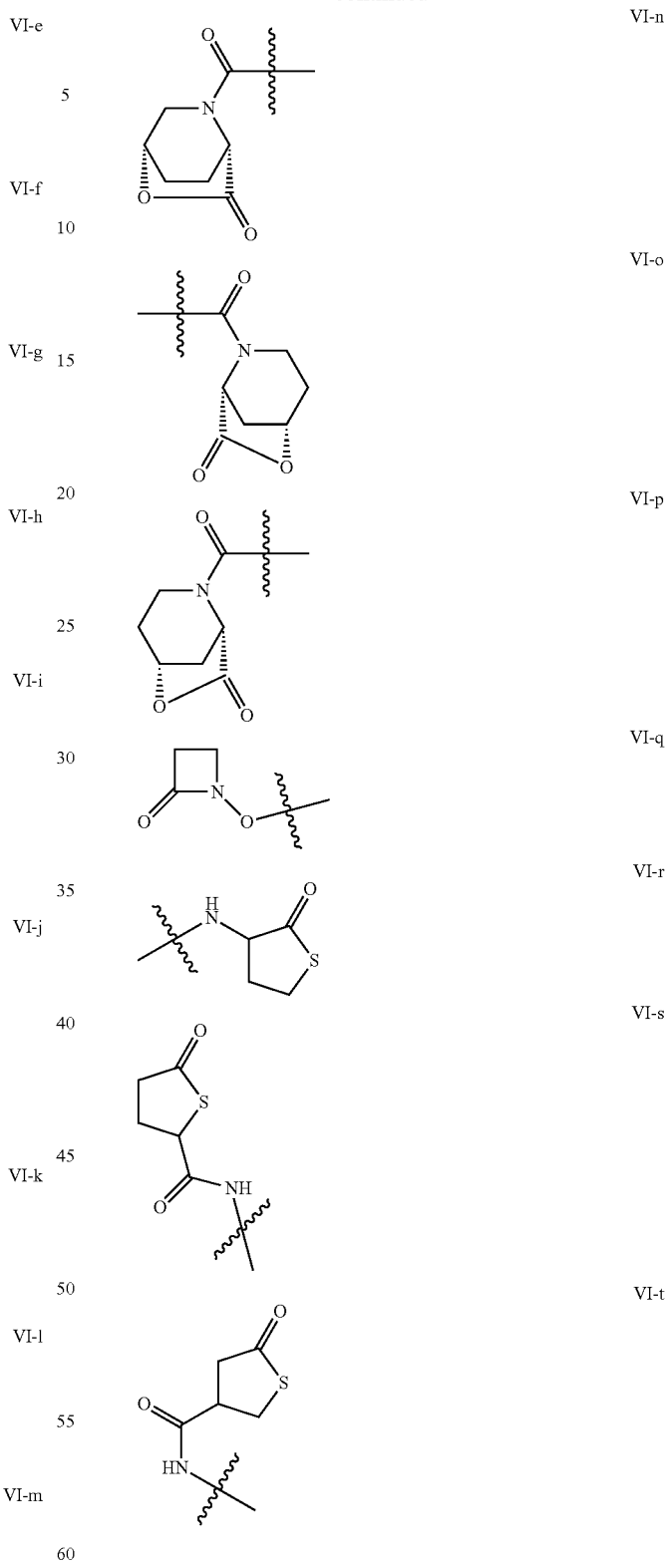

wherein, $R_{zz}$ is hydrogen, methyl, ethyl, propyl, isopropyl, cyclopropyl, —$CH_2OCH_3$, or —$CH_2CH_2OCH_3$.

In some embodiments, Tether is null, a bond, or a bivalent $C_1$-$C_{15}$ saturated, unsaturated, straight, branched, cyclic, bicyclic, tricyclic alkyl, alkenyl, alkynyl; bridged bicyclic, heterocycle, heteroaryl, or aryl moiety; wherein optionally one or more methylene units of the hydrocarbon chain are independently replaced by —NR₁—, —O—, —C(O)—, —S—, —SO—, —SO₂—, —C(=S)—, or C(=NR₁)—; R₁ is hydrogen or C₁-C₈ alkyl; and optionally one or more hydrogens are independently replaced by heteroatoms; and optionally one or more methine groups of the C₁-C₁₅ alkyl, when present, are independently replaced by

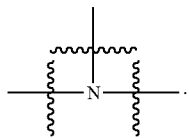

In certain embodiments, the Scaffold is selected from the group consisting of Formulas VII, VIII, IX-a, IX-b, XI, XII, XVI, XVII, XVIII, XIX, XX, XXI, XXII, XXIII, XXXIV, XXV, XXVI, XXVII, XXVIII, XXIX, XXXVi, and XXXVII.

VII. COMPOUNDS OF THE INVENTION

The present disclosure provides compounds capable of covalently binding to lysine residues of a protein thereby inhibiting the function of the protein. Described herein are compounds of the Formula I:

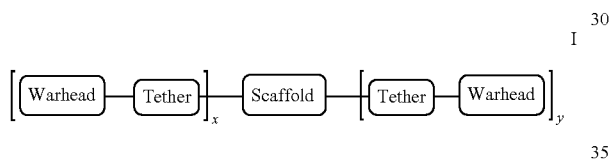

wherein Scaffold, Warhead, Tether, x, y are as defined above for Formula I,
with the proviso that the compound of Formula I is not:
wortmannin:

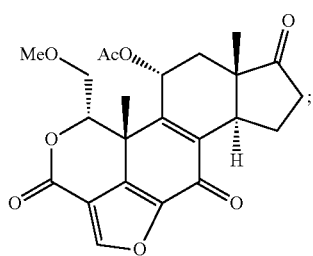 [SMILES: COC[C@H]1OC(=O)c2coc3c2[C@@]1(C)C1=C(C3=O)[C@@H]2CCC(=O)[C@@]2(C)C[C@H]1OC(C)=O]

known analogues of wortmannin that covalently modify lysine through substantially the same mechanism as wortmannin:

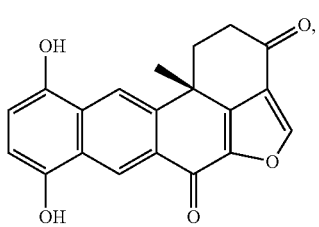

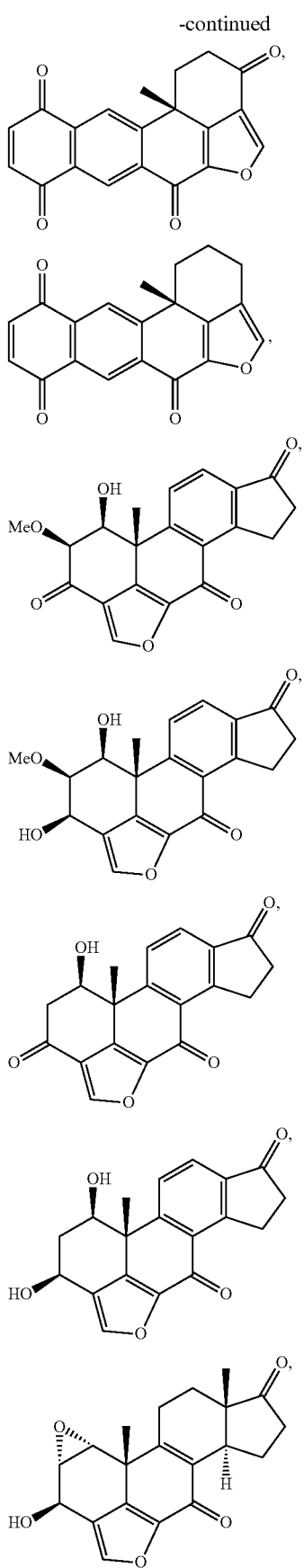

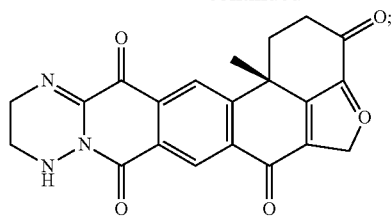
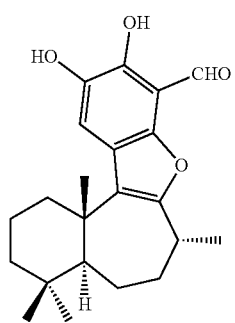
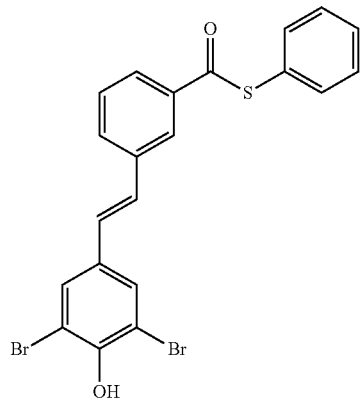
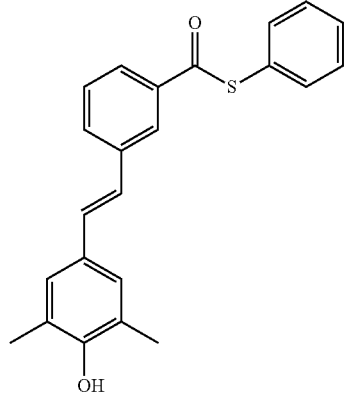
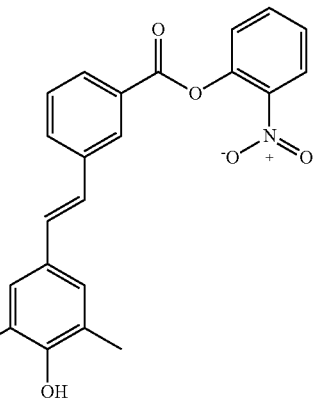
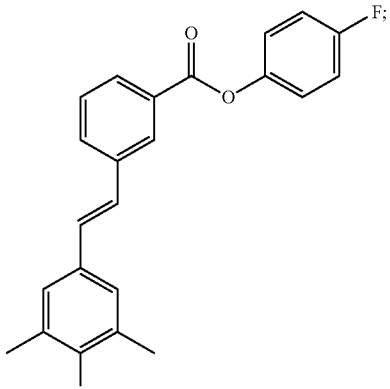
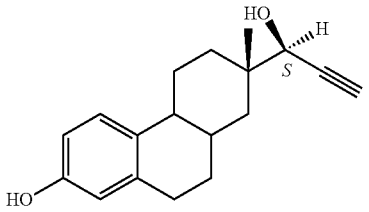
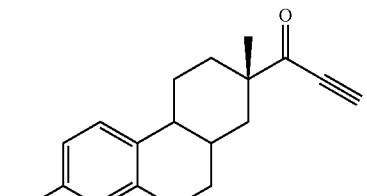
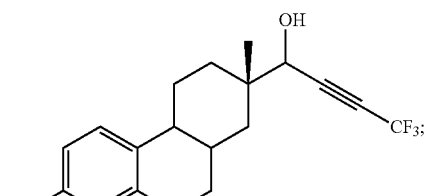
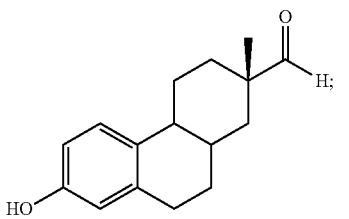

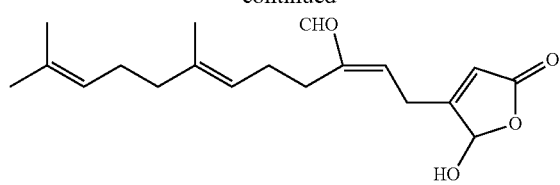

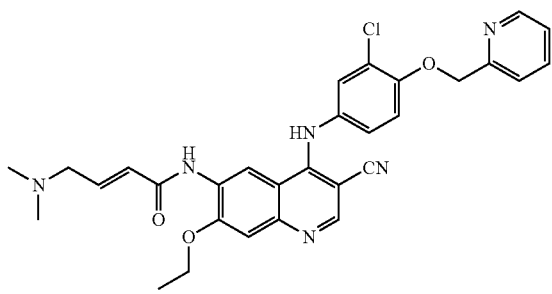

azaphilone core analogues such as

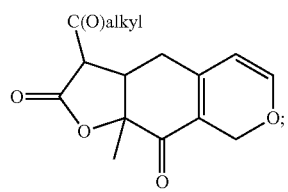

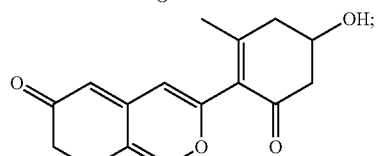

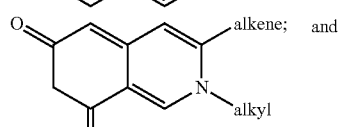

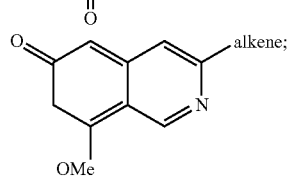

and any mechanism-based irreversible inhibitors.

In certain embodiments, the compound of Formula I is a compound of Formula I',

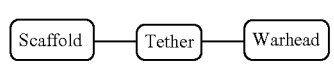

I' wherein Scaffold, Warhead and Tether are as defined above in the embodiments of Formula I.

In certain embodiments, the Warhead is a radical resulting from the removal of a hydrogen of a compound of Formula I-a, I-b, I-c, I-d, I-e, I-f, I-g, I-h, I-j, I-k, I-l, I-m, I-n, I-o, I-p, I-q, I-r, I-s, and I-t:

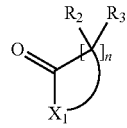 I-a

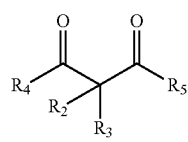 I-b

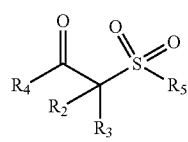 I-c

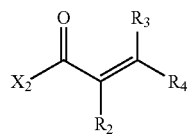 I-d

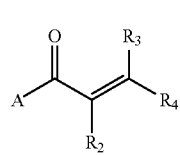 I-e

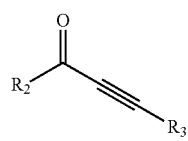 I-f

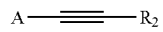 I-g

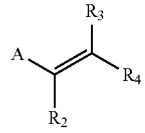 I-h

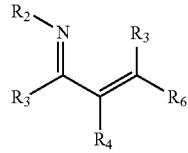 I-i

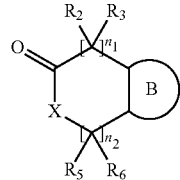 I-j

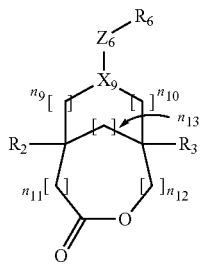

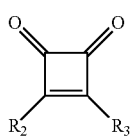

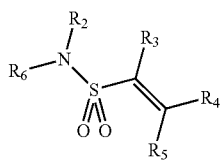

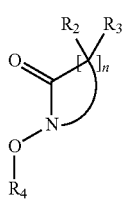

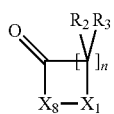

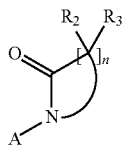

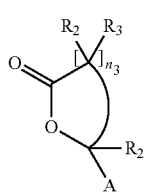

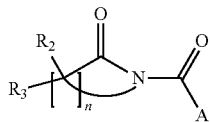

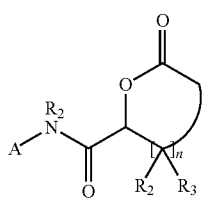

I-k

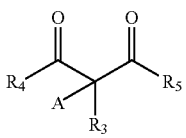

I-l

I-m

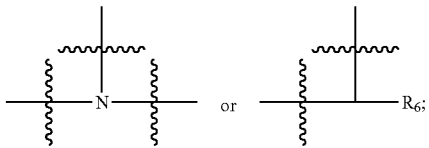

I-n

I-o

I-p

I-q

I-r

I-s

I-t wherein each $X_1$ and $X_8$ is independently —O—, —S—, or —$NR_6$—;

each $X_2$ is independently —$R_6$, —$OR_6$, or —$NR_6R_7$;

each $X_9$ is independently

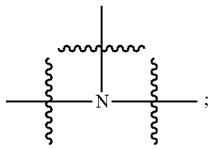 [SMILES: *N(*)*]

each $R_2$, $R_3$, $R_4$, $R_5$, $R_6$, $R_7$, and $R_8$ is independently hydrogen or $C_1$-$C_6$ alkyl; wherein one or more methylene groups of the $C_1$-$C_6$ alkyl can be replaced by —$NR_1$—, —O—, —C(O)—, —S—, —SO—, —$SO_2$-, or —C(=S)—; one or more methine groups of the $C_1$-$C_6$ alkyl, when present, can be independently replaced by $R_1$ is hydrogen or $C_1$-$C_8$ alkyl;

wherein optionally when proper any two of $R_2$, $R_3$, $R_4$, $R_5$, $R_6$, $R_7$, and $R_8$ when taken together form a 3- to 8-membered carbocyclic or heterocyclic ring or an aryl or heteroaryl group; and optionally $X_2$ and any one of $R_2$, $R_3$, and $R_4$ when taken together form a 3- to 8-membered carbocyclic or heterocyclic ring or an aryl or heteroaryl group;

A and B are each independently an optionally substituted monocyclic, bicyclic, or tricyclic aryl or heteroaryl; and n is an integer from 2-4; each $n_1$ and $n_2$ is independently an integer from 0-2; $n_3$ is an integer from 1-2; $n_4$ is an integer from 1-3; and each one of $n_9$, $n_{10}$, $n_{11}$, and $n_{12}$ is an integer from 0-1; and $n_{13}$ is an integer from 0-2, wherein when any one of the foregoing n integers is more than 1, the adjacent carbons represented by the integer can form a single or double bond.

In some embodiments, at least one of $R_2$ and $R_3$ of the compounds of Formula I-b and I-c is hydrogen.

In other embodiments, the compound of Formula I-a, I-d, I-e, I-j, I-k, or I-l is a compound of Formula II-a, II-b, II-c, II-d, II-e, II-f, II-g, II-h, II-j, II-k, II-l, II-m, II-n, II-o, II-p, II-q, II-r, II-s, II-t, II-u, II-v, II-w, II-x, II-y, II-z, II-aa, II-bb, II-cc, II-dd, II-ee, II-ff, II-gg, II-hh, II-jj, II-kk, II-ll, II-mm, II-nn, II-oo, or II-pp.

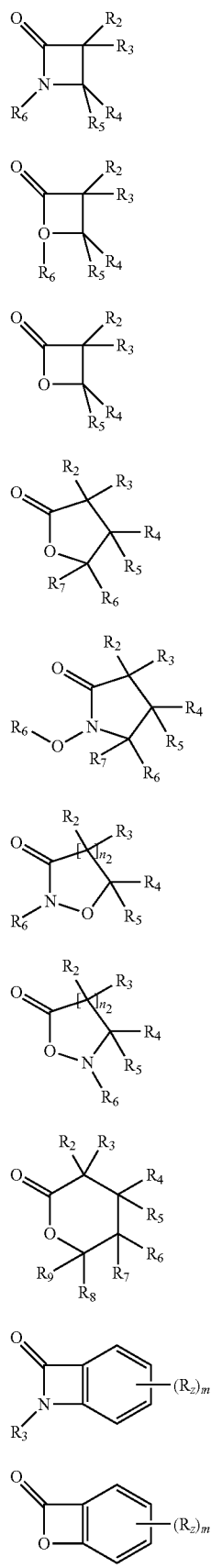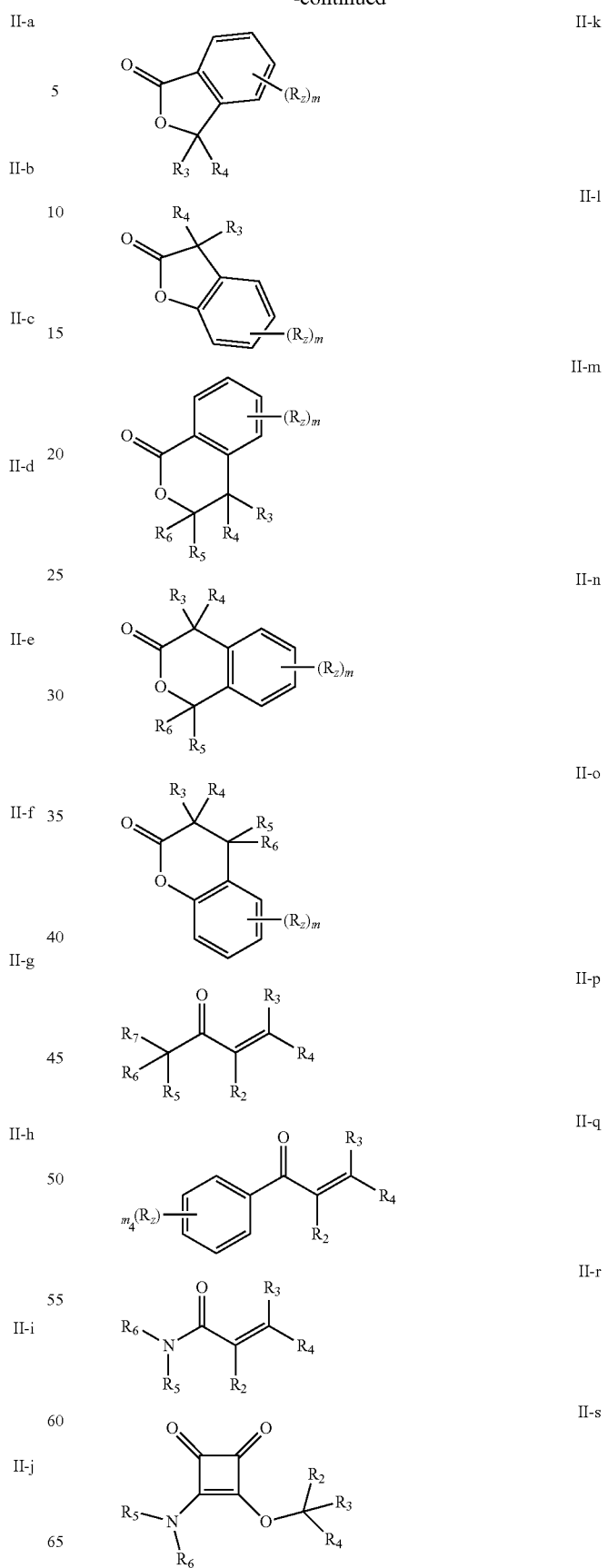

-continued
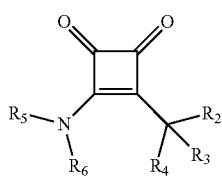
II-t
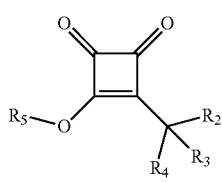
II-u
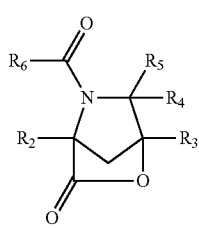
II-v
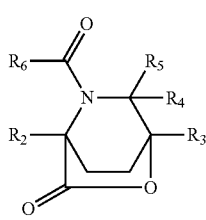
II-w
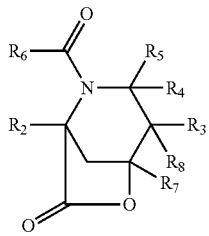
II-x
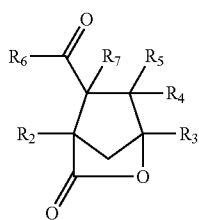
II-y
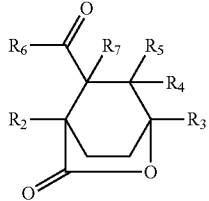
II-z
-continued
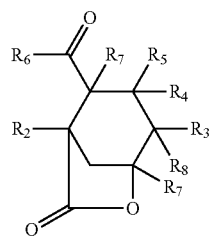
II-aa
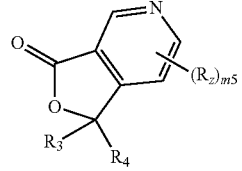
II-bb
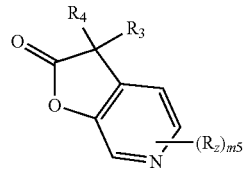
II-cc
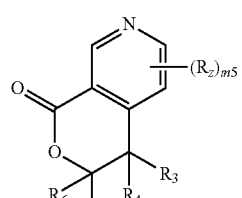
II-dd
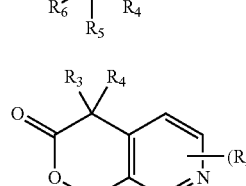
II-ee
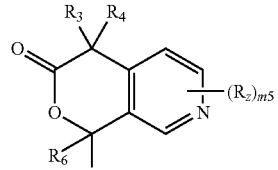
II-ff
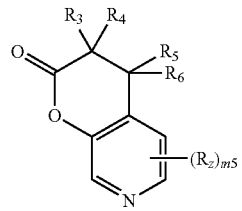
II-ff
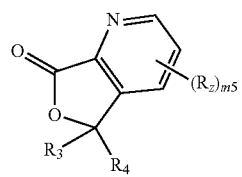
II-gg
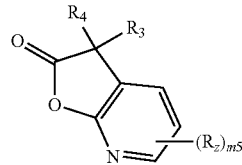
II-hh

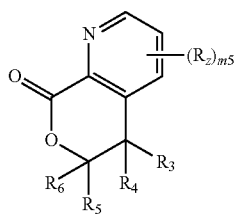
II-ii

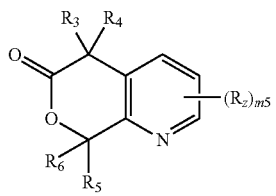
II-jj

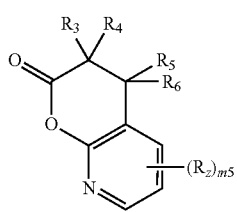
II-kk

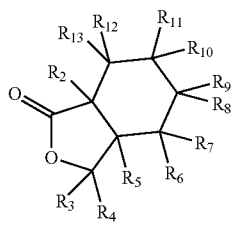
II-ll

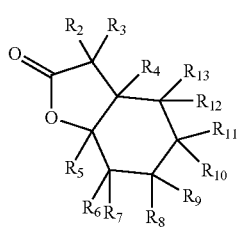
II-mm

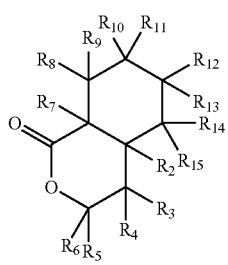
II-nn

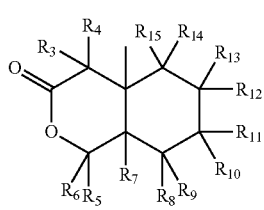
II-oo

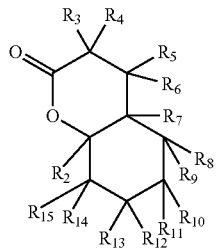
II-pp wherein
each m is independently an integer from 0-4;
each $m_5$ is independently an integer from 0-3;
each $m_4$ is independently an integer from 0-5;
each $n_2$ is independently an integer from 0-2;
each $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ is independently hydrogen or $C_1$-$C_6$ alkyl; $R_z$ is hydrogen, $C_1$-$C_6$ alkyl, halogen, $CF_3$, or nitro; wherein one or more methylene groups of the $C_1$-$C_6$ alkyl can be replaced by —$NR_1$—, —O—, —C(O)—, —S—, —SO—, —$SO_2$—, or —C(=S)—; one or more methine groups of the $C_1$-$C_6$ alkyl, when present, can be independently replaced by

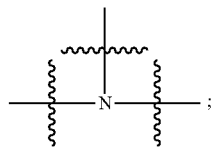 [SMILES: *N(*)*]

optionally when proper any two of $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ when taken together form a 3- to 8-membered carbocyclic or heterocyclic ring or an aryl or heteroaryl group; and $R_1$ is hydrogen or $C_1$-$C_8$ alkyl.

In yet another embodiment, the compound of Formula I-d or I-h is a compound of Formula III-a, III-b, III-c, III-d, III-e, III-f, III-g, III-h, or III-i:

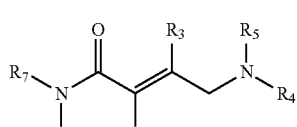
III-a

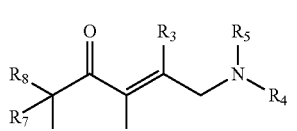
III-b

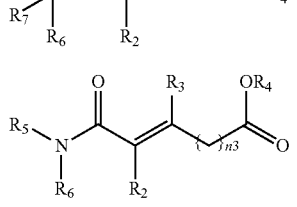
III-c

-continued

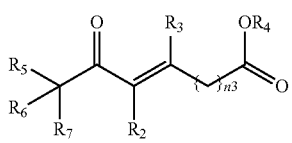
III-d

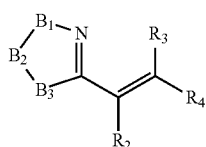
III-e

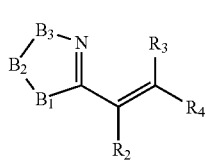
III-f

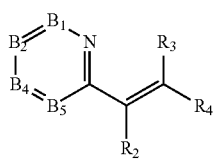
III-g

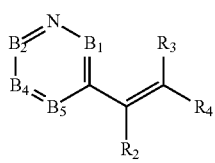
III-h

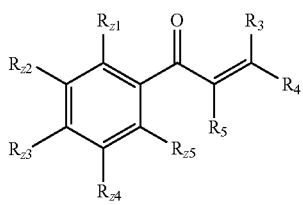
III-i wherein $n_3$ is an integer from 0-2;

each $R_2$, $R_3$, $R_4$, $R_5$, $R_6$, $R_7$, and $R_8$ is independently hydrogen or $C_1$-$C_6$ alkyl;

each $B_1$, $B_2$, $B_4$, and $B_5$ is independently $CR_7$ or N and each $B_3$ is $NR_7$, O, or S;

each $R_{z1}$, $R_{z2}$, $R_{z3}$, $R_{z4}$, and $R_{z5}$ is hydrogen, $C_1$-$C_6$ alkyl, halogen, $CF_3$, or nitro;

one or more methylene groups of the $C_1$-$C_6$ alkyl can be optionally replaced by —NR$_1$—, —O—, —C(O)—, —S—, —SO—, —SO$_2$—, or —C(=S)—; one or more methine groups of the $C_1$-$C_6$ alkyl, when present, can be independently replaced by

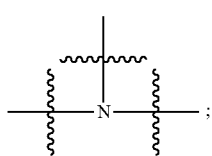 [SMILES: *N(*)*]

$R_1$ is hydrogen or $C_1$-$C_8$ alkyl; and optionally when proper any two of $R_2$, $R_3$, $R_4$, $R_5$, $R_6$, $R_7$, and $R_8$ when taken together form a 3- to 8-membered carbocyclic or heterocyclic ring or an aryl or heteroaryl group.

In certain embodiments, the compound of Formula I-h is a compound of Formula IV-a, IV-b, IV-c, IV-d, IV-e, IV-f, IV-g, IV-h, or IV-i:

IV-a

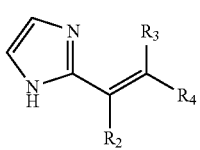
IV-b

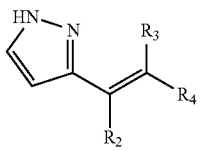
IV-c

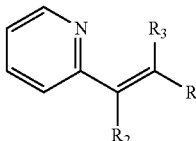
IV-d

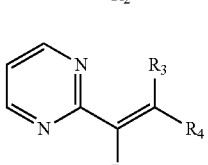
IV-e

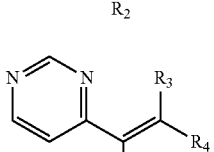
IV-f

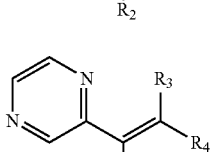
IV-g

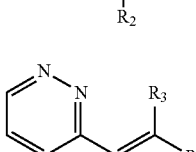
IV-h

-continued

IV-i

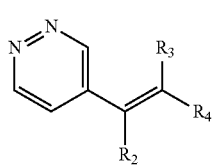

wherein R$_2$, R$_3$ and R$_4$ are defined above for Formula I-d or I-h; and the hydrogen on the nitrogen heterocycle of the compound of Formula IV-a, IV-b, and IV-c can be substituted with alkyl, alkoxy, amido, acyl, acyloxy, oxoacyl, and halogen.

In other embodiments, the radical resulting from the removal of a hydrogen of a compound of Formula I-a, I-d, I-k, or I-m is a radical of Formula V-a, V-b, V-c, V-d, V-e, V-f, V-g, V-h, V-i, or V-j:

V-a

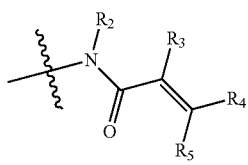

V-b

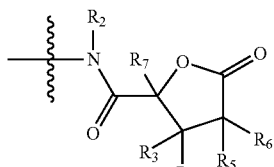

V-c

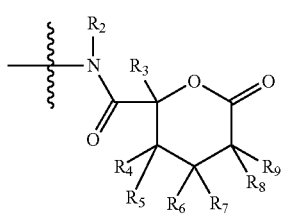

V-d

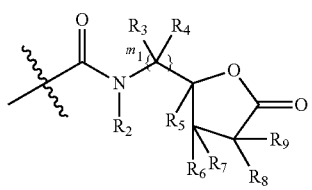

V-e

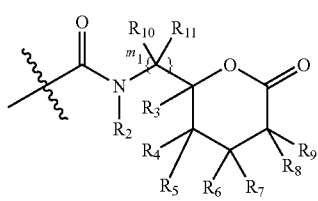

V-f

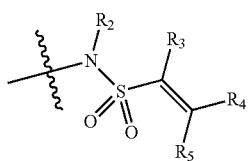

V-g

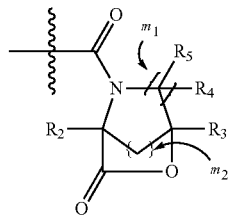

V-h

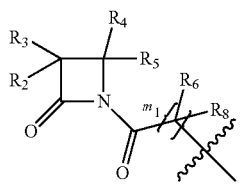

V-i

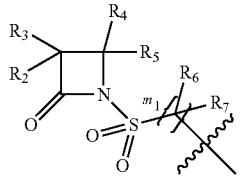

V-j

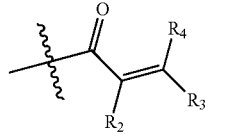

wherein m$_1$ and m$_2$ are each independently an integer from 0 to 2; each R$_2$, R$_3$, R$_4$, R$_5$, R$_6$, R$_7$, R$_8$, R$_9$, R$_{10}$, and R$_{11}$ is independently hydrogen or C$_1$-C$_6$ alkyl, wherein one or more methylene groups of the C$_1$-C$_6$ alkyl can be optionally replaced by —NR$_1$—, —O—, —C(O)—, —S—, —SO—, —SO$_2$—, or —C(=S)—; one or more methine groups of the C$_1$-C$_6$ alkyl, when present, can be independently replaced by

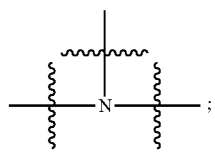 [SMILES: *N(*)*]

R$_1$ is hydrogen or C$_1$-C$_8$ alkyl; and optionally when proper any two of R$_2$, R$_3$, R$_4$, R$_5$, R$_6$, R$_7$, R$_8$, R$_9$, R$_{10}$, and R$_{11}$, when taken together, form a 3- to 8-membered carbocyclic or heterocyclic ring or an aryl or heteroaryl group.

In some illustrative embodiments, the compounds of Formulae I-a, I-b, I-c, I-d, I-e, I-f, I-g, I-h, I-j, I-k, I-l, I-m, I-n, I-o, I-p, I-q, I-r, I-s, and I-t are described below:

aa

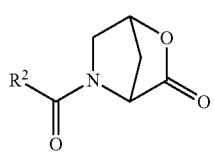

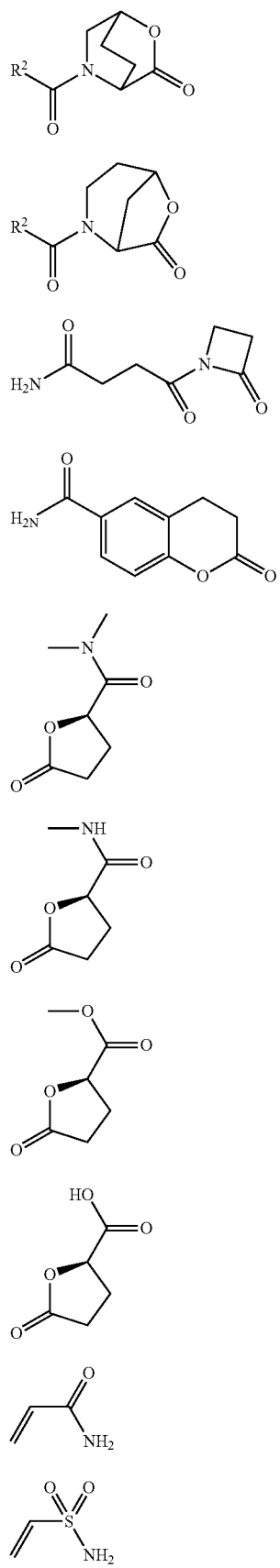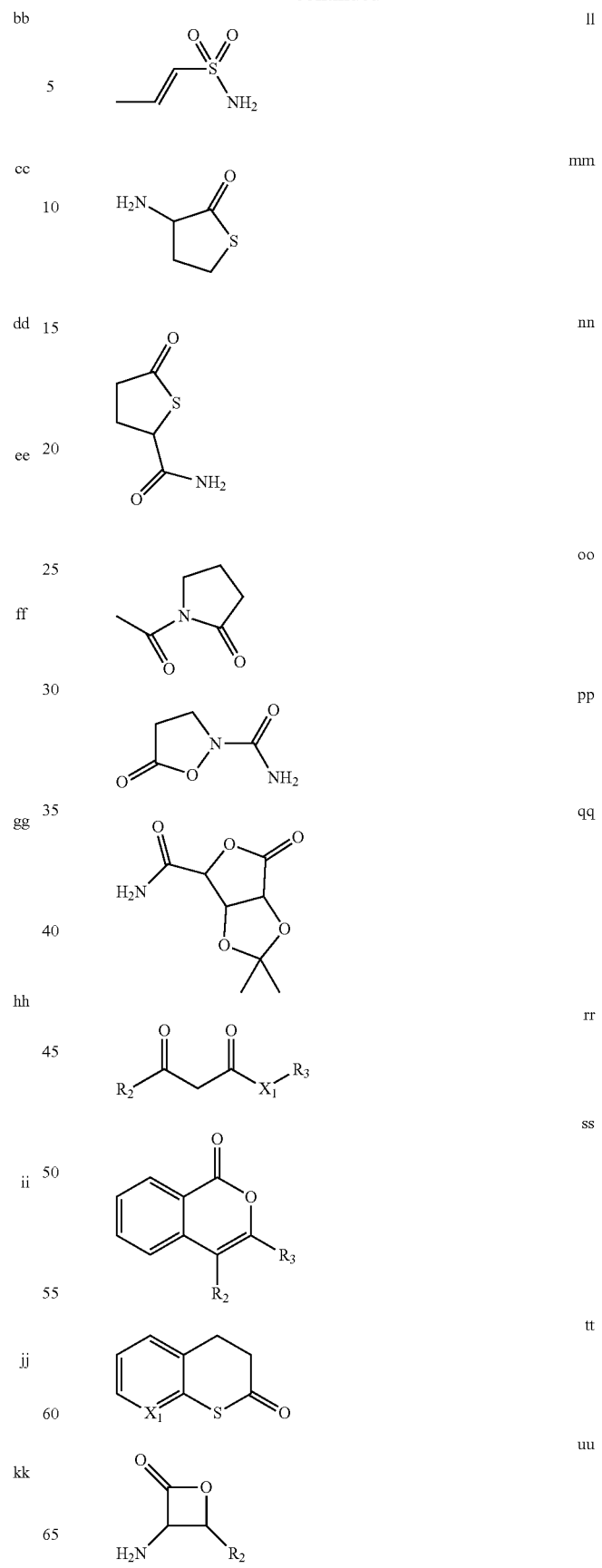

-continued vv 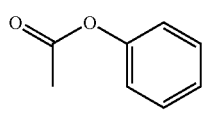

ww 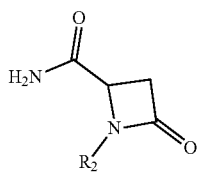

xx 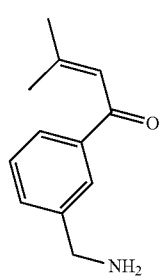

yy 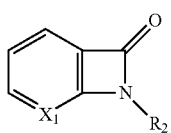

zz 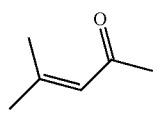

aaa 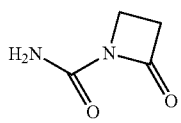

bbb 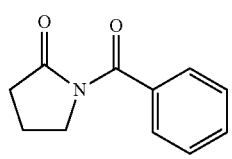

ccc 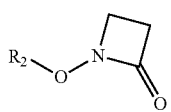

ddd 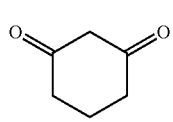

eee 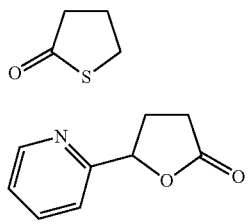

fff 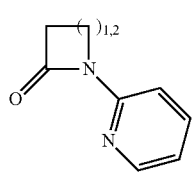

ggg hhh 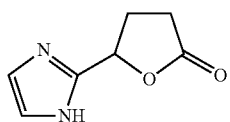

iii 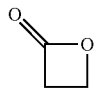

jjj 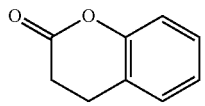

kkk 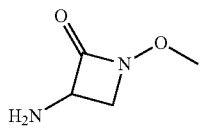

lll 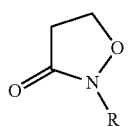

mmm 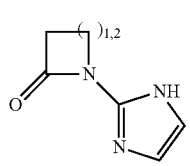

nnn ooo 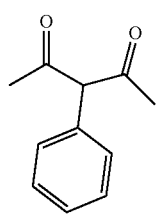

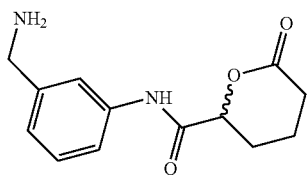

In the foregoing compounds aa-ooo, any substitutable hydrogen may be substituted with the substituents as those defined by $R_2$-$R_8$.

In certain embodiments, the radical resulting from the removal of a hydrogen of a compound of Formula I-a, I-d, I-k, or I-m is a radical of Formula VI-a, VI-b, VI-c, VI-d, VI-e, VI-f, VI-g, VI-h, VI-i, VI-j, VI-k, VI-l, VI-m, VI-n, VI-o, VI-p, or VI-q:

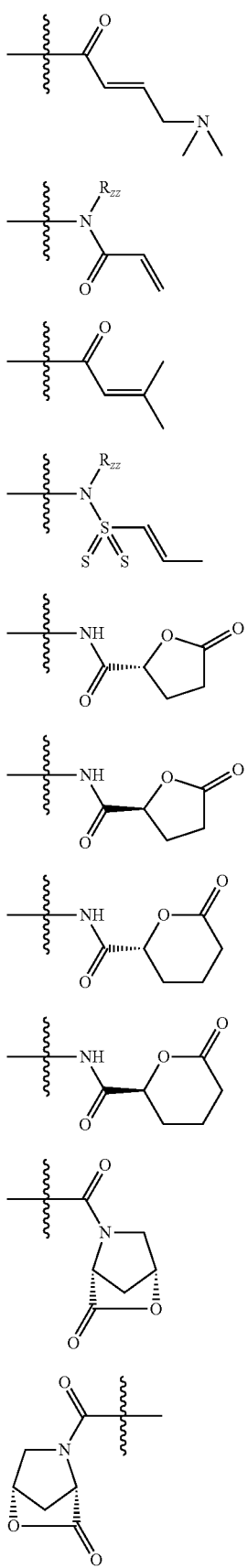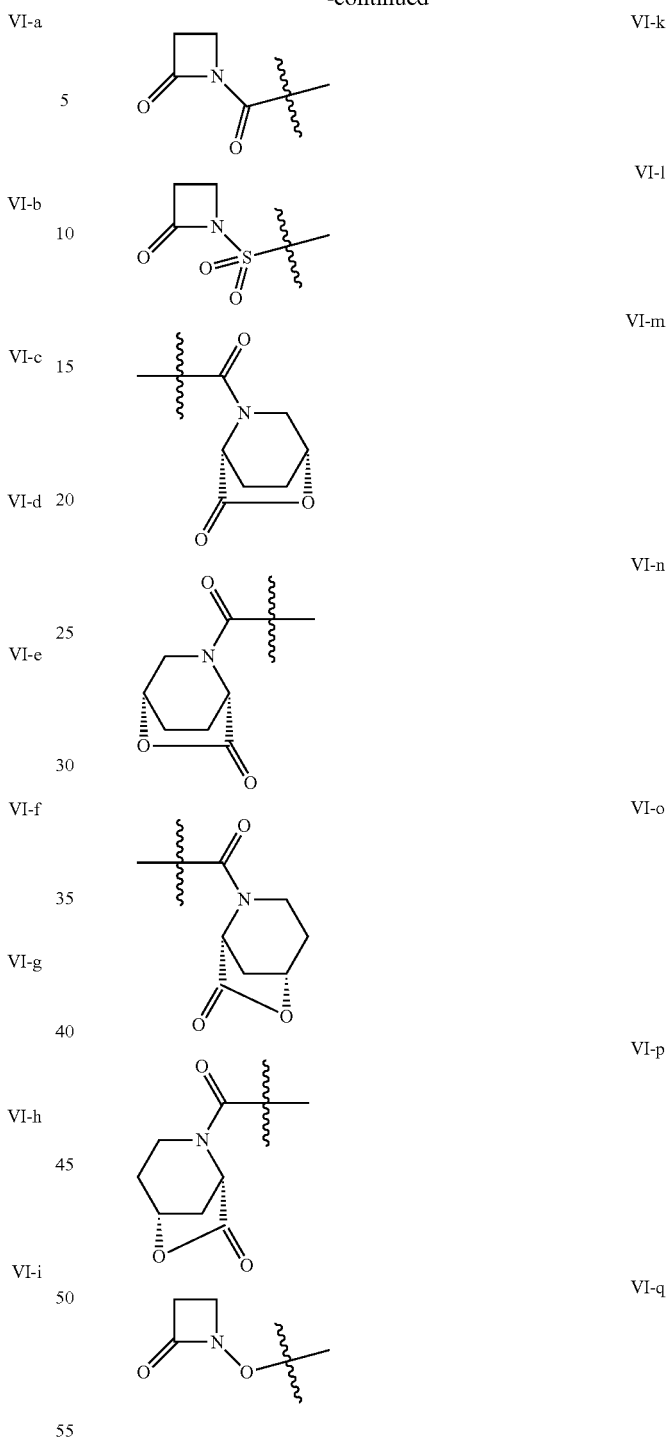

wherein
R_zz is hydrogen, methyl, ethyl, propyl, isopropyl, cyclopropyl, —CH$_2$OCH$_3$, or —CH$_2$CH$_2$OCH$_3$.

In some embodiments of the compound of Formula I, the Tether is null, a bond, or a bivalent C$_1$-C$_{15}$ saturated, unsaturated, straight, branched, cyclic, bicyclic, tricyclic alkyl, alkenyl, alkynyl; bridged bicyclic, heterocycle, heteroaryl, or aryl moiety; wherein optionally one or more methylene units of the hydrocarbon chain are independently replaced by —NR$_1$—, —O—, —C(O)—, —S—, —SO—, —SO$_2$—, —C(=S)—, or C(=NR$_1$)—; optionally, one or more hydrogens are independently replaced by heteroatoms, and optionally, one or more methine groups of the $C_1$-$C_{15}$ alkyl, when present, are independently replaced by

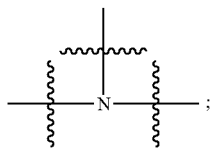 [SMILES: *N(*)*]

and
$R_1$ is hydrogen or $C_1$-$C_8$ alkyl.

In certain embodiments, the Tether is null, a bond, or a bivalent $C_1$-$C_{15}$ saturated, unsaturated, straight, branched, cyclic, bicyclic, tricyclic alkyl, alkenyl, alkynyl; wherein optionally one or more methylene units of the hydrocarbon chain are independently replaced by —$NR_1$—, —O—, —C(O)—, —S—, —SO—, —$SO_2$—, —C(=S)—, or C(=$NR_1$)—; optionally, one or more hydrogens are independently replaced by heteroatoms, and optionally, one or more methine groups of the $C_1$-$C_{15}$ alkyl, when present, are independently replaced by

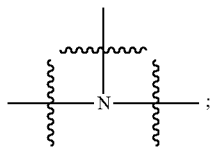

and
$R_1$ is hydrogen or $C_1$-$C_8$ alkyl.

In certain embodiments, the Scaffold is selected from the group consisting of Formulas VII, VIII, IX-a, IX-b, XI, XII, XVI, XVII, XVIII, XIX, XX, XXI, XXII, XXIII, XXXIV, XXV, XXVI, XXVII, XXVIII, XXIX, XXXVi, and XXXVII.

A. IAP Protein Scaffolds

1. Compounds of Formula I Based on Compounds of Formula VII

In some embodiments, the compounds of Formula I are described wherein Scaffold is a radical resulting from the removal of one or more hydrogens of a compound of Formula VII:

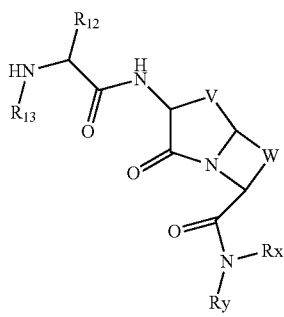

VII wherein
V and W are each independently —$(CR_{14}R_{15})_q X_3 (CR_{16}R_{17})_r$—;
q and r are each independently 0, 1, 2, 3, or 4;
$X_3$ is —$CR_{18}R_{19}$—, or —$NR_{20}$—;

$R_x$, $R_y$, $R_{12}$, $R_{13}$, $R_{14}$, $R_{15}$, $R_{16}$, $R_{17}$, $R_{18}$, $R_{19}$, and $R_{20}$ are each independently hydrogen or $C_1$-$C_6$ alkyl; wherein one or more methylene groups of the $C_1$-$C_6$ alkyl can be replaced by —$NR_1$—, —O—, —C(O)—, —S—, —SO—, —$SO_2$—, —C(=S)—, optionally substituted aryl or heteroaryl groups; one or more methine groups of the $C_1$-$C_6$ alkyl, when present, can be independently replaced by

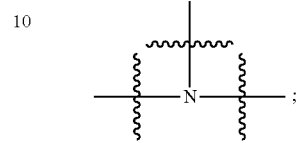

$R_1$ is hydrogen or $C_1$-$C_8$ alkyl; and
Tether and Warhead are as defined above in the embodiments of Formula I.

In some embodiments, the compound of Formula VII is a compound of Formula VII-a:

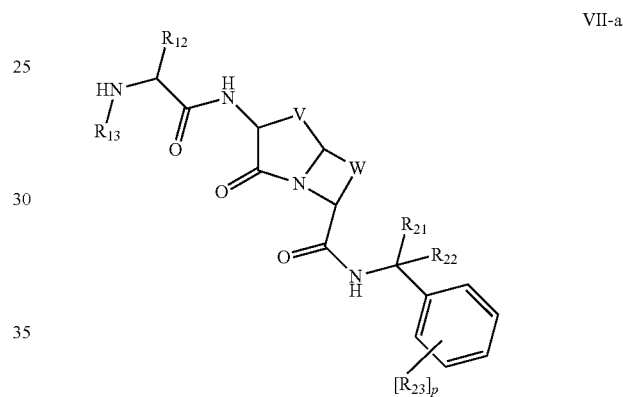

VII-a wherein
V and W are each independently —$(CR_{14}R_{15})_q X_3 (CR_{16}R_{17})_r$—;
q and r are each independently 0, 1, 2, 3, or 4;
$X_3$ is —$CR_{18}R_{19}$—, or —$NR_{20}$—;
p is 0, 1, 2, 3, or 4;
$R_{12}$, $R_{13}$, $R_{14}$, $R_{15}$, $R_{16}$, $R_{17}$, $R_{18}$, $R_{19}$, and $R_{20}$ are each independently hydrogen or $C_1$-$C_6$ alkyl; wherein one or more methylene groups of the $C_1$-$C_6$ alkyl can be replaced by —$NR_1$—, —O—, —C(O)—, —S—, —SO—, —$SO_2$—, —C(=S)—, optionally substituted aryl or heteroaryl groups; one or more methine groups of the $C_1$-$C_6$ alkyl, when present, can be independently replaced by

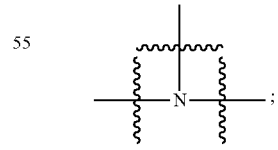

$R_1$ is hydrogen or $C_1$-$C_8$ alkyl; and;
$R_{23}$ is hydrogen, $C_1$-$C_6$ alkyl, halogen, amino, or nitro; wherein one or more methylene groups of $C_1$-$C_6$ alkyl can be optionally replaced by —$NR_1$—, —O—, —C(O)—, —S—, —SO—, —$SO_2$—, or —C(=S)—; one or more methine groups of the $C_1$-$C_6$ alkyl, when present, can be independently replaced by

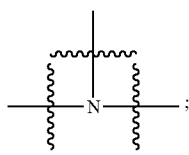

and optionally $R_{21}$ and $R_{23}$ taken together can form a 4- to 8-membered carbocyclic or heterocyclic ring.

In other embodiments, the compound of Formula I' is a compound of Formula VII-b.

VII-b

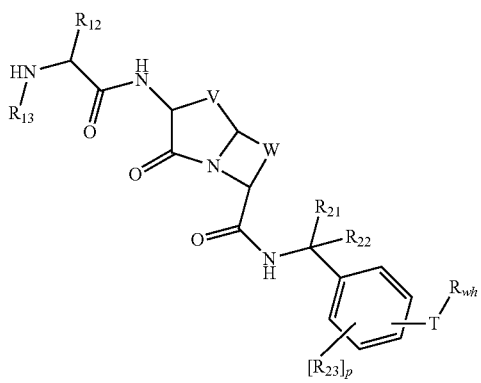

wherein $R_{12}$, $R_{13}$, $R_{21}$, $R_{22}$, $R_{23}$, V, W, p, are as defined above for Formula VII-a and T and $R_{wh}$ are as defined above in the embodiments of Formula I.

In certain embodiments, the compound of Formula VII-b is a compound of Formula VII-h.

VII-h

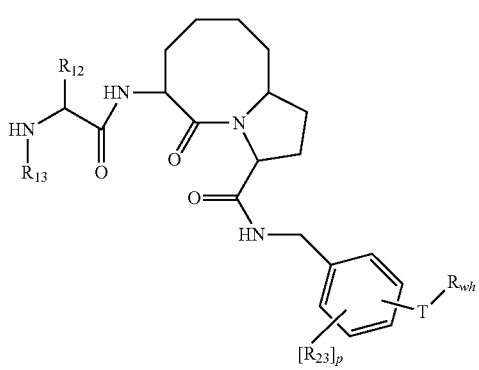

wherein T, $R_{wh}$, p, $R_{12}$, $R_{13}$, $R_{23}$, and p are as described above for Formula VII-b.

In other embodiments, the compound of Formula VII-h is a compound of Formula VII-j, VII-k, VII-l, VII-m, VII-n, or VII-o:

VII-j

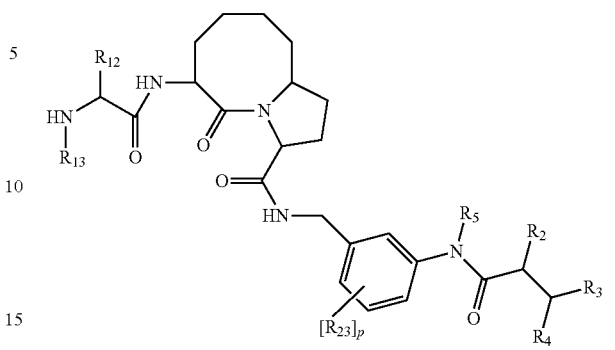

VII-k

VII-l

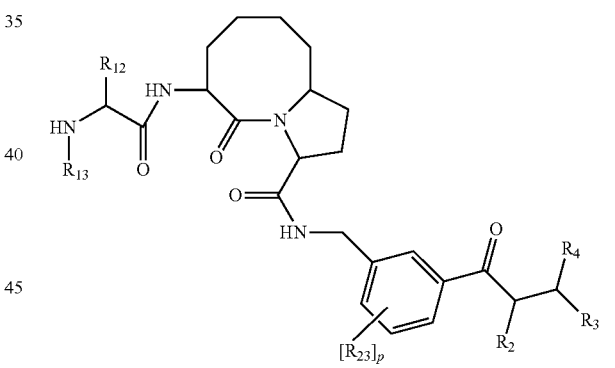

VII-m

VII-n
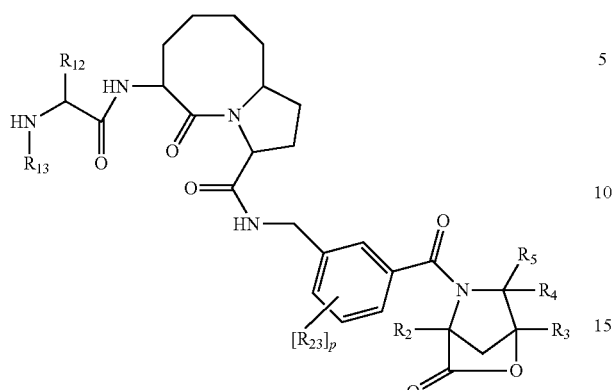
VII-o
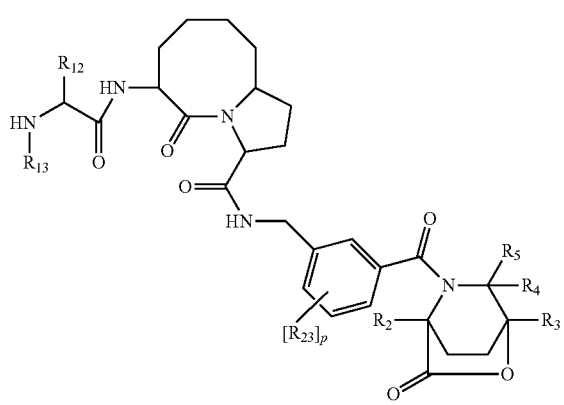
wherein, $R_2$, $R_3$, $R_4$, $R_5$, $R_6$, $R_7$ are as described above for embodiments of Formula I, and $R_{12}$, $R_{13}$, $R_{23}$, and p are as described above for Formulas VII and VII-h.
Non-limiting examples of compounds of Formula VII are as set forth below.
VII-1
VII-2
VII-3
VII-4
VII-5
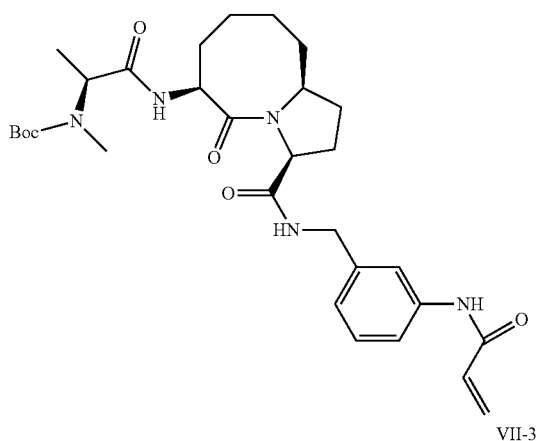
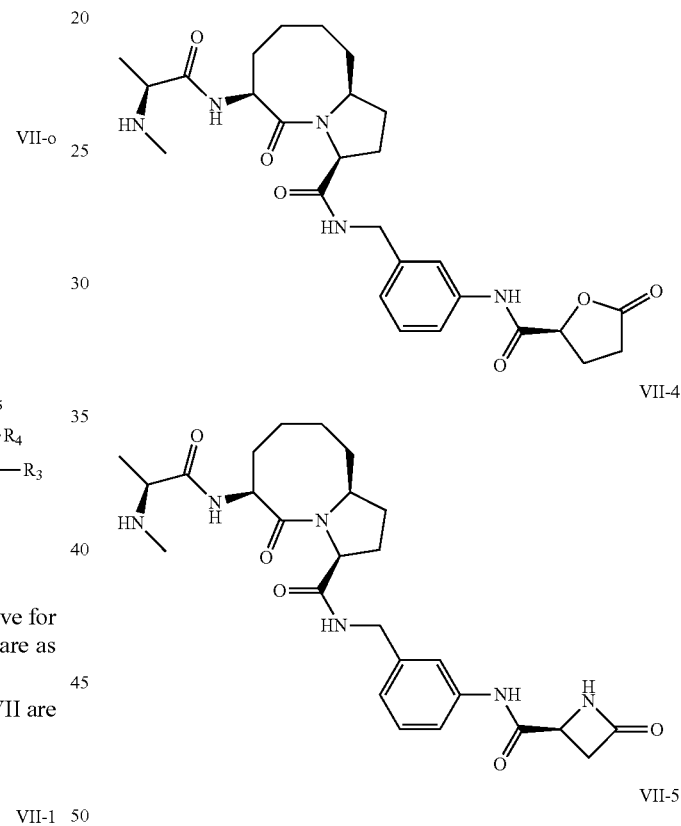
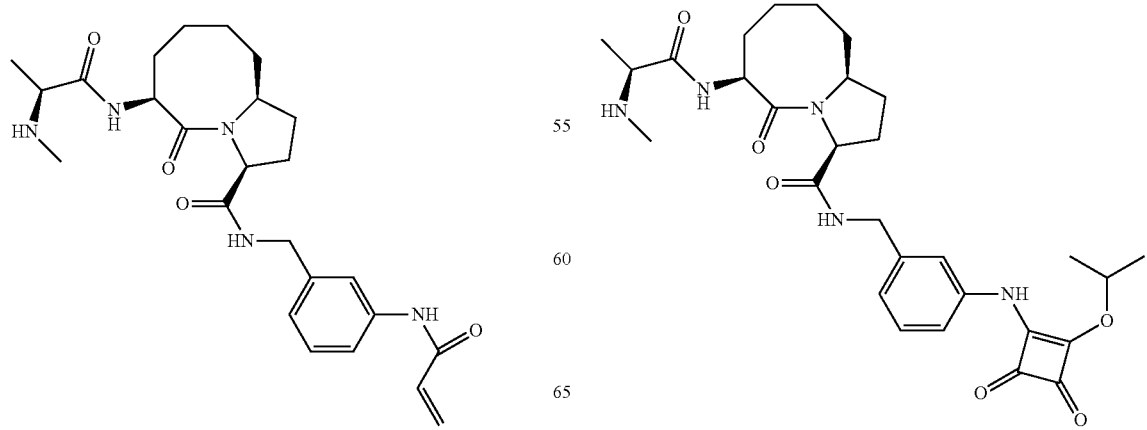

VII-6
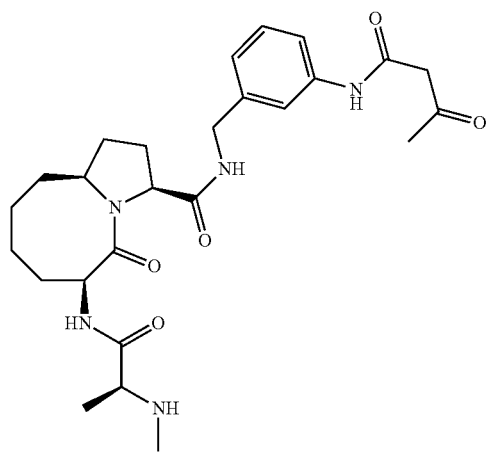
VII-7
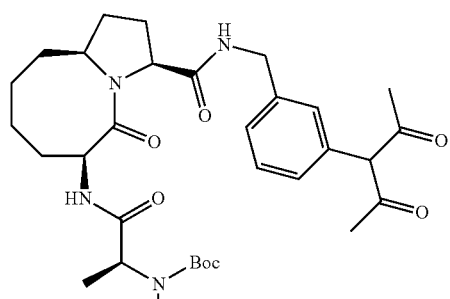
VII-8
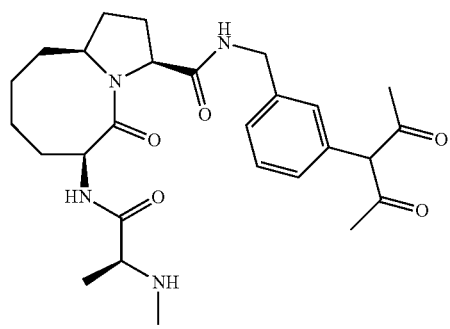
VII-9
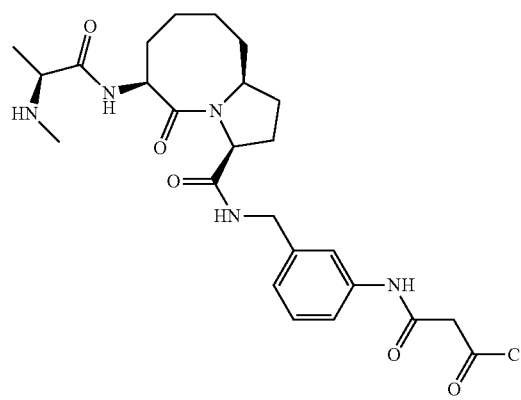
VII-10
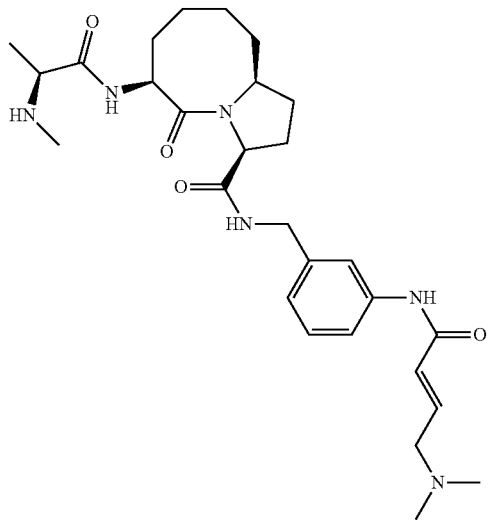
VII-11
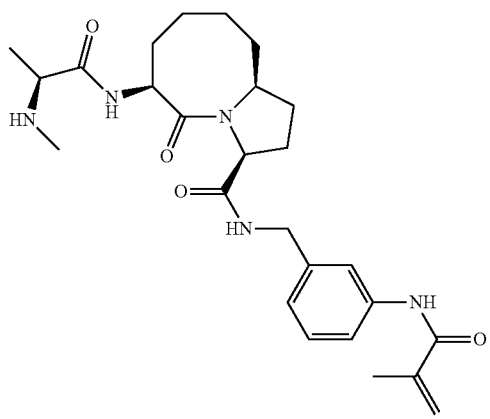
VII-12
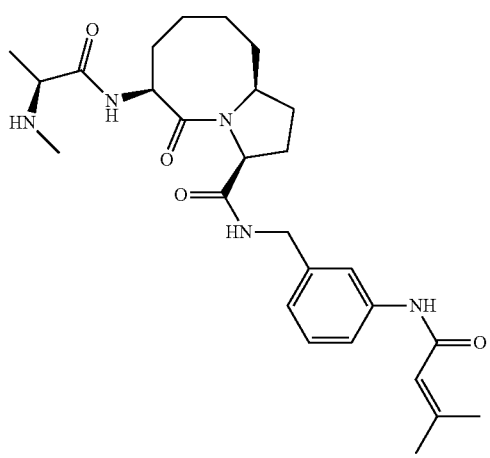

VII-13
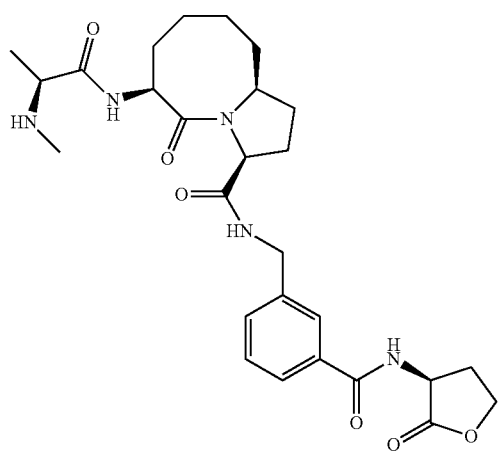
VII-14
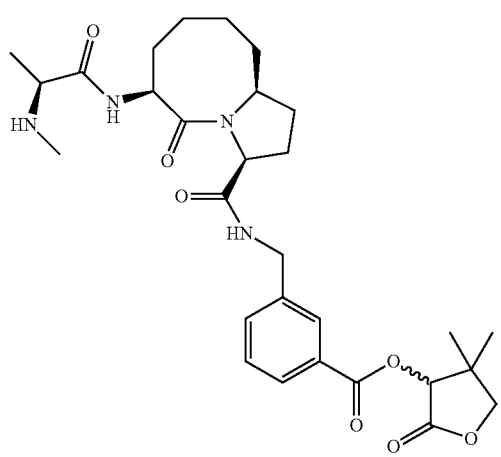
VII-15
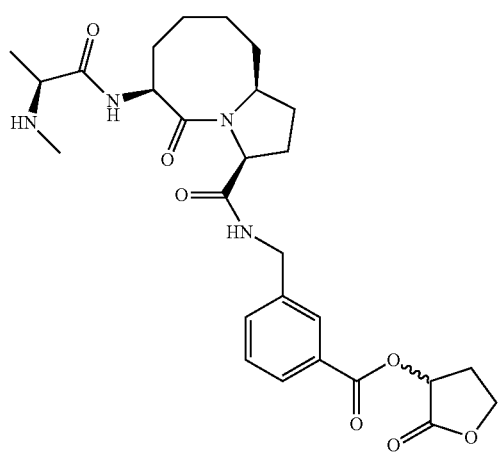
VII-16
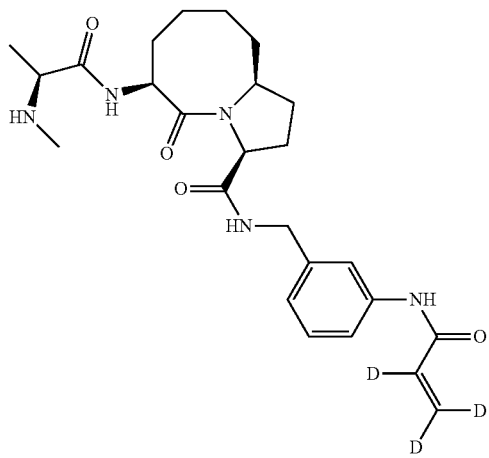
VII-17
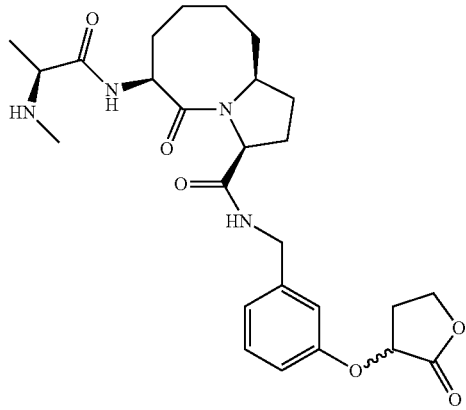
VII-18
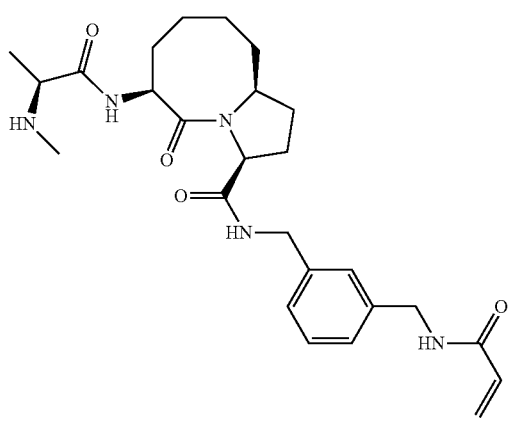

VII-19
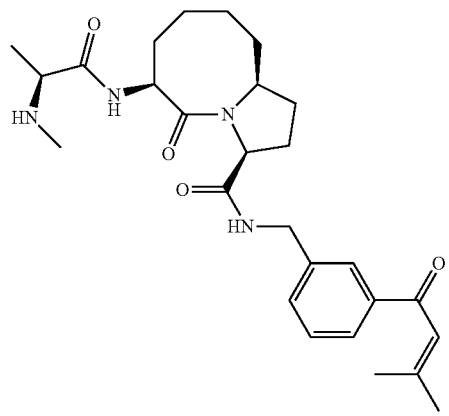
VII-22
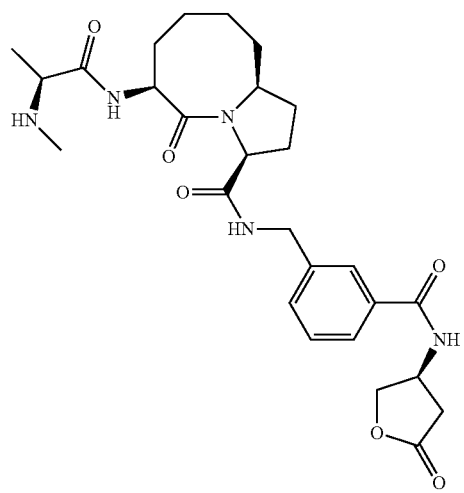
VII-20
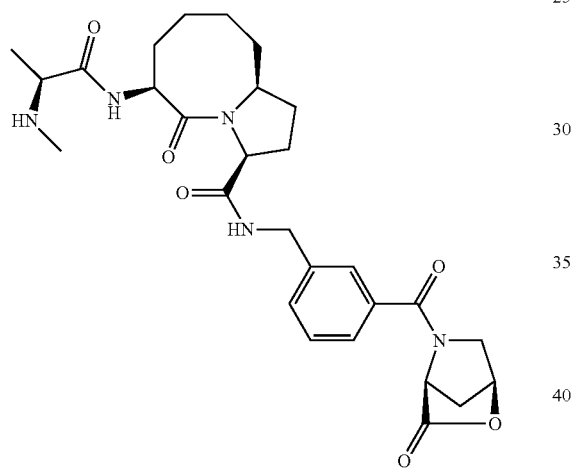
VII-23
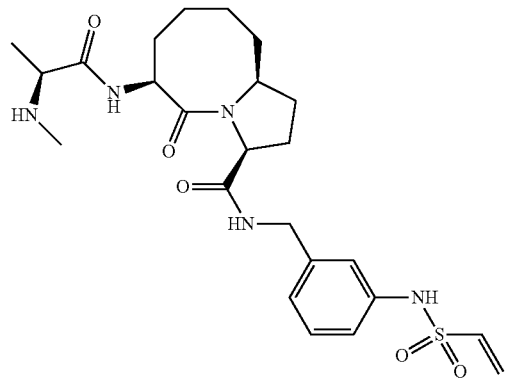
VII-21
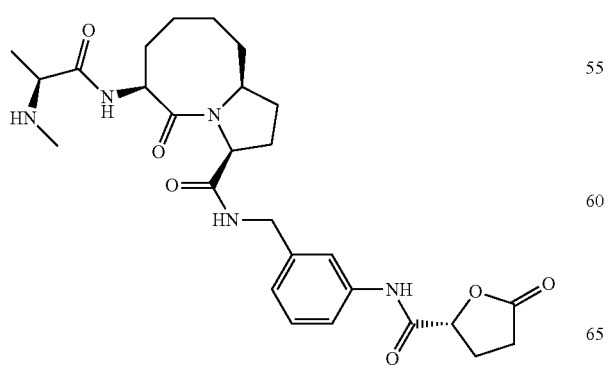
VII-24
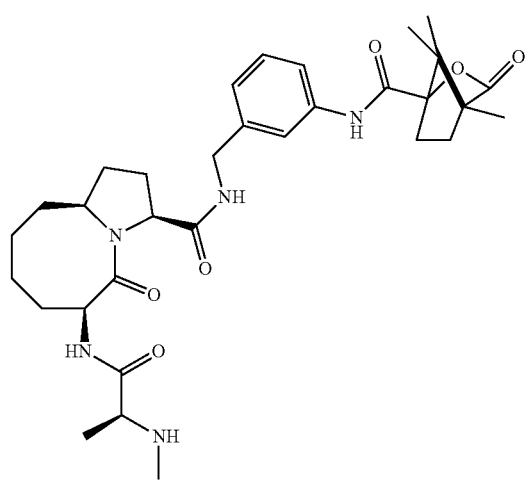

VII-25
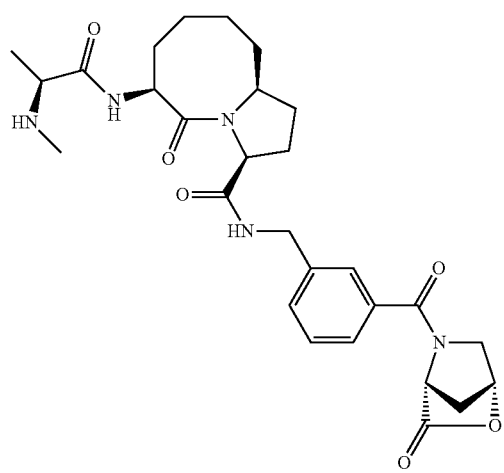
VII-29
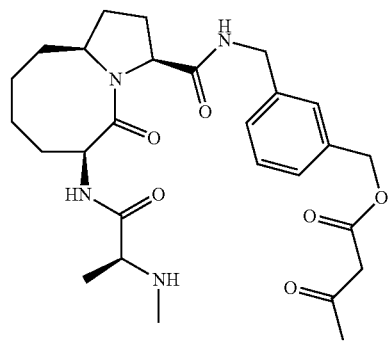
VII-26
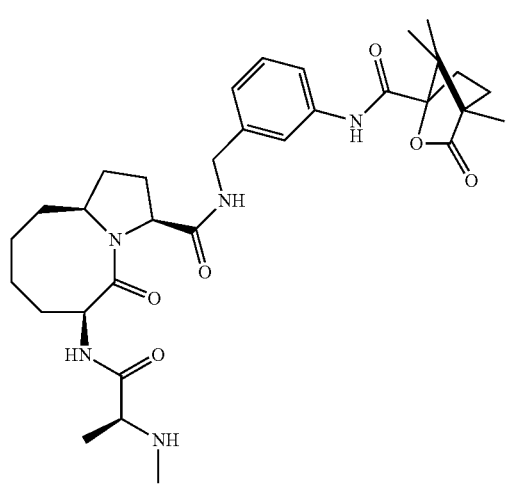
VII-30
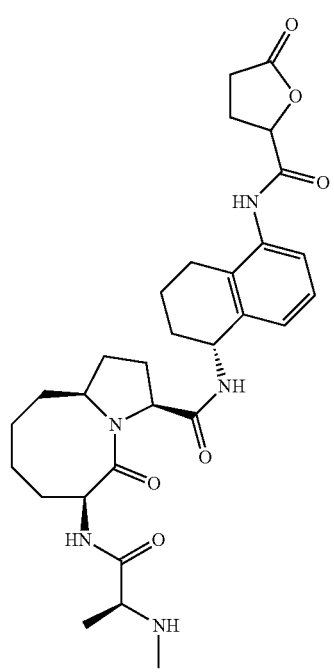
VII-27
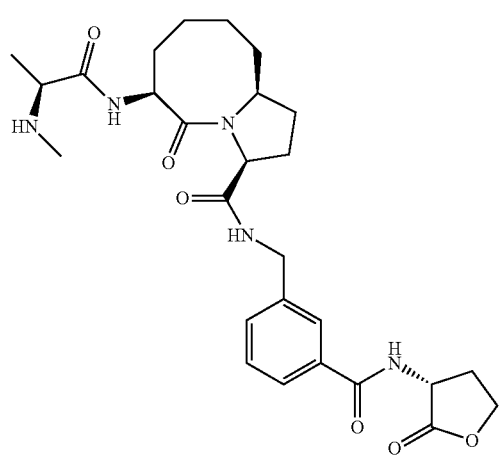
VII-31
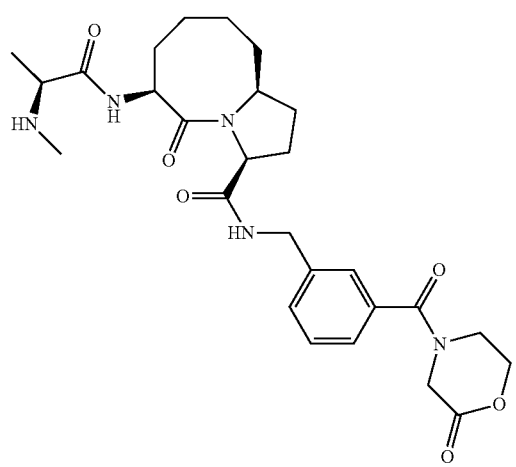

VII-32
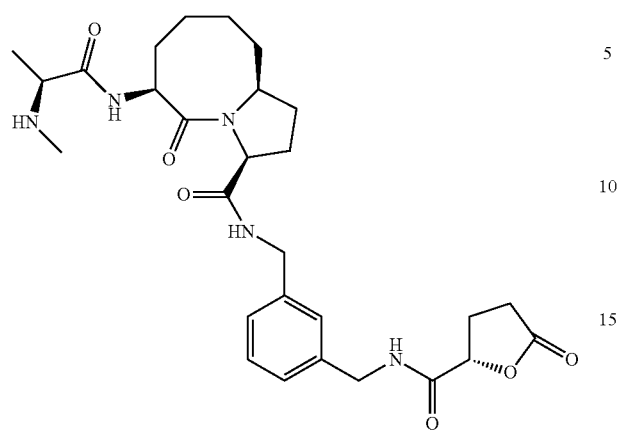
VII-33
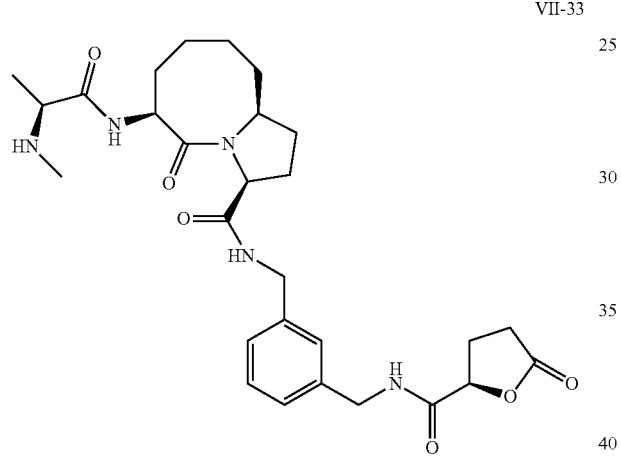
VII-34
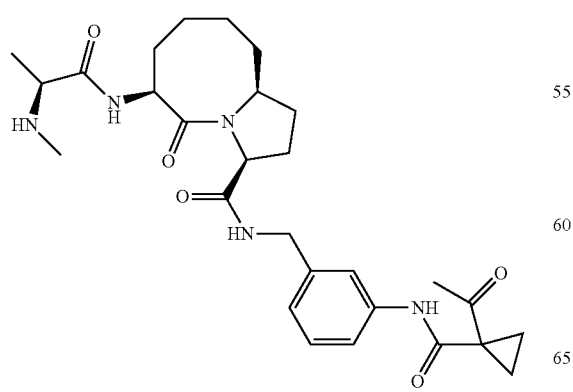
VII-38
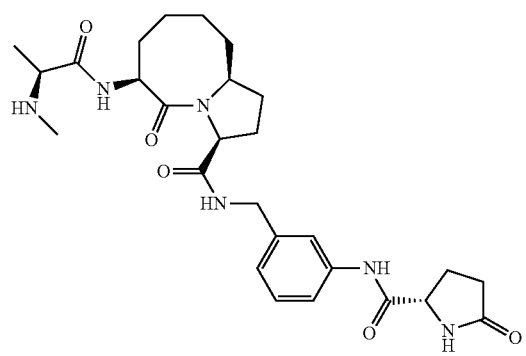
VII-39
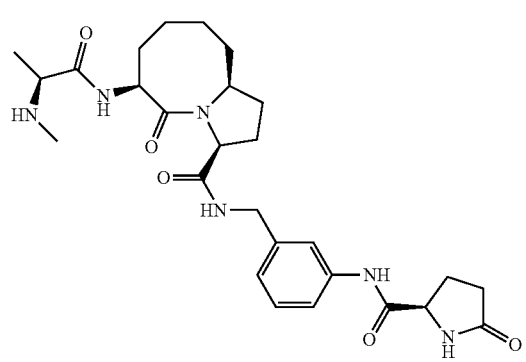
VII-41
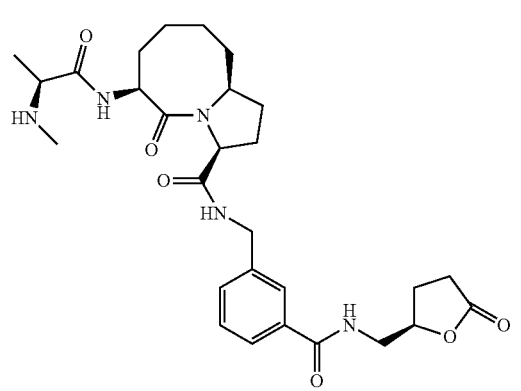
VII-42
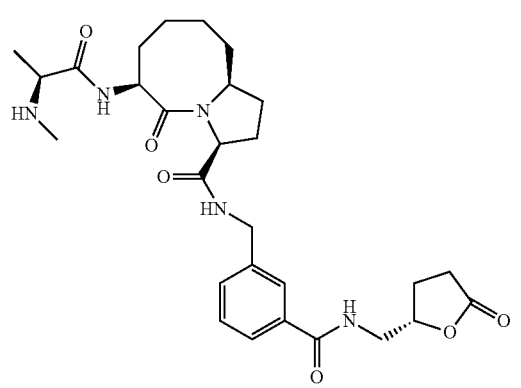

VII-43
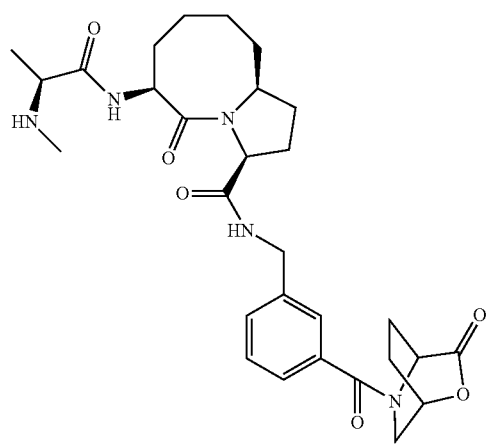
VII-44
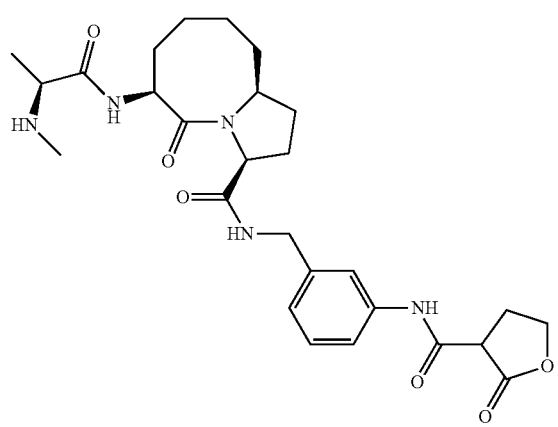
VI-45
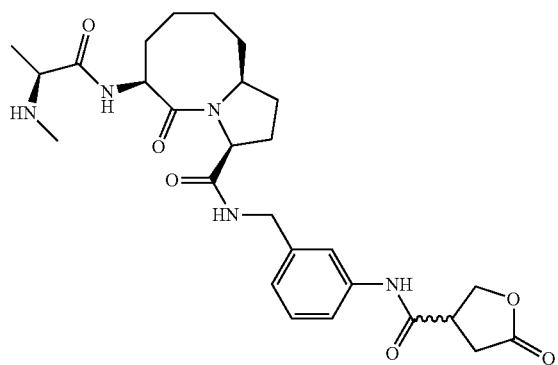
VII-46
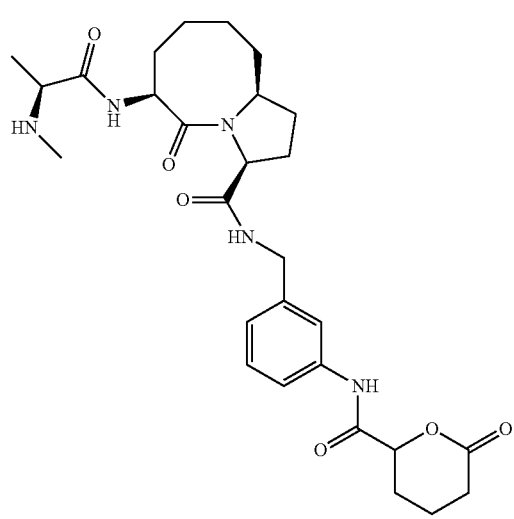
VII-47
VII-48
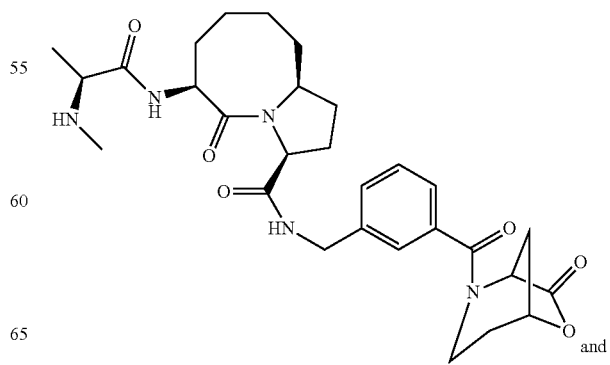
and -continued

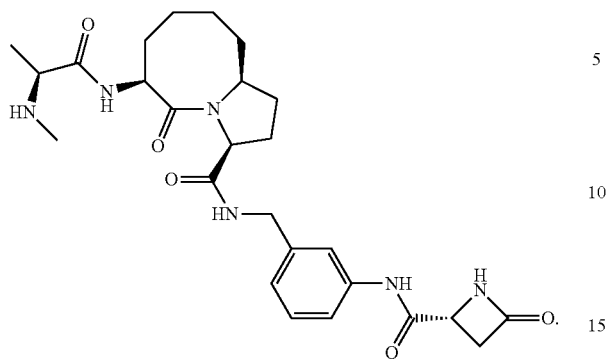
VII-49

2. Compounds of Formula I Based on Compounds of Formula VIII

In other embodiments, compounds of Formula I are described wherein Scaffold is a radical resulting from the removal of a hydrogen of a compound of Formula VIII:

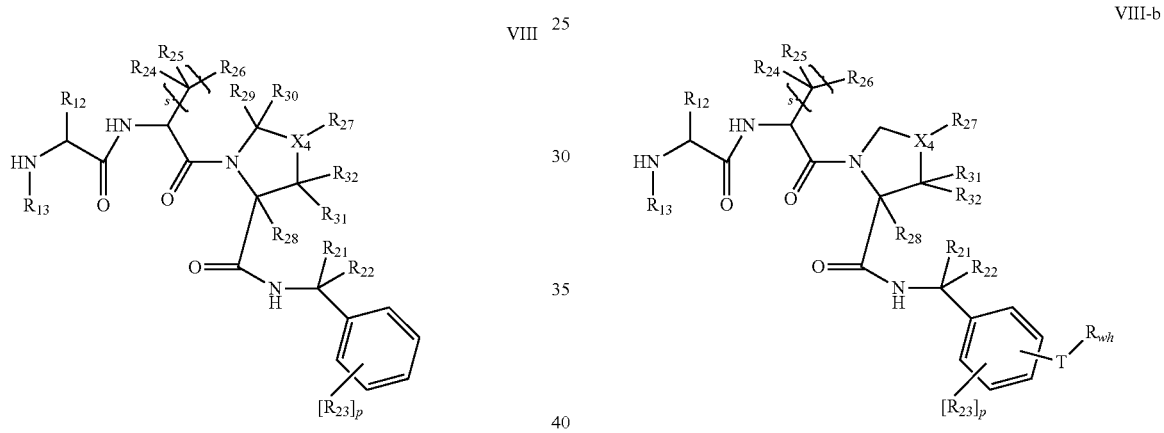
VIII wherein
$X_4$ is —$CR_{33}$— or —N—;
p and s are each independently 0, 1, 2, 3, or 4;
$R_{12}$, $R_{13}$, $R_{21}$, $R_{22}$, $R_{24}$, $R_{25}$, $R_{26}$, $R_{27}$, $R_{28}$, $R_{29}$, $R_{30}$, $R_{31}$, $R_{32}$, and $R_{33}$ are each independently hydrogen or $C_1$-$C_6$ alkyl;
$R_{23}$ is hydrogen, $C_1$-$C_6$ alkyl, halogen, amino, or nitro; wherein one or more methylene groups of $C_1$-$C_6$ alkyl can be optionally replaced by —$NR_1$—, —O—, —C(O)—, —S—, —SO—, —$SO_2$—, or —C(=S)—; one or more methine groups of the $C_1$-$C_6$ alkyl, when present, can be independently replaced by

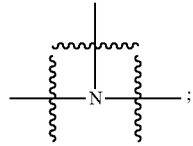
;

$R_1$ is hydrogen or $C_1$-$C_8$ alkyl; and
optionally $R_{21}$ and $R_{23}$ taken together can form a 4- to 8-membered carbocyclic or heterocyclic ring; and
Tether and Warhead are as defined above in the embodiments of Formula I.

In certain embodiments, the compound of Formula I is a compound of Formula VIII-a or VIII-b.

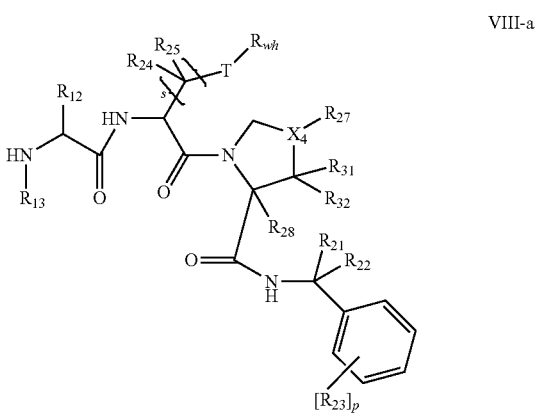
VIII-a

VIII-b wherein $X_4$, p, s, $R_{12}$, $R_{13}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, are as defined above for Formula VIII, and T and $R_{wh}$ are as defined above in the embodiments of Formula I.

Non-limiting examples of compounds of Formula VIII are as set forth below.

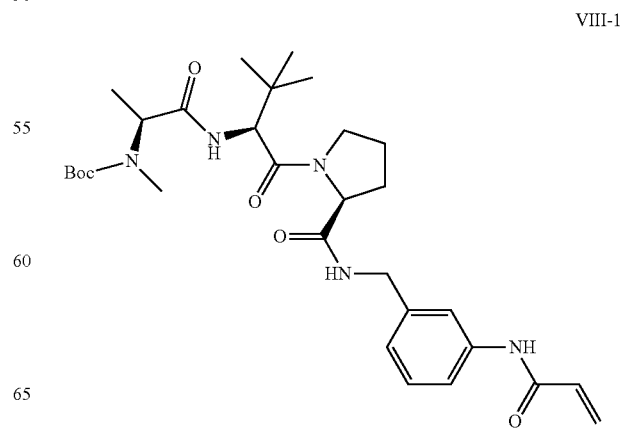
VIII-1

VIII-2
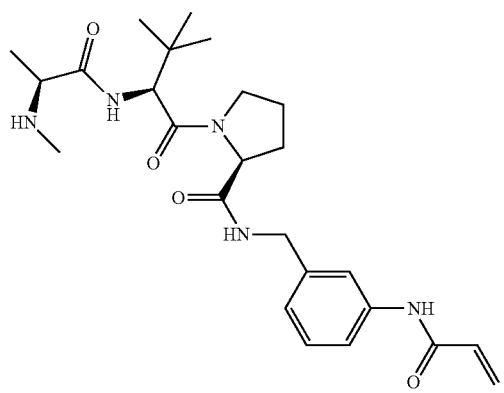
VIII-5
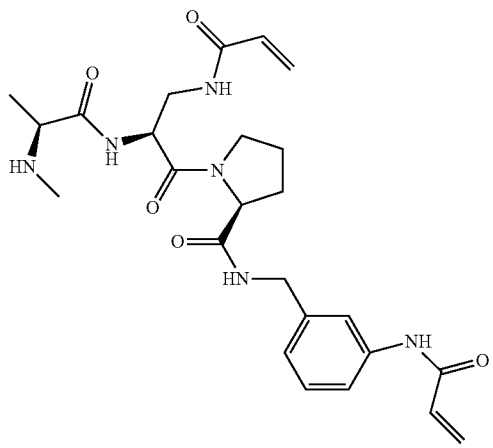
VIII-3
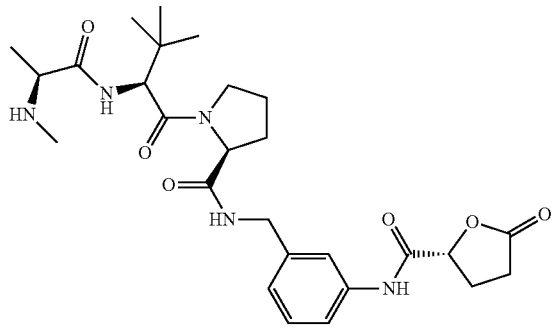
VIII-7
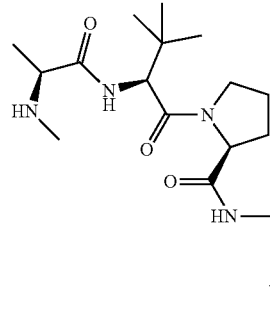
3. Compounds of Formula I Based on Compounds of Formulas IX-A and IX-B
In other embodiments, compounds of Formula I are described wherein Scaffold is a radical resulting from the removal of a hydrogen of a compound of Formula IX-a or IX-b:
VIII-4
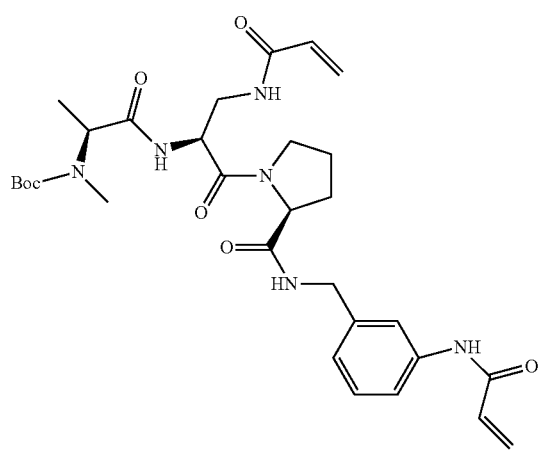
IX-a
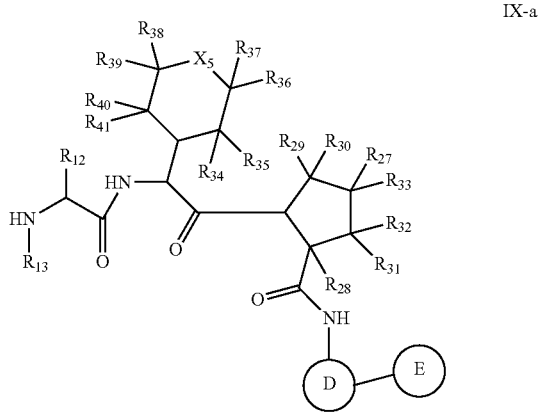

-continued

IX-b

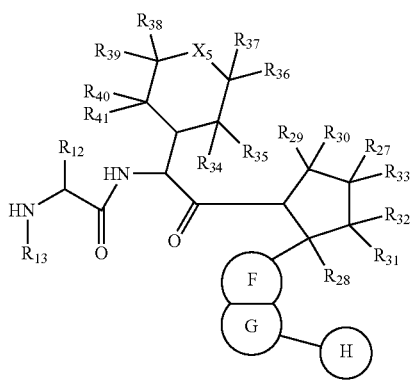

wherein $X_5$ is —O—, —CR$_{42}$R$_{43}$— or —NR$_{42}$—, $R_{12}$, $R_{13}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, and $R_{43}$ are each independently hydrogen or $C_1$-$C_6$ alkyl; wherein one or more methylene groups of $C_1$-$C_6$ alkyl can be optionally replaced by —NR$_1$—, —O—, —C(O)—, —S—, —SO—, —SO$_2$—, or —C(=S)—;

$R_1$ is hydrogen or $C_1$-$C_8$ alkyl; one or more methine groups of the $C_1$-$C_6$ alkyl, when present, can be independently replaced by

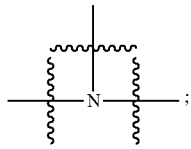 [SMILES: *N(*)*]

D, E, F, G, and H are each independently optionally substituted aryl or heteroaryl;

wherein F and G are fused together to form a bicyclic optionally substituted aryl or heteroaryl; and Tether and Warhead are as defined above in the embodiments of Formula I.

In yet another embodiment, the compound of Formula I is a compound of Formula IX-c or IX-d:

IX-c

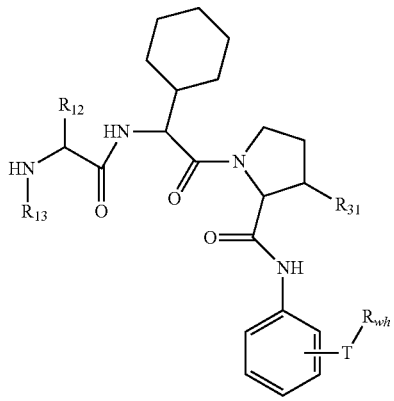

-continued

IX-d

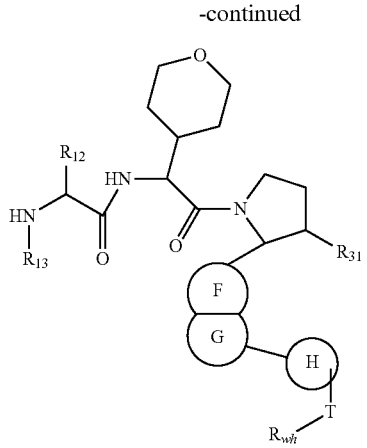

wherein $R_{12}$, $R_{13}$, $R_{31}$, F, G, and H are as defined above for Formulas IX-a and IX-b, and T and $R_{wh}$ are Tether and Warhead, respectively, and are as defined above in the embodiments of Formula I.

4. Compounds of Formula XVII

In some embodiments, compounds of Formula I are described by compounds of the Formula XVII:

XVII

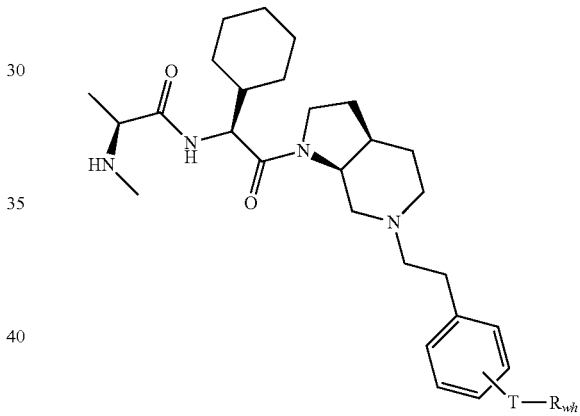

wherein T is Tether and $R_{wh}$ is Warhead and are as defined above in the embodiments of Formula I.

Nonlimiting examples of the compounds of Formula XVII are set forth below.

XVII-1

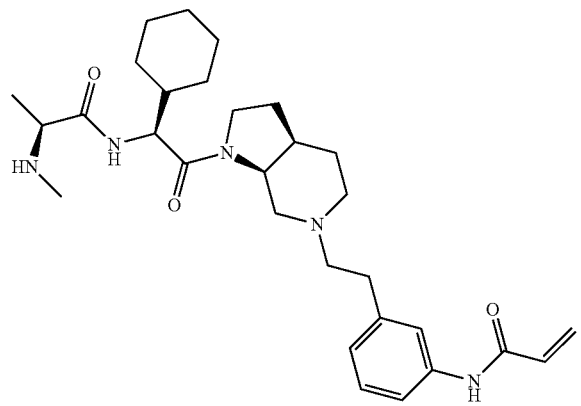

XVII-2
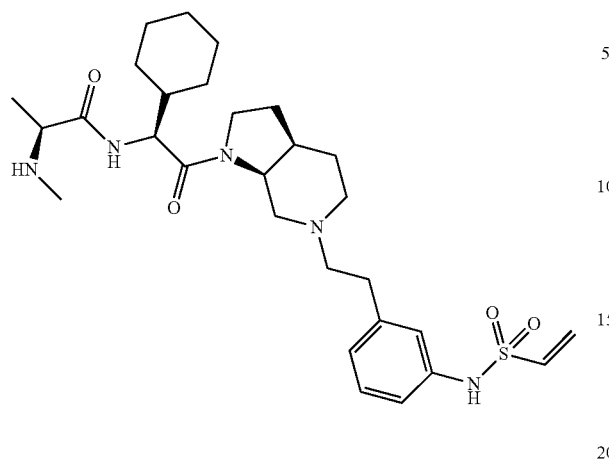
XVII-5
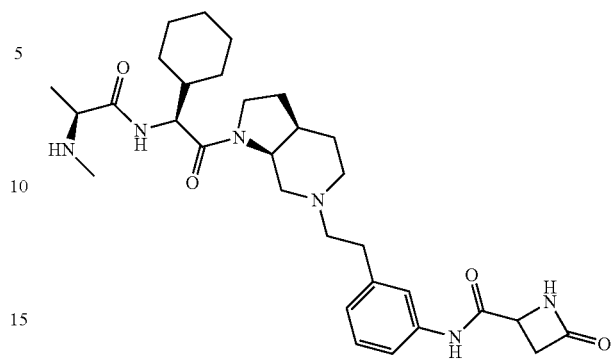
XVII-3
XVII-6
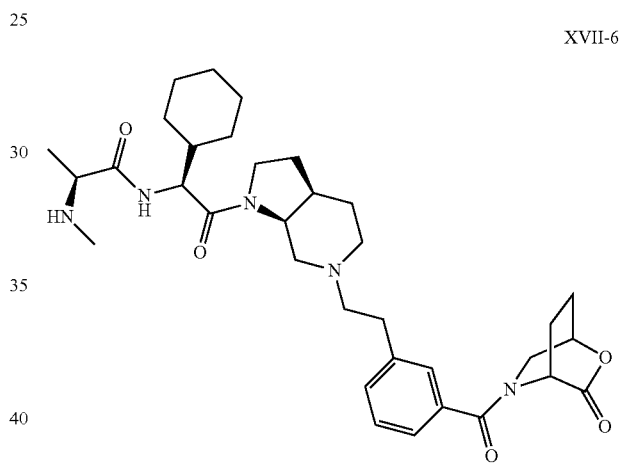
XVII-4
XVII-7
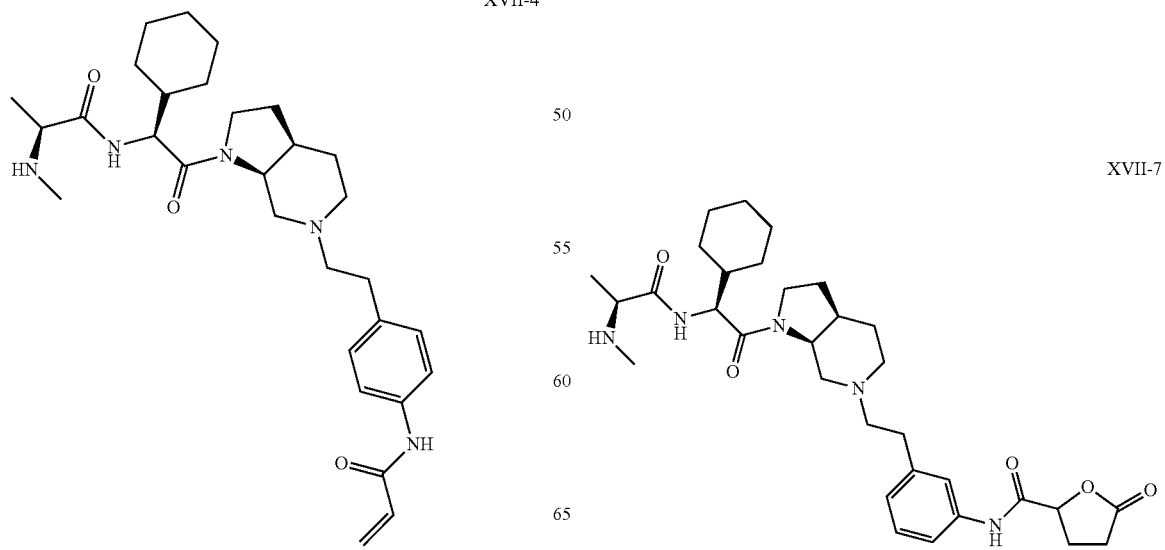

XVII-8
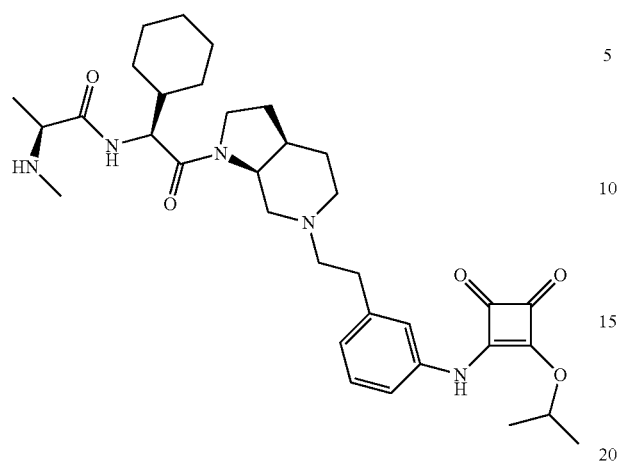
5. Compounds of Formula XVIII
In some embodiments, compounds of Formula I are described by compounds of the Formula XVIII:
XVIII
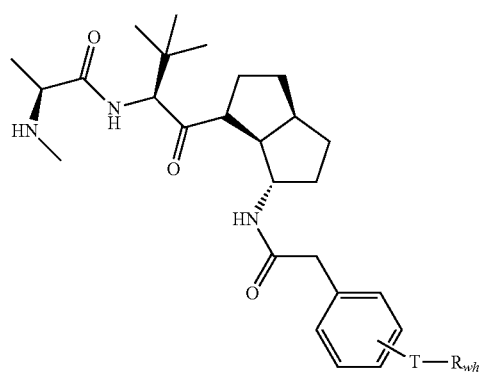
wherein T is Tether and $R_{wh}$ is Warhead and are as defined above in the embodiments of Formula I.
Nonlimiting examples of the compounds of Formula XVIII are set forth below.
XVIII-1
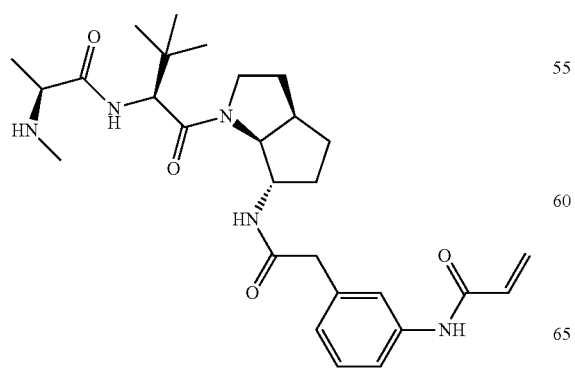
XVIII-2
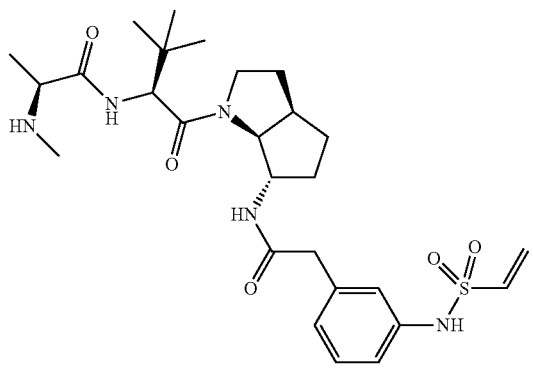
XVIII-3
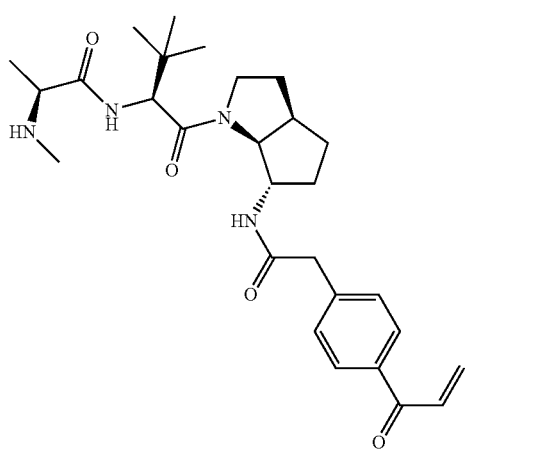
XVIII-4
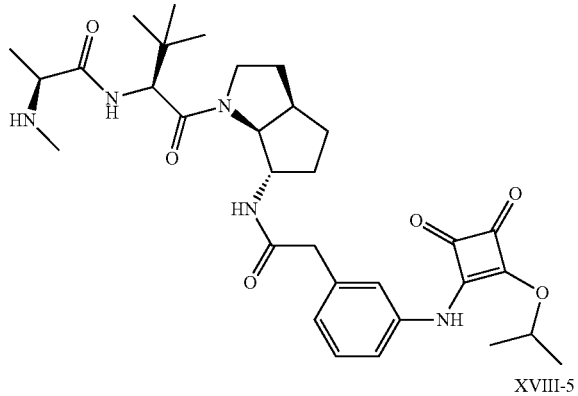
XVIII-5
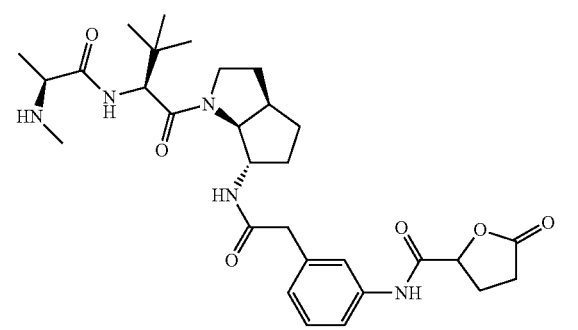

-continued
XVIII-6
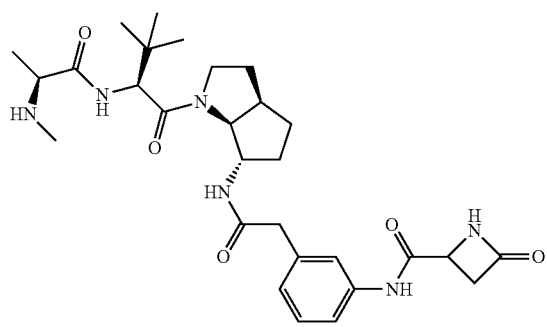
XVIII-7
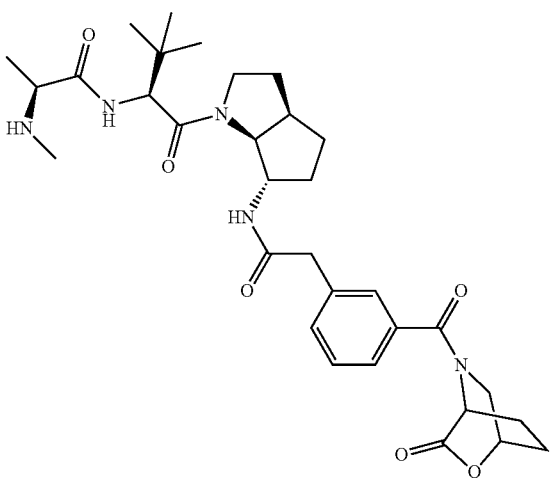
6. Compounds of Formula XIX
In some embodiments, compounds of Formula I are described by compounds of Formula XIX:
XIX
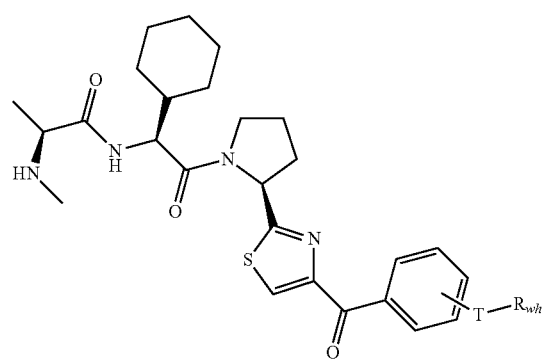
wherein T is Tether and $R_{wh}$ is Warhead and are as defined above in the embodiments of Formula I.
Nonlimiting examples of the compounds of Formula XIX are set forth below.
XIX-1
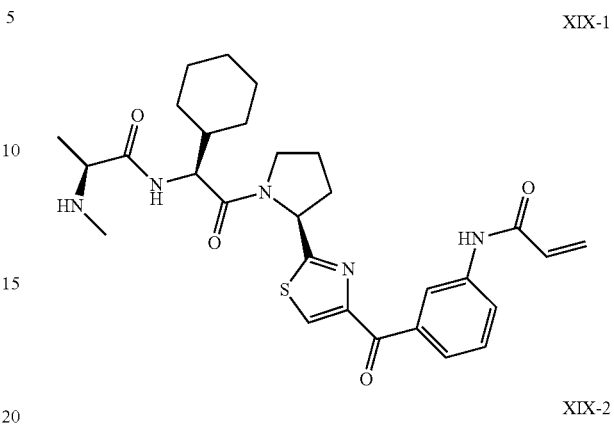
XIX-2
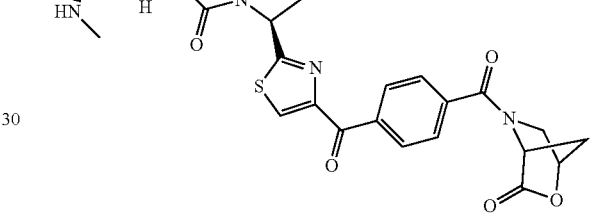
XIX-3
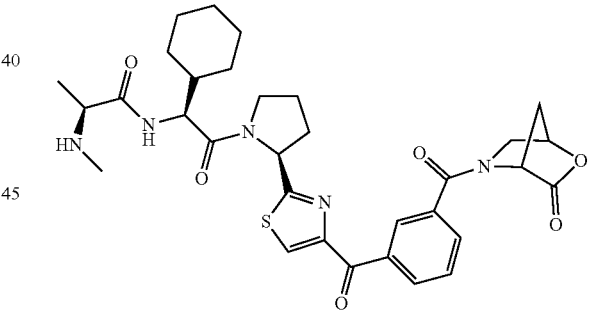
XIX-4
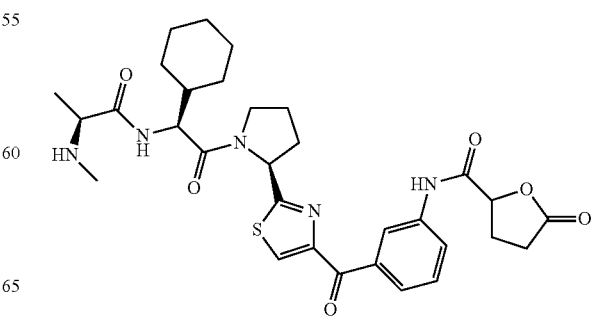

XIX-5

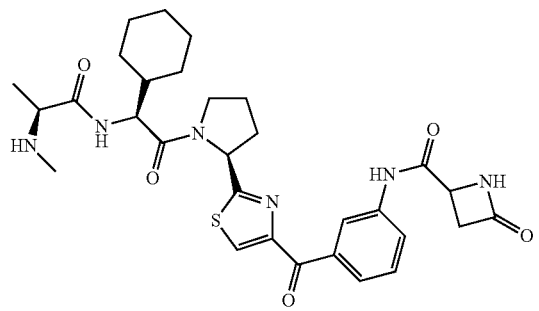

XX-b

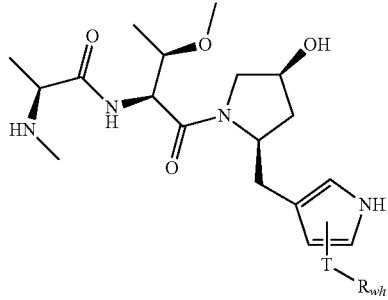

wherein
$R_{1000}$ is C(H) or N, wherein -T-$R_{wh}$ can be attached to any carbon or the NH of the heteroaryl moiety of Formula XX-a and Formula XX-b; and T and $R_{wh}$ are Tether and Warhead, respectively, and are as defined above in the embodiments of Formula I.

Nonlimiting examples of the compounds of Formula XX-a and Formula XX-b are set forth below.

XX-1

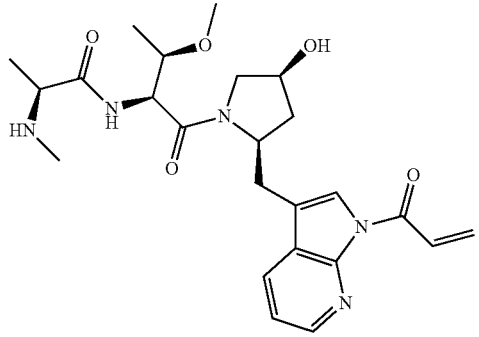

XIX-6

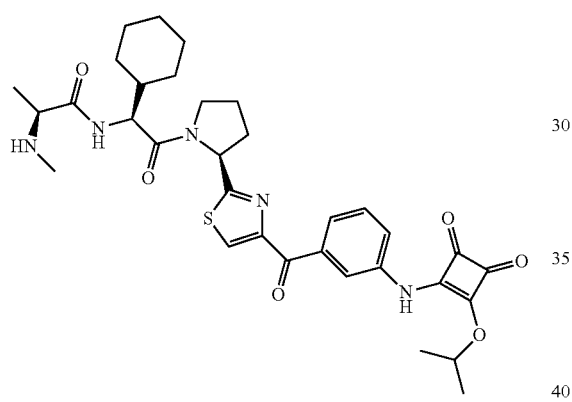

XX-2

7. Compounds of Formula XX-a and XX-b

In some embodiments, compounds of Formula I are described by compounds of Formula XX-a and Formula XX-b:

XX-a

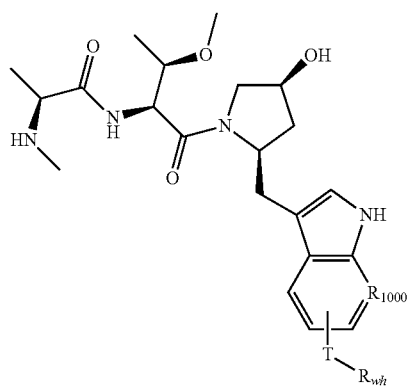

XX-3

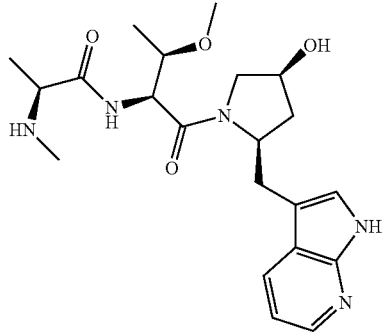

XX-4
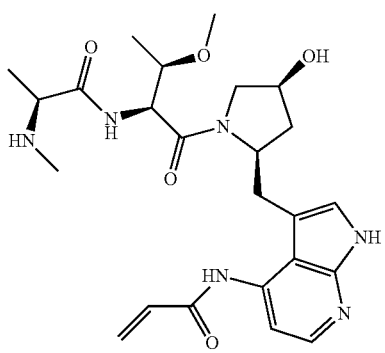

XX-5
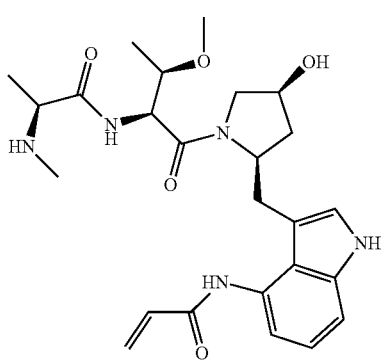

XX-6
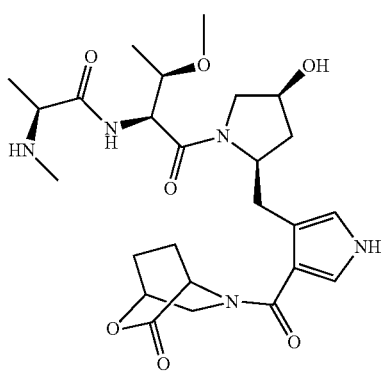

XX-7
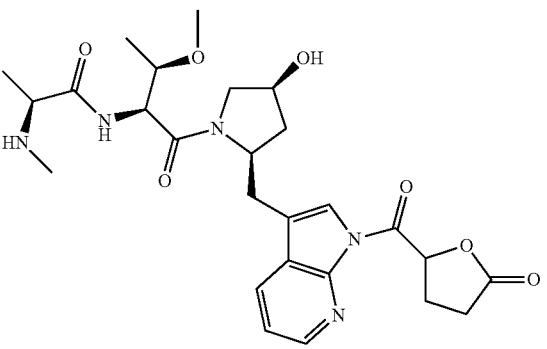

XX-8
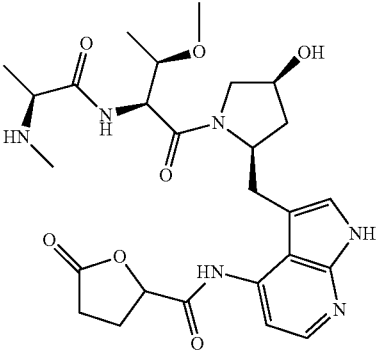

8. Compounds of Formula XXI-a, XXI-b, AND XXI-c

In some embodiments, compounds of Formula I are described by compounds of Formula XXI-a, Formula XXI-b, and Formula XXI-c:

XXI-a
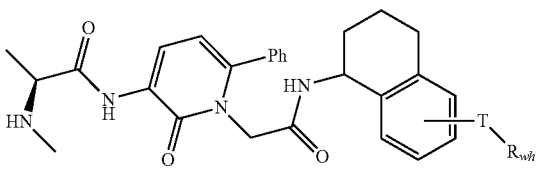

XXI-b
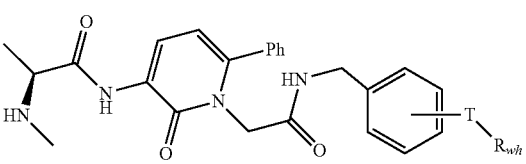

XXI-c
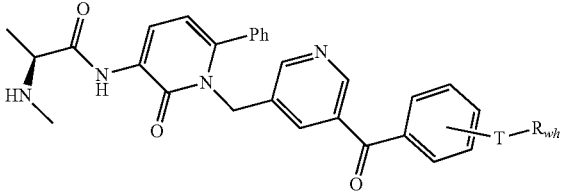

wherein T and $R_{wh}$ are Tether and Warhead, respectively, and are as defined above in the embodiments of Formula I.

Nonlimiting examples of the compounds of Formula XXI-a, Formula XXI-b, and Formula XXI-c are set forth below.

XXI-1
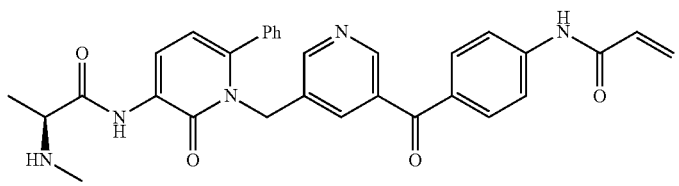
XXI-2
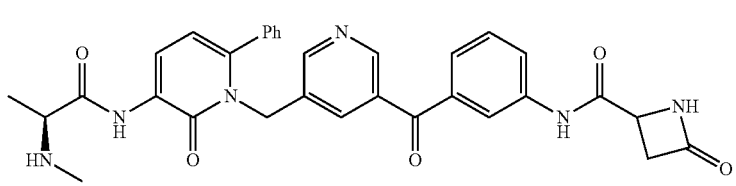
XXI-3
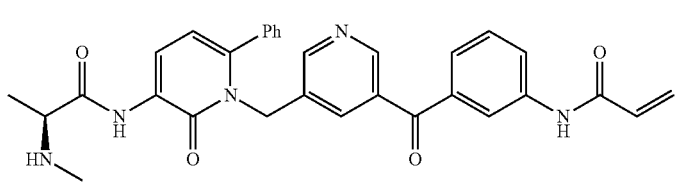
XXI-4
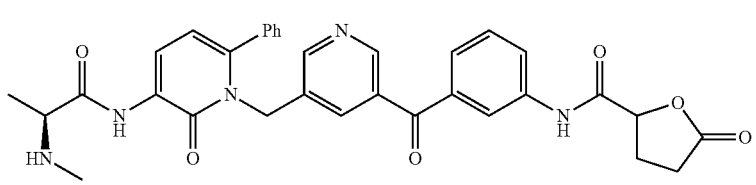
XXI-5
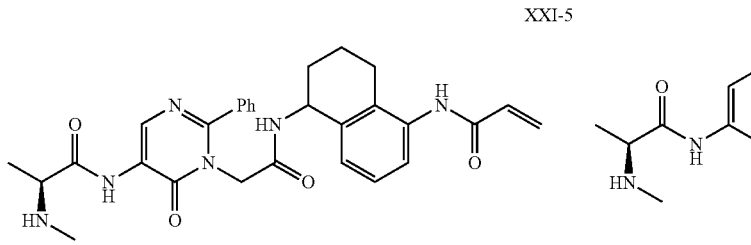
XXI-6
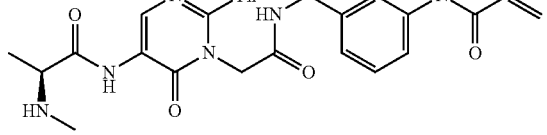
XXI-7
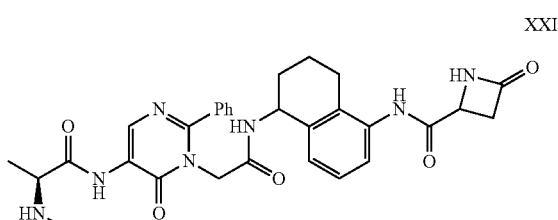
XXI-8
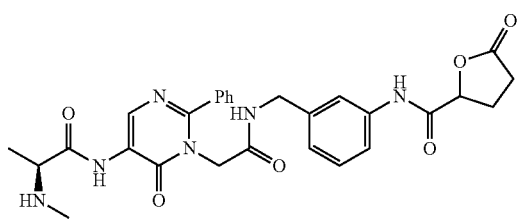
XXI-9
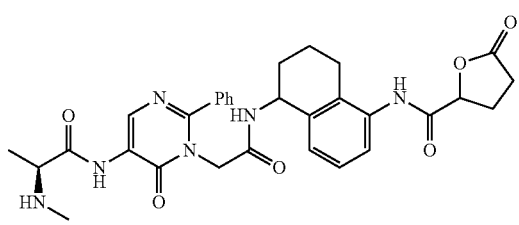
XXI-10

B. PDPK1 Protein Scaffolds

1. Compounds of Formula XI

In some embodiments, compounds of Formula I are described by compounds of Formula XI:

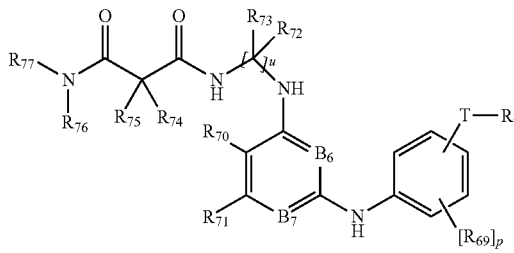

XI wherein $B_6$ and $B_7$ are each independently $CR_7$ or N;

$R_{69}$ is hydrogen, $C_1$-$C_6$ alkyl, halogen, amino, nitro, or —NH(CO)$NR_{78}R_{79}$;

$R_{70}$ is hydrogen, $C_1$-$C_6$ alkyl, halogen, amino, nitro;

$R_7$, $R_{71}$, $R_{72}$, $R_{73}$, $R_{74}$, $R_{75}$, $R_{76}$, $R_{77}$, $R_{78}$, and $R_{79}$ are each independently hydrogen or $C_1$-$C_6$ alkyl;

$R_1$ is hydrogen or $C_1$-$C_8$ alkyl; wherein one or more methylene groups of the $C_1$-$C_6$ alkyl can be replaced by —$NR_1$—, —O—, —C(O)—, —S—, —SO—, —SO$_2$—, or —C(=S)—; one or more methine groups of the $C_1$-$C_6$ alkyl, when present, can be independently replaced by

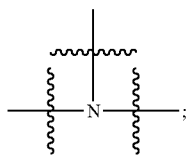 [SMILES: *N(*)*]

optionally $R_{78}$, and $R_{79}$ taken together form a 4- to 8-membered carbocyclic or heterocyclic ring;

p is an integer from 0 to 4, u is an integer from 1 to 4; and

T and $R_{wh}$ are Tether and Warhead respectively, and are as defined above in the embodiments of Formula I;

In other embodiments, the compound of Formula XI is a compound of Formula XI-a, XI-b, or XI-c.

XI-a

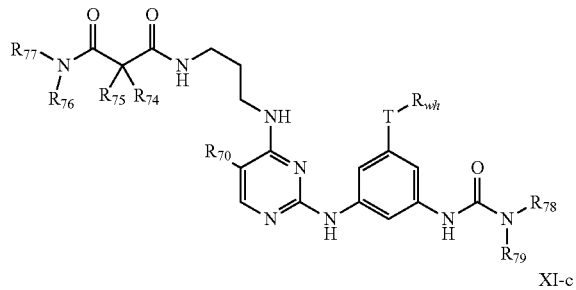

XI-b

XI-c

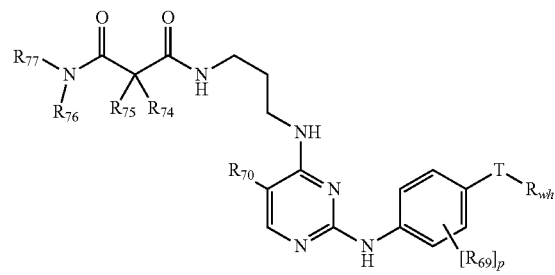

wherein, $R_{69}$, $R_{70}$, $R_{74}$, $R_{75}$, $R_{76}$, $R_{77}$, $R_{78}$, $R_{79}$, T, $R_{wh}$, and p are as defined above for Formula XI.

In yet another embodiment, the compound of Formula XI-a, XI-b or XI-c is a compound of Formula XI-d, XI-e, XI-f, XI-g, XI-h, XI-i, or XI-j.

XI-d

XI-e

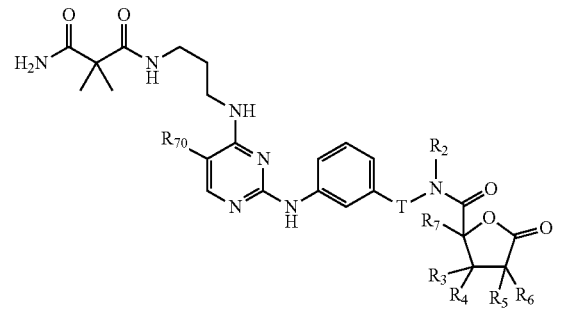

XI-f

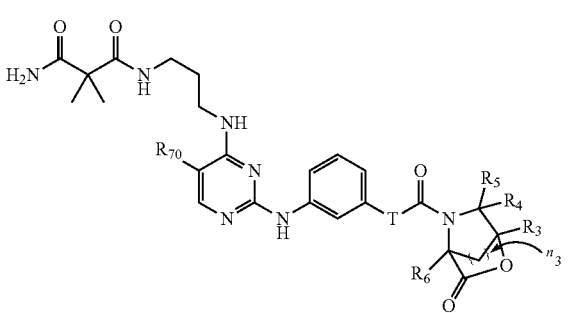

XI-g

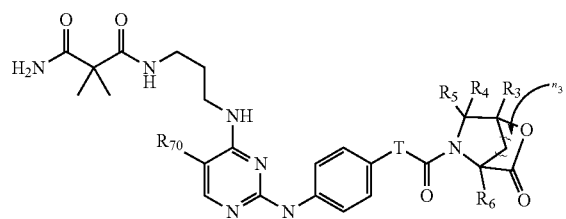

XI-h

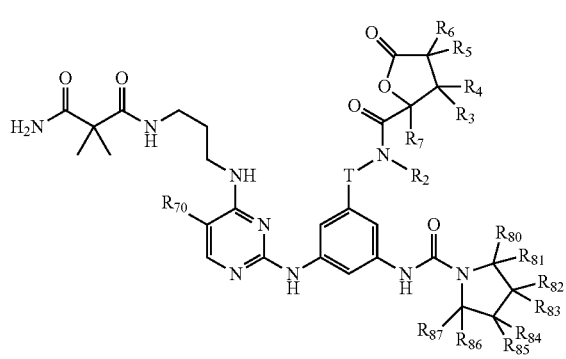

XI-i

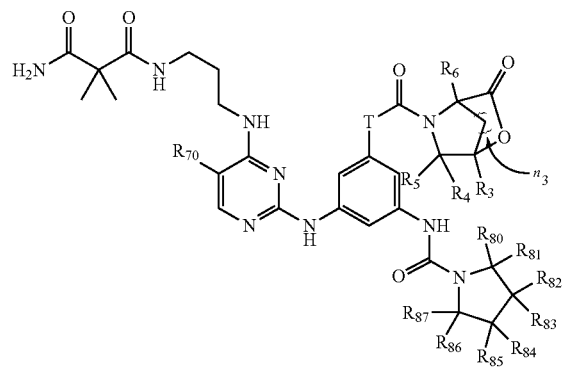

XI-j

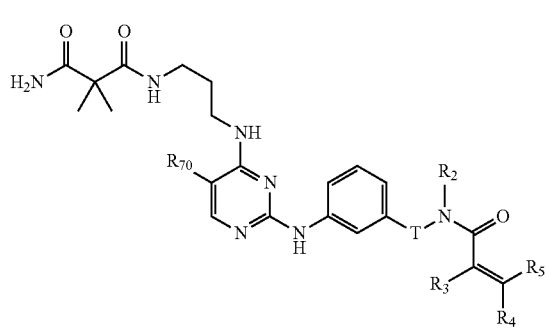

wherein $R_{70}$ and T are as defined above for Formula XI;

$R_1$, $R_2$, $R_3$, $R_4$, $R_5$, $R_6$, $R_{80}$, $R_{81}$, $R_{82}$, $R_{83}$, $R_{84}$, $R_{85}$, $R_{86}$, and $R_{87}$ are each independently hydrogen or $C_1$-$C_6$ alkyl, wherein one or more methylene groups of the $C_1$-$C_6$ alkyl can be replaced by —$NR_1$—, —O—, —S—, —SO—, —$SO_2$—, or —C(=S)—, $R_1$ is hydrogen or $C_1$-$C_8$ alkyl, and one or more methine groups of the $C_1$-$C_6$ alkyl, when present, can be independently replaced by

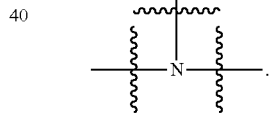

In certain embodiments, the compound of Formula XI-d, XI-e, XI-f, XI-g, XI-h, XI-i, or XI-j is a compound of Formula XI-k, XI-l, XI-m, XI-n, XI-o, XI-p, or XI-q.

XI-k

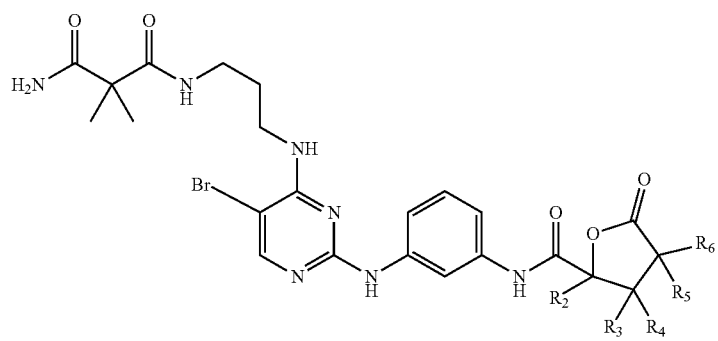

-continued
XI-l
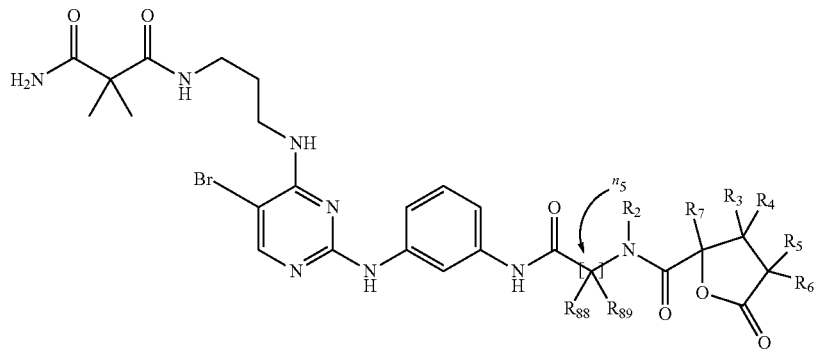
XI-m
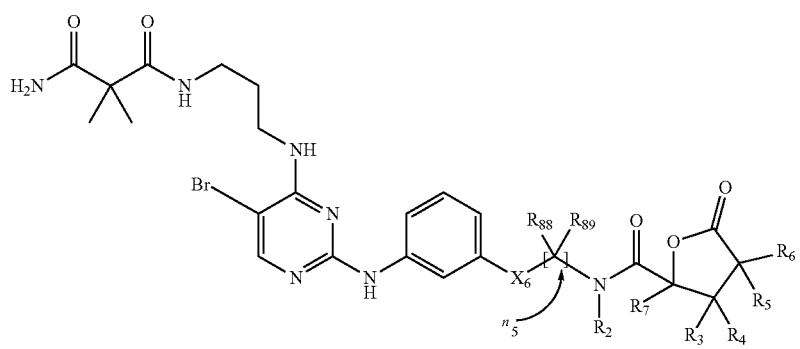
XI-n
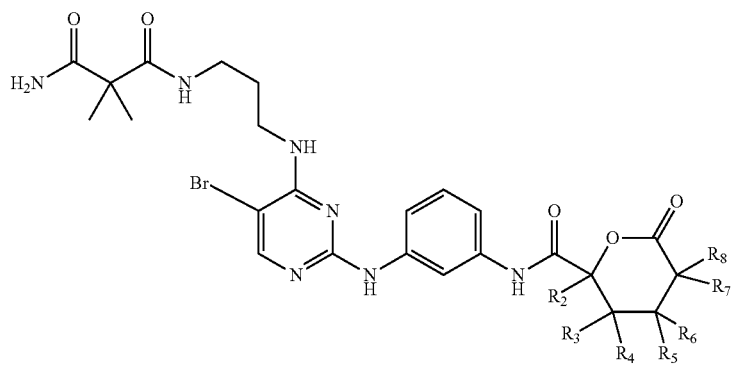
XI-o
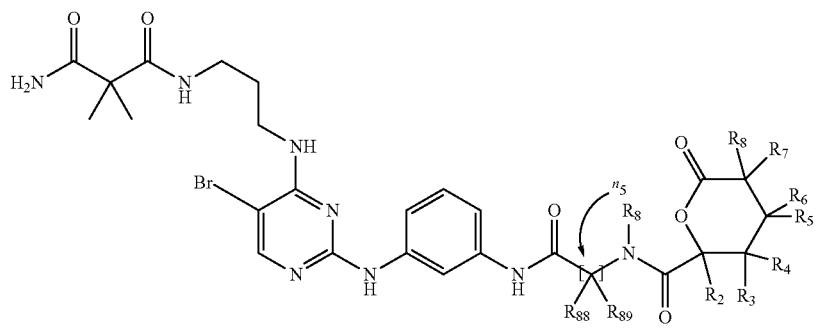

XI-p
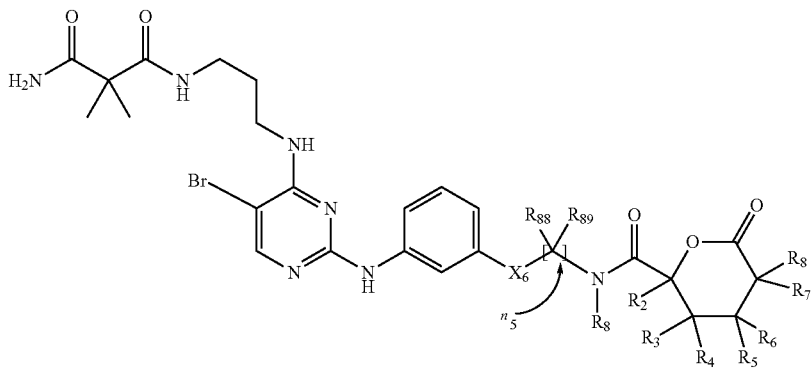
XI-q
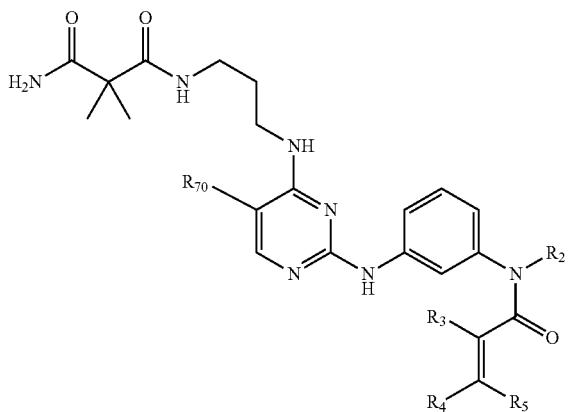
wherein $R_1$-$R_8$, $R_{70}$, $R_{88}$, and $R_{89}$ are as defined above for Formula XI-a, XI-b or XI-c;
$X_6$ is $CH_2$, NH, O, or S; and
$n_5$ is an integer from 0 to 3.
In some embodiments, the compound of Formula XI-e or XI-j is a compound of Formula XI-r, XI-s, XI-t, XI-u, XI-v, XI-w, or XI-x:
XI-r
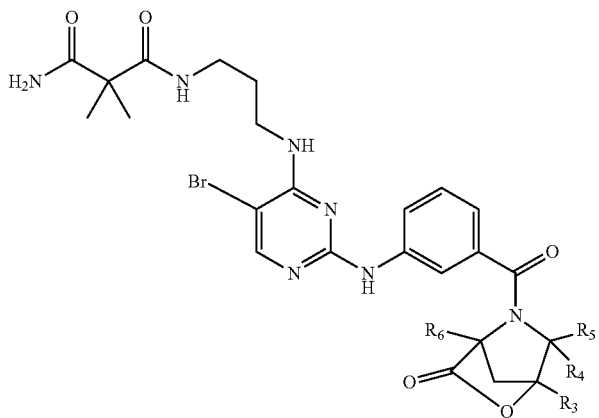

XI-s
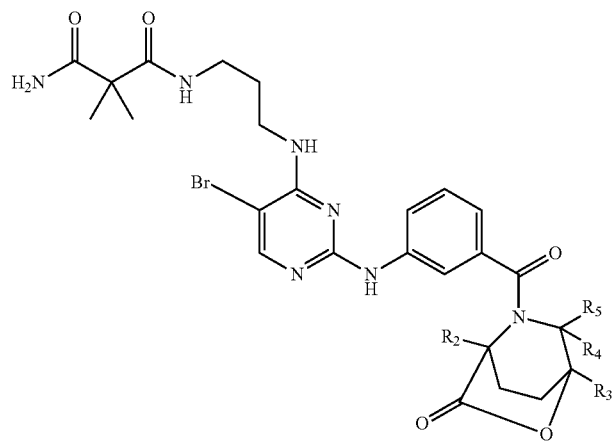
XI-t
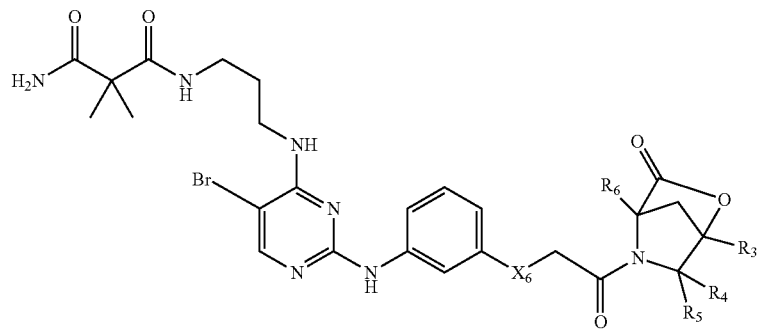
XI-u
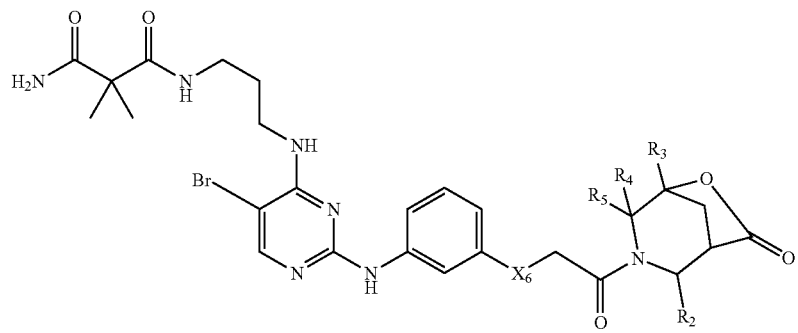
XI-v
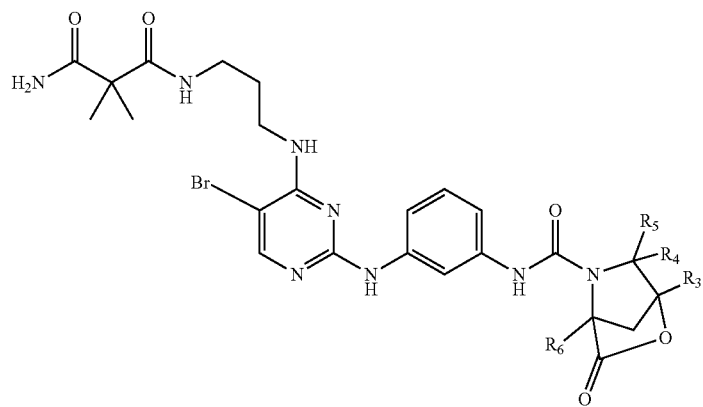

XI-w
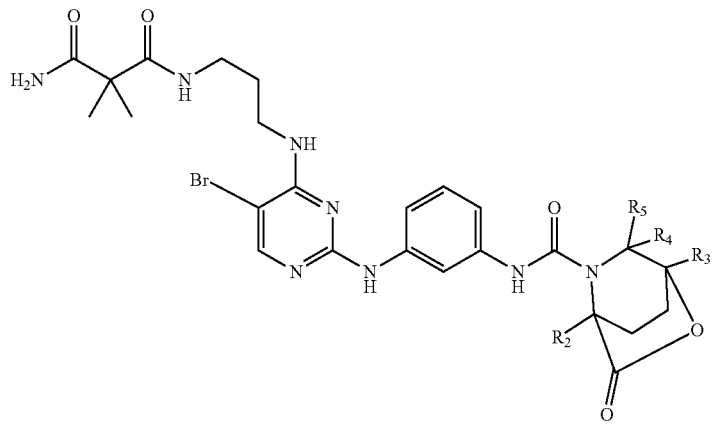
XI-x
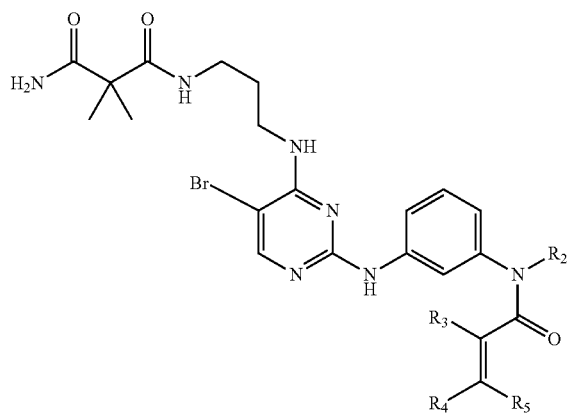
wherein $R_2$, $R_3$, $R_4$, $R_5$, and $R_6$ are as defined above for Formula XI-d, XI-e, XI-f, XI-g, XI-h, XI-i, and XI-j.
In other embodiments, the compound of Formula XI-e, XI-h, XI-i, or XI-j is a compound of Formula XI-y, XI-z, XI-aa, or XI-bb.
XI-y
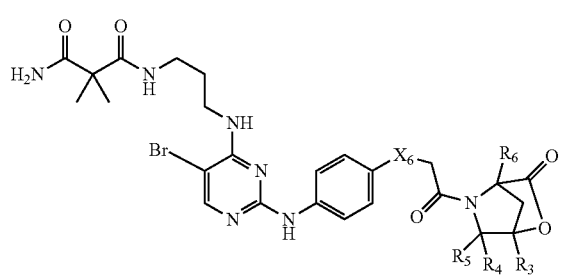
XI-z
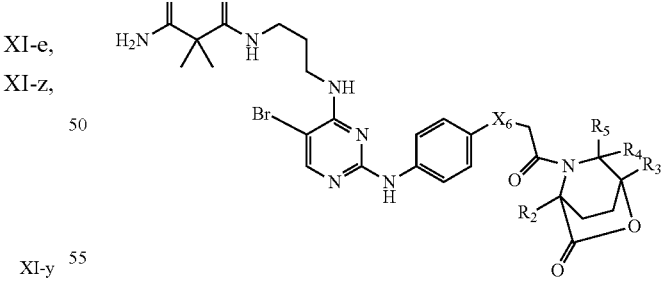
XI-aa
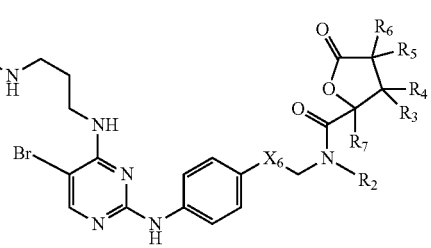

-continued

XI-bb

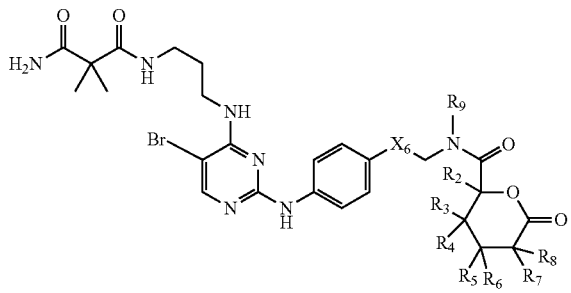

wherein $R_2$-$R_9$ are as defined above for Formula II-a above; and $X_6$ is as defined above for Formula XI-t above.

In certain embodiments, the compound of Formula XI-h or XI-i is a compound of Formula XI-cc, XI-dd, XI-ee, or XI-ff.

XI-cc

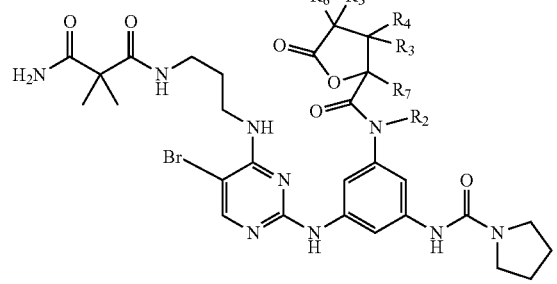

XI-dd

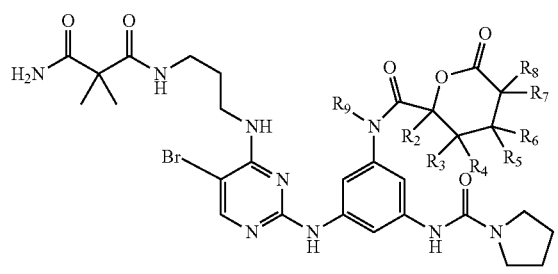

XI-ee

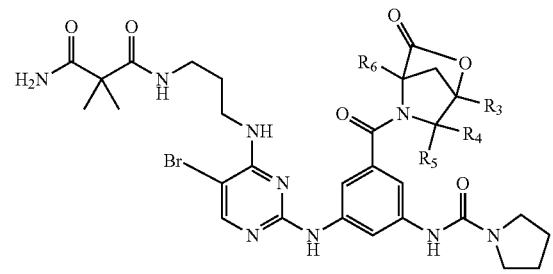

-continued

XI-ff

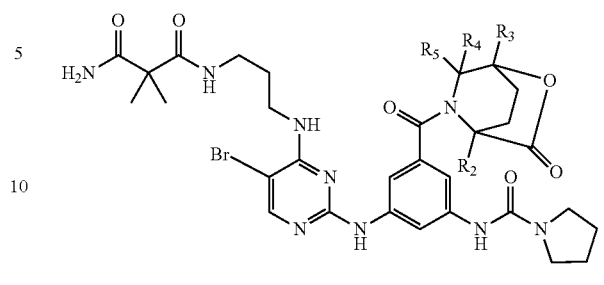

wherein $R_2$-$R_7$, $R_8$, $R_9$, are as defined above for Formula II-a.

Nonlimiting examples of compounds of the Formula XI are set forth below.

XI-1

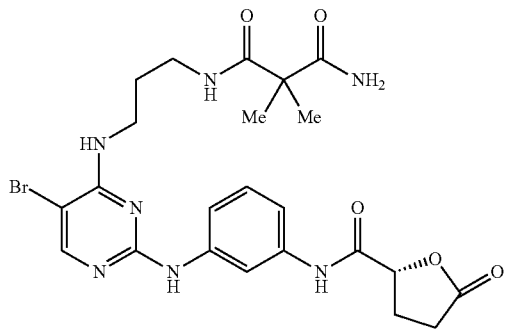

XI-2

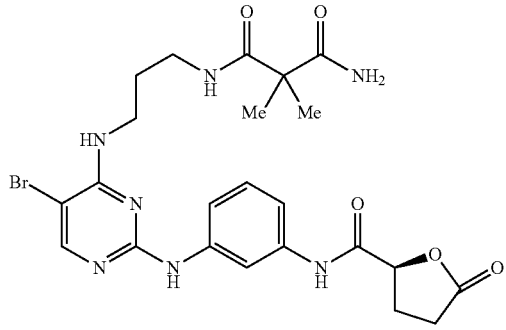

XI-3

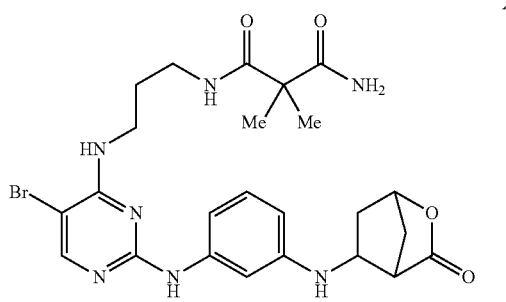

XI-4
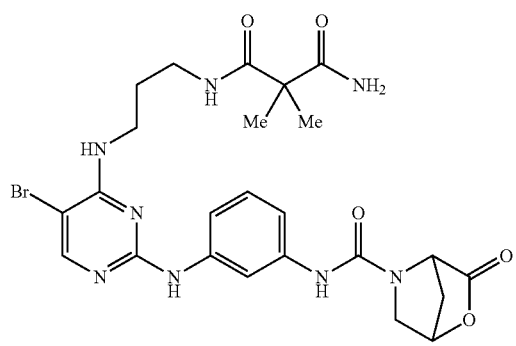
XI-5
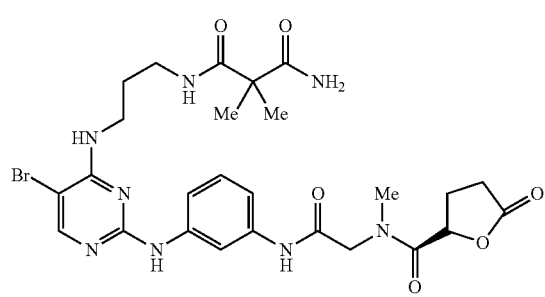
XI-6
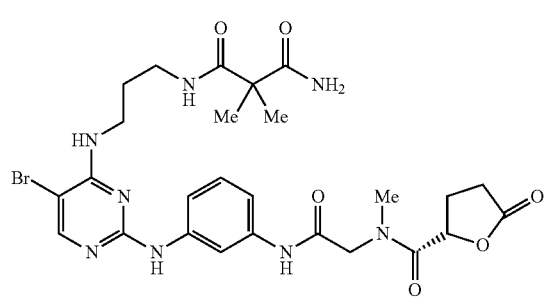
XI-7
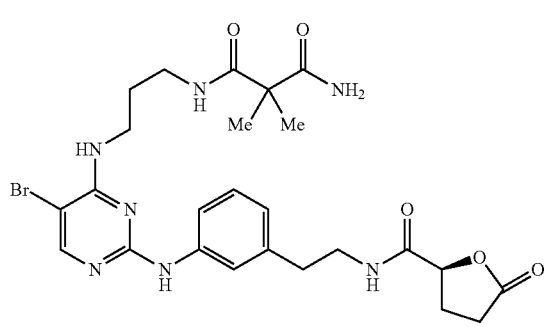
XI-8
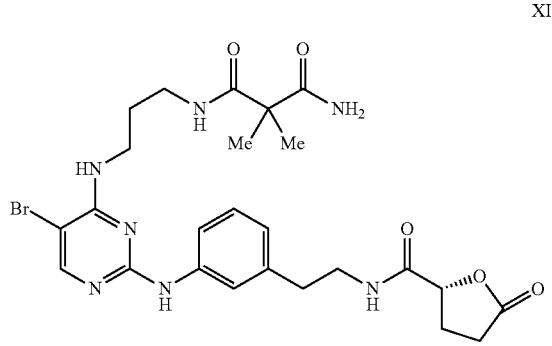
XI-9
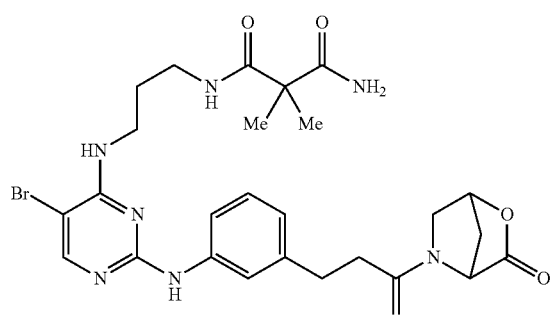
XI-10
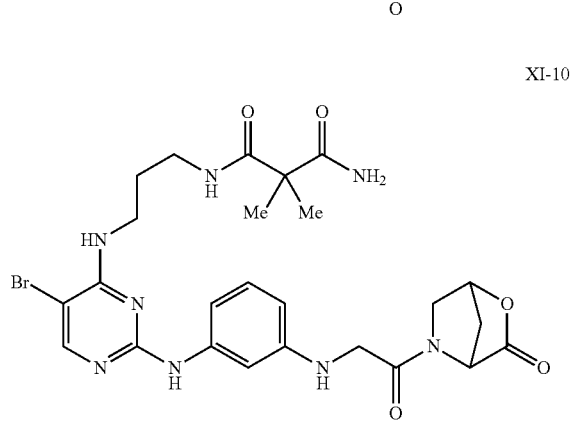
XI-11
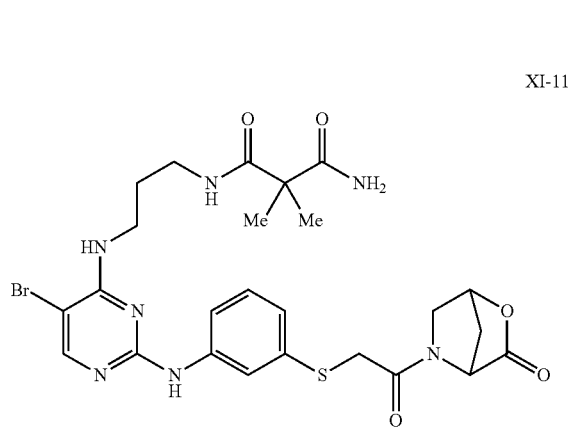
XI-12
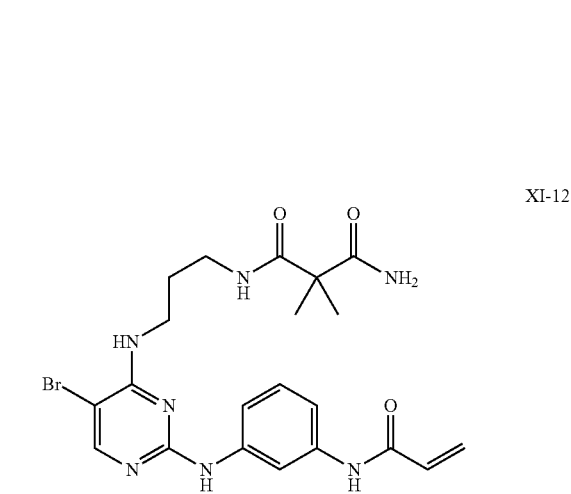

XI-13
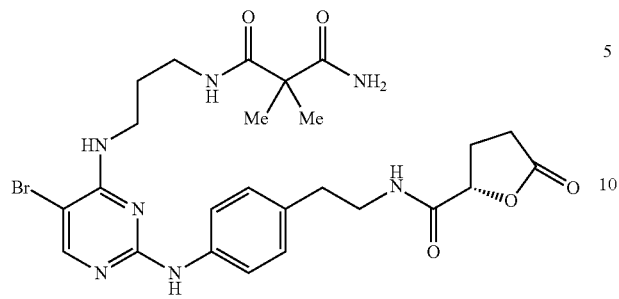
XI-14
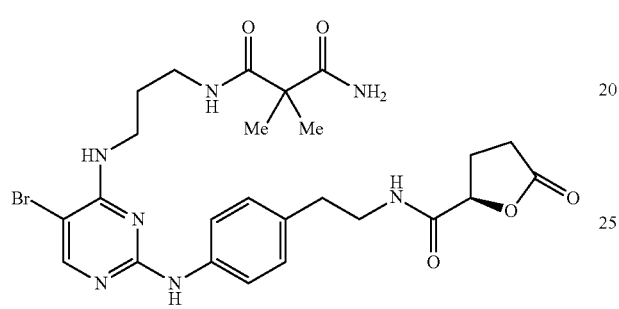
XI-15
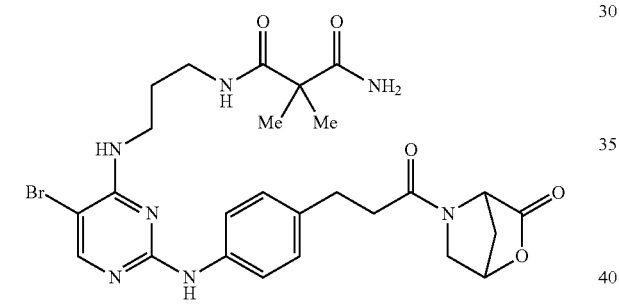
XI-16
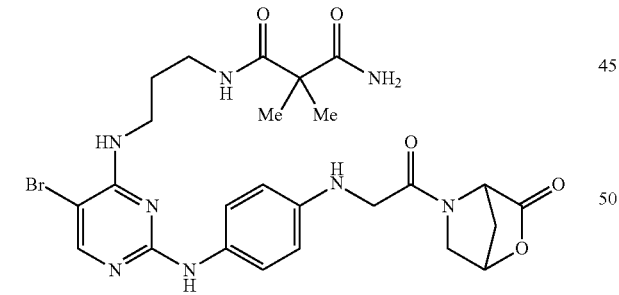
XI-17
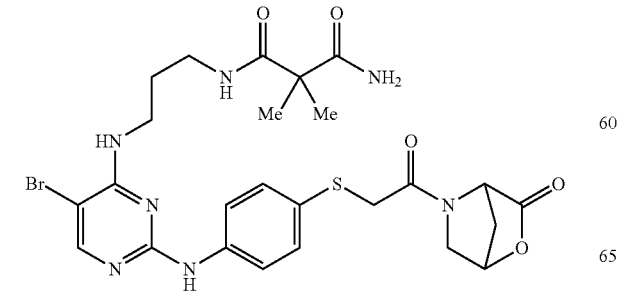
XI-18
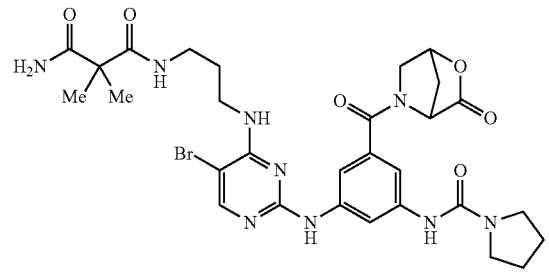
XI-19
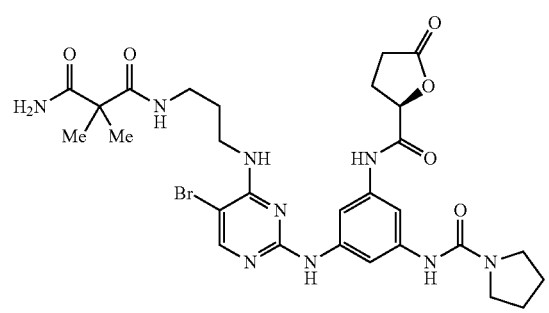
XI-20
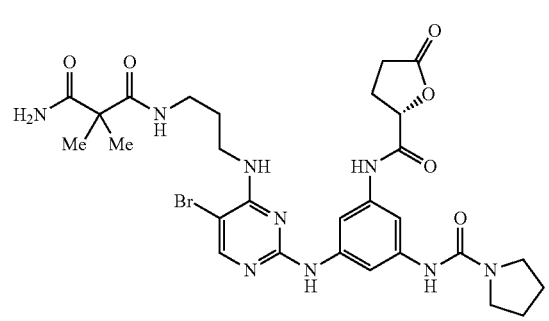
XI-21
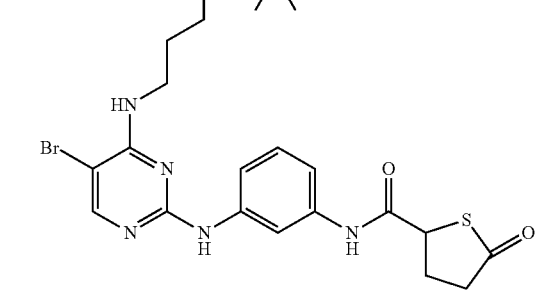

XI-22
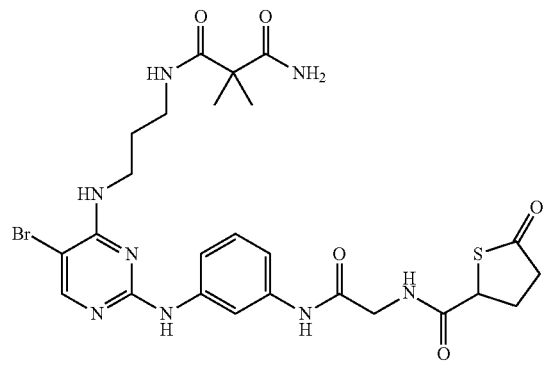
XI-23
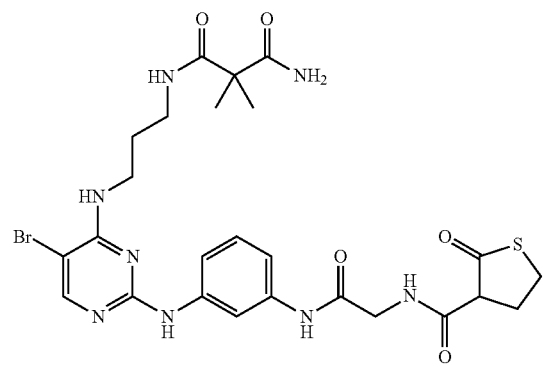
XI-24
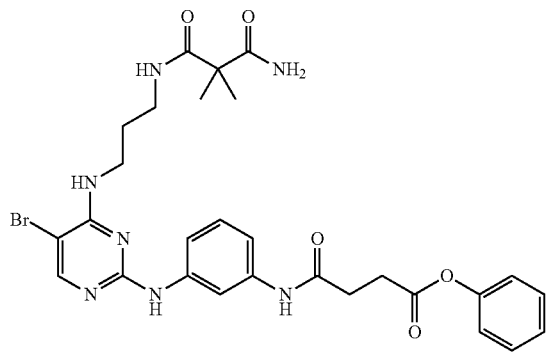
XI-25
XI-26
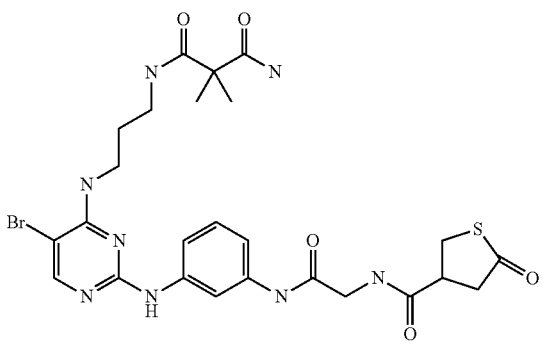
XI-27
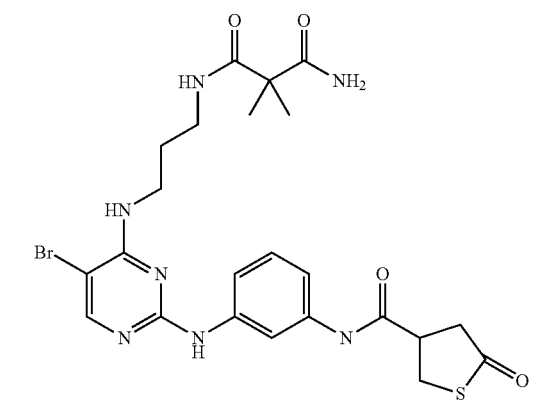
XI-28
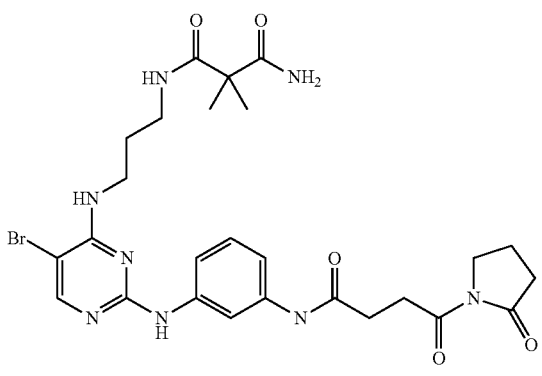
XI-29
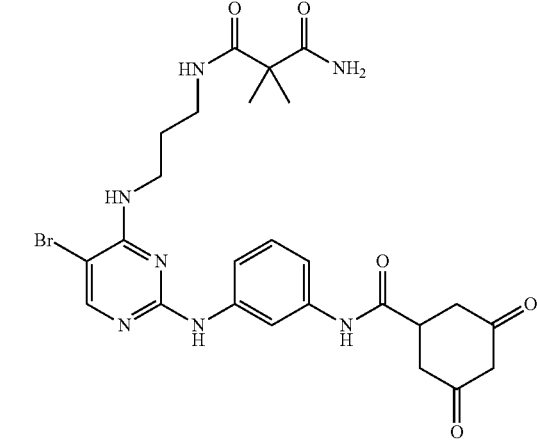

XI-30
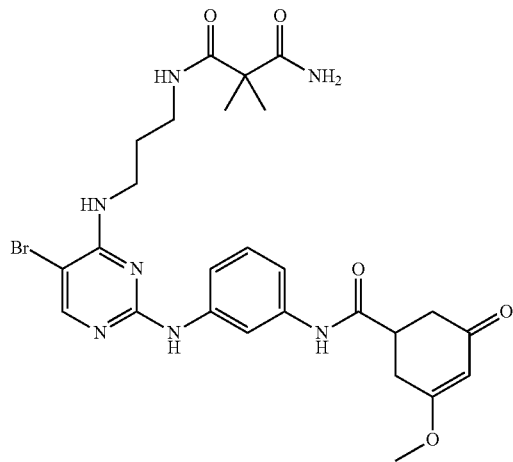
XI-33
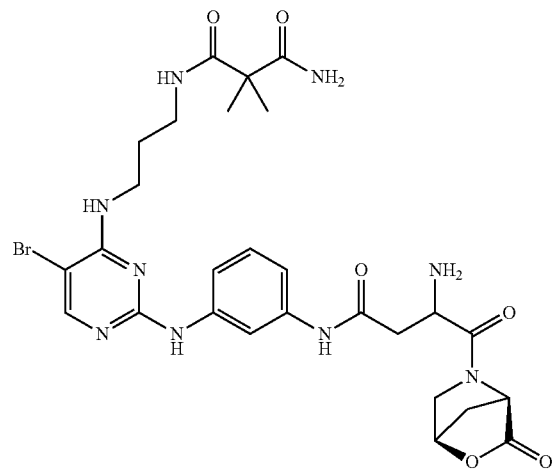
XI-31
XI-34
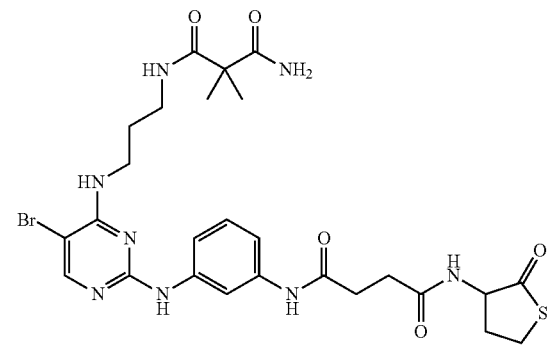
XI-35
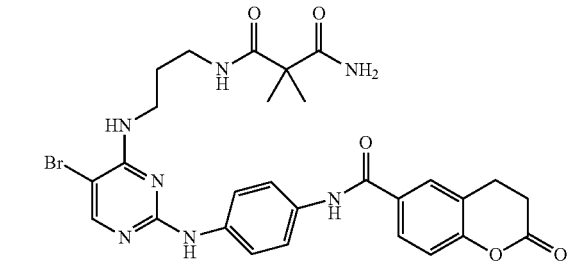
XI-32
XI-36
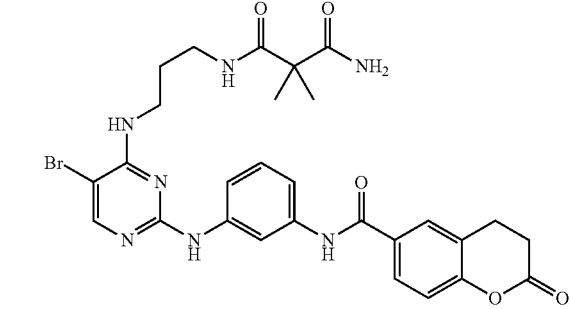

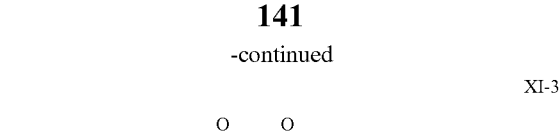
XI-37
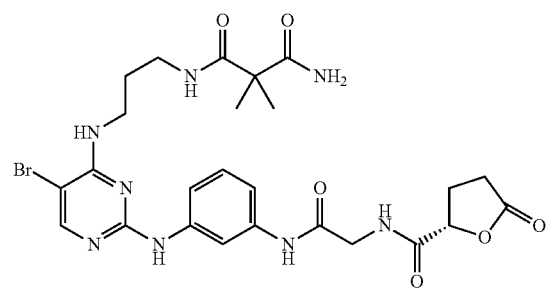
XI-38
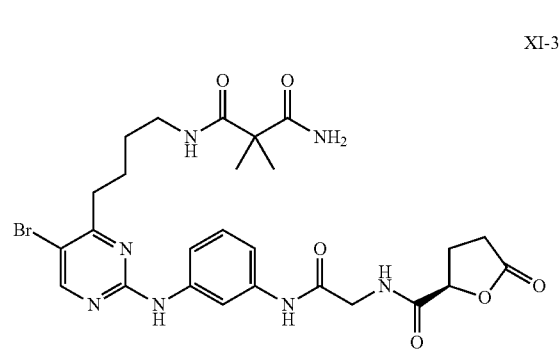
XI-39
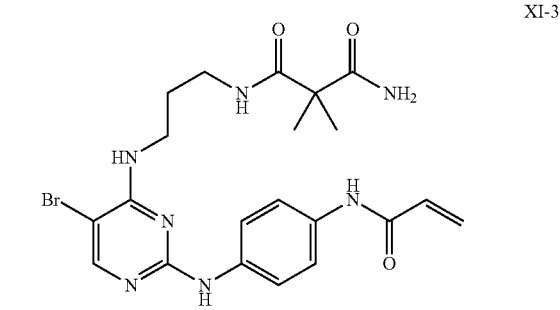
XI-40
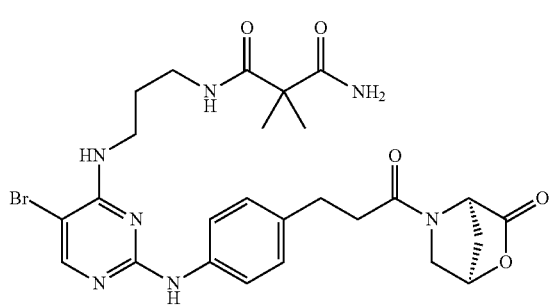
XI-41
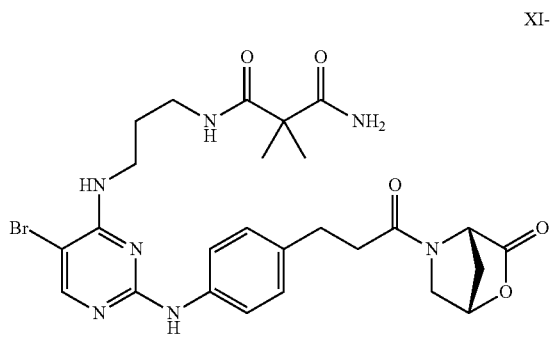
XI-42
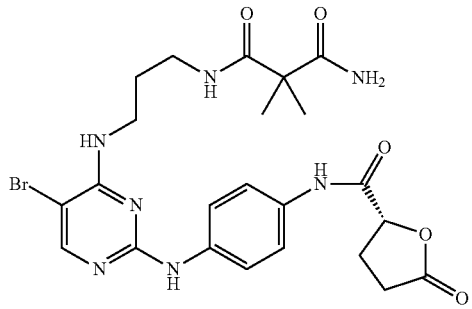
XI-43
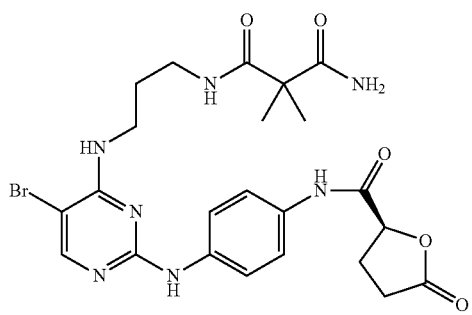
XI-44
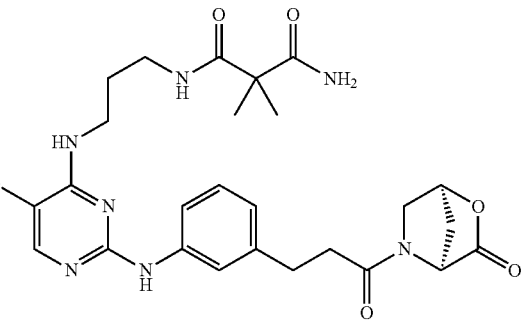
XI-45
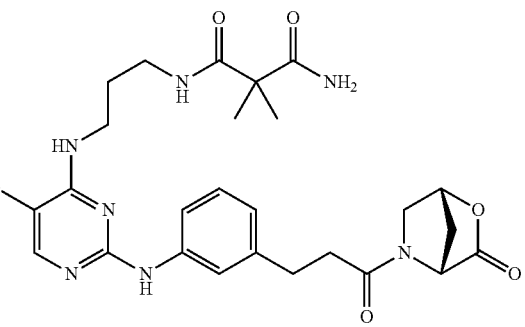

XI-46
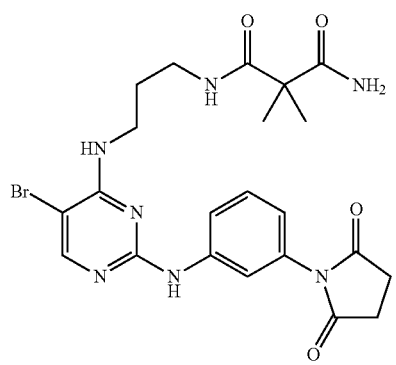
XI-47
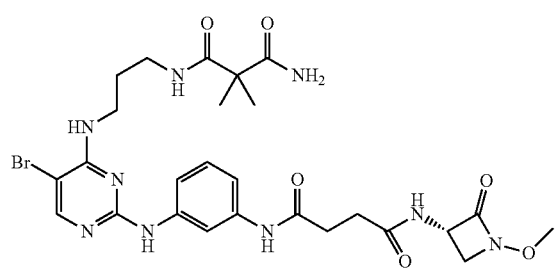
XI-48
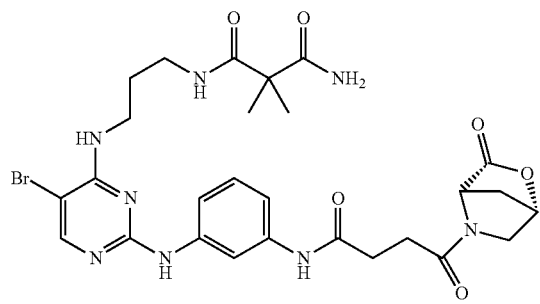
XI-49
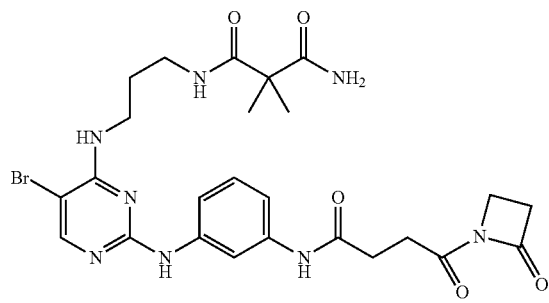
XI-50
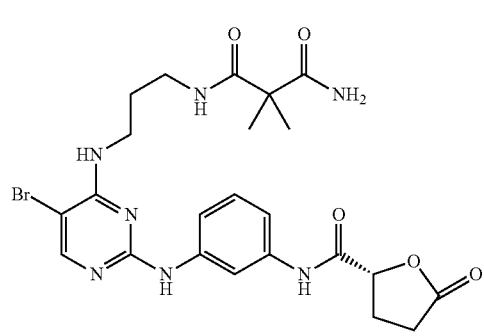
XI-51
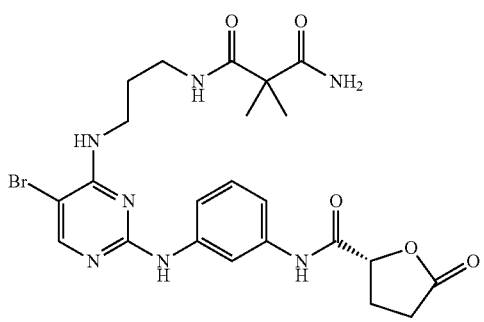
XI-52
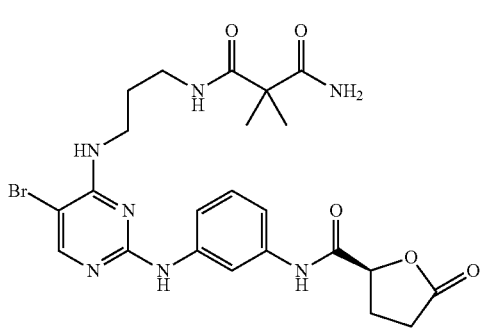
XI-53
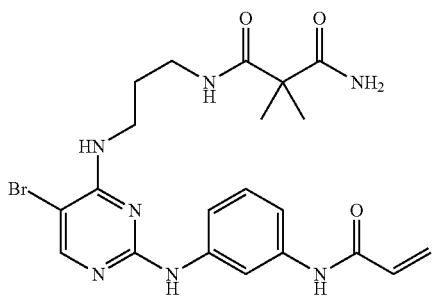
XI-55
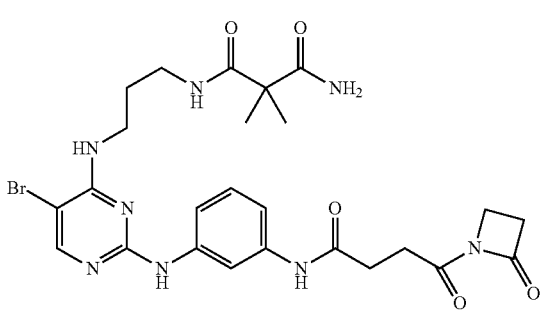

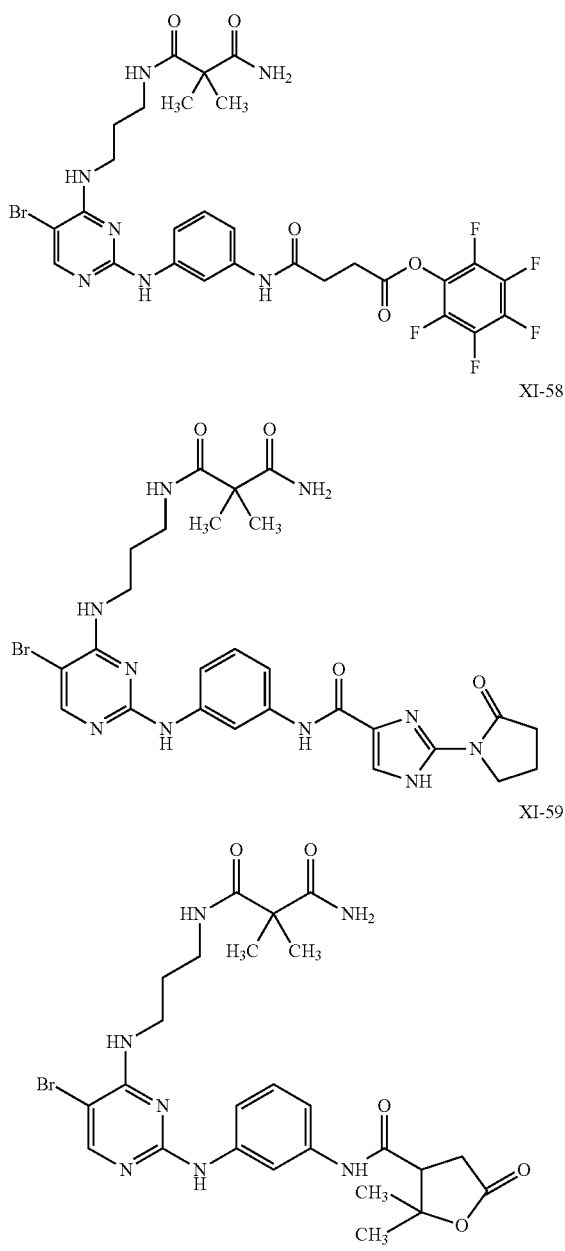

XI-57

XI-58

XI-59

2. Compounds of Formula XII

In some embodiments, compounds of Formula I are described by compounds of Formula XII:

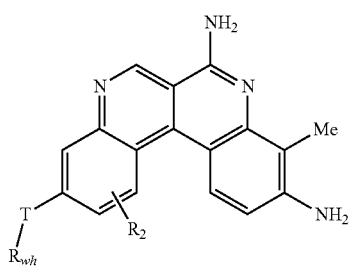

XII wherein T and $R_{wh}$ are Tether and Warhead, respectively, and are as defined above in the embodiments of Formula I; and $R_1$ and $R_2$ are each independently hydrogen or $C_1$-$C_8$ alkyl; wherein one or more methylene groups of the $C_1$-$C_6$ alkyl can be replaced by —$NR_1$—, —O—, —C(O)—, —S—, —SO—, —$SO_2$—, or —C(=S)—; one or more methine groups of the $C_1$-$C_6$ alkyl, when present, can be independently replaced by

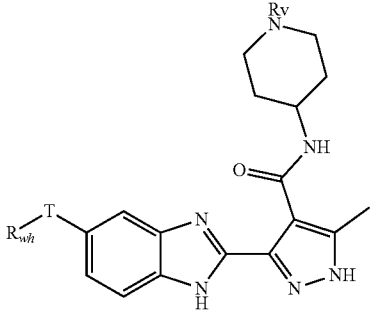

1. Compounds of Formula XXXVI

In some embodiments, compounds of Formula I are described by compounds of Formula XXXVI:

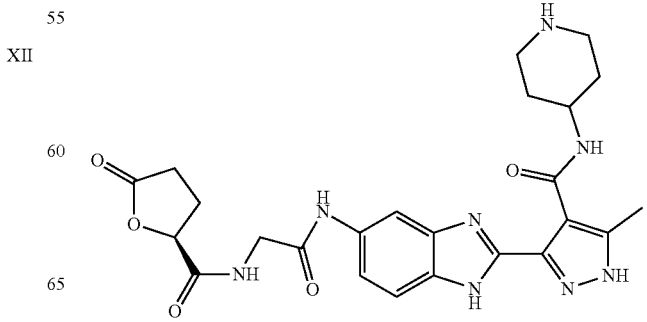

XXXVI wherein

Rv is H, optionally substituted $C_1$-$C_3$ branched or straight chain alkyl, or optionally substituted $C_1$-$C_3$ branched or straight chain acyl; and T and $R_{wh}$ are Tether and Warhead, respectively, and are as defined above in the embodiments of Formula I.

Nonlimiting examples of compounds of the Formula XXXVI are set forth below:

XXXVI-1

-continued

XXXVI-2

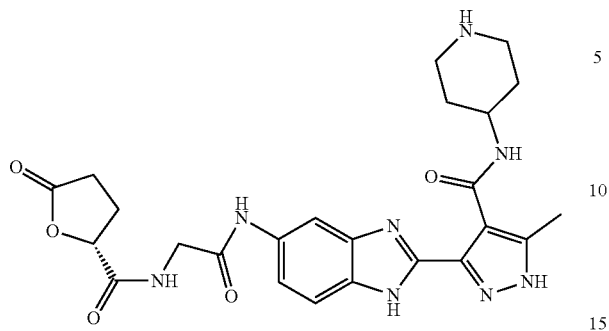

C. HCV Protease

1. Compounds of Formula I Based on Compounds of Formula XVI-a, XVI-b, and XVI-c

In other embodiments, compounds of Formula I are described wherein Scaffold is a radical resulting from the removal of a hydrogen of a compound of Formula XVI-a, XVI-b, or XVI-c:

XVI-a

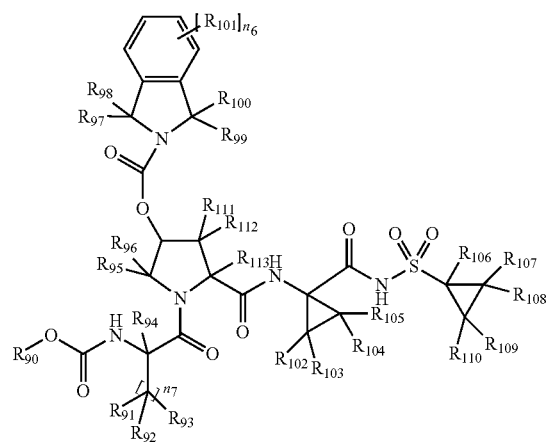

XVI-b

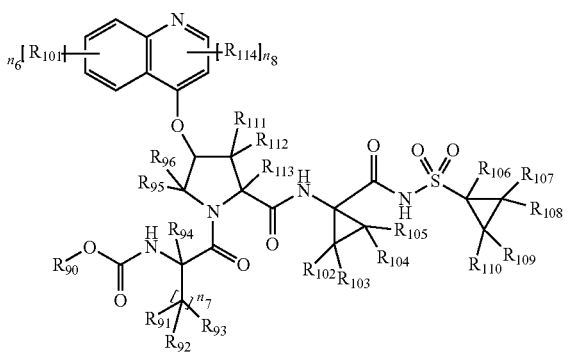

-continued

XVI-c

wherein $R_{90}$, $R_{91}$, $R_{92}$, $R_{93}$, $R_{94}$, $R_{95}$, $R_{96}$, $R_{97}$, $R_{98}$, $R_{99}$, $R_{100}$, $R_{102}$, $R_{104}$, $R_{105}$, $R_{106}$, $R_{107}$, $R_{108}$, $R_{109}$, $R_{110}$, $R_{111}$, $R_{112}$, $R_{113}$, and $R_{114}$ are each independently hydrogen or $C_1$-$C_6$ alkyl; wherein one or more methylene groups of $C_1$-$C_6$ alkyl can be optionally replaced by —$NR_1$—, —O—, —C(O)—, —S—, —SO—, —SO$_2$—, or —C(=S)—;

$R_{103}$ is hydrogen, $C_1$-$C_6$ alkyl, or $C_2$-$C_8$ alkenyl;

one or more methine groups of the $C_1$-$C_6$ alkyl, when present, can be independently replaced by

[structure]

$R_1$ is hydrogen or $C_1$-$C_8$ alkyl;

each $R_{101}$ is independently hydrogen, $C_1$-$C_6$ alkyl, $C_2$-$C_8$ alkenyl, halogen, amino, nitro, optionally substituted aryl or heteroaryl;

$n_6$ and $n_7$ are each independently integer from 0 to 4; $n_8$ is an integer from 0 to 2; and Warhead is a radical resulting from the removal of a hydrogen of a compound of Formula I-b, I-c, I-e, I-j, I-k, I-l, I-n, or I-o;

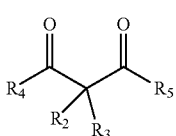

I-b

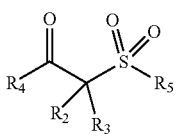

I-c

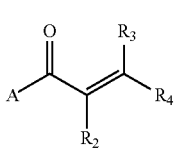

I-e

-continued

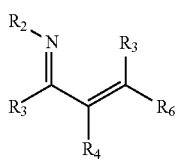

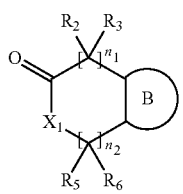

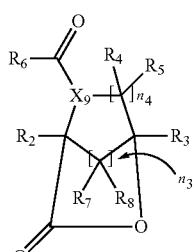

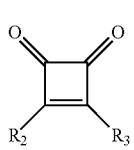

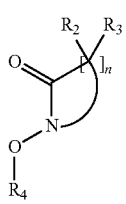

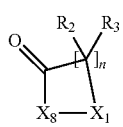

wherein
each $X_1$ and $X_8$ is independently —O—, or —$NR_6$—;
each $X_9$ is independently

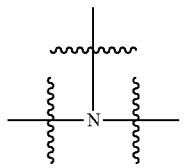

each $R_2$, $R_3$, $R_4$, $R_5$, $R_6$, $R_7$, and $R_8$ is independently hydrogen or $C_1$-$C_6$ alkyl; wherein one or more methylene groups of the $C_1$-$C_6$ alkyl can be replaced by —$NR_1$—, —O—, —C(O)—, —S—, —SO—, —$SO_2$—, or —C(=S)—;
one or more methine groups of the $C_1$-$C_6$ alkyl, when present, can be independently replaced by I-i

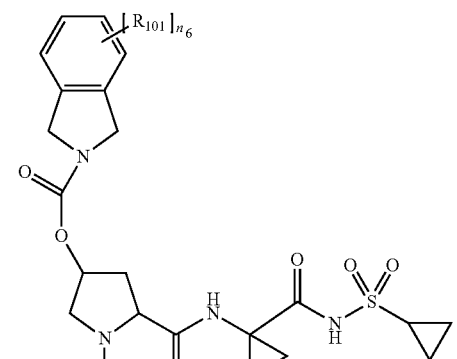

I-j optionally when proper any two of $R_2$, $R_3$, $R_4$, $R_5$, $R_6$, $R_7$, and $R_8$ when taken together form a 3- to 8-membered carbocyclic or heterocyclic ring or an aryl or heteroaryl group;
A and B are each independently an optionally substituted monocyclic, bicyclic, or tricyclic aryl or heteroaryl;
n is an integer from 2-4;

I-k each $n_1$ and $n_2$ are independently an integer from 0-2;
$n_3$ is an integer from 1-2;
$n_4$ is an integer from 1-3;
T is Tether and is null, a bond, or a bivalent $C_1$-$C_{15}$ saturated, unsaturated, straight, branched, cyclic, bicyclic, tricyclic alkyl, alkenyl, alkynyl; bridged bicyclic, heterocycle, heteroaryl, or aryl moiety; wherein optionally one or more methylene units of the hydrocarbon chain are independently replaced by —$NR_1$—, —O—, —C(O)—, —S—, —SO—, —$SO_2$—, —C(=S)—, or C(=$NR_1$)—; optionally, one or more hydrogens are independently replaced by heteroatoms, and optionally, one or more methine groups of the $C_1$-$C_{15}$ alkyl, when present, are independently replaced by I-l I-n and I-o $R_1$ is hydrogen or $C_1$-$C_8$ alkyl.
In some embodiments, the compound of Formula I is a compound of Formula XVI-d, XVI-e, or XVI-f:

XVI-d

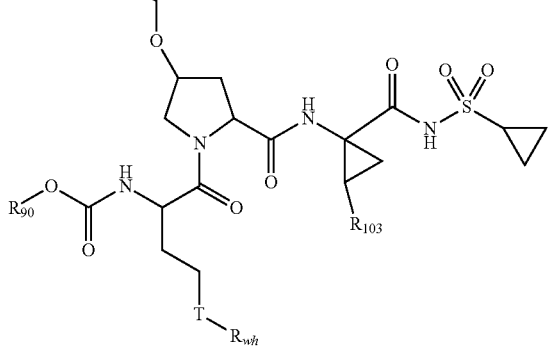

-continued
XVI-e
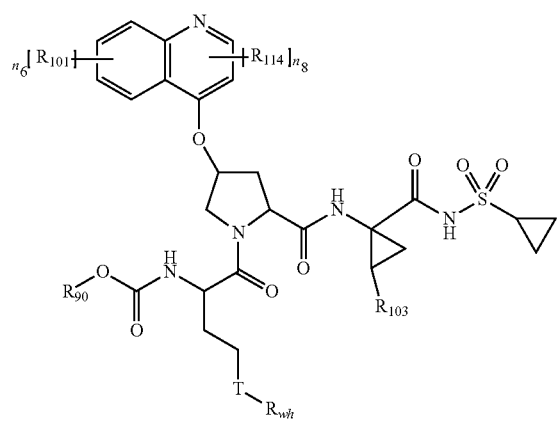
XVI-g
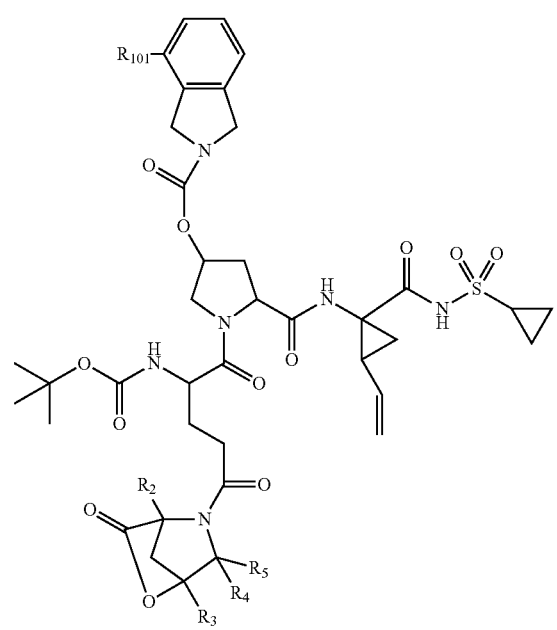
XVI-f
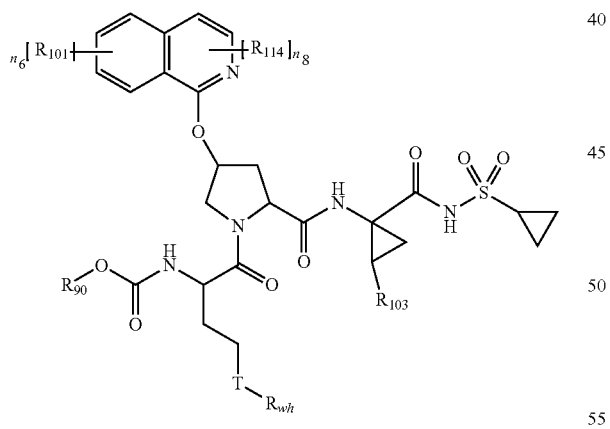
wherein
$R_{90}$, $R_{101}$, $R_{114}$, $n_6$, $n_8$, T and $R_{wh}$ are as defined above for Formula XV-a; and
$R_{103}$ is hydrogen or $C_2$-$C_8$ alkenyl.
In certain embodiments, the compound of Formulas XVI-d, XVI-e, or XVI-f is a compound of Formula XVI-g, XVI-h, or XVI-i:
XVI-h
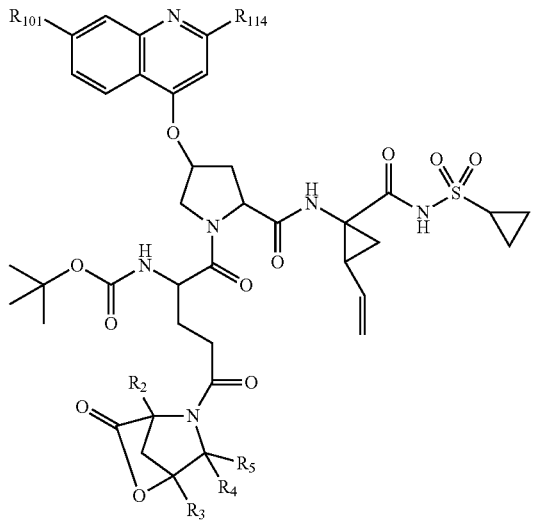

XVI-i
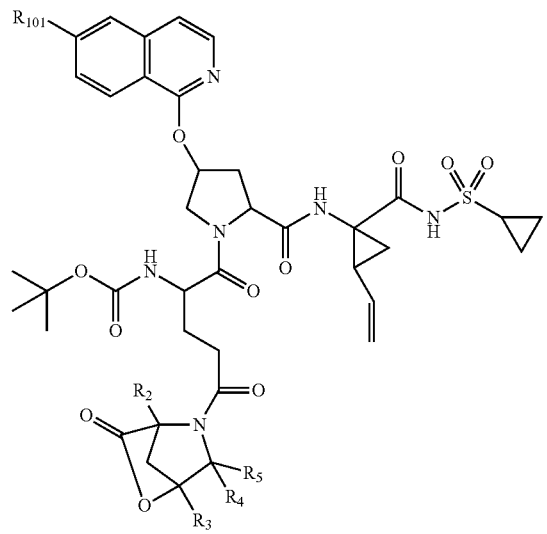
wherein, $R_2$, $R_3$, $R_4$, $R_5$, $R_{101}$, $R_{114}$ are as defined above for Formulas XVI-a.
Non-limiting examples of compounds of Formula XVI-a, Formula XVI-b, and Formula XVI-c are as set forth below.
XVI-2
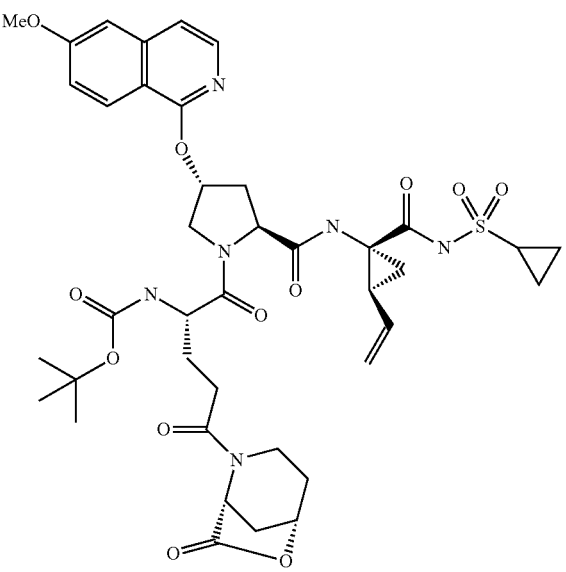
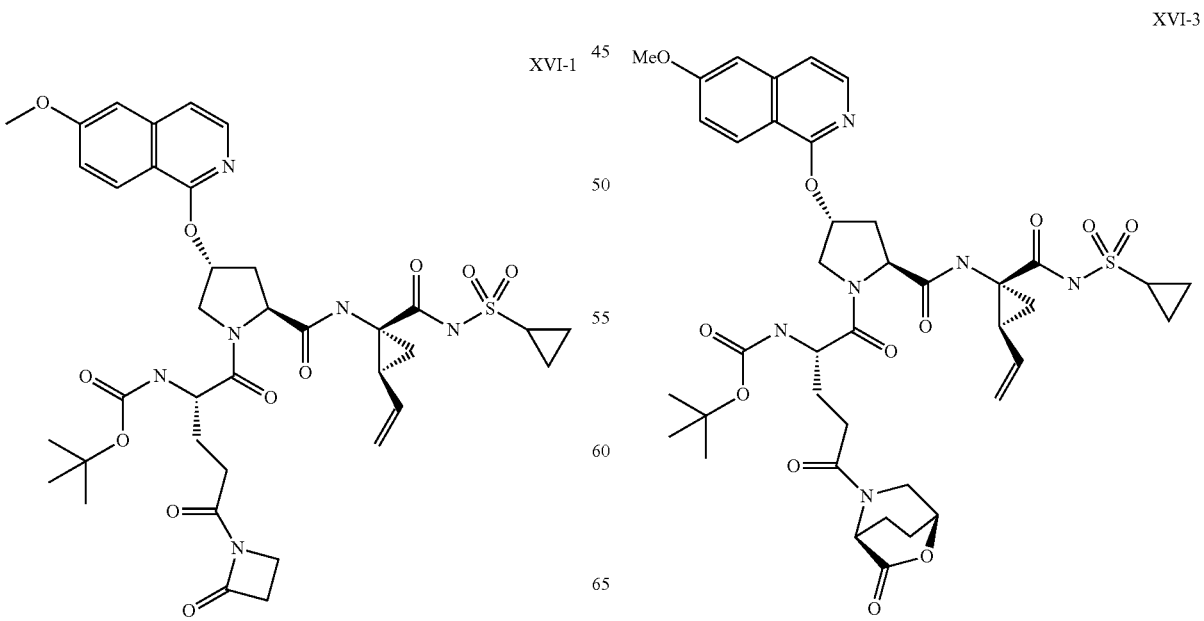
XVI-1
XVI-3

XVI-4
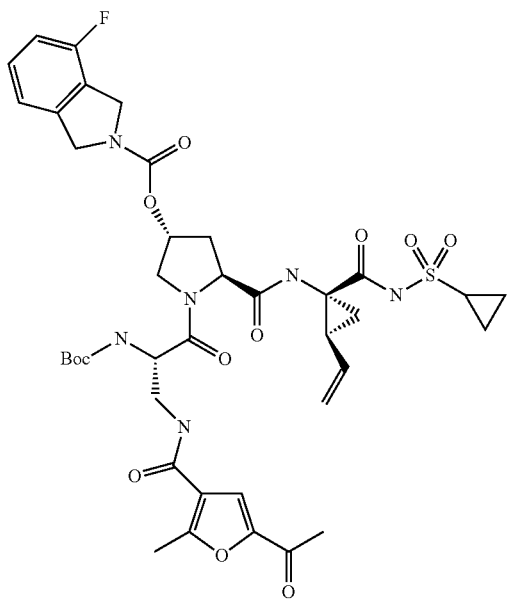
XVI-6
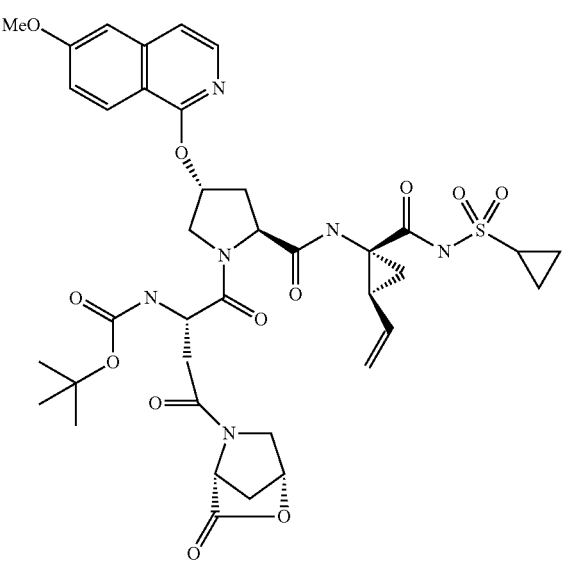
XVI-5
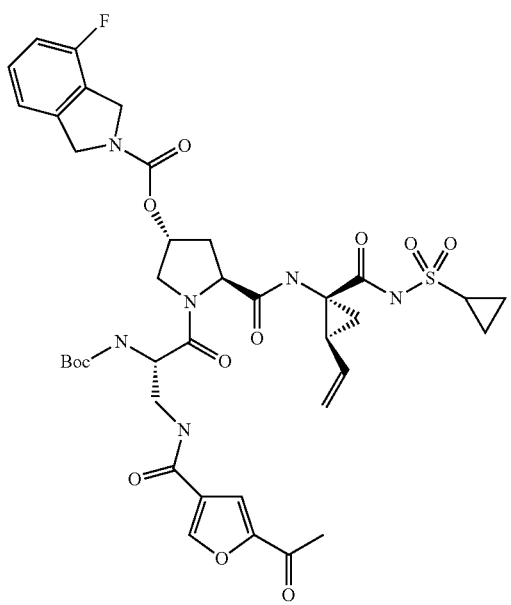
XVI-7
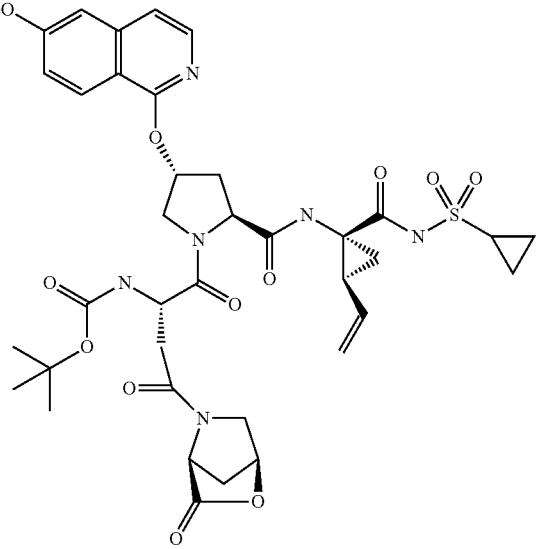

-continued
XVI-8
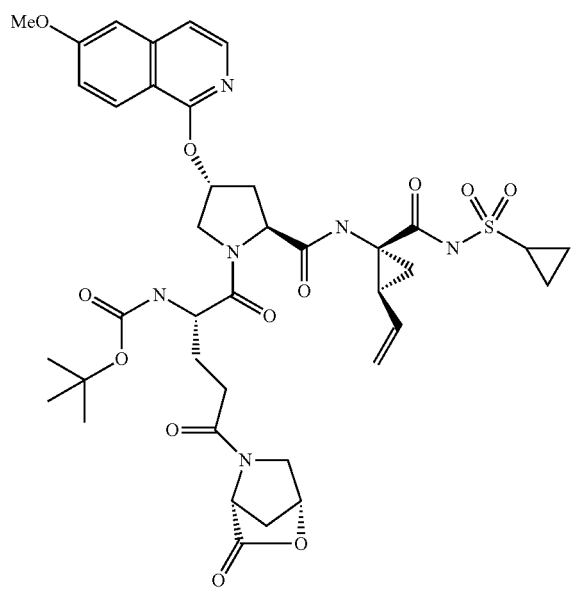
XVI-10
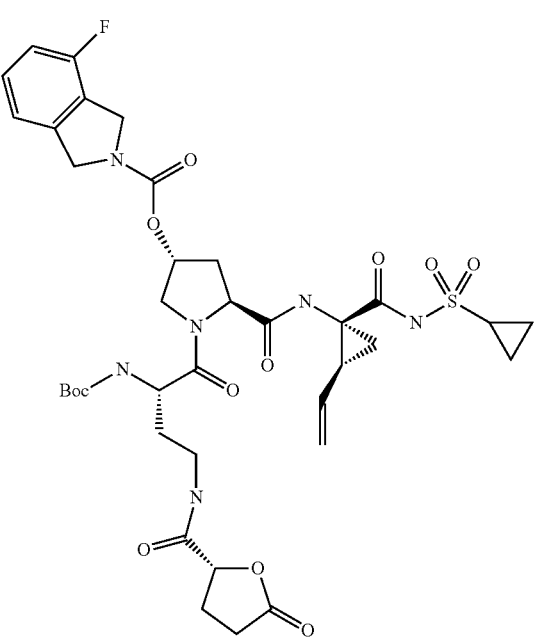
XVI-9
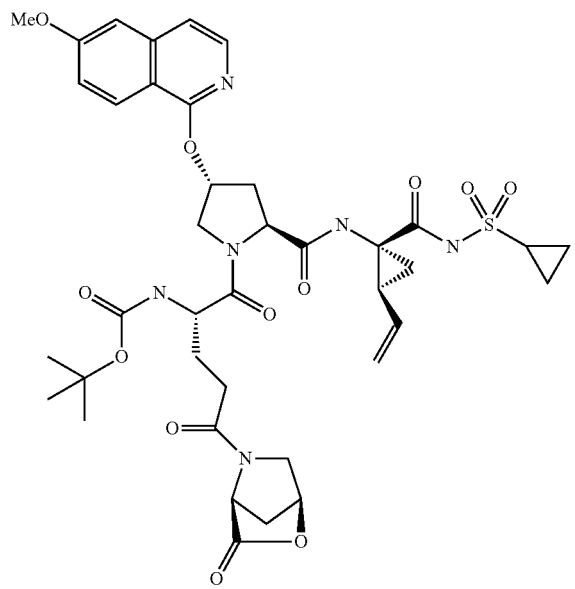
XVI-11
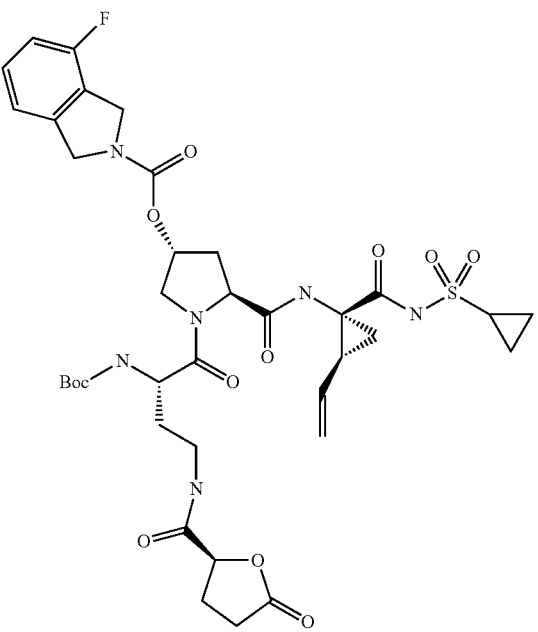

XVI-12
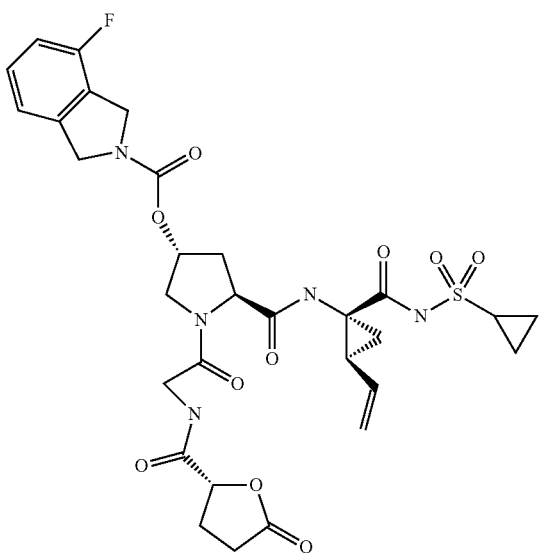
XVI-14
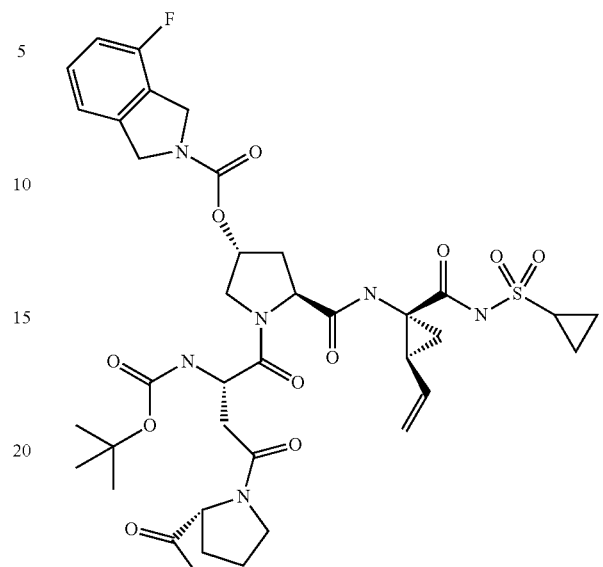
XVI-13
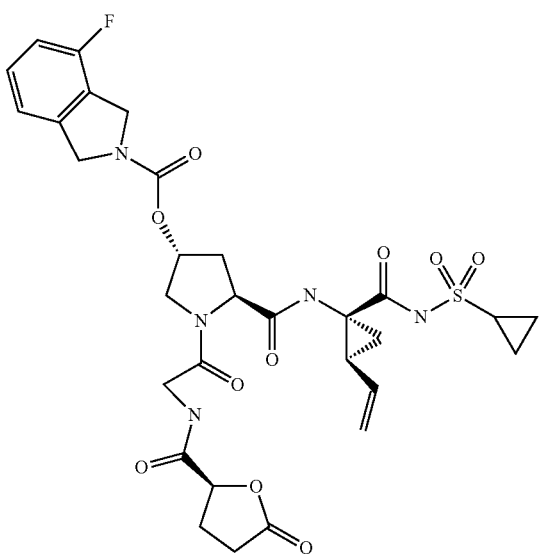
XVI-15
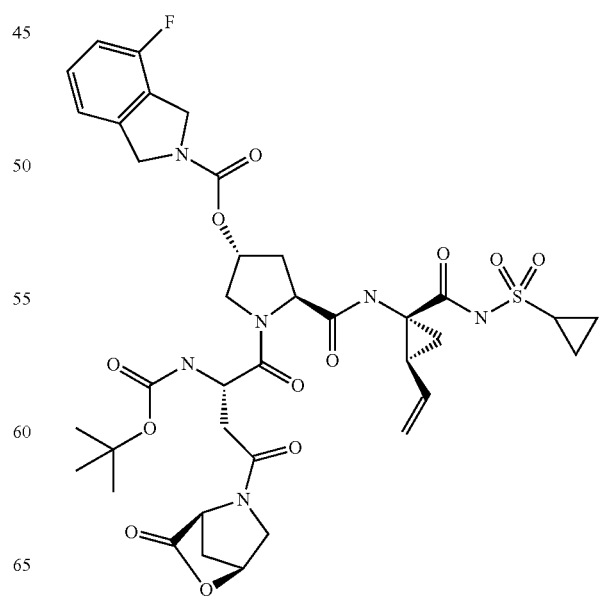

161
-continued
XVI-16
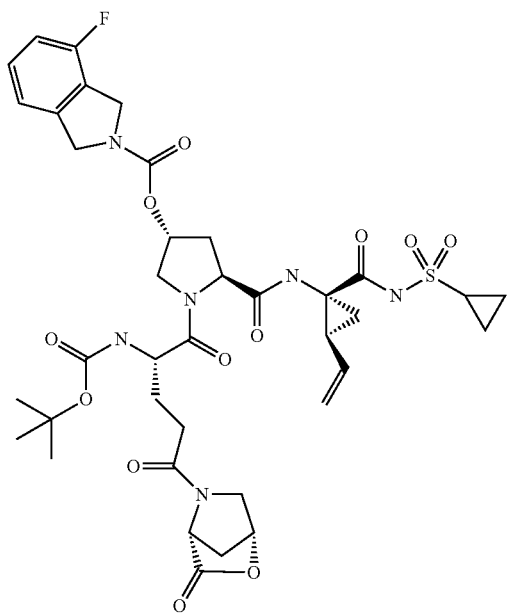
XVI-17
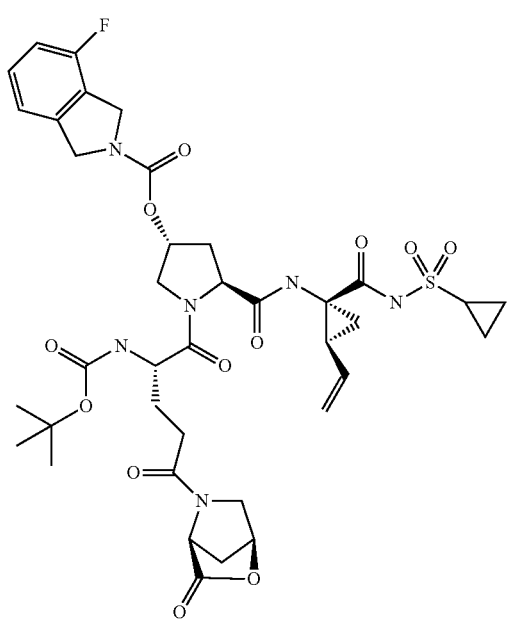
162
-continued
XVI-18
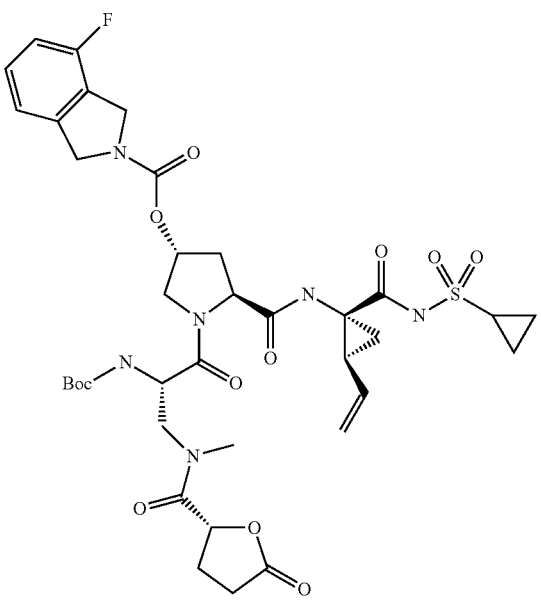
XVI-19
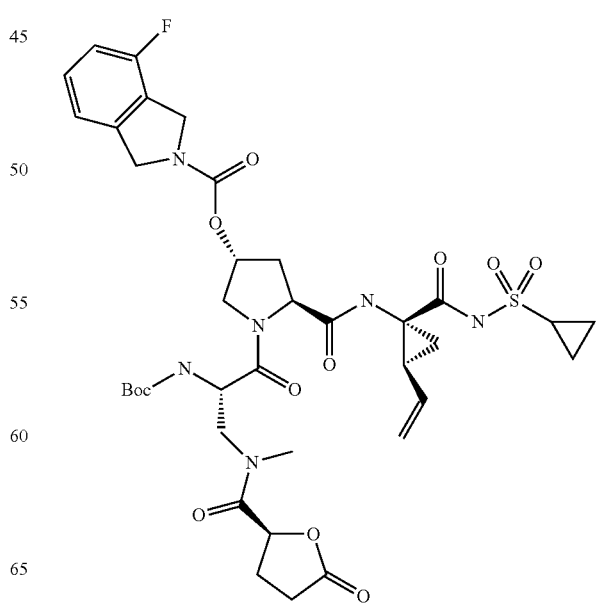

-continued
XVI-20
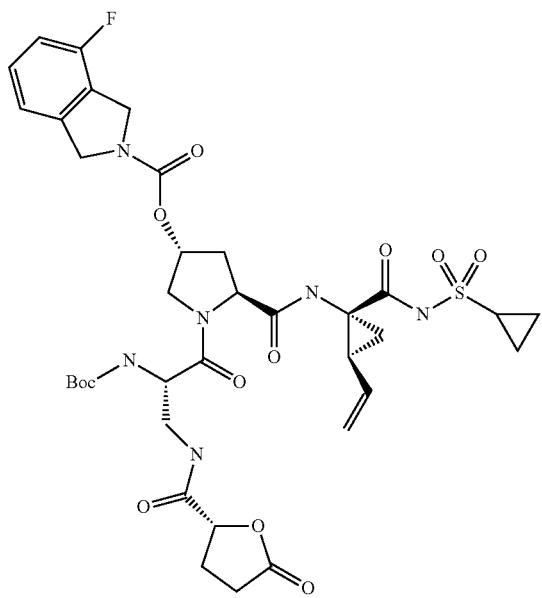
XVI-21
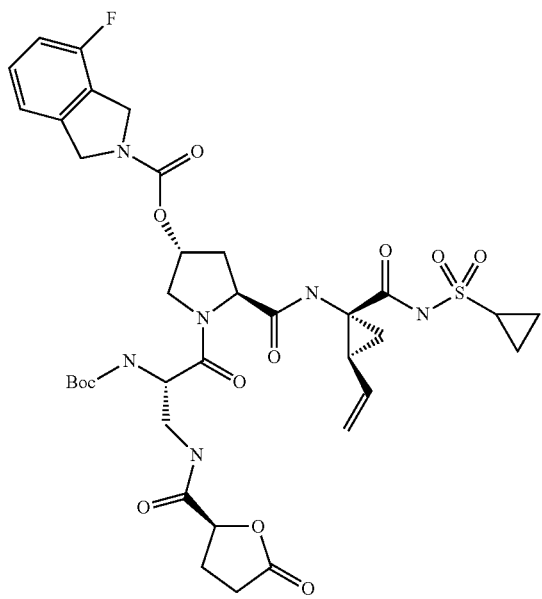
-continued
XVI-22
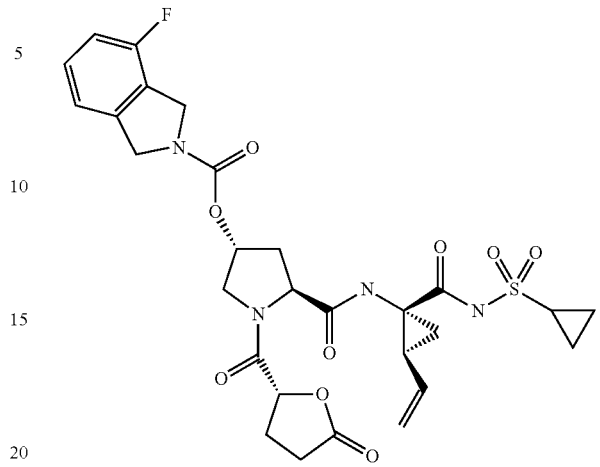
XVI-23
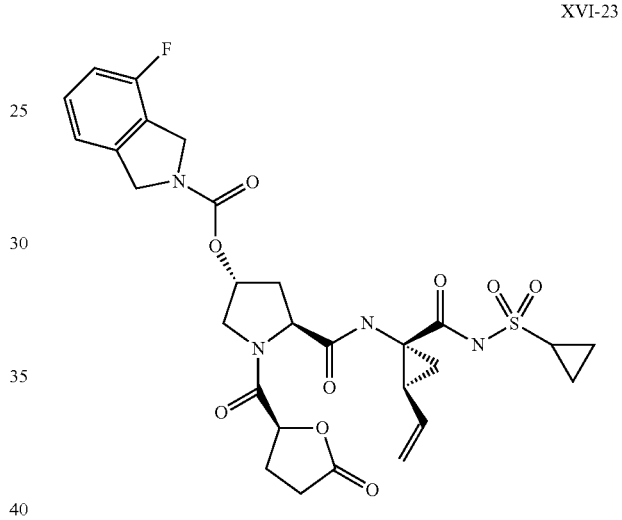
XVI-24
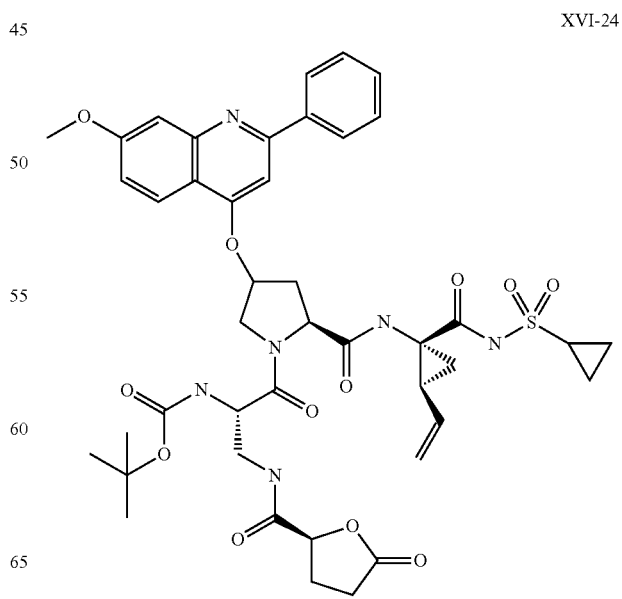

-continued

XVI-25

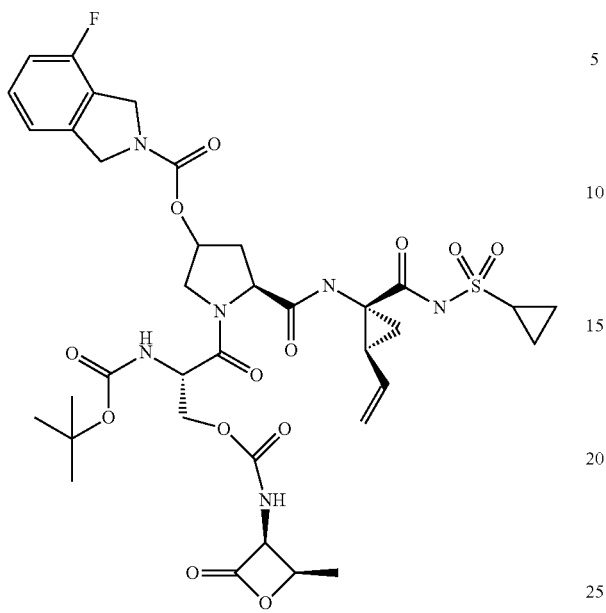

XVI-26

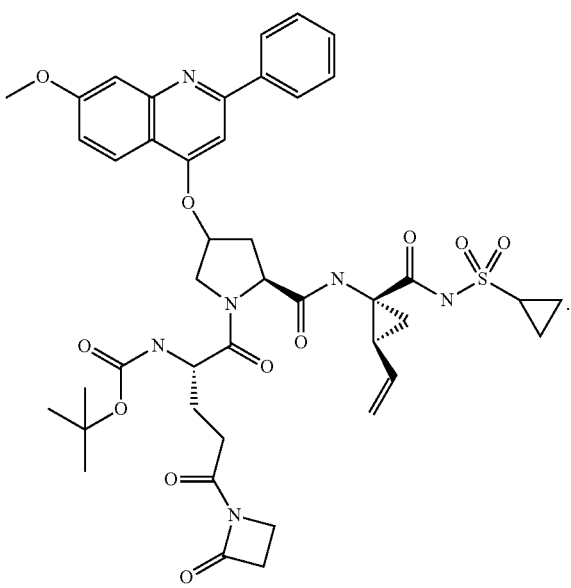

D. PI3Kβ and PI3Kγ Protein Scaffolds

1. COMPOUNDS OF FORMULA XXII-a, FORMULA XXII-b, OR FORMULA XXII-c

In some embodiments, the compound of Formula I is a compound of Formula XXII-a, Formula XXII-b, or Formula XXII-c:

XXII-a

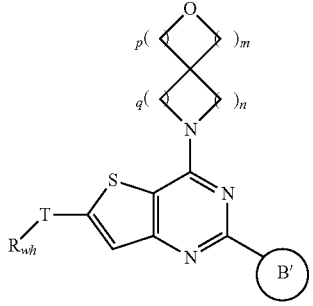

XXII-b

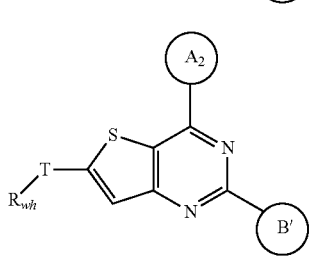

XXII-c

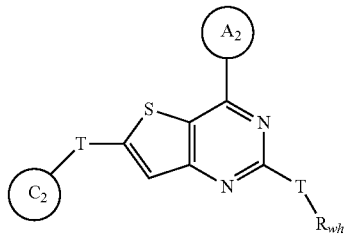

wherein
n, m, p, and q for Formula XXII-a and Formula XXII-b are each independently 0, 1, 2, 3; provided that
n and q are not 0 at the same time, and
m and q are not 0 at the same time;
T and $R_{wh}$ are as defined for Formula I and each T can be the same or different;
$A^2$ is an optionally substituted ring selected from a 4-8 membered saturated or partially unsaturated heterocyclic ring having one or two heteroatoms independently selected from nitrogen, oxygen, or sulfur, or a 5-10 membered saturated or partially unsaturated bridged bicyclic heterocyclic ring having at least one nitrogen, at least one oxygen, and optionally 1-2 additional heteroatoms independently selected from nitrogen, oxygen, or sulfur;
B' is an optionally substituted group selected from phenyl, an 8- to 10-membered bicyclic aryl ring, a 5- to 6-membered heteroaryl ring having 1-4 heteroatoms independently selected from nitrogen, oxygen, or sulfur, or an 8- to 10-membered bicyclic heteroaryl ring having 1-4 heteroatoms independently selected from nitrogen, oxygen, or sulfur; or -T-Rwh; and
$C^2$ is hydrogen or an optionally substituted ring selected from a 3- to 7-membered saturated or partially unsaturated carbocyclic ring, a 7- to 10-membered saturated or partially unsaturated bicyclic carbocyclic ring, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, an 8- to 10-membered bicyclic aryl ring, a 5- to 6-membered heteroaryl ring having 1-3 heteroatoms independently selected from nitrogen, oxygen, or sulfur, or an 8- to 10-membered bicyclic heteroaryl ring having 1-4 heteroatoms independently selected from nitrogen, oxygen, or sulfur.
Nonlimiting examples of compounds for Formula XXII-a and Formula XXII-b are set forth below.
XXII-1
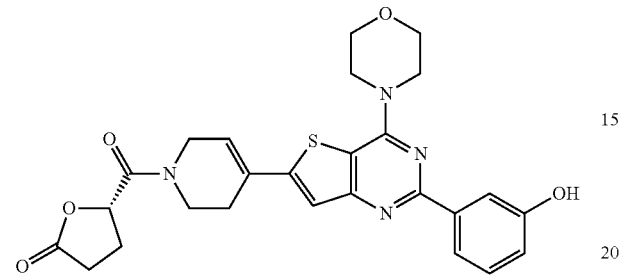
XXII-2
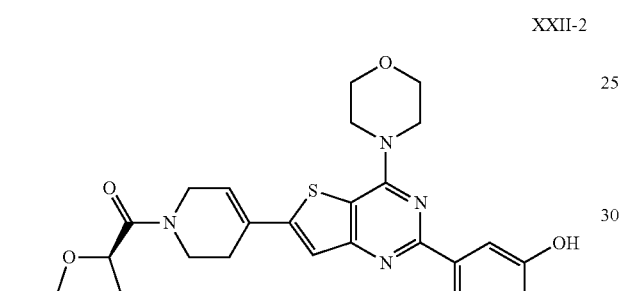
XXII-3
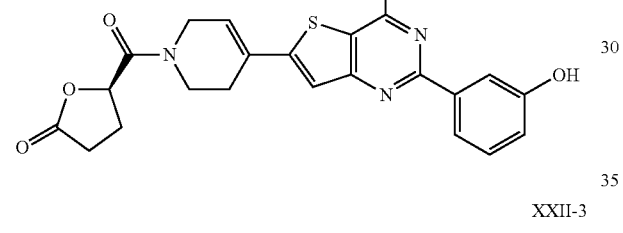
XXII-4
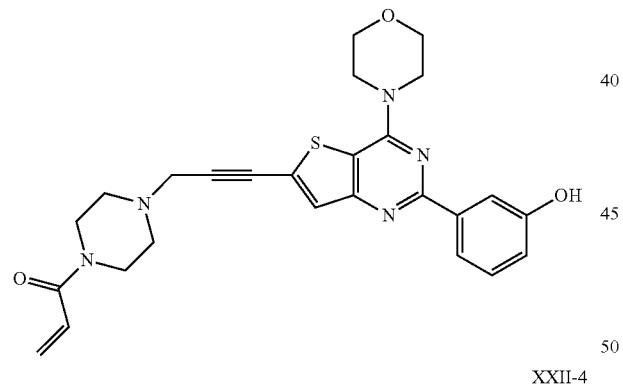
XXII-5
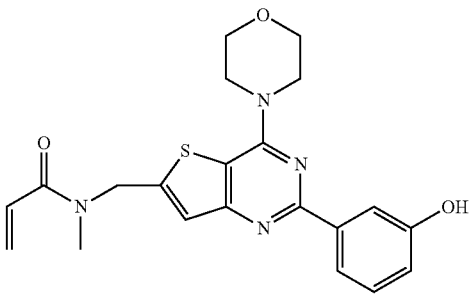
XXII-6
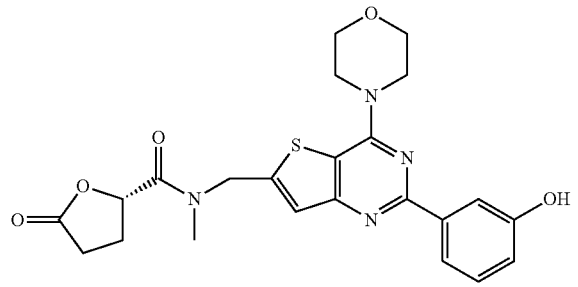
XXII-7
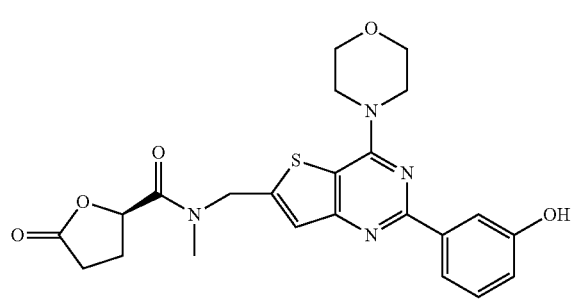
XXII-8
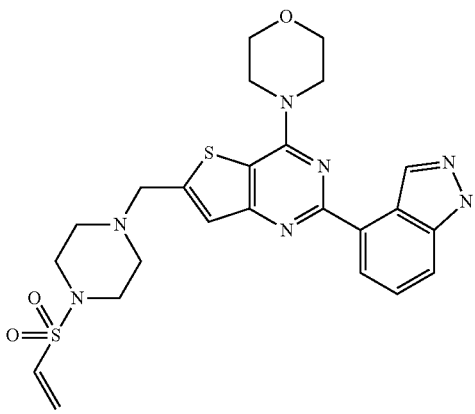

169
-continued
XXII-9
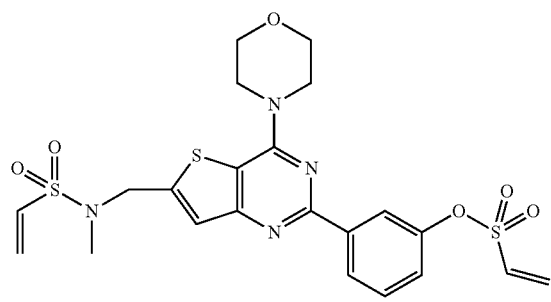
XXII-10
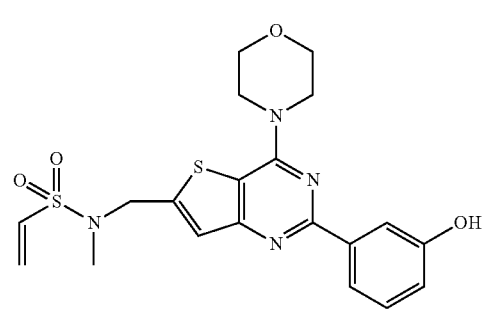
XXII-11
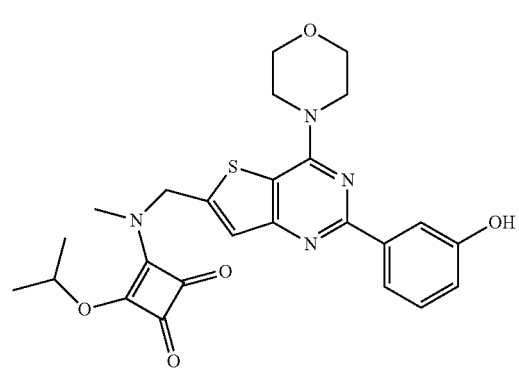
XXII-12
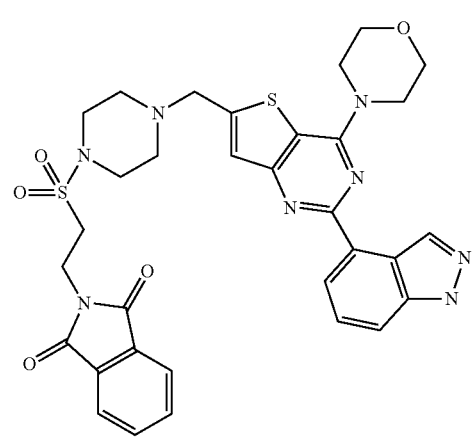
170
-continued
XXII-13
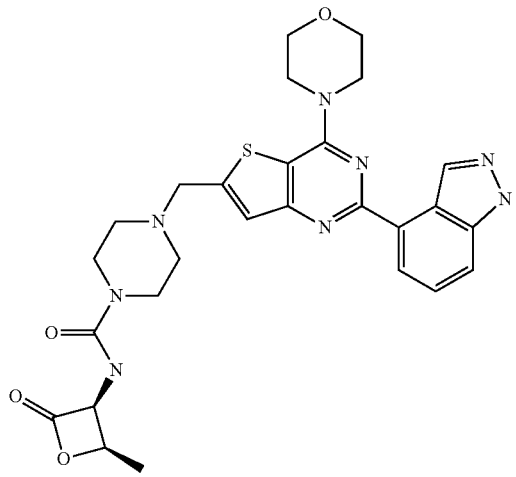
XXII-14
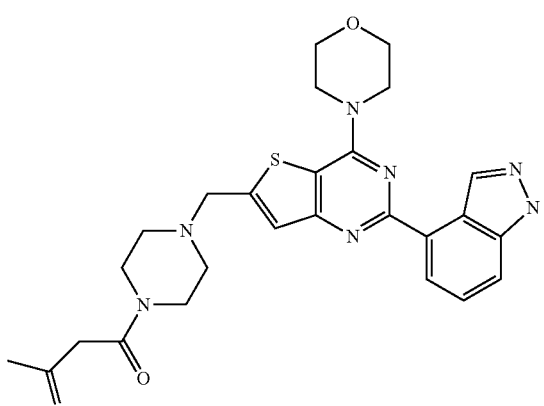
XXII-15
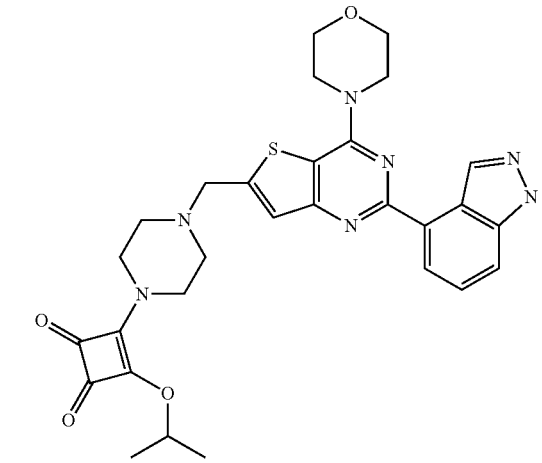

XXII-16
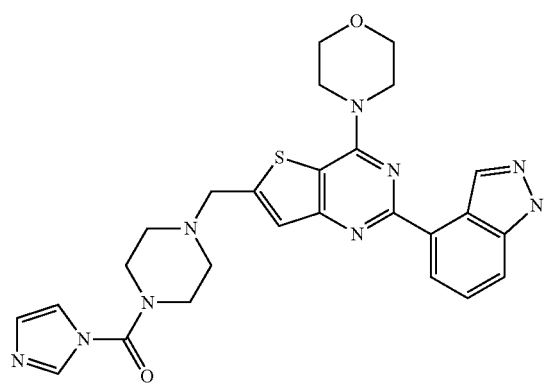
XXII-17
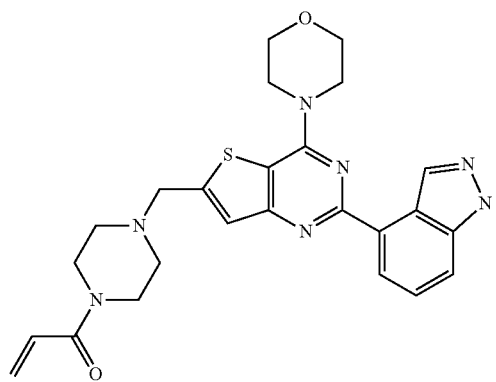
XXII-18
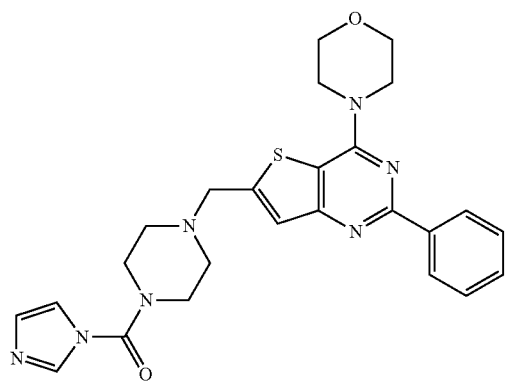
XXII-19
XXII-20
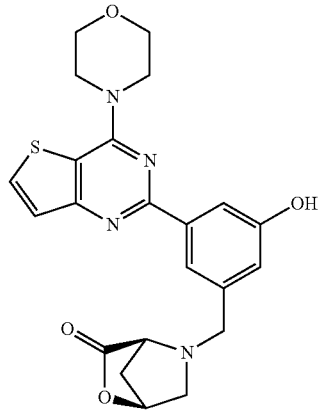
XXII-21
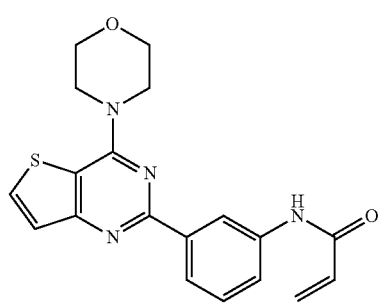
XXII-22
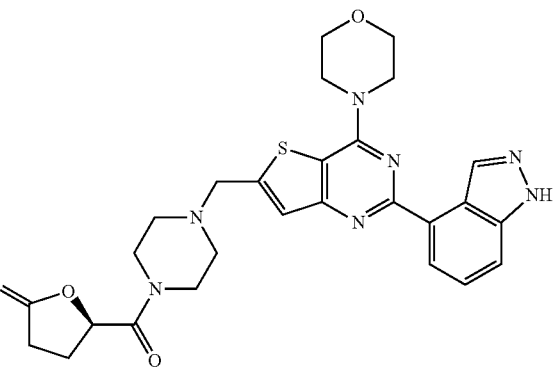
XXII-23
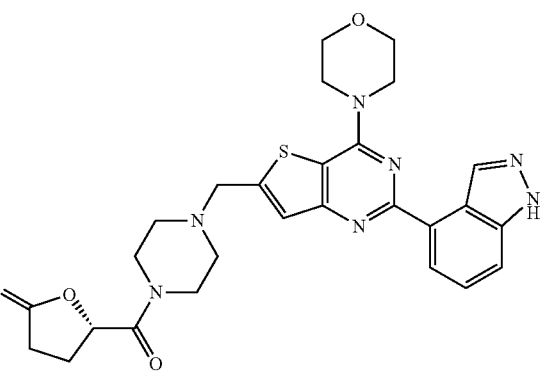

XXII-24
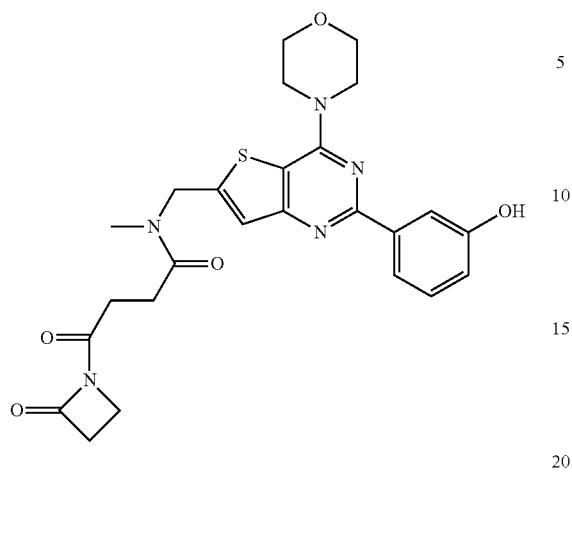
XXII-25
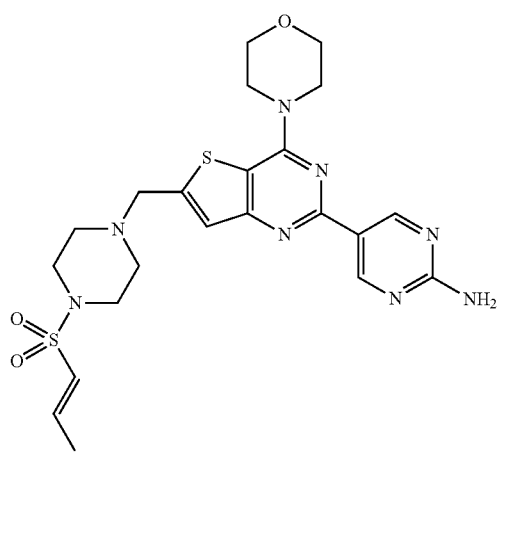
XXII-26
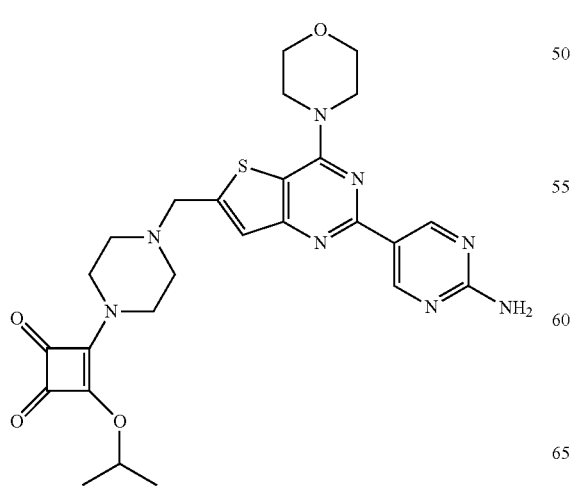
XXII-27
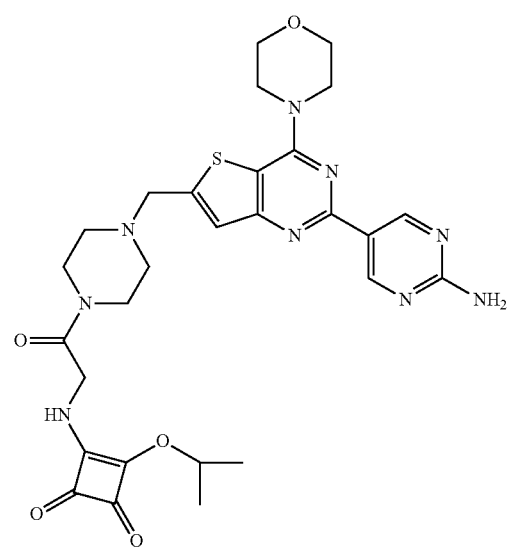
XXII-28
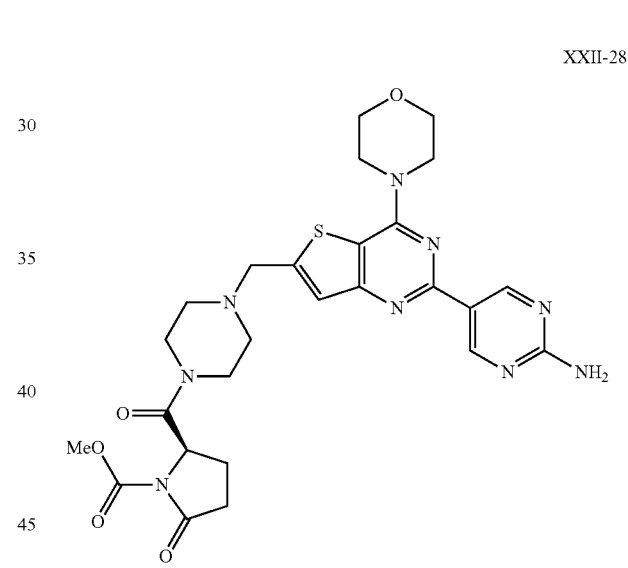
XXII-29
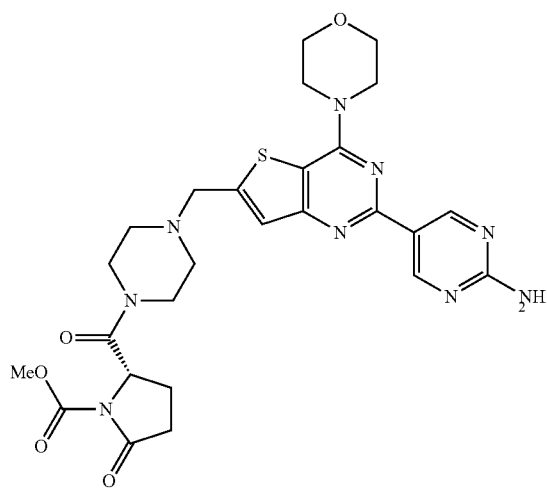

XXII-30
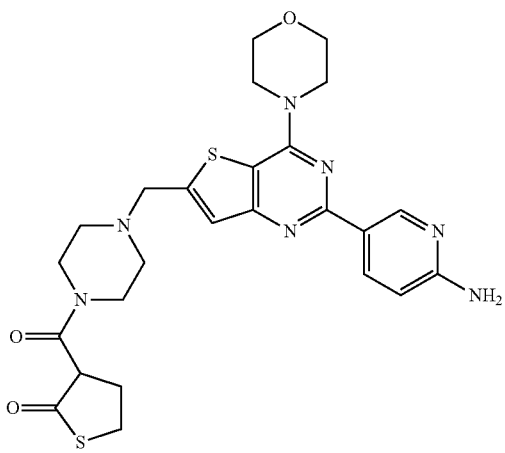
XXII-31
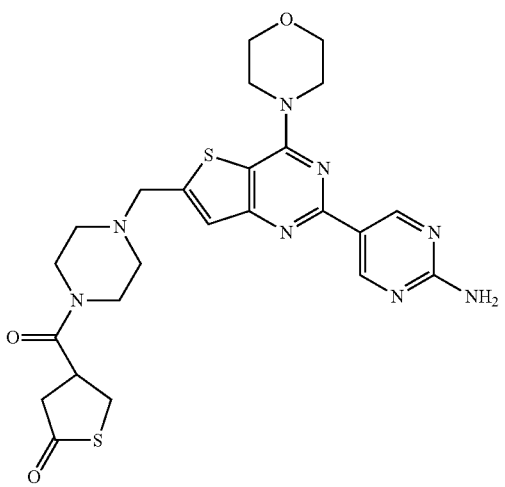
XXII-32
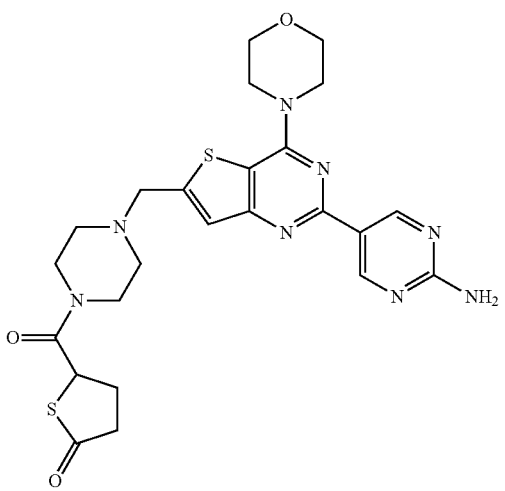
XXII-33
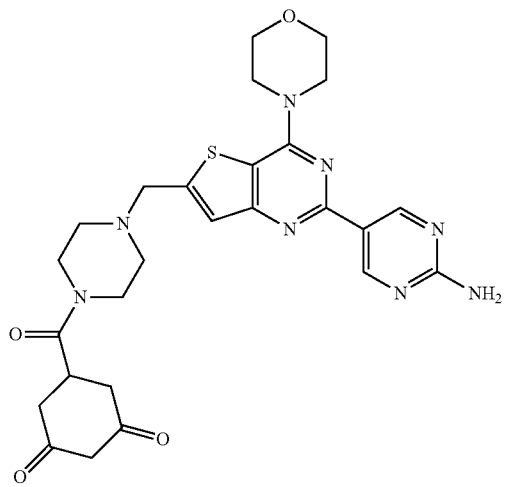
XXII-34
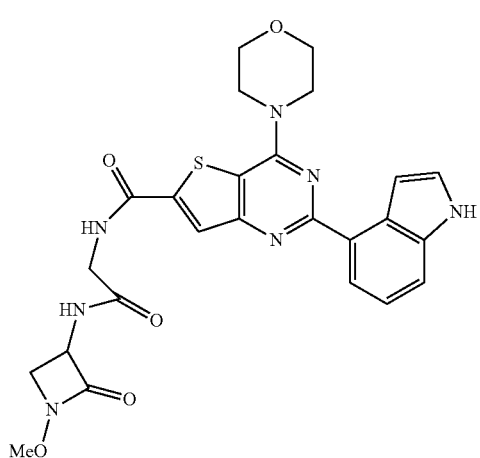
2. COMPOUNDS OF FORMULA XXIII
In some embodiments, the compound of Formula I is a compound of Formula XXIII:
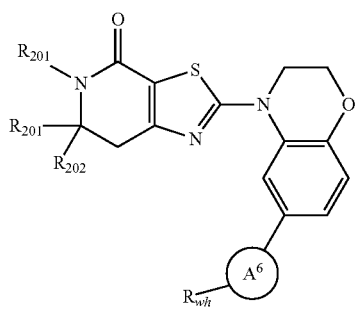
XXIII
wherein:
$R_{wh}$ is a warhead group and is as defined above in the embodiments of Formula I;
$R_{201}$ is hydrogen or $C_{1-6}$ alkyl;
$R_{202}$ is hydrogen or an optionally substituted group selected from $C_{1-6}$ alkyl, $C_{1-6}$ alkoxy, or $(C_{1-6}$ alkylene)-$R_{203}$; or $R_{201}$ and $R_{202}$ are taken together with the intervening carbon to form an optionally substituted ring selected from a 3- to 7-membered carbocyclic ring or a 4- to 7-membered heterocyclic ring having 1-2 heteroatoms independently selected from nitrogen, oxygen, or sulfur;

$R_{203}$ is a 3- to 7-membered saturated or partially unsaturated carbocyclic ring, a 7- to 10-membered saturated or partially unsaturated bicyclic carbocyclic ring, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, a 8- to 10-membered bicyclic aryl ring, a 5- to 6-membered heteroaryl ring having 1-3 heteroatoms independently selected from nitrogen, oxygen, or sulfur, or a 8- to 10-membered bicyclic heteroaryl ring having 1-4 heteroatoms independently selected from nitrogen, oxygen, or sulfur; and Ring $A^6$ is absent or an optionally substituted group selected from a 4- to 7-membered heterocyclic ring having 1-2 heteroatoms independently selected from nitrogen, oxygen, or sulfur, or a 5- to 6-membered heteroaryl ring having 1-3 heteroatoms independently selected from nitrogen, oxygen, or sulfur.

Non-limiting examples of the compounds of Formula XXIII are listed below:

XXIII-1
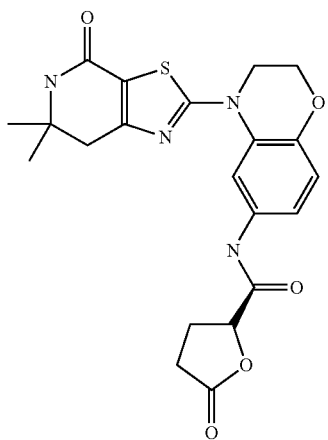

XXIII-2
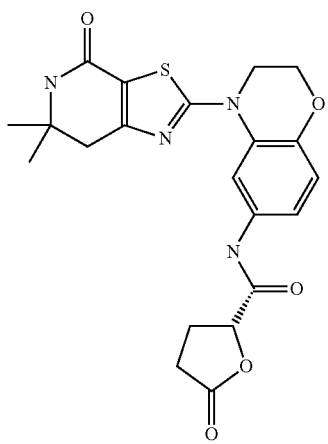

XXIII-3
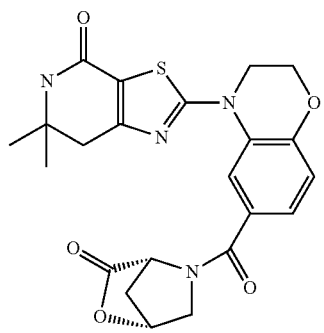

XXIII-4
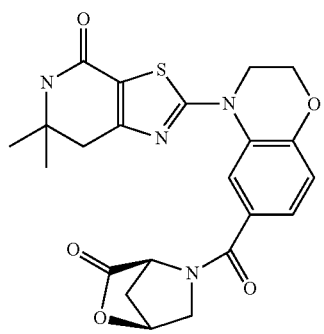

XXIII-5
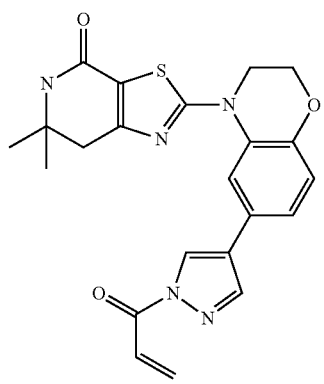

XXIII-6
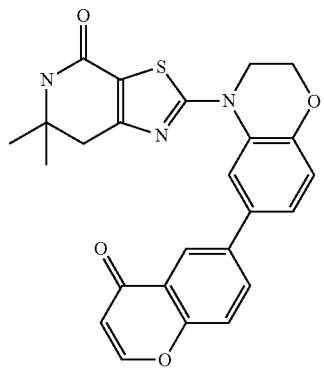

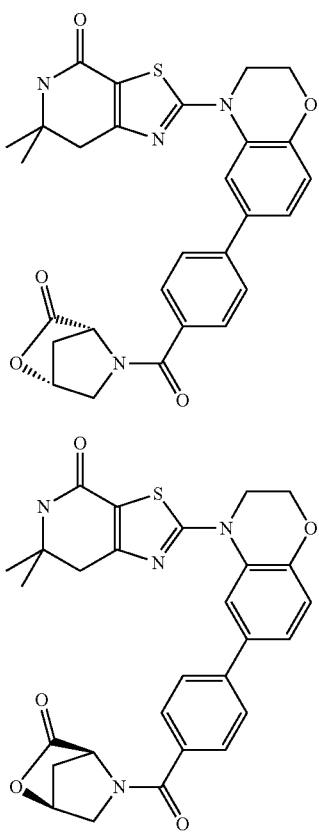

3. COMPOUNDS OF FORMULA XXIV-a AND XXIV-b

In some embodiments, the compound of Formula I is a compound of Formula XXIV-a or Formula XXIV-b:

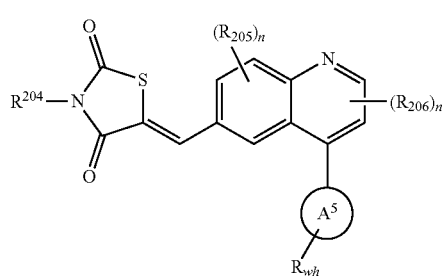

XXIV-a

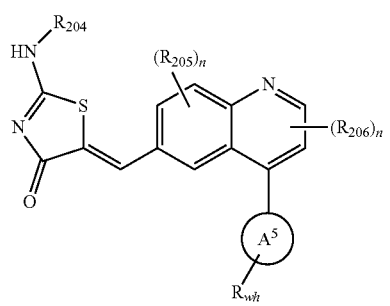

XXIV-b or a pharmaceutically acceptable salt thereof, wherein $R_{wh}$ is a warhead group;

$R_{204}$ is an hydrogen or an optionally substituted group selected from $C_{1-6}$ aliphatic, —$(CH_2)_m$-(3- to 7-membered saturated or partially unsaturated carbocyclic ring), —$(CH_2)_m$-(7- to 10-membered saturated or partially unsaturated bicyclic carbocyclic ring), —$(CH_2)_m$-(4- to 7-membered saturated or partially unsaturated heterocyclic ring having 1-2 heteroatoms independently selected from nitrogen, oxygen, or sulfur), —$(CH_2)_m$-(7- to 10-membered saturated or partially unsaturated bicyclic heterocyclic ring having 1-3 heteroatoms independently selected from nitrogen, oxygen, or sulfur), —$(CH_2)_m$phenyl, —$(CH_2)_m$-(8- to 10-membered bicyclic aryl ring), —$(CH_2)_m$-(5- to 6-membered heteroaryl ring having 1-3 heteroatoms independently selected from nitrogen, oxygen, or sulfur), or —$(CH_2)_m$-(8- to 10-membered bicyclic heteroaryl ring having 1-4 heteroatoms independently selected from nitrogen, oxygen, or sulfur);

each $R_{205}$ and $R_{206}$ is independently —R", halogen, —$NO_2$, —CN, —OR", —SR", —N(R")$_2$, —C(O)R", —$CO_2$R", —C(O)C(O)R", —C(O)CH$_2$C(O)R", —S(O)R", —S(O)$_2$R", —C(O)N(R")$_2$, —SO$_2$N(R")$_2$, —OC(O)R", —N(R")C(O)R", —N(R")N(R")$_2$, —N(R")C(=NR") N(R")$_2$, —C(=NR")N(R")$_2$, —C=NOR", —N(R")C(O)N (R")$_2$, —N(R")SO$_2$N(R")$_2$, —N(R")SO$_2$R", or —OC(O)N (R")$_2$;

each R" is independently hydrogen or an optionally substituted group selected from $C_{1-6}$ aliphatic, a 3- to 7-membered saturated or partially unsaturated carbocyclic ring, a 7- to 10-membered saturated or partially unsaturated bicyclic carbocyclic ring, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, an 8- to 10-membered bicyclic aryl ring, a 5- to 6-membered heteroaryl ring having 1-3 heteroatoms independently selected from nitrogen, oxygen, or sulfur, or an 8- to 10-membered bicyclic heteroaryl ring having 1-4 heteroatoms independently selected from nitrogen, oxygen, or sulfur; or two R" groups on the same nitrogen are taken together with the nitrogen to which they are attached to form an optionally substituted 5-8 membered saturated, partially unsaturated, or aromatic ring having 1-4 heteroatoms independently selected from nitrogen, oxygen, or sulfur;

m is an integer from 0 to 6, inclusive;

each n for Formula XXIV-a or Formula XXIV-b is independently 0, 1, or 2; and

Ring $A^5$ is an optionally substituted 6-membered heterocyclic or heteroaryl ring having 1-2 nitrogens.

Non-limiting examples of compounds of Formula XXIV-a and XXIV-b are set forth below:

XXIV-1

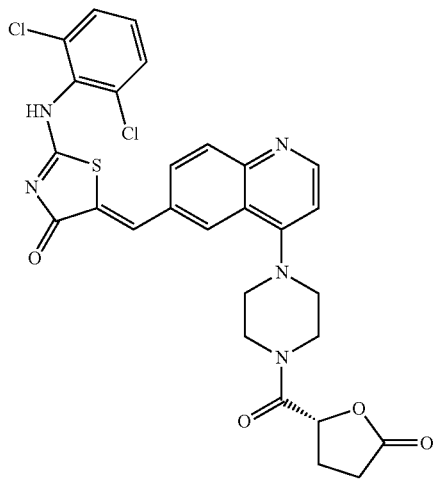

XXIV-2

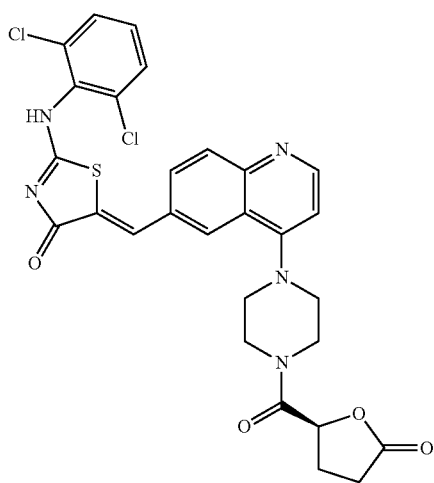

XXIV-3

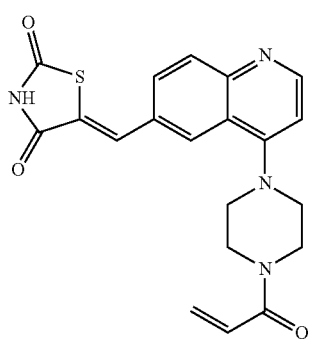

4. COMPOUNDS OF FORMULA XXV

In some embodiments, the compound of Formula I is a compound of Formula XXV:

XXV

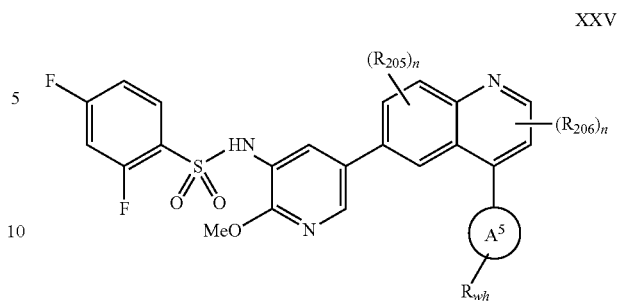

or a pharmaceutically acceptable salt thereof;
wherein
$R_{wh}$ is a warhead group
each $R_{205}$ and $R_{206}$ is independently —R", halogen, —NO$_2$, —CN, —OR", —SR", —N(R")$_2$, —C(O)R", —CO$_2$R", —C(O)C(O)R", —C(O)CH$_2$C(O)R", —S(O)R", —S(O)$_2$R", —C(O)N(R")$_2$, —SO$_2$N(R")$_2$, —OC(O)R", —N(R")C(O)R", —N(R")N(R")$_2$, —N(R")C(=NR")N(R")$_2$, —C(=NR")N(R")$_2$, —C=NOR", —N(R")C(O)N(R")$_2$, —N(R")SO$_2$N(R")$_2$, —N(R")SO$_2$R", or —OC(O)N(R")$_2$;

each R" is independently hydrogen or an optionally substituted group selected from $C_{1-6}$ aliphatic, a 3- to 7-membered saturated or partially unsaturated carbocyclic ring, a 7- to 10-membered saturated or partially unsaturated bicyclic carbocyclic ring, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, an 8- to 10-membered bicyclic aryl ring, a 5- to 6-membered heteroaryl ring having 1-3 heteroatoms independently selected from nitrogen, oxygen, or sulfur, or an 8- to 10-membered bicyclic heteroaryl ring having 1-4 heteroatoms independently selected from nitrogen, oxygen, or sulfur; or optionally, two R" groups on the same nitrogen are taken together with the nitrogen to which they are attached to form an optionally substituted 5-8 membered saturated, partially unsaturated, or aromatic ring having 1-4 heteroatoms independently selected from nitrogen, oxygen, or sulfur;

m is an integer from 0 to 6, inclusive;
each n is independently 0, 1, or 2; and
Ring $A^5$ is an optionally substituted 6-membered heterocyclic or heteroaryl ring having 1-2 nitrogens.

In other nonlimiting illustrative embodiments, compounds of Formula XXV are shown below:

XXV-1

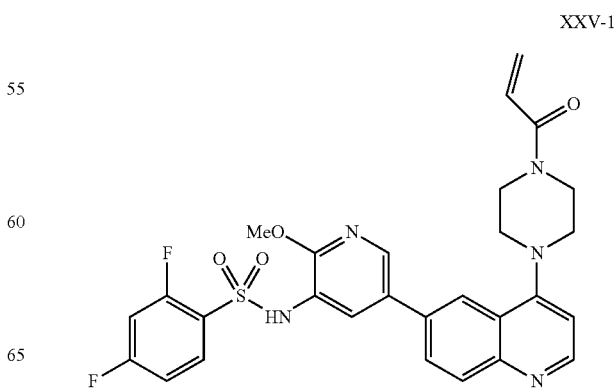

-continued
XXV-2
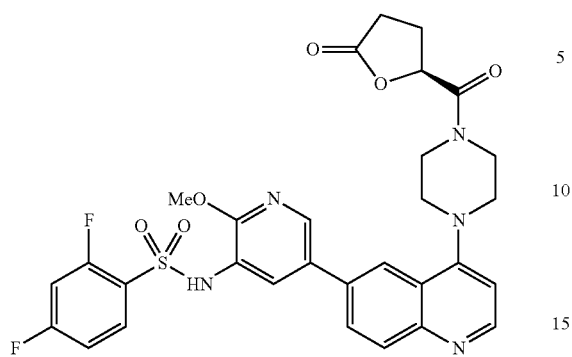
XXV-3
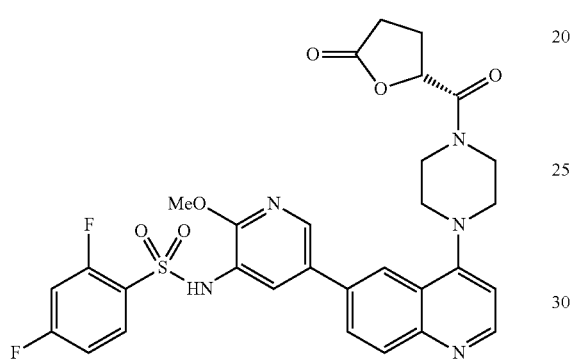
XXV-4
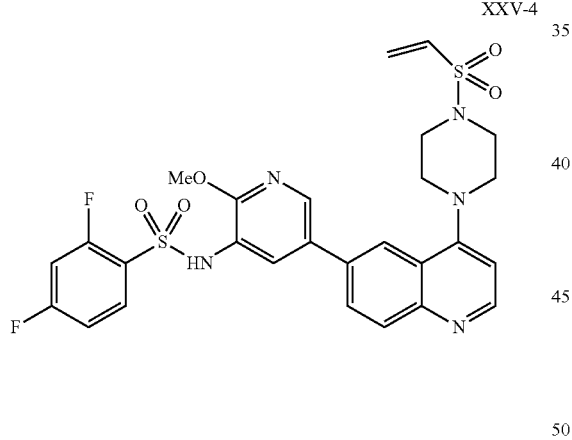
XXV-5
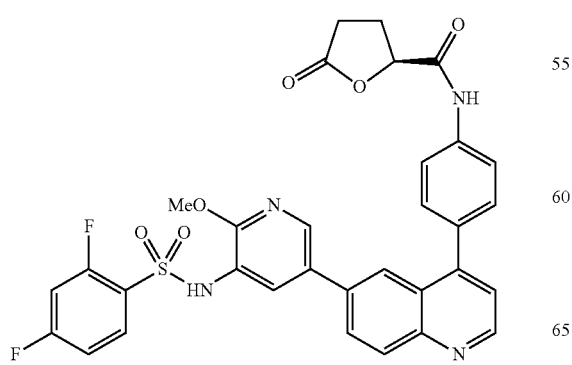
-continued
XXV-6
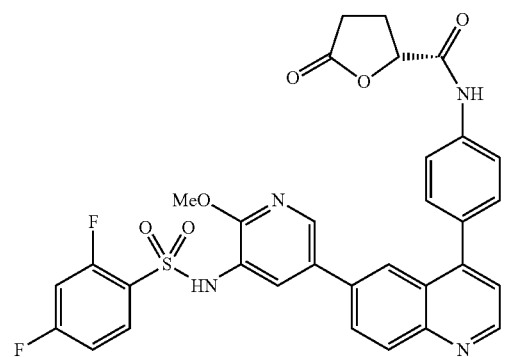
XXV-7
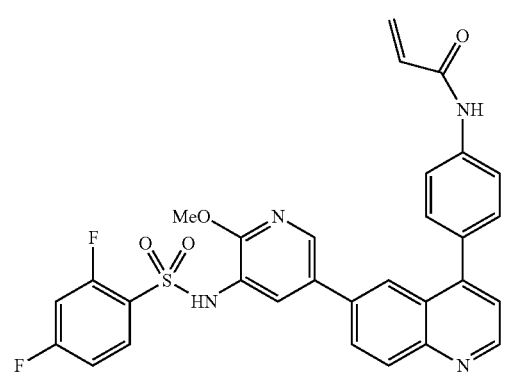
XXV-8
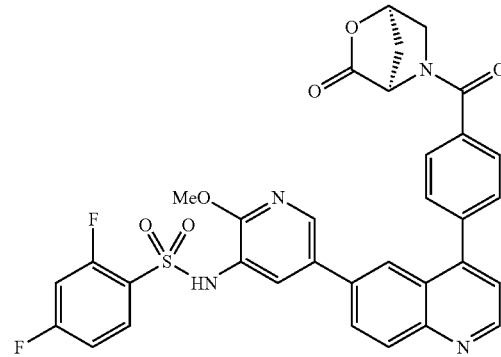
XXV-9
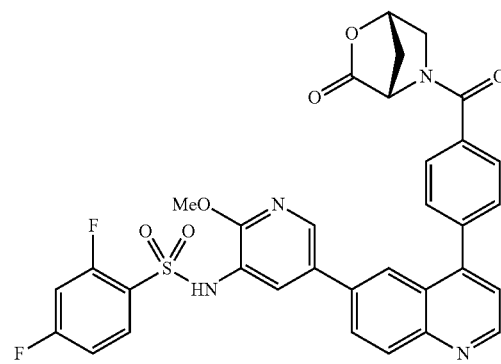

XXV-10
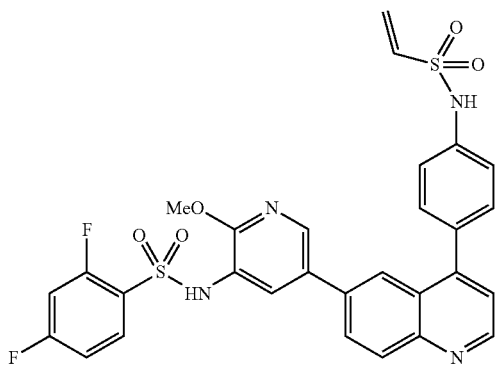

XXV-11
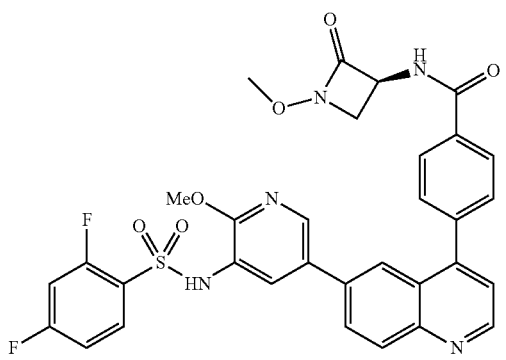

XXV-12
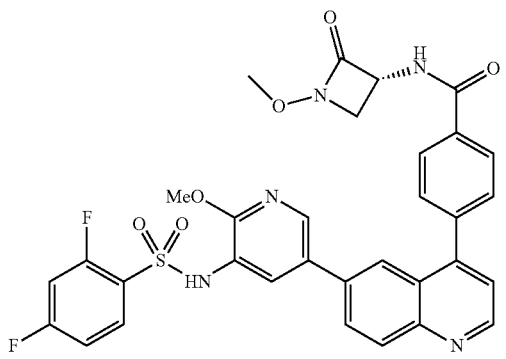

XXV-13
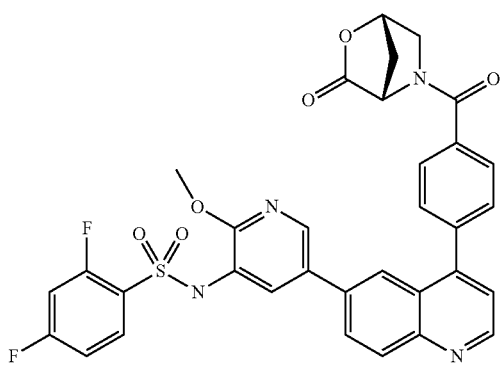

XXV-14
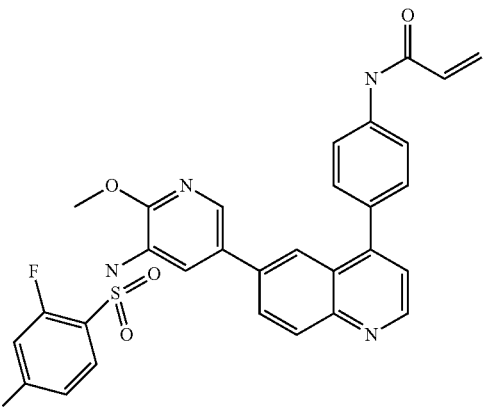

XXV-15
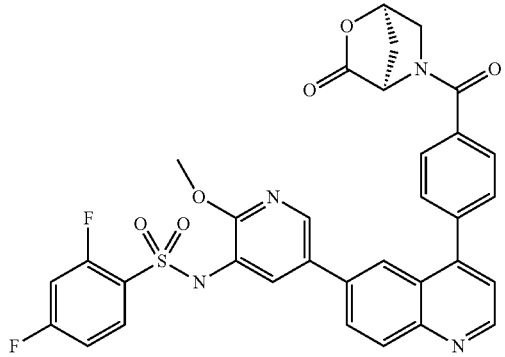

5. COMPOUNDS OF FORMULA XXVI

In some embodiments, the compound of Formula I is a compound of Formula XXVI:

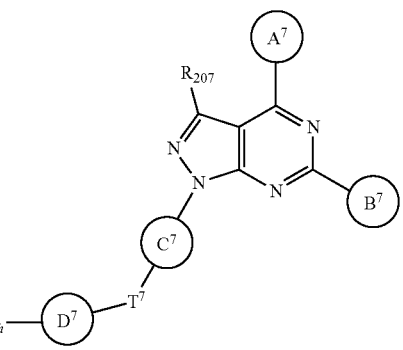

XXVI or a pharmaceutically acceptable salt thereof;
wherein:
$R_{wh}$ is a warhead group and is as defined above in the embodiments of Formula I;
Ring $A^7$ is an optionally substituted ring selected from a 4- to 8-membered saturated or partially unsaturated heterocyclic ring having one or two heteroatoms independently selected from nitrogen, oxygen, or sulfur, or a 5-10 membered saturated or partially unsaturated bridged bicyclic heterocyclic ring having at least one nitrogen, at least one oxygen, and optionally 1-2 additional heteroatoms independently selected from nitrogen, oxygen, or sulfur;

$R_{207}$ is R''', halogen, —OR''', —CN, —NO$_2$, —SO$_2$R''', —SOR''', —C(O)R''', —CO$_2$R''', —C(O)N(R''')$_2$, —NRC(O)R''', —NR'''C(O)N(R''')$_2$, —NRSO$_2$R''', or —N(R''')$_2$;

each R''' is independently hydrogen or an optionally substituted group selected from C$_{1-6}$ aliphatic, aryl, a 4- to 7-membered heterocylic ring having 1-2 heteroatoms independently selected from nitrogen, oxygen, or sulfur, or a 5- to 6-membered monocyclic heteroaryl ring having 1-4 heteroatoms independently selected from nitrogen, oxygen, or sulfur, or:

optionally two R''' groups on the same nitrogen are taken together with the nitrogen atom to which they are attached to form a 4- to 7-membered saturated, partially unsaturated, or heteroaryl ring having 1-4 heteroatoms independently selected from nitrogen, oxygen, or sulfur;

Ring B$^7$ is an optionally substituted group selected from phenyl, an 8- to 10-membered bicyclic aryl ring, a 5- to 6-membered heteroaryl ring having 1-4 heteroatoms independently selected from nitrogen, oxygen, or sulfur, or an 8- to 10-membered bicyclic heteroaryl ring having 1-4 heteroatoms independently selected from nitrogen, oxygen, or sulfur;

T$^7$ is a covalent bond or a bivalent straight or branched, saturated or unsaturated C$_{1-6}$ hydrocarbon chain wherein one or more methylene units of T$^7$ are optionally replaced by —O—, —S—, —N(R''')—, —C(O)—, —OC(O)—, —C(O)O—, —C(O)N(R''')—, —N(R''')C(O)—, —N(R''')C(O)N(R''')—, —SO$_2$—, —SO$_2$N(R''')—, —N(R''')SO$_2$—, or —N(R''')SO$_2$N(R''')—;

Ring C$^7$ is an optionally substituted ring selected from a 3- to 7-membered saturated or partially unsaturated carbocyclic ring, a 7- to 10-membered saturated or partially unsaturated bicyclic carbocyclic ring, a 7- to 12-membered saturated or partially unsaturated bridged bicyclic ring having 0-4 heteroatoms independently selected from nitrogen, oxygen, or sulfur, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, an 8- to 10-membered bicyclic aryl ring, a 5- to 6-membered heteroaryl ring having 1-3 heteroatoms independently selected from nitrogen, oxygen, or sulfur, or an 8- to 10-membered bicyclic heteroaryl ring having 1-4 heteroatoms independently selected from nitrogen, oxygen, or sulfur; and Ring D$^7$ is absent or an optionally substituted ring selected from a 3- to 7-membered saturated or partially unsaturated carbocyclic ring, a 7- to 10-membered saturated or partially unsaturated bicyclic carbocyclic ring, a 7- to 12-membered saturated or partially unsaturated bridged bicyclic ring having 0-4 heteroatoms independently selected from nitrogen, oxygen, or sulfur, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, an 8- to 10-membered bicyclic aryl ring, a 5- to 6-membered heteroaryl ring having 1-3 heteroatoms independently selected from nitrogen, oxygen, or sulfur, or an 8- to 10-membered bicyclic heteroaryl ring having 1-4 heteroatoms independently selected from nitrogen, oxygen, or sulfur.

Nonlimiting examples of the compounds of Formula XXVI are set forth below.

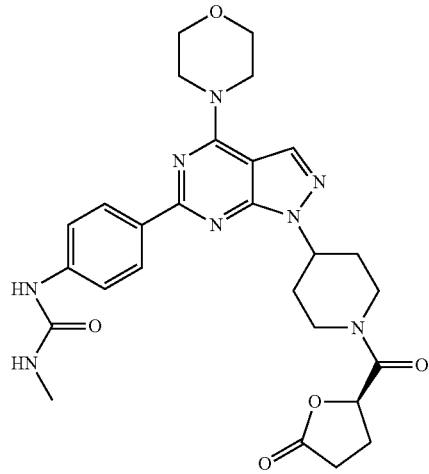

XXVI-1

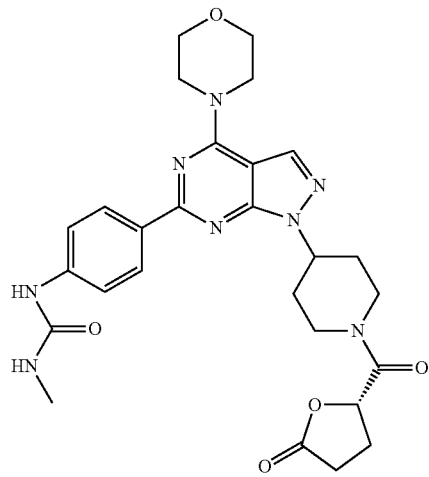

XXVI-2

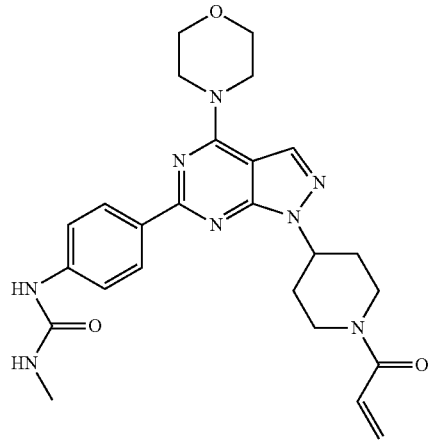

XXVI-3

XXVI-4
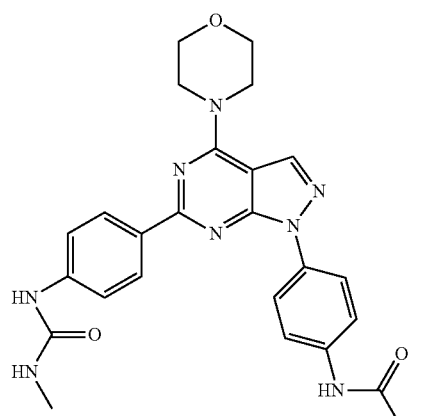
XXVI-5
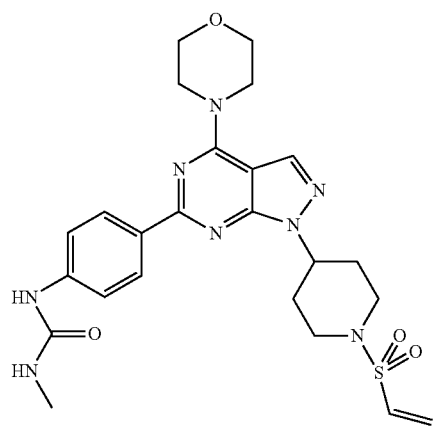
XXVI-6
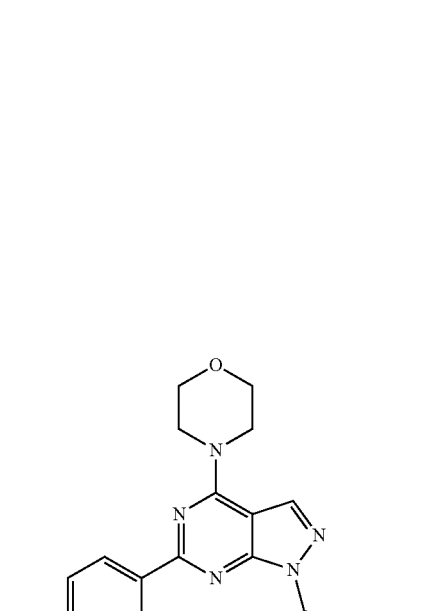
XXVI-7
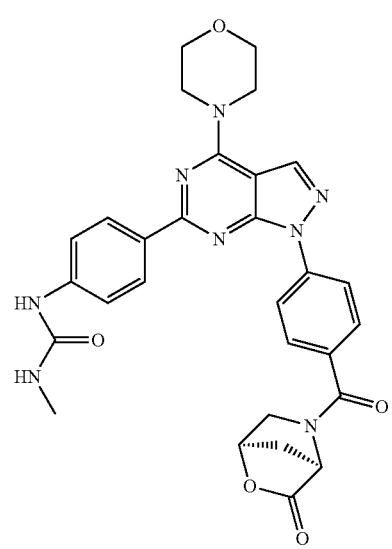
XXVI-8
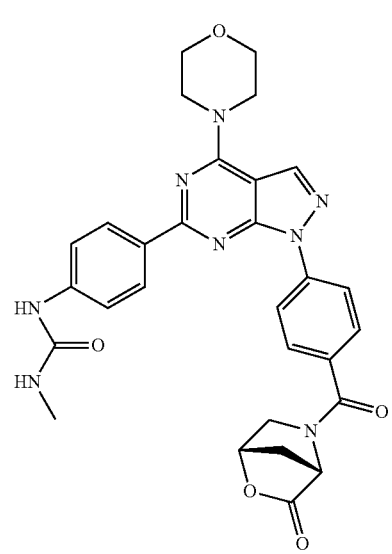
XXVI-9
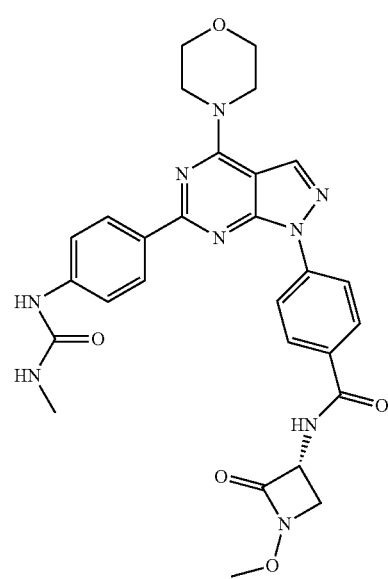

XXVI-10

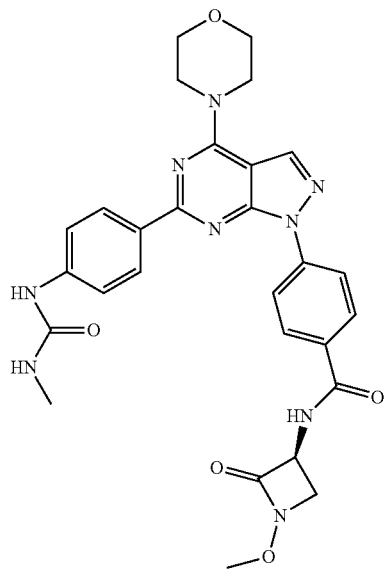

6. COMPOUNDS OF FORMULA XXVII

In some embodiments, the compound of Formula I is a compound of Formula XXVII:

XXVII

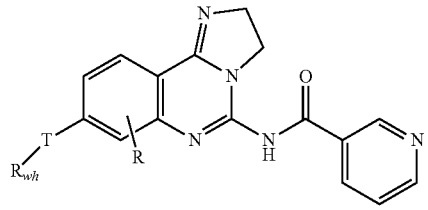

or a pharmaceutically acceptable salt thereof;
wherein:
T and $R_{wh}$ are as defined above in the embodiments of Formula I.
R is H, alkyl, or alkoxy.
Nonlimiting examples of the compounds of the Formula XXVII are set forth below.

XXVII-1

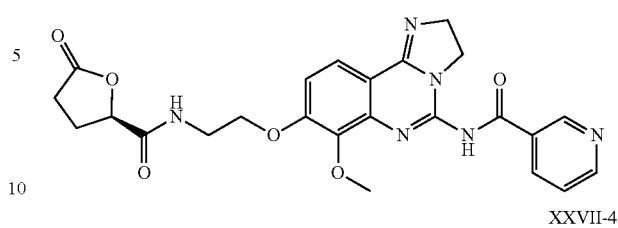

XXVII-2

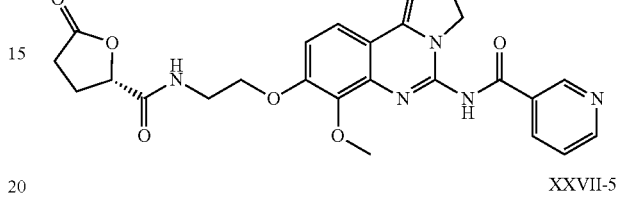

XXVII-3

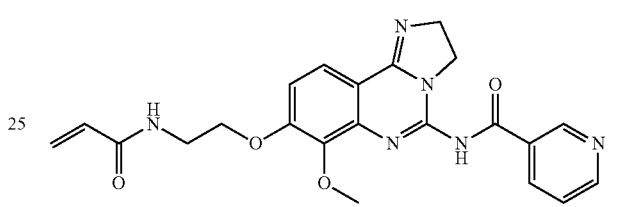

XXVII-4

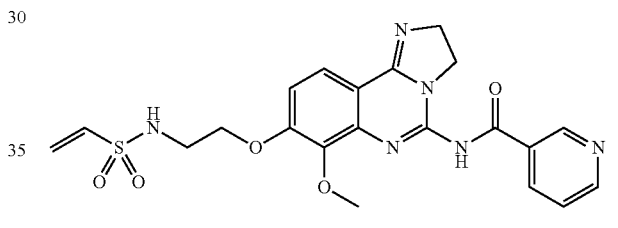

XXVII-5

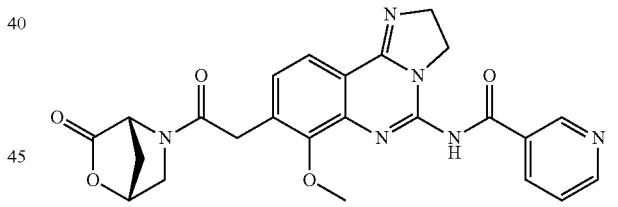

XXVII-6

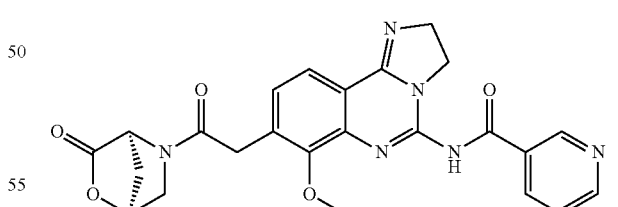

XXVII-7

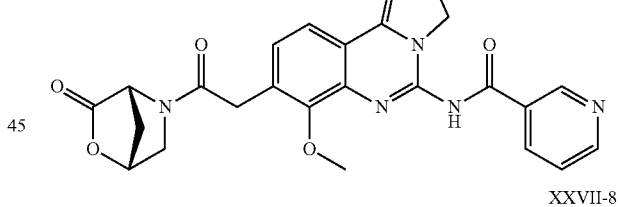

XXVII-8

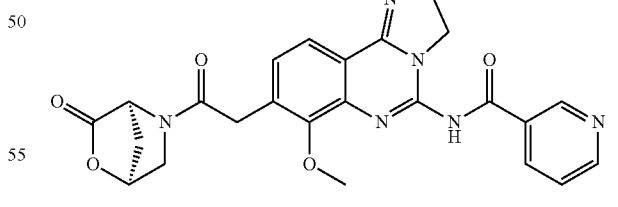

XXVII-9

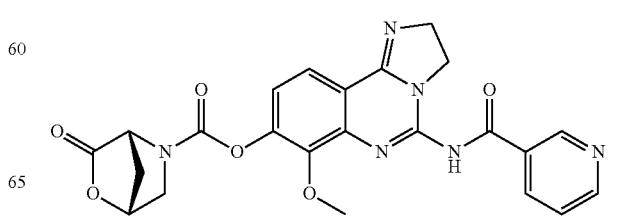

XXVII-10
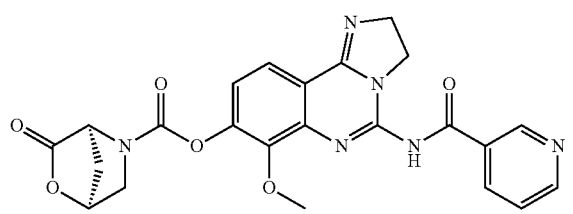
XXVII-11
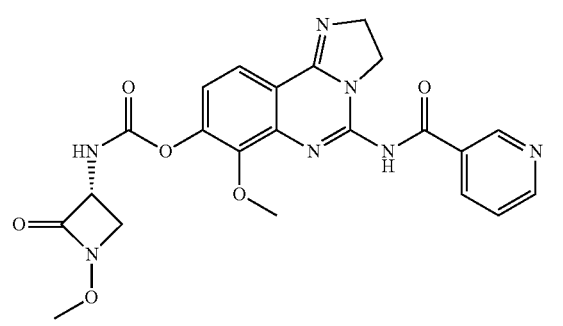
XXVII-12
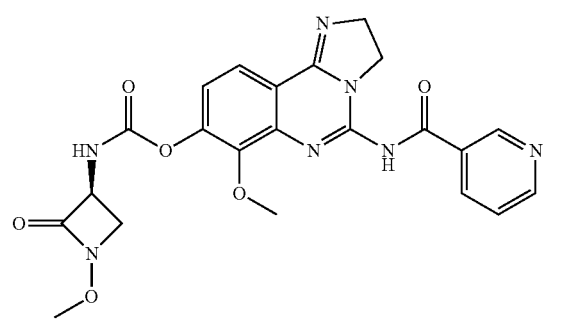
XXVII-13
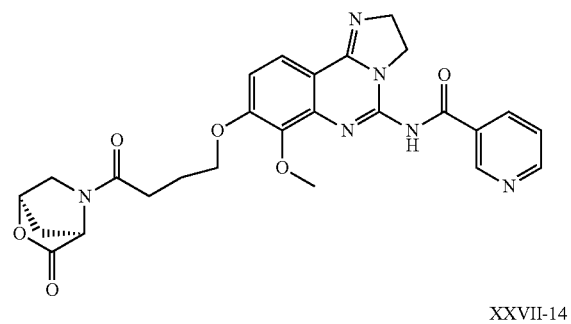
XXVII-14
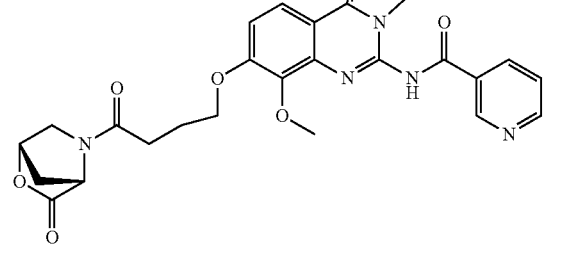
7. COMPOUNDS OF FORMULA XXVIII
In some embodiments, the compound of Formula I is a compound of Formula XXVIII:
XXVIII
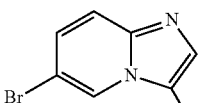
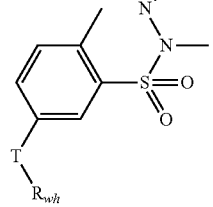
and pharmaceutically acceptable salts thereof;
wherein
T and $R_{wh}$ and are as defined above in the embodiments of Formula I.
Non-limiting examples of the compounds of Formula XXVIII are set forth below:
XXVIII-1
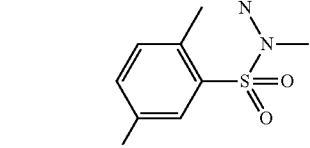
XXVIII-2
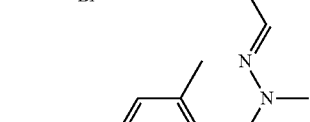

XXVIII-3

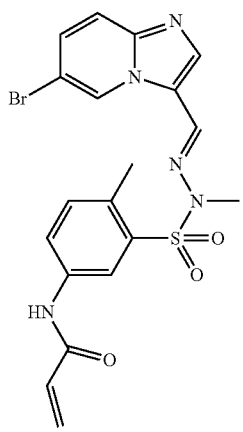

XXVIII-4

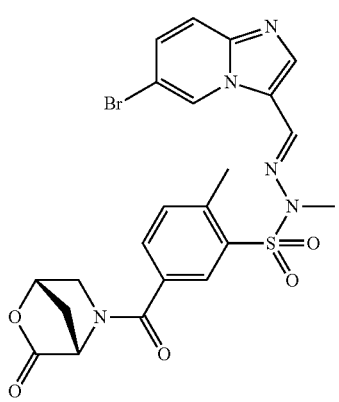

XXVIII-5

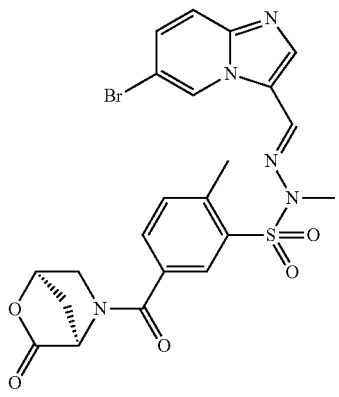

XXVIII-6

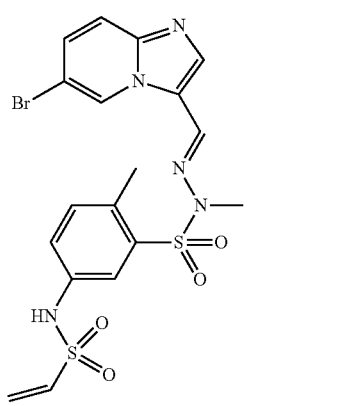

8. COMPOUNDS OF FORMULA XXIX

In some embodiments, the compound of Formula I is a compound of Formula XXIX:

XXIX

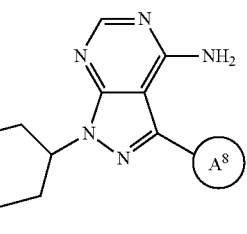

and pharmaceutically acceptable salts thereof;
wherein

T and $R_{wh}$ are Tether and Warhead, respectively, and are as defined as above for Formula I; and $A^8$ is an optionally substituted aryl, biaryl, or heteroaryl.

Non-limiting examples of the compounds of Formula XXIX are set forth below:

XXIX-1

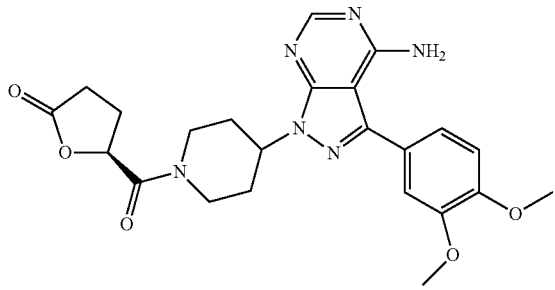

XXIX-2

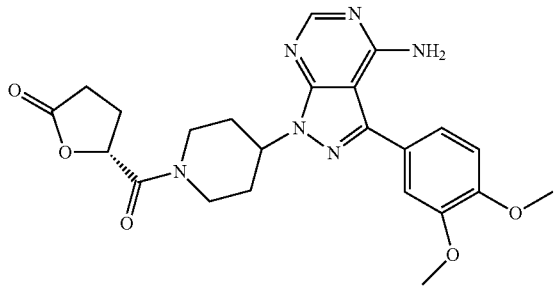

XXIX-3

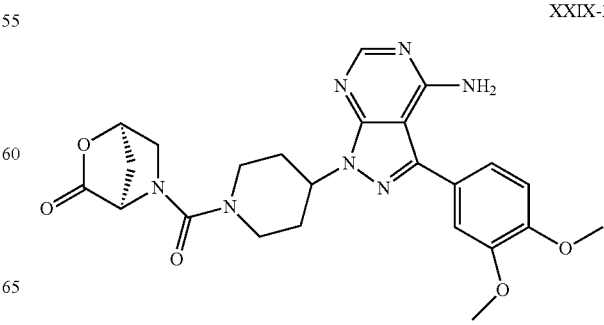

XXIX-4

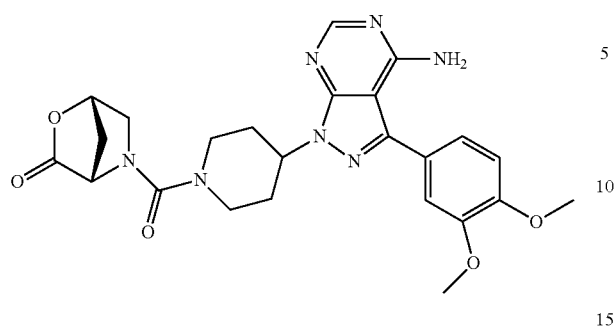

XXXVII-1

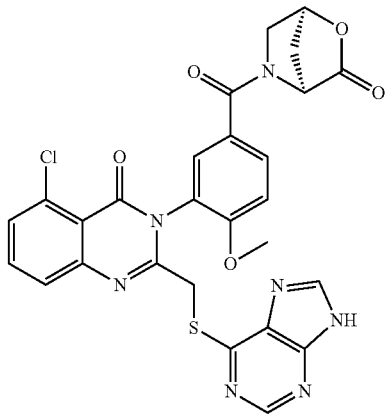

XXXVII-2

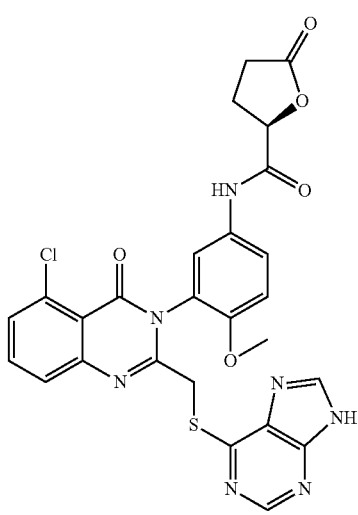

XXIX-5

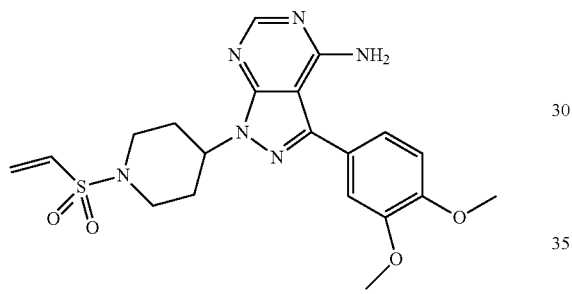

9. Compounds of Formula XXXVII

In some embodiments, the compound of Formula I is a compound of Formula XXXVII:

XXXVII

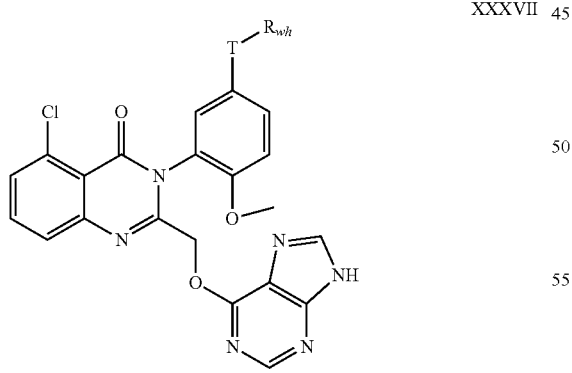

and pharmaceutically acceptable salts thereof;
wherein

T and $R_{wh}$ are Tether and Warhead, respectively, and are as defined as above for Formula I.

Non-limiting examples of the compounds of Formula XXXVII are set forth below

XXXVII-3

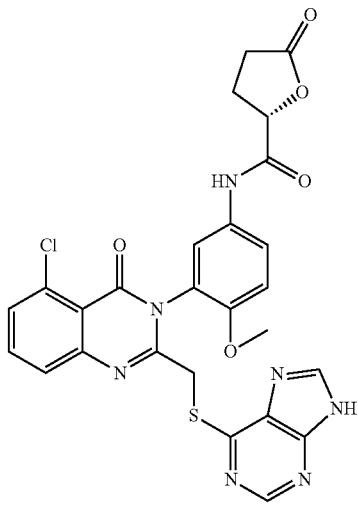

XXXVII-4

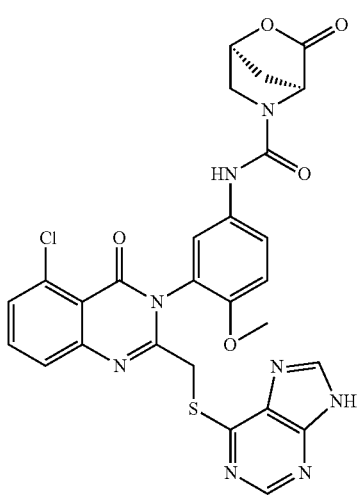

XXXVII-5

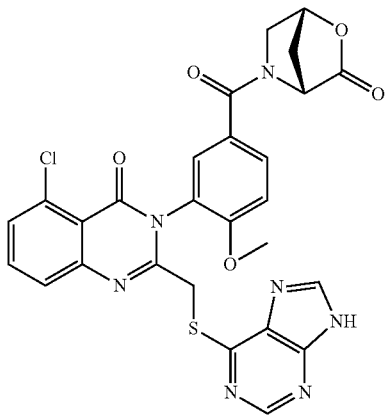

One of ordinary skill in the art will recognize that a variety of warhead groups, as defined herein, are suitable for covalent bonding to lysine. Such $R_{wh}$ groups include, but are not limited to, those described herein and depicted in Formulas VI-a-VI-t, and aa-ooo, inclusive, supra. That these warheads are suitable for covalent bonding to the primary amine of a lysine residue was determined by performing mass spectrometric experiments using the protocol described in detail in Examples 50-54, 88, 163-164, and 174-175 infra, the results of which are depicted in FIGS. 3-9, and 12-22. These experiments show that the compounds described herein covalently modify a target lysine residue in HCV-NS3 protease, XIAP, PI3K, and PDPK-1.

VIII. IN A FURTHER ASPECT, THE INVENTION PROVIDES PROTEIN-MODIFIER-LIGAND CONJUGATES OF THE FORMULA XIII

XIII

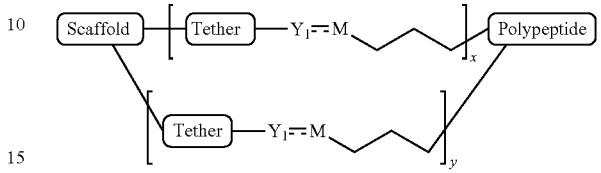

wherein

Scaffold is
a) a radical resulting from the removal of a hydrogen of a ligand capable of binding to, or in proximity to, the ligand-binding site; or
b) a portion of a pharmacophore of a ligand resulting from truncation of the pharmacophore, such that the Scaffold is capable of binding to, or in proximity to, the ligand-binding site;

Warhead is an organic moiety optionally containing one or more heteroatoms selected from O, N, and S; the organic moiety having a molecular weight of about 14 daltons to about 200 daltons; Warhead being capable of reaction with a side chain primary amine group of a lysine residue; and Warhead being attached to Scaffold through Tether; and Tether is null, a bond, or a bivalent $C_1$-$C_{15}$ saturated, unsaturated, straight, branched, cyclic, bicyclic, tricyclic alkyl, alkenyl, alkynyl; bridged bicyclic, heterocycle, heteroaryl, or aryl moiety; wherein optionally one or more methylene units of the hydrocarbon chain are independently replaced by —$NR_1$—, —O—, —C(O)—, —S—, —SO—, —$SO_2$—, —C(=S)—, or C(=$NR_1$)—; optionally, one or more hydrogens are independently replaced by heteroatoms, and optionally, one or more methine groups of the $C_1$-$C_6$ alkyl, when present, are independently replaced by $$\begin{array}{c}|\\-N-\\\end{array};$$

x is 0, 1, or 2;
y is 1, 2, or 3;
$R_1$ is hydrogen or $C_1$-$C_8$ alkyl; and
$Y_1$ is a bivalent or trivalent moiety resulting from the removal of a hydrogen of a radical of Formula XIV-a, XIV-b, XIV-c, XIV-d, XIV-e, XIV-f, XIV-g, XIV-h, or XIV-i, XIV-a

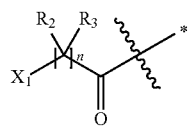

-continued

XIV-b 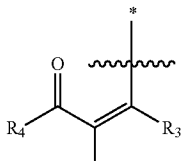

XIV-c 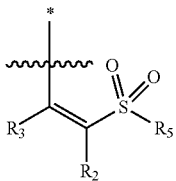

XIV-d 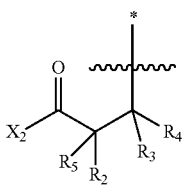

XIV-e 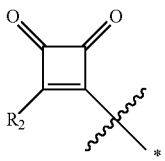

XIV-f 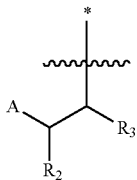

XIV-g 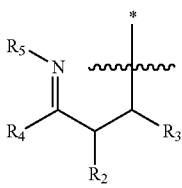

XIV-h 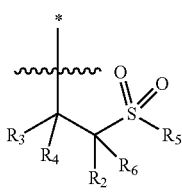

-continued

XIV-i 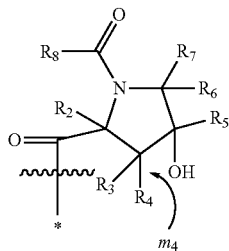

wherein each $X_1$ and $X_2$ is independently —$CR_2R_3R_4$, —$OR_2$, or —$NR_2R_3$;

each $R_2$, $R_3$, $R_4$, $R_5$, $R_6$, $R_7$, and $R_8$ is independently hydrogen or $C_1$-$C_6$ alkyl;

optionally when proper any two of $R_2$, $R_3$, $R_4$, $R_5$, $R_6$, $R_7$, and $R_8$ can be linked together to form a 3- to 8-membered carbocyclic or heterocyclic ring;

one or more methylene groups of the $C_1$-$C_6$ alkyl can be replaced by —O—, —C(O)—, —S—, —SO—, —$SO_2$—, or —C(=S)—; one or more methine groups of the $C_1$-$C_6$ alkyl, when present, can be independently replaced by

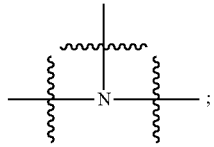

and n is an integer from 2-4, $m_4$ is an integer from 1 to 2;

A is an optionally substituted aryl or heteroaryl;

═══ is a single or a double bond;

a hydrogen of a radical of Formula XIV-a, XIV-b, XIV-c, XIV-d, XIV-e, XIV-f, XIV-g, XIV-h, or XIV-i, is substituted by Tether-Scaffold; and M is connected to the position labeled as "*" and is —NH— or =N—, the nitrogen atom of M being a nitrogen from the side chain primary amine group of the lysine residue of the protein.

In some embodiments, the conjugate of Formula XIII, is a conjugate of Formula

XIII'

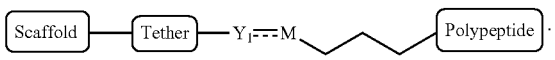

In some embodiments, the Scaffold is selected from the group consisting of Formulas VII, VIII, IX-a, IX-b, XI, XII, XVI, XVII, XVIII, XIX, XX, XXI, XXII, XXIII, XXXIV, XXV, XXVI, XXVII, XXVIII, XXIX, XXXVI, and XXXVII.

In other embodiments, $M(CH_2)_4$-Protein, is selected from the group consisting of $M(CH_2)_4$-K1236-HCV-NS3, $M(CH_2)_4$-K2016-HCV-NS3, $M(CH_2)_4$-K2560-HCV-NS3, $M(CH_2)_4$-K191-(Baculoviral IAP repeat-containing protein 1), $M(CH_2)_4$-K199-(Baculoviral IAP repeat-containing protein 1), $M(CH_2)_4$-K305-(Baculoviral IAP repeat-containing protein 2), $M(CH_2)_4$-K291-(Baculoviral IAP repeat-containing protein 3), $M(CH_2)_4$-K297-(Baculoviral IAP repeat-containing protein 4), M(CH₂)₄-K299-(Baculoviral IAP repeat-containing protein 4), M(CH₂)₄-K311-(Baculoviral IAP repeat-containing protein 4), M(CH₂)₄-K062-(Baculoviral IAP repeat-containing protein 5), M(CH₂)₄-K079-(Baculoviral IAP repeat-containing protein 5), M(CH₂)₄-K121-(Baculoviral IAP repeat-containing protein 7), M(CH₂)₄-K135-(Baculoviral IAP repeat-containing protein 7), M(CH₂)₄-K146-(Baculoviral IAP repeat-containing protein 7), M(CH₂)₄-K036-(Baculoviral IAP repeat-containing protein 8), M(CH₂)₄-K050-(Baculoviral IAP repeat-containing protein 8), M(CH₂)₄-K061-(Baculoviral IAP repeat-containing protein 8), M(CH₂)₄-K776-(Phosphatidylinositol-4,5-bisphosphate 3-kinase catalytic subunit alpha isoform), M(CH₂)₄-K802-(Phosphatidylinositol-4,5-bisphosphate 3-kinase catalytic subunit alpha isoform), M(CH₂)₄-K777-(Phosphatidylinositol-4,5-bisphosphate 3-kinase catalytic subunit beta isoform), M(CH₂)₄-K805-(Phosphatidylinositol-4,5-bisphosphate 3-kinase catalytic subunit beta isoform), M(CH₂)₄-K802-(Phosphatidylinositol-4,5-bisphosphate 3-kinase catalytic subunit gamma isoform), M(CH₂)₄-K807-(Phosphatidylinositol-4,5-bisphosphate 3-kinase catalytic subunit gamma isoform), M(CH₂)₄-K833-(Phosphatidylinositol-4,5-bisphosphate 3-kinase catalytic subunit gamma isoform), M(CH₂)₄-K890-(Phosphatidylinositol-4,5-bisphosphate 3-kinase catalytic subunit gamma isoform), M(CH₂)₄-K086-(3-phosphoinositide-dependent protein kinase 1), M(CH₂)₄-K163-(3-phosphoinositide-dependent protein kinase 1), M(CH₂)₄-K169-(3-phosphoinositide-dependent protein kinase 1), and M(CH₂)₄-K207-(3-phosphoinositide-dependent protein kinase 1).

In other embodiments, the bivalent or trivalent moiety resulting from the removal of a hydrogen of a radical of Formula XIV-a, XIV-d, XIV-h, or XIV-i is a moiety of Formula XV-a, XV-b, XV-c, XV-d, XV-e, XV-f, or XV-g;

XV-a
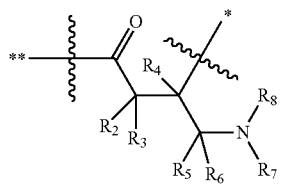

XV-b
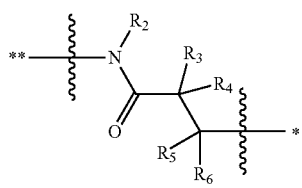

XV-c
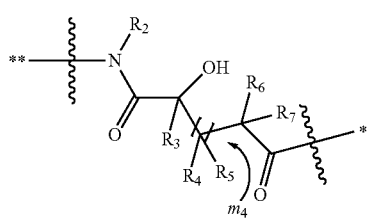

XV-d
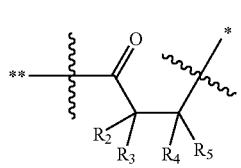

XV-e
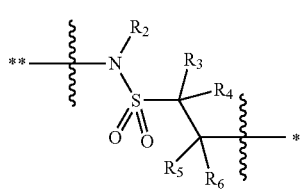

XV-f
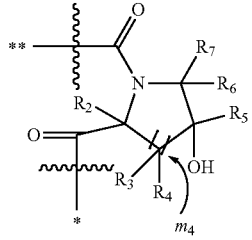

XV-g
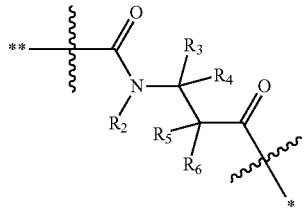

wherein
m₄ is an integer from 1 to 2;
each $R_2$, $R_3$, $R_4$, $R_5$ and $R_6$ is independently hydrogen or $C_1$-$C_6$ alkyl; wherein
optionally when proper any two of $R_2$, $R_3$, $R_4$, $R_5$ and $R_6$ can be linked together to form a 3- to 8-membered carbocyclic or heterocyclic ring; and
one or more methylene groups of the $C_1$-$C_6$ alkyl can be replaced by —NR₁—, —O—, —C(O)—, —S—, —SO—, —SO₂—, or —C(=S)—;
one or more methine groups of the $C_1$-$C_6$ alkyl, when present, can be independently replaced by

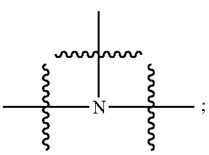 [SMILES: *N(*)*]

M is connected to the position of Y₁ labeled as "*"; and
Tether is connected to the position of Y₁ labeled as "**".
In some embodiments, the bivalent moiety of Formula XV-a, XV-b, XV-c, XV-d, XV-e, XV-f, or XV-g is a bivalent moiety of Formula XV-h, XV-i, XV-j, XV-k, XV-l, XV-m, XV-n, XV-o, XV-p, XV-q, XV-r, XV-s, or XV-t;

XV-h
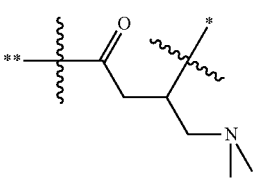

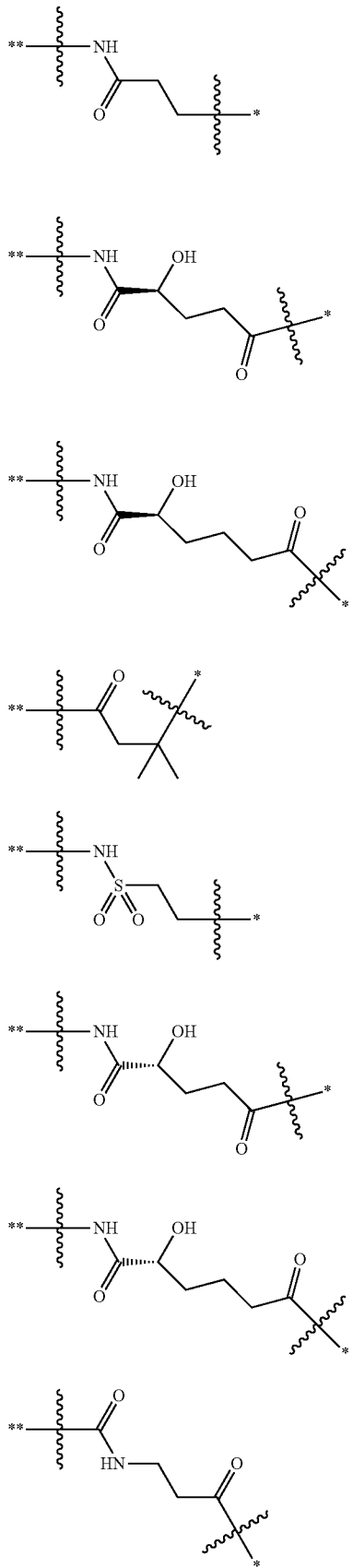

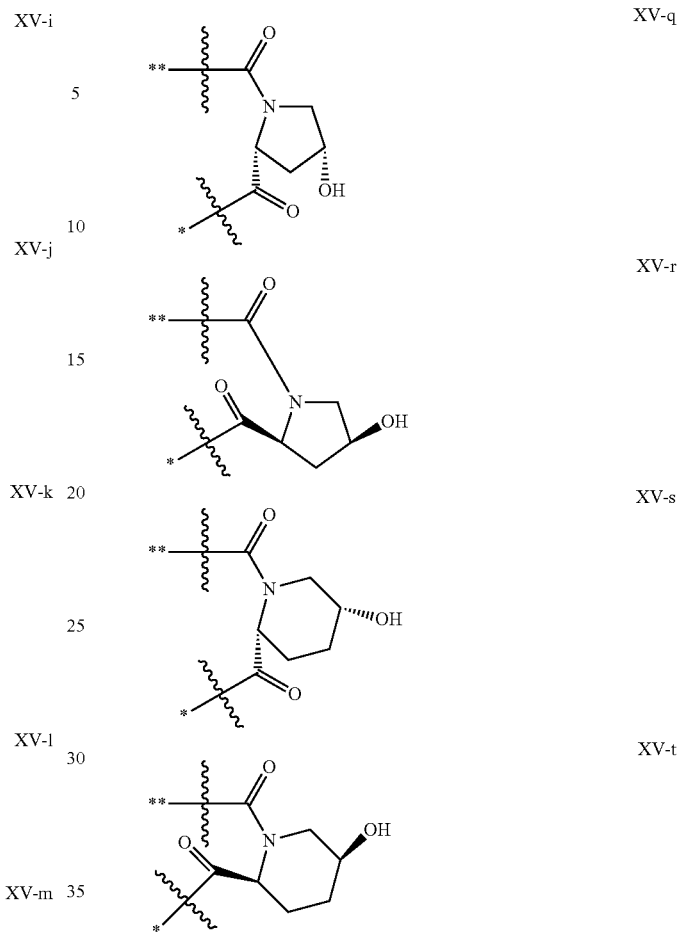

wherein

M is connected to the position of $Y_1$ labeled as "*"; and
Tether is connected to the position of $Y_1$ labeled as "**".

As defined generally above, $R_{wh}$ is a warhead group. Without wishing to be bound by any particular theory, it is believed that such $R_{wh}$ groups, i.e. warhead groups, are particularly suitable for covalently binding to a key lysine residue in the binding domain of, for example, but not limited to, XIAP, PDPK-1, HCV protease, and PI3K. One of ordinary skill in the art will appreciate that XIAP, PDPK-1, HCV protease, and PI3K, and mutants thereof, have at least one lysine residue in the binding domain of each protein.

In certain embodiments, compounds of the present invention have a warhead group characterized in that inventive compounds may target the K297 lysine residue of XIAP. In certain embodiments, compounds of the present invention have a warhead group characterized in that inventive compounds target the K86 lysine residue of PDPK-1. In certain embodiments, compounds of the present invention have a warhead group characterized in that inventive compounds target the K169 lysine residue of PDPK-1. In certain embodiments, compounds of the present invention have a warhead group characterized in that inventive compounds target the K173 lysine residue of PDPK-1. In other embodiments, compounds of the present invention have a warhead group characterized in that inventive compounds target the K136 lysine residue of HCV protease. In other embodiments, compounds of the present invention have a warhead group characterized in that inventive compounds target the K777 lysine residue of PI3Kβ. In other embodiments, compounds of the present invention have a warhead group characterized in that inventive compounds target the K802 lysine residue of PI3Kγ. In other embodiments, compounds of the present invention have a warhead group characterized in that inventive compounds target the K890 lysine residue of PI3Kγ.

Thus, in some embodiments, $R_{wh}$ is characterized in that the -T-$R_{wh}$ moiety is capable of covalently binding to a lysine residue thereby irreversibly inhibiting the enzyme.

According to another aspect, the present invention provides a conjugate comprising XIAP, or a mutant thereof, covalently bonded to an inhibitor at K297. In some embodiments, the inhibitor moiety is bonded via a linker moiety. In certain embodiments, the present invention provides a conjugate of the Formula K297-linker-inhibitor moiety. One of ordinary skill in the art will recognize that the "linker" group corresponds to a -T-$R_{wh}$ as described herein. Accordingly, in certain embodiments, the linker group is as defined for -T-$R_{wh}$ was defined above and described in classes and subclasses herein. It will be appreciated, however, that the linker group is bivalent and, therefore, the corresponding -T-$R_{wh}$ group is also intended to be bivalent resulting from the reaction of the warhead with the K297 of XIAP, or a mutant thereof.

In certain embodiments for XIAP, the inhibitor moiety is a compound of Formula A:

optionally $R_{21}$ and $R_{23}$ taken together can form a 4- to 8-membered carbocyclic or heterocyclic ring.

Thus, in certain embodiments, the present invention provides a conjugate of the formula:

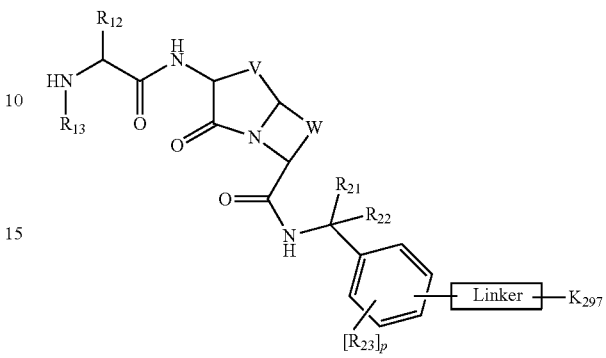

wherein $R_{12}$, $R_{13}$, $R_{21}$, $R_{22}$, $R_{23}$, V, W, and p are as defined above for formula A.

In certain embodiments, the inhibitor moiety is a compound of formula B:

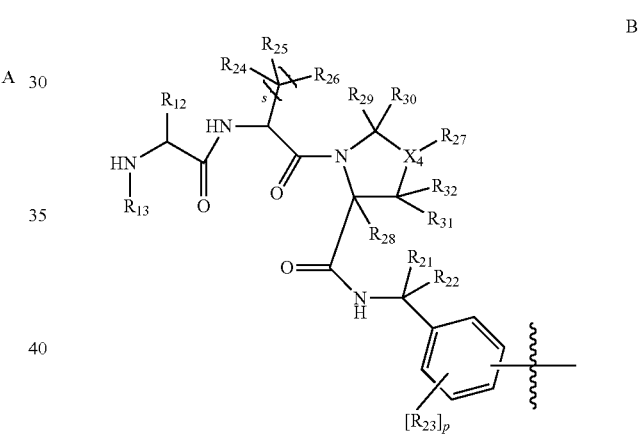

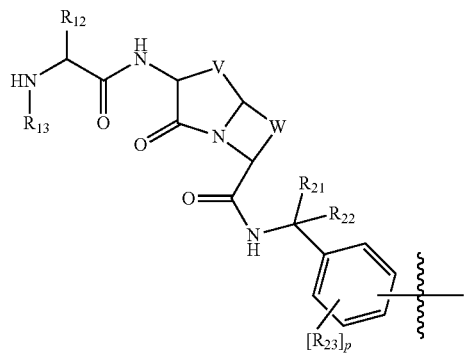

wherein
V and W are each independently —(CR$_{14}$R$_{15}$)$_q$X$_3$(CR$_{16}$R$_{17}$)$_r$—;
p, q and r are each independently 0, 1, 2, 3, or 4;
X$_3$ is —CR$_{18}$R$_{19}$—, or —NR$_{20}$—; and
R$_{21}$ and R$_{22}$ are each independently hydrogen or C$_1$-C$_6$ alkyl;
R$_{23}$ is hydrogen, C$_1$-C$_6$ alkyl, halogen, amino, or nitro; wherein one or more methylene groups of C$_1$-C$_6$ alkyl can be optionally replaced by —NR$_1$—, —O—, —C(O)—, —S—, —SO—, —SO$_2$—, or —C(=S)—; one or more methine groups of the C$_1$-C$_6$ alkyl, when present, can be independently replaced by wherein
X$_4$ is —CR$_{33}$— or —N—;
p and s are each independently 0, 1, 2, 3, or 4;
R$_{12}$, R$_{13}$, R$_{21}$, R$_{22}$, R$_{24}$, R$_{25}$, R$_{26}$, R$_{27}$, R$_{28}$, R$_{29}$, R$_{30}$, R$_{31}$, R$_{32}$, and R$_{33}$ are each independently hydrogen or C$_1$-C$_6$ alkyl;
R$_{23}$ is hydrogen, C$_1$-C$_6$ alkyl, halogen, amino, or nitro; wherein one or more methylene groups of C$_1$-C$_6$ alkyl can be optionally replaced by —NR$_1$—, —O—, —C(O)—, —S—, —SO—, —SO$_2$—, or —C(=S)—; one or more methine groups of the C$_1$-C$_6$ alkyl, when present, can be independently replaced by

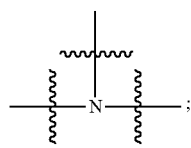

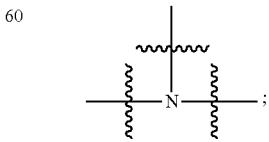

$R_1$ is hydrogen or C$_1$-C$_8$ alkyl; and $R_1$ is hydrogen or C$_1$-C$_8$ alkyl; and optionally $R_{21}$ and $R_{23}$ taken together can form a 4- to 8-membered carbocyclic or heterocyclic ring.

Thus, in certain embodiments, the present invention provides a conjugate of the formula:

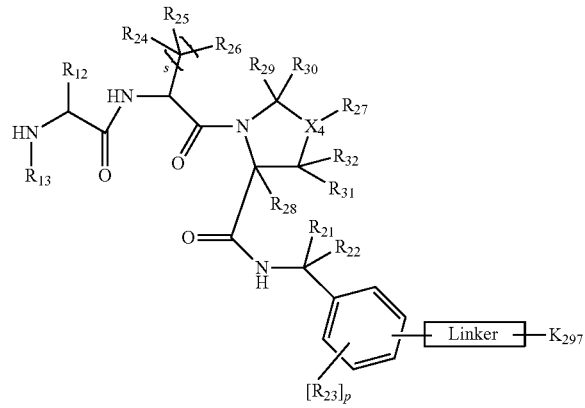

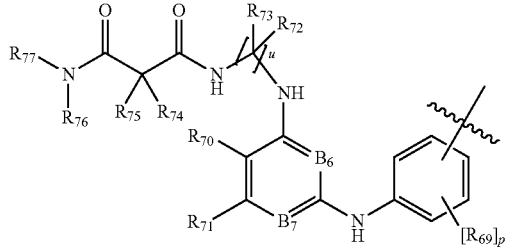

C wherein $X_4$, p, s, $R_{12}$, $R_{13}$, $R_{21}$, $R_{22}$, $R_{24}$, $R_{25}$, $R_{26}$, $R_{27}$, $R_{28}$, $R_{29}$, $R_{30}$, $R_{31}$, $R_{32}$, $R_{33}$, and $R_{23}$ are as defined above for Formula B.

PDPK-1

In certain embodiments, compounds of the present invention have a warhead group characterized in that inventive compounds target the K86 lysine residue of PDPK-1. In certain embodiments, compounds of the present invention have a warhead group characterized in that inventive compounds target the K169 lysine residue of PDPK-1. In certain embodiments, compounds of the present invention have a warhead group characterized in that inventive compounds target the K173 lysine residue of PDPK-1.

In some embodiments, $R_{wh}$ is characterized in that the -T-$R_{wh}$ moiety is capable of covalently binding to a lysine residue thereby irreversibly inhibiting the enzyme. In certain embodiments, the lysine residue is K86 lysine residue of PDPK-1, or a mutant thereof.

According to another aspect, the present invention provides a conjugate comprising PDPK-1, or a mutant thereof, covalently bonded to an inhibitor at K86. In some embodiments, the inhibitor is covalently bonded via a linker moiety.

In certain embodiments, the present invention provides a conjugate of the formula K86-linker-inhibitor moiety. In certain embodiments, the present invention provides a conjugate of the formula K169-linker-inhibitor moiety. In certain embodiments, the present invention provides a conjugate of the formula K173-linker-inhibitor moiety. One of ordinary skill in the art will recognize that the "linker" group corresponds to a -T-$R_{wh}$ as described herein. Accordingly, in certain embodiments, the linker group is as defined for -T-$R_{wh}$ was defined above and described in classes and subclasses herein. It will be appreciated, however, that the linker group is bivalent and, therefore, the corresponding -T-$R_{wh}$ group is also intended to be bivalent resulting from the reaction of the warhead with the K86, K169, or K173 of PDPK-1, or a mutant thereof.

In certain embodiments for PDPK-1, the inhibitor moiety is a compound of Formula C:

wherein $B_6$ and $B_7$ are each independently $CR_7$ or N;

$R_{69}$ is hydrogen, $C_1$-$C_6$ alkyl, halogen, amino, nitro, or —NH(CO)N$R_{78}R_{79}$;

$R_{70}$ is hydrogen, $C_1$-$C_6$ alkyl, halogen, amino, nitro;

$R_7$, $R_{71}$, $R_{72}$, $R_{73}$, $R_{74}$, $R_{75}$, $R_{76}$, $R_{77}$, $R_{78}$, and $R_{79}$ are each independently hydrogen or $C_1$-$C_6$ alkyl;

$R_1$ is hydrogen or $C_1$-$C_8$ alkyl; wherein one or more methylene groups of the $C_1$-$C_6$ alkyl can be replaced by —N$R_1$—, —O—, —C(O)—, —S—, —SO—, —SO$_2$—, or —C(=S)—; one or more methine groups of the $C_1$-$C_6$ alkyl, when present, can be independently replaced by

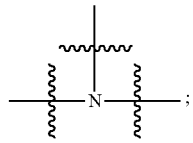

optionally $R_{78}$, and $R_{79}$ taken together form a 4- to 8-membered carbocyclic or heterocyclic ring; and p is an integer from 0 to 4, u is an integer from 1 to 4.

Thus, in certain embodiments, the present invention provides a conjugate of the formula:

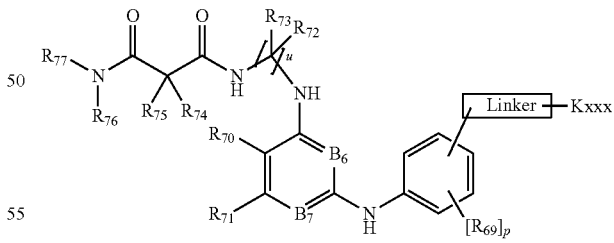

wherein $B_6$, $B_7$, $R_{69}$, $R_{70}$, $R_7$, $R_{71}$, $R_{72}$, $R_{73}$, $R_{74}$, $R_{75}$, $R_{76}$, $R_{77}$, $R_{78}$, $R_{79}$, $R_1$ and p are as defined above for Formula C and Kxxx is K86, K169, or K173.

In some embodiments, Kxxx is K86 of PDPK-1.

In some embodiments, Kxxx is K169 of PDPK-1.

In some embodiments, Kxxx is K173 of PDPK-1.

In certain embodiments for PDPK-1, the inhibitor moiety is a compound of Formula D:

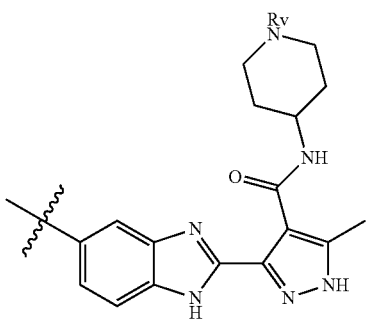

wherein $R_v$ is H, optionally substituted $C_1$-$C_3$ branched or straight chain alkyl, or optionally substituted $C_1$-$C_3$ branched or straight chain acyl.

Thus, in certain embodiments, the present invention provides a conjugate of the formula:

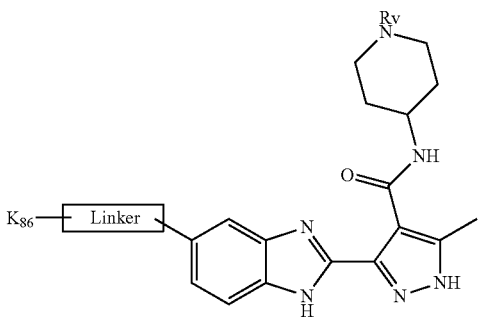

wherein $R_v$ is as defined above for Formula D.

Thus, in certain embodiments, the present invention provides a conjugate of the formula:

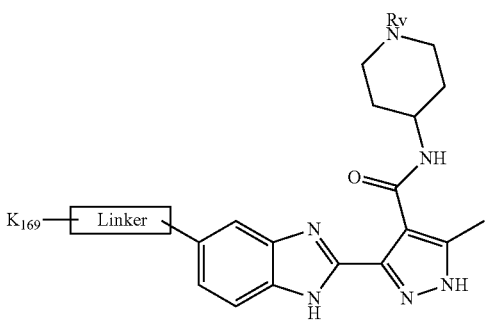

wherein $R_v$ is as defined above for Formula D.

Thus, in certain embodiments, the present invention provides a conjugate of the formula:

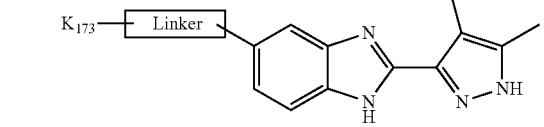

wherein $R_v$ is as defined above for Formula D.

HCV Protease

In certain embodiments, compounds of the present invention have a warhead group characterized in that inventive compounds target the K136 lysine residue of HCV protease.

In some embodiments, $R_{wh}$ is characterized in that the -T-$R_{wh}$ moiety is capable of covalently binding to a lysine residue thereby irreversibly inhibiting the enzyme. In certain embodiments, the lysine residue is K136 lysine residue of HCV protease, or a mutant thereof.

According to another aspect, the present invention provides a conjugate comprising HCV protease, or a mutant thereof, covalently bonded to an inhibitor at K136. In some embodiments, the inhibitor is covalently bonded via a linker moiety.

In certain embodiments, the present invention provides a conjugate of the formula K136-linker-inhibitor moiety. One of ordinary skill in the art will recognize that the "linker" group corresponds to a -T-$R_{wh}$ as described herein. Accordingly, in certain embodiments, the linker group is as defined for -T-$R_{wh}$ was defined above and described in classes and subclasses herein. It will be appreciated, however, that the linker group is bivalent and, therefore, the corresponding -T-$R_{wh}$ group is also intended to be bivalent resulting from the reaction of the warhead with the K136 of HCV protease, or a mutant thereof.

In certain embodiments for HCV protease, the inhibitor moiety is a compound of E, F, or G:

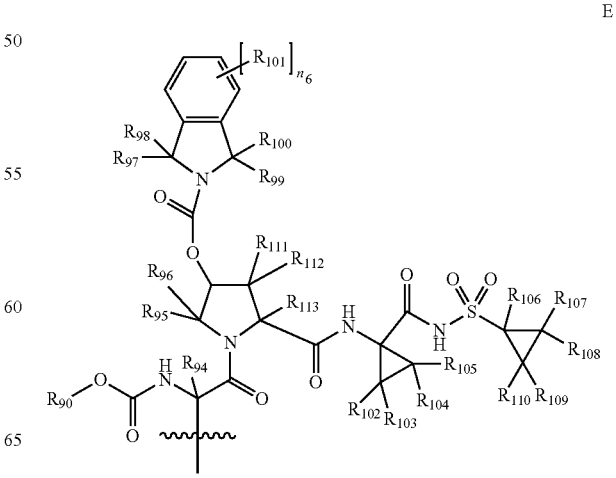

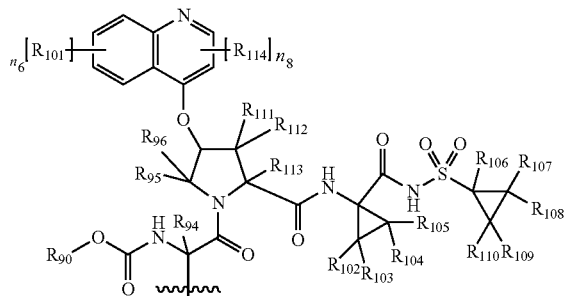

F

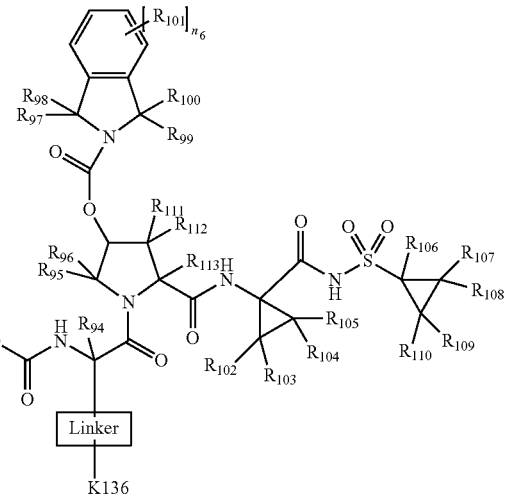

G where $R_1$, $R_{90}$, $R_{94}$, $R_{95}$, $R_{96}$, $R_{97}$, $R_{98}$, $R_{99}$, $R_{100}$, $R_{101}$, $R_{102}$, $R_{103}$, $R_{104}$, $R_{105}$, $R_{106}$, $R_{107}$, $R_{108}$, $R_{109}$, $R_{110}$, $R_{111}$, $R_{112}$, $R_{113}$, $R_{114}$, $n_6$, and $n_8$ are as defined above for Formula E.

Thus, in certain embodiments, the present invention provides a conjugate of the formula:

wherein $R_{90}$, $R_{94}$, $R_{95}$, $R_{96}$, $R_{97}$, $R_{98}$, $R_{99}$, $R_{100}$, $R_{102}$, $R_{104}$, $R_{105}$, $R_{106}$, $R_{107}$, $R_{108}$, $R_{109}$, $R_{110}$, $R_{111}$, $R_{112}$, $R_{113}$, and $R_{114}$ are each independently hydrogen or $C_1$-$C_6$ alkyl; wherein one or more methylene groups of $C_1$-$C_6$ alkyl can be optionally replaced by —$NR_1$—, —O—, —C(O)—, —S—, —SO—, —$SO_2$—, or —C(=S)—;

$R_{103}$ is hydrogen, $C_1$-$C_6$ alkyl, or $C_2$-$C_8$ alkenyl;

one or more methine groups of the $C_1$-$C_6$ alkyl, when present, can be independently replaced by

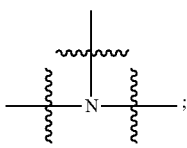 [SMILES: *N(*)*]

$R_1$ is hydrogen or $C_1$-$C_8$ alkyl;

each $R_{101}$ is independently hydrogen, $C_1$-$C_6$ alkyl, $C_2$-$C_8$ alkenyl, halogen, amino, nitro, optionally substituted aryl or heteroaryl; $n_6$ is an integer from 0 to 4; and $n_8$ is an integer from 0 to 2.

Thus, in certain embodiments, the present invention provides a conjugate of the formula:

where $R_1$, $R_{90}$, $R_{94}$, $R_{95}$, $R_{96}$, $R_{97}$, $R_{98}$, $R_{99}$, $R_{100}$, $R_{101}$, $R_{102}$, $R_{103}$, $R_{104}$, $R_{105}$, $R_{106}$, $R_{107}$, $R_{108}$, $R_{109}$, $R_{110}$, $R_{111}$, $R_{112}$, $R_{113}$, $R_{114}$, $n_6$, and $n_8$ are as defined above for Formula F.

Thus, in certain embodiments, the present invention provides a conjugate of the formula:

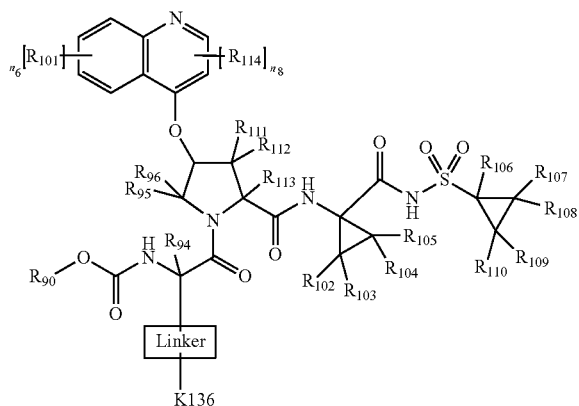

where $R_1$, $R_{90}$, $R_{94}$, $R_{95}$, $R_{96}$, $R_{97}$, $R_{98}$, $R_{99}$, $R_{100}$, $R_{101}$, $R_{102}$, $R_{103}$, $R_{104}$, $R_{105}$, $R_{106}$, $R_{107}$, $R_{108}$, $R_{109}$, $R_{110}$, $R_{111}$, $R_{112}$, $R_{113}$, $R_{114}$, $n_6$, and $n_8$ are as defined above for Formula G.

PI3K

In certain embodiments, compounds of the present invention have a warhead group characterized in that inventive compounds target the K777 lysine residue of PI3Kβ. In certain embodiments, compounds of the present invention have a warhead group characterized in that inventive compounds target the K802 lysine residue of PI3Kγ. In certain embodiments, compounds of the present invention have a warhead group characterized in that inventive compounds target the K890 lysine residue of PI3Kγ.

In some embodiments, $R_{wh}$ is characterized in that the -T-$R_{wh}$ moiety is capable of covalently binding to a lysine residue thereby irreversibly inhibiting the enzyme. In certain embodiments, the lysine residue is K777 lysine residue of PI3Kβ, or a mutant thereof.

According to another aspect, the present invention provides a conjugate comprising PI3Kβ, or a mutant thereof, covalently bonded to an inhibitor at K777. In some embodiments, the inhibitor is covalently bonded via a linker moiety.

In certain embodiments, the present invention provides a conjugate of the formula K777-linker-inhibitor moiety. In certain embodiments, the present invention provides a conjugate of the formula K802-linker-inhibitor moiety. In certain embodiments, the present invention provides a conjugate of the formula K890-linker-inhibitor moiety. One of ordinary skill in the art will recognize that the "linker" group corresponds to a -T-$R_{wh}$ as described herein. Accordingly, in certain embodiments, the linker group is as defined for -T-$R_{wh}$ was defined above and described in classes and subclasses herein. It will be appreciated, however, that the linker group is bivalent and, therefore, the corresponding -T-$R_{wh}$ group is also intended to be bivalent resulting from the reaction of the warhead with the K777 of PI3Kβ, or from the reaction of the warhead with the K802 or K890 of PI3Kγ, or a mutant thereof.

In certain embodiments for PI3K, the inhibitor moiety is a compound of Formula H, J or K:

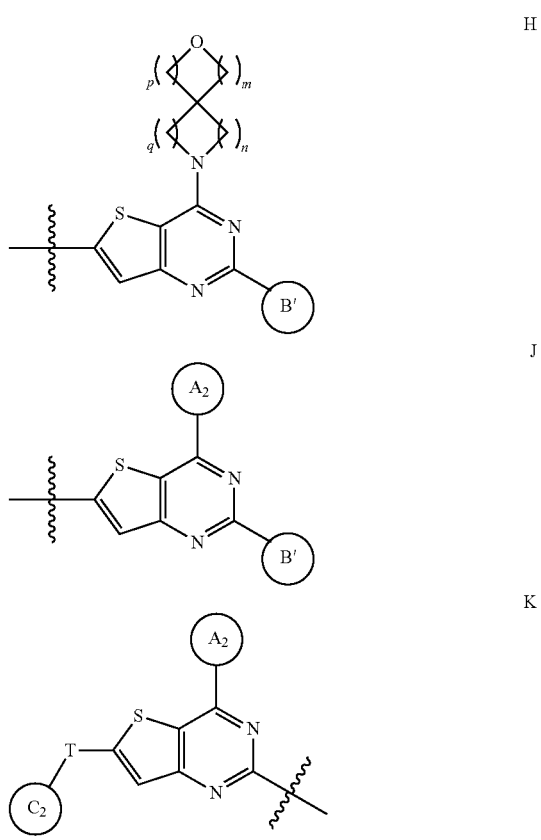

wherein
n, m, p, and q are each independently 0, 1, 2, 3; provided that n and q are not 0 at the same time, and m and q are not 0 at the same time;

$A^2$ is an optionally substituted ring selected from a 4-8 membered saturated or partially unsaturated heterocyclic ring having one or two heteroatoms independently selected from nitrogen, oxygen, or sulfur, or a 5-10 membered saturated or partially unsaturated bridged bicyclic heterocyclic ring having at least one nitrogen, at least one oxygen, and optionally 1-2 additional heteroatoms independently selected from nitrogen, oxygen, or sulfur;

B' is an optionally substituted group selected from phenyl, an 8- to 10-membered bicyclic aryl ring, a 5- to 6-membered heteroaryl ring having 1-4 heteroatoms independently selected from nitrogen, oxygen, or sulfur, or an 8- to 10-membered bicyclic heteroaryl ring having 1-4 heteroatoms independently selected from nitrogen, oxygen, or sulfur; or -T-Rwh; and $C^2$ is hydrogen or an optionally substituted ring selected from a 3- to 7-membered saturated or partially unsaturated carbocyclic ring, a 7- to 10-membered saturated or partially unsaturated bicyclic carbocyclic ring, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, an 8- to 10-membered bicyclic aryl ring, a 5- to 6-membered heteroaryl ring having 1-3 heteroatoms independently selected from nitrogen, oxygen, or sulfur, or an 8- to 10-membered bicyclic heteroaryl ring having 1-4 heteroatoms independently selected from nitrogen, oxygen, or sulfur.

Thus, in certain embodiments, the present invention provides a conjugate of the formula:

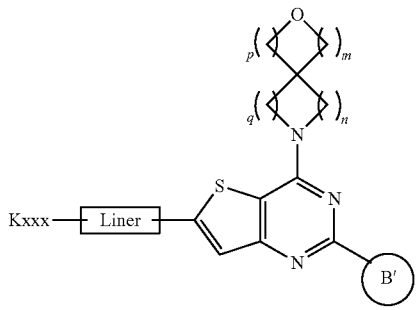

wherein m, n, o, p and B' are as defined above for Formula H, and Kxxx is K777 of PI3Kβ, or K802 or K890 of PI3Kγ.

In some embodiments, Kxxx is K777 of PI3Kβ.

In some embodiments, Kxxx is K802 of PI3Kγ.

In other embodiments, Kxxx is K890 of PI3Kγ.

Thus, in certain embodiments, the present invention provides a conjugate of the formula:

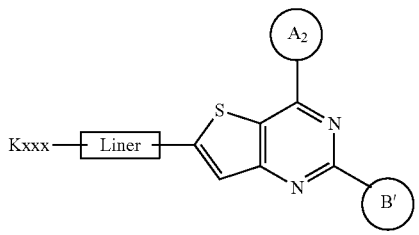

wherein B' and $A_2$ are as defined above for Formula J, and $K_{xxx}$ is K777 of PI3Kβ, or K802 or K890 of PI3Kγ.

In some embodiments, Kxxx is K777 of PI3Kβ.

In some embodiments, Kxxx is K802 of PI3Kγ.

In other embodiments, Kxxx is K890 of PI3Kγ.

Thus, in certain embodiments, the present invention provides a conjugate of the formula:

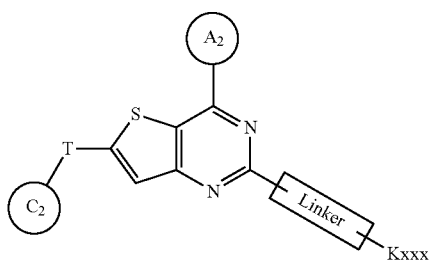

wherein $A_2$ and $C_2$ are as defined above for Formula K, and $K_{xxx}$ is K777 of PI3Kβ, or K802 or K890 of PI3Kγ.

In some embodiments, Kxxx is K777 of PI3Kβ.

In some embodiments, Kxxx is K802 of PI3Kγ.

In other embodiments, Kxxx is K890 of PI3Kγ.

In certain embodiments for PI3K, the inhibitor moiety is a compound of Formula L or M:

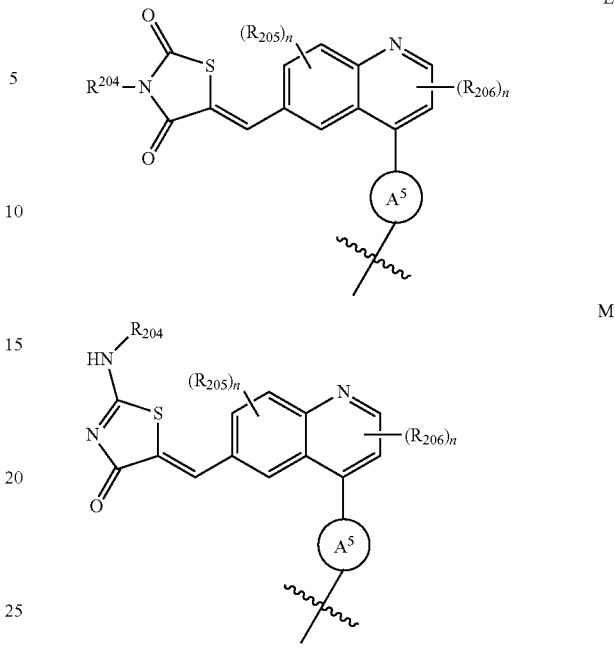

wherein $R_{204}$ is an hydrogen or an optionally substituted group selected from $C_{1-6}$ aliphatic, —$(CH_2)_m$-(3- to 7-membered saturated or partially unsaturated carbocyclic ring), —$(CH_2)_m$-(7- to 10-membered saturated or partially unsaturated bicyclic carbocyclic ring), —$(CH_2)_m$-(4- to 7-membered saturated or partially unsaturated heterocyclic ring having 1-2 heteroatoms independently selected from nitrogen, oxygen, or sulfur), —$(CH_2)_m$-(7- to 10-membered saturated or partially unsaturated bicyclic heterocyclic ring having 1-3 heteroatoms independently selected from nitrogen, oxygen, or sulfur), —$(CH_2)_m$-phenyl, —$(CH_2)_m$-(8- to 10-membered bicyclic aryl ring), —$(CH_2)_m$-(5- to 6-membered heteroaryl ring having 1-3 heteroatoms independently selected from nitrogen, oxygen, or sulfur), or —$(CH_2)_m$-(8- to 10-membered bicyclic heteroaryl ring having 1-4 heteroatoms independently selected from nitrogen, oxygen, or sulfur);

each $R_{205}$ and $R_{206}$ is independently —R", halogen, —$NO_2$, —CN, —OR", —SR", —N(R")$_2$, —C(O)R", —$CO_2$R", —C(O)C(O)R", —C(O)CH$_2$C(O)R", —S(O)R", —S(O)$_2$R", —C(O)N(R")$_2$, —SO$_2$N(R")$_2$, —OC(O)R", —N(R")C(O)R", —N(R")N(R")$_2$, —N(R")C(=NR") N(R")$_2$, —C(=NR")N(R")$_2$, —C=NOR", —N(R")C(O)N (R")$_2$, —N(R")SO$_2$N(R")$_2$, —N(R")SO$_2$R", or —OC(O)N (R")$_2$;

each R" is independently hydrogen or an optionally substituted group selected from $C_{1-6}$ aliphatic, a 3- to 7-membered saturated or partially unsaturated carbocyclic ring, a 7- to 10-membered saturated or partially unsaturated bicyclic carbocyclic ring, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, an 8- to 10-membered bicyclic aryl ring, a 5- to 6-membered heteroaryl ring having 1-3 heteroatoms independently selected from nitrogen, oxygen, or sulfur, or an 8- to 10-membered bicyclic heteroaryl ring having 1-4 heteroatoms independently selected from nitrogen, oxygen, or sulfur; or two R" groups on the same nitrogen are taken together with the nitrogen to which they are attached to form an optionally substituted 5-8 membered saturated, partially unsaturated, or aromatic ring having 1-4 heteroatoms independently selected from nitrogen, oxygen, or sulfur;

m is an integer from 0 to 6, inclusive;

each n is independently 0, 1, or 2; and

Ring $A^5$ is an optionally substituted 6-membered heterocyclic or heteroaryl ring having 1-2 nitrogens.

Thus, in certain embodiments, the present invention provides a conjugate of the formula:

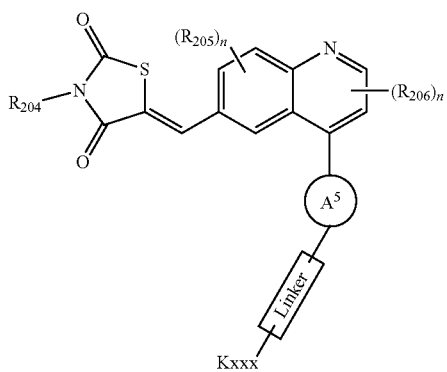

wherein $R_{204}$, $R_{205}$, $R_{206}$, n, and $A^5$ defined as above for Formula L and $K_{xxx}$ is K777 of PI3Kβ, or K802 or K890 of PI3Kγ.

In some embodiments, $K_{xxx}$ is K777 of PI3Kβ.

In some embodiments, $K_{xxx}$ is K802 of PI3Kγ.

In other embodiments, $K_{xxx}$ is K890 of PI3Kγ.

Thus, in certain embodiments, the present invention provides a conjugate of the formula:

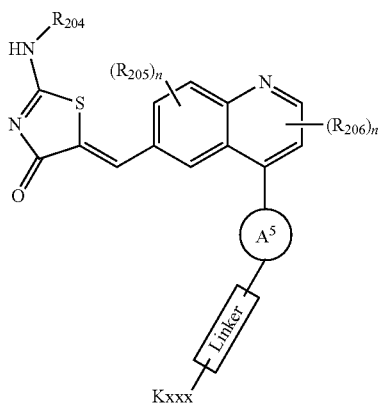

wherein $R_{204}$, $R_{205}$, $R_{206}$, n, and $A^5$ defined as above for Formula M and $K_{xxx}$ is K777 of PI3Kβ, or K802 or K890 of PI3Kγ.

In some embodiments, Kxxx is K777 of PI3Kβ.

In some embodiments, Kxxx is K802 of PI3Kγ.

In other embodiments, Kxxx is K890 of PI3Kγ.

In certain embodiments for PI3K, the inhibitor moiety is a compound of Formula N:

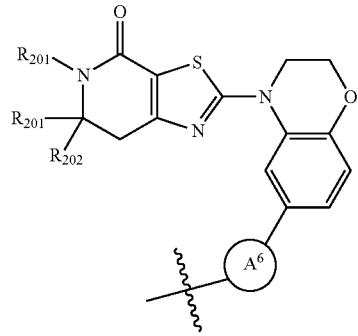

wherein:

$R_{201}$ is hydrogen or $C_{1-6}$ alkyl;

$R_{202}$ is hydrogen or an optionally substituted group selected from $C_{1-6}$ alkyl, $C_{1-6}$ alkoxy, or $(C_{1-6}$ alkylene)-$R_{203}$; or $R_{201}$ and $R_{202}$ are taken together with the intervening carbon to form an optionally substituted ring selected from a 3- to 7-membered carbocyclic ring or a 4- to 7-membered heterocyclic ring having 1-2 heteroatoms independently selected from nitrogen, oxygen, or sulfur;

$R_{203}$ is a 3- to 7-membered saturated or partially unsaturated carbocyclic ring, a 7- to 10-membered saturated or partially unsaturated bicyclic carbocyclic ring, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, a 8- to 10-membered bicyclic aryl ring, a 5- to 6-membered heteroaryl ring having 1-3 heteroatoms independently selected from nitrogen, oxygen, or sulfur, or a 8- to 10-membered bicyclic heteroaryl ring having 1-4 heteroatoms independently selected from nitrogen, oxygen, or sulfur; and Ring $A^6$ is absent or an optionally substituted group selected from a 4- to 7-membered heterocyclic ring having 1-2 heteroatoms independently selected from nitrogen, oxygen, or sulfur, or a 5- to 6-membered heteroaryl ring having 1-3 heteroatoms independently selected from nitrogen, oxygen, or sulfur.

Thus, in certain embodiments, the present invention provides a conjugate of the formula:

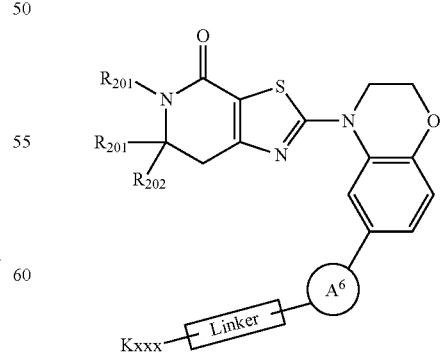

wherein $R_{201}$, $R_{202}$, $R_{203}$ and $A^6$ are as defined above for Formula N, and Kxxx is K777 of PI3Kβ, or K802 or K890 of PI3Kγ.

In some embodiments, Kxxx is K777 of PI3Kβ.

In some embodiments, Kxxx is K802 of PI3Kγ.

In other embodiments, Kxxx is K890 of PI3Kγ.

In certain embodiments for PI3K, the inhibitor moiety is a compound of Formula O:

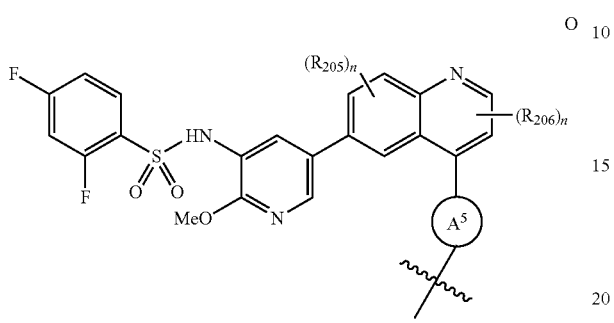

wherein each $R_{205}$ and $R_{206}$ is independently —R″, halogen, —NO$_2$, —CN, —OR″, —SR″, —N(R″)$_2$, —C(O)R″, —CO$_2$R″, —C(O)C(O)R″, —C(O)CH$_2$C(O)R″, —S(O)R″, —S(O)$_2$R″, —C(O)N(R″)$_2$, —SO$_2$N(R″)$_2$, —OC(O)R″, —N(R″)C(O)R″, —N(R″)N(R″)$_2$, —N(R″)C(=NR″)N(R″)$_2$, —C(=NR″)N(R″)$_2$, —C=NOR″, —N(R″)C(O)N(R″)$_2$, —N(R″)SO$_2$N(R″)$_2$, —N(R″)SO$_2$R″, or —OC(O)N(R″)$_2$;

each R″ is independently hydrogen or an optionally substituted group selected from $C_{1-6}$ aliphatic, a 3- to 7-membered saturated or partially unsaturated carbocyclic ring, a 7- to 10-membered saturated or partially unsaturated bicyclic carbocyclic ring, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, an 8- to 10-membered bicyclic aryl ring, a 5- to 6-membered heteroaryl ring having 1-3 heteroatoms independently selected from nitrogen, oxygen, or sulfur, or an 8- to 10-membered bicyclic heteroaryl ring having 1-4 heteroatoms independently selected from nitrogen, oxygen, or sulfur; or optionally, two R″ groups on the same nitrogen are taken together with the nitrogen to which they are attached to form an optionally substituted 5-8 membered saturated, partially unsaturated, or aromatic ring having 1-4 heteroatoms independently selected from nitrogen, oxygen, or sulfur;

m is an integer from 0 to 6, inclusive;

each n is independently 0, 1, or 2; and

Ring $A^5$ is an optionally substituted 6-membered heterocyclic or heteroaryl ring having 1-2 nitrogens.

Thus, in certain embodiments, the present invention provides a conjugate of the formula:

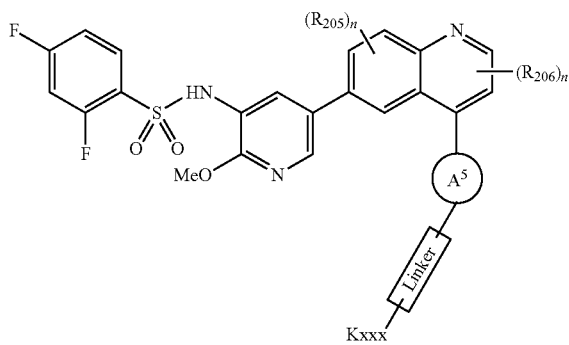

wherein $R_{205}$, $R_{206}$, n and $A^5$ are as defined above for formula O, and Kxxx is K777 of PI3Kβ, or K802 or K890 of PI3Kγ.

In some embodiments, Kxxx is K777 of PI3Kβ.

In some embodiments, Kxxx is K802 of PI3Kγ.

In other embodiments, Kxxx is K890 of PI3Kγ.

In certain embodiments for PI3K, the inhibitor moiety is a compound of Formula P:

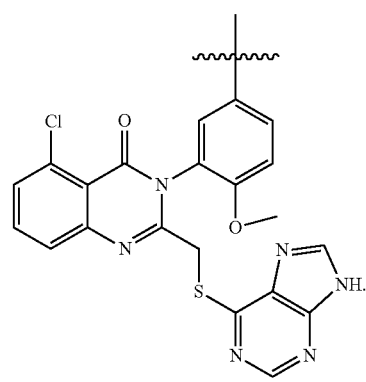

Thus, in certain embodiments, the present invention provides a conjugate of the formula:

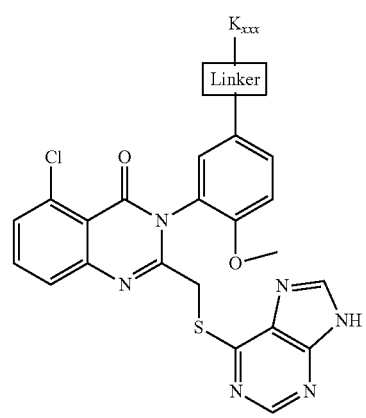

wherein $K_{xxx}$ is K777 of PI3Kβ, or K802 or K890 of PI3Kγ.

In some embodiments, Kxxx is K777 of PI3Kβ.

In some embodiments, Kxxx is K802 of PI3Kγ.

In other embodiments, Kxxx is K890 of PI3Kγ.

As used herein, the term "inhibitor moiety" refers to a Scaffold group that binds in the active site of a protein. Such Scaffold groups are well known in the art and include those described in, for example, but not limited to, Formulae VII, VIII, IX-a, IX-b, XI, XII, XVI, XVII, XVIII, XIX, XX, XXI, XXII, XXIII, XXXIV, XXV, XXVI, XXVII, XXVIII, XXIX, XXXVI, and XXXVII.

One of ordinary skill in the art will recognize that certain compounds described herein are reversible inhibitors. In certain embodiments, such compounds are useful as assay comparator compounds. In some embodiments, such reversible compounds are useful as inhibitors of the proteins disclosed herein, or a mutants thereof, and are therefore useful for treating one or more disorders as described herein. In some embodiments, provided compounds are reversible counterparts of provided irreversible inhibitors.

A. Truncation of Pharmacophores

In some embodiments, when truncating a pharmacophore, the key elements of the pharmacophore required for non-covalent binding to the target protein are retained. Whether the key elements of the pharmacophore are retained for binding is demonstrated when the non-covalent affinity conferred by the Scaffold is sufficient to further confer selective binding of the ligand and also covalent bonding.

1. The Pharmacophore is GDC-0941

Non-limiting examples of Scaffolds derived from the truncation of a pharmacophore, as described in the present disclosure, are set forth below in Formulas XXX, XXXI, XXXII, XXXIII, XXXIV, and XXXV.

In Formulas XXX, XXXI, and XXXII, the Scaffolds are based on truncating the pharmacophore GDC-0941:

GDC-0941

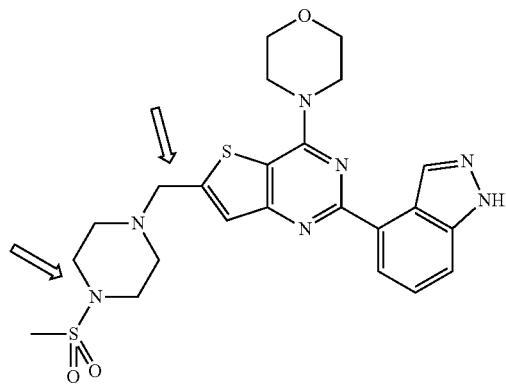

wherein the arrows indicate the possible sites of truncation.

One non-limiting example of a truncated form of GDC-0941 is described by Formula XXX:

Formula XXX

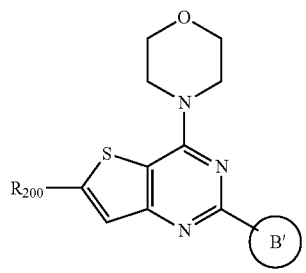

wherein $R_{200}$ is located at the site of truncation and is -Tether-$R_{wh}$, where Tether and $R_{wh}$ are as defined for Formula I; and Ring B' is an optionally substituted group selected from phenyl, an 8- to 10-membered bicyclic aryl ring, a 5- to 6-membered heteroaryl ring having 1-4 heteroatoms independently selected from nitrogen, oxygen, or sulfur, or an 8- to 10-membered bicyclic heteroaryl ring having 1-4 heteroatoms independently selected from nitrogen, oxygen, or sulfur.

Non-limiting examples of Scaffold of the Formula XXX above are set forth below:

XXII-1

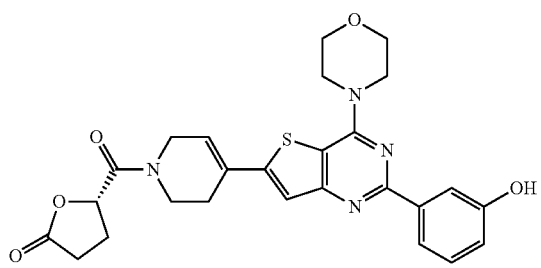

XXII-2

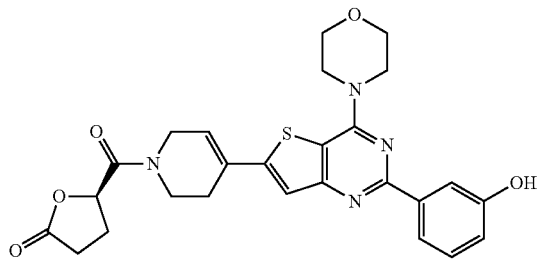

XXII-5

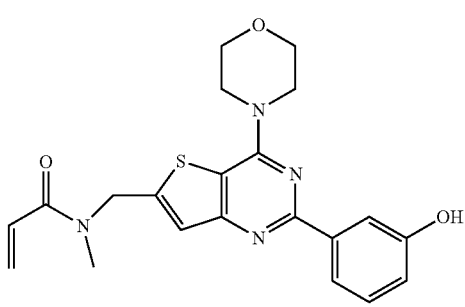

-continued

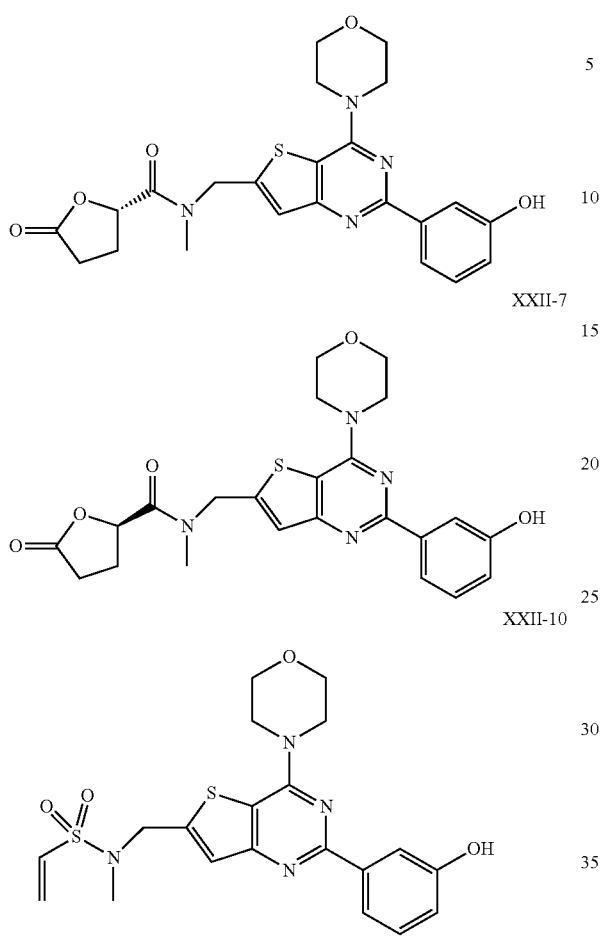

XXII-6

XXII-7

XXII-10

Another non-limiting example of a Scaffold that has been truncated as described in the present disclosure is set forth below in Formula XXXI:

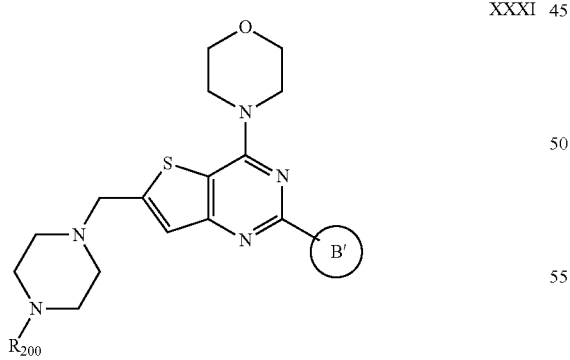

XXXI wherein

R$_{200}$ is located at the site of truncation and is -Tether-R$_{WH}$, where Tether and R$_{wh}$ are as defined in Formula I; and Ring B' is an optionally substituted group selected from phenyl, an 8- to 10-membered bicyclic aryl ring, a 5- to 6-membered heteroaryl ring having 1-4 heteroatoms independently selected from nitrogen, oxygen, or sulfur, or an 8- to 10-membered bicyclic heteroaryl ring having 1-4 heteroatoms independently selected from nitrogen, oxygen, or sulfur.

Non-limiting examples of Scaffolds of the Formula XXXI above are set forth below:

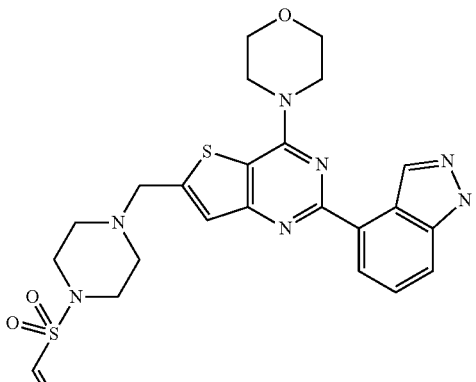

XXII-8

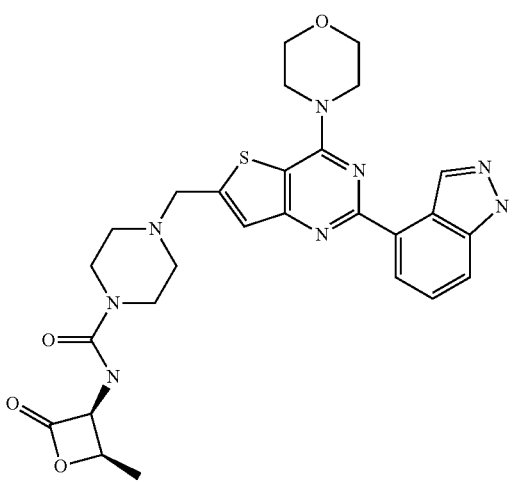

XXII-13

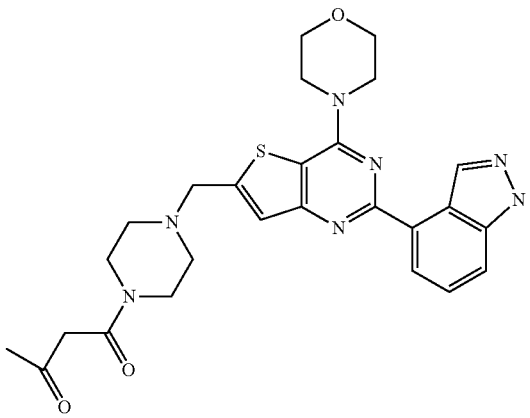

XXII-14

-continued

XXII-15

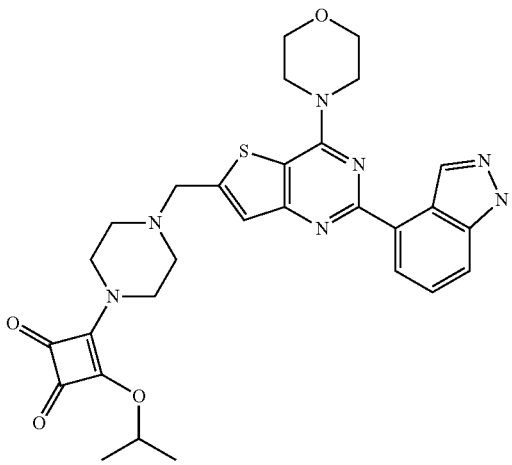

XXII-16

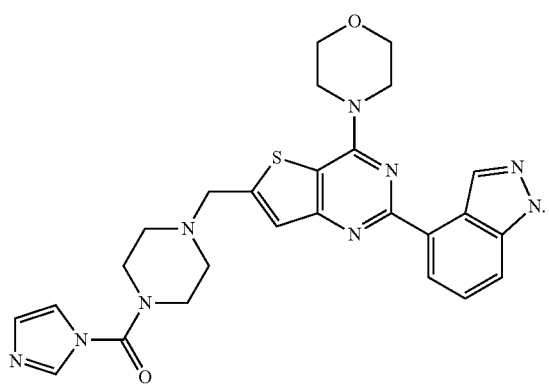

Another non-limiting example of a Scaffold that has been truncated as described in the present disclosure is set forth below in Formula XXXII:

XXXII

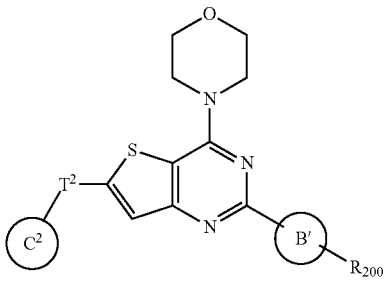

wherein $R_{200}$ is at the site of truncation and is -Tether-$R_{WH}$, where Tether and $R_{wh}$ are as defined above in the embodiments of Formula I;

$T^2$ is a covalent bond or a bivalent straight or branched, saturated or unsaturated $C_{1-6}$ hydrocarbon chain wherein one or more methylene units of $T^2$ are optionally replaced by —O—, —S, —N($R_1$)—, —C(O)—, —OC(O)—, —C(O)O—, —C(O)N($R_1$)—, —N($R_1$)C(O)—, —N($R_1$)C(O)N($R_1$)—, —SO$_2$—, —SO$_2$N($R_1$)—, —N($R_1$)SO$_2$—, or —N($R_1$)SO$_2$N($R_1$)—;

$C^2$ is hydrogen or an optionally substituted ring selected from a 3- to 7-membered saturated or partially unsaturated carbocyclic ring, a 7- to 10-membered saturated or partially unsaturated bicyclic carbocyclic ring, a 4- to 7-membered saturated or partially unsaturated heterocyclic ring having 1-2 heteroatoms independently selected from nitrogen, oxygen, or sulfur, a 7- to 10-membered saturated or partially unsaturated bicyclic heterocyclic ring having 1-3 heteroatoms independently selected from nitrogen, oxygen, or sulfur, phenyl, an 8- to 10-membered bicyclic aryl ring, a 5- to 6-membered heteroaryl ring having 1-3 heteroatoms independently selected from nitrogen, oxygen, or sulfur, or an 8- to 10-membered bicyclic heteroaryl ring having 1-4 heteroatoms independently selected from nitrogen, oxygen, or sulfur; and B' is an optionally substituted group selected from phenyl, an 8- to 10-membered bicyclic aryl ring, a 5- to 6-membered heteroaryl ring having 1-4 heteroatoms independently selected from nitrogen, oxygen, or sulfur, or an 8- to 10-membered bicyclic heteroaryl ring having 1-4 heteroatoms independently selected from nitrogen, oxygen, or sulfur.

Non-limiting examples of Scaffolds of the Formula XXXII above include:

XXII-20

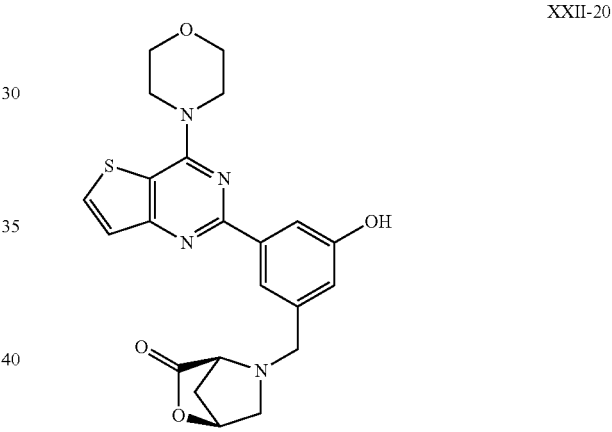

XXII-21

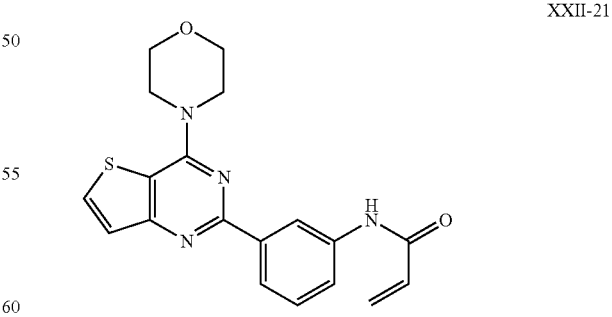

2. Scaffolds of Formula XXXIII Through the Truncation of Dihydroimidazoquinazoline:

In another embodiment, the Scaffolds described by Formula XXXIII are based on truncating the pharmacophore dihydroimidazoquinazoline:

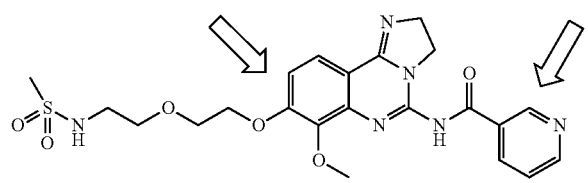 [SMILES: COc1c(OCCOCCNS(C)(=O)=O)ccc2c1N=C(NC(=O)c1cccnc1)N1CCN=C21]

wherein the arrows indicate the possible sites of truncation.

Another non-limiting example of a Scaffold that has been truncated as described in the present disclosure is set forth below in Formula XXXIII

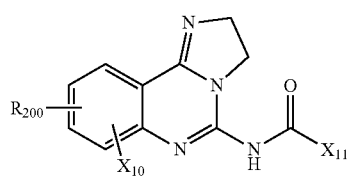

XXXIII wherein $R_{200}$ is at the site of truncation and is -Tether-$R_{WH}$, where Tether and $R_{wh}$ are as defined previously;

$X_{10}$ is hydrogen, alkoxy, heterocycloalkyl, heterocycloalkoxy;

$X_{11}$ is an optionally substituted group selected from phenyl, an 8- to 10-membered bicyclic aryl ring, a 5- to 6-membered heteroaryl ring having 1-4 heteroatoms independently selected from nitrogen, oxygen, or sulfur, or an 8- to 10-membered bicyclic heteroaryl ring having 1-4 heteroatoms independently selected from nitrogen, oxygen, or sulfur.

3. IAP Scaffolds of Formula XXXIV and Formula XXXV Through the Truncation of SM-337 and SM-122

In another embodiment, the Scaffolds described by Formula XXXIV and Formula XXXV are based on truncating the pharmacophore SM-337 and SM-122.

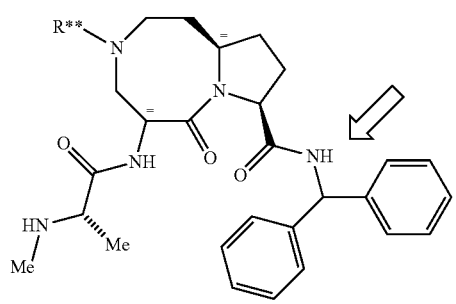

SM-337

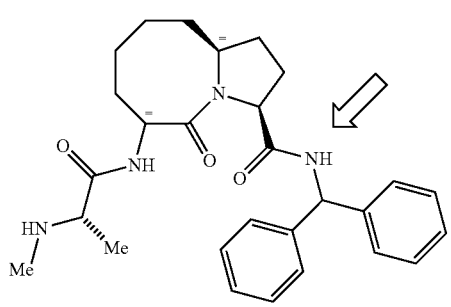

SM-122 wherein the arrows indicate the possible sites of truncation; and R** is phenylacetamide.

Compounds of the truncated form of SM-337 are described by the formula XXXIV:

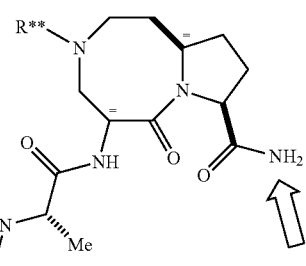

XXXIV wherein R** is phenylacetamide and the arrow denotes the site of attachment for T-$R_{WH}$, both of which are as described herein.

Compounds of the truncated form of SM-122 are described by the formula XXXV:

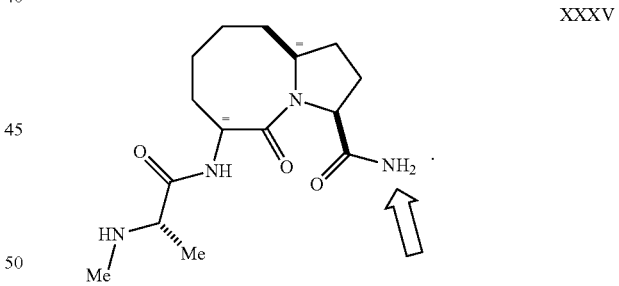

XXXV wherein the arrow denotes the site of attachment of T-$R_{wh}$; where T is Tether; and $R_{wh}$ is Warhead, both of which are as defined herein.

B. Methods of Using

1. IAP

X-linked Inhibitor of Apoptosis Protein (XIAP) is a member of the inhibitor of apoptosis family of proteins (IAP). Other family members of IAP include cIAP1, cIAP2 and ML-IAP. IAPs were initially identified in baculoviruses, but XIAP is one of the homologous proteins found in mammals. It is so called because it was first discovered by a 273 base pair site on the X chromosome.

Deregulation of XIAP can result in cancer, neurodegenerative disorders, and autoimmunity. High proportions of XIAP may function as a tumor marker. In the development of lung cancer NCI-H460, the overexpression of XIAP not only inhibits caspase, but also stops the apoptotic activity of cytochrome c (Apoptosis). In developing prostate cancer, XIAP is one of four IAPs overexpressed in the prostatic epithelium, indicating that a molecule that inhibits all IAPs may be necessary for effective treatment.

Among the diseases and disorders associated with XIAP deregulation include, but are not limited to, acute myelogenous leukemia (AML), Addison's disease, adrenoleukodystrophy (ALD), alcoholism, Alexander's disease, alopecia greata, Alper's disease, Alzheimer's disease, amyotrophic lateral sclerosis (Lou Gehrig's Disease), angiitis, ankylosing spondylitis, antiphospholipid syndrome, ataxia telangiectasia, autism, autoimmune haemolytic anaemia, autoimmune hepatitis, Batten disease (also known as Spielmeyer-Vogt-Sjögren-Batten disease), Behcet's syndrome, Berger's disease, bovine spongiform encephalopathy (BSE), bullous pemphigoid, Canavan disease, cardiomyopathy, Chagas disease, chronic fatigue syndrome (CFS, CFIDS), chronic inflammatory polyneuropathy, chronic obstructive pulmonary disease, Churg-Strauss syndrome, Cockayne syndrome, coeliac disease, corticobasal degeneration, CREST syndrome, Creutzfeldt-Jakob disease, Crohns Disease (one of two types of idiopathic inflammatory bowel disease or IBD), dermatomyositis, diabetes mellitus type 1, endometriosis, familial fatal insomnia, fibromyalgia, giant cell arteritis, frontotemporal lobar degeneration, Goodpasture's syndrome, Graves' disease, Guillain-Barré syndrome (GBS), Hashimoto's thyroiditis, hidradenitis suppurativa, HIV-associated dementia, Huntington's disease, idiopathic pulmonary fibrosis, idiopathic thrombocytopenia purpura (ITP), idiopathic thrombocytopenic purpura, IgA nephropathy, interstitial cystitis, Kawasaki disease, Kennedy's disease, Krabbe's disease, lactic acidosis and stroke (MELAS), Lewy body dementia, lichen planus, lung cancer, lupus erythematosus, Machado-Joseph disease (Spinocerebellar ataxia type 3), malignant lymphoma, malignant gliomas, Meniere's disease, mitochondrial encephalopathy, mixed connective tissue disease, morphea, multiple system atrophy, multiple sclerosis, myasthenia gravis, narcolepsy, neuroborreliosis, neuromyotonia, Niemann Pick disease, Parkinson's disease, Pelizaeus-Merzbacher disease, Pemphigus vulgaris pernicious anaemia, Pick's disease, polyarteritis nodosa, polymyalgia rheumatica, polymyositis, primary biliary cirrhosis, primary lateral sclerosis, prion diseases, psoriasis, psoriatic arthritis, Raynaud's disease, Refsum's disease, Reiter's syndrome, relapsing polychondritis, progressive supranuclear palsy, rheumatic fever, rheumatoid arthritis (RA), Sandhoff disease, sarcoidosis, Schilder's disease, schizophrenia, scleroderma, Sjögren's syndrome, Spielmeyer-Vogt-Sjogren-Batten disease (also known as Batten disease), spinal muscular atrophy, spinocerebellar ataxia (multiple types with varying characteristics), Steele-Richardson-Olszewski disease, stiff person syndrome, subacute combined degeneration of spinal cord secondary to pernicious anaemia, Tabes dorsalis, temporal arteritis (also known as giant cell arteritis), toxic encephalopathy and X-linked lymphoproliferative disease (XLP), ulcerative colitis (one of two types of idiopathic inflammatory bowel disease or IBD), uveitis, vasculitis, vitiligo, and Wegener's granulomatosis.

In some embodiments, the invention provides compositions useful for treating or preventing a proliferative disorder or an autoimmune disease. The compositions are suitable for internal use and comprise an effective amount of a IAP inhibitor and a physiologically acceptable carrier or vehicle, useful for treating or preventing cancer, neurodegenerative disorders, and autoimmunity.

A XIAP inhibitor can be administered in amounts that are effective to treat or prevent or reduce the severity of a proliferative disorder in a subject. Proliferative disorders include, but are not limited to, solid tumor cancers such as malignant lymphoma, malignant gliomas, X-linked lymphoproliferative disease (XLP), acute myelogenous leukemia (AML), fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, Leiomyosarcoma, rhabdomyosarcoma, brain cancer, colon cancer, colorectal cancer, kidney cancer, liver cancer, pancreatic cancer, bone cancer, breast cancer, ovarian cancer, prostate cancer, esophageal cancer, stomach cancer, oral cancer, nasal cancer, throat cancer, head and neck cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, cancer of the central nervous system, epithelial carcinoma, skin cancer, melanoma, neuroblastoma, and retinoblastoma.

In some embodiments, the invention provides compositions of a IAP inhibitor useful for treating or preventing an autoimmune disease. Autoimmune diseases include, but are not limited to, autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, acute pancreatitis, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

A XIAP inhibitor can be administered in amounts that are effective to treat or prevent an autoimmune disease in a subject. Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

A cIAP inhibitor can be administered in amounts that are effective to treat or prevent or reduce the severity of a proliferative disorder in a subject. Proliferative disorders include, but are not limited to, mucosa associated lymphoid tissue lymphoma (MALT lymphoma) which is a subset of non-Hodgkin's lymphoma, breast cancer, prostate cancer, pancreatic cancer, lung cancer, ovarian cancer, colon cancer, malignant gliomas, and acute myelogenous leukemia (AML).

2. PI3Kβ/γ

The phosphatidylinositol 3-kinase ("PI3Kβ/γ") pathway is a central signaling pathway that exerts its effect on numerous cellular functions including cell cycle progression, proliferation, motility, metabolism and survival (Marone, et al. *Biochim. Biophys. Acta* (2008) 1784: 159-185). Activation of receptor tyrosine kinases in the case of Class IA PI3Ks, or G-proteins in the case of Class IB PI3Kγ, causes phosphorylation of phosphatidylinositol-(4,5)-diphosphate, resulting in membrane-bound phosphatidylinositol-(3,4,5)-triphosphate. The latter promotes the transfer of a variety of protein kinases from the cytoplasm to the plasma membrane by binding of phosphatidylinositol-(3,4,5)-triphosphate to the pleckstrin-homology (PH) domain of the kinase.

Kinases that are downstream targets of PI3K include phosphatidylinositide-dependent kinase 1 (PI3K) and Akt (also known as Protein Kinase B or PKB). Phosphorylation of such kinases then allows for the activation or deactivation of numerous other pathways, involving mediators such as GSK3, mTOR, PRAS40, FKHD, NF-κB, BAD, Caspase-9, and others. These pathways are involved in many cellular processes, such as cell cycle progression, cell survival and apoptosis, cell growth, transcription, translation, metabolism, degranulation, and cell motility.

An important negative feedback mechanism for the PI3K pathway is PTEN, a phosphatase that catalyzes the dephosphorylation of phosphatidylinositol-(3,4,5)-triphosphate to phosphatidylinositol-(4,5)-diphosphate. In more than 60% of all solid tumors, PTEN is mutated into an inactive form, permitting a constitutive activation of the PI3K pathway. As many cancers are solid tumors, such an observation provides evidence that a targeting of PI3K itself or individual downstream kinases in the PI3K pathway provide a promising approach to mitigate or even abolish the disregulation in many cancers and thus restore normal cell function and behavior.

Diseases and disorders treatable by regulating the function of PI3K include, but are not limited to, cancer, neurofibromatosis, ocular angiogenesis, stroke, diabetes, hepatomegaly, cardiovascular disease, Alzheimer's disease, cystic fibrosis, viral diseases, autoimmune diseases, atherosclerosis, restenosis, psoriasis, allergic disorders, inflammation, neurological disorders, angiogenic disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. Such proliferative diseases/disorders include, but are not limited to, solid tumor cancers such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, Leiomyosarcoma, rhabdomyosarcoma, brain cancer, colon cancer, colorectal cancer, kidney cancer, liver cancer, pancreatic cancer, bone cancer, breast cancer, ovarian cancer, prostate cancer, esophageal cancer, stomach cancer, oral cancer, nasal cancer, throat cancer, head and neck cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, cancer of the central nervous system, epithelial carcinoma, skin cancer, melanoma, neuroblastoma, and retinoblastoma.

A PI3K inhibitor can be administered in amounts that are effective to treat or prevent or reduce the severity of a proliferative disorder in a subject. More specifically, compounds of the current invention are useful in the treatment of a proliferative disease selected from a benign or malignant tumor, carcinoma of the brain, kidney, liver, bile duct, adrenal gland, bladder, breast, esophagus, stomach, gastric tumors, ovaries, colon, rectum, prostate, pancreas, lung (including small cell lung cancer, non-small cell lung cancer and bronchioalveolar cancer), stomach, vagina, endometrial, uterus, cervix and vulva, testes, genitourinary tract, larynx, skin, bone or thyroid, sarcoma, glioblastomas, neuroblastomas, multiple myeloma and lymphomas, gastrointestinal cancer, especially colon carcinoma or colorectal adenoma, a tumor of the neck and head, a cancer of the central nervous system, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins, a mammary carcinoma, follicular carcinoma, undifferentiated carcinoma, papillary carcinoma, seminoma, melanoma, or leukemias (including ALL and CML). Other diseases include Cowden syndrome, Lhermitte-Dudos disease and Bannayan-Zonana syndrome, or diseases in which the PI3K/PKB pathway is aberrantly activated.

A PI3K inhibitor can be administered in amounts that are effective to treat or prevent or reduce the severity of a neurodegenerative disease/disorder in a subject. Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

A PI3K inhibitor can be administered in amounts that are effective to treat or prevent an autoimmune disease in a subject. Autoimmune diseases include, but are not limited to, autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, acute pancreatitis, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

In certain embodiments, the present invention provides a method of using the disclosed compounds to prevent, treat, or reduce the severity of neurofibromatosis type I (NF1), neurofibromatosis type II (NF2) Schwann cell neoplasms (e.g. MPNST's), or Schwannomas.

Furthermore, compounds disclosed herein are useful to prevent, treat, or reduce the severity of inflammatory or obstructive airways diseases associated with PI3K. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping." "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

In yet another embodiment, compounds of the current invention can be used to prevent, treat, or reduce the severity of other inflammatory or obstructive airways diseases and conditions associated with PI3K including, but not limited to, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, the methods disclosed herein may be used to treat eosinophil related disorders associated with PI3K, e.g. eosinsophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

As PI3K has been implicated in inflammatory and allergies, the methods disclosed herein are also useful to prevent, treat, or reduce the severity of psoriasis, contact dermatitis, atopic dermatitis, alopecia areata, erythema multiforma, dermatitis herpetiformis, scleroderma, vitiligo, hypersensitivity angiitis, urticaria, bullous pemphigoid, systemic lupus erythematosus, pemphisus, epidermolysis bullosa acquisita, and other inflammatory or allergic conditions of the skin.

Furthermore, diseases or conditions having an inflammatory component caused by aberrant PI3K may also be prevented, treated, or used to reduce the severity by the methods disclosed herein. These diseases and disorders include, but are not limited to, diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, acute pancreatitis, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Cardiovascular diseases which can be prevent, treated, or used to reduce the severity according to the methods of this invention include, but are not limited to, restenosis, cardiomegaly, atherosclerosis, myocardial infarction, ischemic stroke and congestive heart failure.

In one embodiment, the invention provides compositions useful for treating or preventing cancer, neurofibromatosis, ocular angiogenesis, stroke, diabetes, hepatomegaly, cardiovascular disease, Alzheimer's disease, cystic fibrosis, viral diseases, autoimmune diseases, atherosclerosis, restenosis, psoriasis, allergic disorders, inflammation, neurological disorders, angiogenic disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient.

Because PI3K is pro-angiogenic (Graupera et al. Nature (2008) 453(7195):662-6), the methods of the present invention may be advantageous for inhibiting angiogenesis, for example, to treat eye disease associated with ocular angiogenesis, such as by topical administration of the subject compounds. Compounds according to the invention can be formulated for topical administration. For example, the irreversible inhibitor can be formulated for topical delivery to the lung (e.g., as an aerosol, such as a dry powder or liquid formulation) to treat asthma, as a cream, ointment, lotion or the like for topical application to the skin to treat psoriasis, or as an ocular formulation for topical application to the eye to treat an ocular disease. Such a formulation will contain a subject inhibitor and a pharmaceutically acceptable carrier. Additional components, such as preservatives, and agents to increase viscosity of the formulation such as natural or synthetic polymers may also be present. The ocular formulation can be in any suitable form, such as a liquid, an ointment, a hydrogel or a powder. Compounds of the current invention can be administered together with another therapeutic agent, such as an anti-VEGF agent, for example ranibizumab a Fab fragment of an antibody that binds VEGFA, or another anti-angiogenic compound as described further below.

3. PDPK1

3-Phosphoinositide-dependent kinase 1 (PDPK1) phosphorylates the activation loop of a number of protein serine/threonine kinases of the AGC kinase superfamily, including protein kinase B (PKB; also called Akt), serum and glucocorticoid-induced kinase, protein kinase C isoforms, and the p70 ribosomal S6 kinase. The phosphoinositide 3-kinase/3-phosphoinositide-dependent kinase 1 (PDPK1)/Akt signaling pathway plays a key role in cancer cell growth, survival, and tumor angiogenesis and represents a promising target for anti-cancer drugs.

A proliferative disorder can be prevented, treated, or reduce the severity of by administration of an effective amount of a PDPK1 inhibitor to a subject in need thereof. Proliferative disorders that can be prevented, treated, or reduce the severity of by administering an effective amount of a PDPK1 inhibitor include, but are not limited to, cancer, uterine fibroids, benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, an inflammatory bowel disease, transplantation rejection, endotoxic shock, a fungal infection, a defective apoptosis-associated condition, or a proliferative disease that is dependent on PDPK1 activity.

Because PDPK1 is a downstream target of PI3K, diseases and disorders that are regulated by PI3K are also implicated in aberrant PDPK1 function. Accordingly diseases treatable by regulating PDPK1 activity include, but are not limited to, cancer, neurofibromatosis, ocular angiogenesis, stroke, diabetes, hepatomegaly, cardiovascular disease, Alzheimer's disease, cystic fibrosis, viral diseases, autoimmune diseases, atherosclerosis, restenosis, psoriasis, allergic disorders, inflammation, neurological disorders, angiogenic disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. Such proliferative diseases/disorders include, but are not limited to, solid tumor cancers such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, Leiomyosarcoma, rhabdomyosarcoma, brain cancer, colon cancer, colorectal cancer, kidney cancer, liver cancer, pancreatic cancer, bone cancer, breast cancer, ovarian cancer, prostate cancer, esophageal cancer, stomach cancer, oral cancer, nasal cancer, throat cancer, head and neck cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, cancer of the central nervous system, epithelial carcinoma, skin cancer, melanoma, neuroblastoma, and retinoblastoma.

A PDPK1 inhibitor can be administered in amounts that are effective to treat or prevent or reduce the severity of a proliferative disorder in a subject. More specifically, compounds of the current invention are useful in the treatment of a proliferative disease selected from a benign or malignant tumor, carcinoma of the brain, kidney, liver, bile duct, adrenal gland, bladder, breast, esophagus, stomach, gastric tumors, ovaries, colon, rectum, prostate, pancreas, lung (including small cell lung cancer, non-small cell lung cancer and bronchoalveolar cancer), stomach, vagina, endometrial, uterus, cervix and vulva, testes, genitourinary tract, larynx, skin, bone or thyroid, sarcoma, glioblastomas, neuroblastomas, multiple myeloma and lymphomas, gastrointestinal cancer, especially colon carcinoma or colorectal adenoma, a tumor of the neck and head, a cancer of the central nervous system, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins, a mammary carcinoma, follicular carcinoma, undifferentiated carcinoma, papillary carcinoma, seminoma, melanoma, or leukemias (including ALL and CML). Other diseases include Cowden syndrome, Lhermitte-Dudos disease and Bannayan-Zonana syndrome, or diseases in which the PI3K/PKB pathway is aberrantly activated.

A PDPK1 inhibitor can be administered in amounts that are effective to treat or prevent or reduce the severity of a neurodegenerative disease/disorder in a subject. Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

A PDPK1 inhibitor can be administered in amounts that are effective to treat or prevent an autoimmune disease in a subject. Autoimmune diseases include, but are not limited to, autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, acute pancreatitis, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Blood-borne cancers implicated in aberrant PDPK1 expression include, but are not limited to, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, and myeloma.

Lymphomas where PDPK1 is implicated include, but are not limited to, Hodgkin's disease, non-Hodgkin's lymphomas, multiple myeloma, Waldenström's macroglobulinemia, heavy chain disease, and polycythemia vera.

CNS and brain cancers where aberrant PDPK1 expression include, but not limited to, glioma, pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, and meningioma.

Virally-mediated cancers have also been implicated in overexpression of PDPK1. Such viruses include human papilloma virus, which can lead to cervical cancer (see, e.g., Hernandez-Avila et al., Archives of Medical Research (1997) 28:265-271); Epstein-Barr virus (EBV), which can lead to lymphoma (see, e.g., Herrmann et al., J Pathol (2003) 199(2):140-5); hepatitis B or C virus, which can lead to liver carcinoma (see, e.g., El-Serag, J Clin Gastroenterol (2002) 35(5 Suppl 2):572-8); human T cell leukemia virus (HTLV)-I, which can lead to T-cell leukemia (see e.g., Mortreux et al., Leukemia (2003) 17(1):26-38);
human herpesvirus-8 infection, which can lead to Kaposi's sarcoma (see, e.g., Kadow et al., Curr Opin Investig Drugs (2002) 3(11): 1574-9); and Human Immune deficiency Virus (HIV) infection, which can lead to cancer as a consequence of immunodeficiency (see, e.g., Dal Maso et al., Lancet Oncol (2003) 4(2):110-9).

The invention provides methods for treating or preventing these aforementioned cancers, disorders and diseases, comprising administering to a subject in need of such treatment or prevention an effective amount of a PDPK1 inhibitor.

4. HCV

HCV is a positive-stranded RNA virus whose genome encodes a polyprotein of approximately 3000 amino acids. This precursor protein is processed into at least 10 viral structural and nonstructural proteins: C, E1, E2, p7, NS2, NS3, NS4A, NS4B, NS5A, and NS5B (Blight, K. J., et al., Antiviral Ther. 3, Suppl. 3: 71-81, 1998). HCV nonstructural (NS) proteins are derived by proteolytic cleavage of the polyprotein and are presumed to provide the essential catalytic machinery for viral replication.

NS3 is an approximately 68 Kda protein, and has both an N-terminal serine protease domain and an RNA-dependent ATPase domain at its C-terminus. It has been shown that the NS4A protein serves as a co-factor for the serine protease activity of NS3. NS3 functions as a proteolytic enzyme that cleaves sites liberating other nonstructural proteins necessary for HCV replication and is a validated therapeutic target for antiviral chemotherapy.

No vaccines are available for HCV, and the established therapy of interferon treatment is effective in only 15-20% of patients (Weiland, O., FEMS Microbiol. Rev. 14: 279-88, 1994), and has significant side effects (Walker, M. A., et al., DDT 4: 518-29, 1999; Moradpour, D., et al., Eur. J. Gastroenterol. Hepatol. 11: 1199-1202, 1999). While the current standard of care, pegylated interferon α in combination with ribavirin, is more efficacious and appears to decrease hepatocellular carcinoma in patients with HCV-related cirrhosis (Hung, C. H., et al., J Viral Hepatitis 13(6): 409-414, 2006), this treatment has also been shown to produce side effects such as thyroid dysfunction (Huang, J. F., et al., J Viral Hepatitis 13(6): 396-401, 2006).

Symptoms of HCV infection can either be acute or chronic. Acute symptoms include decreased appetite, fatigue, abdominal pain, jaundice, itching, and flu-like symptoms. Most patients diagnosed with HCV infection with acute symptoms eventually develop chronic symptoms, which include fatigue, flu-like symptoms, joint pains, itching, sleep disturbances, appetite changes, nausea, and depression. Chronic HCV infection eventually leads to liver inflammation, fibrosis, and eventually cirrhosis all of which lead to decreased liver function and eventually liver failure. Chronic hepatitis C can also be associated with extrahepatic manifestations associated with the presence of HCV such as porphyria cutanea tarda, cryoglobulinemia (a form of small-vessel vasculitis) and glomerulonephritis (inflammation of the kidney), specifically membranoproliferative glomerulonephritis (MPGN).

In one embodiment, the invention provides compositions useful for treating or preventing a an HCV infection. The compositions are suitable for internal use and comprise an effective amount of a HCV inhibitor and a physiologically acceptable carrier or vehicle.

A HCV inhibitor can be administered in amounts that are effective to treat or prevent or reduce the severity of an HCV infection in a subject.

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or composition thereof, is administered in combination with another inhibitor of HCV protease, or a variant thereof. In some embodiments, a provided compound, or composition thereof, is administered in combination with another antiviral agent. Such antiviral agents include, but are not limited to, immunomodulatory agents, such as α-, β-, and γ-interferons, pegylated derivatized interferon-a compounds, and thymosin; other anti-viral agents, such as ribavirin, amantadine, and telbivudine; other inhibitors of hepatitis C proteases (NS2-NS3 inhibitors and NS3-NS4A inhibitors, e.g. BILN 2061 and VX-950); inhibitors of other targets in the HCV life cycle, including helicase and polymerase inhibitors; inhibitors of internal ribosome entry; broad-spectrum viral inhibitors, such as IMPDH inhibitors (e.g., mycophenolic acid and derivatives thereof); or combinations of any of the above.

In certain embodiments, a combination of 2 or more antiviral agents may be administered. In certain embodiments, a combination of 3 or more antiviral agents may be administered. In some embodiments, the antiviral agents are selected from ribavirin or interferon. In other embodiments, the antiviral agent is α-interferon.

Other examples of agents the inhibitors of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

5. Dosage

The methods of the present invention may be used to prevent, treat, or reduce the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of
the specific compound employed; the duration of the treatment; drugs used in combination or coincidental with the specific compound employed, and like factors well known in the medical arts. The term "patient", as used herein, means an animal, preferably a mammal, and most preferably a human.

Administration of an inhibitor or pharmaceutically active agent described herein can be accomplished via any mode of administration for therapeutic agents. These modes include systemic or local administration such as oral, nasal, parenteral, transdermal, subcutaneous, vaginal, buccal, rectal or topical administration modes. In some instances, administration will result in the release of the inhibitor or pharmaceutically active agent described herein into the bloodstream.

In one embodiment, the inhibitor or pharmaceutically active agent described herein is administered orally.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, preferably in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using dissolution or suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, aqueous dextrose, glycerol, ethanol, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions of the inhibitor or pharmaceutically active agent described herein for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders or diluents such as starches, lactose, sucrose, glucose, mannitol, cellulose, saccharin, glycine, and silicic acid, b) binders such as, for example, magnesium aluminum silicate, starch paste, tragacanth, carboxymethylcellulose, methyl cellulose, alginates, gelatin, polyvinylpyrrolidinone, magnesium carbonate, natural sugars, corn sweeteners, sucrose, waxes and natural or synthetic gums such as acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators or disintegrants such as quaternary ammonium compounds, starches, agar, methyl cellulose, bentonite, xanthangum, algiic acid, and effervescent mixtures, g) wetting agents such as, for example, cetyl alcohol and glycerol monostearate, h) absorbents such as kaolin and bentonite clay, and i) lubricants such as talc, silica, stearic acid, calcium stearate, magnesium stearate, sodium oleate, sodium acetate, sodium chloride, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The inhibitor or pharmaceutically active agent described herein can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

The inhibitor or pharmaceutically active agent described herein can also be delivered by the use of monoclonal antibodies as individual carriers to which the inhibitor or pharmaceutically active agent described herein are coupled. The inhibitor or pharmaceutically active agent described herein can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the inhibitor or pharmaceutically active agent described herein can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Parenteral injectable administration can be used for subcutaneous, intramuscular or intravenous injections and infusions. Injectables can be prepared in conventional forms, either as liquid solutions or suspensions or solid forms suitable for dissolving in liquid prior to injection.

One embodiment, for parenteral administration employs the implantation of a slow-release or sustained-released system, according to U.S. Pat. No. 3,710,795, incorporated herein by reference.

The compositions can be sterilized or contain non-toxic amounts of adjuvants, such as preserving, stabilizing, wetting or emulsifying agents, solution promoters, salts for regulating the osmotic pressure, pH buffering agents, and other substances, including, but not limited to, sodium acetate or triethanolamine oleate. In addition, they can also contain other therapeutically valuable substances.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compositions can be prepared according to conventional mixing, granulating or coating methods, respectively, and the present pharmaceutical compositions can contain from about 0.1% to about 99%, preferably from about 1% to about 70% of the inhibitor or pharmaceutically active agent described herein by weight or volume.

The dosage regimen utilizing the inhibitor or pharmaceutically active agent described herein can be selected in accordance with a variety of factors including type, species, age, weight, sex and medical condition of the subject; the severity of the condition to be treated; the route of administration; the renal or hepatic function of the subject; and the particular inhibitor or pharmaceutically active agent described herein employed. A person skilled in the art can readily determine and prescribe the effective amount of the drug useful for treating or preventing a proliferative disorder.

Effective dosage amounts of the inhibitor or pharmaceutically active agent described herein, when administered to a subject, range from about 0.05 to about 1000 mg of inhibitor or pharmaceutically active agent described herein per day. Compositions for in vivo or in vitro use can contain about 0.5, 1.0, 2.5, 5.0, 10.0, 15.0, 25.0, 50.0, 100.0, 250.0, 500.0 or 1000.0 mg of the inhibitor described herein. In one embodiment, the compositions are in the form of a tablet that can be scored. Effective plasma levels of the inhibitor or pharmaceutically active agent described herein can range from about 0.002 mg to about 50 mg per kg of body weight per day. The amount of an inhibitor or pharmaceutically active agent described herein that is effective in the treatment or prevention of cancer can be determined by clinical techniques that are known to those of skill in the art. In addition, in vitro and in vivo assays can optionally be employed to help identify optimal dosage ranges. The precise dose to be employed can also depend on the route of administration, and the seriousness of the proliferative disorder being treated and can be decided according to the judgment of the practitioner and each subject's circumstances in view of, e.g., published clinical studies. Suitable effective dosage amounts, however, can range from about 10 micrograms to about 5 grams about every 4 h, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one inhibitor or pharmaceutically active agent described herein is administered, the effective dosage amounts correspond to the total amount administered.

The dosage regimen utilizing the inhibitor or pharmaceutically active agent described herein can be selected in accordance with a variety of factors including type, species, age, weight, sex and medical condition of the subject; the severity of the proliferative disorder to be treated; the route of administration; the renal or hepatic function of the subject; and the particular inhibitor or pharmaceutically active agent described herein employed. A person skilled in the art can readily determine and prescribe the effective amount of the drug required to prevent, counter or arrest the progress of the proliferative disorder.

The inhibitor or pharmaceutically active agent described herein can be administered in a single daily dose, or the total daily dosage can be administered in divided doses of two, three or four times daily. Furthermore, the inhibitor or pharmaceutically active agent described herein can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the inhibitor or pharmaceutically active agent described herein ranges from about 0.1% to about 15%, w/w or w/v.

6. Combination

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated". In a combination of an inhibitor described herein and additional therapeutic agent, the additional therapeutic agent is not a competitive binder for the active binding site within the target protein for the inhibitor used in the combination.

In certain embodiments, an inhibitor or pharmaceutically active agent provided herein, or composition thereof, is administered in combination with another pharmaceutically active agent, or a variant thereof. In some embodiments, a provided compound, or composition thereof, is administered in combination with one or more additional pharmaceutically active agent. Such additional pharmaceutically active agents include, but are not limited to, treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the compositions comprise an amount of an anticancer inhibitor described herein, e.g., a XIAP inhibitor, and another anticancer agent which together are effective to treat or prevent cancer. In another embodiment, the amount of the anticancer inhibitor described herein and another anticancer agent is at least about 0.01% of the combined combination chemotherapy agents by weight of the composition. When intended for oral administration, this amount can be varied from about 0.1% to about 80% by weight of the composition. Some oral compositions can comprise from about 4% to about 50% of the anticancer inhibitor described herein and another anticancer agent. Other compositions of the present invention are prepared so that a parenteral dosage unit contains from about 0.01% to about 2% by weight of the composition.

The present methods for treating or preventing cancer in a subject in need thereof can further comprise administering another prophylactic or therapeutic agent to the subject being administered an anticancer inhibitor described herein. In one embodiment the other prophylactic or therapeutic agent is administered in an effective amount. The other prophylactic or therapeutic agent includes, but is not limited to, an anti-inflammatory agent, an anti-renal failure agent, an anti-diabetic agent, an anti-cardiovascular disease agent, an antiemetic agent, a hematopoietic colony stimulating factor, an anxiolytic agent, and an opioid or non-opioid analgesic agent.

In a further embodiment, the anticancer inhibitor described herein can be administered prior to, concurrently with, or after an antiemetic agent, or on the same day, or within 1 hour, 2 hours, 12 hours, 24 hours, 48 hours or 72 hours of each other.

In another embodiment, the anticancer inhibitor described herein can be administered prior to, concurrently with, or after a hematopoietic colony stimulating factor, or on the same day, or within 1 hour, 2 hours, 12 hours, 24 hours, 48 hours, 72 hours, 1 week, 2 weeks, 3 weeks or 4 weeks of each other.

In still another embodiment, the anticancer inhibitor described herein can be administered prior to, concurrently with, or after an opioid or non-opioid analgesic agent, or on the same day, or within 1 hour, 2 hours, 12 hours, 24 hours, 48 hours or 72 hours of each other.

In yet another embodiment, the anticancer inhibitor described herein can be administered prior to, concurrently with, or after an anxiolytic agent, or on the same day, or within 1 hour, 2 hours, 12 hours, 24 hours, 48 hours or 72 hours of each other.

Effective amounts of the other therapeutic agents are well known to those skilled in the art. However, it is well within the skilled artisan's purview to determine the other therapeutic agent's optimal effective amount range. In one embodiment of the invention, where, another therapeutic agent is administered to a subject, the effective amount of the anticancer inhibitor described herein is less than its effective amount would be where the other therapeutic agent is not administered. In this case, without being bound by theory, it is believed that the anticancer inhibitor described herein and the other therapeutic agent act synergistically to treat or prevent cancer.

Antiemetic agents useful in the methods of the present invention include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, and tropisetron.

Hematopoietic colony stimulating factors useful in the methods of the present invention include, but are not limited to, filgrastim, sargramostim, molgramostim and epoietin alfa.

Opioid analgesic agents useful in the methods of the present invention include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene.

Non-opioid analgesic agents useful in the methods of the present invention include, but are not limited to, aspirin, celecoxib, rofecoxib, diclofenac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

Anxiolytic agents useful in the methods of the present invention include, but are not limited to, buspirone, and benzodiazepines such as diazepam, lorazepam, oxazapam, chlorazepate, clonazepam, chlordiazepoxide and alprazolam.

The invention encompasses kits that can simplify the administration of a ligand that covalently binds to a target polypeptide having a lysine residue present in the active site to a subject.

A typical kit of the invention comprises a unit dosage form of a ligand that covalently binds to a target polypeptide having a lysine residue present in the active site. In one embodiment the unit dosage form is a container, which can be sterile, containing an effective amount of a ligand that covalently binds to a target polypeptide having a lysine residue present in the active site and a physiologically acceptable carrier or vehicle. The kit can further comprise a label or printed instructions instructing the use of the ligand that covalently binds to a target polypeptide having a lysine residue present in the active site to treat or prevent cancer. The kit can also further comprise a unit dosage form of another prophylactic or therapeutic agent, for example, a container containing an effective amount of another prophylactic or therapeutic agent or another anticancer agent. In one embodiment the kit comprises a container containing an effective amount of a ligand that covalently binds to a target polypeptide having a lysine residue present in the active site and an effective amount of another prophylactic or therapeutic agent. Examples of other prophylactic or therapeutic agents and other anticancer agents include, but are not limited to, those listed above.

C. Probe Compounds

A compound of the present invention may be tethered to a detectable moiety. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Nonlimiting exemplary probe compounds are as set forth below.

VII-28

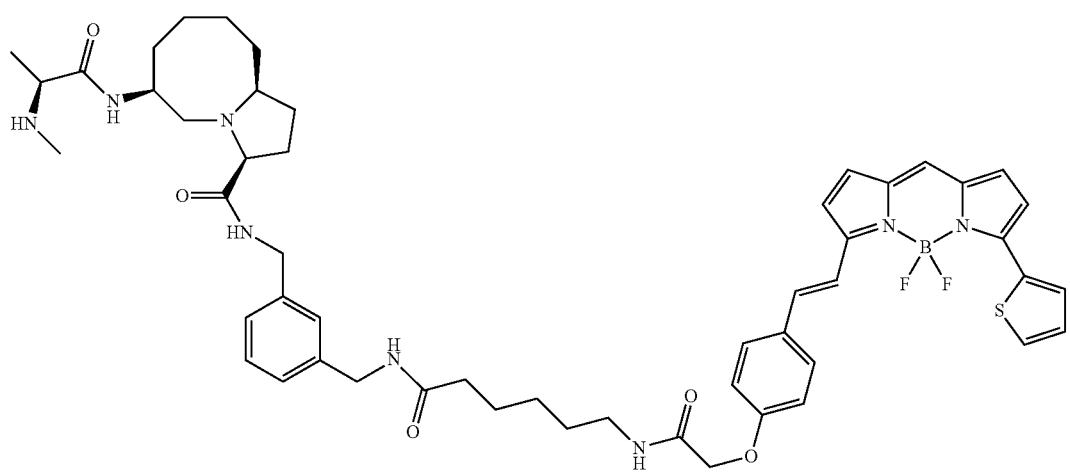

-continued
VII-35
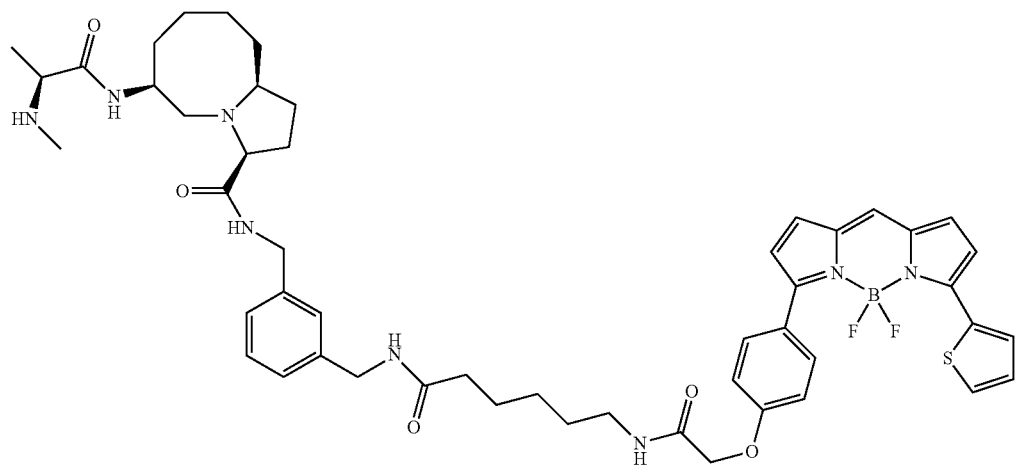
VIII-6
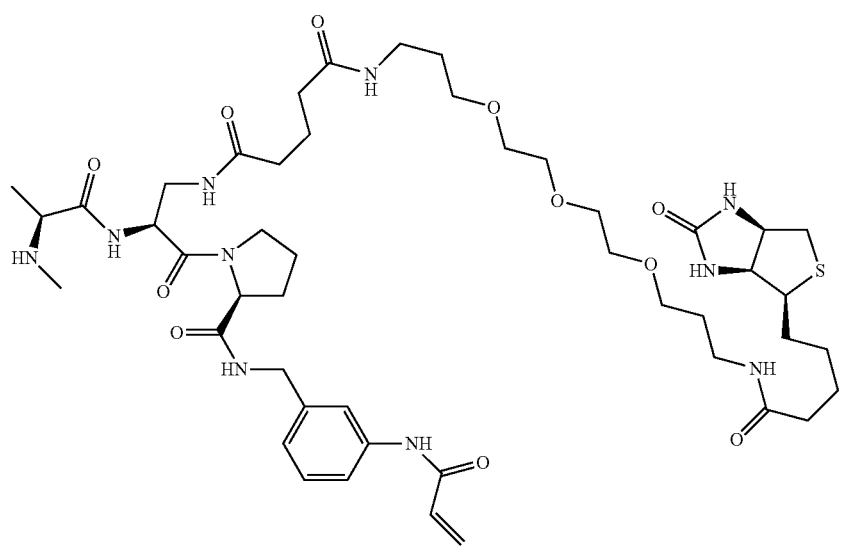
XVI-27
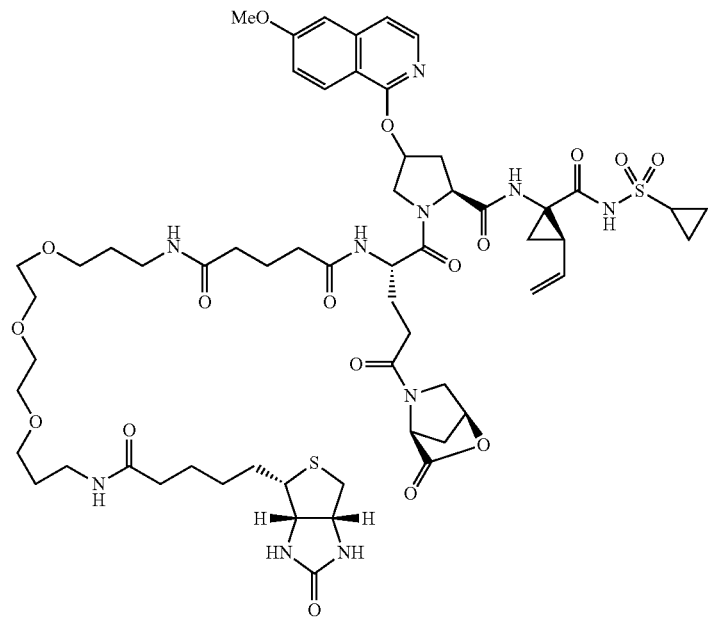

XI-56

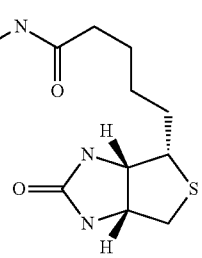
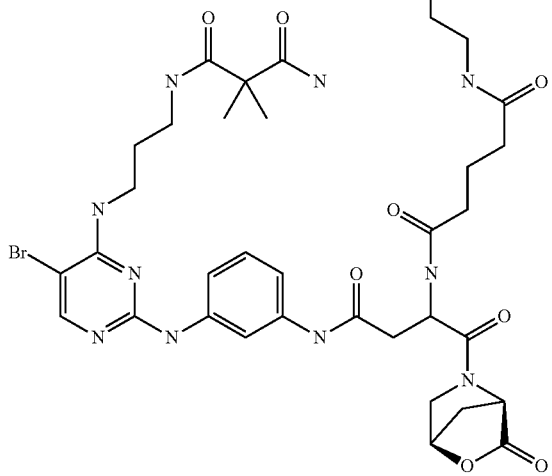

Primary labels, such as radioisotopes (e.g., tritium, $^{32}$P, $^{33}$P, $^{35}$S, $^{14}$C, $^{123}$I, $^{124}$I, $^{125}$I, or $^{131}$I), mass-tags including, but not limited to, stable isotopes (e.g., $^{13}$O, $^{2}$H, $^{17}$O, $^{18}$O, $^{15}$N, $^{19}$F, and $^{127}$I), positron emitting isotopes (e.g., $^{11}$C, $^{18}$F, $^{13}$N, $^{124}$I, and $^{15}$O) and fluorescent labels are signal generating reporter groups which can be detected without further modifications. Detectable moities may be analyzed by methods including, but not limited to fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromo-sulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags. Stable isotopes (e.g., $^{13}C$, $^2H$, $^{17}O$, $^{18}O$, and $^{15}N$) may also be used as mass-tags.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "moiety incorporating a heavy atom," as used herein, refers to a group which incorporates an ion of atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a linkage with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitril radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering moiety, such as a bivalent saturated or unsaturated hydrocarbon chain.

In some embodiments, detectable moieties are attached to a provided compound via click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57. In some embodiments, a click ready inhibitor moiety is provided and reacted with a click ready -$T^P$-$R^P$ moiety. As used herein, "click ready" refers to a moiety containing an azide or alkyne for use in a click chemistry reaction. In some embodiments, the click ready inhibitor moiety comprises an azide. In certain embodiments, the click ready -$T^P$-$R^P$ moiety comprises a strained cyclooctyne for use in a copper-free click chemistry reaction (for example, using methods described in Baskin et al., Proc. Natl. Acad. Sci. USA 2007, 104, 16793-16797).

9. EXEMPLIFICATION

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

A. Design of an Irreversible Inhibitor of XIAP

Example 1

(3 S,6S,10aR)-6-((S)-2-(methylamino)propanamido)-5-oxo-N-((R)-1,2,3,4-tetrahydronaphthalen-1-yl)decahydropyrrolo[1,2-a]azocine-3-carboxamide (Compound A) is a reversible inhibitor of XIAP (Ki 26 nM) (Sun et al., J. Med. Chem. 52, 593-596 (2009). Using the structure-based design algorithm described herein, Compound A was converted from a reversible inhibitor into Compound VII-1, a potent and irreversible inhibitor of XIAP. The process for the conversion of Compound A to Compound VII-1 is described below.

A

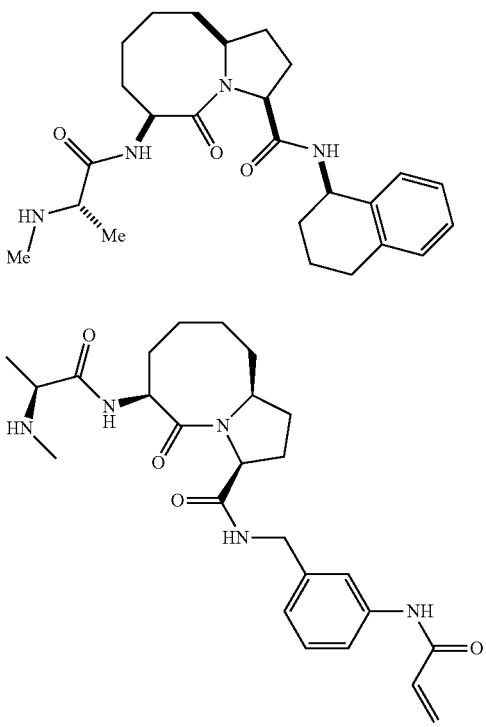

The X-ray crystal structure of XIAP complexed with Compound B, a related compound to Compound A, has been reported (Sun, H., et al., J. Med. Chem. 51, 7169-7180 (2008)) and was obtained from the protein databank (pdb-code 2JK7 at www.rcsb.org). The X-ray complex of Compound B bound to XIAP was used to

B

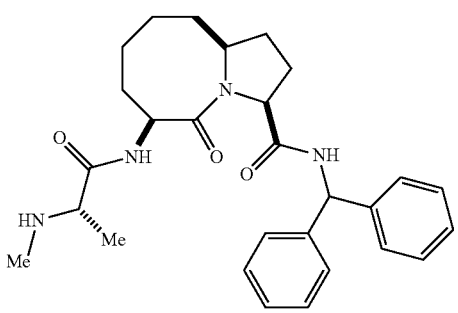

design covalent inhibitors of XIAP using the design algorithm described herein. The three-dimensional structure of Compound B was docked into the XIAP ligand-binding site using the CDOCKER method in Discovery Studio (www.accelrys.com). The ligand-binding site of XIAP was defined using the sphere that has a 7.5 angstroms radius around the reference ligand. The docking results demonstrated that the inhibitor Compound A, bound to XIAP in a similar fashion to that seen in the X-ray complex of Compound B bound to XIAP. After docking Compound B in the ligand-binding site of XIAP, all lysine residues (Lys) of XIAP within 15 angstroms in the XIAP-Compound B complex were identified: Lys281, Lys297, Lys299, Lys311, Lys322, Lys328 and Lys334.

Using the modeled coordinates of Compound A, a library of virtual covalent inhibitors was created by building an acrylamide warhead at each of the $A_1$ (ortho-, meta- and para-), $A_2$ and $A_3$ positions shown below in Template X.

Template X

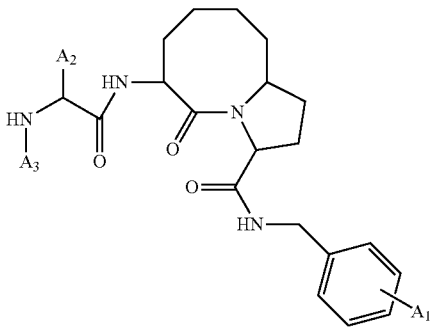

To sample the flexibility of the warheads and the side chain positions, a molecular dynamics simulation of the warheads and XIAP side chain positions was performed and analyzed to determine if the warhead was within 6 angstroms of any of the Lys residues in the binding site. Additionally, an analysis of possible steric clashes between the warheads and the residues was performed. Standard settings were used in the Standard Dynamics Cascade Simulations protocol of Discovery Studio, along with Merck Molecular Force Field, for the molecular dynamics simulations (www.accelrys.com). The coordinates of the non-warhead positions and the Lys main-chain atoms were held fixed during the molecular dynamics simulation. The modeling demonstrated that the VII-1 ($A_1$=meta-substituted acrylamide) was close to Lys297 and also Lys299 in XIAP. To confirm that VII-1 was able to form a bond with either of these Lys residues, a model of the reaction product between XIAP and Lys297 or Lys299 was built. In both cases, the reaction product could be formed without any significant change in the geometry of the model, thereby supporting bond formation.

Subsequently, VII-1 was synthesized and inhibited XIAP at a Ki of 161 nM, (see Table 2 below), while Compound VII-2, an inactive control compound demonstrated a Ki of >10,000 nM. Mass spectrometric analysis of the reaction product of VII-1 incubated with XIAP demonstrates that VII-1 covalently modifies XIAP (see Examples 50 and 51, below).

VII-2

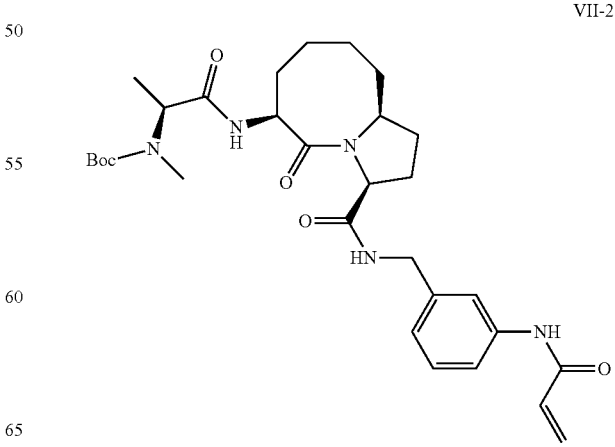

B. XIAP Inhibitors Synthetic Examples
Example 1A
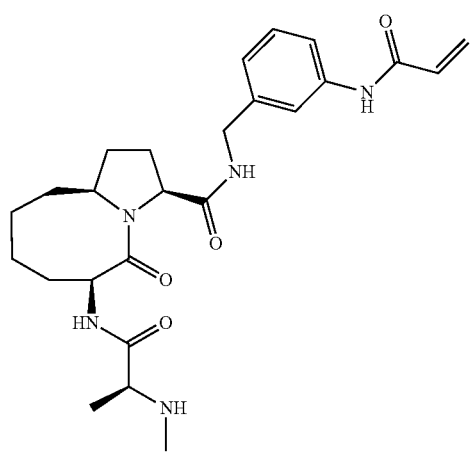
(3S,6S,10aS)-N-(3-acrylamidobenzyl)-6-((S)-2-(methylamino)propanamido)-5-oxodecahydropyrrolo[1,2-a]azocine-3-carboxamide
The title compound was prepared according to the steps and intermediates as described below.
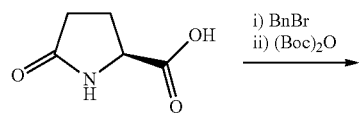
i) BnBr
ii) (Boc)$_2$O
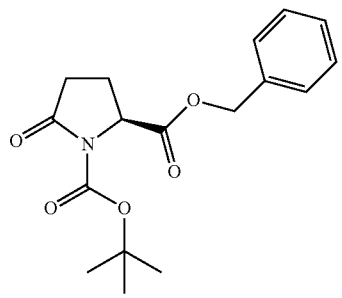 [SMILES: CC(C)(C)OC(=O)N1C(=O)CC[C@H]1C(=O)OCc1ccccc1]
1a
Superhydride
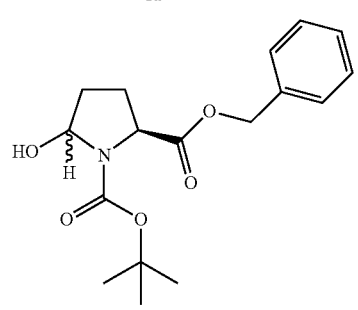 [SMILES: CC(C)(C)OC(=O)N1C(O)CC[C@H]1C(=O)OCc1ccccc1]
1b
PTSA
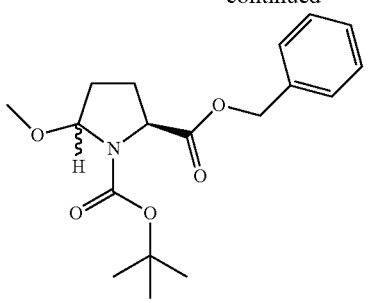
1c
BF$_3$·Et$_2$O
allyltributyltin
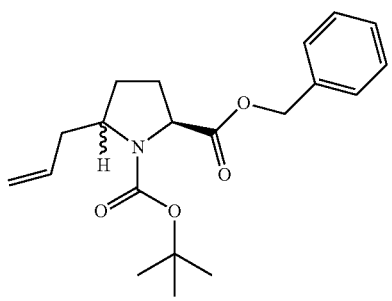
1d
TFA
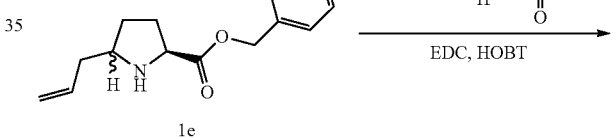
1e
EDC, HOBT
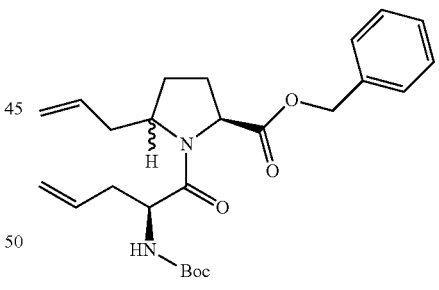
1f
Grubbs' catalyst
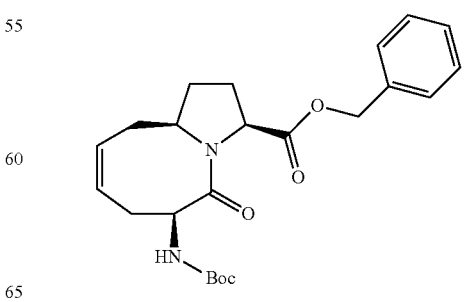
1g
TFA -continued

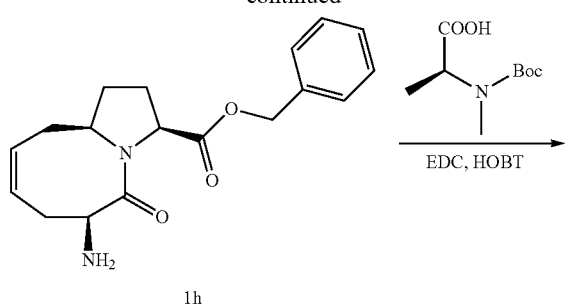

1h

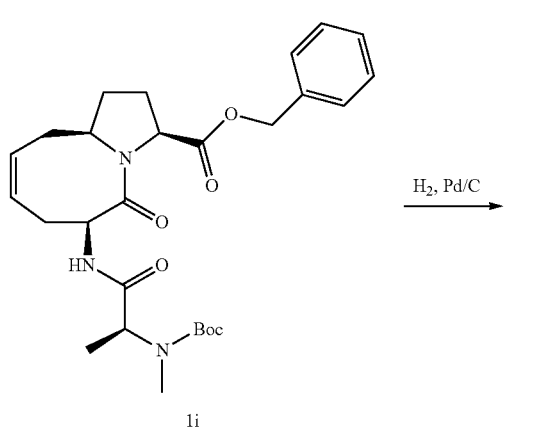

1i

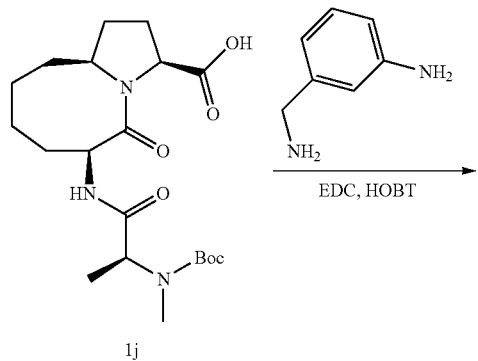

1j

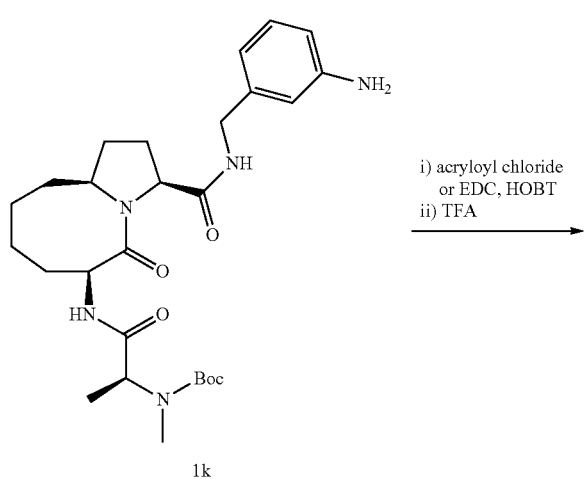

1k

-continued

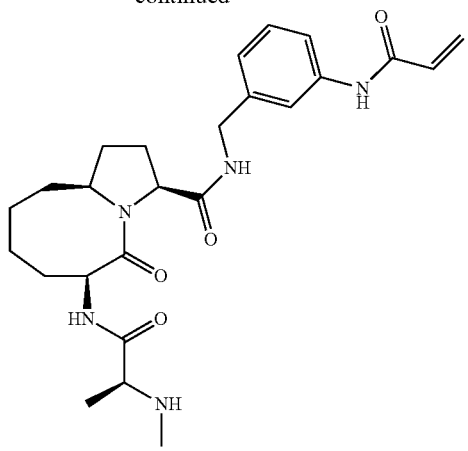

(S)-2-benzyl 1-tert-butyl 5-oxopyrrolidine-1,2-dicarboxylate (1a)

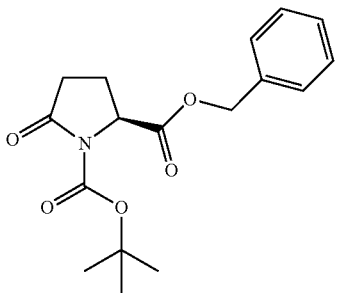

To a stirred solution of L-pyroglutamic acid (75 g, 0.58 mol) and N,N-diisopropylethylamine (87.3 g, 0.676 mol) in dry dichloromethane (1.0 L) at 0° C. was added benzyl bromide (98.84 g, 0.58 mol) dropwise. The reaction mixture was heated under reflux for 5 h, cooled to RT and washed with aqueous NaH₂PO₄. The aqueous layer was extracted with CH₂Cl₂; the combined organic layers were washed with brine, dried over Na₂SO₄, filtered and concentrated under reduced pressure. The residue obtained was then taken in acetonitrile (1.5 L) and 4-dimethylaminopyridine (7.09 g, 58.0 mmol) and Boc-anhydride (150.0 g, 0.688 mol) were added and stirred at RT for 3 hrs. The reaction mixture was concentrated; the residue obtained was treated with water and extracted with ethyl acetate. The ethyl acetate layer was washed with aqueous NaH₂PO₄ and brine, dried over Na₂SO₄, filtered, and concentrated under reduced pressure to give pale yellow viscous oil. It was crystallized with ethyl acetate-petroleum ether to give 1a (150 g, 80.8%) as a pale yellow solid.

(2S)-2-benzyl 1-tert-butyl 5-hydroxypyrrolidine-1,2-dicarboxylate (1b)

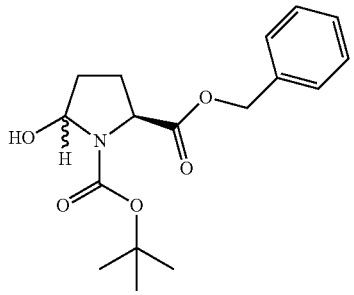

To a stirred solution of 1a (100.0 g, 313.1 mmol) in THF (1000 mL) at −78° C. under nitrogen was added Super Hydride® (1M in THF, 469 mL, 469 mmol) slowly and the mixture was stirred at −78° C. for 2 h. Saturated aq. sodium hydrogen carbonate (300 mL) was added and the reaction mixture was stirred at 0° C. for 30 min. The reaction mixture was concentrated to remove most of THF and the residue was extracted with ethyl acetate. The combined organic extracts were dried over $Na_2SO_4$, filtered, and concentrated under reduced pressure to get 1b (100 g, 99.3%) as colorless oil. It was taken for the next step without further purification.

(2S)-2-benzyl 1-tert-butyl 5-methoxypyrrolidine-1,2-dicarboxylate (1c)

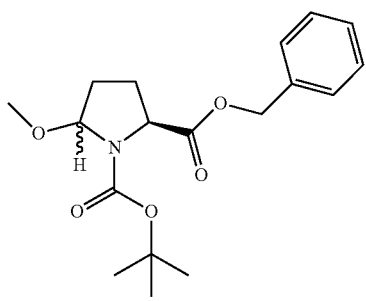 [SMILES: COC1CC[C@@H](C(=O)OCc2ccccc2)N1C(=O)OC(C)(C)C]

To a stirred solution of 1b (100 g, 311.1 mmol) in methanol (1000 mL) was added p-toluenesulfonic acid monohydrate (5.89 g, 30.96 mmol) and stirred at RT for 16 h. Sat. sodium hydrogen carbonate solution (500 mL) was added and then concentrated under reduced pressure to remove most of methanol. The residue was extracted with MTBE and the combined MTBE extract was washed with brine, dried over $Na_2SO_4$, filtered, and concentrated under reduced pressure to get 1c (88 g, 84.3%) as colorless oil. It was taken for the next step without further purification.

(2S)-2-benzyl 1-tert-butyl 5-allylpyrrolidine-1,2-dicarboxylate (1d)

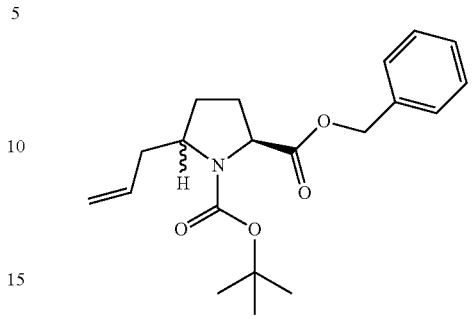

To a stirred solution of 1c (25 g, 74.4 mmol) in dichloromethane (250 mL) at −78° C. was added borontrifluoride-diethyletherate (9.2 mL, 74.5 mmol) slowly and the solution was stirred at −78° C. for 1 h. Allytributylstannane (28 mL, 90.3 mmol) was added slowly and the reaction mixture was stirred further at −78° C. for 3 h. De-ionized water (300 mL) was added and the solution was allowed to warm to RT. It was filtered through Celite, layers were separated and the aqueous layer was extracted with dichloromethane. The combined organic extracts were washed with water and brine, dried over $Na_2SO_4$, filtered, and concentrated under reduced pressure to get the crude. The crude product obtained was purified by column chromatography ($SiO_2$, ethyl acetate: petroleum ether, 8:92) to get 1d (15 g, 58.3%) as colorless oil.

(2S)-benzyl 5-allylpyrrolidine-2-carboxylate (1e)

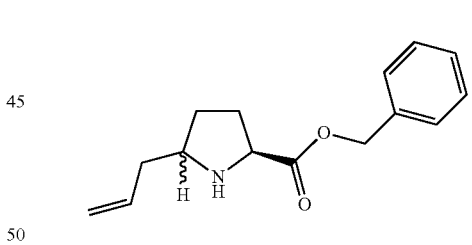

To a stirred solution of 1d (30 g, 86.7 mmol) in dichloromethane (300 mL) at 0° C. was added trifluoroacetic acid (45 mL) slowly and the solution was stirred at RT for 2 h under nitrogen. The reaction mixture was concentrated under reduced pressure and the residue obtained was taken in dichloromethane-water (2:1, 150 mL), stirred vigorously and triethylamine (50 mL, 356.4 mmol) was added. Stirring was continued at RT for 2 h. The phases were separated and the aqueous phase was extracted with dichloromethane. The combined organic extracts were dried over $Na_2SO_4$, filtered, and concentrated under reduced pressure to get 1e (20 g, 93.9%) as a pale yellow oil and was taken for the next step without further purification.

265

(2S)-benzyl 5-allyl-1-((S)-2-(tert-butoxycarbonylamino)pent-4-enoyl)pyrrolidine-2-carboxylate (1f)

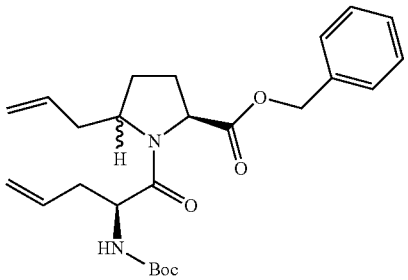 [SMILES: C=CCC1CC[C@@H](C(=O)OCc2ccccc2)N1C(=O)[C@H](CC=C)NC(=O)OC(C)(C)C]

To a stirred solution of 1e (11 g, 44.9 mmol) in DMF (110 mL) were added (S)-2-(tert-butoxycarbonylamino)pent-4-enoic acid (9.65 g, 44.9 mmol), EDC.HCl (12.87 g, 67.35 mmol), HOBt (2.42 g, 17.96 mmol) and DIPEA (11.63 mL, 67.35 mmol). The reaction mixture was stirred at room temperature for 18 h under nitrogen atmosphere. It was diluted with cold water and extracted with ethyl acetate. The combined organic extracts were washed with water and brine, dried over $Na_2SO_4$, filtered, and concentrated under reduced pressure to get a residue. The crude product obtained was mixed with the crude obtained from another similar batch and purified by column chromatography ($SiO_2$, 15-20% ethyl acetate in petroleum ether) to get 1f (25 g, 62.9%) as a pale yellow oil.

(3S,6S,10aR,Z)-benzyl 6-(tert-butoxycarbonylamino)-5-oxo-1,2,3,5,6,7,10,10a-octahydropyrrolo[1,2-a]azocine-3-carboxylate (1g)

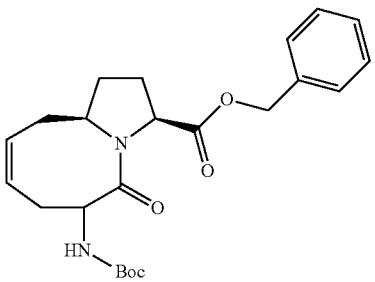

To a solution of 1f (25 g, 56.49 mmol) in dichloromethane (500 mL) was added bis(tricyclohexylphosphine)benzylideneruthenium(IV) dichloride (Grubbs' catalyst) (9.3 g, 11.29 mmol) and stirred at reflux for 24 h. Cooled to RT, concentrated under reduced pressure, the residue was taken in MTBE and filtered through Celite, filtrate concentrated under reduced pressure to get 1g (50 g) as dark green residue. It was taken for the next step without further purification.

266

(3S,6S,10aR,Z)-benzyl 6-amino-5-oxo-1,2,3,5,6,7,10,10a-octahydropyrrolo[1,2-a]azocine-3-carboxylate (1h)

To a stirred solution of 1g (~50 g, crude) in dichloromethane (500 mL) at 0° C. was added trifluoroacetic acid (50 mL) slowly and the solution was stirred at RT for 2 h under nitrogen. The reaction mixture was concentrated under reduced pressure and the residue obtained was taken up in water. It was washed with MTBE; the aqueous layer was basified with 10% NaOH solution and extracted with ethyl acetate. Combined ethyl acetate extracts were washed with water and brine, dried over $Na_2SO_4$, filtered, and concentrated under reduced pressure to get 1h (9 g, 50.7% yield in two steps) as yellow oil which was found to be sufficiently pure.

(3S,6S,10aR,Z)-benzyl 6-((S)-2-(tert-butoxycarbonyl(methyl)amino)propanamido)-5-oxo-1,2,3,5,6,7,10,10a-octahydropyrrolo[1,2-a]azocine-3-carboxylate (1i)

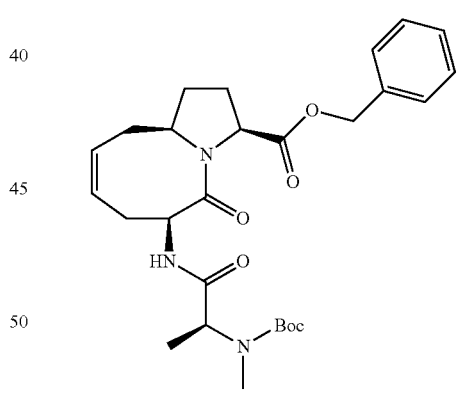

To a stirred solution of 1h (7.3 g, 23.22 mmol) in dichloromethane (150 mL) were added (R)-2-(tert-butoxycarbonyl(methyl)amino)propanoic acid (4.71 g, 23.22 mmol), EDC.HCl (6.59 g, 34.5 mmol), HOBt (1.55 g, 11.5 mmol) and DIPEA (5.96 mL, 34.5 mmol) and stirred at room temperature for 18 h under nitrogen atmosphere. The reaction mixture was concentrated under reduced pressure and the residue obtained was taken up in water and extracted with ethyl acetate. The combined organic extracts were washed with water and brine, dried over $Na_2SO_4$, filtered, and concentrated under reduced pressure to get a residue. It was purified by column chromatography ($SiO_2$, 1-2% methanol in chloroform) to get 1i (10 g, 86.2%) as a pale oil.

(3S,6S,10aS)-6-((S)-2-(tert-butoxycarbonyl(methyl)amino)propanamido)-5-oxodecahydropyrrolo[1,2-a]azocine-3-carboxylic acid (1j)

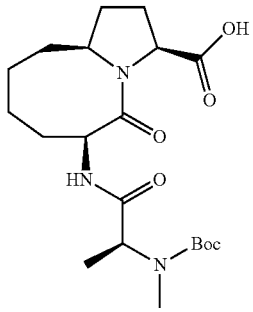 [SMILES: C[C@@H](C(=O)N[C@H]1CCCC[C@H]2CC[C@@H](C(=O)O)N2C1=O)N(C)C(=O)OC(C)(C)C]

To a solution of 1i (2.5 g, 5.01 mmol) in ethanol (100 mL) was added 10% palladium on carbon (1.0 g) and stirred at RT for 6 h using a hydrogen balloon. The reaction mixture was filtered through Celite and the filtrate was concentrated under reduced pressure to get a residue. It was dissolved in dichloromethane and filtered through Celite to remove any undissolved material and the filtrate was concentrated under reduced pressure to get 1j (1.8 g, 87.8%) as a white solid. $^1$H NMR (400 MHz, DMSO-$d_6$): ☐=1.21 (d, J=7.16 Hz, 3H), 1.39 (s, 9H), 1.53-1.92 (m, 10H), 1.99-2.10 (m, 1H), 2.18-2.28 (m, 1H), 2.73 (s, 3H), 4.16-4.24 (m, 2H), 4.33-4.75 (m, 2H), 7.76 (d, J=7 Hz, 1H), 12.45 (brs, 1H).

tert-butyl(S)-1-((3S,6S,10aS)-3-(3-aminobenzylcarbamoyl)-5-oxodecahydropyrrolo[1,2-a]azocin-6-ylamino)-1-oxopropan-2-yl(methyl)carbamate (1k)

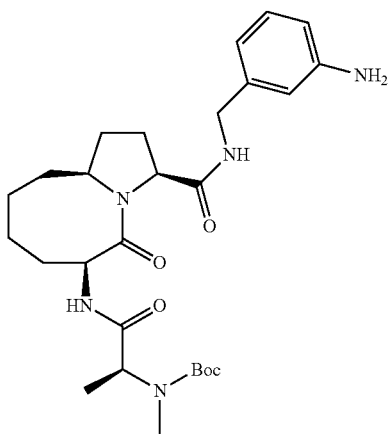 [SMILES: C[C@@H](C(=O)N[C@H]1CCCC[C@H]2CC[C@@H](C(=O)NCc3cccc(N)c3)N2C1=O)N(C)C(=O)OC(C)(C)C]

A mixture of 1j (488 mg), 3-aminobenzylamine (173 mg), EDC.HCl (272 mg), HOBt (192 mg), N-methylmorpholine (0.39 mL) in acetonitrile (16 mL) was stirred overnight at RT. After concentrating under reduced pressure, the residue was directly purified by column chromatography (SiO$_2$, isopropanol: dichloromethane, 7:93) to afford 420 mg of the desired aniline 1k as white solid. $^1$H NMR (400 MHz, CDCl$_3$): ☐=7.08 (m, 2H), 6.59 (m, 3H), 4.88 (m, 1H), 4.55 (t, J=6.9 Hz, 1H), 4.34 (ddd, J=2.8, 6.0, 14.7 Hz, 2H), 4.18 (t, J=10.0 Hz, 1H), 2.79 (s, 2H), 2.5 (m, 1H), 2.1-1.4 (m), 1.48 (s, 9H), 1.32 (d, J=7.3 Hz, 3H); LCMS: m/e 516.3 (M+1).

(3S,6S,10aS)-N-(3-acrylamidobenzyl)-6-((S)-2-(methylamino)propanamido)-5-oxodecahydropyrrolo[1,2-a]azocine-3-carboxamide (VII-1)

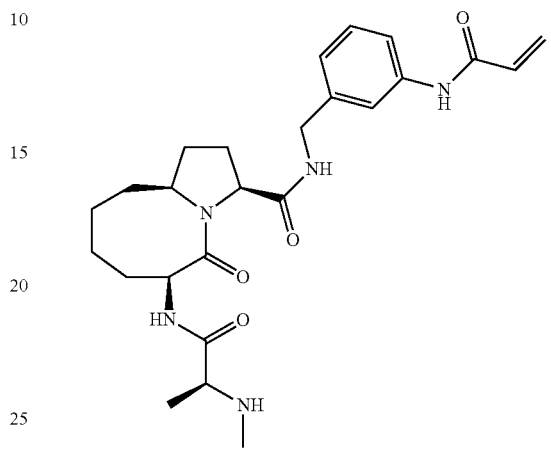

To a mixture of the aniline 1k (60 mg) and triethylamine (80 μl) in dry dichloromethane (2 mL) was added acryloyl chloride (19 μl) dropwise at 0° C. After stirring for 10 min at 0° C., trifluoroacetic acid (1 mL) was added to the reaction mixture and stirred 10 min at rt. The reaction mixture was concentrated and the residue was purified using semi-prep HPLC (TFA modifier) to give a white solid (VII-1) as TFA salt. $^1$H NMR (400 MHz, DMSO-$d_6$): ☐=10.1 (s, 1H), 8.70 (m, 2H), 8.47 (t, J=5.5 Hz, 1H), 7.57 (s, 1H), 7.50 (d, J=9.2 Hz, 1H), 7.24 (t, J=7.8 Hz, 1H), 6.98 (d, J=7.8 Hz, 1H), 6.42 (dd, J=10.1, 14.6 Hz, 1H), 6.23 (dd, J=2.3, 17.0 Hz, 1H), 5.72 (dd, J=2.3 Hz, 10.1 Hz, 1H), 4.78 (m, 1H), 4.31 (m, 2H), 4.17 (m, 2H), 3.7-1.3 (m), 1.31 (d, J=6.9 Hz, 3H); LCMS: m/e 470.2 (M+1).

VII-2

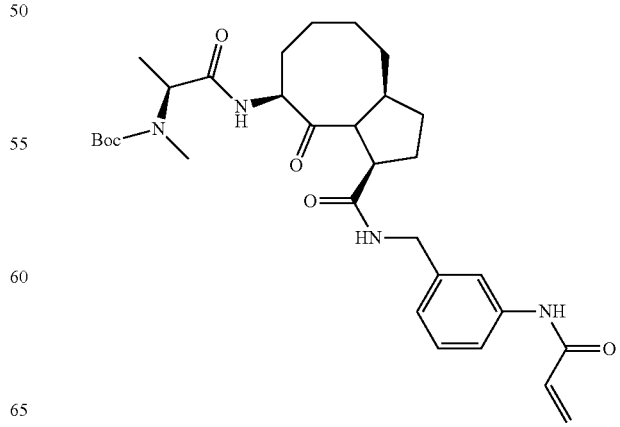

Example 2 tert-Butyl(S)-1-((3S,6S,10aS)-3-(3-acrylamidobenzylcarbamoyl)-5-oxodecahydropyrrolo[1,2-a]azocin-6-ylamino)-1-oxopropan-2-yl(methyl)carbamate The title compound was prepared according to the steps and intermediates as described below.

To a mixture of the aniline 1k (60 mg) and triethylamine (80 μl) in dry dichloromethane (2 mL) was added acryloyl chloride (19 μl) dropwise at 0° C. The reaction mixture was concentrated and the residue was purified using semi-prep HPLC (TFA modifier) to give a white solid. LCMS: m/e 470.3 (M+1-$^t$Bu).

Example 3

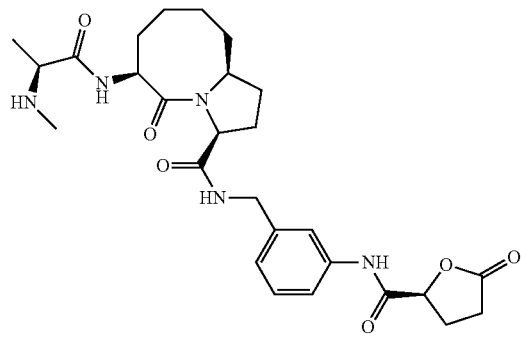

VII-3

(3S,6S,10aS)-6-((S)-2-(methylamino)propanamido)-5-oxo-N-(3-((S)-5-oxotetrahydrofuran-2-carboxamido)benzyl)decahydropyrrolo[1,2-a]azocine-3-carboxamide The title compound was prepared according to the steps and intermediates as described below.

To a mixture of the aniline 1k (19.8 mg), (S)-5-oxo-2-tetrahydrofurancarboxylic acid (6 mg), EDC.HCl (12 mg), HOBt (9 mg), N-methylmorpholine (20 μl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 528.3 (M+1).

Example 4

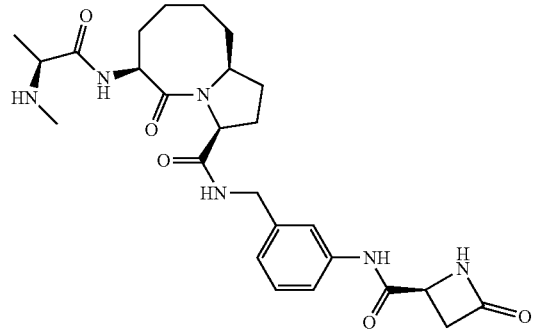

VII-4

(3S,6S,10aS)-6-((S)-2-(methylamino)propanamido)-5-oxo-N-(3-((S)-4-oxoazetidine-2-carboxamido)benzyl)decahydropyrrolo[1,2-a]azocine-3-carboxamide The title compound was prepared according to the steps and intermediates as described below.

To a mixture of the aniline 1k (24.5 mg), (S)-4-oxo-2-azetidinecarboxylic acid (6.6 mg), EDC.HCl (12 mg), HOBt (9 mg), N-methylmorpholine (20 μl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 513.3 (M+1).

Example 5

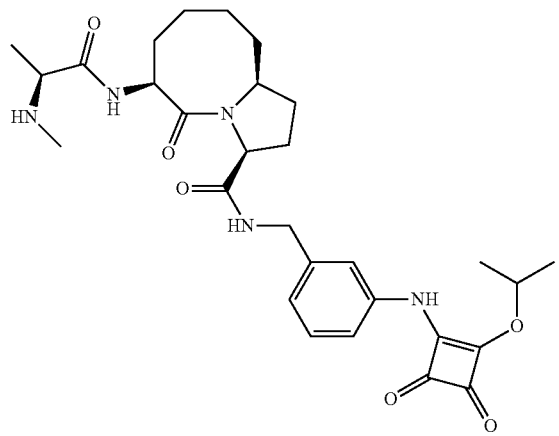

VII-5

271

(3S,6S,10aS)-N-(3-(2-isopropoxy-3,4-dioxocyclobut-1-enylamino)benzyl)-6-((S)-2-(methylamino)propanamido)-5-oxodecahydropyrrolo[1,2-a]azocine-3-carboxamide The title compound was prepared according to the steps and intermediates as described below.

To a mixture of the aniline 1k (37.7 mg), 3,4-diisopropyl-3-cyclobutene-1,2-dione (16 mg), triethylamine (20 µl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt.

LCMS: m/e 554.2 (M+1).

Example 6

VII-6

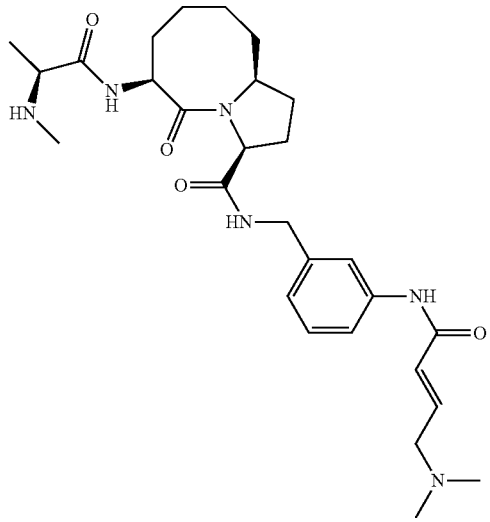

(3S,6S,10aS)-6-((S)-2-(methylamino)propanamido)-5-oxo-N-(3-(3-oxobutanamido)benzyl)decahydropyrrolo[1,2-a]azocine-3-carboxamide The title compound was prepared according to the steps and intermediates as described below.

To a mixture of the aniline 1k (20 mg), 2,2,4-trimethyl-6-keto-1,3-dioxin (10 µl) in dioxane (1 mL) was stirred overnight at 80° C. The mixture was concentrated and diluted with dichloromethane (1 mL). Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 500.3 (M+1).

272

Example 7

VII-9

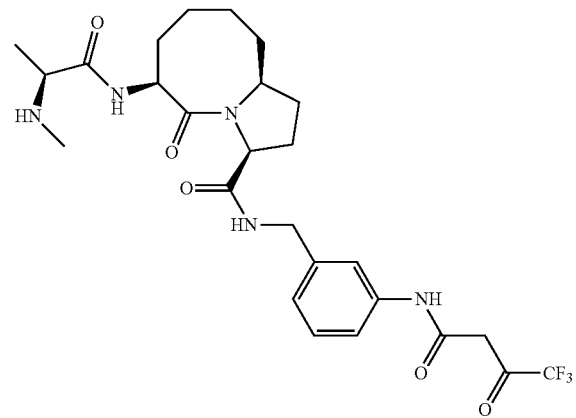

(3S,6S,10aS)-6-((S)-2-(methylamino)propanamido)-5-oxo-N-(3-(4,4,4-trifluoro-3-oxobutanamido)benzyl)decahydropyrrolo[1,2-a]azocine-3-carboxamide The title compound was prepared according to the steps and intermediates as described below.

To a mixture of the aniline 1k (12 mg), ethyl 4,4,4-trifluoroacetoacetate (100 µl) in toluene (1 mL) was stirred for 2 h at 80° C. The mixture was concentrated and diluted with dichloromethane (1 mL). Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 554.2 (M+1).

Example 8

VII-10

(3S,6S,10aS)-N-(3-((E)-4-(dimethylamino)but-2-enamido)benzyl)-6-((S)-2-(methylamino)propanamido)-5-oxodecahydropyrrolo[1,2-a]azocine-3-carboxamide The title compound was prepared according to the steps and intermediates as described below.

To a mixture of the aniline 1k (12.7 mg) and diisopropylethylamine (100 µl) in dry dichloromethane (1 mL) was added (E)-4-(dimethylamino)but-2-enoyl chloride (20 µl) dropwise at 0° C. After stirring for 10 min at 0° C., trifluoroacetic acid (1 mL) was added to the reaction mixture and stirred 10 min at rt. The reaction mixture was concentrated and the residue was purified using semi-prep HPLC (TFA modifier) to give a white solid as TFA salt. LCMS: m/e 527.3 (M+1).

Example 9

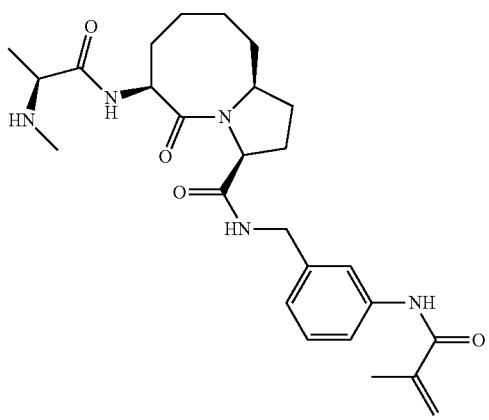

VII-11

(3S,6S,10aS)-N-(3-methacrylamidobenzyl)-6-((S)-2-(methylamino)propanamido)-5-oxodecahydropyrrolo[1,2-a]azocine-3-carboxamide The title compound was prepared according to the steps and intermediates as described below.

To a mixture of the aniline 1k (10 mg) and diisopropylethylamine (50 µl) in dry dichloromethane (1 mL) was added methacryloyl chloride (20 µl) dropwise at 0° C. After stirring for 10 min at 0° C., trifluoroacetic acid (1 mL) was added to the reaction mixture and stirred 10 min at rt. The reaction mixture was concentrated and the residue was purified using semi-prep HPLC (TFA modifier) to give a white solid as TFA salt. LCMS: m/e 484.4 (M+1).

Example 10

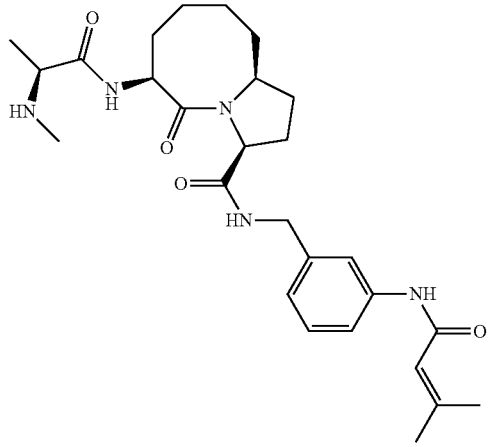

VII-12

(3S,6S,10aS)-6-((S)-2-(methylamino)propanamido)-N-(3-(3-methylbut-2-enamido)benzyl)-5-oxodecahydropyrrolo[1,2-a]azocine-3-carboxamide The title compound was prepared according to the steps and intermediates as described below.

To a mixture of the aniline 1k (10 mg) and diisopropylethylamine (50 µl) in dry dichloromethane (1 mL) was added 3-methylbut-2-enoyl chloride (20 µl) dropwise at 0° C. After stirring for 10 min at 0° C., trifluoroacetic acid (1 mL) was added to the reaction mixture and stirred 10 min at rt. The reaction mixture was concentrated and the residue was purified using semi-prep HPLC (TFA modifier) to give a white solid as TFA salt. LCMS: m/e 498.3 (M+1).

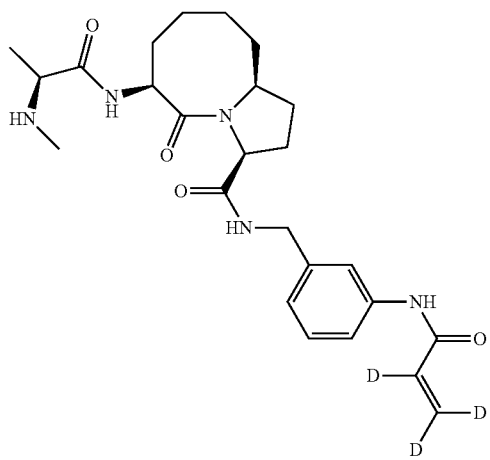

VII-16

Example 11

VII-16 was prepared according to the steps and intermediates as described below.

To a mixture of the aniline 1k (13.2 mg), acrylic acid-d4 (1.7 µl), EDC.HCl (8 mg), HOBt (6 mg), N-methylmorpholine (13 µl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 473.2 (M+1).

VII-21

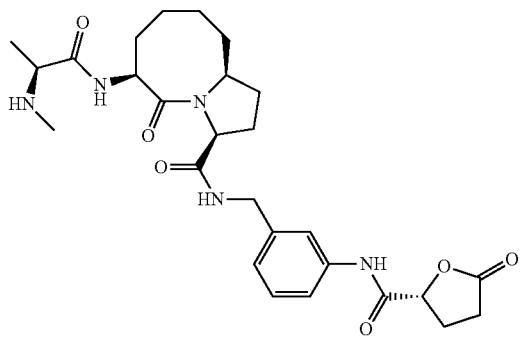

Example 12

(3S,6S,10aS)-6-((S)-2-(methylamino)propanamido)-5-oxo-N-(3-((R)-5-oxotetrahydrofuran-2-carboxamido)benzyl)decahydropyrrolo[1,2-a]azocine-3-carboxamide The title compound was prepared according to the steps and intermediates as described below.

To a mixture of the aniline 1k (8.1 mg), (R)-5-oxo-2-tetrahydrofurancarboxylic acid (2.4 mg), EDC.HCl (5 mg), HOBt (4 mg), N-methylmorpholine (10 µl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 528.3 (M+1).

Example 13

VII-23

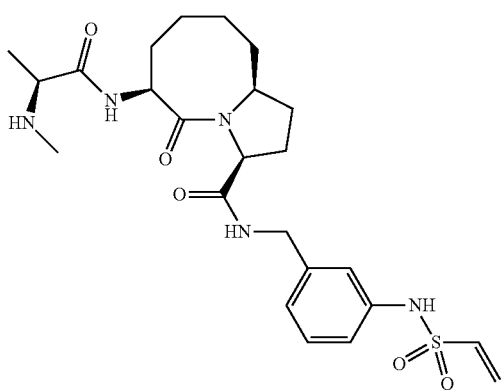

(3S,6S,10aS)-6-((S)-2-(methylamino)propanamido)-5-oxo-N-(3-(vinylsulfonamido)benzyl)decahydropyrrolo[1,2-a]azocine-3-carboxamide The title compound was prepared according to the steps and intermediates as described below.

To a mixture of the aniline 1k (30 mg) and diisopropylethylamine (50 µl) in dry dichloromethane (1 mL) was added 2-chloro-1-ethanesulfonyl chloride (5 µl) dropwise at 0° C. After stirring for 30 min at 0° C. to rt, trifluoroacetic acid (1 mL) was added to the reaction mixture and stirred 10 min at rt. The reaction mixture was concentrated and the residue was purified using semi-prep HPLC (TFA modifier) to give a white solid as TFA salt. LCMS: m/e 506.2 (M+1).

Example 14

VII-24

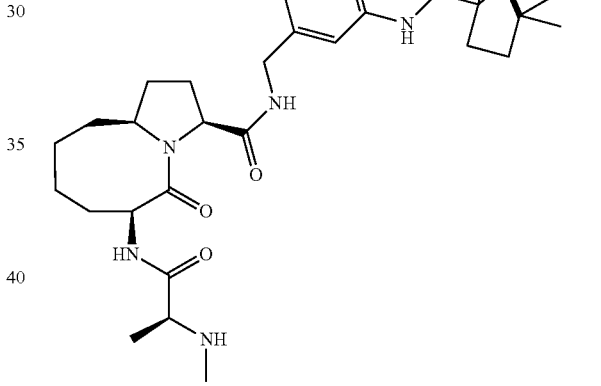

(3S,6S,10aS)-6-((S)-2-(methylamino)propanamido)-5-oxo-N-(3-((4R)-4,7,7-trimethyl-3-oxo-2-oxabicyclo[2.2.1]heptane-1-carboxamido)benzyl)decahydropyrrolo[1,2-a]azocine-3-carboxamide The title compound was prepared according to the steps and intermediates as described below.

To a mixture of the aniline 1k (8.0 mg), (1S)-(−)-camphanic acid (6.0 mg), EDC.HCl (8 mg), HOBt (6 mg), N-methylmorpholine (10 µl) in dichloromethane (1 mL) was stirred 2 days at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 596.4 (M+1).

Example 15

VII-26

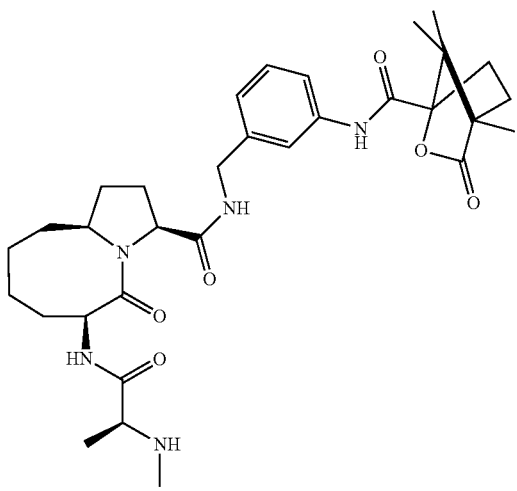

(3S,6S,10aS)-6-((S)-2-(methylamino)propanamido)-5-oxo-N-(3-((4S)-4,7,7-trimethyl-3-oxo-2-oxabicyclo[2.2.1]heptane-1-carboxamido)benzyl)decahydropyrrolo[1,2-a]azocine-3-carboxamide The title compound was prepared according to the steps and intermediates as described below.

To a mixture of the aniline 1k (8.1 mg), (1R)-(+)-camphanic acid (12 mg), EDC.HCl (16 mg), HOBt (12 mg), N-methylmorpholine (10 µl) in dichloromethane (1 mL) was stirred 3 days at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 596.3 (M+1).

Example 16

VII-34

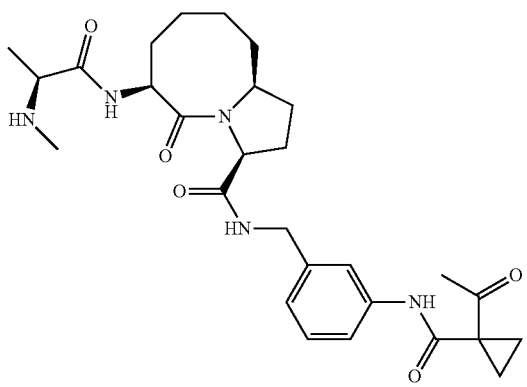

(3S,6S,10aS)-N-(3-(1-acetylcyclopropanecarboxamido)benzyl)-6-((S)-2-(methylamino)propanamido)-5-oxodecahydropyrrolo[1,2-a]azocine-3-carboxamide The title compound was prepared according to the steps and intermediates as described below.

To a mixture of the aniline 1k (14.2 mg), 1-acetylcyclopropanecarboxylic acid (10 mg), HATU (20 mg), diisopropylethylamine (10 µl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 526.3 (M+1).

Example 17

VII-38

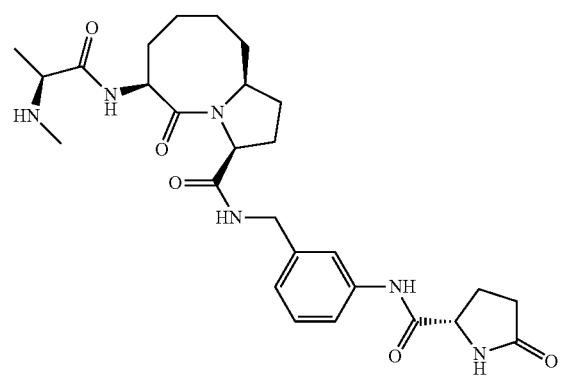

(3S,6S,10aS)-6-((S)-2-(methylamino)propanamido)-5-oxo-N-(3-((S)-5-oxopyrrolidine-2-carboxamido)benzyl)decahydropyrrolo[1,2-a]azocine-3-carboxamide The title compound was prepared according to the steps and intermediates as described below.

To a mixture of the aniline 1k (8 mg), (S)-2-pyrrolidine-5-carboxylic acid (5 mg), EDC.HCl (10 mg), HOBt (7 mg), diisopropylethylamine (10 µl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 527.2 (M+1).

Example 18

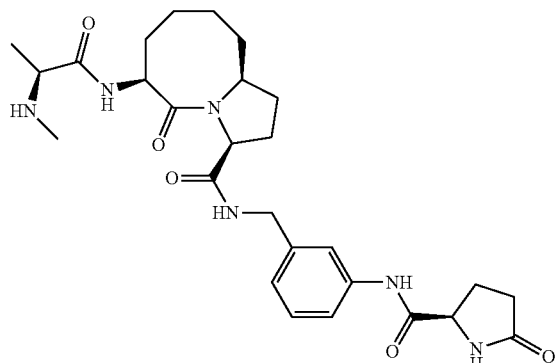

VII-39

(3S,6S,10aS)-6-((S)-2-(methylamino)propanamido)-5-oxo-N-(3-((R)-5-oxopyrrolidine-2-carboxamido)benzyl)decahydropyrrolo[1,2-a]azocine-3-carboxamide The title compound was prepared according to the steps and intermediates as described below.

To a mixture of the aniline 1k (8 mg), (R)-2-pyrrolidine-5-carboxylic acid (5 mg), EDC.HCl (10 mg), HOBt (7 mg), diisopropylethylamine (10 μl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 527.2 (M+1).

Example 19

VII-44

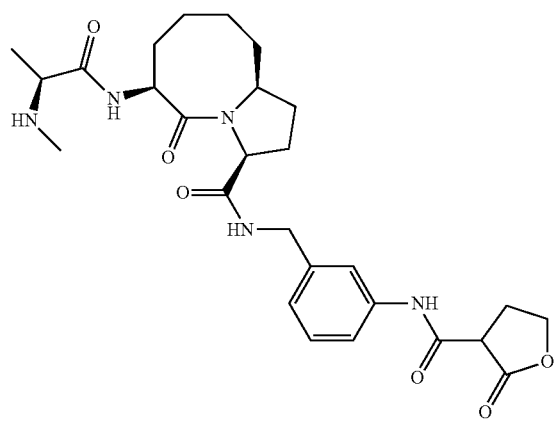

(3S,6S,10aS)-6-((S)-2-(methylamino)propanamido)-5-oxo-N-(3-(2-oxotetrahydrofuran-3-carboxamido)benzyl)decahydropyrrolo[1,2-a]azocine-3-carboxamide The title compound was prepared according to the steps and intermediates as described below.

To a mixture of the aniline 1k (8 mg), 2-oxo-3-tetrahydrofurancarboxylic acid (10 mg), EDC.HCl (10 mg), HOBt (7 mg), diisopropylethylamine (10 μl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 528.3 (M+1).

Example 20

VII-45

(3S,6S,10aS)-6-((S)-2-(methylamino)propanamido)-5-oxo-N-(3-(5-oxotetrahydrofuran-3-carboxamido)benzyl)decahydropyrrolo[1,2-a]azocine-3-carboxamide The title compound was prepared according to the steps and intermediates as described below.

To a mixture of the aniline 1k (8 mg), 2-oxo-4-tetrahydrofurancarboxylic acid (10 mg), EDC.HCl (10 mg), HOBt (7 mg), diisopropylethylamine (10 μl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 528.3 (M+1).

Example 21

VII-49

281

(3S,6S,10aS)-6-((S)-2-(methylamino)propanamido)-5-oxo-N-(3-((R)-4-oxoazetidine-2-carboxamido)benzyl)decahydropyrrolo[1,2-a]azocine-3-carboxamide The title compound was prepared according to the steps and intermediates as described below.

To a mixture of the aniline 1k (16 mg), (R)-4-oxo-2-azetidinecarboxylic acid (12 mg), EDC.HCl (20 mg), HOBt (14 mg), disoppropylethylamine (20 µl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 513.3 (M+1).

Example 22

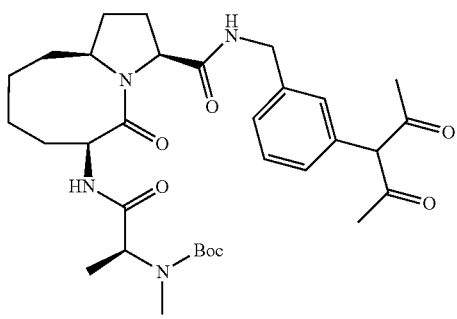

VII-7 tert-butyl(S)-1-((3S,6S,10aS)-3-(3-(2,4-dioxopentan-3-yl)benzylcarbamoyl)-5-oxodecahydropyrrolo[1,2-a]azocin-6-ylamino)-1-oxopropan-2-yl(methyl)carbamate The title compound was prepared according to the steps and intermediates as described below.

A mixture of 1j (250 mg), 3-iodobenzylamine (97 ul), EDC.HCl (152 mg), HOBt (99 mg), N-methylmorpholine (0.20 mL) in acetonitrile (10 mL) was stirred overnight at RT. After concentrating under reduced pressure, the residue was directly purified by column chromatography (SiO$_2$, isopropanol: dichloromethane, 7:93) to afford 300 mg of the desired iodide. LCMS: m/e 527.2 (M+1-$^t$Bu).

To the prepared iodide (32 mg) in DMSO (1 mL) were added copper iodide (1.0 mg), L-proline (1.2 mg), cesium carbonate (66 mg) and acetyl acetone (10 ul) and stirred at 90° C. for 2 h. The reaction mixture was filtered and the filtrate was purified using semi-prep HPLC (TFA modifier) to give a solid. LCMS: m/e 499.2 (M+1-$^t$Bu).

282

Example 23

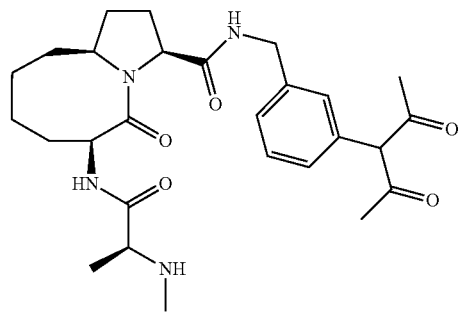

VII-8

(3S,6S,10aS)-N-(3-(2,4-dioxopentan-3-yl)benzyl)-6-((S)-2-(methylamino)propanamido)-5-oxodecahydropyrrolo[1,2-a]azocine-3-carboxamide The title compound was prepared according to the steps and intermediates as described below.

To the tert-butyl (S)-1-((3S,6S,10aS)-3-(3-(2,4-dioxopentan-3-yl)benzylcarbamoyl)-5-oxodecahydropyrrolo[1,2-a]azocin-6-ylamino)-1-oxopropan-2-yl(methyl)carbamate (VII-7) (7 mg) in dichloromethane (1 mL) was added trifluoroacetic acid (0.3 mL) and stirred 10 min at rt. The reaction mixture was concentrated and the residue was purified using semi-prep HPLC (TFA modifier) to give a white solid as TFA salt. LCMS: m/e 499.2 (M+1).

Example 24

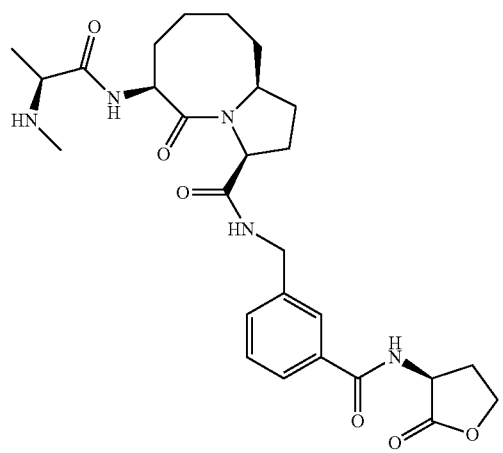

VII-13

283

(3S,6S,10aS)-6-((S)-2-(methylamino)propanamido)-5-oxo-N-(3-((S)-2-oxotetrahydrofuran-3-ylcarbamoyl)benzyl)decahydropyrrolo[1,2-a]azocine-3-carboxamide The title compound was prepared according to the steps and intermediates as described below.

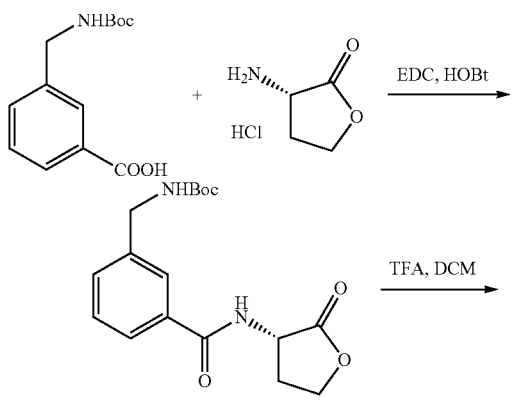

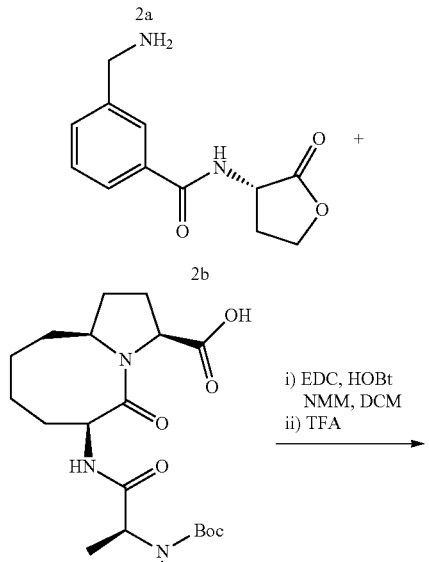

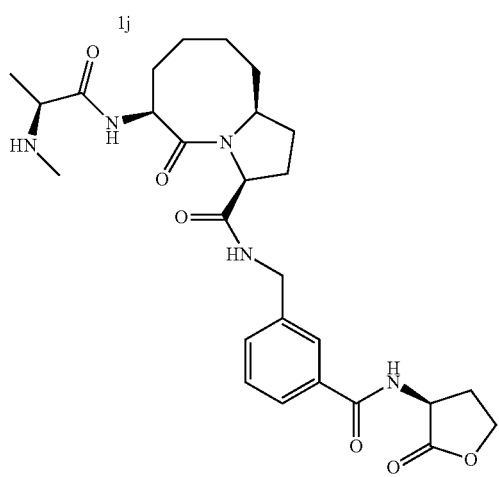

284

(S)-tert-butyl 3-(2-oxotetrahydrofuran-3-ylcarbamoyl)benzylcarbamate (2a)

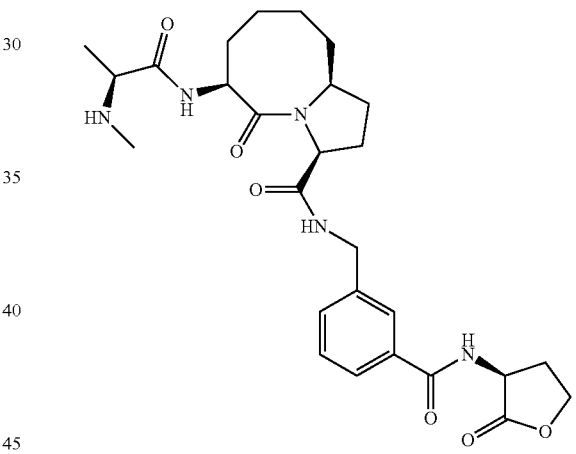

A mixture of 3-((tert-butoxycarbonylamino)methyl)benzoic acid (100 mg), (S)-3-aminodihydrofuran-2(3H)-one hydrochloride (55 mg), EDC.HCl (92 mg), HOBt (64 mg), N-methylmorpholine (0.13 mL) in acetonitrile (2 mL) was stirred overnight at RT. After concentrating under reduced pressure, the residue was directly purified by column chromatography (SiO$_2$, heptane:ethyl acetate, 10:90) to afford 120 mg of the desired aniline 2a as white solid. $^1$H NMR (400 MHz, CDCl$_3$): □=7.7-7.2 (m, 6H), 5.21 (s, 1H), 4.96 (m, 1H), 4.54 (t, J=9.2 Hz, 1H), 4.32 (m, 3H), 2.86 (m, 1H), 2.31 (m, 1H), 1.47 (s, 9H).

VII-13

(3S,6S,10aS)-6-((S)-2-(methylamino)propanamido)-5-oxo-N-(3-((S)-2-oxotetrahydrofuran-3-ylcarbamoyl)benzyl)decahydropyrrolo[1,2-a]azocine-3-carboxamide To a lactone 2a (40 mg) in dry dichloromethane (1 mL) was added trifluoroacetic acid (0.3 mL) dropwise at rt. After stirring for 10 min at rt, the reaction mixture was completely concentrated under reduced pressure. To this residue 2b in dry dichloromethane (1 mL) were added 1j (12 mg), EDC.HCl (5.6 mg), HOBt (4.3 mg), N-methylmorpholine (9.6 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid VII-13 as TFA salt. $^1$H NMR (400 MHz, DMSO-d$_6$): □=8.95 (d, J=8.2 Hz, 1H), 8.75 (m, 2H), 8.70 (d, J=6.8 Hz, 1H), 8.55 (t, J=6.0 Hz, 1H), 7.72 (m, 2H), 7.44 (m, 2H), 4.76 (m, 2H), 4.43-4.15 (m, 5H), 3.80 (q, J=6.4 Hz, 1H), 2.5-1.4 (m), 1.31 (d, J=6.8 Hz, 3H); LCMS: m/e 528.3 (M+1).

Example 25

VII-46

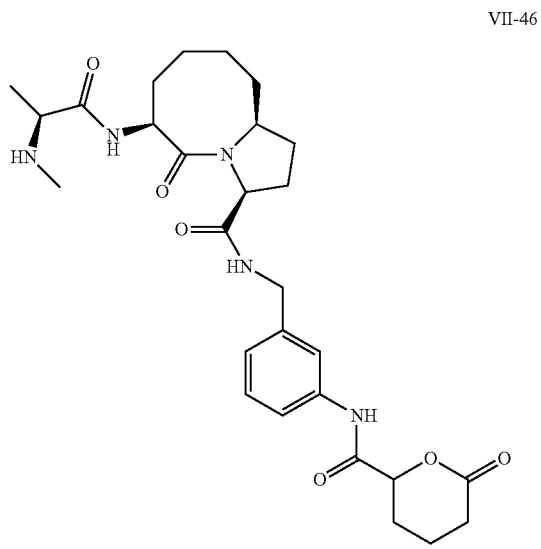 [SMILES: CN[C@@H](C)C(=O)N[C@H]1CCCC[C@H]2CC[C@@H](C(=O)NCc3cccc(NC(=O)C4CCCC(=O)O4)c3)N2C1=O]

(3S,6S,10aS)-6-((S)-2-(methylamino)propanamido)-5-oxo-N-(3-(6-oxotetrahydro-2H-pyran-2-carboxamido)benzyl)decahydropyrrolo[1,2-a]azocine-3-carboxamide The title compound was prepared according to the steps and intermediates as described below.

To a tert-butyl 3-(6-oxotetrahydro-2H-pyran-2-carboxamido)benzylcarbamate (20 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (12 mg), EDC.HCl (20 mg), HOBt (14 mg), N-methylmorpholine (20 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 542.3 (M+1).

Example 26

VII-14

4,4-dimethyl-2-oxotetrahydrofuran-3-yl 3-(((3S,6S,10aS)-6-((S)-2-(methylamino)propanamido)-5-oxo-decahydropyrrolo[1,2-a]azocine-3-carboxamido)methyl)benzoate The title compound was prepared according to the steps and intermediates as described below.

To a 4,4-dimethyl-2-oxotetrahydrofuran-3-yl 3-((tert-butoxycarbonylamino)methyl)benzoate (40 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (12 mg), EDC.HCl (5.6 mg), HOBt (4.3 mg), N-methylmorpholine (9.6 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 557.3 (M+1).

Example 27

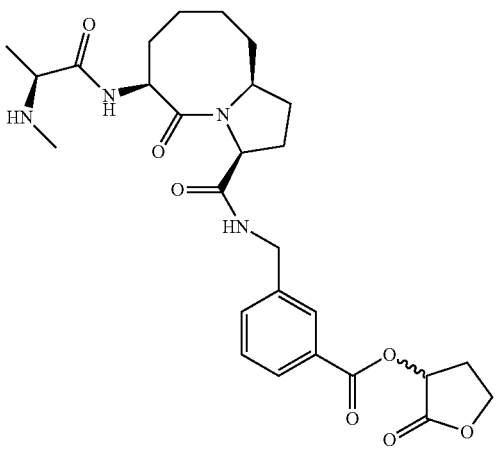

VII-15

2-oxotetrahydrofuran-3-yl 3-(((3S,6S,10aS)-6-((S)-2-(methylamino)propanamido)-5-oxodecahydropyrrolo[1,2-a]azocine-3-carboxamido)methyl)benzoate The title compound was prepared according to the steps and intermediates as described below.

To a 2-oxotetrahydrofuran-3-yl 3-((tert-butoxycarbonylamino)methyl)benzoate (40 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (12 mg), EDC.HCl (5.6 mg), HOBt (4.3 mg), N-methylmorpholine (9.6 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 529.3 (M+1).

Example 28

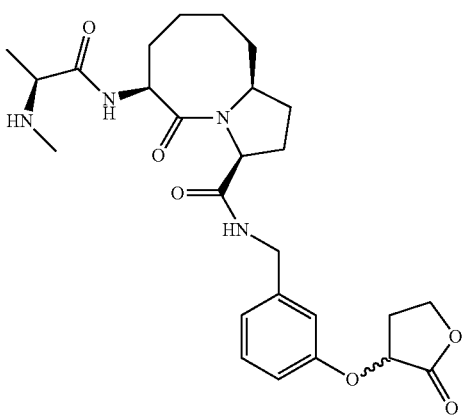

VII-17

(3S,6S,10aS)-6-((S)-2-(methylamino)propanamido)-5-oxo-N-(3-(2-oxotetrahydrofuran-3-yloxy)benzyl)decahydropyrrolo[1,2-a]azocine-3-carboxamide The title compound was prepared according to the steps and intermediates as described below.

To 3-(3-(aminomethyl)phenoxy)dihydrofuran-2(3H)-one (10 mg) in dry dichloromethane (1 mL) were added 1j (12 mg), EDC.HCl (5.6 mg), HOBt (4.3 mg), N-methylmorpholine (9.6 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 501.3 (M+1).

Example 29

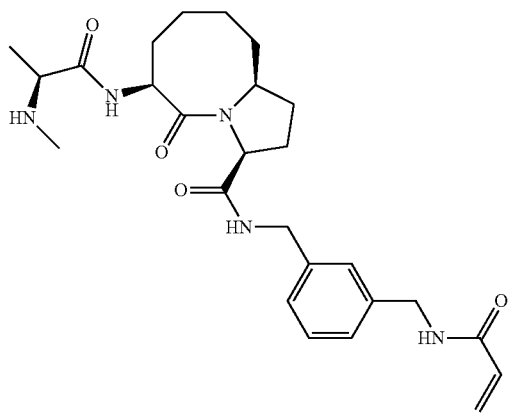

VII-18

(3S,6S,10aS)-N-(3-(acrylamidomethyl)benzyl)-6-((S)-2-(methylamino)propanamido)-5-oxodecahydropyrrolo[1,2-a]azocine-3-carboxamide The title compound was prepared according to the steps and intermediates as described below.

To 1,3-phenylenedimethanamine (0.1 mL) in dry dichloromethane (1 mL) were added 1j (12 mg), EDC.HCl (5.6 mg), HOBt (4.3 mg), N-methylmorpholine (9.6 µl) and the resulting mixture was stirred overnight at rt. At 0° C., acryloyl chloride was added and stirred for 10 min at 0° C. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 484.3 (M+1).

Example 30

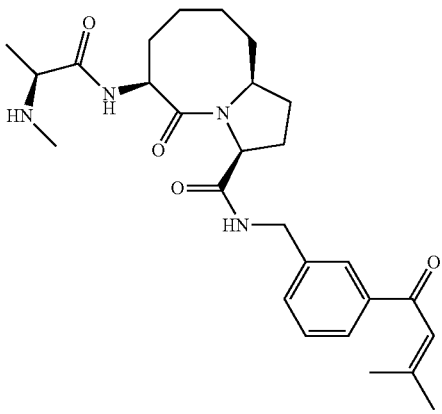

VII-19

(3S,6S,10aS)-6-((S)-2-(methylamino)propanamido)-
N-(3-(3-methylbut-2-enoyl)benzyl)-5-oxodecahydro-
pyrrolo[1,2-a]azocine-3-carboxamide The title compound was prepared according to the steps and intermediates as described below.

To a tert-butyl 3-(3-methylbut-2-enoyl)benzylcarbamate (40 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (28 mg), EDC.HCl (17.3 mg), HOBt (12.2 mg), N-methylmorpholine (25 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 483.3 (M+1).

Example 31

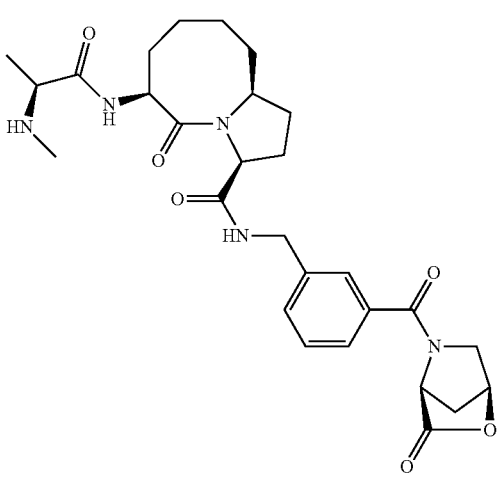

VII-20

(3S,6S,10aS)-6-((S)-2-(methylamino)propanamido)-
5-oxo-N-(3-((1S,4S)-3-oxo-2-oxa-5-azabicyclo
[2.2.1]heptane-5-carbonyl)benzyl)decahydropyrrolo
[1,2-a]azocine-3-carboxamide The title compound was prepared according to the steps and intermediates as described below.

To a tert-butyl 3-((1S,4S)-3-oxo-2-oxa-5-azabicyclo[2.2.1]heptane-5-carbonyl)benzylcarbamate (55 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (28 mg), EDC.HCl (17.3 mg), HOBt (12.2 mg), N-methylmorpholine (25 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 540.3 (M+1). VII-20

Example 32

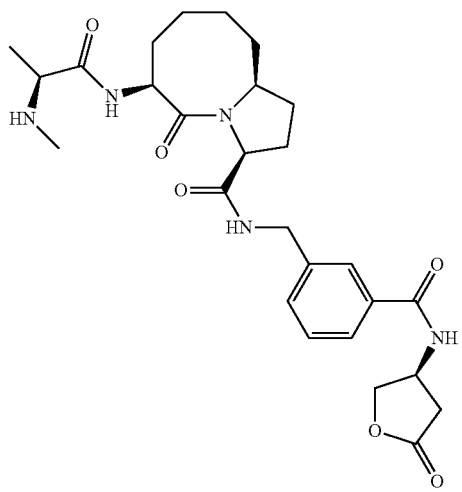

VII-22

(3S,6S,10aS)-6-((S)-2-(methylamino)propanamido)-
5-oxo-N-(3-((S)-5-oxotetrahydrofuran-3-ylcarbam-
oyl)benzyl)decahydropyrrolo[1,2-a]azocine-3-car-
boxamide The title compound was prepared according to the steps and intermediates as described below.

To a (S)-tert-butyl 3-(5-oxotetrahydrofuran-3-ylcarbamoyl)benzylcarbamate (20 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (20 mg), EDC.HCl (17.3 mg), HOBt (12.2 mg), N-methylmorpholine (50 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 528.3 (M+1).

Example 33

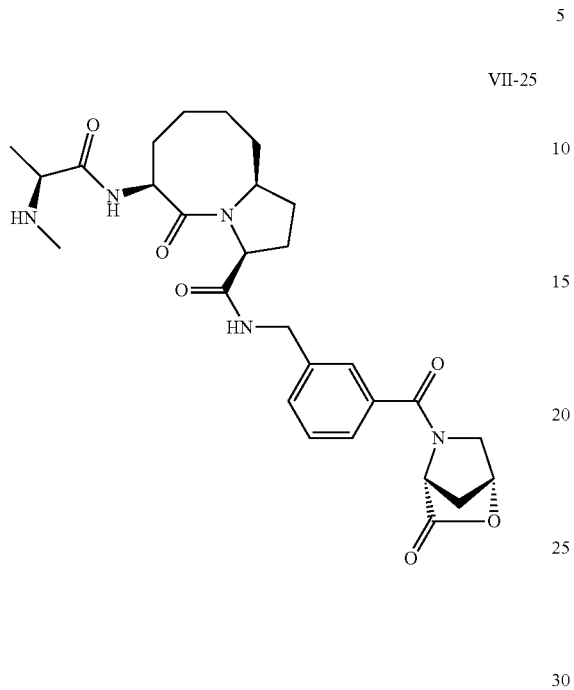

VII-25

(3S,6S,10aS)-6-((S)-2-(methylamino)propanamido)-5-oxo-N-(3-((1R,4R)-3-oxo-2-oxa-5-azabicyclo[2.2.1]heptane-5-carbonyl)benzyl)decahydropyrrolo[1,2-a]azocine-3-carboxamide The title compound was prepared according to the steps and intermediates as described below.

To a tert-butyl 3-((1R,4R)-3-oxo-2-oxa-5-azabicyclo[2.2.1]heptane-5-carbonyl)benzylcarbamate (30 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (11.5 mg), EDC.HCl (17 mg), HOBt (12 mg), N-methylmorpholine (10 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 540.3 (M+1).

Example 34

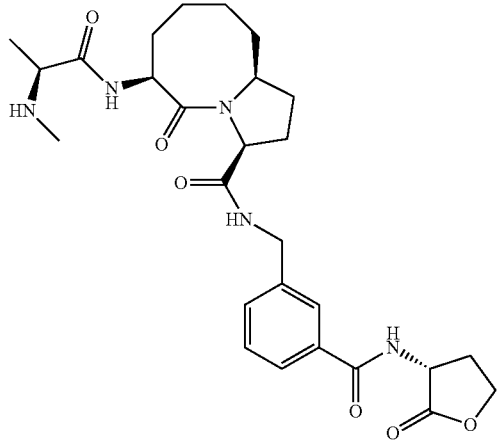

VII-27

(3S,6S,10aS)-6-((S)-2-(methylamino)propanamido)-5-oxo-N-(3-((R)-2-oxotetrahydrofuran-3-ylcarbamoyl)benzyl)decahydropyrrolo[1,2-a]azocine-3-carboxamide The title compound was prepared according to the steps and intermediates as described below.

To a (R)-tert-butyl 3-(5-oxotetrahydrofuran-3-ylcarbamoyl)benzylcarbamate (37 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (10 mg), EDC.HCl (17.3 mg), HOBt (12.2 mg), N-methylmorpholine (10 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 528.3 (M+1).

Example 35

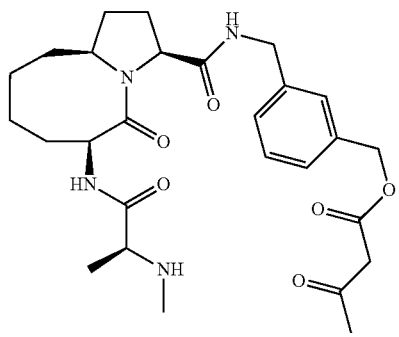

VII-29

3-(((3S,6S,10aS)-6-((S)-2-(methylamino)propanamido)-5-oxodecahydropyrrolo[1,2-a]azocine-3-carboxamido)methyl)benzyl 3-oxobutanoate The title compound was prepared according to the steps and intermediates as described below.

To (3-(aminomethyl)phenyl)methanol (10 mg) in dry dichloromethane (1 mL) were added 1j (13.7 mg), EDC.HCl (7 mg), HOBt (5.0 mg), N-methylmorpholine (10 µl) and the resulting mixture was purified using semi-prep HPLC (TFA modifier). To a mixture of the isolated product (5 mg), 2,2,4-trimethyl-6-keto-1,3-dioxin (10 µl) in dimethoxyethane (1 mL) was stirred overnight at 80° C. The mixture was concentrated and diluted with dichloromethane (1 mL). Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 515.2 (M+1).

Example 36

VII-31

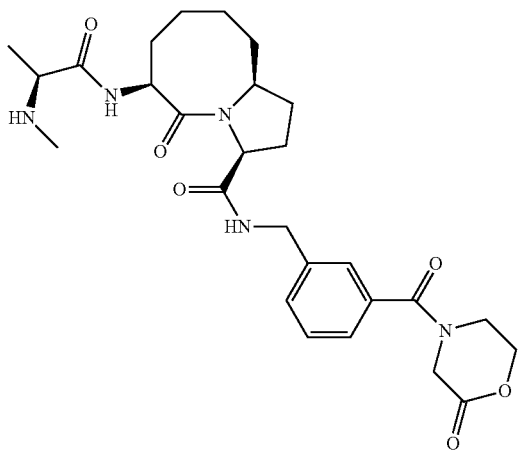

3S,6S,10aS)-6-((S)-2-(methylamino)propanamido)-5-oxo-N-(3-(2-oxomorpholine-4-carbonyl)benzyl)decahydropyrrolo[1,2-a]azocine-3-carboxamide The title compound was prepared according to the steps and intermediates as described below.

To a tert-butyl 3-(2-oxomorpholine-4-carbonyl)benzylcarbamate (20 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (10 mg), EDC.HCl (10 mg), HOBt (7 mg), N-methylmorpholine (10 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 528.3 (M+1).

Example 37

VII-32

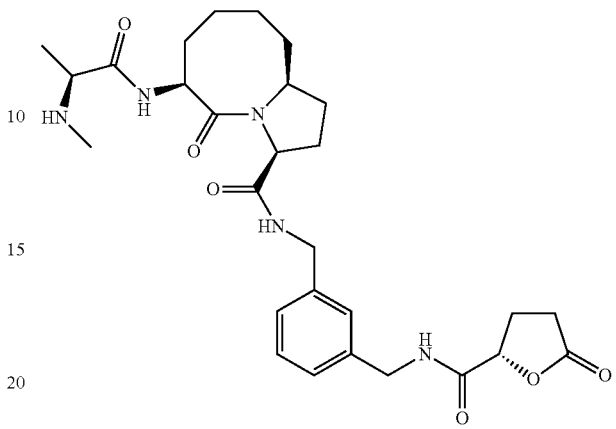

3S,6S,10aS)-6-((S)-2-(methylamino)propanamido)-5-oxo-N-(3-(((S)-5-oxotetrahydrofuran-2-carboxamido)methyl)benzyl)decahydropyrrolo[1,2-a]azocine-3-carboxamide The title compound was prepared according to the steps and intermediates as described below.

To a (S)-tert-butyl 3-((5-oxotetrahydrofuran-2-carboxamido)methyl)benzylcarbamate (10 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (10 mg), EDC.HCl (10 mg), HOBt (7 mg), N-methylmorpholine (10 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 542.3 (M+1).

Example 38

VII-33

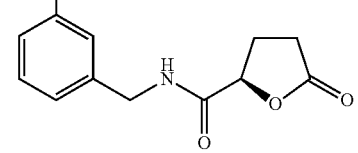

3S,6S,10aS)-6-((S)-2-(methylamino)propanamido)-5-oxo-N-(3-(((R)-5-oxotetrahydrofuran-2-carboxamido)methyl)benzyl)decahydropyrrolo[1,2-a]azocine-3-carboxamide The title compound was prepared according to the steps and intermediates as described below.

To a (R)-tert-butyl 3-((5-oxotetrahydrofuran-2-carboxamido)methyl)benzylcarbamate (10 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (10 mg), EDC.HCl (10 mg), HOBt (7 mg), N-methylmorpholine (10 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 542.3 (M+1).

Example 39

VII-41

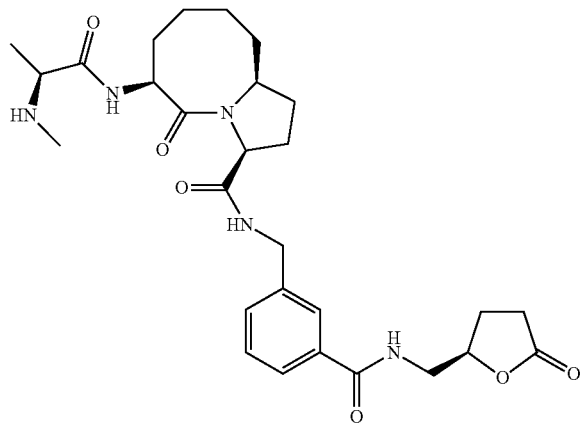

3S,6S,10aS)-6-((S)-2-(methylamino)propanamido)-5-oxo-N-(3-(((R)-5-oxotetrahydrofuran-2-yl)methylcarbamoyl)benzyl)decahydropyrrolo[1,2-a]azocine-3-carboxamide The title compound was prepared according to the steps and intermediates as described below.

To a (R)-tert-butyl 3-((5-oxotetrahydrofuran-2-yl)methylcarbamoyl)benzylcarbamate (20 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (10 mg), EDC.HCl (20 mg), HOBt (14 mg), N-methylmorpholine (20 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 542.3 (M+1).

Example 40

VII-42

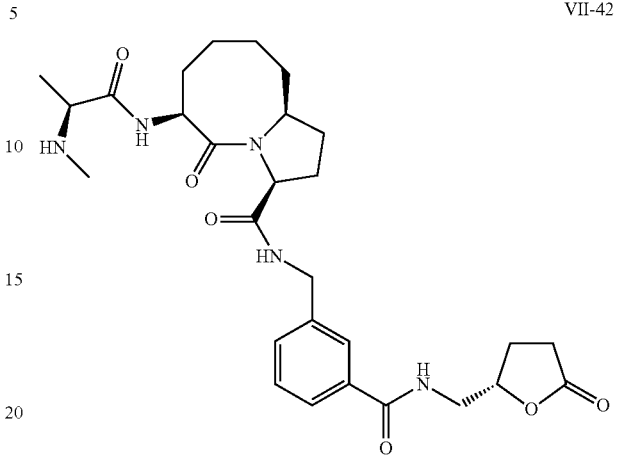

3S,6S,10aS)-6-((S)-2-(methylamino)propanamido)-5-oxo-N-(3-(((S)-5-oxotetrahydrofuran-2-yl)methylcarbamoyl)benzyl)decahydropyrrolo[1,2-a]azocine-3-carboxamide The title compound was prepared according to the steps and intermediates as described below.

To a (S)-tert-butyl 3-((5-oxotetrahydrofuran-2-yl)methylcarbamoyl)benzylcarbamate (20 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (10 mg), EDC.HCl (20 mg), HOBt (14 mg), N-methylmorpholine (20 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 542.3 (M+1).

Example 41

VII-43

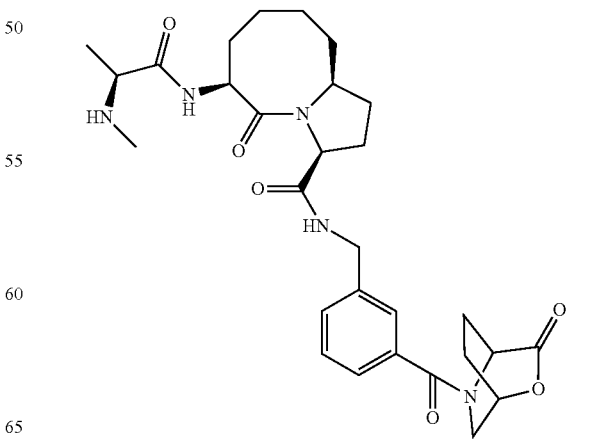

3S,6S,10aS)-6-((S)-2-(methylamino)propanamido)-
5-oxo-N-(3-(3-oxo-2-oxa-5-azabicyclo[2.2.2]octane-
5-carbonyl)benzyl)decahydropyrrolo[1,2-a]azocine-
3-carboxamide The title compound was prepared according to the steps and intermediates as described below.

To a tert-butyl 3-((1S,4S)-3-oxo-2-oxa-5-azabicyclo[2.2.2]octane-5-carbonyl)benzylcarbamate (20 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (10 mg), EDC.HCl (20 mg), HOBt (14 mg), N-methylmorpholine (20 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 544.3 (M+1).

Example 42

VII-47

3S,6S,10aS)-6-((S)-2-(methylamino)propanamido)-
5-oxo-N-(3-((1S)-7-oxo-6-oxa-2-azabicyclo[3.2.1]
octane-2-carbonyl)benzyl)decahydropyrrolo[1,2-a]
azocine-3-carboxamide The title compound was prepared according to the steps and intermediates as described below.

To a tert-butyl 3-((1R,5 S)-7-oxo-6-oxa-2-azabicyclo[3.2.1]octane-2-carbonyl)benzylcarbamate (18 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (10 mg), EDC.HCl (20 mg), HOBt (14 mg), N-methylmorpholine (20 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 554.3 (M+1).

Example 43

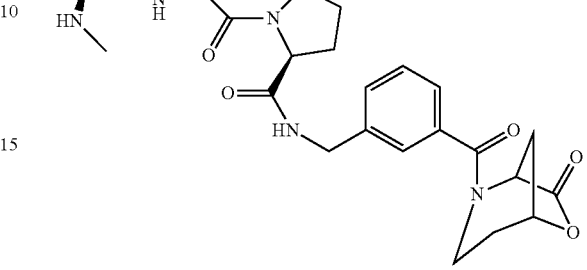

VII-48

3S,6S,10aS)-6-((S)-2-(methylamino)propanamido)-
5-oxo-N-(3-(7-oxo-6-oxa-2-azabicyclo[3.2.1]octane-
2-carbonyl)benzyl)decahydropyrrolo[1,2-a]azocine-
3-carboxamide The title compound was prepared according to the steps and intermediates as described below.

To a tert-butyl 3-((1 S,5R)-7-oxo-6-oxa-2-azabicyclo[3.2.1]octane-2-carbonyl)benzylcarbamate (9.0 mg) in dry dichloromethane (1 mL) was added trifluoroacetic acid (0.3 mL) dropwise at rt. After stirring for 10 min at rt, the reaction mixture was completely concentrated under reduced pressure. To this residue in dry dichloromethane (1 mL) were added 1j (10 mg), EDC.HCl (10 mg), HOBt (7 mg), N-methylmorpholine (10 µl) and the resulting mixture was stirred overnight at rt. Trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 554.3 (M+1).

Example 44

VIII-2

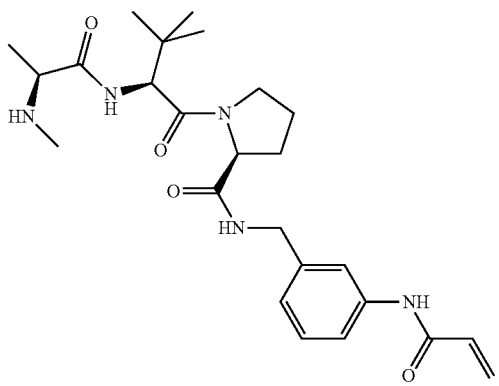

(S)-N-(3-acrylamidobenzyl)-1-((S)-3,3-dimethyl-2-((S)-2-(methylamino)propanamido)butanoyl)pyrrolidine-2-carboxamide
The title compound was prepared according to the steps and intermediates as described below.
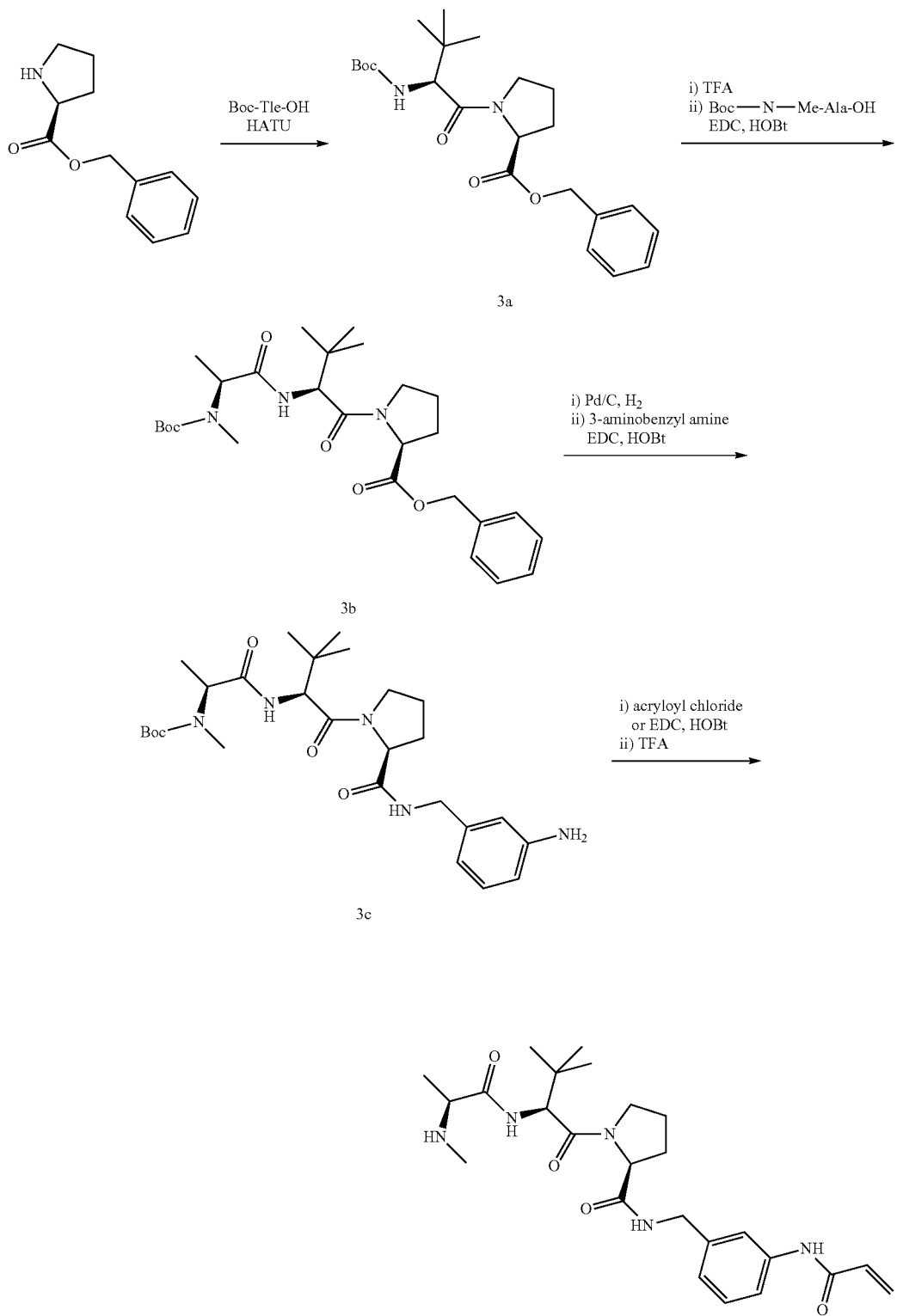

301

(S)-benzyl 1-((S)-2-(tert-butoxycarbonylamino)-3,3-dimethylbutanoyl)pyrrolidine-2-carboxylate (3a)

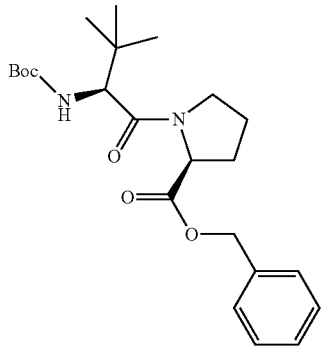 [SMILES: CC(C)(C)OC(=O)N[C@H](C(=O)N1CCC[C@H]1C(=O)OCc1ccccc1)C(C)(C)C]

A mixture of proline benzyl ester (1.0 g), Boc-Tle-OH (1.05 g), HATU (1.73 g), diisopropylethylamine (0.5 mL) in DMF (10 mL) was stirred overnight at RT. After concentrating under reduced pressure, the residue was partitioned into EtOAc and saturated sodium bicarbonate. The organic layer was dried over sodium sulfate and filtered. The residue was purified by column chromatography (SiO$_2$, heptane:ethyl acetate, 60:40) to afford the desired 3a as white solid. LCMS: m/e 319.1 (M+1-$^t$Bu).

(S)-benzyl 1-((S)-2-((S)-2-(tert-butoxycarbonyl(methyl)amino)propanamido)-3,3-dimethylbutanoyl)pyrrolidine-2-carboxylate (3b)

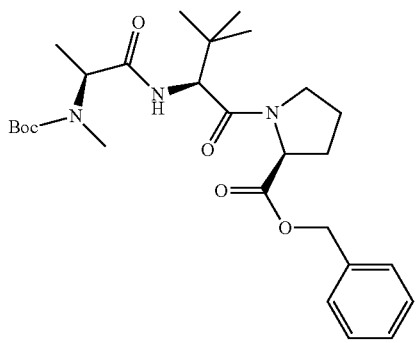 [SMILES: C[C@@H](C(=O)N[C@H](C(=O)N1CCC[C@H]1C(=O)OCc1ccccc1)C(C)(C)C)N(C)C(=O)OC(C)(C)C]

To 3a (110 mg) in dry dichloromethane (2 mL) was added trifluoroacetic acid (1 mL) dropwise at rt. After stirring for 10 min at rt, the mixture was concentrated under reduced pressure. To the residue in dry dichloromethane (3 mL) was treated with Boc-N-Me-Ala-OH (59 mg), EDC.HCl (61 mg), HOBt (39 mg), diisopropylethylamine (0.10 mL), and the resulting mixture was stirred overnight at rt. The reaction mixture was partitioned into EtOAc and washed with saturated sodium bicarbonate. The organic layer was dried over sodium sulfate and filtered. The residue was purified by column chromatography (SiO$_2$, heptane:ethyl acetate, 40:60) to give the desired 3b as colorless oil. $^1$H NMR (400 MHz, CDCl$_3$): ☐=7.34 (m, 5H), 5.19 (d, J=11.9 Hz, 1H), 5.12 (d, J=11.9 Hz, 1H), 4.7 (m, 1H), 4.61 (d, J=14.0 Hz, 1H), 4.57 (m, 1H), 3.86 (m, 1H), 3.69 (m, 1H), 2.79 (s, 3H), 2.22 (m, 1H), 1.97 (m, 2H), 1.48 (s, 9H), 1.35 (m, 1H), 0.98 (s, 9H); LCMS: m/e 404.3 (M+1-$^t$Bu).

302 tert-butyl (S)-1-((S)-1-((S)-2-(3-aminobenzylcarbamoyl)pyrrolidin-1-yl)-3,3-dimethyl-1-oxobutan-2-ylamino)-1-oxopropan-2-yl(methyl)carbamate (3c)

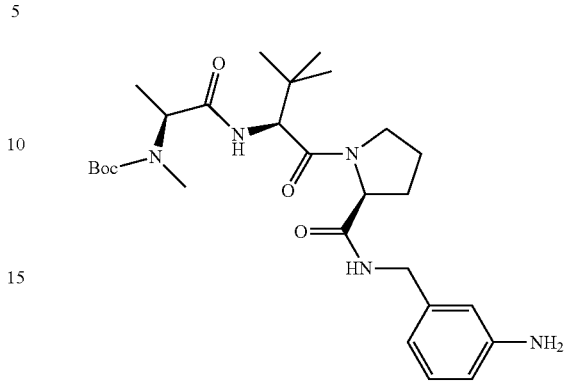

Benzyl ester 3b (100 mg) in dry methanol (10 mL) was hydrogenated in the presence of palladium on carbon (10%, wet type) for 2 h. The mixture was filtered and the filtrate was concentrated under reduced pressure. To the residue in dry dichloromethane (3 mL) was treated with 3-aminobenzylamine (30 mg), EDC.HCl (61 mg), HOBt (39 mg), diisopropylethylamine (0.10 mL), and the resulting mixture was stirred overnight at rt. The reaction mixture was partitioned into EtOAc and washed with saturated sodium bicarbonate. The organic layer was dried over sodium sulfate and filtered. The residue was purified by column chromatography (SiO$_2$, dichloromethane:isopropanol, 90:10) to give the desired 3c as colorless oil. $^1$H NMR (400 MHz, CDCl$_3$): LCMS: m/e 418.2 (M+1-$^t$Bu).

VIII-2

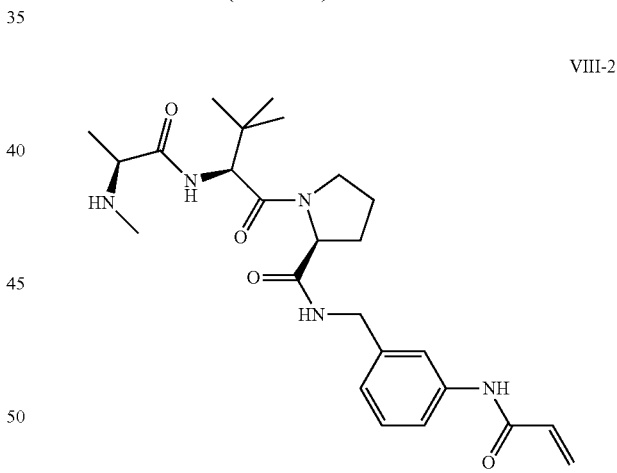

S)-N-(3-acrylamidobenzyl)-1-((S)-3,3-dimethyl-2-((S)-2-(methylamino)propanamido)butanoyl)pyrrolidine-2-carboxamide To a mixture of the aniline 3c (14 mg) and triethylamine (20 µl) in dry dichloromethane (1 mL) was added acryloyl chloride (10 µl) dropwise at 0° C. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid 4 as TFA salt. $^1$H NMR (400 MHz, DMSO-d$_6$): ☐=10.0 (s, 1H), 8.75 (m, 2H), 8.53 (d, J=8.7 Hz, 1H), 8.37 (t, J=6.0 Hz, 1H), 7.52 (s, 1H), 7.45 (d, J=8.2 Hz, 1H), 7.17 (t, J=8.2 Hz, 1H), 6.95 (d, J=7.8 Hz, 1H), 6.38 (dd, J=10.1, 16.9 Hz, 1H), 6.19 (dd, J=2.3, 16.9 Hz, 1H), 5.69 (dd, J=2.3, 10.1 Hz, 1H), 4.46 (d, J=8.7 Hz, 1H), 4.29 (m, 1H), 4.19 (m, 1H), 3.87 (m, 1H), 3.65 (m, 2H), 2.04 (m, 1H), 1.93 (m, 1H), 1.78 (m, 2H), 1.25 (d, J=6.9 Hz, 3H), 0.95 (s, 9H); LCMS: m/e 472.2 (M+1).

Example 45

VIII-1

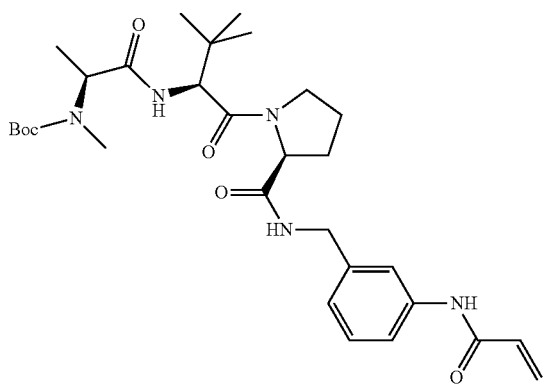

tert-butyl (S)-1-((S)-1-((S)-2-(3-acrylamidobenzyl-carbamoyl)pyrrolidin-1-yl)-3,3-dimethyl-1-oxobutan-2-ylamino)-1-oxopropan-2-yl(methyl)carbamate The title compound was prepared according to the steps and intermediates as described below.

To a mixture of the aniline 3c (14 mg) and triethylamine (20 μl) in dry dichloromethane (1 mL) was added acryloyl chloride (10 μl) dropwise at 0° C. After stirring for 10 min at 0° C., the reaction mixture was concentrated and the residue was purified using semi-prep HPLC (TFA modifier) to give a white solid 4. LCMS: m/e 472.2 (M+1-ᵗBu).

Example 46

VIII-3

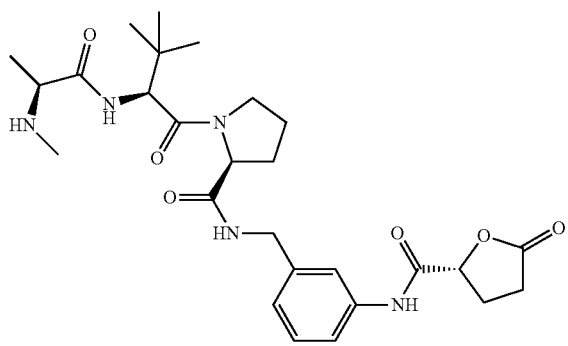

(S)-1-((S)-3,3-dimethyl-2-((S)-2-(methylamino)propanamido)butanoyl)-N-(3-((R)-5-oxotetrahydrofuran-2-carboxamido)benzyl)pyrrolidine-2-carboxamide The title compound was prepared according to the steps and intermediates as described below.

To a mixture of the aniline 3c (12 mg), (R)-5-oxo-2-tetrahydrofurancarboxylic acid (6 mg), EDC.HCl (10 mg), HOBt (7 mg), diisopropylethylamine (10 μl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 530.3 (M+1).

Example 47

VIII-7

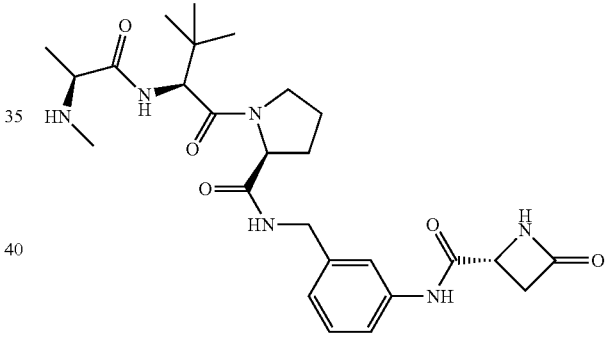

(S)-1-((S)-3,3-dimethyl-2-((S)-2-(methylamino)propanamido)butanoyl)-N-(3-((R)-4-oxoazetidine-2-carboxamido)benzyl)pyrrolidine-2-carboxamide The title compound was prepared according to the steps and intermediates as described below.

To a mixture of the aniline 3c (12 mg), (R)-4-oxo-2-azetidinecarboxylic acid (6 mg), EDC.HCl (10 mg), HOBt (7 mg), diisopropylethylamine (10 μl) in dichloromethane (1 mL) was stirred overnight at RT. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid as TFA salt. LCMS: m/e 515.3 (M+1).

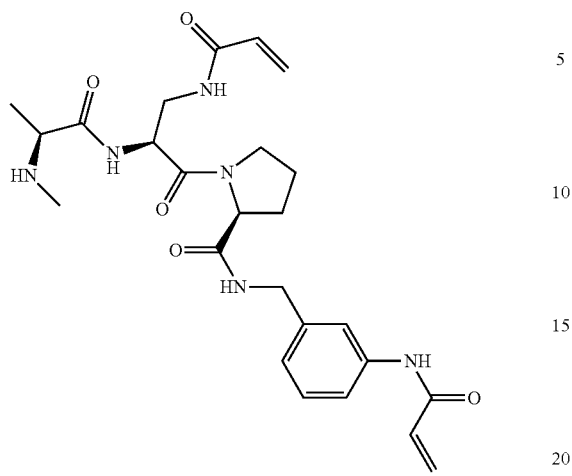
Example 48
(S)-1-((S)-3-acrylamido-2-((S)-2-(methylamino)propanamido)propanoyl)-N-(3-acrylamidobenzyl)pyrrolidine-2-carboxamide
The title compound was prepared according to the steps and intermediates as described below.
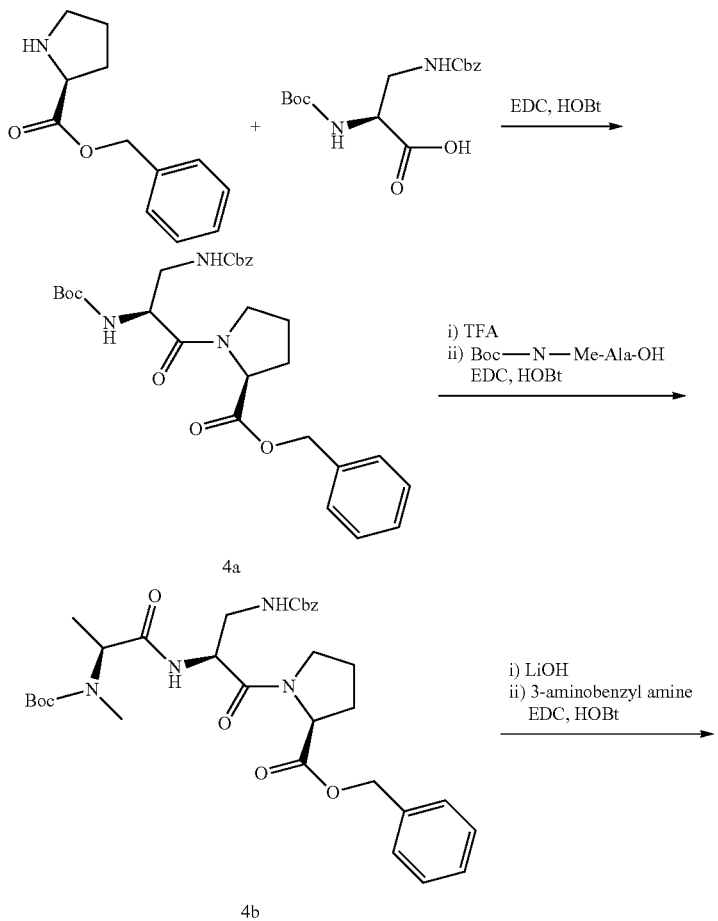

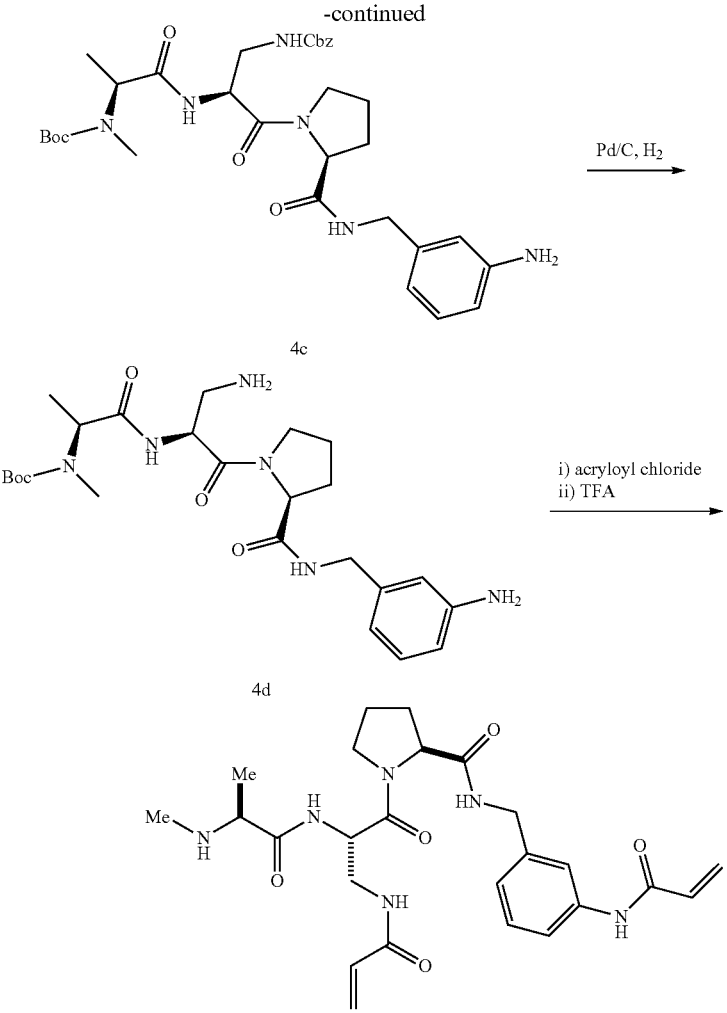

4c

4d

(S)-benzyl 1-((S)-3-(benzyloxycarbonylamino)-2-(tert-butoxycarbonylamino)propanoyl)pyrrolidine-2-carboxylate (4a)

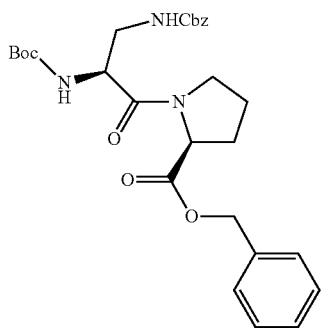 [SMILES: CC(C)(C)OC(=O)N[C@@H](CNC(=O)OCc1ccccc1)C(=O)N1CCC[C@H]1C(=O)OCc1ccccc1]

A mixture of proline benzyl ester (0.66 g), Boc-Dap(Z)—OH (1.1 g), EDC.HCl (0.58 g), HOBt (370 mg), diisopropylethylamine (1.0 mL), in DCM (10 mL) was stirred overnight at RT. After concentrating under reduced pressure, the residue was partitioned into EtOAc and saturated sodium bicarbonate. The organic layer was dried over sodium sulfate and filtered. The residue was purified by column chromatography (SiO$_2$, heptane:ethyl acetate, 60:40) to afford the desired 4a as white foam. LCMS: m/e 426.2 (M+1-$^t$Bu).

(S)-benzyl 1-((S)-3-(benzyloxycarbonylamino)-2-((S)-2-(tert-butoxycarbonyl(methyl)amino)propanamido)propanoyl)pyrrolidine-2-carboxylate (4b)

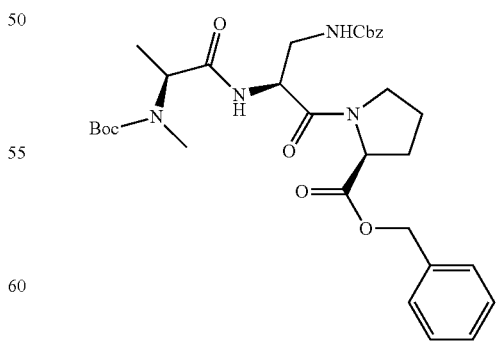

To 4a (1.15 g) in dry dichloromethane (10 mL) was added trifluoroacetic acid (3 mL) dropwise at rt. After stirring for 10 min at rt, the mixture was concentrated under reduced pressure. To the residue in dry dichloromethane (10 mL) was treated with Boc-N-Me-Ala-OH (489 mg), EDC.HCl (505 mg), HOBt (325 mg), diisopropylethylamine (0.60 mL), and the resulting mixture was stirred overnight at rt. The reaction mixture was partitioned into EtOAc and washed with saturated sodium bicarbonate. The organic layer was dried over sodium sulfate and filtered. The residue was purified by column chromatography (SiO$_2$, heptane:ethyl acetate, 40:60) to give the desired 4b as white solid. LCMS: m/e 511.2 (M+1-$^t$Bu).

tert-butyl (S)-1-((S)-3-(benzyloxycarbonylamino)-1-((S)-2-(3-aminobenzylcarbamoyl)pyrrolidin-1-yl)-1-oxopropan-2-ylamino)-1-oxopropan-2-yl(methyl)carbamate (4c)

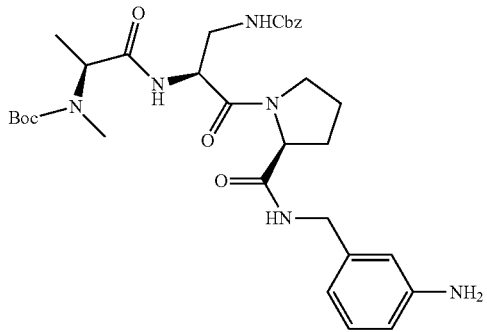 [SMILES: C[C@@H](C(=O)N[C@@H](CNC(=O)OCc1ccccc1)C(=O)N1CCC[C@H]1C(=O)NCc1cccc(N)c1)N(C)C(=O)OC(C)(C)C]

To 4b (540 mg) in water (3 mL) was added 74 mg of lithium hydroxide in 3 mL of methanol at 0° C. After 30 min, the mixture was acidified to pH 3.0 using 1 N—HCl and partitioned into ethyl acetate The organic layer was dried over sodium sulfate. The mixture was filtered and the filtrate was concentrated under reduced pressure. To the residue in dry dichloromethane (10 mL) was treated with 3-aminobenzylamine (130 mg), EDC.HCl (204 mg), HOBt (131 mg), diisopropylethylamine (0.60 mL), and the resulting mixture was stirred overnight at rt. The reaction mixture was partitioned into EtOAc and washed with saturated sodium bicarbonate. The organic layer was dried over sodium sulfate and filtered. The residue was purified by column chromatography (SiO$_2$, dichloromethane:isopropanol, 90:10) to give the desired 4c as white solid. $^1$H NMR (400 MHz, CDCl$_3$): LCMS: m/e 625.3 (M+1).

tert-butyl (S)-1-((S)-3-amino-1-((S)-2-(3-aminobenzylcarbamoyl)pyrrolidin-1-yl)-1-oxopropan-2-ylamino)-1-oxopropan-2-yl(methyl)carbamate (4d)

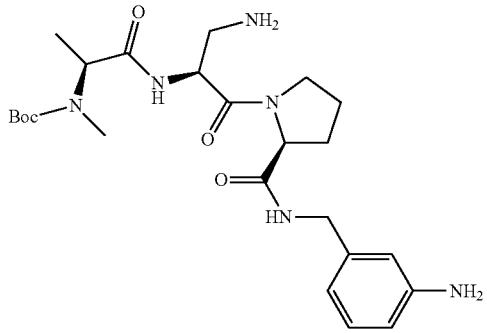 [SMILES: C[C@@H](C(=O)N[C@@H](CN)C(=O)N1CCC[C@H]1C(=O)NCc1cccc(N)c1)N(C)C(=O)OC(C)(C)C]

To 4b (30 mg) in dry methanol (5 mL) was hydrogenated in the presence of palladium on carbon (10%, wet type) for 2 h. The mixture was filtered and the filtrate was concentrated under reduced pressure to provide 4d. LCMS: m/e 491.3 (M+1).

(S)-1-((S)-3-acrylamido-2-((S)-2-(methylamino)propanamido)propanoyl)-N-(3-acrylamidobenzyl)pyrrolidine-2-carboxamide (VIII-5)

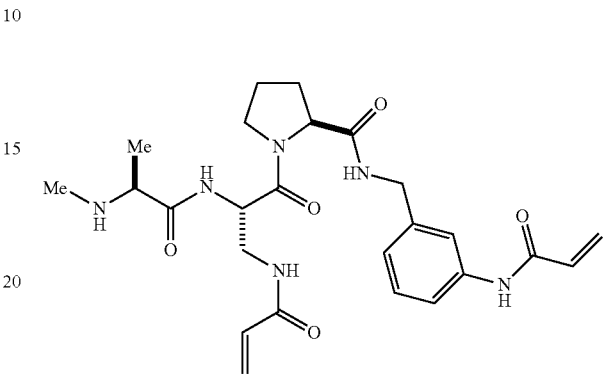

To a mixture of the aniline 4d (14 mg) and triethylamine (20 μl) in dry dichloromethane (1 mL) was added acryloyl chloride (10 μl) dropwise at 0° C. After stirring for 10 min at 0° C., trifluoroacetic acid (0.3 mL) was added to the reaction mixture and stirred 10 min at rt. The reaction mixture was concentrated and the residue was purified using semi-prep HPLC (TFA modifier) to give a white solid VIII-5 as TFA salt. LCMS: m/e 499.2 (M+1).

VIII-4

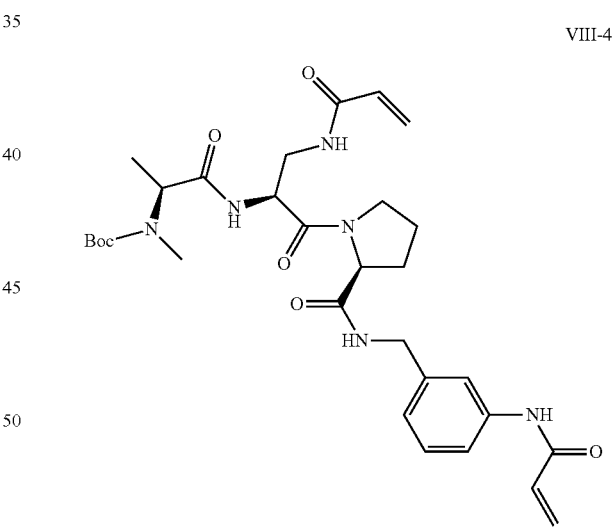

Example 49 tert-butyl (S)-1-((S)-3-acrylamido-1-((S)-2-(3-acrylamidobenzylcarbamoyl)pyrrolidin-1-yl)-1-oxopropan-2-ylamino)-1-oxopropan-2-yl(methyl)carbamate The title compound was prepared according to the steps and intermediates as described below.

To a mixture of the aniline 4d (14 mg) and triethylamine (20 μl) in dry dichloromethane (1 mL) was added acryloyl chloride (10 μl) dropwise at 0° C. After stirring for 10 min at 0° C., the reaction mixture was concentrated and the residue was purified using semi-prep HPLC (TFA modifier) to give a white solid. LCMS: m/e 499.2 (M+1-$^t$Bu).

C. XIAP Biological Data

Example 50

Homogeneous, Fluorescence Polarization, Competition Binding Assay Protocol for Affinity Assessment of Compound Binding to XIAP, cIAP-1 and ML-IAPβ BIR3 Domains 1× stocks of recombinant human XIAP; BIR3 domain (895-XB), recombinant human cIAP-1 (818-IA) or recombinant human ML-IAPβ (818-IA) from R&D Systems and Fluorescence Polarization (FP) assay tracer (Atto-647 tagged IAP inhibitor probe compound) were prepared in assay buffer consisting of 25 mM Tris-HCL, pH 7.5 (Sigma), 10 mM NaCl$_2$ (Sigma), 1 mM DTT (Fluka) and 0.005% TritonX-100 (Pierce). While IAP protein and tracer equilibrated at ambient temp in the dark (30-60 min), 100× stocks of test compound were prepared in 50% DMSO:H$_2$O, serially diluted and spotted (0.5 □L/well) in duplicate wells of a 384-well, flat bottom, polypropylene, black assay plate (Greiner #781209). Amounts used with respect to each protein were as follows: [XIAP]=120 nM, [Assay Tracer]=20 nM (Tracer:Protein K$_d$=83-61 nM; 0-3 hr); [cIAP-1]=30 nM, [Assay Tracer]=10 nM (Tracer:Protein K$_d$=37-14 nM; 0-1 hr); and [ML-IAPβ]=100 nM, [Assay Tracer]=15 nM (Tracer:Protein K$_d$=43-55 nM; 0-3 hr). Competition binding between test compounds and assay tracer was initiated by the addition of 50 □L/well of pre-equilibrated IAP protein and assay tracer. Displacement of the assay tracer was measured in a Synergy plate reader from BioTek (Winooski, Vt.) at $\lambda_{ex}$620/$\lambda_{em}$680 through a 660 nm half-sized dicroich mirror and S/P polarizing filters every 30 min for 3 hr. (See Huang, X., *Journal of Biomolecular Screening* 8, 2003). The resulting compound dose response data were fit to a one-site binding K$_i$ model in GraphPad Prism from GraphPad Software (San Diego, Calif.).

Table 2 shows the activity of selected compounds of this invention in the Ki (XIAP), Ki (c-IAP-1, 3 h), and Ki (ML-IAP, 2 h) Assays. Compounds having an activity designated as "A" provide an IC50≤10 nM; compounds having an activity designated as "B" provide an IC50>10 nM and ≤100 nM; compounds having an activity designated as "C" provide an IC50>100 nM and ≤1000 nM; compounds having an activity designated as "D" provide an IC50>1000 nM and <10,000 nM; and compounds having an activity designated as "E" provide an IC50≥10,000 nM.

TABLE 2

| Compound | Enzyme/Ki | Inhibition Designation |
|---|---|---|
| VII-1 | XIAP | C |
| | c-IAP-1 | C |
| | ML-IAP | C |
| VII-2 | XIAP | E |
| | c-IAP-1 | E |
| | ML-IAP | E |
| VII-3 | XIAP | C |
| | c-IAP-1 | C |
| VII-4 | XIAP | C |
| | c-IAP-1 | C |
| VII-5 | XIAP | B |
| | c-IAP-1 | C |
| VII-6 | XIAP | C |
| | c-IAP-1 | B |
| VII-7 | XIAP | E |
| | c-IAP-1 | E |
| VII-8 | XIAP | B |
| | c-IAP-1 | C |
| VII-9 | XIAP | B |
| | c-IAP-1 | C |
| VII-10 | XIAP | C |
| | c-IAP-1 | C |
| VII-11 | XIAP | C |
| | c-IAP-1 | C |
| VII-12 | XIAP | C |
| | c-IAP-1 | B |
| VII-13 | XIAP | C |
| | c-IAP-1 | C |
| VII-14 | XIAP | C |
| | c-IAP-1 | D |
| VII-15 | XIAP | B |
| | c-IAP-1 | C |
| VII-16 | XIAP | C |
| | c-IAP-1 | C |
| | ML-IAP | C |
| VII-17 | XIAP | B |
| | c-IAP-1 | C |
| VII-18 | XIAP | C |
| | c-IAP-1 | C |
| VII-19 | XIAP | C |
| | c-IAP-1 | B |
| VII-20 | XIAP | B |
| | c-IAP-1 | C |
| VII-21 | XIAP | C |
| | c-IAP-1 | C |
| | ML-IAP | D |
| VII-22 | XIAP | C |
| | c-IAP-1 | C |
| VII-23 | XIAP | B |
| | c-IAP-1 | A |
| | ML-IAP | B |
| VII-24 | XIAP | C |
| | c-IAP-1 | C |
| VII-25 | XIAP | C |
| | c-IAP-1 | C |
| VII-26 | XIAP | C |
| | c-IAP-1 | C |
| VII-27 | XIAP | C |
| | c-IAP-1 | C |
| VII-28 | XIAP | B |
| | c-IAP-1 | B |
| VII-29 | XIAP | C |
| | c-IAP-1 | D |
| | ML-IAP | B |
| VII-30 | XIAP | B |
| | c-IAP-1 | B |
| | ML-IAP | B |
| VII-31 | XIAP | C |
| | c-IAP-1 | C |
| VII-32 | XIAP | C |
| | c-IAP-1 | C |
| VII-33 | XIAP | C |
| | c-IAP-1 | D |
| VII-34 | XIAP | C |
| | c-IAP-1 | C |
| VII-35 | XIAP | B |
| | c-IAP-1 | A |
| VII-36 | XIAP | C |
| | c-IAP-1 | C |
| | ML-IAP | D |
| VII-37 | XIAP | C |
| | c-IAP-1 | C |
| VII-38 | XIAP | C |
| | c-IAP-1 | D |
| VII-39 | XIAP | C |
| | c-IAP-1 | C |
| VII-40 | XIAP | C |
| | c-IAP-1 | C |
| VII-41 | XIAP | C |
| | c-IAP-1 | C |
| VII-42 | XIAP | C |
| | c-IAP-1 | C |

TABLE 2-continued

| Compound | Enzyme/Ki | Inhibition Designation |
|---|---|---|
| VII-43 | XIAP | C |
| | c-IAP-1 | D |
| | ML-IAP | E |
| VII-44 | XIAP | C |
| | c-IAP-1 | C |
| VII-45 | XIAP | C |
| | c-IAP-1 | D |
| VII-46 | XIAP | B |
| | c-IAP-1 | C |
| VII-47 | XIAP | C |
| | c-IAP-1 | D |
| VII-48 | XIAP | C |
| | c-IAP-1 | C |

D. Mass Spectrometric Analysis of XIAP Contacted with Compounds of the Invention

Example 51

Figure 6:
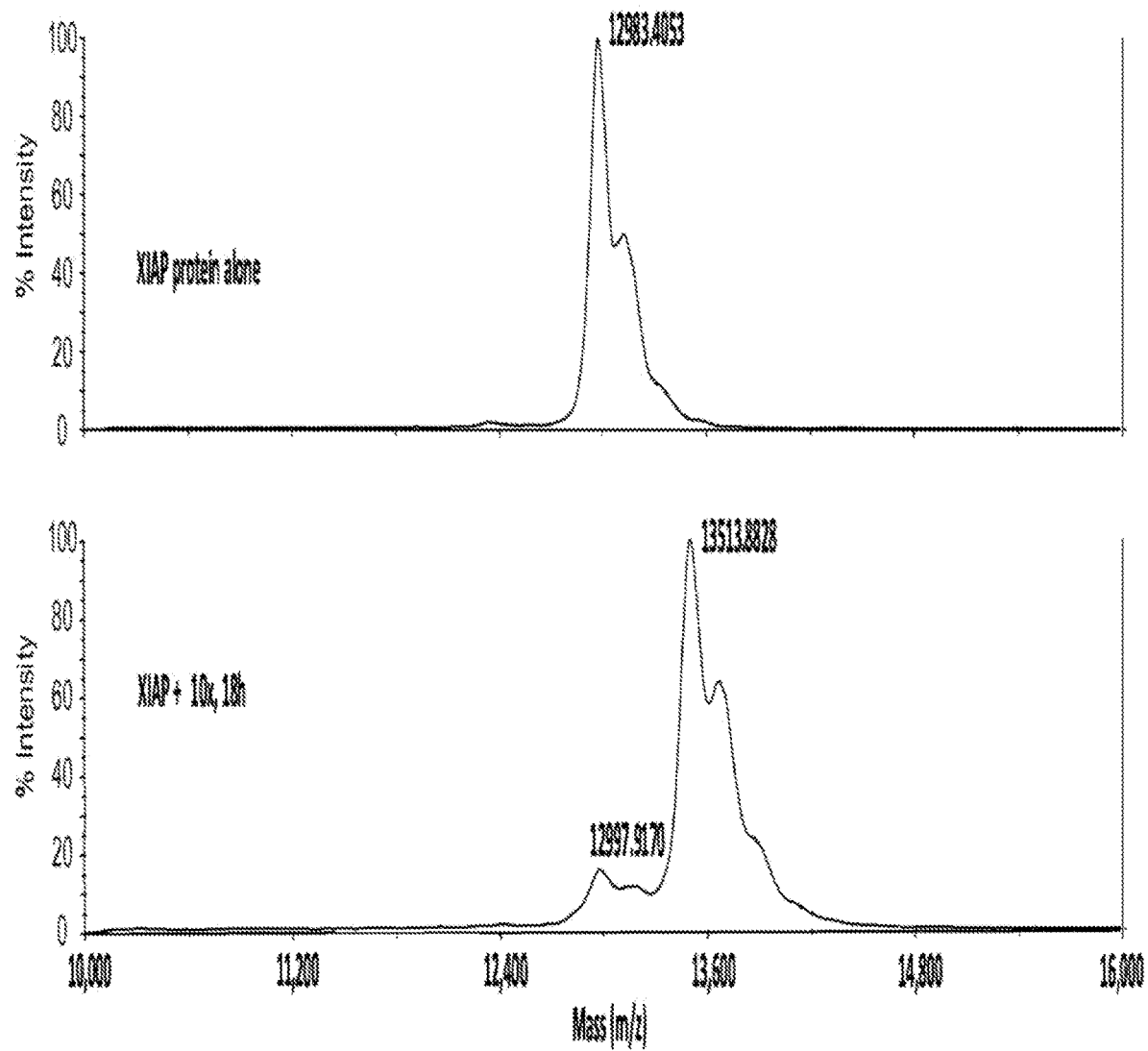
FIG. 6 depicts the mass spectrometric analysis of compound VII-1 contacted with XIAP.

Intact XIAP was incubated for 18 hr at a 10-fold excess of VII-1 to protein. 3ul aliquots of the samples were diluted with 10 ul of 0.1% TFA prior to micro C4 ZipTipping directly onto the MALDI target using Sinapinic acid as the desorption matrix (10 mg/mL in 0.1% TFA:Acetonitrile 50:50). The top panel of FIG. 6 shows mass spectrometric trace of the intact XIAP protein (m/z 13,096 Da). The bottom panel of FIG. 6 shows mass spectrometric trace of XIAP incubated with VII-1(mw=469.59) for 18 hr (m/z of 13,513), which shows a mass shift of 417 Da, with no m/z of 13,096, which indicates complete modification of XIAP by VII-1 within 18 h.

Example 52

Intact XIAP was incubated for 18 hr at a 10-fold excess of VII-1 to protein. After incubation, the protein was cleaned using a low volume ZEBA desalting column and then diluted with an equal volume of 0.2M ammonium bicarbonate with 1 mM DTT. The protein was then reduced by heating at 56° C. for 45 min. After incubation, the sample was allowed to cool to room temperature and a 1.9 μg/μL iodoacetamide solution was added and incubated for 30 min at room temperature to alkylate cysteine residues. Sequencing grade trypsin (promega) was added at a 1:20 (protease:protein) ratio and incubated at 37° C. for 16 hours. Peptides are then purified and enriched using C4 packed pipette tips (Millipore) and spotted directly on the MALDI target plate with alpha-cyano-4-hydroxy-cinnamic acid as the matrix (10 mg/mL in 0.1% TFA:Acetonitrile 50:50).

Figure 7:
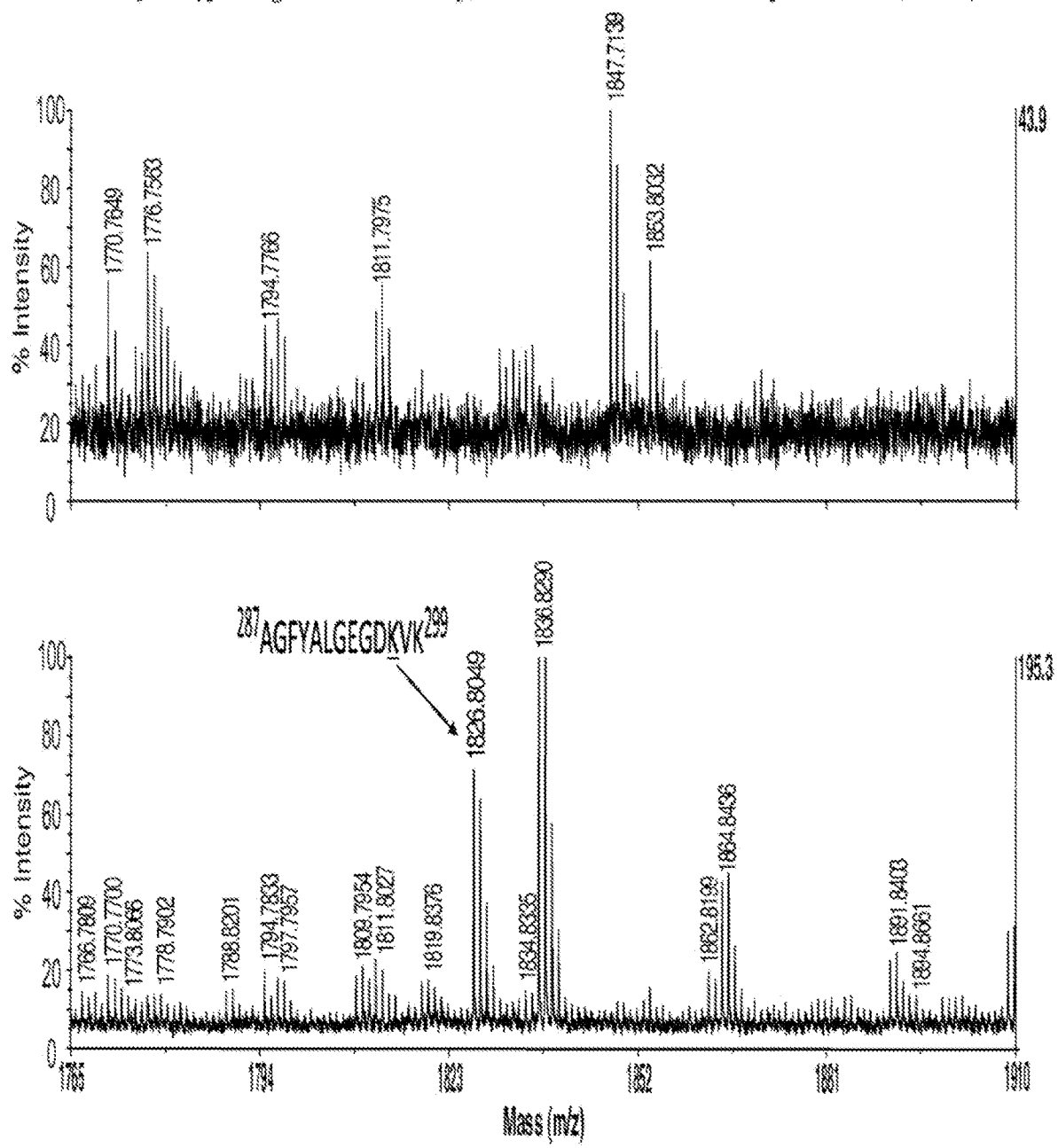
FIG. 7 depicts the mass spectrometric analysis of chymotrypsin digestion of XIAP (top) and XIAP contacted with compound VII-1 (bottom).

The top panel of FIG. 7 shows the mass spectrometric trace of the mass region for the control XIAP digest, and the bottom panel of FIG. 7 shows the mass spectrometric trace for the digest of XIAP incubated with VII-1. A peptide with a m/z of 1,826 Da is identified in the XIAP+VII-21 digest, but was not observed in the control XIAP digest, which corresponds to the mass of the peptide amino acids 287-299 (AGFYALGEGDKVK (SEQ ID NO: 174)) from XIAP containing a single VII-1 modification. Modification of the peptide occurred at lysine K297 and not at K299, because if the modification had occurred at K299, the trypsin digest would not occur at that site, indicating that VII-1 binds to K297 of XIAP.

Example 53

Figure 8:
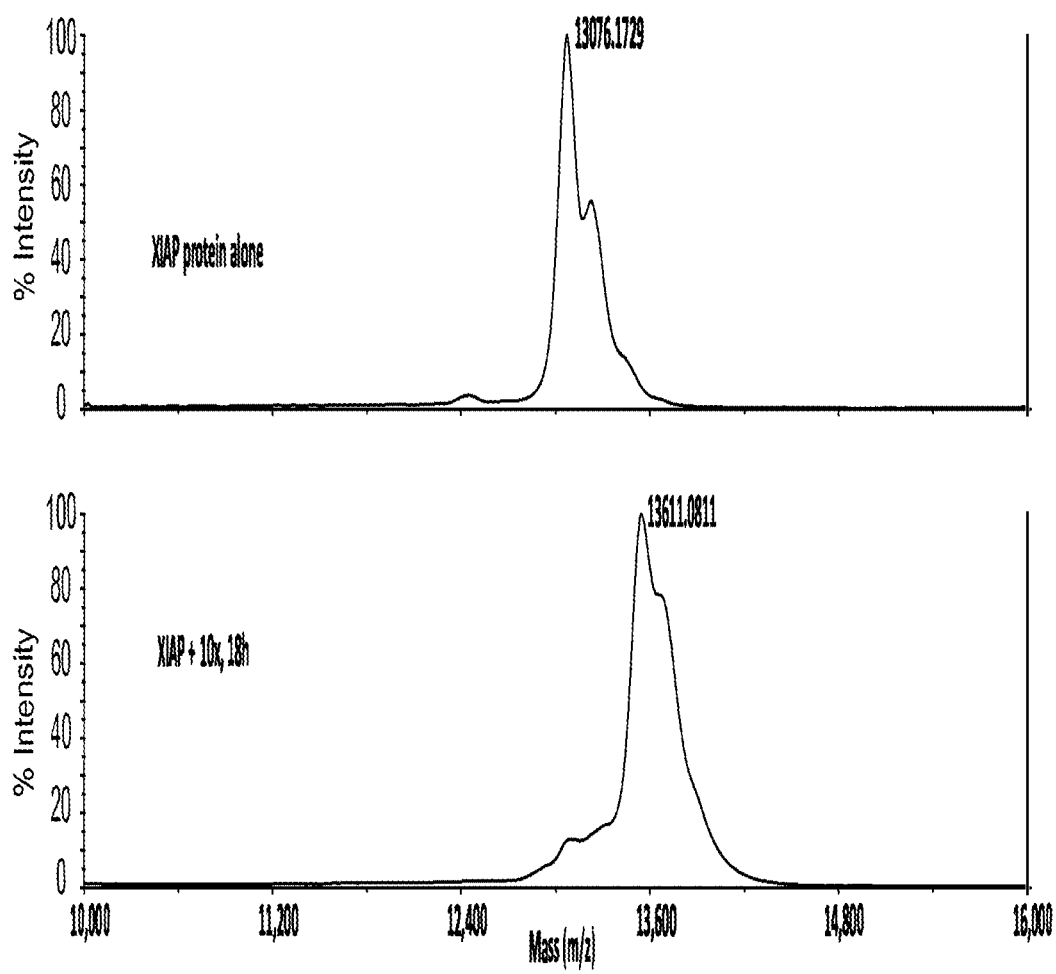
FIG. 8 depicts the mass spectrometric analysis of compound VII-21 contacted with XIAP.

Intact XIAP was incubated for 18 hr at a 10-fold excess of VII-21 to protein. 3 ul aliquots of the samples were diluted with 10 ul of 0.1% TFA prior to micro C4 ZipTipping directly onto the MALDI target using Sinapinic acid as the desorption matrix (10 mg/mL in 0.1% TFA:Acetonitrile 50:50). Results: The top panel of FIG. 8 shows the mass spectrometric trace of intact XIAP protein (m/z 12,994 Da). The bottom panel of FIG. 8 shows the mass spectrometric trace of XIAP incubated with VII-21 (mw=572.62) for 18 hr (m/z of 13,516), which shows a mass shift of 522 Da, and no m/z at 12,994 Da, indicating complete modification of XIAP by VII-21 within 18h.

Example 54

Intact XIAP was incubated for 18 hr at a 10-fold excess of VII-21 to protein. After incubation the protein was cleaned using a low volume ZEBA desalting column and then diluted with an equal volume of 100 mM TrisHCl, 10 mM $CaCl_2$, with 1 mM DTT pH 7.8. The protein was then reduced by heating at 56° C. for 45 min. After incubation, the sample was then allowed to cool to room temperature and then a 1.9 μg/μL iodoacetamide solution was added and incubated for 30 min at room temperature to alkylate cysteine residues. Finally, chymotrypsin (Roche) was added at a 1:20 (protease:protein) ratio and incubated at room temperature for 16 hours. Peptides were then purified and enriched using C4 packed pipette tips (Millipore) and spotted directly on the MALDI target plate with alpha-cyano-4-hydroxy-cinnamic acid as the matrix (10 mg/mL in 0.1% TFA:Acetonitrile 50:50).

Figure 9:
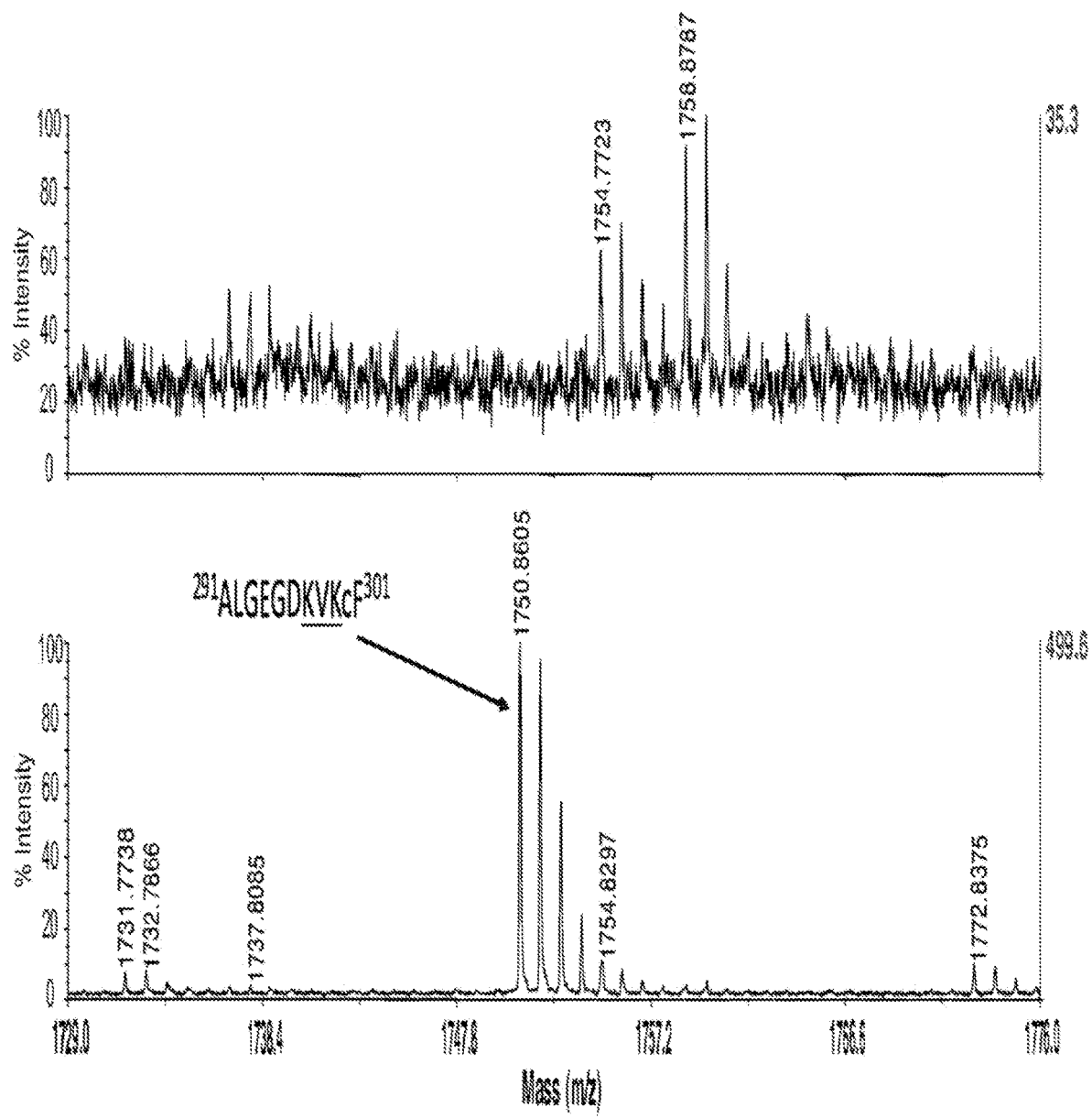
FIG. 9 depicts the mass spectrometric analysis of chymotrypsin digestion of XIAP (top) and XIAP contacted with compound VII-21 (bottom).

The top panel of FIG. 9 shows the mass spectrometric trace of the mass region of the molecular weight for the control XIAP digest, and the bottom panel of FIG. 9 shows the mass spectrometric trace of the digest of XIAP incubated with VII-21. A peptide with an m/z of 1,750 Da is identified in the XIAP+VII-21 digest that is absent in the control XIAP digest. This peptide corresponds to the mass of the peptide of amino acids 291-301 (ALGEGDKVKCF (SEQ ID NO: 175)) from XIAP containing a single VII-21 modification and the cysteine alkylated iodoacetamide.

E. HCV Protease Synthetic Examples

Example 55

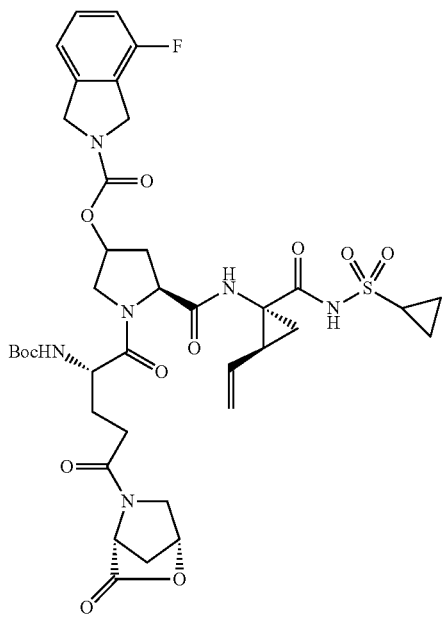

XVI-16

(5S)-1-((S)-2-(tert-butoxycarbonylamino)-5-oxo-5-((1R,4R)-3-oxo-2-oxa-5-azabicyclo[2.2.1]heptan-5-yl)pentanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate The title compound was prepared according to the steps and intermediates as described below.

Intermediate 1a

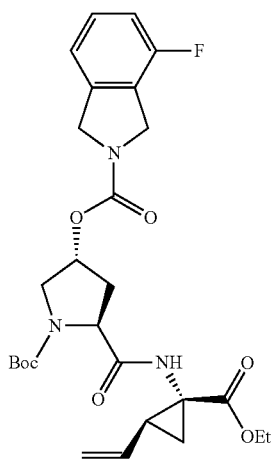 [SMILES: C=C[C@@H]1C[C@]1(NC(=O)[C@@H]1C[C@@H](OC(=O)N2Cc3cccc(F)c3C2)CN1C(=O)OC(C)(C)C)C(=O)OCC]

To a solution of (1R,2S)-1-amino-2-vinylcyclopropane carboxylic acid ethyl ester toluenesulfonic acid (0.33 g, 1.0 mmol) and (2S,4R)-1-(tert-butoxycarbonyl)-4-(4-fluoroisoindoline-2-carbonyloxy)pyrrolidine-2-carboxylic acid (0.4 g, 1.0 mmol) in 10 mL of acetonitrile was added HATU (0.44 g, 1.2 mmol) and then DIEA (0.46 mL, 2.5 mmol) under stirring. The mixture was stirred at r.t. for two hours. After the complete consumption of starting materials, the reaction mixture was evaporated. The residue was dissolved in 30 mL ethyl acetate and washed with water and brine twice and dried over $Na_2SO_4$. After removal of solvent, the crude product was subjected to chromatography on silica gel (hexane:EtOAc=1:1). 0.35 g of the title compound was obtained: MS m/z: 532.0 (ES+).

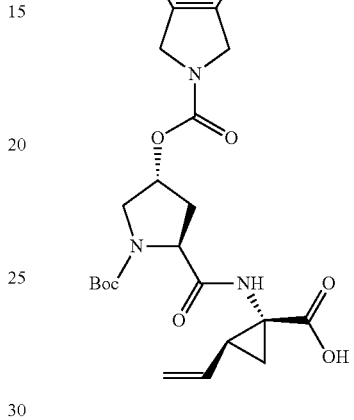

Intermediate 1b

To a solution of the product of step 1a (0.35 g, 0.66 mmol) in 5 mL of THF/MeOH (1:1) was added 1N LiOH aqueous solution (2 mL, 2.0 mmol). After stirring at r.t. for 10 hours, the reaction mixture was neutralized with 1.0 N HCl. The organic solvents were evaporated under vacuum, and the remaining aqueous phase was acidified to pH~3 using 1.0 N HCl and was extracted with EtOAc. The organic layer was washed with brine, and was dried over anhydrous magnesium sulfate. After removal of solvent, 0.3 g of the title compound was obtained: MS m/z: 526.2 (M+Na+).

Intermediate 1c

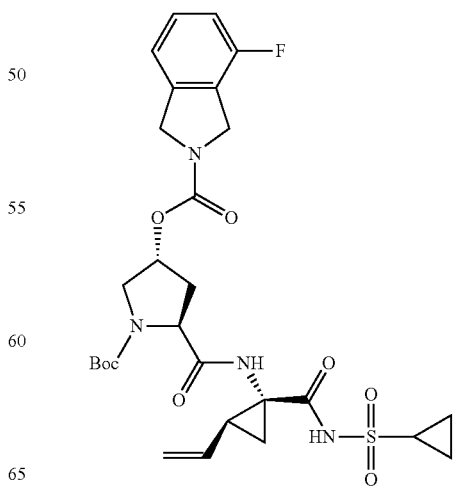

To a solution of the product of step 1b (0.30 g, 0.6 mmol) in 10 mL of DCM was added CDI (0.16 g, 1.0 mmol) and the resulting solution was stirred at 40° C. for 1 hour. cyclopropylsulfonamide (0.18 g, 1.5 mmol) and DBU (0.16 g, 1.0 mmol) were added to the reaction mixture. The mixture was stirred at 40° C. for additional 10 hours. The solvent was then removed and the residue was diluted with EtOAc and was washed with aqueous NaOAc buffer (pH~5, 2×10 mL), NaHCO$_3$ solution and brine. After drying over Na$_2$SO$_4$ and removal of solvent, the residue was subjected to chromatography on silica gel using hexane/EtOAc (1:1~1:2). A total of 0.30 g of the title compound was obtained: R$_f$ 0.1 (EtOAc:hexane=1:1), MS m/z: 605.0 (ES−).

Intermediate 1d

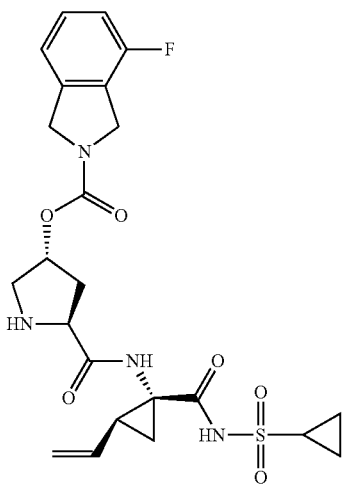 [SMILES: C=C[C@@H]1C[C@]1(NC(=O)[C@@H]1C[C@@H](OC(=O)N2Cc3cccc(F)c3C2)CN1)C(=O)NS(=O)(=O)C1CC1]

The product from step 1c (0.25 g, 0.41 mmol) was dissolved in 4 N HCl in dioxane. The mixture was stirred at r.t. for 1 hour. After removal of solvents, a 10-mL portion of DCM was poured in followed by evaporation to dryness. This process of DCM addition followed by evaporation was repeated four times to give a residue solid which was used directly for the next step: MS m/z: 507.0 (M+H$^+$).

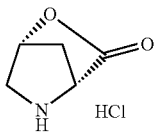

Intermediate 1e

To a stirring solution of 213 mg (1R,4R)-3-Oxo-2-oxa-5-aza-bicyclo[2.2.1]heptane-5-carboxylic acid tert-butyl ester (213 mg, 1 mmol) in 1 mL of DCM, was added 2.0 mL of 4 M HCl in dioxane. The resulting mixture was stirred at rt for 30 min, and evaporated to dryness, giving desired HCl salt used directly for the following step.

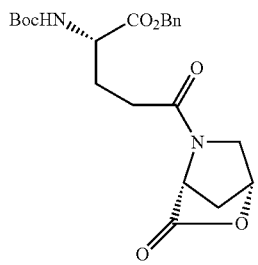 [SMILES: CC(C)(C)OC(=O)N[C@@H](CCC(=O)N1C[C@H]2C[C@@H]1C(=O)O2)C(=O)OCc1ccccc1]

Intermediate 1f

To a stirring mixture of 1-benzyl-N-Boc-L-glutamate (170 mg, 0.5 mmol), 0.5 mmol of intermediate 1e, and 250 µl of Hunig's base in 2 mL of DCM, was added 1.5 mL of 0.5 M 2-chloro-1,3-dimethyl-imidazolidinium chlorides solution in DCM. The resulting mixture was stirred at rt for 30 min, and concentrate. The residue was subject to routine workup with EtOAc, 1N aqueous HCl, dried over anhydrous sodium sulfate. After filtration and concentration, the product was purified by flash column chromatography on silica gel with heptane/EtOAc giving 146 mg of color less oil (67%). LC-MS: 333.2 (ES+, M-Boc)

Intermediate 1g

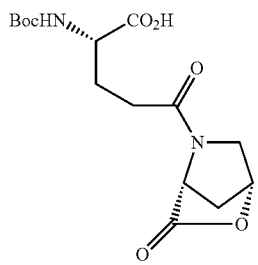

140 mg of benzyl ester from previous step was subject to hydrogenationi with 20 mg of Pd(OH)$_2$ as catalyst in anhydrous MeOH. After 1 hr at rt, LC-MS showed completion of the removal of benzyl group. The reaction mixture was filtered through celite, and concentrated to give desired acid as foamy solid. LC-MS: 243.2 (ES+, M-Boc).

Intermediate 1h

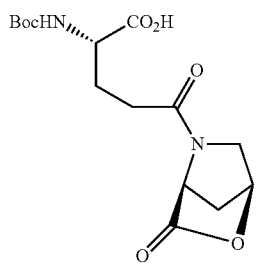 [SMILES: CC(C)(C)OC(=O)N[C@@H](CCC(=O)N1C[C@@H]2C[C@H]1C(=O)O2)C(=O)O]

Intermediate 1h was synthesized in the same way as for preparing intermediate 1g while using enantiomeric bicyclic lactone as starting material in the step for making intermediate 1e.

Intermediate 1i

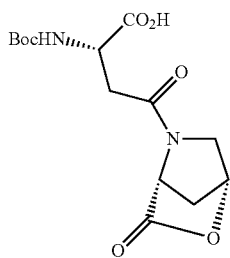 [SMILES: CC(C)(C)OC(=O)N[C@@H](CC(=O)N1C[C@H]2C[C@@H]1C(=O)O2)C(=O)O]

Intermediate 1i was synthesized in the same way for preparing intermediate 1g using 1-benzyl-N-Boc-aspartate for making intermediate 1f instead of 1-benzyl-N-boc-L-glutamate.

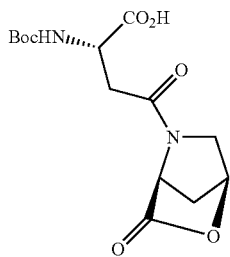 [SMILES: CC(C)(C)OC(=O)N[C@@H](CC(=O)N1C[C@@H]2C[C@H]1C(=O)O2)C(=O)O]

Intermediate 1j

Intermediate 1j was synthesized in the same way for preparing intermediate 1h using 1-benzyl-N-Boc-L-aspartate for making intermediate 1f instead of 1-benzyl-N-boc-L-glutamate.

XVI-16

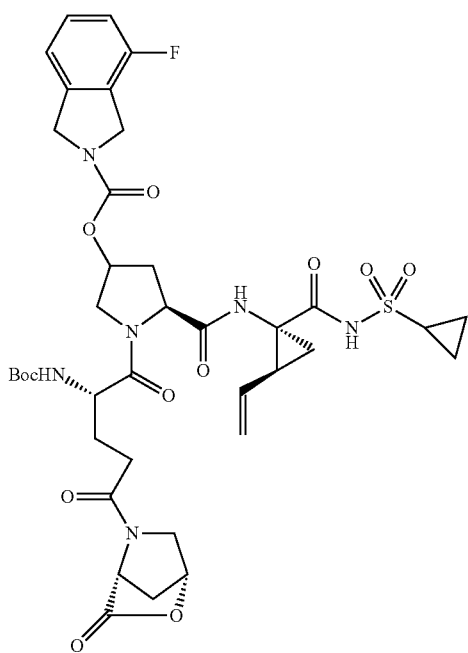

(5S)-1-((S)-2-(tert-butoxycarbonylamino)-5-oxo-5-((1R,4R)-3-oxo-2-oxa-5-azabicyclo[2.2.1]heptan-5-yl)pentanoyl)-5-((1R,2 S)-1-(cyclopropyl sulfonyl-carbamoyl)-2-vinylcyclopropylcarbamoyl)pyrrolidin-3-yl 4-fluoroisoindoline-2-carboxylate (XVI-16): To a mixture of 15 mg of intermediate 1d, 8 mg of intermediate 1g, and 20 µl of Hunig's base in 1 mL of DMA, was added 20 mg of HATU. After stirring at rt for 20 min, the resulting mixture was purified by Prep-HPLC, giving XVI-16. LC-MS: 829.2 (ES−).

Example 56

XVI-17

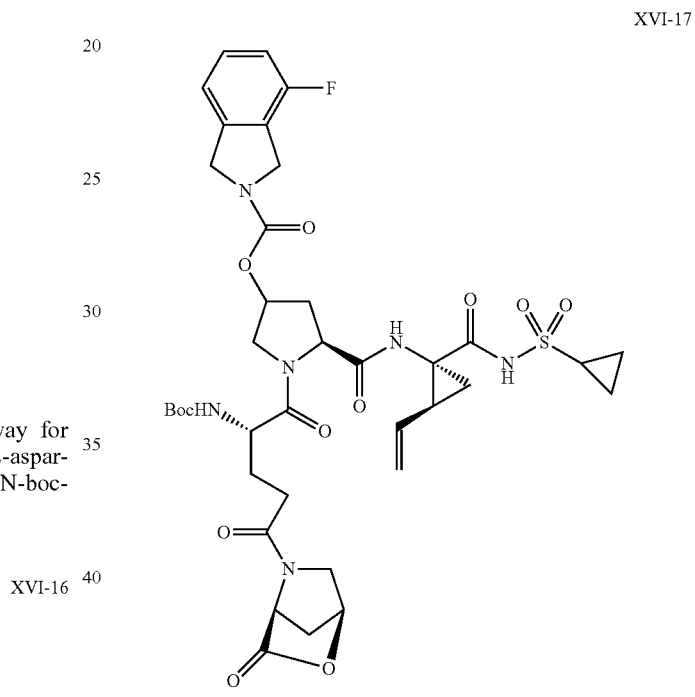

(5S)-1-((S)-2-(tert-butoxycarbonylamino)-5-oxo-5-((1S,4S)-3-oxo-2-oxa-5-azabicyclo[2.2.1]heptan-5-yl)pentanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate The title compound was prepared according to the steps and intermediates as described below.

(5 S)-1-((S)-2-(tert-butoxycarbonylamino)-5-oxo-5-((1S,4S)-3-oxo-2-oxa-5-azabicyclo[2.2.1]heptan-5-yl)pentanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate (XVI-17)

The title compound was prepared in the same manner as for XVI-16, using intermediate 1h for the final step instead of intermediate 1g. LC-MS: 829.2 (ES−).

Example 57

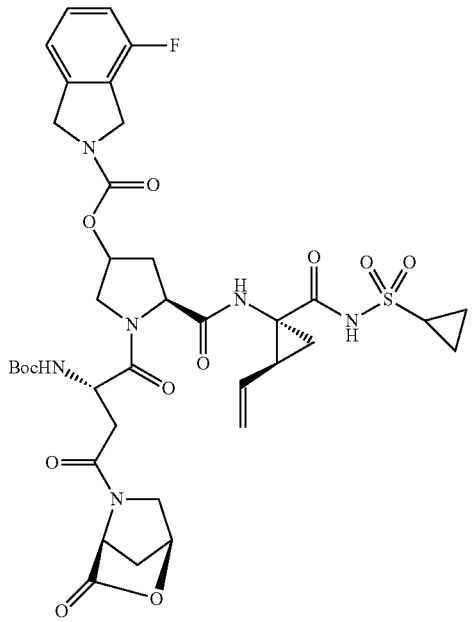

XVI-15

(5S)-1-((S)-2-(tert-butoxycarbonylamino)-4-oxo-4-((1S,4S)-3-oxo-2-oxa-5-azabicyclo[2.2.1]heptan-5-yl)butanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate The title compound was prepared according to the steps and intermediates as described below.

(5 S)-1-((S)-2-(tert-butoxycarbonylamino)-4-oxo-4-((1S,4S)-3-oxo-2-oxa-5-azabicyclo[2.2.1]heptan-5-yl)butanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate (XVI-15)

The title compound was prepared in the same manner as for XVI-16, using intermediate 1i for the final step instead of intermediate 1g. LC-MS: 815.3 (ES−).

Example 58

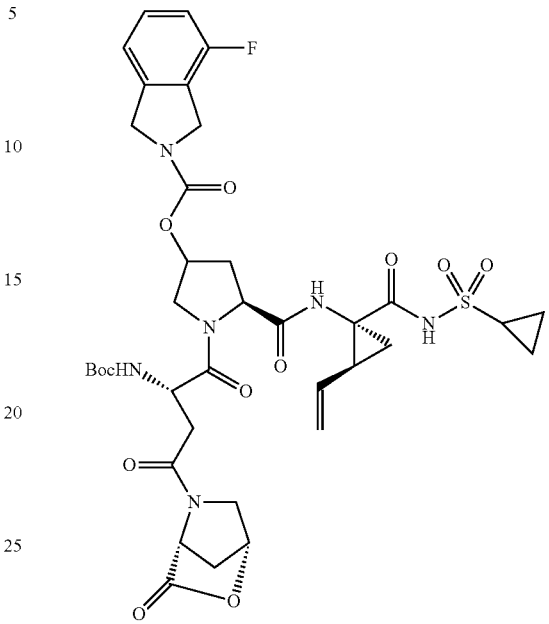

XVI-14

(5S)-1-((S)-2-(tert-butoxycarbonylamino)-4-oxo-4-((1R,4R)-3-oxo-2-oxa-5-azabicyclo[2.2.1]heptan-5-yl)butanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate The title compound was prepared according to the steps and intermediates as described below.

(5 S)-1-((S)-2-(tert-butoxycarbonylamino)-4-oxo-4-((1R,4R)-3-oxo-2-oxa-5-azabicyclo[2.2.1]heptan-5-yl)butanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate (XVI-14): The title compound was prepared in the same manner as for XVI-16, using intermediate 1j for the final step instead of intermediate 1g. LC-MS: 815.3 (ES−).

Example 59

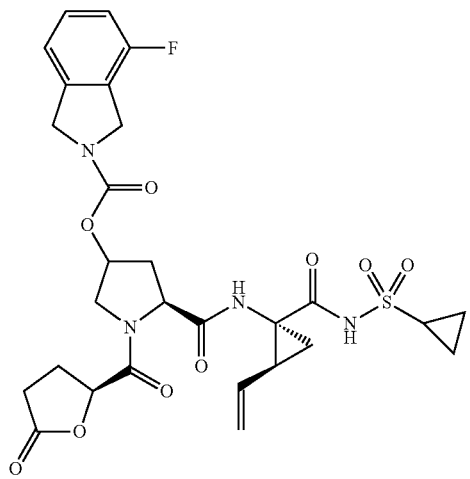

XVI-23

(5S)-5-((1R,2S)-1-(cyclopropylsulfonylcarbamoyl)-2-vinylcyclopropylcarbamoyl)-1-((S)-5-oxotetrahydrofuran-2-carbonyl)pyrrolidin-3-yl 4-fluoroisoindoline-2-carboxylate (XVI-23)

The title compound was synthesized in the same chemistry as preparation for XVI-16 using intermediate 1d to couple with (2S)-5-oxo-tetrahydro-furan-2-carboxylic acid. LC-MS: 617.2 (ES−).

Example 60

XVI-22

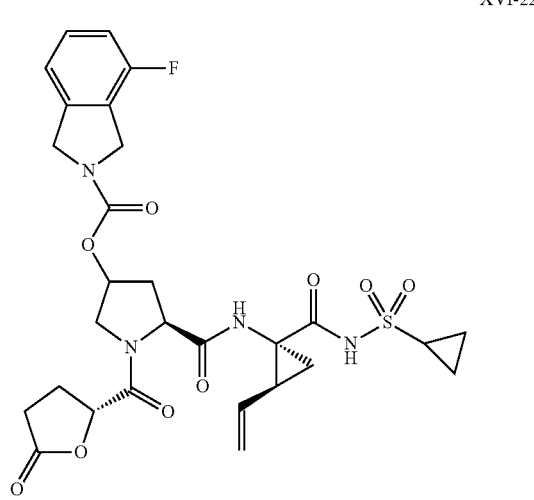

(5S)-5-((1R,2S)-1-(cyclopropylsulfonylcarbamoyl)-2-vinylcyclopropylcarbamoyl)-1-((R)-5-oxotetrahydrofuran-2-carbonyl)pyrrolidin-3-yl 4-fluoroisoindoline-2-carboxylate (XVI-22)

The title compound was synthesized in the same chemistry as preparation for XVI-16 using intermediate 1d to couple with (2R)-5-oxo-tetrahydro-furan-2-carboxylic acid. LC-MS: 617.2 (ES−).

Example 61

XVI-13

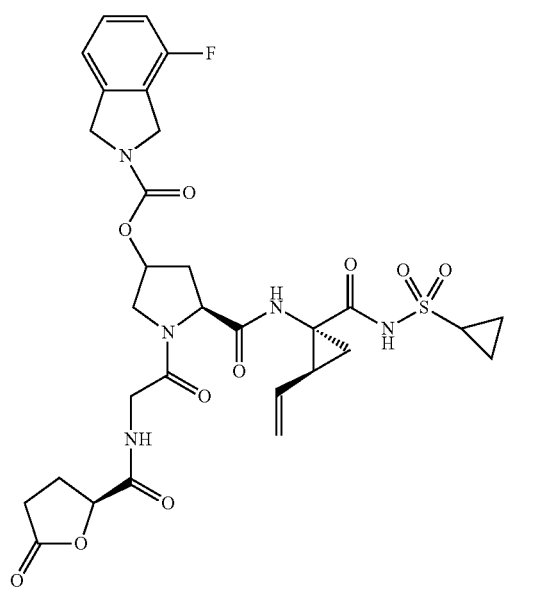

(5S)-5-((1R,2S)-1-(cyclopropylsulfonylcarbamoyl)-2-vinylcyclopropylcarbamoyl)-1-(2-((S)-5-oxotetrahydrofuran-2-carboxamido)acetyl)pyrrolidin-3-yl 4-fluoroisoindoline-2-carboxylate The title compound was prepared according to the steps and intermediates as described below.

Intermediate 2a

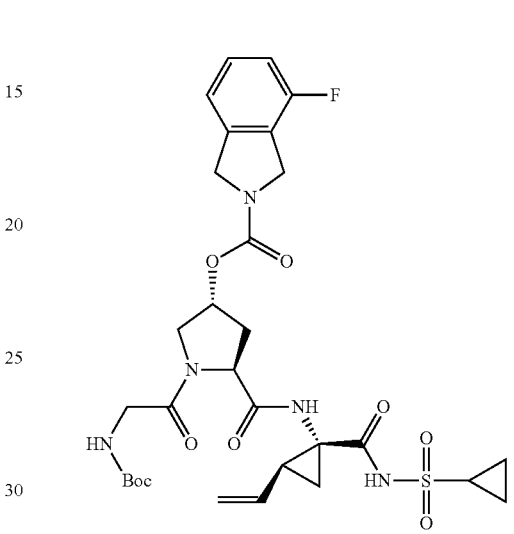

To a solution of intermediate 1d (0.12 g, 0.22 mmol) and N-Boc-glycine (0.054 g, 0.31 mmol) in 4.0 mL of acetonitrile was added HATU (133 mg, 0.35 mmol) and DIEA (0.12 mL, 0.66 mmol) at r.t. under stirring. The reaction mixture was stirred for 2 h. LC-MS and TLC analysis indicated completion of the coupling reaction. A 20-mL of EtOAc was poured in and the mixture was washed with a buffer (pH~4, AcONa/AcOH), NaHCO$_3$ and brine, and was dried over Na$_2$SO$_4$. After removal of solvent, the crude product was subjected to chromatography on silica gel (eluents: EtOAc/hexane). A total of 0.10 g of the title compound was obtained: R$_f$ 0.2 (EtOAc); MS m/z: 664.0 (M+H$^+$).

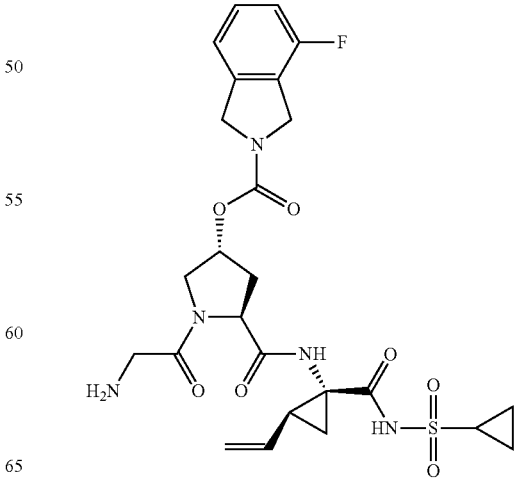

Intermediate 2b

The intermediate 2a (0.10 g, 0.15 mmol) was dissolved in 2 mL of 4 N HCl in dioxane and the reaction was stirred for 1 hour at RT. After removal of solvents, a 3-mL portion of DCM was poured in followed by evaporation to dryness. This process of DCM addition followed by evaporation was repeated three times to give the title compound Intermediate 2b as its HCl salt (0.10 g). MS m/z: 564.0 (M+H$^+$).

Example 62

XVI-13

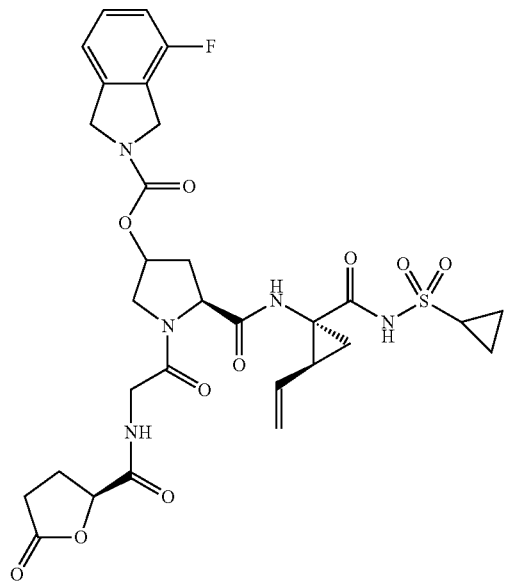

(5S)-5-((1R,2S)-1-(cyclopropylsulfonylcarbamoyl)-2-vinylcyclopropylcarbamoyl)-1-(2-((S)-5-oxotetrahydrofuran-2-carboxamido)acetyl)pyrrolidin-3-yl 4-fluoroisoindoline-2-carboxylate (XVI-13)

The title compound was synthesized in the same chemistry as preparation for XVI-23 using intermediate 2b to couple with (2S)-5-oxo-tetrahydro-furan-2-carboxylic acid. LC-MS: 676.2 (ES+), 674.1 (ES−).

XVI-12

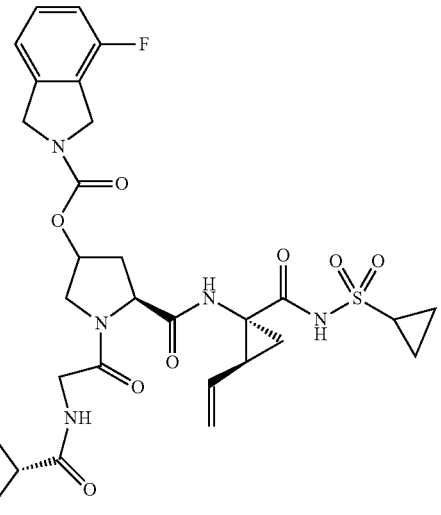

Example 63

(5S)-5-((1R,2S)-1-(cyclopropylsulfonylcarbamoyl)-2-vinylcyclopropylcarbamoyl)-1-(2-((R)-5-oxotetrahydrofuran-2-carboxamido)acetyl)pyrrolidin-3-yl 4-fluoroisoindoline-2-carboxylate (XVI-12)

The title compound was synthesized in the same chemistry as preparation for XVI-13 using intermediate 2b to couple with (2R)-5-oxo-tetrahydro-furan-2-carboxylic acid. LC-MS: 676.2 (ES+), 674.1 (ES−).

Example 64

XVI-21

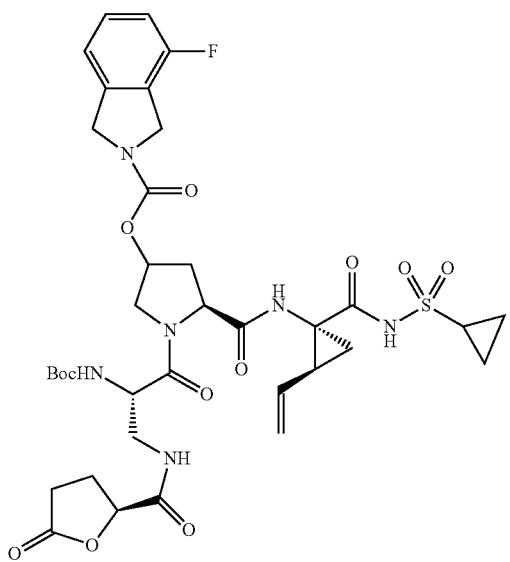

327

(5S)-1-((S)-2-(tert-butoxycarbonylamino)-3-((S)-5-oxotetrahydrofuran-2-carboxamido)propanoyl)-5-((1R,2S)-1-(cyclopropylsulfonylcarbamoyl)-2-vinyl-cyclopropylcarbamoyl)pyrrolidin-3-yl 4-fluoroisoindoline-2-carboxylate The title compound was prepared according to the steps and intermediates as described below.

Intermediate 3a

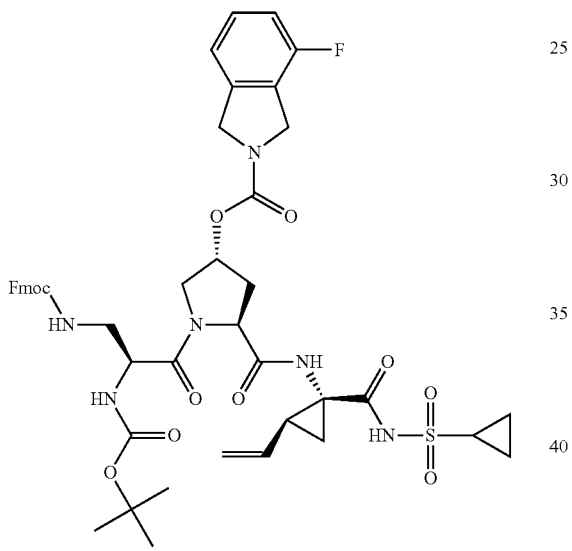

To a solution of intermediate 1d (0.16 g, 0.28 mmol) and N-Boc-3-(Fmoc)amino-L-alanine (0.15 g, 0.35 mmol) in 5.0 mL of DMF was added HATU (125 mg, 0.33 mmol) and DIEA (130 mg, 1.0 mmol) at r.t. under stirring. TLC analysis indicated completion of the coupling reaction had occurred after one hour. A 20-mL portion of EtOAc was poured in and the mixture was washed with a buffer (pH~4, AcONa/AcOH), NaHCO₃ and brine, and was dried over MgSO₄. After removal of solvent, the crude oil product was subjected to chromatography on silica gel (eluents: EtOAc/hexane). A total of 0.14 g of the title compound was obtained. LC-MS: 915.9 (ES+)

328

Intermediate 3b

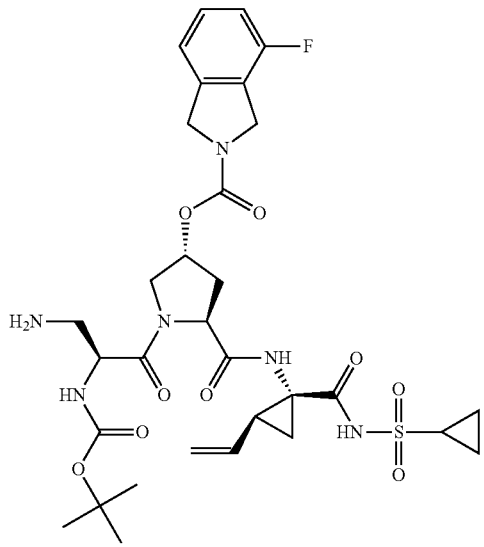 [SMILES: C=C[C@@H]1C[C@]1(NC(=O)[C@@H]1C[C@@H](OC(=O)N2Cc3cccc(F)c3C2)CN1C(=O)[C@H](CN)NC(=O)OC(C)(C)C)C(=O)NS(=O)(=O)C1CC1]

A solution of 0.10 g of the product of intermediate 3a in 1 mL of DMF with 12% piperidine was stirred for 1.5 hours at r.t. and then was evaporated to dryness under high vacuum. The residue was triturated with hexane/ether (4:1) to yield 70 mg of the title compound. LC-MS: 693.2 (ES+), 691.2 (ES-).

Example 65

XVI-21

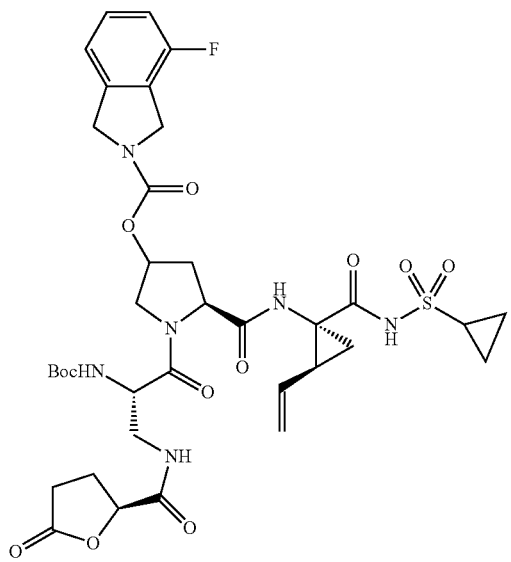

(5S)-1-((S)-2-(tert-butoxycarbonylamino)-3-((S)-5-
oxotetrahydrofuran-2-carboxamido)propanoyl)-5-
((1R,2S)-1-(cyclopropylsulfonylcarbamoyl)-2-vinyl-
cyclopropylcarbamoyl)pyrrolidin-3-yl
4-fluoroisoindoline-2-carboxylate (XVI-21)

The title compound was synthesized in the same chemistry as preparation for XVI-23 using intermediate 3b to couple with (2S)-5-oxo-tetrahydro-furan-2-carboxylic acid. LC-MS: 803.2 (ES−).

Example 66

XVI-20

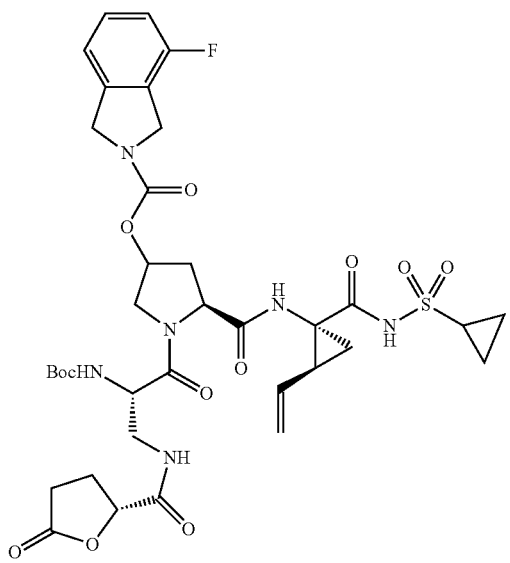

(5S)-1-((S)-2-(tert-butoxycarbonylamino)-3-((R)-5-
oxotetrahydrofuran-2-carboxamido)propanoyl)-5-
((1R,2S)-1-(cyclopropylsulfonylcarbamoyl)-2-vinyl-
cyclopropylcarbamoyl)pyrrolidin-3-yl
4-fluoroisoindoline-2-carboxylate (XVI-20)

The title compound was synthesized in the same chemistry as preparation for XVI-21 using intermediate 3b to couple with (2R)-5-oxo-tetrahydro-furan-2-carboxylic acid. LC-MS: 803.2 (ES−).

Example 67

XVI-19

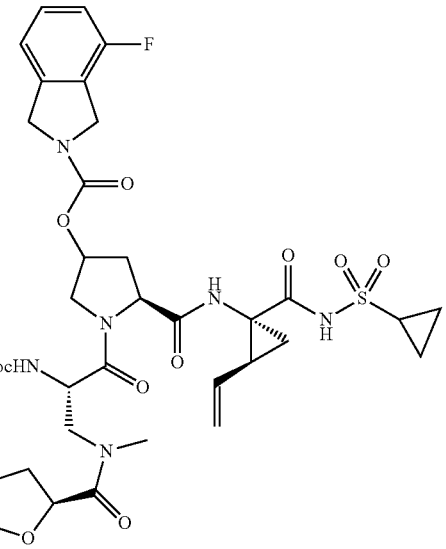

(5S)-1-((S)-2-(tert-butoxycarbonylamino)-3-((S)-N-
methyl-5-oxotetrahydrofuran-2-carboxamido)pro-
panoyl)-5-((1R,2S)-1-(cyclopropylsulfonylcarbam-
oyl)-2-vinylcyclopropylcarbamoyl)pyrrolidin-3-yl
4-fluoroisoindoline-2-carboxylate The title compound was prepared according to the steps and intermediates as described below.

Intermediate 4a

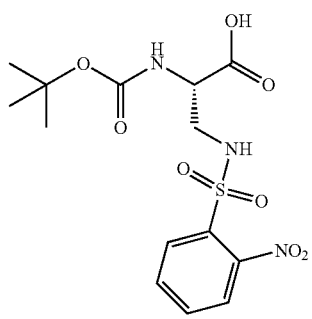 [SMILES: CC(C)(C)OC(=O)N[C@@H](CNS(=O)(=O)c1ccccc1[N+](=O)[O-])C(=O)O]

To a solution of (S)-3-amino-2-(tert-butoxycarbonylamino)propanoic acid (2.04 g, 10 mmol), TEA (4.5 mL, 30 mmol) in 50 mL CH$_2$Cl$_2$ was added nitrobenzenesulfonyl chloride (2.9 g, 13.0 mmol) at RT. The mixture was stirred for 10 hours at RT. The solvent was removed under vacuum followed by the addition of 100 mL EtOAc. The organic layer was washed with 1 N HCl (to pH 3), water and brine. The organic layer was dried over Na$_2$SO$_4$, filtered and the solvent was removed to afford the crude Intermediate 4a (4.0 g).

Intermediate 4b

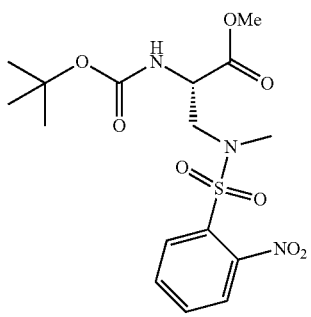 [SMILES: COC(=O)[C@H](CN(C)S(=O)(=O)c1ccccc1[N+](=O)[O-])NC(=O)OC(C)(C)C]

The crude Intermediate 4a (2.0 g), K₂CO₃ (1.5, 4 equiv.) were dissolved in 10 mL DMF. MeI (0.8 mL, 4 equiv.) was added to the reaction at RT. The resulting mixture was stirred for 20 hours. The DMF was mostly removed under vacuum and 100 mL EtOAc was added and the mixture was washed with water and brine. The organic layer was dried over Na₂SO₄. After removal of solvent, the crude product was subject to a short silica gel column (eluents: EtOAc/hexane) to produce 1.62 g of the Intermediate 4b. MS m/z: 439.9 (M+Na⁺).

Intermediate 4c

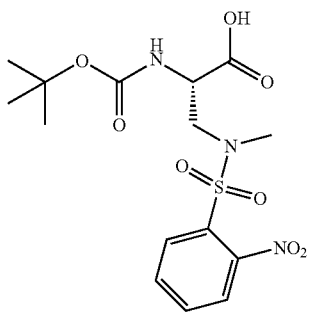 [SMILES: CN(C[C@H](NC(=O)OC(C)(C)C)C(=O)O)S(=O)(=O)c1ccccc1[N+](=O)[O-]]

To a solution of Intermediate 4b (1.6 g, 3.8 mmol) in 10 mL of THF/MeOH (1:1) was added 1 N LiOH aqueous solution (5.8 mL, 5.8 mmol). After stirring at r.t. for 10 hours, the reaction mixture was neutralized with 1.0 N HCl. The organic solvent was evaporated under vacuum, and the remaining aqueous phase was acidified to pH~3 using 1.0 N HCl and was extracted with EtOAc. The organic layer was washed with brine, and was dried over anhydrous sodium sulfate. After removal of solvent, 1.5 g of Intermediate 4c was obtained. MS m/z: 402.0 (ES−).

Intermediate 4d

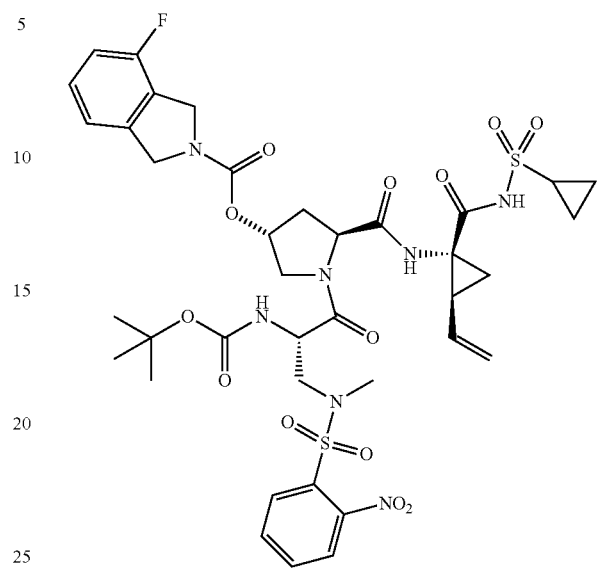

To a solution of Intermediate 1d (0.12 g, 0.20 mmol) and Intermediate 4c (0.12 g, 0.3 mmol) in 5.0 mL of anhydrous acetonitrile was added HATU (0.11 g, 0.3 mmol) and DIEA (0.14 mL, 0.9 mmol) at r.t. under stirring. TLC analysis and LC-MS indicated completion of the coupling reaction after one hour. A 20-mL portion of EtOAc was poured in and the mixture was washed with a buffer (pH~4, AcONa/AcOH), NaHCO₃ and brine. The organic layer was dried over Na₂SO₄. After removal of solvent, the crude product was subjected to chromatography on silica gel (eluents: EtOAc/hexane). A total of 0.10 g of Intermediate 4d was obtained: $R_f$ 0.1 (EtOAc); MS m/z: 891.8 (M+H⁺).

Intermediate 4e

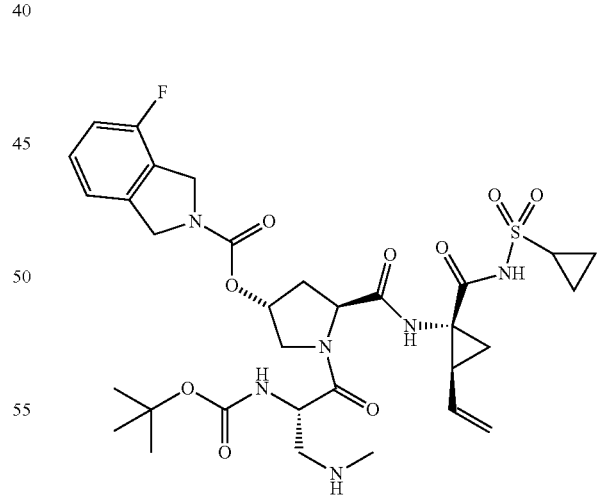

To a solution of Intermediate 4d (0.10 g, 0.11 mmol) in 3 mL DMF was added phenylthiol (30 mg, 0.26 mmol) and K₂CO₃ (40 mg, 0.3 mmol). The resulting mixture was stirred for 20 hours at RT. 30 mL EtOAc was added and the mixture was washed with water and brine and water. The organic layer was dried over Na₂SO₄. After removal of solvent, the crude product was subjected to chromatography on silica gel (eluents: EtOAc/hexane) to produce 0.1 g of crude Intermediate 4e. MS m/z: 706.9 (M+H⁺).

Example 68

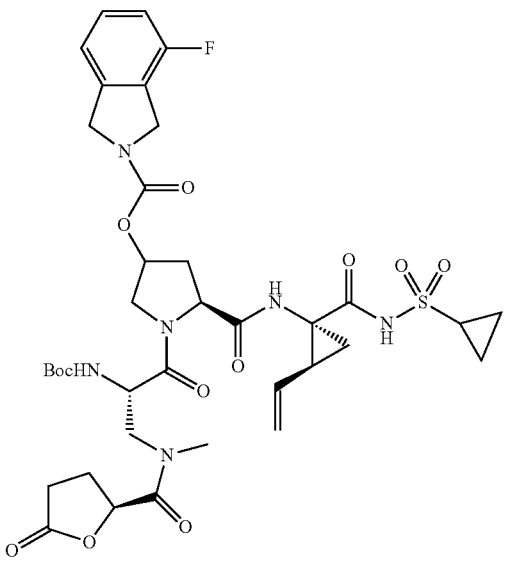

XVI-19

(5S)-1-((S)-2-(tert-butoxycarbonylamino)-3-((S)-N-methyl-5-oxotetrahydrofuran-2-carboxamido)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate (XVI-19)

The title compound was synthesized in the same chemistry as preparation for XVI-21 using intermediate 4e instead of intermediate 3b to couple with (2R)-5-oxo-tetrahydrofuran-2-carboxylic acid. LC-MS: 817.2 (ES−).

Example 69

XVI-18

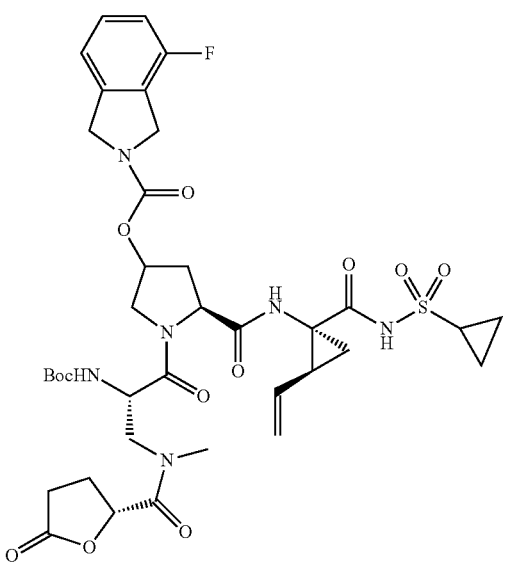

(5S)-1-((S)-2-(tert-butoxycarbonylamino)-3-((R)-N-methyl-5-oxotetrahydrofuran-2-carboxamido)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate (XVI-18)

The title compound was synthesized in the same chemistry as preparation for XVI-20 using intermediate 4e instead of intermediate 3b to couple with (2S)-5-oxo-tetrahydrofuran-2-carboxylic acid. LC-MS: 817.2 (ES−).

Example 70

XVI-11

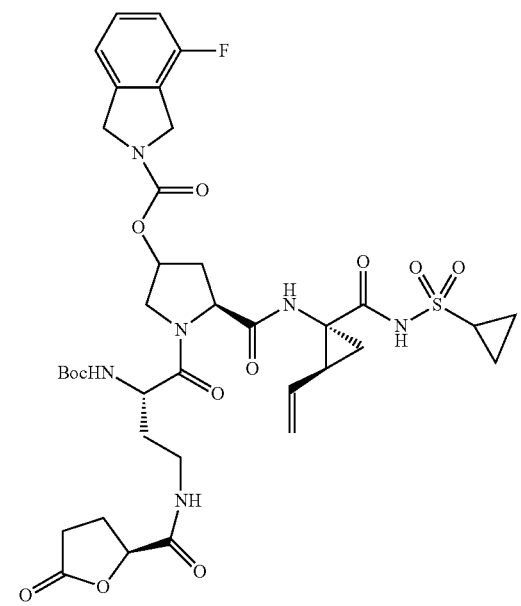

(5S)-1-((S)-2-(tert-butoxycarbonylamino)-4-((S)-5-oxotetrahydrofuran-2-carboxamido)butanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate The title compound was prepared according to the steps and intermediates as described below.

Intermediate 5a

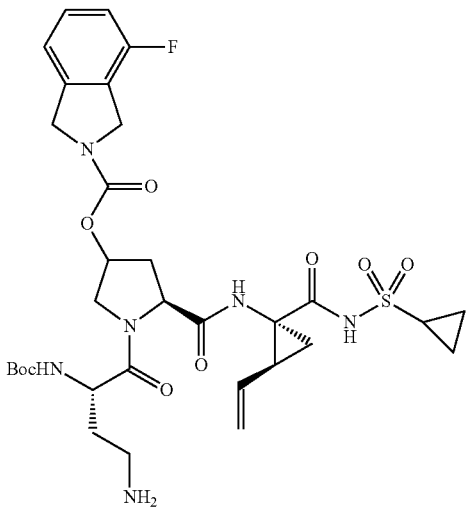 [SMILES: C=C[C@@H]1C[C@]1(NC(=O)[C@@H]1CC(OC(=O)N2Cc3cccc(F)c3C2)CN1C(=O)[C@H](CCN)NC(=O)OC(C)(C)C)C(=O)NS(=O)(=O)C1CC1]

Intermediate 5a was prepared in the same way as for intermediate 3b using (S)-4-(((9H-fluoren-9-yl)methoxy)carbonylamino)-2-(tert-butoxycarbonylamino)butanoic acid instead of N-Boc-3-(Fmoc)amino-L-alanine. LC-MS: 707.2 (ES+)

Example 71

XVI-11

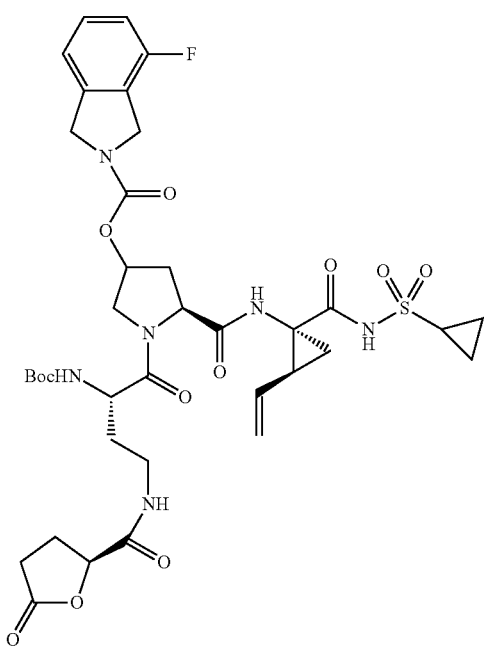

(5S)-1-((S)-2-(tert-butoxycarbonylamino)-4-((S)-5-oxotetrahydrofuran-2-carboxamido)butanoyl)-5-((1R,2S)-1-(cyclopropylsulfonylcarbamoyl)-2-vinyl-cyclopropylcarbamoyl)pyrrolidin-3-yl 4-fluoroisoindoline-2-carboxylate (XVI-11)

The title compound was synthesized in the same chemistry as preparation for XVI-19 using intermediate 5a instead of intermediate 4e to couple with (2S)-5-oxo-tetrahydro-furan-2-carboxylic acid. LC-MS: 817.2 (ES−).

Example 72

XVI-10

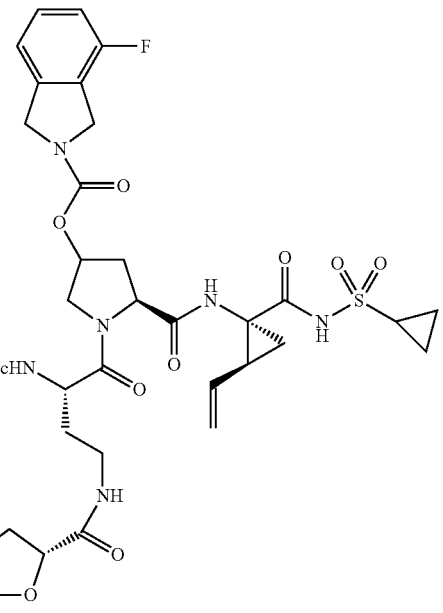

(5S)-1-((S)-2-(tert-butoxycarbonylamino)-4-((R)-5-oxotetrahydrofuran-2-carboxamido)butanoyl)-5-((1R,2S)-1-(cyclopropylsulfonylcarbamoyl)-2-vinyl-cyclopropylcarbamoyl)pyrrolidin-3-yl 4-fluoroisoindoline-2-carboxylate (XVI-10)

The title compound was synthesized in the same chemistry as preparation for XVI-18 using intermediate 5a instead of intermediate 4e to couple with (2S)-5-oxo-tetrahydro-furan-2-carboxylic acid. LC-MS: 817.2 (ES−).

Example 73

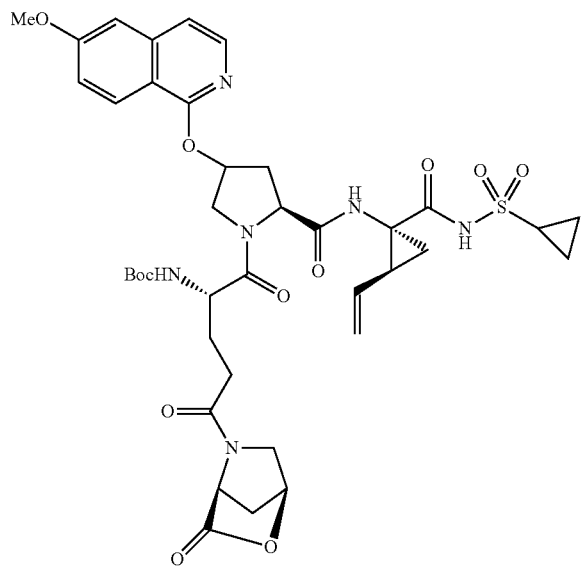

tert-butyl(2S)-1-((2S)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxo-5-((1S,4S)-3-oxo-2-oxa-5-azabicyclo[2.2.1]heptan-5-yl)pentan-2-ylcarbamate The title compound was prepared according to the steps and intermediates as described below.

Intermediate 6a

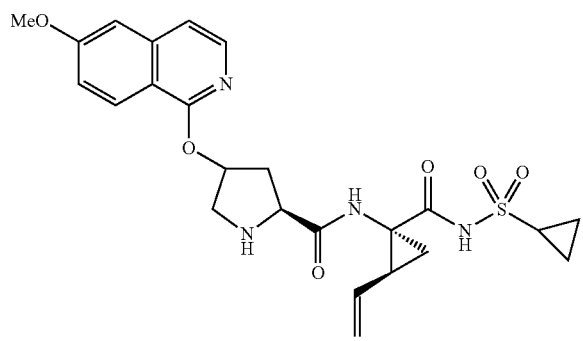 [SMILES: C=C[C@@H]1C[C@]1(NC(=O)[C@@H]1CC(Oc2nccc3cc(OC)ccc23)CN1)C(=O)NS(=O)(=O)C1CC1]

Intermediate 6a was prepared following the procedure published in WO 2006086381.

Intermediate 6b

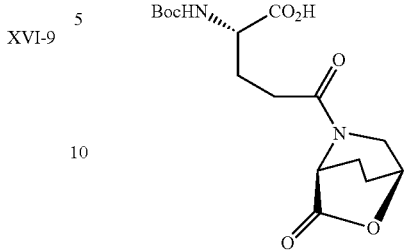

Intermediate 6b was synthesized in the same way for preparing intermediate 1g using (1S,4S)-tert-butyl 3-oxo-2-oxa-5-azabicyclo[2.2.2]octane-5-carboxylate as starting material in preparing intermediate 1e instead of (1R,4R)-3-Oxo-2-oxa-5-aza-bicyclo[2.2.1]heptane-5-carboxylic acid tert-butyl ester. LC-MS: 355.1 (ES−).

Intermediate 6c

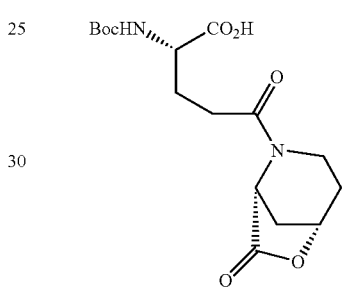

Intermediate 6c was synthesized in the same way for preparing intermediate 1g using (1S,5S)-6-oxa-2-aza-bicyclo[3.2.1]octan-7-one in preparing intermediate 1e instead of (1R,4R)-3-Oxo-2-oxa-5-aza-bicyclo[2.2.1]heptane-5-carboxylic acid tert-butyl ester. LC-MS: 355.1 (ES−).

Example 74

XVI-9

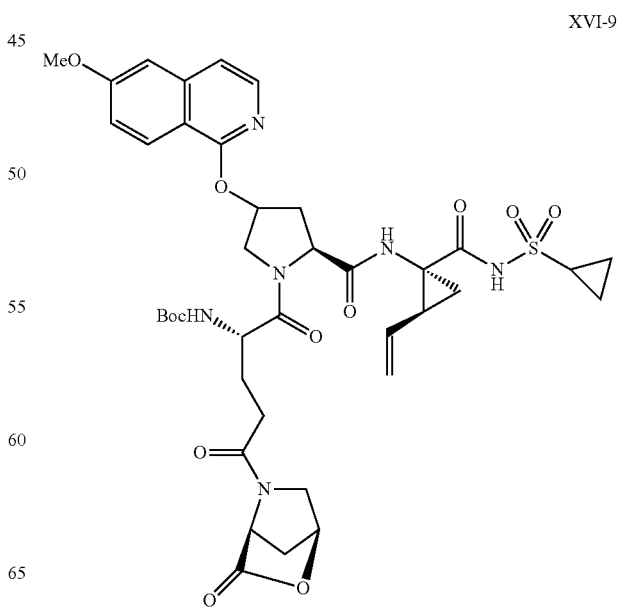

339 tert-butyl(2S)-1-((2S)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxo-5-((1S,4S)-3-oxo-2-oxa-5-azabicyclo[2.2.1]heptan-5-yl)pentan-2-ylcarbamate (XVI-9)

The title compound was synthesized in the same way as for XVI-17 using intermediate 6a as starting material instead of intermediate 1d. LC-MS: 825.3 (ES+), 823.2 (ES−).

Example 75

340 tert-butyl(2S)-1-(2S)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxo-5-((1R,4R)-3-oxo-2-oxa-5-azabicyclo[2.2.1]heptan-5-yl)pentan-2-ylcarbamate (XVI-8)

The title compound was synthesized in the same way as for XVI-16 using intermediate 6a as starting material instead of intermediate 1d. LC-MS: 825.3 (ES+), 823.2 (ES−).

Example 76

XVI-8

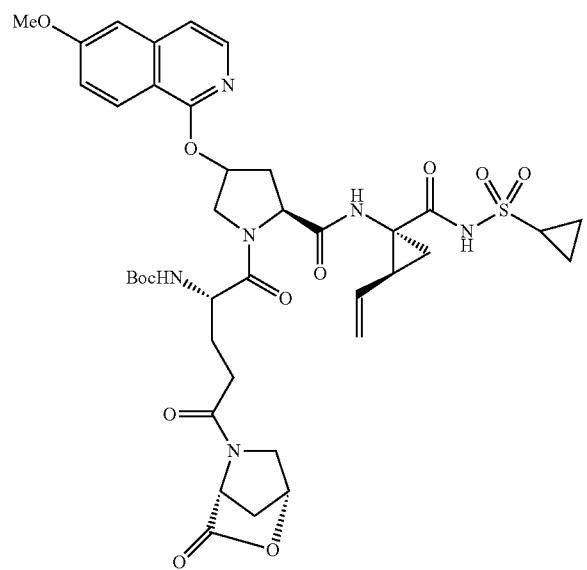

XVI-7

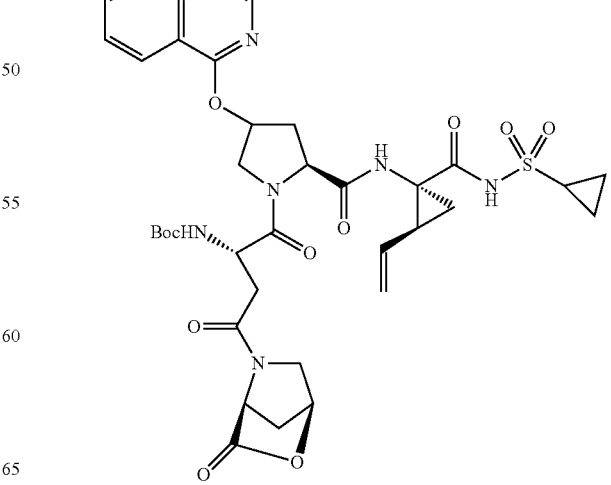

tert-butyl(2S)-1-(2S)-2-((1R,2S)-1-(cyclopropy-lsulfonylcarbamoyl)-2-vinylcyclopropylcarbamoyl)-4-(6-methoxyisoquinolin-1-yloxy)pyrrolidin-1-yl)-1,4-dioxo-4-((1S,4S)-3-oxo-2-oxa-5-azabicyclo[2.2.1]heptan-5-yl)butan-2-ylcarbamate (XVI-7)

The title compound was synthesized in the same way as for XVI-15 using intermediate 6a as starting material instead of intermediate 1d. LC-MS: 811.2 (ES+), 809.1 (ES−).

Example 77

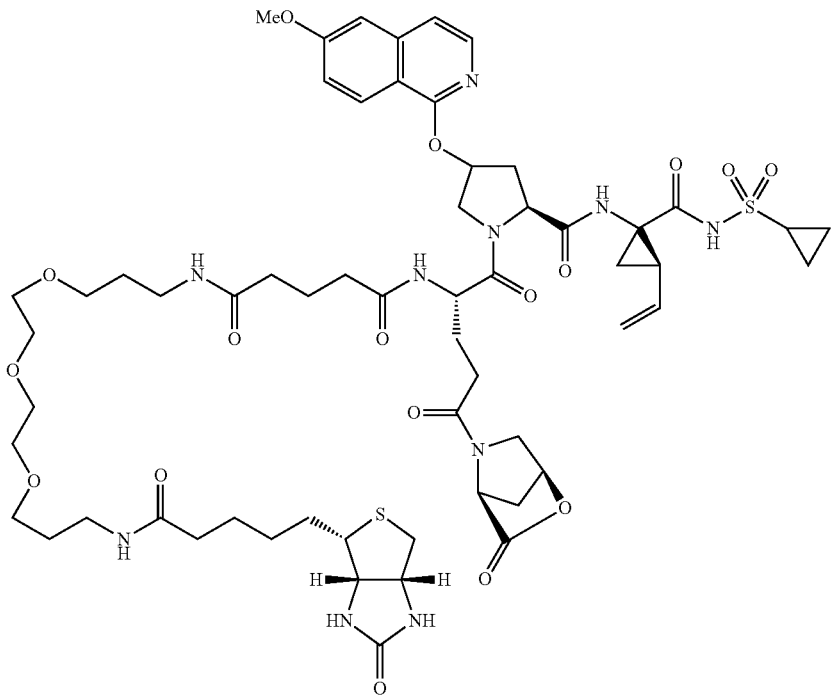

XVI-27

N1-((2S)-1-((2S)-2-((1S,2R)-1-(cyclopropylsulfo-nylcarbamoyl)-2-vinylcyclopropylcarbamoyl)-4-(6-methoxyisoquinolin-1-yloxy)pyrrolidin-1-yl)-1,5-dioxo-5-((1S,4S)-3-oxo-2-oxa-5-azabicyclo[2.2.1]heptan-5-yl)pentan-2-yl)-N5-(15-oxo-19-((3aS,4S,6aR)-2-oxohexahydro-1H-thieno[3,4-d]imidazol-4-yl)-4,7,10-trioxa-14-azanonadecyl)glutaramide (XVI-27)

To a solution of 2 mg of XVI-7 in 100 uL of anhydrous DCM, was added 50 uL of TFA. After stirring at rt for 1 hr, the solvent was removed under reduced pressure, and the residue was dried in vacuum for 2 hr. 0.5 mL of anhydrous acetonitrile was then added, followed by 50 uL of Hunig's base, 5 mg of 5,21-dioxo-25-((3aS,4S,6aR)-2-oxohexahydro-1H-thieno[3,4-d]imidazol-4-yl)-10,13,16-trioxa-6,20-diazapentacosan-1-oic acid and 6 mg of HATU. The reaction mixture was stirred at rt for 1 hr, then purified by prep-HPLC, giving desired tool compound XVI-27 as white powder after lyophilization. LC-MS: 1267.5 (ES+), 1265.6 (ES−)

Example 78

XVI-6

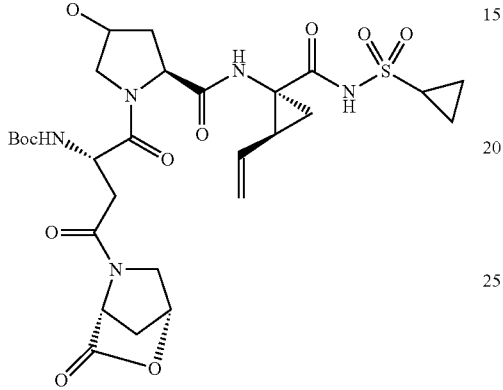

tert-butyl(2S)-1-(2S)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,4-dioxo-4-((1R,4R)-3-oxo-2-oxa-5-azabicyclo[2.2.1]heptan-5-yl)butan-2-ylcarbamate (XVI-6)

The title compound was synthesized in the same way as for XVI-14 using intermediate 6a as starting material instead of intermediate 1d. LC-MS: 811.2 (ES+), 809.1 (ES−).

Example 79

XVI-3

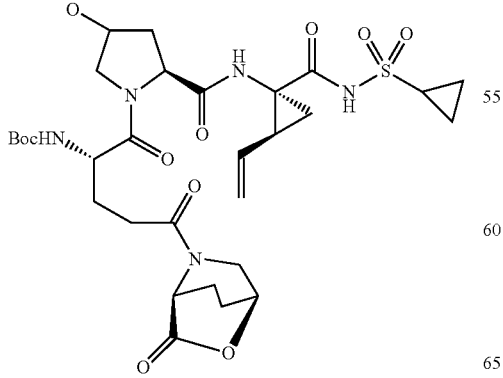

tert-butyl(2S)-1-((2S)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxo-5-((1S,4S)-3-oxo-2-oxa-5-azabicyclo[2.2.2]octan-5-yl)pentan-2-ylcarbamate (XVI-3)

The title compound was synthesized in the same way as for XVI-9 using intermediate 6b as coupling acid of intermediate 1h. LC-MS: 839.3 (ES+), 837.3 (ES).

Example 80

XVI-2

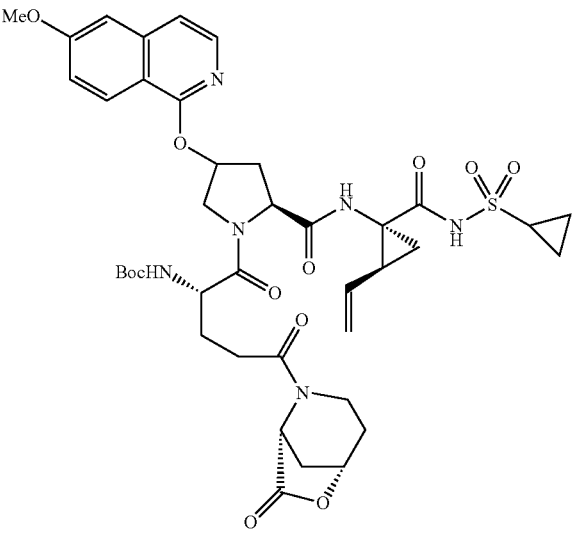

tert-butyl(2S)-1-(2S)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxo-5-((1R,5S)-7-oxo-6-oxa-2-azabicyclo[3.2.1]octan-2-yl)pentan-2-ylcarbamate (XVI-2)

The title compound was synthesized in the same way as for XVI-3 using intermediate 6c as coupling acid of intermediate 6b. LC-MS: 839.3 (ES+), 837.3 (ES−).

Example 81

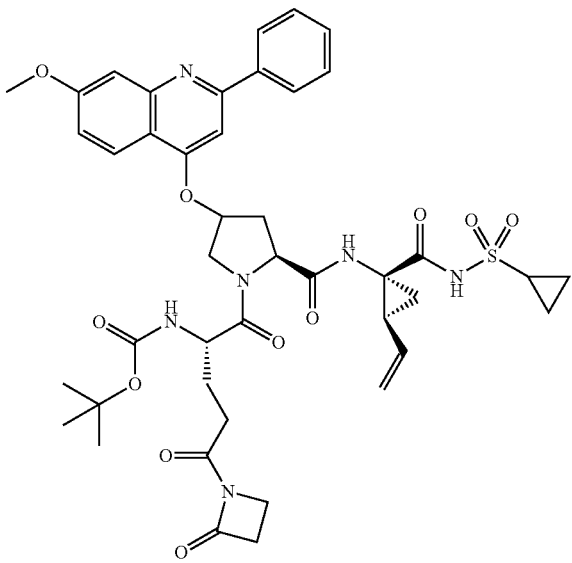

tert-butyl(2S)-1-(2S)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1,5-dioxo-5-(2-oxoazetidin-1-yl)pentan-2-ylcarbamate The title compound was prepared according to the steps and intermediates as described below.

Intermediate 7a

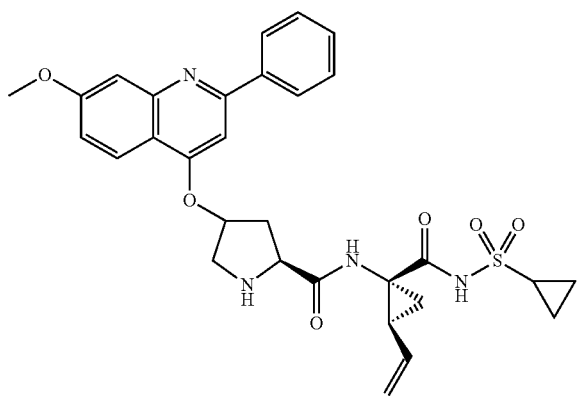 [SMILES: C=C[C@@H]1C[C@]1(NC(=O)[C@@H]1CC(Oc2cc(-c3ccccc3)nc3cc(OC)ccc23)CN1)C(=O)NS(=O)(=O)C1CC1]

Intermediate 7a was prepared following the published procedure as in WO2006086381.

Intermediate 7b

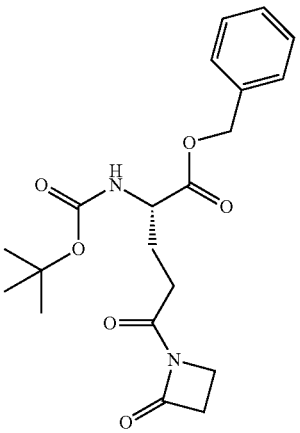 [SMILES: CC(C)(C)OC(=O)N[C@@H](CCC(=O)N1CCC1=O)C(=O)OCc1ccccc1]

To a stirring solution of azetidin-2-one (36 mg, 0.5 mmol) in 5 mL anhydrous THF was added n-BuLi (1.6 M, 0.31 mL) at −78° C. The solution was stirred for 0.5 h at −78° C. and warmed up to RT. This solution was then transferred into a stirred solution of (S)-5-(benzyloxy)-4-(tert-butoxycarbonylamino)-5-oxopentanoic acid (0.25 g, 0.75 mmol) and DCC (0.16 g, 0.75 mmol) in 5 mL dichloromethane (pre stirred for 10 minutes). To the mixture was then added DIEA (0.55 mmol) and DMAP (0.2 mmol) and the solution was stirred at RT for 10 hours. The solvent was removed and the crude was purified by flash column chromatography on silica gel with heptane/EtOAc (1:1) to afford 30 mg of white solid (20%) as intermediate 7b. LC-MS: 291.1 (ES+, M-Boc).

Intermediate 7c

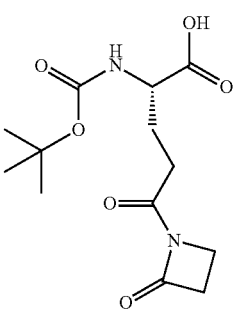 [SMILES: CC(C)(C)OC(=O)N[C@@H](CCC(=O)N1CCC1=O)C(=O)O]

Intermediate 7b (30 mg) was hydrogenated in ethyl acetate ($H_2$, Pd/C, 1h) to give the de-protected carboxylic acid 30 mg (100%). LC-MS: 299.1 (ES−).

347

Example 82

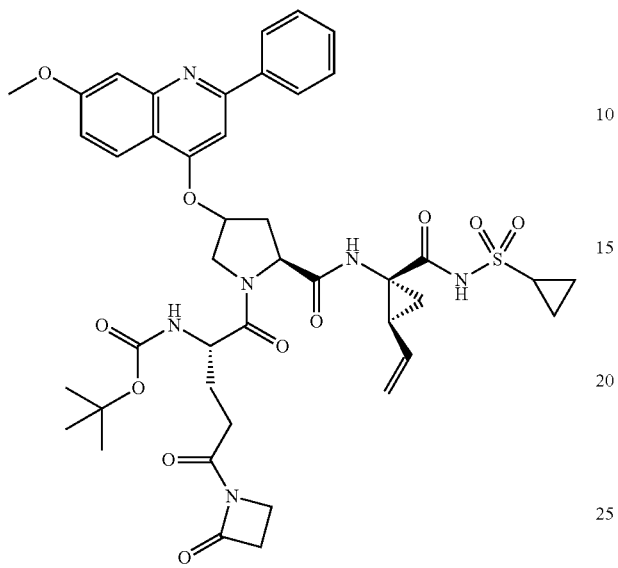

tert-butyl(2S)-1-(2S)-2-((1R,2S)-1-(cyclopropy-
lsulfonylcarbamoyl)-2-vinylcyclopropylcarbamoyl)-
4-(7-methoxy-2-phenylquinolin-4-yloxy)pyrrolidin-
1-yl)-1,5-dioxo-5-(2-oxoazetidin-1-yl)pentan-2-
ylcarbamate (XVI-26)

The title compound was synthesized using intermediate 7a and intermediate 7c via the chemistry as described for XVI-16. LC-MS: 859.3 (ES+).

Example 83

XVI-1

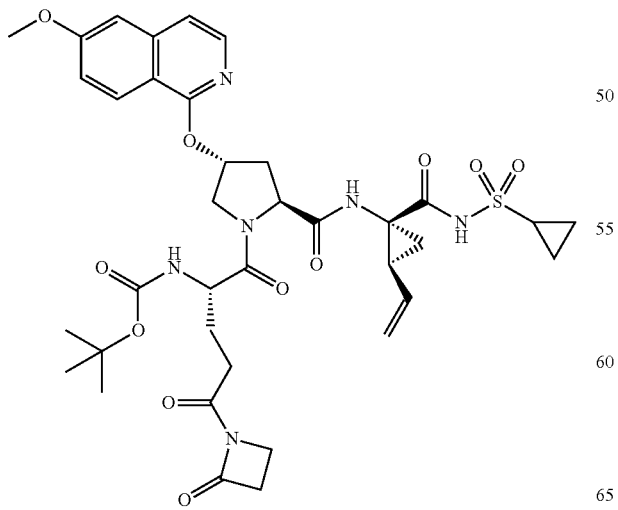

348 tert-butyl (S)-1-((2S,4R)-2-((1R,2S)-1-(cyclopropy-
lsulfonylcarbamoyl)-2-vinylcyclopropylcarbamoyl)-
4-(6-methoxyisoquinolin-1-yloxy)pyrrolidin-1-yl)-1,
5-dioxo-5-(2-oxoazetidin-1-yl)pentan-2-ylcarbamate
(XVI-1)

The title compound was synthesized in a similar way as for XVI-26 using intermediate 6a and intermediate 7c as reactants. LC-MS: 783.3 (ES+).

Example 84

XVI-25

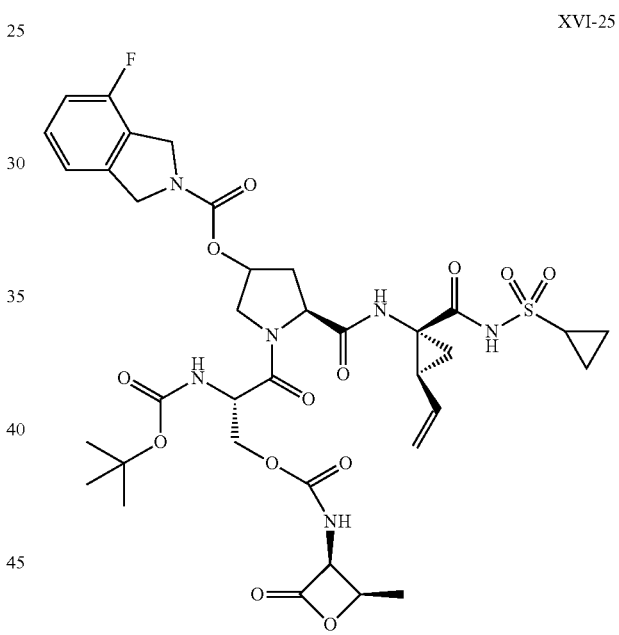

(5S)-1-((S)-2-(tert-butoxycarbonylamino)-3-((2R,
3S)-2-methyl-4-oxooxetan-3-ylcarbamoyloxy)pro-
panoyl)-5-((1R,2S)-1-(cyclopropylsulfonylcarbam-
oyl)-2-vinylcyclopropylcarbamoyl)pyrrolidin-3-yl
4-fluoroisoindoline-2-carboxylate The title compound was prepared according to the steps and intermediates as described below.

Intermediate 8a

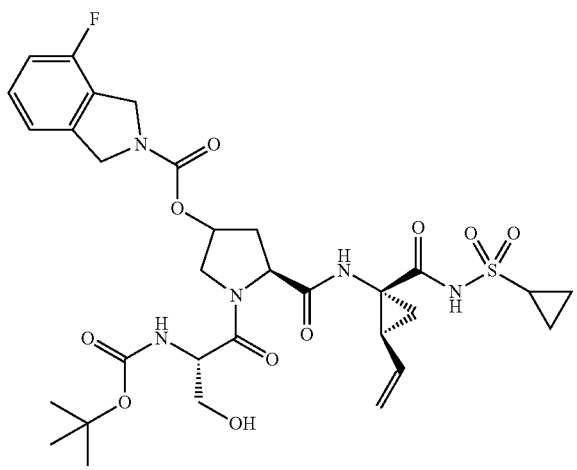 [SMILES: C=C[C@@H]1C[C@]1(NC(=O)[C@@H]1CC(OC(=O)N2Cc3cccc(F)c3C2)CN1C(=O)[C@H](CO)NC(=O)OC(C)(C)C)C(=O)NS(=O)(=O)C1CC1]

Intermediate 8a was prepared through HATU coupling reaction using intermediate 1d with N-Boc-L-serine. LC-MS: 692.2 (ES−).

Example 85

XVI-25

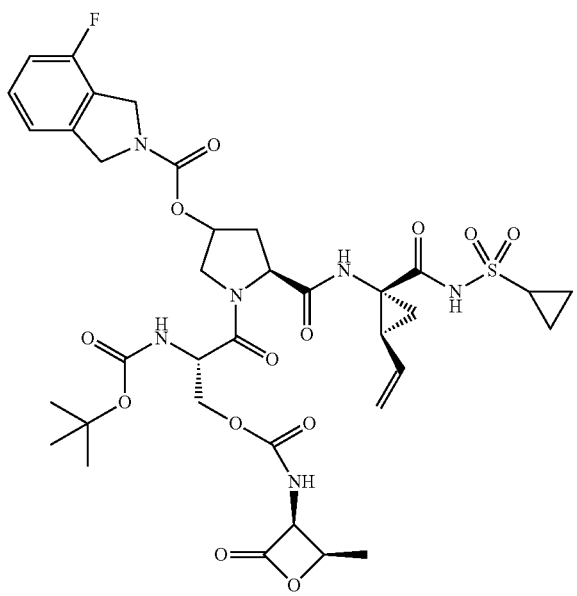

(5S)-1-((S)-2-(tert-butoxycarbonylamino)-3-((2R,3S)-2-methyl-4-oxooxetan-3-ylcarbamoyloxy)propanoyl)-5-((1R,2S)-1-(cyclopropylsulfonylcarbamoyl)-2-vinylcyclopropylcarbamoyl)pyrrolidin-3-yl 4-fluoroisoindoline-2-carboxylate (XVI-25)

Intermediate 8a was treated with 2 equivalent of phosgene in DCM at 0° C. for 1 hr. The resulting mixture was evaporated under reduced pressure. 1 equivalent (3S,4R)-3-amino-4-methyloxetan-2-one and 2 equiv of Hunig's base in acetonitrile was added in, the resulting mixture was stirred at rt for 1 hr. After concentration, the resulting residue was subject to prep-HPLC purification, giving desired XVI-25. LC-MS: 843.1 (ES+, M+Na)

Example 86

XVI-24

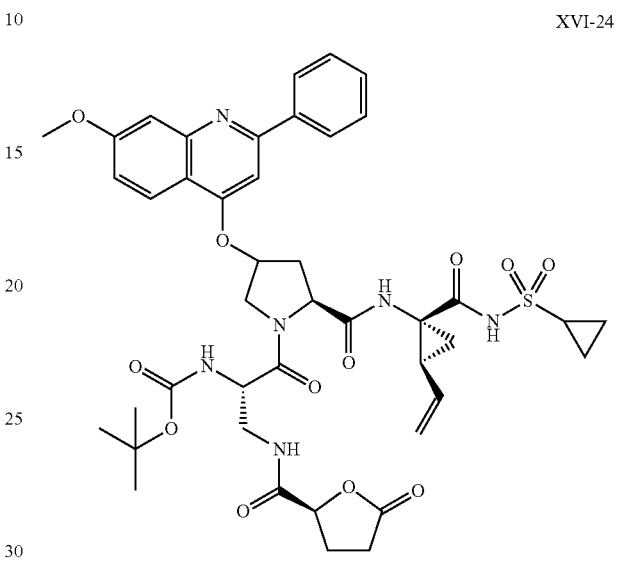

tert-butyl(2S)-1-((2S)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1-oxo-3-((S)-5-oxotetrahydrofuran-2-carboxamido)propan-2-ylcarbamate The title compound was prepared according to the steps and intermediates as described below.

Intermediate 9a

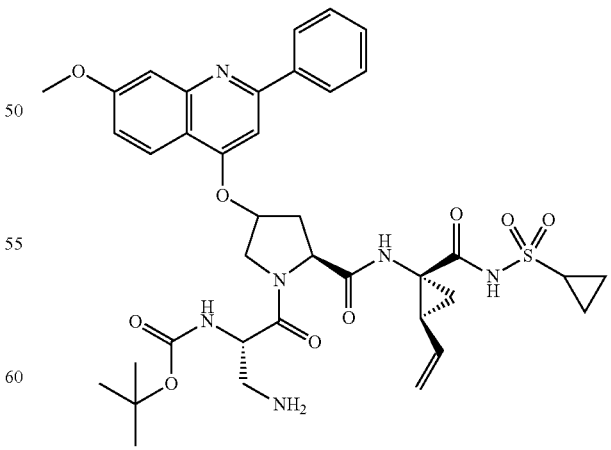

Intermediate 9a was prepared in the same way as for intermediate 3b starting from intermediate 7a instead of intermediate 1d. LC-MS: 763.3 (ES+).

Example 87

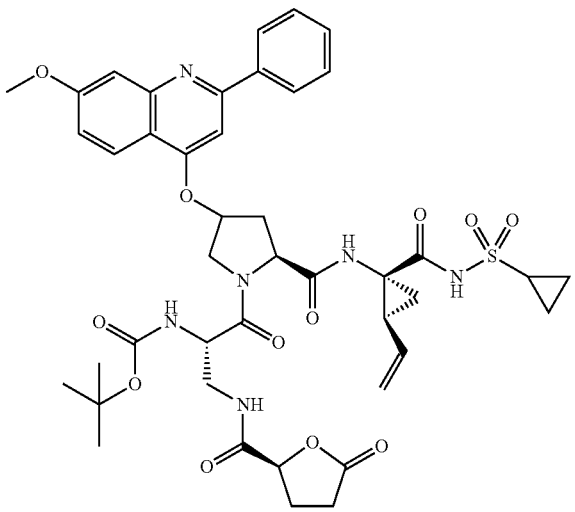

XVI-24 tert-butyl(2S)-1-((2S)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1-oxo-3-((S)-5-oxotetrahydrofuran-2-carboxamido)propan-2-ylcarbamate (XVI-24)

The title compound was made in the same way as for XVI-21 using intermediate 9a instead of intermediate 3b. LC-MS: 875.3. (ES+).

HCV-NS3 Biological Data

Table 3 shows the activity of selected compounds of this invention in the NS3/4A_App (nM), MS_HCVNS3_INTACT_NS3 WT 1b 1 HR, MS_HCVNS3_INTACT C139S_3HR, MS_HCVNS3_INTACT_K136A_3HR Assays. Compounds having an activity designated as "A" provide an IC50≤1 nM; compounds having an activity designated as "B" provide an IC50>1 nM and ≤10 nM; compounds having an activity designated as "C" provide an IC50>10 nM and ≤100 nM; compounds having an activity designated as "D" provide an IC50>100 nM and ≤1000 nM; and compounds having an activity designated as "E" provide an IC50≥1000 nM.

Compounds having an activity designated as "F" provide complete modification; compounds having an activity designated as "G" provide >70% modification; compounds having an activity designated as "H" provide >50% and ≤70% modification; compounds having an activity designated as "I" provide >30% and ≤50% modification; and compounds having an activity designated as "K" provide ≤30% modification.

TABLE 3

| Compound Designation | Enzyme/Assay | Inhibition/Modification Designation |
|---|---|---|
| XVI-1 | NS3/4A_App (nM) | A |
| | MS_HCVNS3_INTACT_NS3 WT 1b 1 HR | G |
| | MS_HCVNS3_INTACT_C139S_3 HR | F |
| | MS_HCVNS3_INTACT_K136A_3 HR | K |
| XVI-2 | NS3/4A_App (nM) | A |
| | MS_HCVNS3_INTACT_NS3 WT 1b 1 HR | K |
| XVI-3 | NS3/4A_App (nM) | A |
| | MS_HCVNS3_INTACT_NS3 WT 1b 1 HR | K |
| | MS_HCVNS3_INTACT_K136A_3 HR | K |
| XVI-4 | NS3/4A_App (nM) | D |
| | MS_HCVNS3_INTACT_NS3 WT 1b 1 HR | K |
| XVI-5 | NS3/4A_App (nM) | D |
| | MS_HCVNS3_INTACT_NS3 WT 1b 1 HR | K |
| XVI-6 | NS3/4A_App (nM) | B |
| | MS_HCVNS3_INTACT_NS3 WT 1b 1 HR | H |
| XVI-7 | NS3/4A_App (nM) | B |
| | MS_HCVNS3_INTACT_NS3 WT 1b 1 HR | H |
| XVI-8 | NS3/4A_App (nM) | A |
| | MS_HCVNS3_INTACT_NS3 WT 1b 1 HR | G |
| XVI-9 | NS3/4A_App (nM) | A |
| | MS_HCVNS3_INTACT_NS3 WT 1b 1 HR | H |
| | MS_HCVNS3_INTACT_K136A_3 HR | K |
| XVI-10 | NS3/4A_App (nM) | D |
| XVI-11 | NS3/4A_App (nM) | D |
| XVI-12 | NS3/4A_App (nM) | D |
| XVI-13 | NS3/4A_App (nM) | D |
| XVI-14 | NS3/4A_App (nM) | A |
| | MS_HCVNS3_INTACT_NS3 WT 1b 1 HR | H |
| | MS_HCVNS3_INTACT_C139S_3 HR | I |
| | MS_HCVNS3_INTACT_K136A_3 HR | I |
| XVI-15 | NS3/4A_App (nM) | A |
| | MS_HCVNS3_INTACT_NS3 WT 1b 1 HR | H |
| | MS_HCVNS3_INTACT_C139S_3 HR | H |
| | MS_HCVNS3_INTACT_K136A_3 HR | H |
| XVI-16 | NS3/4A_App (nM) | A |
| | MS_HCVNS3_INTACT_NS3 WT 1b 1 HR | H |
| | MS_HCVNS3_INTACT_C139S_3 HR | F |
| | MS_HCVNS3_INTACT_K136A_3 HR | F |
| XVI-17 | NS3/4A_App (nM) | A |
| | MS_HCVNS3_INTACT_NS3 WT 1b 1 HR | G |
| | MS_HCVNS3_INTACT_C139S_3 HR | F |
| | MS_HCVNS3_INTACT_K136A_3 HR | F |
| XVI-18 | NS3/4A_App (nM) | B |
| XVI-19 | NS3/4A_App (nM) | B |
| | MS_HCVNS3_INTACT_C139S_3 HR | K |
| XVI-20 | NS3/4A_App (nM) | B |
| XVI-21 | NS3/4A_App (nM) | B |
| XVI-22 | NS3/4A_App (nM) | E |
| XVI-23 | NS3/4A_App (nM) | D |
| XVI-24 | NS3/4A_App (nM) | B |
| | MS_HCVNS3_INTACT_NS3 WT 1b 1 HR | K |
| XVI-25 | NS3/4A_App (nM) | A |
| | MS_HCVNS3_INTACT_NS3 WT 1b 1 HR | K |
| XVI-26 | NS3/4A_App (nM) | A |
| | MS_HCVNS3_INTACT_NS3 WT 1b 1 HR | H |
| | MS_HCVNS3_INTACT_C139S_3 HR | F |

Some of the HCV Protease inhibitors, such as compounds XVI-1, XVI-8, XVI-17, XVI-16, and XVI-26, provide >70% modification of HCV Protease, or mutants thereof. Some of the HCV Protease inhibitors, such as compounds XVI-6, XVI-7, XVI-9, XVI-14, XVI-15, XV-16, and XVI-26 provide >50% up to ≤70% modification of HCV Protease, or mutants thereof. Some of the HCV Protease inhibitors, such as compound XVI-14 provide >30% and ≤50% modification of HCV Protease, or mutants thereof. Some of the HCV Protease inhibitors, such as compounds XVI-1, XVI-2, XVI-3, XVI-4, XVI-5, XVI-9, XVI-19, XVI-24, and XVI-25 provide ≤30% modification of HCV Protease, or mutants thereof.

F. Mass Spectrometric Analysis of HCV Protease Contacted with Compounds of the Invention Example 88

Figure 3:
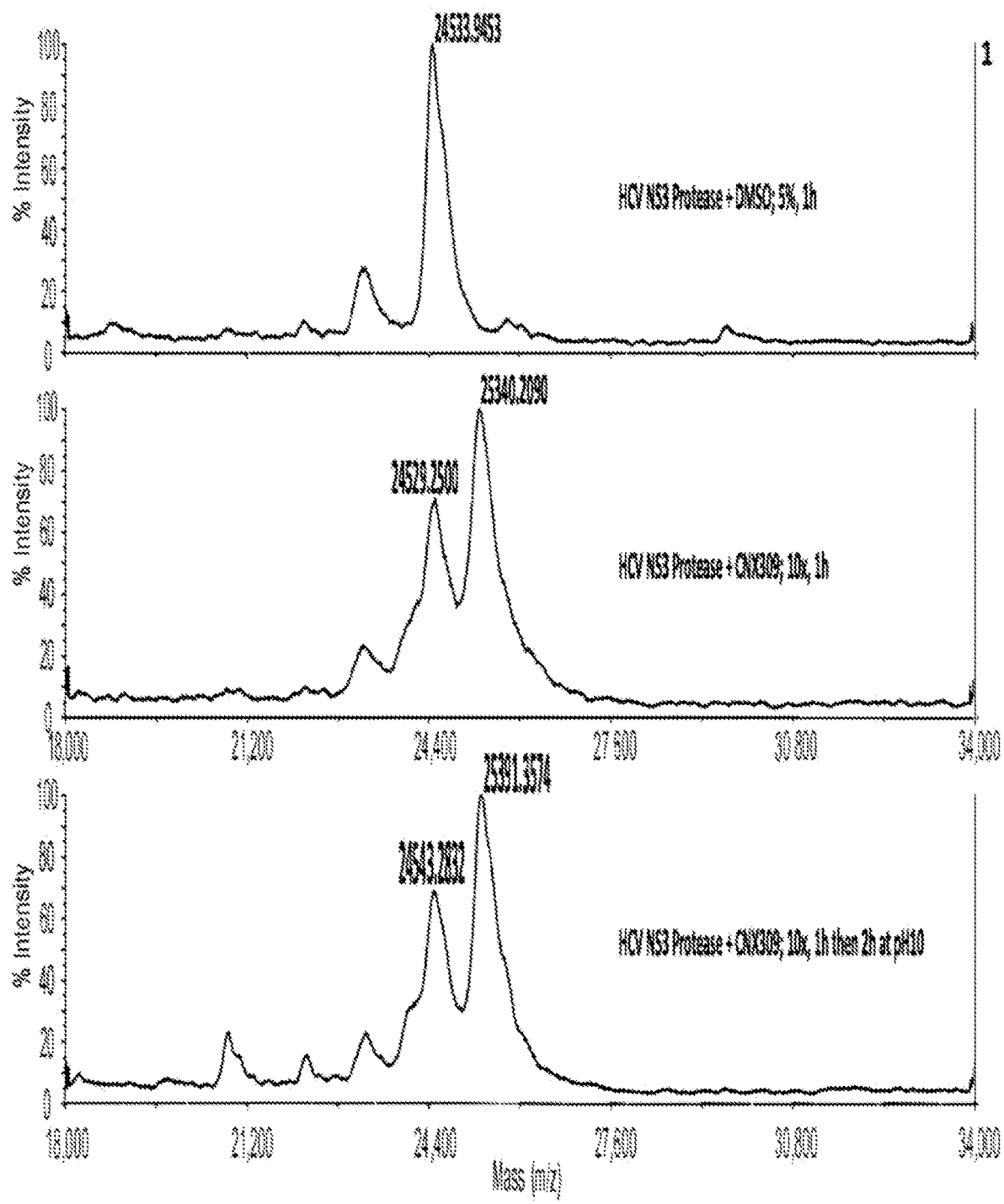
FIG. 3 depicts the mass spectrometric analysis of Compound XVI-26 contacted with HCV NS3 Protease.

Intact HCV (protease) 1bWT was incubated for 1 hr at a 10× fold excess of XVI-26 to protein. 3 ul aliquots of the samples were diluted with 10 ul of 0.1% TFA prior to micro C4 ZipTipping directly onto the MALDI target using Sinapinic acid as the desorption matrix (10 mg/mL in 0.1% TFA:Acetonitrile 50:50). The top panel in FIG. 3 shows the mass spectrometric trace of the intact HCV 1bWT protein (m/z 24,529 Da). The middle panel in FIG. 3 shows the mass spectrometric trace when HCV 1bWT was incubated with XVI-26 (mw=858.9). The centroid mass (m/z=25,340 Da) shows a positive shift of about 811 Da, indicating modification of HCV 1bWT by XVI-26. Due to likely protein misfolding during protein purification, a small portion of the misfolded protein was not modified.

In order to determine whether the modification of the protein occurred at lysine, the pH from the above experiment was increased from 7.4 to 10.0. Because the compound lysine adduct would be an amide any increase in pH would have minimal effect on the modified protein. If however, the modification occurred at cysteine the resultant thioester bond would be unstable and the compound would hydrolyze off the protein. The bottom panel of FIG. 3 shows a mass spectrometric trace of HCV 1bWT reaction with XVI-26 for 1 hour at pH 7.4 followed by 2 hours at pH 10, and XVI-26 did not come off of the protein implying the adduct was occurring on a lysine.

Figure 4:
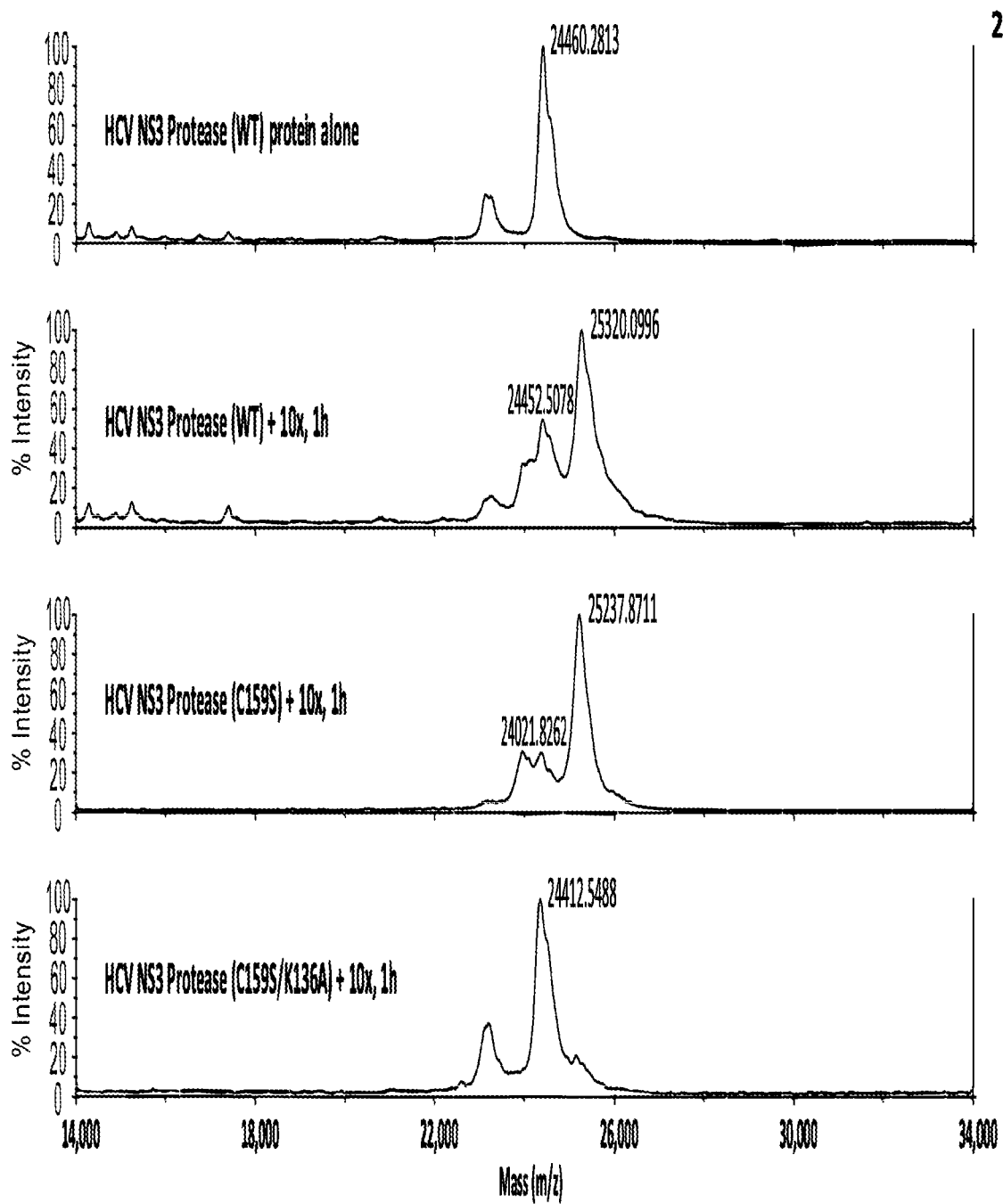
FIG. 4 depicts the mass spectrometric analysis of Compound XVI-26 treated with HCV NS3 Protease (WT); HCV NS3 Protease (C159S); and HCV NS3 protease (C159S/K136A).

Intact HCV (protease) 1bWT, C159S, and C159S/K136A were incubated for 1 hr at a 10× fold excess of XVI-26 to protein. 3 µl aliquots of the samples were diluted with 10 µl of 0.1% TFA prior to micro C4 ZipTipping directly onto the MALDI target using Sinapinic acid as the desorption matrix (10 mg/mL in 0.1% TFA:Acetonitrile 50:50). The first panel of FIG. 4 shows the mass spectrometric trace of the intact HCV 1bWT protein (m/z 24,460 Da). The second panel of FIG. 4 shows the mass spectrometric trace when HCV 1bWT was incubated with XVI-26 (mw=858.9), the centroid mass (m/z=25,320 Da) shows a positive shift of about 860 Da, indicating modification of HCV 1bWT by XVI-26. The third panel of FIG. 4 shows the mass spectrometric trace when HCV C159S mutant was incubated with XVI-26 and the centroid mass (m/z=25,237 Da) shows a positive shift of 770 Da, indicating modification of HCV C159S by XVI-26. The fourth panel of FIG. 4 shows the mass spectrometric trace when HCV C159S/K136A double mutant was incubated with XVI-26, the centroid mass (m/z=24,412 Da) is consistent with the mass of unmodified HCV C159S/K136A, indicating no modification of HCV C159S/K136A by XVI-26. This data shows that K136 is the amino acid modified by XVI-26.

Figure 5:
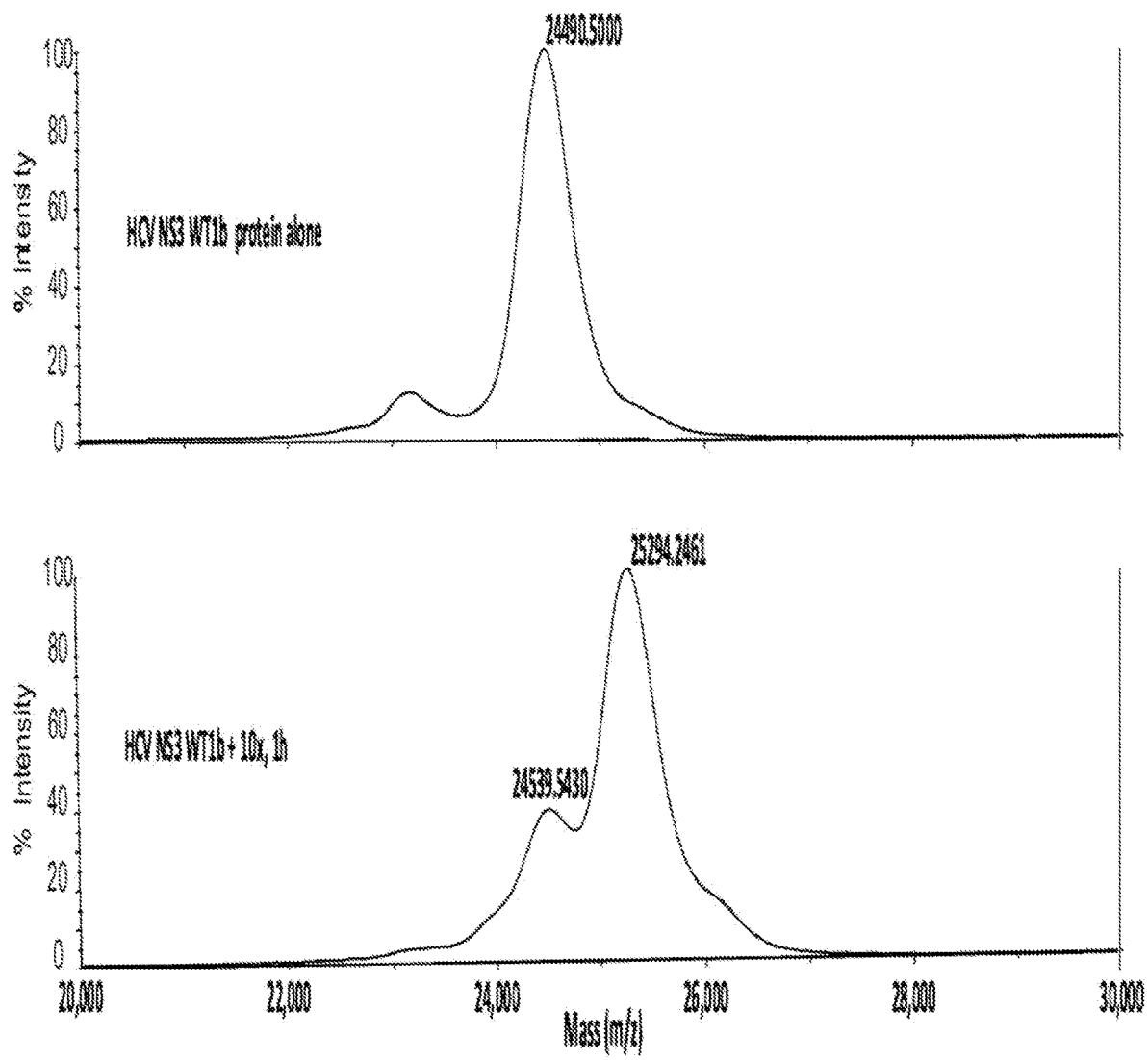
FIG. 5 depicts the mass spectrometric analysis of compound XVI-1 treated with HCV NS3 Protease (WT1b).

Intact HCV (protease) WT1b was incubated for 1 hr at a 10× fold excess of XVI-1 (mw=782.87) to protein. 3 µl aliquots of the samples were diluted with 10 µl of 0.1% TFA prior to micro C4 ZipTipping directly onto the MALDI target using Sinapinic acid as the desorption matrix (10 mg/mL in 0.1% TFA:Acetonitrile 50:50). The top panel of FIG. 5 shows the mass spectrometric trace of HCV NS3 protein (m/z 24,550 Da) and the bottom panel of FIG. 5 shows the 1 hr time point (m/z of 24,611 & 25,372), which shows a mass shift of +755 (~72% conversion) showing that XVI-1 modified HCV NS3 WT1b. Due to some protein misfolding during the purification of the protein, the unfolded portion of the protein can not react with XVI-1.

Example 89

Single Chain HCV Protease (wt) Peptide Expression and Purification

The single-chain proteolytic domain (NS4A$_{21-32}$-GSGS-NS$_{33-631}$) was cloned into pET-14b (Novagen, Madison, Wis.) and transformed into DH10B cells (Invitrogen). The resulting plasmid was transferred into *Escherichia coli* BL21 (Novagen) for protein expression and purification. Briefly, the cultures were grown at 37° C. in LB medium containing 100 µg/ml of ampicillin until the optical density at 600 nm (OD600) reached 1.0 and were induced by addition of isopropyl-β-D-thiogalactopyranoside (IPTG) to 1 mM. After an additional incubation at 18° C. for 20 h, bacteria were harvested by centrifugation at 6,000×g for 10 minutes and resuspended in a lysis buffer containing 50 mM Na$_3$PO$_4$, pH 8.0, 300 mM NaCl, 5 mM 2-mercaptoethanol, 10% glycerol, 0.5% Igepal CA630, and a protease inhibitor cocktail consisting of 1 mM phenylmethylsulfonyl fluoride, 0.5 µg/ml leupeptin, pepstatin A, and 2 mM benzamidine. Cells were lysed by freezing and thawing, followed by sonication. Cell debris was removed by centrifugation at 12,000×g for 30 min. The supernatant was further clarified by passing through a 0.45-µm filter (Corning) and then loaded onto a HiTrap chelating column charged with NiSO$_4$ (Amersham Pharmacia Biotech). The bound protein was eluted with an imidazole solution in a 100-to-500 mM linear gradient. Selected fractions were run through Ni$^{2+}$ column chromatography and were analyzed on a 10% sodium dodecyl sulfate (SDS)-polyacrylamide gel. The purified protein was resolved by electrophoresis in a 12% SDS-PAGE gel and then transferred onto a nitrocellulose membrane. The protein was analyzed by Western blot analysis using monoclonal antibodies against NS3. Proteins were visualized by using a chemiluminescence kit (Roche) with horseradish peroxidase-conjugated goat anti-mouse antibodies (Pierce) as secondary antibodies. The protein was aliquoted and stored at −80° C.

Example 90

Cloning and Expression of HCV Protease A156S, A156T, D168A, D168V Drug-Resistance Mutants and C159S Variant The mutant DNA fragments of NS4A/NS3 were generated by PCR and cloned into pET expression vector. After transformation into BL21 competent cells, the expression was induced with IPTG for 2 hours. The His-tagged fusion proteins were purified using affinity column followed by size exclusion chromatography.

Example 91

Figure 10:
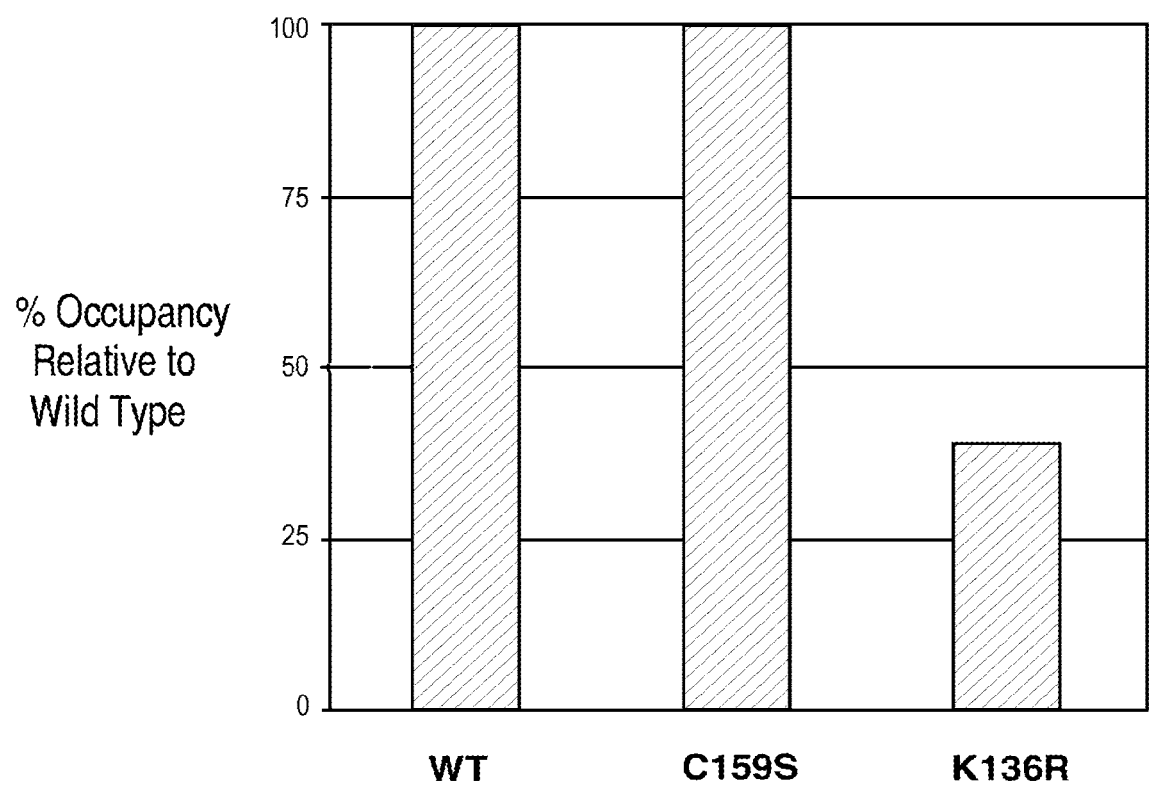
FIG. 10 depicts that the probe compound XVI-27, modifies NS3/4A C159S.

Plasmids Used for Lys Washout and Covalent Probe:

FIG. 10 depicts lysine covalent probe compound XVI-27 modifying NS3/4A C159S. The pCI-Neo-FLAG-NS3/4a-WT plasmid was constructed by amplifying the NS3 and 4a sequence from the pFK-I389-luc-ubi-neo-NS3-3'ET vector using Accuprime Pfx (Invitrogen) according to manufacturer's instructions and with primers that added an NheI site and FLAG epitope tag to the 5' end and an XbaI site to the 3' end.

```
                                            (SEQ ID NO: 176)
(FTAATAAGCTAGCACCATGGACTACAAAGATGATGACGATAAAGGAGCG

CCTATTACGGCCTACTCCCAACAG, (SEQ ID NO: 177)
R-TTATTATCTAGACTAGCACTCTTCCATCTCATCGAACTCCCGGTAA

AG).
```

The resulting PCR product was then digested with NheI and XbaI and ligated into the same sites of the pCI-Neo vector (Invitrogen). The WT construct was then used as a template for site-directed mutagenesis using the Quickchange II Site-Directed Mutagenesis kit (Qiagen) and primers containing the K136R or C159S mutations (below).

```
NS3-C159S-F
                                            (SEQ ID NO: 178)
ATCTTTCGGGCTGCCGTGAGCACCCGAGGGGTTGCGAAG

NS3-C159S-R
                                            (SEQ ID NO: 179)
CTTCGCAACCCCTCGGGTGCTCACGGCAGCCCGAAAGAT

NS3-K136R-F
                                            (SEQ ID NO: 180)
GTCTCCTACTTGAGGGGCTCTTCGGGCGGT

NS3-K136R-R
                                            (SEQ ID NO: 181)
ACCGCCCGAAGAGCCCCTCAAGTAGGAGAC
```

Example 92

Demonstration of Prolonged Duration of Action (Washout)

Figure 11:
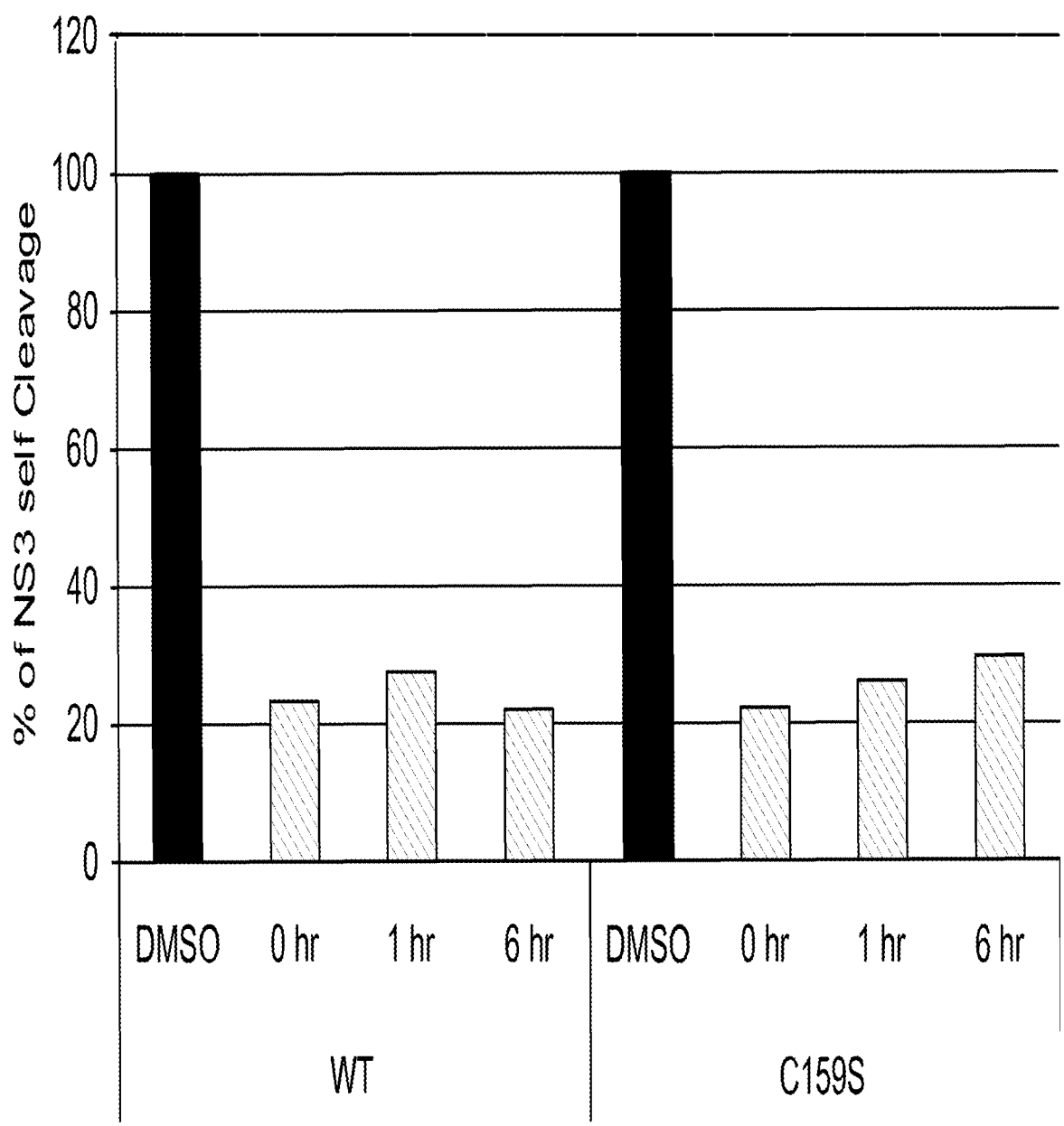
FIG. 11 depicts the prolonged duration of action of XVI-26.

FIG. 11 depicts the prolonged duration of action with XVI-26. Parental Huh-7 cells were plated at a density of 1.75×10$^6$ cells per 100 mm dish in media with 10% FBS. The following day, cells were transfected in OptiMEM using 28 ug of plasmid and 112 ul of Lipfectamine 2000 (Invitrogen), according to manufacturer's instructions. After 4 hours incubation with the transfection complex, the media was changed to Replicon Assay Medium (RPMI supplemented with 5% FBS, 1× non-essential amino acids and pen/strep). The next morning, the cells were trypsinized, counted and replated in Replicon Media at a density of 20,000 cells/well of a 12 well plate (4 wells per genotype). Cells were allowed to adhere to the plate, then the media was removed and replaced with 1 ml media containing XVI-26, (3 wells per compound) and 0.02% DMSO and returned to the incubator overnight. Sixteen hours later 1 treated well from each genotype (0 hr sample) and 1 untreated well were washed with PBS, then lysed and scraped into 30 ul of Cell Extraction Buffer (Biosource, Camarillo, Calif.) plus Complete Protease Inhibitor (Roche, Indianapolis, Ind.). The remaining wells were rinsed 2× with PBS then fed with Replicon Media and returned to the incubator. Cells were washed once every hour by removing the old media and replacing it with fresh media and were lysed and collected at 1 and 6 hours following the first collection. Lysates were resolved using standard immunoblotting methods and NS3 self-cleavage activity was assessed and quantified relative to untreated samples.

Example 93

Demonstration of Lysine Modification Using Covalent Probe

As illustrated in FIG. 11, 200 µg of total cell lysate was used for either NS3/4A WT, C159S or K136R respectively. Lysates were treated with 1 µM of biotinylated covalent probe, XVI-27, for 1h and immunoprecipitated with anti-NS3 antibody (mouse). Immunoblots were probed with streptavidin and anti-NS3 antibody (goat). Successful modification by the covalent probe was assessed and quantified relative to WT NS3.

Example 94

Assay buffer: 2% CHAPS, 50 mM Tris pH 7.5, 50% glycerol, 2 uM M-2235 (Bachem) substrate. In a 50 ul reaction, add 49 ul assay buffer, 1 ul (1U) HCV serine protease (Bioenza). Incubate 20 minutes at room temperature. The plate was read at either 350/460 nm (excitation/emission) on a fluorescent micro-plate reader or monitored at one-minute intervals to achieve the kinetic curve.

The enzyme tolerated 1% DMSO and 2% methanol. In the experiments of testing compounds, the compounds in pure DMSO were diluted 10 times with 20% methanol (10% DMSO and 20% methanol). This compound solution was added to the reaction (not exceeding 10% of the final reaction volume). The final concentration of the organic solvents was: 1% DMSO and 2% methanol.

Example 95

HCV Protease FRET Assay for WT and Mutated NS3/4A 1b Enzymes ($IC_{50\_APP}$).

The following protocol was used to generate "apparent" $IC_{50}$ ($IC_{50\_APP}$) values as depicted in Table 6, below. Without wishing to be bound by any particular theory, it is believed that $IC_{50\_APP}$, contrasted with $IC_{50}$ values, may provide a more useful indication of time-dependent inhibition, and are thus more representative of binding affinity. The protocol is a modified FRET-based assay (v_03) developed to evaluate compound potency, rank-order and resistance profiles against wild type and C159S, A156S, A156T, D168A, D168V, R155K mutants of the HCV NS3/4A 1b protease enzyme as follows: 10× stocks of NS3/4A protease enzyme from Bioenza (Mountain View, Calif.) and 1.13×5-FAM/QXL™520 FRET peptide substrate from Anaspec (San Jose, Calif.) were prepared in 50 mM Tris-HCl, pH 7.5, 5 mM DTT, 2% CHAPS and 20% glycerol. 5 µL of each enzyme were added to Corning (#3575) 384-well, black, microtiter plates (Corning, N.Y.) after spotting a 0.5 µL volume of 50% DMSO and serially diluted compounds prepared in 50% DMSO. Protease reactions were immediately started after enzyme addition with the addition of 45 µL of the FRET substrate and monitored for 60-90 minutes at $\lambda_{ex}485/\lambda_{em}520$ in a Synergy plate reader from BioTek (Winooski, Vt.). At the conclusion of each assay, progress curves from each well were examined for linear reaction kinetics and fit statistics ($R^2$, 95% confidence intervals, absolute sum of squares). Initial velocity (0 minutes to 15+ minutes) from each reaction was determined from the slope of a plot of relative fluorescence units vs time (minutes) and then plotted against inhibitor concentration as a percent of the no inhibitor and no enzyme controls to estimate apparent $IC_{50}$ from log [Inhibitor] vs Response. (Variable Slope model in GraphPad Prism from GraphPad Software (San Diego, Calif.).)

G. PI3 Kinase Inhibitors (LYS) Synthetic Examples
Example 96
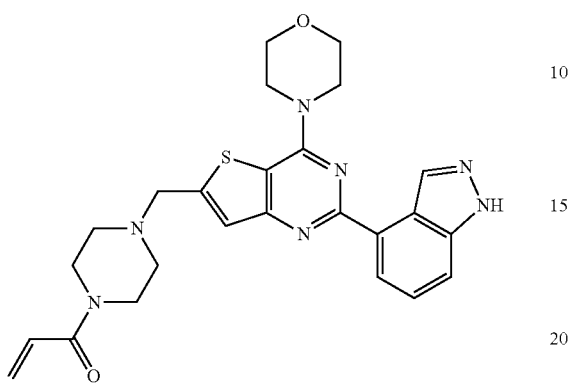
XXII-17
1-(4-((2-(1H-indazol-4-yl)-4-morpholinothieno[3,2-d]pyrimidin-6-yl)methyl)piperazin-1-yl)prop-2-en-1-one
The title compound was prepared according to the steps and intermediates as described below.
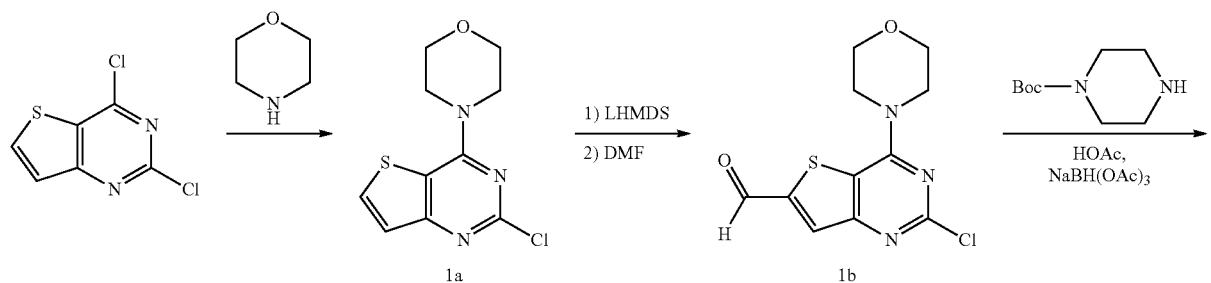
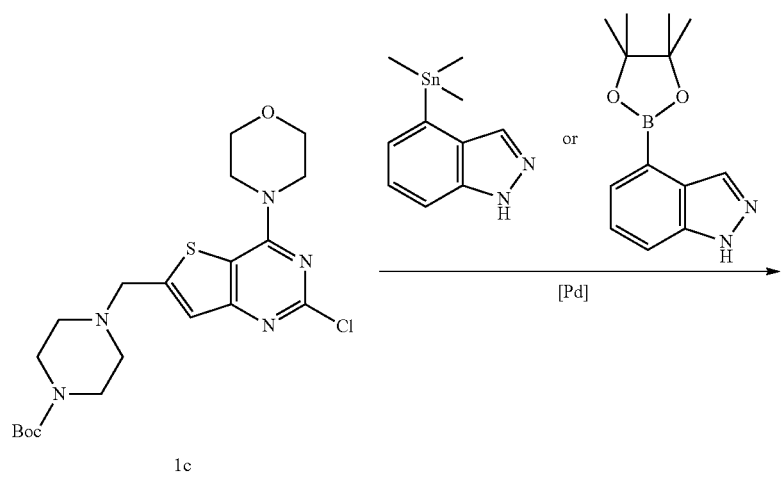

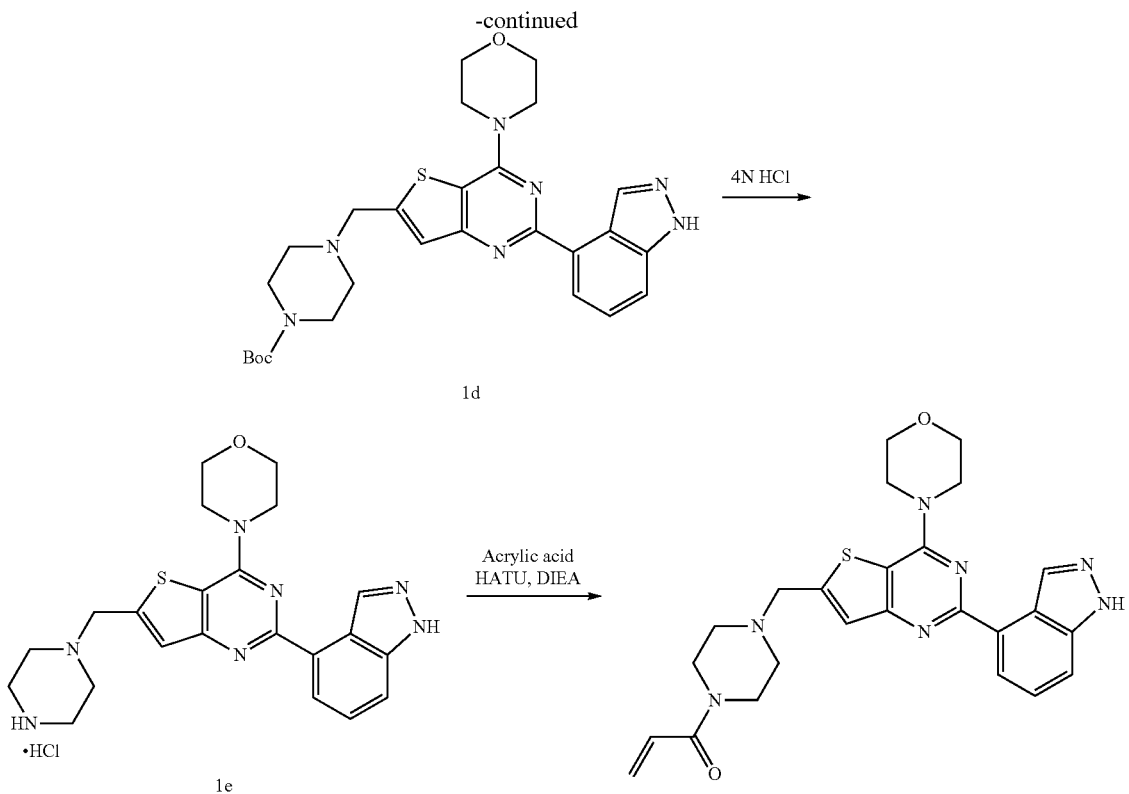

Step 1a: 4-(2-chlorothieno[3,2-d]pyrimidin-4-yl)morpholine (Intermediate 1a)

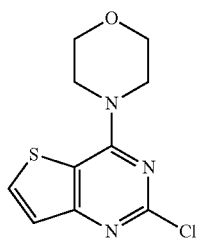 [SMILES: Clc1nc(N2CCOCC2)c2sccc2n1]

To a solution of 2,4-dichlorothieno[3,2-d]pyrimidine (2.0 g, 9.7 mmol) in 30 mL MeOH was added 1.9 mL morpholine. After stirring at room temperature for one hour, the reaction mixture was filtered; the solid was washed with water and methanol to provide 2.0 g of the title compound. MS m/z: 256.0, 258.1 (M+1). 1H NMR (400 MHz, CDCl3): □: 7.78 (1H, d, J=5.48 Hz), 7.38 (1H, d, J=5.48 Hz), 4.02 (4H, t, J=4.80 Hz), 3.85 (4H, t, J=4.82 Hz).

Step 1b: 2-chloro-4-morpholinothieno[3,2-d]pyrimidine-6-carbaldehyde (Intermediate 1b)

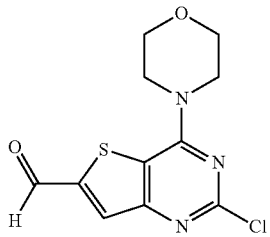 [SMILES: O=Cc1cc2nc(Cl)nc(N3CCOCC3)c2s1]

To a suspension of Intermediate 1a (1.02 g, 4.0 mmol) in 30 mL THF at −78° C. was added LiHMDS (1.0 N, 6.0 mL, 6.0 mmol) slowly. The reaction mixture was stirred at −78° C. for 1 h, DMF (0.5 mL) was added and reaction mixture was allowed to warm up to room temperature over 2 hours. The reaction was quenched with NH$_4$Cl aqueous solution and the THF was removed under vacuum. A 50-mL portion of EtOAc was added in and the mixture was washed with aqueous NaHCO$_3$ and brine. The organic layer was separated and was dried over Na$_2$SO$_4$. After removal of solvent, the crude product was subjected to chromatography on silica gel (eluents: EtOAc/hexane). A total of 0.6 g of the title compound was obtained (60%). MS m/z: 284.2 (ES+, M+1).

Step 1c: tert-butyl 4-((2-chloro-4-morpholinothieno[3,2-d]pyrimidin-6-yl)methyl)piperazine-1-carboxylate (Intermediate 1c)

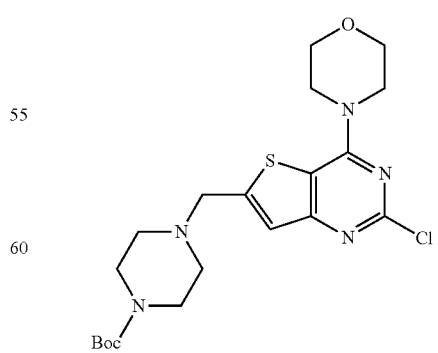

Intermediate 1b (0.40 g, 1.5 mmol), tert-butyl piperazine-1-carboxylate and 0.2 mL acetic acid were dissolved in 12 mL dichloroethane. The mixture was stirred at room temperature for 2 hours. NaBH(OAc)$_3$ (0.54 g, 2.5 mmol) was added to the reaction mixture and the resulting mixture was stirred at room temperature for 10 hours. A 20-mL of NaHCO$_3$ aqueous solution and 10 mL of DCM were added. The organic layer was separated and dried over Na$_2$SO$_4$. After removal of solvent, the crude product was subjected to chromatography on silica gel (eluents: EtOAc/hexane 3:7). A total of 0.30 g of the title compound was obtained. MS m/z: 454.2 (ES+, M+1).

Step 1d: tert-butyl 4-((2-(1H-indazol-4-yl)-4-morpholinothieno[3,2-d]pyrimidin-6-yl)methyl)piperazine-1-carboxylate (Intermediate 1d)

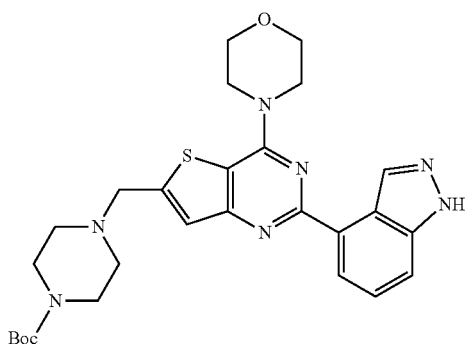 [SMILES: CC(C)(C)OC(=O)N1CCN(Cc2cc3nc(-c4cccc5[nH]ncc45)nc(N4CCOCC4)c3s2)CC1]

Intermediate 1c (0.14 g, 0.31 mmol), 4-(trimethylstannyl)-1H-indazole (0.10 g, 0.37 mmol) and tetrakis(triphenylphosphine)palladium (35 mg, 0.03 mmol) were dissolved in 5 mL toluene. The solution was degassed and flushed with N$_2$. The reaction mixture was heated to 135° C. for 40 hours in a sealed vial. The solvent was removed under vacuum and the residue was purified by chromatography on silica gel (eluents: EtOAc/hexane 5:5). A total of 0.10 g of the title compound was obtained. MS m/z: 536.1 (M+1).

Alternatively, Intermediate 1d can be prepared by the following Suzuki coupling procedures: Intermediate 1c (70 mg, 0.15 mmol), 4-(4,4,5,5-tetramethyl-1,3,2-dioxaborolan-2-yl)-1H-indazole (56 mg, 0.23 mmol), Pd(PPh$_3$)$_2$Cl$_2$ (10 mg, 0.015 mmol) and sodium carbonate (60 mg, 0.56 mmoL) were dissolved in toluene/ethanol/water (2.5 mL/1.5 mL/0.7 mL). The solution was degassed and flushed with argon. The reaction mixture was heated to 125° C. for 10 hours in a sealed vial. The reaction was then worked up by adding ethyl acetate 10 mL and washed with water and brine. The organic layer was separated and was dried over Na$_2$SO$_4$. After removal of solvent, the crude product was subjected to chromatography on silica gel (eluents: EtOAc/hexane 1:1 to 4:1) to give the title compound. MS m/z: 536.1 (M+1).

Step 1e: 4-(2-(1H-indazol-4-yl)-6-(piperazin-1-ylmethyl)thieno[3,2-d]pyrimidin-4-yl)morpholine (Intermediate 1e)

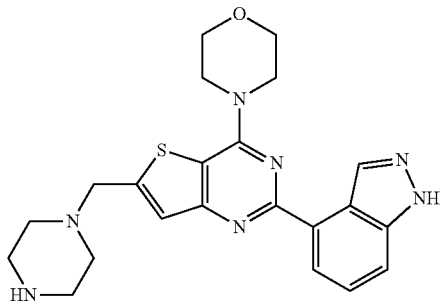 [SMILES: c1cc(-c2nc(N3CCOCC3)c3sc(CN4CCNCC4)cc3n2)c2cn[nH]c2c1]

Intermediate 1d (100 mg, 0.18 mmol) was dissolved in 3 mL of 4N HCl in dixoxane and the reaction was stirred for 3 hours at room temperature. After removal of solvents, a 3-mL portion of DCM was poured in followed by evaporation to dryness. This process of DCM addition followed by evaporation was repeated three times to give a white solid and was used directly for the next step. MS m/z: 436.2 (M+H$^+$).

Step 1f: 1-(4-((2-(1H-indazol-4-yl)-4-morpholinothieno[3,2-d]pyrimidin-6-yl)methyl)piperazin-1-yl)prop-2-en-1-one

XXII-17

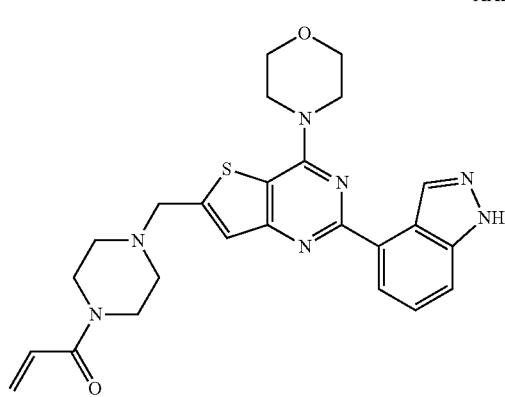

To a solution of Intermediate 1e (10 mg, 0.02 mmol) and acrylic acid (2.0 mg, 0.025 mmol) in 1.0 mL of anhydrous acetonitrile was added HATU (9.1 mg, 0.024 mmol) and DIEA (15 mg, 0.1 mmol) at −40° C. while stirring. The reaction mixture was stirred for 10 min at ~−10° C. A 10-mL portion of EtOAc and 5 mL of NaHCO$_3$ aqueous solution were added. The organic layer was separated and was dried over Na$_2$SO$_4$. After removal of solvent, the crude product was subjected to chromatography on silica gel (eluents: EtOAc/hexane 9:1). A total of 6 mg of the title compound was obtained. MS m/z: 490.2 (M+H$^+$). $^1$H NMR (400 MHz, CDCl$_3$): □: 9.01 (1H d, J=0.88 Hz), 8.27 (1H d, J=7.32 Hz), 7.58 (1H d, J=7.0 Hz), 7.51 (1H t, J=6.84 Hz), 7.39 (1H, s), 6.56 (1H dd, J=10.56, 16.96 Hz), 6.32 (1H d, 16.96 Hz), 5.70 (1H d, 10.52 Hz), 4.09 (4H, m), 3.93 (6H, m), 3.79 (2H, s), 3.62 (2H, s), 2.60 (4H, s).

In similar fashion, using Intermediate 1e and coupling with (R)-5-oxotetrahydrofuran-2-carboxylic acid, the following compound was prepared:

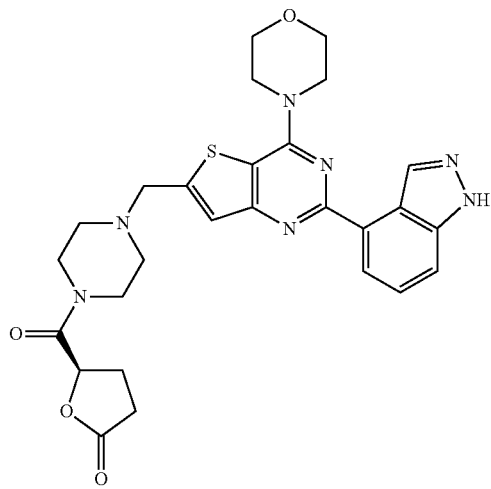 [SMILES: O=C1CC[C@H](C(=O)N2CCN(Cc3cc4nc(-c5cccc6[nH]ncc56)nc(N5CCOCC5)c4s3)CC2)O1]

In similar fashion, using Intermediate 1e and coupling with (S)-5-oxotetrahydrofuran-2-carboxylic acid, the following compound was prepared:

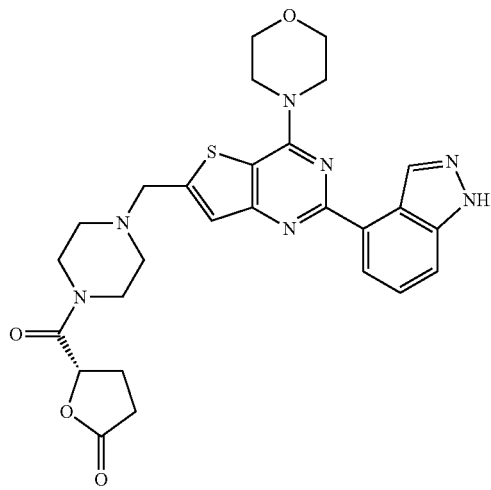 [SMILES: O=C1CC[C@@H](C(=O)N2CCN(Cc3cc4nc(-c5cccc6[nH]ncc56)nc(N5CCOCC5)c4s3)CC2)O1]

Example 97

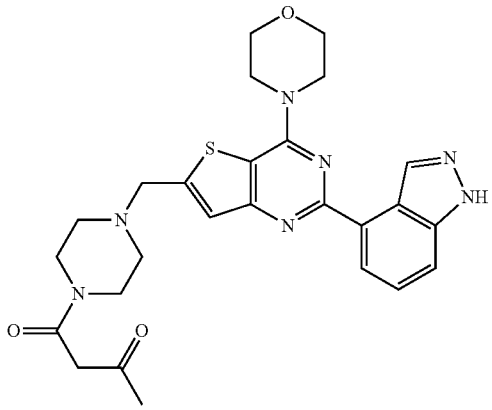

XXII-14

1-(4-((2-(1H-indazol-4-yl)-4-morpholinothieno[3,2-d]pyrimidin-6-yl)methyl)piperazin-1-yl)butane-1,3-dione In similar fashion, using Intermediate 1e and suitable carboxylic acids, the title compound was prepared: MS m/z: 520.1 (M+H⁺).

Example 98

XXII-13

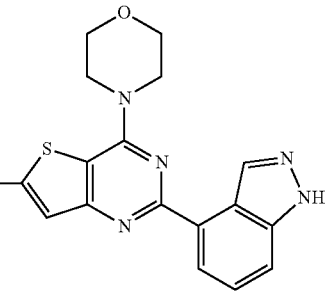

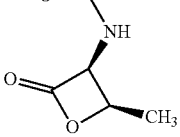

4-((2-(1H-indazol-4-yl)-4-morpholinothieno[3,2-d]pyrimidin-6-yl)methyl)-N-((2R,3S)-2-methyl-4-oxooxetan-3-yl)piperazine-1-carboxamide In similar fashion, using Intermediate 1e and suitable carboxylic acids, the title compound was prepared: MS m/z: 563.3 (M+H⁺).

Example 99

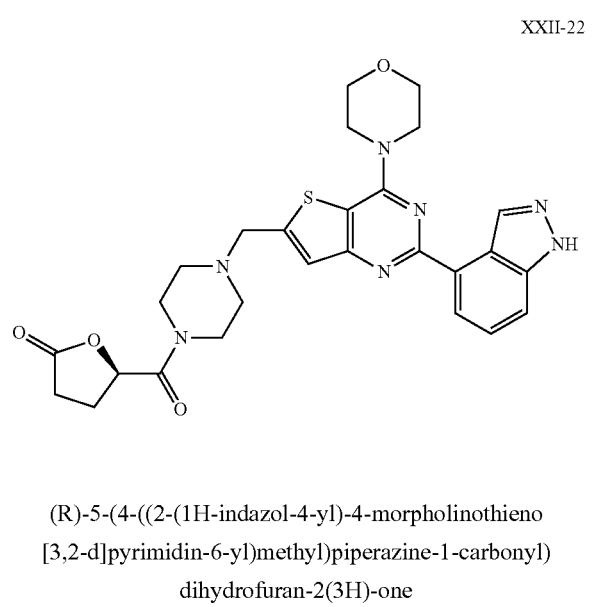

XXII-22

(R)-5-(4-((2-(1H-indazol-4-yl)-4-morpholinothieno[3,2-d]pyrimidin-6-yl)methyl)piperazine-1-carbonyl)dihydrofuran-2(3H)-one In similar fashion, using Intermediate 1e and suitable carboxylic acids, the titled compounds was prepared: MS m/z: 548.1 (M+H$^+$).

Example 100

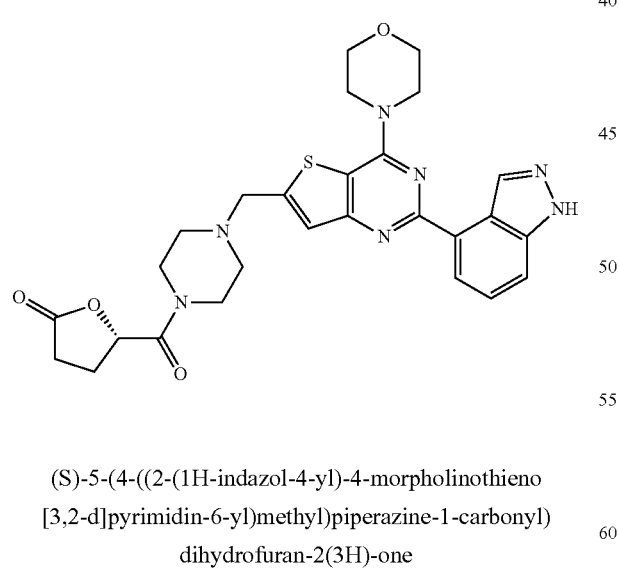

XXII-23

(S)-5-(4-((2-(1H-indazol-4-yl)-4-morpholinothieno[3,2-d]pyrimidin-6-yl)methyl)piperazine-1-carbonyl)dihydrofuran-2(3H)-one In similar fashion, using Intermediate 1e and suitable carboxylic acids, the titled compounds was prepared: MS m/z: 548.1 (M+H$^+$).

Example 101

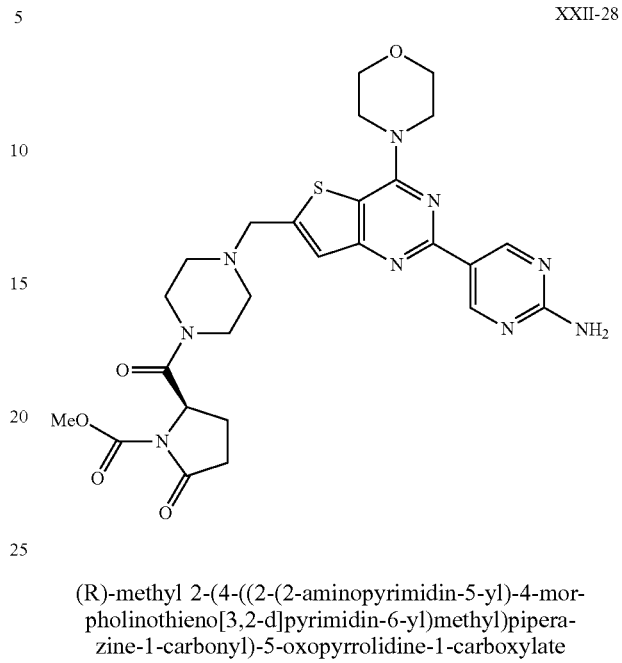

XXII-28

(R)-methyl 2-(4-((2-(2-aminopyrimidin-5-yl)-4-morpholinothieno[3,2-d]pyrimidin-6-yl)methyl)piperazine-1-carbonyl)-5-oxopyrrolidine-1-carboxylate In similar fashion, using Intermediate 1e and suitable carboxylic acids, the titled compounds was prepared: MS m/z: 582.2 (M+H$^+$).

Example 102

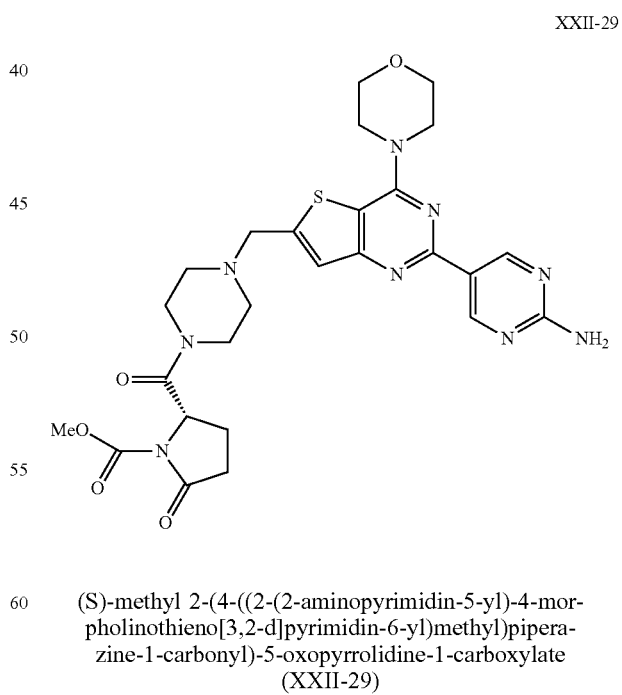

XXII-29

(S)-methyl 2-(4-((2-(2-aminopyrimidin-5-yl)-4-morpholinothieno[3,2-d]pyrimidin-6-yl)methyl)piperazine-1-carbonyl)-5-oxopyrrolidine-1-carboxylate (XXII-29)

In similar fashion, using Intermediate 1e and suitable carboxylic acids, the titled compounds was prepared: MS m/z: 582.2 (M+H$^+$).

Example 103

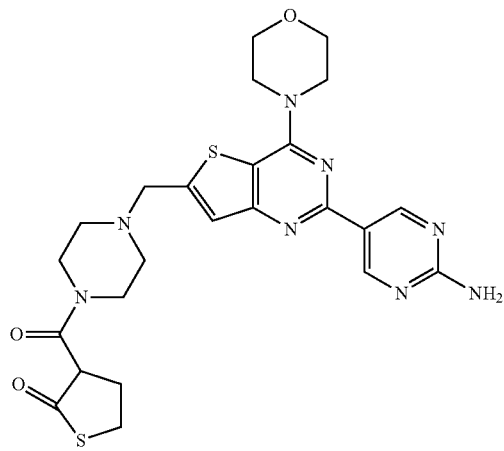

3-(4-((2-(2-aminopyrimidin-5-yl)-4-morpholinothieno[3,2-d]pyrimidin-6-yl)methyl)piperazine-1-carbonyl)dihydrothiophen-2(3H)-one (XXII-30)

In similar fashion, using Intermediate 1e and suitable carboxylic acids, the titled compounds was prepared: MS m/z: 541.1 (M+H⁺).

Example 104

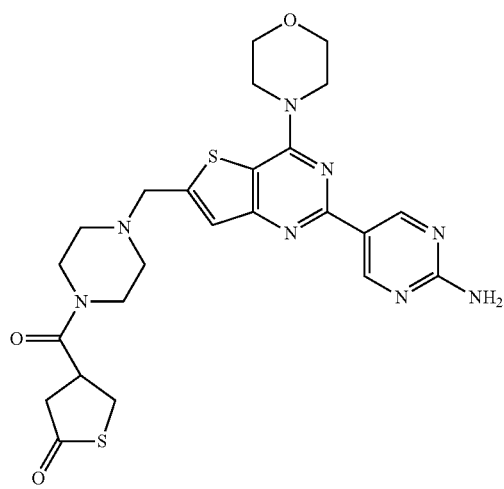

4-(4-((2-(2-aminopyrimidin-5-yl)-4-morpholinothieno[3,2-d]pyrimidin-6-yl)methyl)piperazine-1-carbonyl)dihydrothiophen-2(3H)-one (XXII-31)

In similar fashion, using Intermediate 1e and suitable carboxylic acids, the titled compounds was prepared: MS m/z: 541.1 (M+H⁺).

Example 105

5-(4-((2-(2-aminopyrimidin-5-yl)-4-morpholinothieno[3,2-d]pyrimidin-6-yl)methyl)piperazine-1-carbonyl)dihydrothiophen-2(3H)-one (XXII-32)

In similar fashion, using Intermediate 1e and suitable carboxylic acids, the titled compounds was prepared: MS m/z: 541.1 (M+H⁺).

Example 106

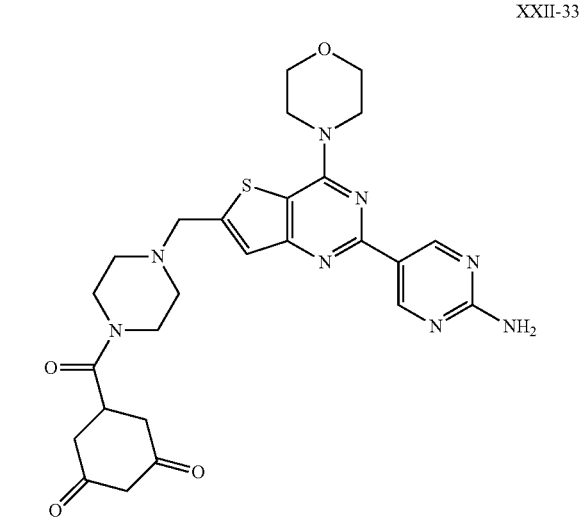 [SMILES: Nc1ncc(-c2nc(N3CCOCC3)c3sc(CN4CCN(C(=O)C5CC(=O)CC(=O)C5)CC4)cc3n2)cn1]

5-(4-((2-(2-aminopyrimidin-5-yl)-4-morpholinothieno[3,2-d]pyrimidin-6-yl)methyl)piperazine-1-carbonyl)cyclohexane-1,3-dione (XXII-33)

In similar fashion, using Intermediate 1e and suitable carboxylic acids, the titled compounds was prepared: MS m/z: 551.2 (M+H⁺).

Example 107

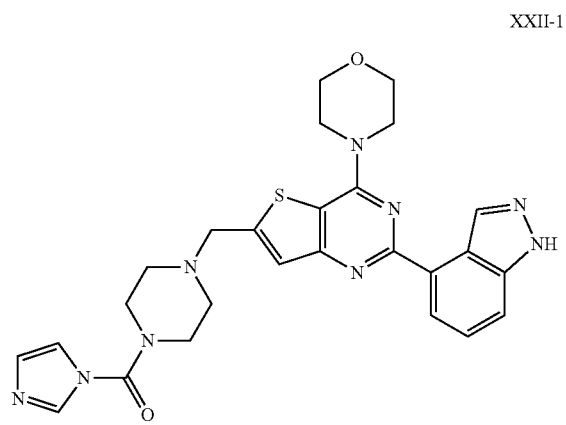

XXII-16

(4-((2-(1H-indazol-4-yl)-4-morpholinothieno[3,2-d]pyrimidin-6-yl)methyl)piperazin-1-yl)(1H-imidazol-1-yl)methanone In similar fashion, using Intermediate 1e and coupling with CDI at the presence of TEA in dichloromethane, (4-((2-(1H-indazol-4-yl)-4-morpholinothieno[3,2-d]pyrimidin-6-yl)methyl)piperazin-1-yl)(1H-imidazol-1-yl)methanone (XXII-16) was prepared: MS m/z: 530.2 (M+H$^+$).

Example 108

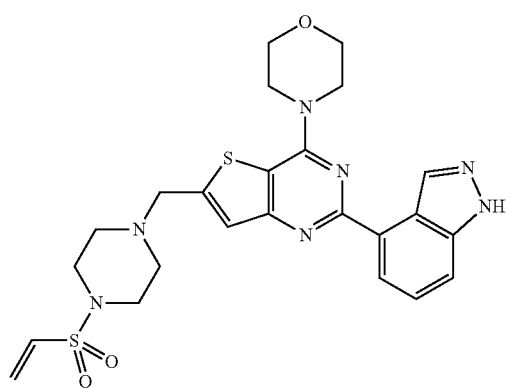

XXII-12

4-(2-(1H-indazol-4-yl)-6-((4-(vinylsulfonyl)piperazin-1-yl)methyl)thieno[3,2-d]pyrimidin-4-yl)morpholine In similar fashion, using Intermediate 1e and coupling with 2-chloroethanesulfonyl chloride in the presence of TEA, 4-(2-(1H-indazol-4-yl)-6-((4-(vinylsulfonyl)piperazin-1-yl)methyl)thieno[3,2-d]pyrimidin-4-yl)morpholine (XXII-8) was prepared: MS m/z: 526.2 (M+H$^+$).

Example 109

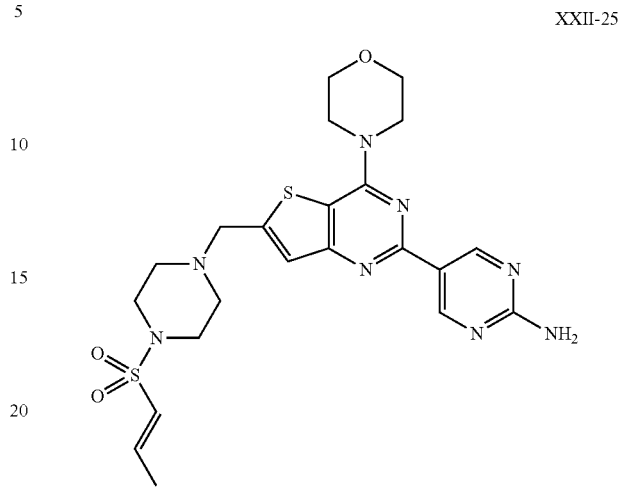

XXII-25

(E)-5-(4-morpholino-6-((4-(prop-1-enylsulfonyl)piperazin-1-yl)methyl)thieno[3,2-d]pyrimidin-2-yl)pyrimidin-2-amine (XXII-25)

In similar fashion, using Intermediate 1e and (E)-prop-1-ene-1-sulfonyl chloride, the titled compounds was prepared: MS m/z: 517.2 (M+H$^+$).

Example 110

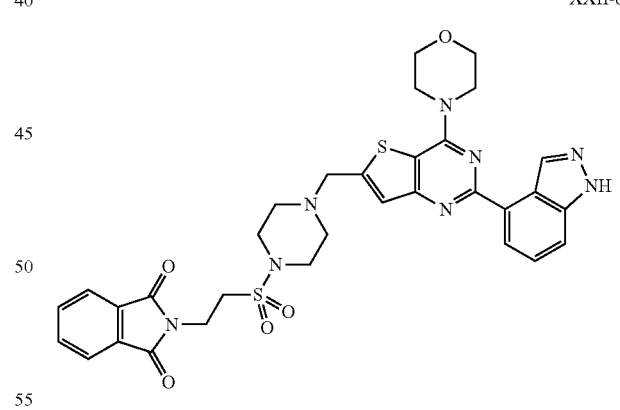

XXII-8

2-(2-(4-((2-(1H-indazol-4-yl)-4-morpholinothieno[3,2-d]pyrimidin-6-yl)methyl)piperazin-1-ylsulfonyl)ethyl)isoindoline-1,3-dione In similar fashion, using Intermediate 1e and coupling with 2-(1,3-dioxoisoindolin-2-yl)ethanesulfonyl chloride in the presence of TEA, the following compound was prepared: MS m/z: 673.2 (M+H$^+$).

Example 111

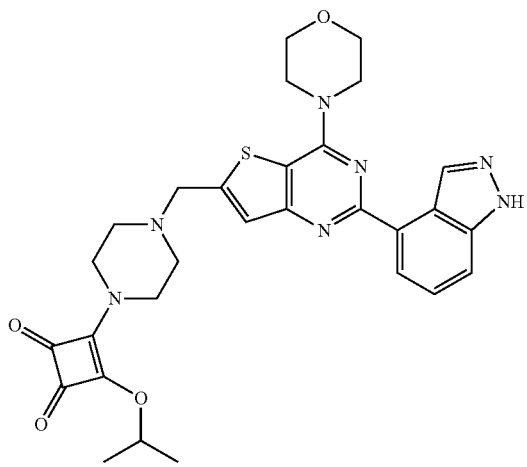

XXII-15

3-(4-((2-(1H-indazol-4-yl)-4-morpholinothieno[3,2-d]pyrimidin-6-yl)methyl)piperazin-1-yl)-4-isopropoxycyclobut-3-ene-1,2-dione In similar fashion, treating Intermediate 1e with 3,4-diisopropoxycyclobut-3-ene-1,2-dione in the presence of TEA in acetonitrile, the following compound was prepared: MS m/z: 574.2 (M+H⁺).

Example 112

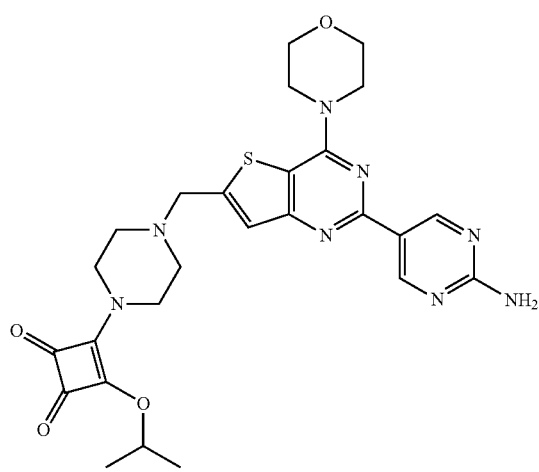

XXII-26

3-(4-((2-(2-aminopyrimidin-5-yl)-4-morpholinothieno[3,2-d]pyrimidin-6-yl)methyl)piperazin-1-yl)-4-isopropoxycyclobut-3-ene-1,2-dione (XXII-26)

In a similar way, the title compound was prepared. MS m/z: 551.2 (M+1).

Example 113

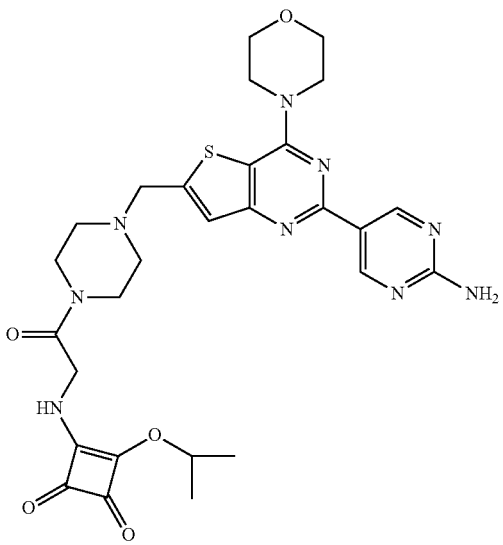

XXII-27

3-(2-(4-((2-(2-aminopyrimidin-5-yl)-4-morpholinothieno[3,2-d]pyrimidin-6-yl)methyl)piperazin-1-yl)-2-oxoethylamino)-4-isopropoxycyclobut-3-ene-1,2-dione (XXII-27)

In a similar way, the title compound was prepared. MS m/z: 608.3 (M+1).

Example 114

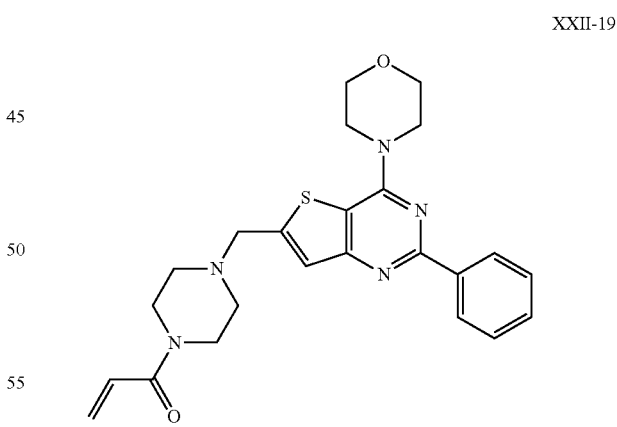

XXII-19

1-(4-((4-morpholino-2-phenylthieno[3,2-d]pyrimidin-6-yl)methyl)piperazin-1-yl)prop-2-en-1-one In similar fashion as described above, when using phenylboronic acid in step 1d instead of 4-(trimethylstannyl)-1H-indazole under a standard Suzuki coupling condition, the following compounds were prepared: MS m/z: 450.2 (M+H⁺).

Example 115
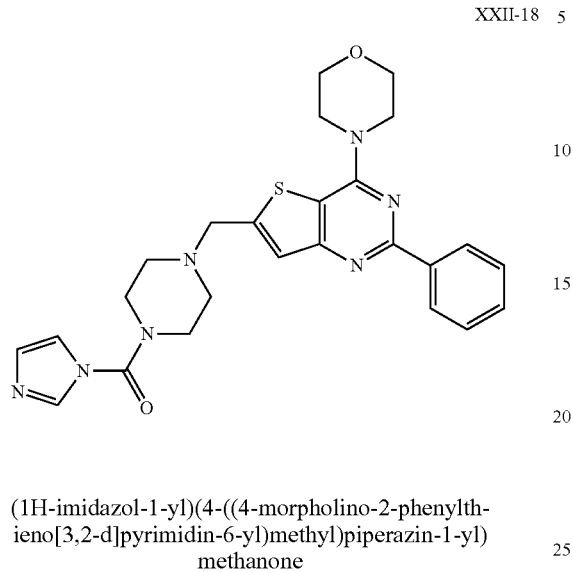
(1H-imidazol-1-yl)(4-((4-morpholino-2-phenylthieno[3,2-d]pyrimidin-6-yl)methyl)piperazin-1-yl)methanone
MS m/z: 490.2 (M+H⁺).
Example 116
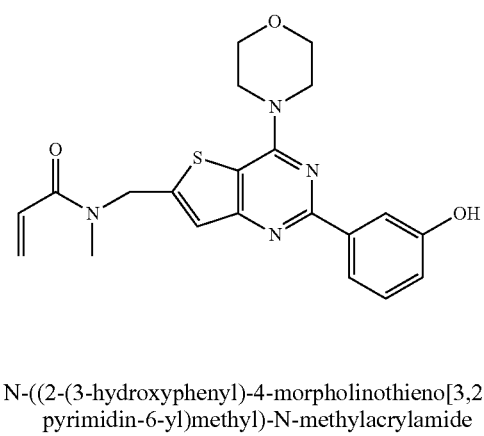
N-((2-(3-hydroxyphenyl)-4-morpholinothieno[3,2-d]pyrimidin-6-yl)methyl)-N-methylacrylamide
The title compound was prepared according to the steps and intermediates as described below.
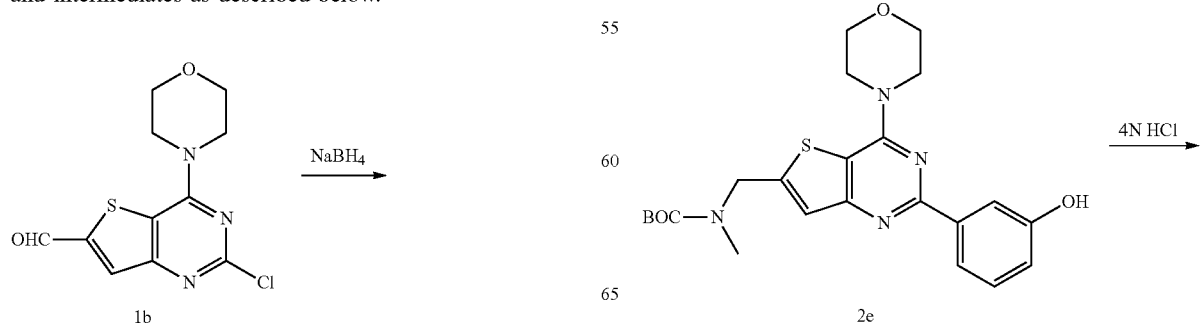

-continued

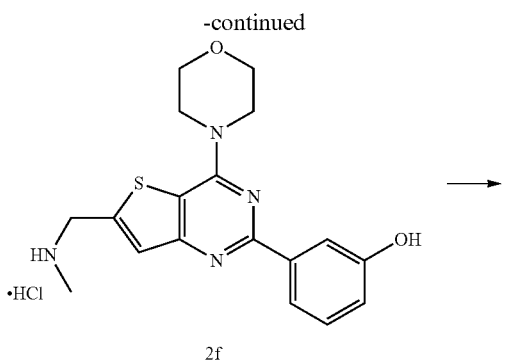

2f

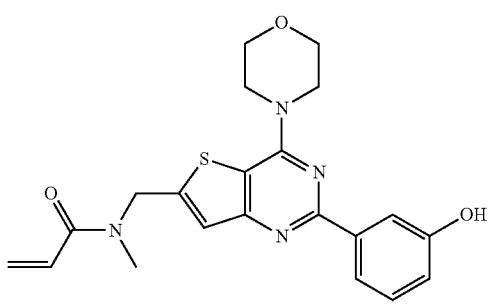

Step 2a: (2-chloro-4-morpholinothieno[3,2-d]pyrimidin-6-yl)methanol (Intermediate 2a)

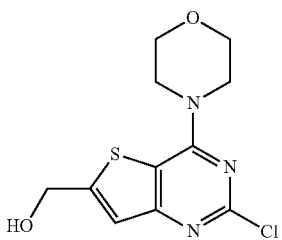 [SMILES: OCc1cc2nc(Cl)nc(N3CCOCC3)c2s1]

To a solution of compound 1b (5 g, 17.6 mmol) in MeOH (50 mL) was added NaBH$_4$ (0.98 g, 26.4 mmol) portion wise at 0° C. and stirred for 5 h at RT. After the completion of reaction (monitored by TLC), the volatiles were removed under reduced pressure, residue dissolved in water and extracted with DCM (3×75 mL). The combined organic phases were washed with water, dried over anhydrous Na$_2$SO$_4$ and concentrated in vacuo to afford intermediate 6a (3 g, 60%) as a light yellow solid. TLC: 80% EtOAc/Hexane (R$_f$: 0.3); $^1$H-NMR (CDCl$_3$, 200 MHz): δ 7.21 (s, 1H), 4.98 (s, 2H), 4.0 (t, J=4.2 Hz, 4H), 3.83 (t, J=4.8 Hz, 4H); Mass: 286 [M$^+$+1]

Step 2b: (2-chloro-4-morpholinothieno[3,2-d]pyrimidin-6-yl)methyl methanesulfonate (Intermediate 2b)

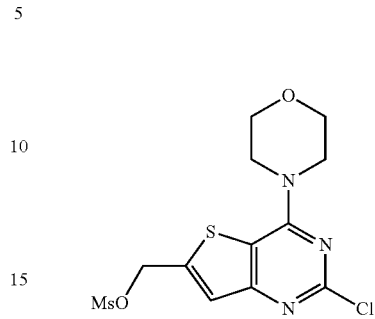

To a solution of Intermediate 2a (1 g, 3.5 mmol) in DCM (10 mL) was added TEA (1.06 g, 10.5 mmol) over a period of 10 minutes and followed by addition of mesyl chloride (0.48 g, 4.2 mmol) at 0° C. The reaction mixture was stirred for 1 h at RT. After the completion of reaction (monitored by TLC), water (25 mL) was added, extracted with DCM (2×50 mL). The combined organic phases were dried over anhydrous Na$_2$SO$_4$ and concentrated in vacuo. The crude compound was purified by silicagel column chromatography (50% EtOAc/hexane) to afford intermediate 2b (0.8 g, 62%) as a yellow solid. TLC: 80% EtOAc/Hexane (R$_f$: 0.6); $^1$H-NMR (CDCl$_3$, 500 MHz) (SAV-A9008-009): δ 7.39 (s, 1H), 5.46 (s, 2H), 4.0 (t, J=4.5 Hz, 4H), 3.84 (t, J=5.0 Hz, 4H), 3.05 (s, 3H); Mass: 364 [M$^+$+1]; Mp: 151.4° C.

Step 2c: 1-(2-chloro-4-morpholinothieno[3,2-d]pyrimidin-6-yl)-N-methylmethanamine (Intermediate 2c)

A solution of Intermediate 2b (0.24 g, 0.67 mmol), 2M methylamine in THF (2.0 mL, 4.0 mmol) and DIEA (0.35 mL, 2.0 mmol) in THF (5 mL) was stirred at RT for 2 hours. LC-MS showed the complete conversion to the product. The solvent was removed in vacuo and the crude was used directly for the next step. MS m/z: 299.1 (M+1).

Step 2d: tert-butyl(2-chloro-4-morpholinothieno[3,2-d]pyrimidin-6-yl)methyl(methyl)carbamate (Intermediate 2d)

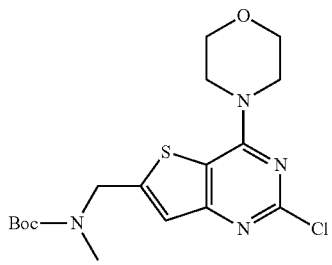 [SMILES: CN(Cc1cc2nc(Cl)nc(N3CCOCC3)c2s1)C(=O)OC(C)(C)C]

The crude Intermediate 2c, Boc₂O (0.22 g, 1.0 mmol), and TEA (0.2 mL) were dissolved in 10 mL dichloromethane and the solution was stirred for 10 hours. LC-MS showed the complete conversion to the product. The solvent was removed in vacuo and the crude was used directly for the next step. MS m/z: 399.1 (M+1).

Step 2e: tert-butyl(2-(3-hydroxyphenyl)-4-morpholinothieno[3,2-d]pyrimidin-6-yl)methyl(methyl)carbamate (Intermediate 2e)

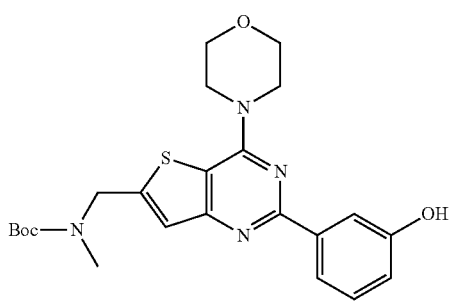 [SMILES: CN(Cc1cc2nc(-c3cccc(O)c3)nc(N3CCOCC3)c2s1)C(=O)OC(C)(C)C]

Intermediate 2d (0.20 g, 0.50 mmol), 3-hydroxyphenylboronic acid (139 mg, 1.0 mmol), Pd(PPh₃)₂Cl₂ (50 mg, 0.067 mmol) and sodium carbonate (0.5 g, 4.1 mmoL) were dissolved in toluene/ethanol/water (5 mL/3 mL/1.5 mL). The solution was degassed and flushed with N₂. The reaction mixture was heated to 120° C. for 3 hours in a sealed vial. The solvent was removed under vacuum and the residue was purified by chromatography on silica gel (eluents: EtOAc/hexane 1:1). A total of 190 mg (66%) of the title compound was obtained. MS m/z: 457.1 (M+1).

Step 2f: 3-(6-((methylamino)methyl)-4-morpholinothieno[3,2-d]pyrimidin-2-yl)phenol (Intermediate 2f)

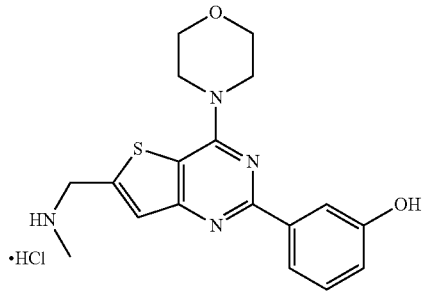 [SMILES: Cl ; CNCc1cc2nc(-c3cccc(O)c3)nc(N3CCOCC3)c2s1]

Intermediate 2e was treated with 4N HCl following the procedure described in Example 102, step 1e to afford the title compound. MS m/z: 357.1 (M+1).

XXII-5

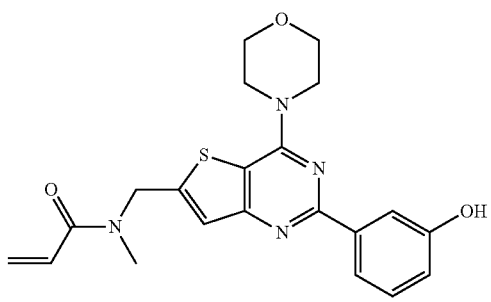

Step 2g: N-((2-(3-hydroxyphenyl)-4-morpholinothieno[3,2-d]pyrimidin-6-yl)methyl)-N-methylacrylamide (XXII-5)

The title compound was prepared by coupling acrylic acid with Intermediate 2f using HATU following the procedure described in Step 1f. MS m/z: 411.1 (M+H⁺).

Example 117

XXII-10

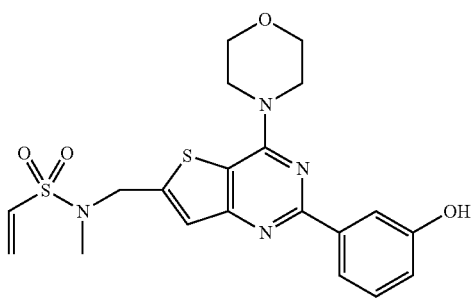

379

N-((2-(3-hydroxyphenyl)-4-morpholinothieno[3,2-d]pyrimidin-6-yl)methyl)-N-methylethenesulfonamide In similar fashion, using Intermediate 2f, the following compounds were prepared: MS m/z: 447.1 (M+1).

Example 118

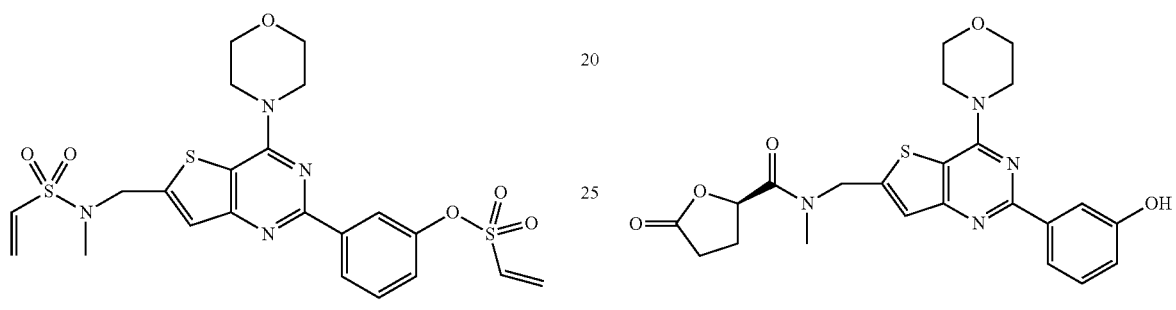

XXII-9

3-(6-((N-methylvinylsulfonamido)methyl)-4-morpholinothieno[3,2-d]pyrimidin-2-yl)phenyl ethenesulfonate MS m/z: 537.2 (M+1).

Example 119

XXII-11

380

3-(((2-(3-hydroxyphenyl)-4-morpholinothieno[3,2-d]pyrimidin-6-yl)methyl)(methyl)amino)-4-isopropoxycyclobut-3-ene-1,2-dione MS m/z: 495.1 (M+1).

Example 120

XXII-7

(R)-N-((2-(3-hydroxyphenyl)-4-morpholinothieno[3,2-d]pyrimidin-6-yl)methyl)-N-methyl-5-oxotetrahydrofuran-2-carboxamide MS m/z: 469.2 (M+1).

Example 121

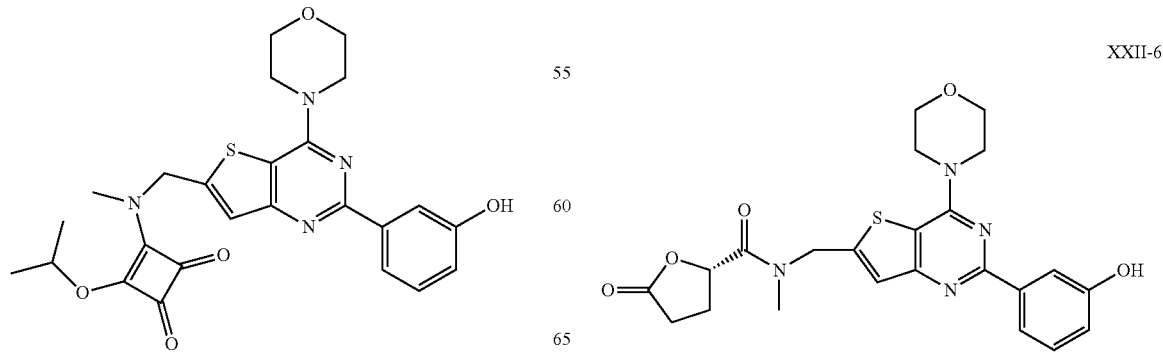

XXII-6

(S)-N-((2-(3-hydroxyphenyl)-4-morpholinothieno[3,2-d]pyrimidin-6-yl)methyl)-N-methyl-5-oxotetrahydrofuran-2-carboxamide MS m/z: 469.2 (M+1).

Example 122

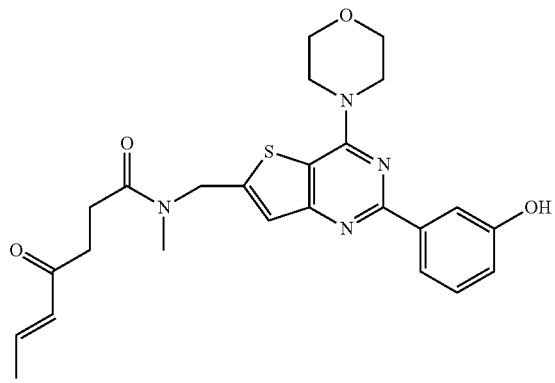

XXII-4

(E)-N-((2-(3-hydroxyphenyl)-4-morpholinothieno[3,2-d]pyrimidin-6-yl)methyl)-N-methyl-4-oxohept-5-enamide MS m/z: 481.2 (M+1).

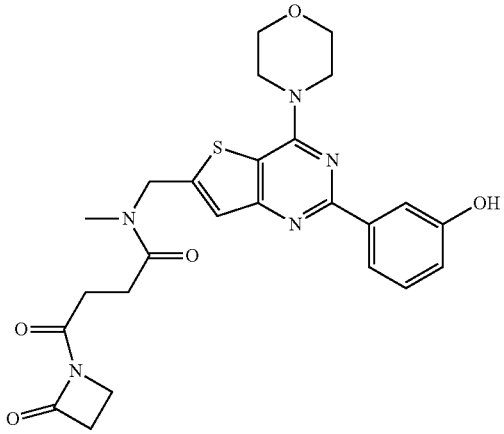

XXII-24

N-((2-(3-hydroxyphenyl)-4-morpholinothieno[3,2-d]pyrimidin-6-yl)methyl)-N-methyl-4-oxo-4-(2-oxoazetidin-1-yl)butanamide (XXII-24)

In similar fashion, using Intermediate 2f, the titled compounds was prepared: MS m/z: 510.2 (M+1).

Example 123

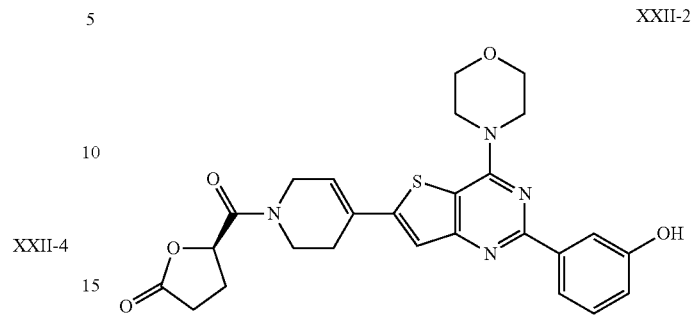

XXII-2

(R)-5-(4-(2-(3-hydroxyphenyl)-4-morpholinothieno[3,2-d]pyrimidin-6-yl)-1,2,3,6-tetrahydropyridine-1-carbonyl)dihydrofuran-2(3H)-one The title compound was prepared according to the steps and intermediates as described below.

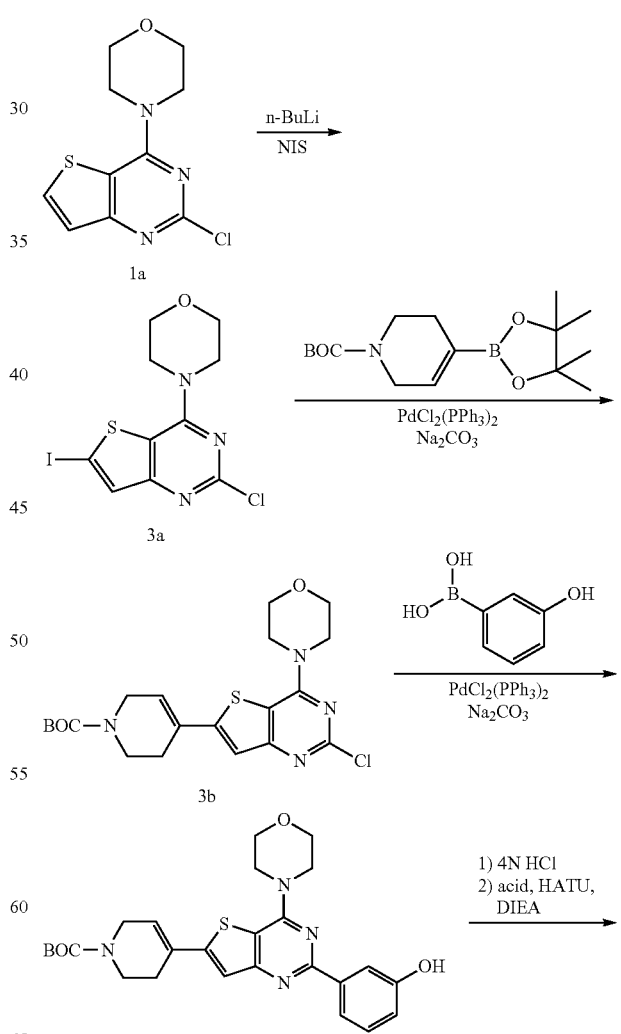

383
-continued

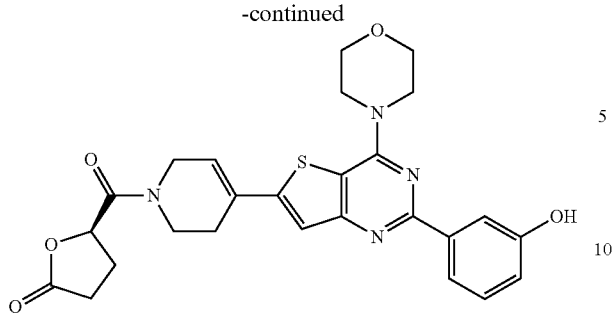

Step 3a: 4-(2-chloro-6-iodothieno[3,2-d]pyrimidin-4-yl)morpholine (Intermediate 3a)

To a stirred solution of Intermediate 1a (5 g, 0.019 mol) in THF (100 mL) was added n-BuLi (2.5 g, 0.03 mol) at −78° C. over a period of 30 minutes, stirred for 2 h at −40° C. followed by addition of iodine (9.9 g, 0.03 mol) in THF (5 mL) at −78° C. The reaction mixture was stirred for 8 h at RT. After the completion of reaction (monitored by TLC), the reaction was quenched with saturated ammonium chloride (100 mL) and extracted with EtOAc (4×200 mL). The organic layer was washed with sodium thiosulphate solution, dried over anhydrous $Na_2SO_4$ and concentrated in vacuo. The crude product was washed with diethyl ether to afford intermediate 3a (7 g, 94%) as off white solid. TLC: 30% Ethyl acetate/hexane ($R_f$: 0.3); $^1$H-NMR (CDCl$_3$, 500 MHz): δ 7.57 (s, 1H), 3.94-3.91 (m, 4H), 3.85-3.80 (m, 4H); Mass: 382 [M$^+$+1], MP: 173.5° C.

Step 3b: tert-butyl 4-(2-chloro-4-morpholinothieno[3,2-d]pyrimidin-6-yl)-5,6-dihydropyridine-1(2H)-carboxylate (Intermediate 3b)

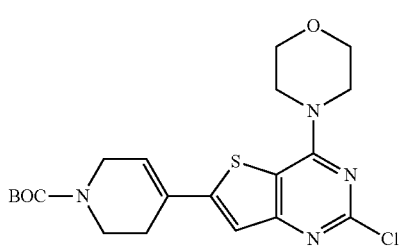

To a stirred solution of 4-(2-chloro-6-iodothieno[3,2-d]pyrimidin-4-yl)morpholine (Intermediate 3a) (0.57 g, 1.5 mmol) in toluene (10 mL), EtOH (6.0 mL), H$_2$O (3.0 mL) was added tert-butyl 4-(4,4,5,5-tetramethyl-1,3,2-dioxaborolan-2-yl)-5, 6-dihydropyridine-1(2H)-carboxylate (0.5 g, 1.6 mmol), Na$_2$CO$_3$ (0.7 g) and Pd(PPh$_3$)$_2$Cl$_2$ (56 mg, 0.08 mmol) at RT. The reaction mixture was degassed with argon and stirred at 40° C. for 3 h. LC-MS showed the completion of the conversion: MS m/z: 437.1 (M+1). The reaction mixture was used directly for the next step.

384
Step 3c: tert-butyl 4-(2-(3-hydroxyphenyl)-4-morpholinothieno[3,2-d]pyrimidin-6-yl)-5,6-dihydropyridine-1(2H)-carboxylate (Intermediate 3c)

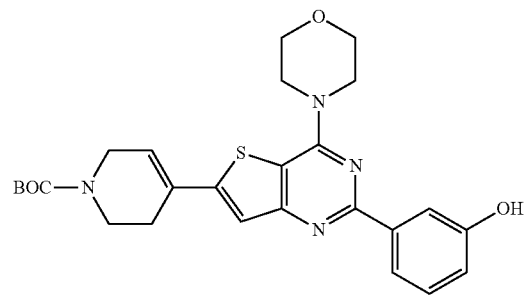

To the reaction mixture from step 3b was added 3-hydroxyphenylboronic acid (0.35 g, 2.5 mmol), Na$_2$CO$_3$ (1.0 g) and Pd(PPh$_3$)$_2$Cl$_2$ (30 mg, 0.04 mmol) at RT. The reaction mixture was degassed with argon and stirred at 130° C. for 3 h. The reaction was then worked up by adding ethyl acetate 50 mL and washed with water and brine. The organic layer was separated and was dried over Na$_2$SO$_4$. After removal of solvent, the crude product was subjected to chromatography on silica gel (eluents: EtOAc/hexane 1:1 to 4:1) to give the title compound. MS m/z: 495.1 (M+1).

XXII-2

Step 3d: (R)-5-(4-(2-(3-hydroxyphenyl)-4-morpholinothieno[3,2-d]pyrimidin-6-yl)-1,2,3,6-tetrahydropyridine-1-carbonyl)dihydrofuran-2(3H)-one The title compound was prepared by following the de-boc and the coupling procedures described in example 1. MS m/z: 507.1 (M+H$^+$).

Example 124

XXII-1

In similar fashion, (S)-5-(4-(2-(3-hydroxyphenyl)-4-morpholinothieno[3,2-d]pyrimidin-6-yl)-1,2,3,6-tetrahydropyridine-1-carbonyl)dihydrofuran-2(3H)-one, was prepared: MS m/z: 507.1 (M+H$^+$)

Example 125

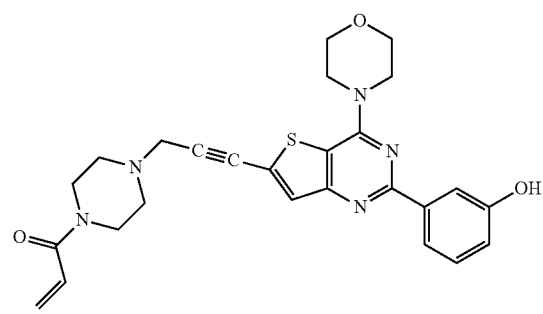

1-(4-(3-(2-(3-hydroxyphenyl)-4-morpholinothieno[3,2-d]pyrimidin-6-yl)prop-2-ynyl)piperazin-1-yl)prop-2-en-1-one The title compound was prepared according to the steps and intermediates as described below.

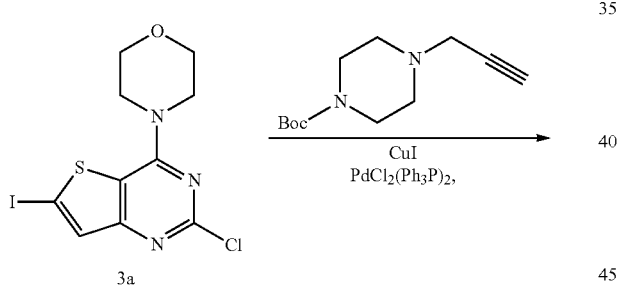

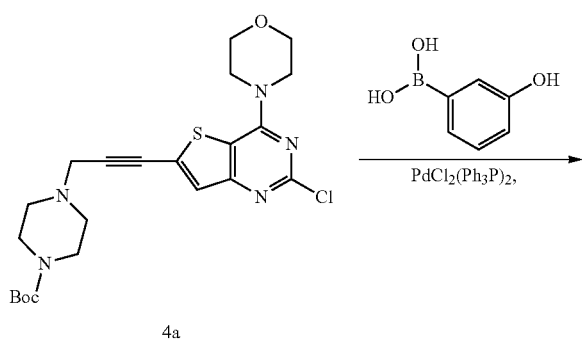

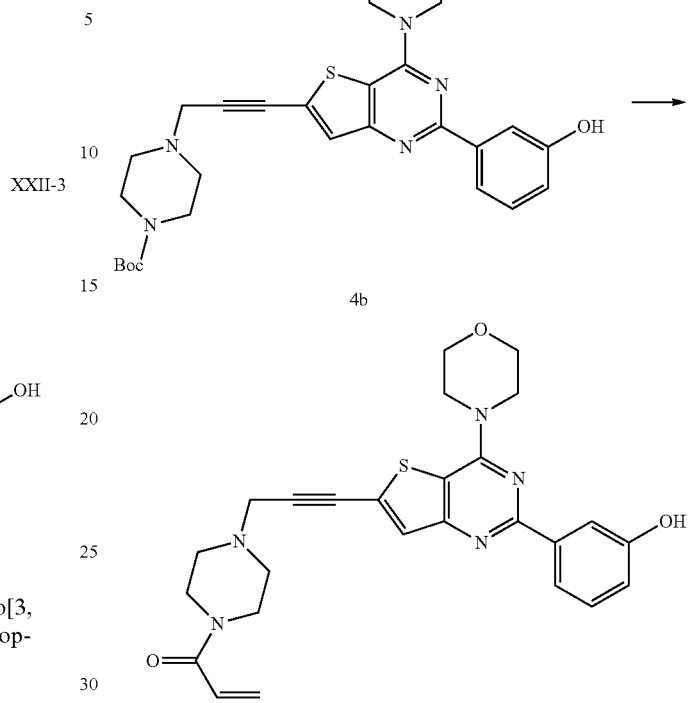

Step 4a: tert-butyl 4-(3-(2-chloro-4-morpholinothieno[3,2-d]pyrimidin-6-yl)prop-2-ynyl)piperazine-1-carboxylate (Intermediate 4a)

To a stirred solution of Intermediate 3a (1.0 g, 2.6 mmol), tert-butyl 4-(prop-2-ynyl)piperazine-1-carboxylate (880 mg, 3.8 mmol) in THF (40 mL) were added TEA (16 mL) followed by Pd(PPh$_3$)$_2$Cl$_2$ (184 mg, 0.26 mmol) at RT, degassed with argon for 30 minutes and CuI (496 mg, 2.6 mmol) was added to the reaction mixture. The reaction mixture was again degassed with argon for 30 minutes. The resulting reaction mixture was refluxed for 3h. After the completion of reaction (monitored by TLC), the reaction mixture was diluted with DCM. The organic layer was washed with water and dried over anhydrous Na$_2$SO$_4$ and concentrated under reduced pressure. The crude material was purified by silica gel column chromatography (20% EtOAc/Hexane) to afford intermediate 4a (0.60 g). Mass: 478 [M$^+$+1].

Step 4b: tert-butyl 4-(3-(2-(3-hydroxyphenyl)-4-morpholinothieno[3,2-d]pyrimidin-6-yl)prop-2-ynyl)piperazine-1-carboxylate (Intermediate 4b)

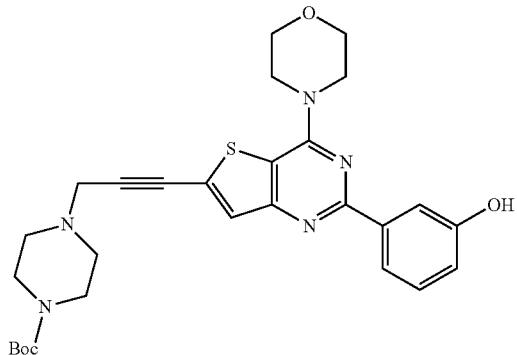 [SMILES: CC(C)(C)OC(=O)N1CCN(CC#Cc2cc3nc(-c4cccc(O)c4)nc(N4CCOCC4)c3s2)CC1]

The title compound was prepared by coupling intermediate 4a and 3-hydroxyphenylboronic acid following the procedures described in step 3c of Example 123. MS m/z: 536.2 (M+H$^+$).

Step 4c: 1-(4-(3-(2-(3-hydroxyphenyl)-4-morpholinothieno[3,2-d]pyrimidin-6-yl)prop-2-ynyl)piperazin-1-yl)prop-2-en-1-one The title compound was prepared by following the procedures described in Example 96, step 1e and 1f. MS m/z: 490.1 (M+H$^+$).

Example 126

XXII-22

(R)-5-(4-(3-(2-(3-hydroxyphenyl)-4-morpholinothieno[3,2-d]pyrimidin-6-yl)prop-2-ynyl)piperazine-1-carbonyl)dihydrofuran-2(3H)-one In similar fashion, starting from intermediate 4b, using a suitable carboxylic acid, the following compounds are made.

Example 127

XXII-23

(S)-5-(4-(3-(2-(3-hydroxyphenyl)-4-morpholinothieno[3,2-d]pyrimidin-6-yl)prop-2-ynyl)piperazine-1-carbonyl)dihydrofuran-2(3H)-one In similar fashion, starting from intermediate 4b, using a suitable carboxylic acid, the following compounds are made.

Example 128

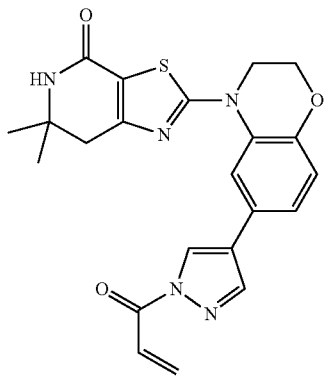

2-(6-(1-acryloyl-1H-pyrazol-4-yl)-2H-benzo[b][1,4]oxazin-4(3H)-yl)-6,6-dimethyl-6,7-dihydrothiazolo[5,4-c]pyridin-4(5H)-one The title compound was prepared according to the steps and intermediates as described below.

Synthesis of Intermediate 5-I

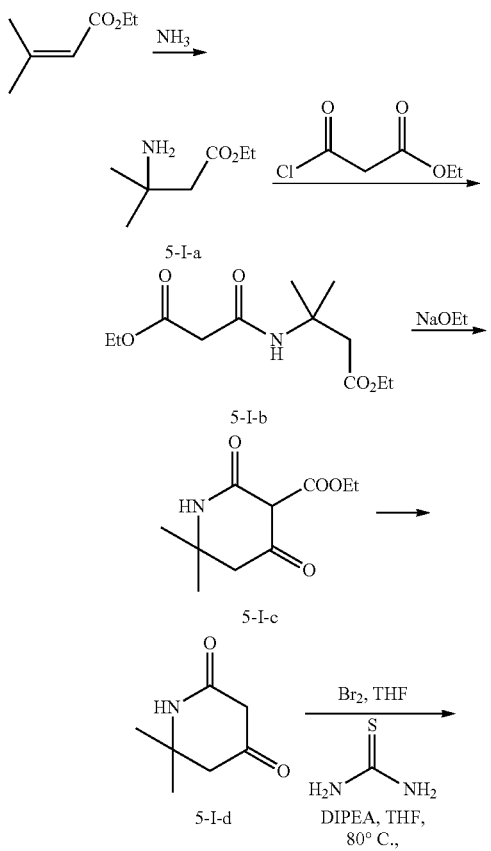

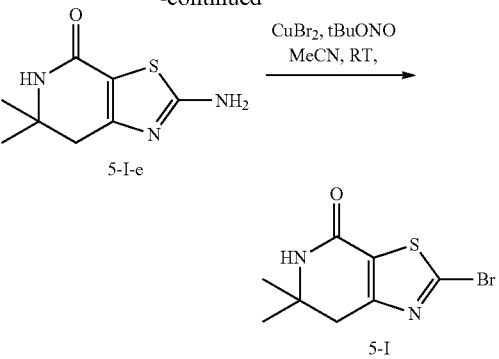

Step 5-I-a: Ethyl 3-amino-3-methylbutanoate hydrochloride salt (5-I-a)

To a solution of ethyl 3-methylbut-2-enoate (15 g, 117 mmol) in EtOH (40 mL) was added liquid ammonia (80 mL) at −70° C. and the reaction mixture stirred in a autoclave (200 Psi) at 45° C. for 16 h. After completion of the reaction (monitored by TLC), excess ammonia was removed by flashing $N_2$, cooled to 0° C. and HCl in dioxane (pH-2) was added. The reaction mixture was stirred for 30 minutes at 0° C., the volatiles were removed under reduced pressure and the obtained solid was washed with diethyl ether to afford 5-I-a-HCl salt (10 g, 58.8%) as white solid; TLC: 10% MeOH/DCM ($R_f$: 0.1); $^1$H-NMR (DMSO $d_6$, 200 MHz): δ 8.33 (bs, 1H), 4.09 (q, J=7.0 Hz, 2H), 2.70 (s, 2H), 1.33 (s, 6H), 1.20 (t, J=7.0 Hz, 3H); Mass: 146 [M$^+$+1].

Step 5-I-b: Ethyl 3-(ethyl 2-carbamoylacetyl)-3-methylbutanoate (5-I-b)

To a solution of compound 5-I-a (11 g, 68.9 mmol) in DCM (150 mL) was added TEA (38.1 mL, 275 mmol) and ethyl malonoyl chloride (8.8 mL, 68.9 mmol) at 0° C. The reaction mixture was stirred at RT for 3 h. After completion of the reaction (monitored by TLC), the reaction was quenched water and extracted with DCM (2×200 mL). The combined organic layer was washed with 1N HCl (100 mL), saturated NaHCO$_3$ (100 mL), dried over anhydrous Na$_2$SO$_4$ and concentrated in vacuo to afford 5-I-b (11 g, 62%) as brown syrup. TLC: 30% EtOAc/Hexane ($R_f$: 0.3); $^1$H-NMR (CDCl$_3$, 200 MHz): δ 4.28-4.07 (m, 4H), 3.24 (s, 2H), 2.74 (s, 2H), 1.45 (s, 6H), 1.35-1.20 (m, 6H); Mass: 260 [M$^+$+1].

Steps 5-I-c and 5-I-d: 6,6-Dimethylpiperidine-2,4-dione (5-I-d)

To a stirred solution of compound 5-I-b (11 g, 42.6 mmol) in toluene (120 mL) was added NaOEt (4.34 g, 63.9 mmol) in toluene (30 mL) and the reaction mixture was stirred at 80° C. for 4 h. After completion of the reaction (monitored by TLC), the reaction was quenched water, and the aqueous layer was extracted with diethyl ether (100 mL). The organic layer was separated; aqueous layer was acidified with 1N HCl and extracted with DCM (2×200 mL). The combined organic layer was dried over Na$_2$SO$_4$ and concentrated in vacuo. The obtained crude 5-I-c was dissolved in 1% H$_2$O/ACN (80 mL) and refluxed for 3 h. After completion of the reaction (monitored by TLC), the volatiles were removed under reduced pressure and the obtained residue was washed with diethyl ether to afford 5-I-d (3.2 g, 53.3%) as off white solid. TLC: 10% MeOH/DCM ($R_f$: 0.3); $^1$H-NMR (CDCl$_3$+ DMSO-d$_6$, 200 MHz): δ 7.28 (bs, NH), 3.21 (s, 2H), 2.56 (s, 2H), 1.34 (s, 6H); Mass: 142 [M$^+$+1].

Step 5-I-e: 2-Amino-6,7-dihydro-6,6-dimethylthiazolo[5,4-c]pyridin-4(5H)-one (5-I-e)

To a stirred solution of compound 5-I-d (3.2 g, 22.7 mmol) in THF (100 mL) was added Br$_2$ (1.13 mL, 22.7 mmol) and the reaction mixture was stirred for 10 minutes at RT followed by addition of thiourea (1.72 g, 22.7 mmol) and DIPEA (12 mL, 68.0 mmol). The reaction mixture was stirred at 80° C. for 2 h. After completion of the reaction (monitored by TLC), the reaction was quenched water and extracted with EtOAc (2×150 mL). The combined organic layer was dried over Na$_2$SO$_4$, concentrated in vacuo and the crude residue was washed with diethyl ether to afford 5-I-e (2.5 g, 56%) as yellow solid. TLC: 10% MeOH/DCM ($R_f$: 0.2); $^1$H-NMR (DMSO d$_6$, 200 MHz): δ 7.63 (bs, 2H), 7.17 (bs, 1H), 2.61 (s, 2H), 1.22 (s, 6H); Mass: 198 [M$^+$+1].

Intermediate 5-I: 2-bromo-6,7-dihydro-6,6-dimethylthiazolo[5,4-c]pyridin-4(5H)-one To a solution of compound 5-I-e (2.5 g, 12.7 mmol) in acetonitrile (70 mL) was added CuBr$_2$ (2.26 g, 10.15 mmol) and tert-butyl nitrite (1.3 g, 12.8 mmol) at RT. The reaction mixture was stirred for 2 h at RT. After completion of reaction (monitored by TLC), the reaction was quenched with 1N HCl and extracted with DCM (2×150 mL). The combined organic layer was dried over Na$_2$SO$_4$, concentrated in vacuo and the crude residue was washed with diethyl ether to afford 5-I (2 g, 60%) as brown solid; TLC: 10% MeOH/DCM ($R_f$: 0.5); $^1$H-NMR (CDCl$_3$, 500 MHz): δ 5.48 (bs, NH), 3.02 (s, 2H), 1.4 (s, 6H); Mass: 283 [M$^+$+Na].

Synthesis of Intermediate 5-II

4-Bromo-1-(1-ethoxyethyl)-1H-pyrazole (5-II-a)

To a solution of 4-bromo-1H-pyrazole (3 g, 20.4 mmol), ethyl vinyl ether (1.76 g, 24.5 mmol) in DCM (30 mL) was added HCl (4M in dioxane, 0.16 mL), and the reaction mixture was stirred for 3 h at RT. After completion of the reaction (monitored by TLC), the reaction was neutralized with saturated NaHCO$_3$ solution and extracted with DCM (3×100 mL). The combined organic layers were dried over anhydrous Na$_2$SO$_4$ and concentrated in vacuo to afford 5-II-a (4.46 g, 89%) as colorless liquid; TLC: 30% EtOAc/Hexane ($R_f$: 0.7); $^1$H-NMR (CDCl$_3$, 200 MHz): δ 7.60 (s, 1H), 7.46 (s, 1H), 5.46 (q, J=6.0 Hz, 1H), 3.55-3.25 (m, 2H), 1.63 (d, J=6.0 Hz, 3H), 1.15 (t, J=7.2 Hz, 3H); MS: 221 [M$^+$+2].

1-(1-ethoxyethyl)-4-(4,4,5,5-tetramethyl-1,3,2-dioxaborolan-2-yl)-1H-pyrazole (5-II)

To a solution of compound 5-II-a (600 mg, 2.73 mmol) in dioxane (15 mL) was added KOAc (800 mg, 8.2 mmol), bis(pinacolato)diboran (1.39 g, 5.4 mmol) and Pd(dppf)Cl$_2$ (0.06 g, 0.08 mmol) at RT. The reaction mixture was degassed by purging with argon for 30 minutes and stirred at 50° C. for 16 h. After completion of the reaction (monitored by TLC), the reaction was quenched with H$_2$O and extracted with EtOAc (3×100 mL). The combined organic layers were dried over anhydrous Na$_2$SO$_4$ and concentrated in vacuo. The crude compound was purified by column chromatography (15% EtOAc/Hexane) to afford 5II (500 mg, 68.5%) as off white solid. TLC: 30% EtOAc/Hexane ($R_f$: 0.4); $^1$H-NMR (CDCl$_3$, 200 MHz): δ 7.90 (s, 1H), 7.79 (s, 1H), 5.56 (q, J=6.0 Hz, 1H), 3.55-3.25 (m, 2H), 1.63 (d, J=6.0 Hz, 3H), 1.35 (s, 12H), 1.15 (t, J=7.2 Hz, 3H); Mass: 267 [M$^+$+1].

Synthesis of XXIII-5

2-(6-(1-acryloyl-1H-pyrazol-4-yl)-2H-benzo[b][1,4]oxazin-4(3H)-yl)-6,6-dimethyl-6,7-dihydrothiazolo[5,4-c]pyridin-4(5H)-one The title compound was prepared according to the steps and intermediates as described below:

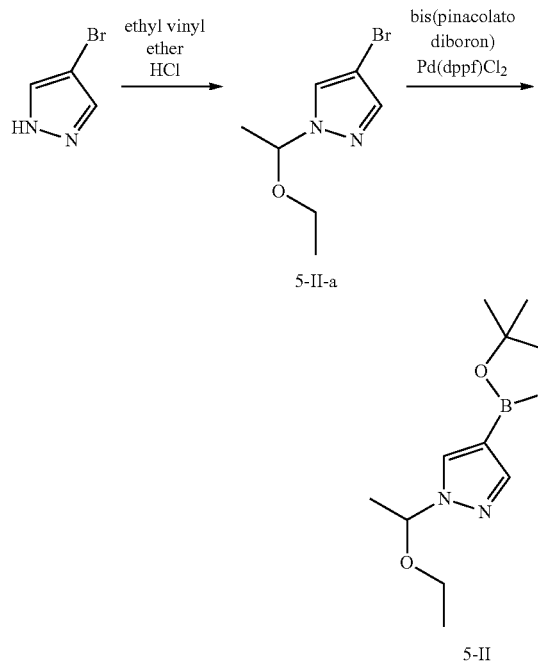

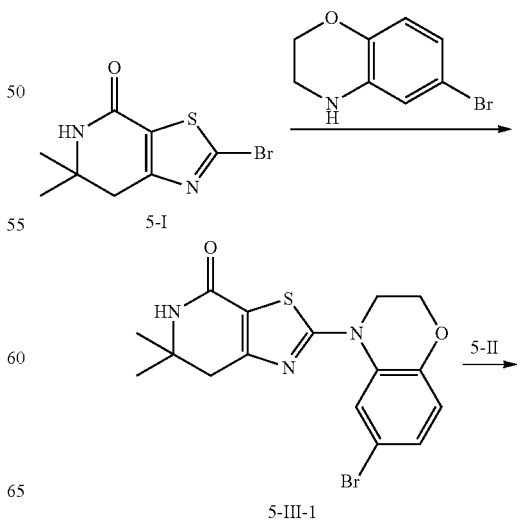

-continued

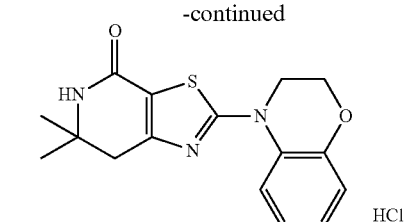

5-III-2

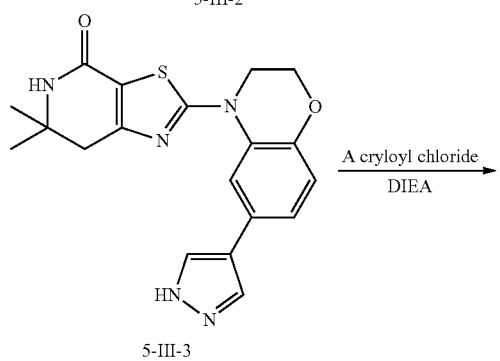

5-III-3

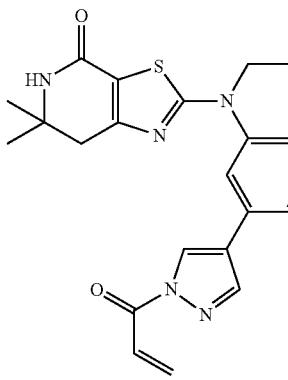

2-(6-bromo-2,3-dihydrobenzo[b][1,4]oxazin-4-yl)-6,7-dihydro-6,6-dimethylthiazolo[5,4-c]pyridin-4(5H)-one To a solution of compound 5-I (2.7 g, 10.3 mmol) in acetonitrile (100 mL) were added Cs$_2$CO$_3$ (6.71 g, 20.6 mmol), Xanthophos (476 mg, 0.82 mmol) and Pd(OAc)$_2$ (139 mg, 0.61 mmol) at room temperature. The reaction mixture was degassed by purging with argon and 6-bromo-3,4-dihydro-2H-benzo[b][1,4]oxazine (2.31 g, 10.3 mmol) in acetonitrile was added. The reaction mixture was degassed for 45 minutes at RT and at 85° C. for 16 h. After completion of the reaction (monitored by TLC), the reaction mixture was filtered through a pad of celite, washed with 5% MeOH/DCM and the filtrate was concentrated in vacuo. The crude compound was purified by washing with diethyl ether to afford compound 5-III-1 (3.24 g, 80%) as brown solid.

TLC: EtOAc (R$_f$: 0.4); $^1$H-NMR (CDCl$_3$, 200 MHz): δ 8.24 (d, J=2.2 Hz, 1H), 7.14 (dd, J=2.4, 8.8 Hz, 1H), 6.83 (d, J=9.0 Hz, 1H), 5.29 (bs, NH), 4.38-4.30 (m, 2H), 4.10-4.02 (m, 2H), 2.90 (s, 2H), 1.40 (s, 6H); Mass: 394.5 [M$^+$+1]; MP: 154.7° C.

2-(6-(1-(1-ethoxyethyl)-1H-pyrazol-4-yl)-2H-benzo[b][1,4]oxazin-4(3H)-yl)-6,6-dimethyl-6,7-dihydrothiazolo[5,4-c]pyridin-4(5H)-one (5-III-2)

To a solution of compound 5-III-1 (2.0 g, 5.0 mmol) in THF (70 mL) were added boronate ester 5-II (3.37 g, 12.7 mmol), Na$_2$CO$_3$ (1.6 g, 15.2 mmol), TBAB (653 mg, 20.3 mmol) and Pd(PPh$_3$)$_4$ (470 mg, 0.4 mmol) at room temperature. The reaction mixture was degassed by purging with argon for 45 minutes and stirred at 100° C. for 36 h. After completion of the reaction (monitored by TLC), the volatiles were removed under reduced pressure and water was added. The aqueous layer was extracted with DCM (3×100 mL), the combined organic layers was dried over anhydrous Na$_2$SO$_4$ and concentrated in vacuo. The crude compound was purified by column chromatography (3% MeOH/DCM) to afford 5-III-2 (850 mg, 37%) as brown solid. TLC: 5% MeOH/DCM (R$_f$: 0.4); $^1$H-NMR (CDCl$_3$, 200 MHz): δ 8.03 (s, 1H), 7.75 (d, J=8.4 Hz, 2H), 7.20 (d, J=2.4, 8.4 Hz, 1H), 6.95 (d, J=8.4 Hz, 1H), 5.55 (q, J=6.0 Hz, 1H), 5.26 (bs, 1H), 4.40-4.30 (m, 2H), 4.25-4.15 (m, 2H), 3.55-3.35 (m, 2H), 2.90 (s, 2H), 1.73 (d, J=6.0 Hz, 3H), 1.43 (s, 6H), 1.15 (t, J=7.2 Hz, 3H); Mass: 476 [M$^+$+Na] and 382 [M-71].

2-(6-(1H-pyrazol-4-yl)-2H-benzo[b][1,4]oxazin-4(3H)-yl)-6,6-dimethyl-6,7-dihydrothiazolo[5,4-c]pyridin-4(5H)-one (5-III-3)

To a solution of compound 5-III-2 (0.85 g, 1.87 mmol) in DCM (10 mL) was added HCl/dioxane (2 mL) at 0° C. and the reaction mixture was stirred for 2 h at RT. After completion of the reaction (monitored by TLC), the volatiles were removed under reduced pressure and the residue was washed with diisopropyl ether followed by 20% EtOAc/hexane to afford 5-III-3 (600 mg, 84%) as off white solid. TLC: 10% MeOH/DCM (R$_f$: 0.3); $^1$H-NMR (DMSO d$_6$, 200 MHz): δ 8.28 (d, J=8.4 Hz, 1H), 7.98 (s, 1H), 7.53 (s, 1H), 7.3 (dd, J=2.2, 8.4 Hz, 1H), 6.94 (d, J=8.4 Hz, 1H), 4.35-4.25 (m, 2H), 4.14-4.05 (m, 2H), 2.83 (s, 2H), 1.28 (s, 6H). Mass: 382 [M$^+$+1].

2-(6-(1-acryloyl-1H-pyrazol-4-yl)-2H-benzo[b][1,4]oxazin-4(3H)-yl)-6,6-dimethyl-6,7-dihydrothiazolo[5,4-c]pyridin-4(5H)-one (XXIII-5)

To a stirred solution of the above compound 5-III-3 (0.01 g, 0.024 mmol) in DCM (1.0 mL) was added TEA (0.008 g, 0.08 mmol) followed by acryloyl chloride (0.0025 g, 0.029 mmol) at RT. The reaction mixture was stirred for 0.5 h. The solvent was removed in vacuo. The crude compound was purified by prep. HPLC (25% to 90% CH3CN aqueous containing 0.1% TFA) to give 7.0 mg of the title compound. MS m/z: 436.0 (M+1).

Example 129

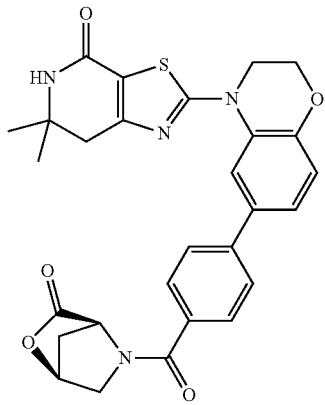

(1S,4S)-5-(4-(4-(6,6-dimethyl-4-oxo-4,5,6,7-tetrahydrothiazolo[5,4-c]pyridin-2-yl)-3,4-dihydro-2H-benzo[b][1,4]oxazin-6-yl)benzoyl)-2-oxa-5-azabicyclo[2.2.1]heptan-3-one The title compound was prepared according to the steps and intermediates as described below.

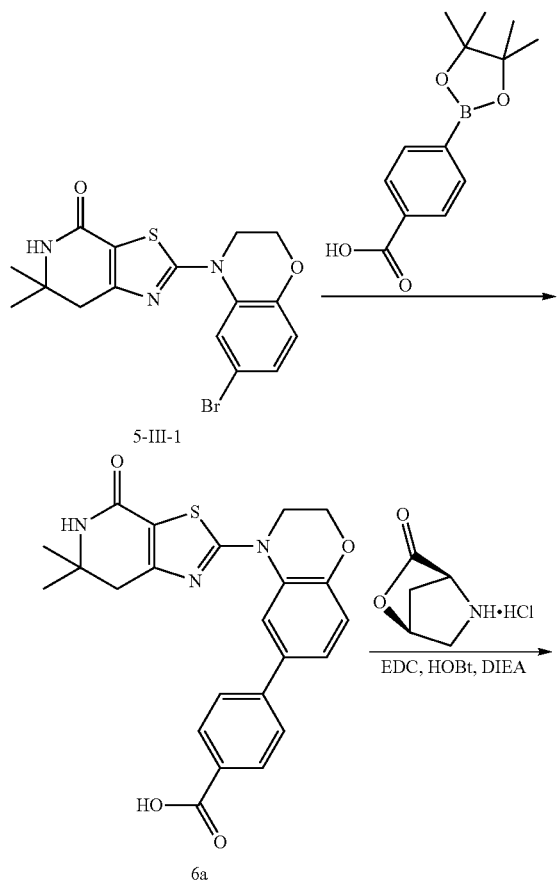

Step 6a: 4-(4-(6,6-dimethyl-4-oxo-4,5,6,7-tetrahydrothiazolo[5,4-c]pyridin-2-yl)-3,4-dihydro-2H-benzo[b][1,4]oxazin-6-yl)benzoic acid

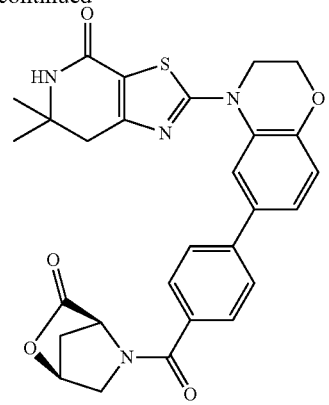

2-(6-bromo-2H-benzo[b][1,4]oxazin-4(3H)-yl)-6,6-dimethyl-6,7-dihydrothiazolo[5,4-c]pyridin-4(5H)-one (compound 5-III-1) and 4-(4,4,5,5-tetramethyl-1,3,2-dioxaborolan-2-yl)benzoic acid were coupled following the Suzuki coupling procedure described in step 3c to afford the title compound (30 mg). MS m/z: 436.2 (M+1).

Step 6b: (1S,4S)-5-(4-(4-(6,6-dimethyl-4-oxo-4,5,6,7-tetrahydrothiazolo[5,4-c]pyridin-2-yl)-3,4-dihydro-2H-benzo[b][1,4]oxazin-6-yl)benzoyl)-2-oxa-5-azabicyclo[2.2.1]heptan-3-one (XXIII-8)

To a solution of intermediate 6a (22 mg, 0.05 mmol) and (1S,4S)-2-oxa-5-azabicyclo[2.2.1]heptan-3-one HCl salt (10 mg, 0.06 mmol) in 2 mL dichloromethane was added EDCI.HCl (15 mg, 0.08 mmol), HOBT (11 mg, 0.08 mmol) and DIEA (0.05 mL). The reaction mixture was stirred at RT for 1 hour. After removal of solvent, the crude product was subject to prep. HPLC (40% to 90% $CH_3CN$ aqueous containing 0.1% TFA) to give 15 mg of the title compound. MS m/z: 531.2 (M+1).

Example 130

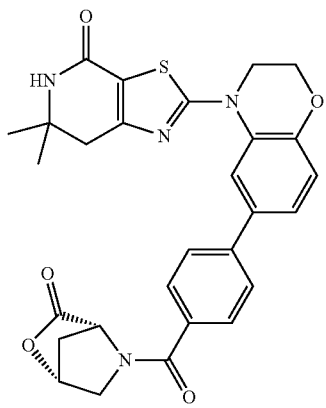

(1R,4R)-5-(4-(4-(6,6-dimethyl-4-oxo-4,5,6,7-tetra-hydrothiazolo[5,4-c]pyridin-2-yl)-3,4-dihydro-2H-benzo[b][1,4]oxazin-6-yl)benzoyl)-2-oxa-5-azabicyclo[2.2.1]heptan-3-one In similar fashion, when using (1R,4R)-2-oxa-5-azabicyclo[2.2.1]heptan-3-one HCl salt in step 6b, the following compound was prepared: MS m/z: 531.2 (M+1).

Example 131

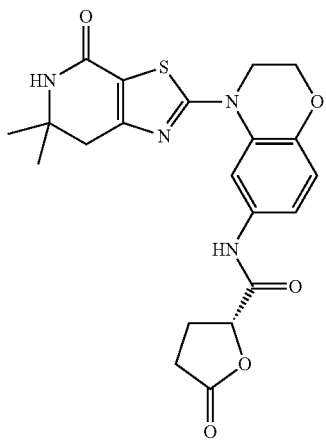

(R)-N-(4-(6,6-dimethyl-4-oxo-4,5,6,7-tetrahydrothiazolo[5,4-c]pyridin-2-yl)-3,4-dihydro-2H-benzo[b][1,4]oxazin-6-yl)-5-oxotetrahydrofuran-2-carboxamide. The title compound was prepared according to the steps and intermediates as described below

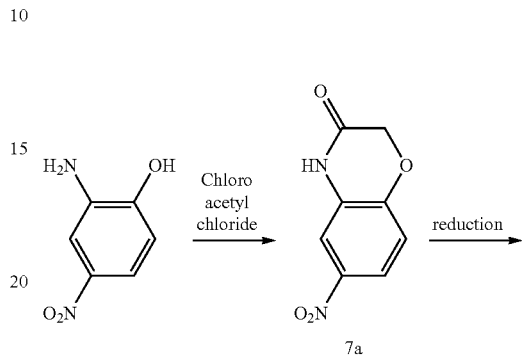

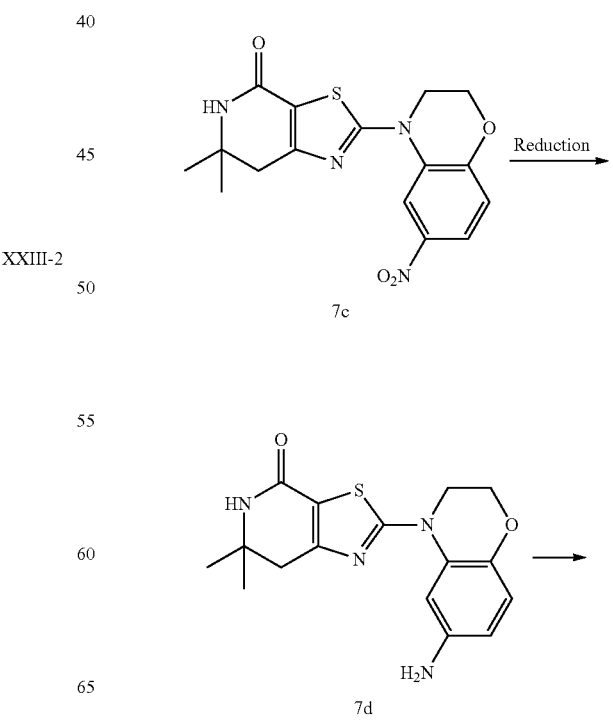

-continued

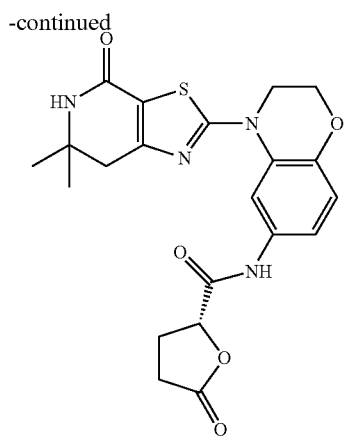

Step 7a: 6-nitro-2H-benzo[b][1,4]oxazin-3(4H)-one (Intermediate 7a)

To a stirred solution of 2-amino-4-nitrophenol (3 g, 19.4 mmol) in DMF (25 mL) was added pyridine (1.6 mL, 19.4 mmol) and chloroacetyl chloride (1.53 mL, 19.4 mmol) at 0° C. The reaction mixture was stirred for 1 h at RT followed by addition of 60% NaH (780 mg, 19.4 mmol) and continued stirring for another 2 h at RT. After the completion of reaction (monitored by TLC), the reaction was quenched with ice cold water (150 mL), precipitated solid was filtered and dried to afford 7a (2 g, 54%) as off white solid. TLC: 60% Ethyl acetate/hexane ($R_f$: 0.4); $^1$H NMR (500 MHz, CDCl$_3$): δ 8.05 (bs, 1H), 7.93 (d, J=9.0 Hz, 1H), 7.73 (s, 1H), 7.08 (d, J=9.0 Hz, 1H), 4.75 (s, 2H).

Step 7b: 3,4-dihydro-6-nitro-2H-benzo[b][1,4]oxazine (Intermediate 7b)

To a stirred solution of 7a (1.7 g, 8.85 mmol) in THF (30 mL) was added BF$_3$ etharate (2.8 mL, 22.13 mmol) at 0° C., the reaction mixture was stirred for 1 h at RT and followed by addition of NaHB$_4$ (836 mg, 22.13 mmol) at 0° C. under inert atmosphere. The reaction mixture was stirred for 16h at RT. After the completion of reaction (monitored by TLC), the reaction mixture was diluted with EtOAc/H$_2$O and aqueous layer was extracted with EtOAc (2×100 mL). The combined organic layer was dried over anhydrous Na$_2$SO$_4$ and concentrated in vacuo. The obtained solid was purified by ether washing to afford 7b (1 g, 63%) as off white solid. TLC: 50% Ethyl acetate/hexane ($R_f$: 0.3); $^1$H NMR (500 MHz, CDCl$_3$): δ 7.56 (dd, J=2.5, 9.0 Hz, 1H), 7.47 (d, J=5.3 Hz, 1H), 6.8 (d, J=9.0 Hz, 1H), 4.33 (t, J=4.0 Hz, 2H), 3.48-3.44 (m, 2H); Mass: 178 [M$^+$+1].

Step 7c: 6,7-Dihydro-2-(2,3-dihydro-6-nitrobenzo[b][1,4]oxazin-4-yl)-6,6-dimethylthiazolo[5,4-c]pyridin-4(5H)-one (Intermediate 7c)

To a stirred solution of 5-I (1 g, 3.8 mmol, from Example 128) in acetonitrile (25 mL) was added compound 7b (680 mg, 3.8 mmol), Xanthophos (176 mg, 0.3 mmol), Pd(OAc)$_2$ (52 mg, 0.2 mmol) and Cs$_2$CO$_3$ (2.5 g, 7.6 mmol) at RT. The reaction mixture was degassed with argon for 45 minutes and stirred for 6 h at 80° C. After the completion of reaction (monitored by TLC), the volatiles were removed in vacuo, diluted with water and extracted with DCM (2×100 mL). The combined organic layer was dried over anhydrous Na$_2$SO$_4$ and concentrated in vacuo. The crude residue was washed with diethyl ether to afford 7c (1 g, 73%) as light brown solid. TLC: Ethyl acetate ($R_f$: 0.3); $^1$H NMR (200 MHz, CDCl$_3$): δ 9.32 (d, J=2.6 Hz, 1H), 7.94 (dd, J=2.6, 9.0 Hz, 1H), 7.04 (d, J=9.0 Hz, 1H), 5.33 (bs, 1H), 4.46 (t, J=4.4 Hz, 2H), 4.07 (t, J=4.6 Hz, 2H), 2.95 (s, 2H) and 1.41 (s, 6H).

Step 7d: 2-(6-amino-2,3-dihydrobenzo[b][1,4]oxazin-4-yl)-6,7-dihydro-6,6-dimethylthiazolo[5,4-c]pyridin-4(5H)-one (Intermediate 7d)

To a stirred solution of 7c (1 g, 2.7 mmol) in EtOAc/MeOH (1:1, 40 mL) was added Pd/C (100 mg). The reaction mixture was stirred under hydrogen atmosphere (60 Psi) for 36 h at RT. After the completion of reaction (monitored by TLC), the reaction mixture was filtered through a pad of celite and filtrate was concentrated in vacuo. The crude residue was recrystallised from DCM/hexane to afford 7d (520 mg, 57%) as off white solid. TLC: 10% MeOH/DCM ($R_f$: 0.4); $^1$H NMR (500 MHz, CDCl$_3$): δ 7.34 (d, J=3.0 Hz, 1H), 6.76 (d, J=8.5 Hz, 1H), 6.42 (dd, J=2.5, 8.0 Hz, 1H), 5.17 (bs, 2H), 4.25 (t, J=4.0 Hz, 2H), 4.11 (t, J=5.5 Hz, 2H), 3.5 (bs, 2H), 2.87 (s, 2H), 1.39 (s, 6H); Mass: 331 [M$^+$+1]; MP: 244.8° C.

Step 7e: (R)-N-(4-(6,6-dimethyl-4-oxo-4,5,6,7-tetrahydrothiazolo[5,4-c]pyridin-2-yl)-3,4-dihydro-2H-benzo[b][1,4]oxazin-6-yl)-5-oxotetrahydrofuran-2-carboxamide The title compound was prepared by coupling intermediate 7d and (R)-5-oxotetrahydrofuran-2-carboxylic acid using HATU as described in step 1f, example 1. MS m/z: 443.2 (M+H$^+$).

Example 132

XXIII-1

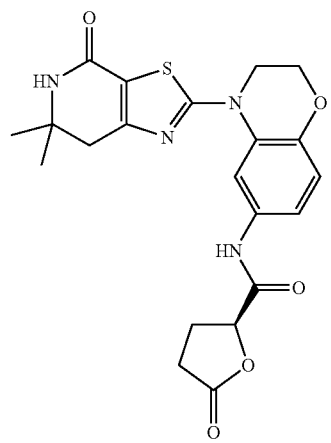

(S)-N-(4-(6,6-dimethyl-4-oxo-4,5,6,7-tetrahydrothiazolo[5,4-c]pyridin-2-yl)-3,4-dihydro-2H-benzo[b][1,4]oxazin-6-yl)-5-oxotetrahydrofuran-2-carboxamide The following compound was prepared by starting with Intermediate 7d and (S)-5-oxotetrahydrofuran-2-carboxylic acid: MS m/z: 443.2 (M+H$^+$).

Example 133

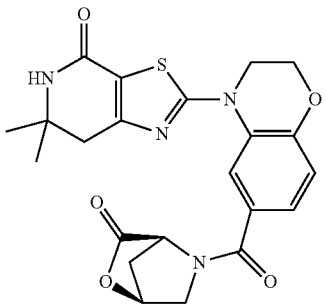

(1S,4S)-5-(4-(6,6-dimethyl-4-oxo-4,5,6,7-tetrahydrothiazolo[5,4-c]pyridin-2-yl)-3,4-dihydro-2H-benzo[b][1,4]oxazine-6-carbonyl)-2-oxa-5-azabicyclo[2.2.1]heptan-3-one The title compound was prepared according to the steps and intermediates as described below.

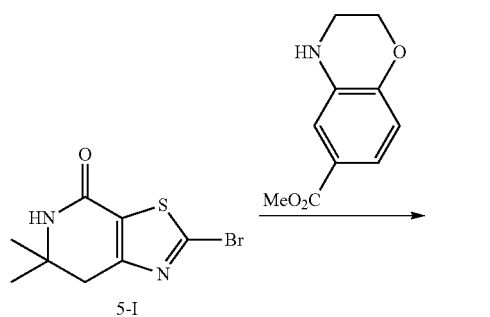

5-I

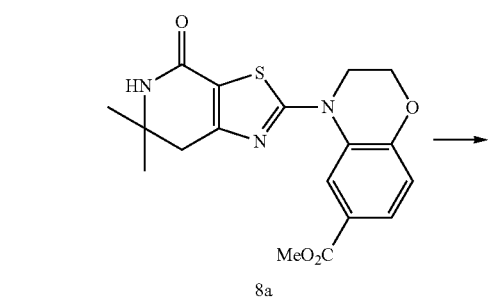

8a

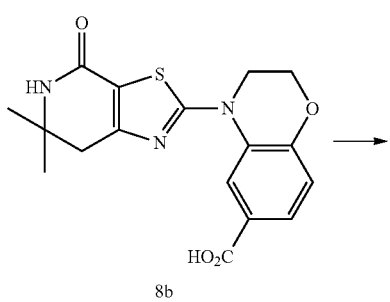

8b

XXIII-4

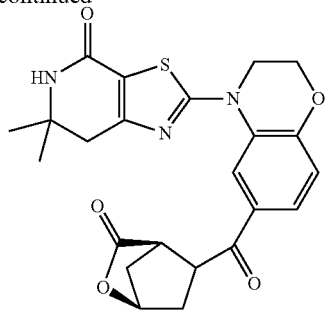

Step 8a: methyl 4-(6,6-dimethyl-4-oxo-4,5,6,7-tetrahydrothiazolo[5,4-c]pyridin-2-yl)-3,4-dihydro-2H-benzo[b][1,4]oxazine-6-carboxylate (Intermediate 8a)

To a stirred solution of compound 5-I (1 g, 3.8 mmol) in acetonitrile (40 mL) was added methyl 3,4-dihydro-2H-benzo[b][1,4]oxazine-6-carboxylate (0.73 g, 3.8 mmol), $Cs_2CO_3$ (2.5 g, 7.6 mmol), $Pd(OAc)_2$ (51 mg, 0.2 mmol) and Xanthophos (176 mg, 0.3 mmol) at room temperature. The reaction mixture was degassed with argon for 45 minutes and stirred for 16 h at 80° C. After completion of the reaction (monitored by TLC), the reaction mixture was filtered through a pad of celite and washed with DCM (100 mL) and the filtrate was washed with water (100 mL), dried over anhydrous $Na_2SO_4$ and concentrated in vacuo. The crude compound was purified by washings with diethyl ether to afford compound 8a (880 mg, 62%) as brown solid. TLC: EtOAc ($R_f$: 0.3). $^1$H-NMR ($CDCl_3$, 200 MHz): δ 8.64 (d, J=2.0 Hz, 1H), 7.76 (dd, J=2.0, 8.6 Hz, 1H), 6.99 (d, J=8.8 Hz, 1H), 5.21 (b s, 1H), 4.43-4.38 (m, 2H), 4.20-4.14 (m, 2H), 3.9 (s, 3H), 2.89 (s, 2H), 1.4 (s, 6H). MS: 374 [M$^+$+1].

Step 8b: 4-(6,6-dimethyl-4-oxo-4,5,6,7-tetrahydrothiazolo[5,4-c]pyridin-2-yl)-3,4-dihydro-2H-benzo[b][1,4]oxazine-6-carboxylic acid (Intermediate 8b)

To a stirred solution of compound 8a (0.87 g, 2.3 mmol) in THF (7 mL) and $H_2O$ (4.6 mL) was added $LiOH.H_2O$ (195 mg, 4.6 mmol) at 0° C. and the reaction mixture was stirred for 16 h at RT. After completion of the reaction (monitored by TLC), the aqueous layer was extracted with diethyl ether (2×30 mL) and organic layer was separated. The aqueous layer was acidified with 10% aqueous $KHSO_4$ (pH-2), stirred for 15 minutes and the obtained solid was filtered and dried to afford intermediate 8b (520 mg, 62%) as an off white solid. TLC: EtOAc ($R_f$: 0.1). $^1$H-NMR (DMSO-$d_6$, 500 MHz): δ 12.80 (bs, 1H), 8.76 (s, 1H), 7.63 (d, J=9.0 Hz, 1H), 7.55 (s, 1H), 7.04 (d, J=8.5 Hz, 1H), 4.39 (t, J=4.0 Hz, 2H), 4.1 (t, J=5.0 Hz, 2H), 2.82 (s, 2H), 1.28 (s, 6H). MS: 360 [M$^+$+1]. IR: 3402, 3193, 2973, 2529, 1892, 1677, 1646, 1525, 1373, 1251, 1104, 751 cm$^{-1}$. MP: 300.5° C.

Step 8c: (1S,4S)-5-(4-(6,6-dimethyl-4-oxo-4,5,6,7-tetrahydrothiazolo[5,4-c]pyridin-2-yl)-3,4-dihydro-2H-benzo[b][1,4]oxazine-6-carbonyl)-2-oxa-5-azabicyclo[2.2.1]heptan-3-one (XXIII-4)

The title compound was prepared by coupling intermediate 8b and (1S,4S)-2-oxa-5-azabicyclo[2.2.1]heptan-3-one TFA salt using HATU as described in step 1f, example 1. MS m/z: 455.1 (M+H⁺).

Example 134

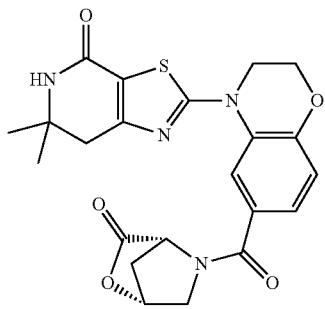

XXIII-3

(1R,4R)-5-(4-(6,6-dimethyl-4-oxo-4,5,6,7-tetrahydrothiazolo[5,4-c]pyridin-2-yl)-3,4-dihydro-2H-benzo[b][1,4]oxazine-6-carbonyl)-2-oxa-5-azabicyclo[2.2.1]heptan-3-one The following compound was prepared by starting with intermediate 8b and (1R,4R)-2-oxa-5-azabicyclo[2.2.1]heptan-3-one TFA salt: MS m/z: 455.1 (M+H⁺).

Example 135

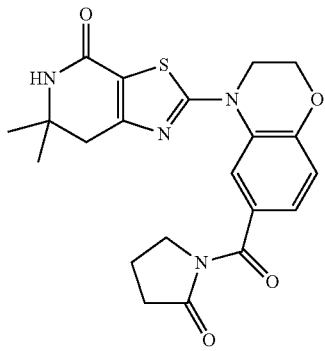

XXII-24

6,6-dimethyl-2-(6-(2-oxopyrrolidine-1-carbonyl)-2H-benzo[b][1,4]oxazin-4(3H)-yl)-6,7-dihydrothiazolo[5,4-c]pyridin-4(5H)-one The title compounds are prepared by starting with intermediate 8b and coupling with a suitable amine or amide.

Example 136

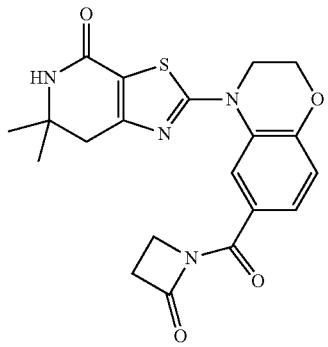

XXIII-25

6,6-dimethyl-2-(6-(2-oxoazetidine-1-carbonyl)-2H-benzo[b][1,4]oxazin-4(3H)-yl)-6,7-dihydrothiazolo[5,4-c]pyridin-4(5H)-one The title compounds are prepared by starting with intermediate 8b and coupling with a suitable amine or amide.

Example 137

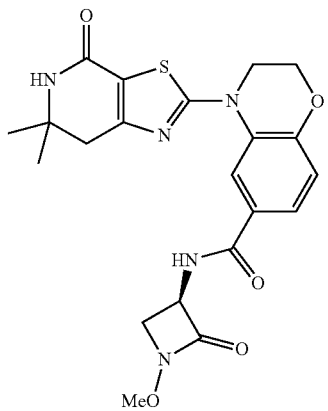

XXIII-26

(R)-4-(6,6-dimethyl-4-oxo-4,5,6,7-tetrahydrothiazolo[5,4-c]pyridin-2-yl)-N-(1-methoxy-2-oxoazetidin-3-yl)-3,4-dihydro-2H-benzo[b][1,4]oxazine-6-carboxamide The title compounds are prepared by starting with intermediate 8b and coupling with a suitable amine or amide.

Example 138

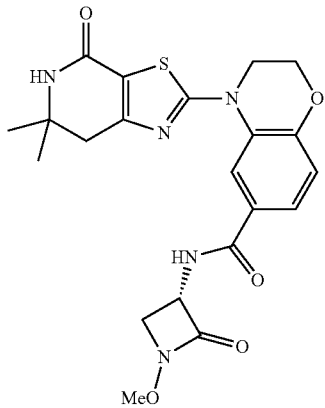

(S)-4-(6,6-dimethyl-4-oxo-4,5,6,7-tetrahydrothiazolo
[5,4-c]pyridin-2-yl)-N-(1-methoxy-2-oxoazetidin-3-
yl)-3,4-dihydro-2H-benzo[b][1,4]oxazine-6-carbox-
amide The title compounds are prepared by starting with intermediate 8b and coupling with a suitable amine or amide.

Example 139

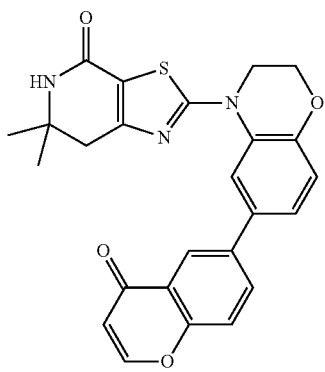

6,6-dimethyl-2-(6-(4-oxo-4H-chromen-6-yl)-2H-
benzo[b][1,4]oxazin-4(3H)-yl)-6,7-dihydrothiazolo
[5,4-c]pyridin-4(5H)-one The title compound was prepared according to the steps and intermediates as described below.

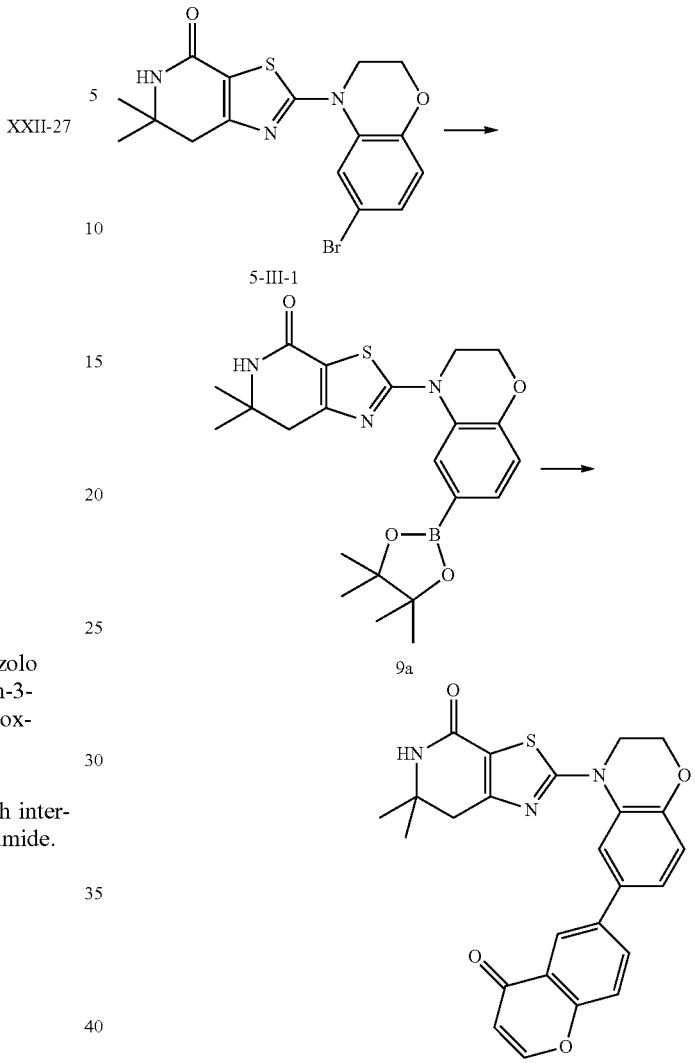

Step 9a: 6,6-dimethyl-2-(6-(4,4,5,5-tetramethyl-1,3,
2-dioxaborolan-2-yl)-2H-benzo[b][1,4]oxazin-4
(3H)-yl)-6,7-dihydrothiazolo[5,4-c]pyridin-4(5H)-
one (9a)

To a stirred solution of compound 5-III-1 from example 5 (1.5 g, 3.8 mmol) in dioxane (30 mL) was added KOAc (1.16 g, 4.5 mmol), bis (pinacolato) diboran (1.12 g, 11.4 mmol) and Pd(dppf)Cl$_2$ (556 mg, 0.7 mmol) at RT. The reaction mixture was degassed by purging with argon for 30 minutes and stirred at 90° C. for 2h. After completion of the reaction (monitored by TLC), the reaction was quenched with H$_2$O and extracted with EtOAc (3×100 mL). The combined organic layer was dried over anhydrous Na$_2$SO$_4$ and concentrated in vacuo. The crude compound was purified by column chromatography (40% EtOAc/Hexane) to afford compound 9a (900 mg, 53%) as off white solid. TLC: EtOAc (R$_f$: 0.5). $^1$H-NMR (CDCl$_3$, 200 MHz): δ 8.16 (s, 1H), 7.52 (d, J=8.4 Hz, 1H), 6.94 (d, J=8.0 Hz, 1H), 5.19 (bs, NH), 4.40-4.31 (m, 2H), 4.24-4.14 (m, 2H), 2.86 (s, 2H), 1.39 (s, 6H), 1.27 (s, 12H).

MS: 442 [M$^+$+1]

Step 9b: 6,6-dimethyl-2-(6-(4-oxo-4H-chromen-6-yl)-2H-benzo[b][1,4]oxazin-4(3H)-yl)-6,7-dihydrothiazolo[5,4-c]pyridin-4(5H)-one The title compound was prepared by treating compound 9a with 6-bromo-4H-chromen-4-one under the standard Suzuki coupling conditions described in step 3c in example 3. MS m/z: 460.1 (M+H$^+$).

Example 140

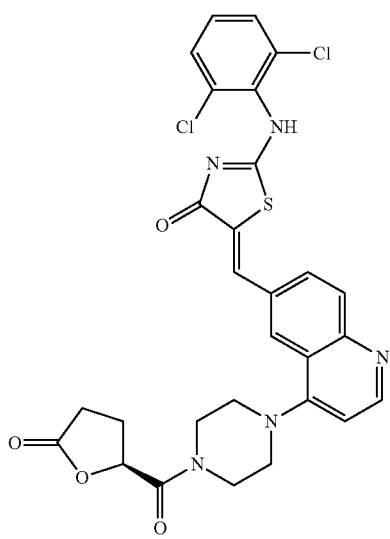

XXIV-2

(S,Z)-2-(2,6-dichlorophenylamino)-5-((4-(4-(5-oxo-tetrahydrofuran-2-carbonyl)piperazin-1-yl)quinolin-6-yl)methylene)thiazol-4(5H)-one The title compound was prepared according to the steps and intermediates as described below.

Step 10a: Methyl 4-(4-(tert-butoxycarbonyl)piperazin-1-yl)quinoline-6-carboxylate To methyl 4-chloroquinoline-6-carboxylate (synthesized according to WO 2007099326) (1.5 g, 6.8 mmol) in isopropanol (30 mL) was added n-Boc-piperazine (1.3 g, 7.0 mmol), and the solution was heated to 90° C. for three days. The reaction was cooled to ambient temperature, filtered and the solvent removed by rotary evaporation. The product was purified by silica chromatography (DCM/EtOAc) to give the title compound (0.51 g, 1.4 mmol). $^1$H NMR (d$_6$DMSO) δ ppm: 8.78 (d, J=5.1 Hz, 1H), 8.66 (d, J=1.9 Hz, 1H), 8.14 (dd, J=8.7, 1.9 Hz, 1H), 8.02 (d, J=8.7 Hz, 1H), 3.91 (s, 3H), 3.64-3.58 (m, 4H), 3.20-3.14 (m, 4H), 1.43 (s, 9H); m/z 372 (M+1).

Step 10b: Tert-butyl 4-(6-(hydroxymethyl)quinolin-4-yl)piperazine-1-carboxylate To methyl 4-(4-(tert-butoxycarbonyl)piperazin-1-yl)quinoline-6-carboxylate (0.51 g, 1.4 mmol) in THF (10 mL) cooled to 0° C. was added lithium aluminum hydride (0.10 g, 2.7 mmol) and the reaction stirred for 30 min. The reaction was quenched by addition of excess water and the product extracted with EtOAc (3×30 mL). The combined organics were dried (MgSO$_4$), filtered, and the solvent removed by rotary evaporation to give the title compound as a yellow oil (0.45 g, 1.3 mmol). $^1$H NMR (d$_6$DMSO) δ ppm: 8.64 (d, J=5.0 Hz, 1H), 7.94 (d, J=0.9 Hz, 1H), 7.89 (d, J=8.7 Hz, 1H), 7.62 (dd, J=8.3, 1.9 Hz, 1H), 6.97 (d, J=5.0 Hz, 1H), 5.38 (dd, J=6.0, 5.5 Hz, 1H), 4.67 (d, J=6.0 Hz, 1H), 3.63-3.57 (m, 4H), 3.14-3.08 (m, 4H), 1.43 (s, 9H). m/z 344 (M+1).

Step 10c: Tert-butyl 4-(6-formylquinolin-4-yl)piperazine-1-carboxylate

To tert-butyl 4-(6-(hydroxymethyl)quinolin-4-yl)piperazine-1-carboxylate (0.45 g, 1.3 mmol) in DCM (10 mL) was added Dess-Martin periodinane (0.62 g, 1.5 mmol). The solution was stirred at ambient temperature overnight. The solution was filtered and the volatiles removed by rotary evaporation. The product was purified by silica chromatography (DCM/EtOAc) to provide the title compound as a yellow foam (0.31 g, 0.91 mmol). $^1$H NMR (d$_6$DMSO) δ ppm: 10.20 (s, 1H), 8.80 (d, J=5.0 Hz, 1H), 8.62 (dd, J=1.4, 0.9 Hz, 1H), 8.06 (s, 1H), 8.05 (s, 1H), 7.10 (d, J=5.0 Hz, 1H), 3.67-3.62 (m, 4H), 3.24-3.21 (m, 4H), 1.44 (s, 9H). m/z 342 (M+1).

Step 10d: (Z)-tert-butyl 4-(6-((2-(2,6-dichlorophenylamino)-4-oxothiazol-5(4H)-ylidene)methyl)quinolin-4-yl)piperazine-1-carboxylate Tert-butyl 4-(6-formylquinolin-4-yl)piperazine-1-carboxylate (0.17 g, 0.50 mmol), 2-(2,6-dichlorophenylamino)thiazol-4(5H)-one (see WO 2006132739) (0.13 g, 0.50 mmol), and piperidine (0.040 g, 0.50 mmol) were combined in a microwave vial and ethanol (2 mL) added. The solution was heated at 150° C. for 30 min. in the microwave. The volatiles were removed on a rotary evaporator and the residue purified by silica chromatography (EtOAc/MeOH).

Step 10e: (S,Z)-2-(2,6-dichlorophenylamino)-5-((4-(4-(5-oxotetrahydrofuran-2-carbonyl)piperazin-1-yl)quinolin-6-yl)methylene)thiazol-4(5H)-one The purified material from above was dissolved in MeOH and treated with 4 N HCl in dioxane. After stirring for 1 h, the volatiles were removed by rotary evaporation. The residue was taken up in EtOAc and washed with saturated NaHCO$_3$ solution. The solution was dried (MgSO4), filtered and the solvent removed by rotary evaporation. The residue was coupled with (S)-5-oxotetrahydrofuran-2-carboxylic acid with HATU following the procedure described in step 1f in Example 96. MS m/z: 597.2 (M+H$^+$).

Example 141

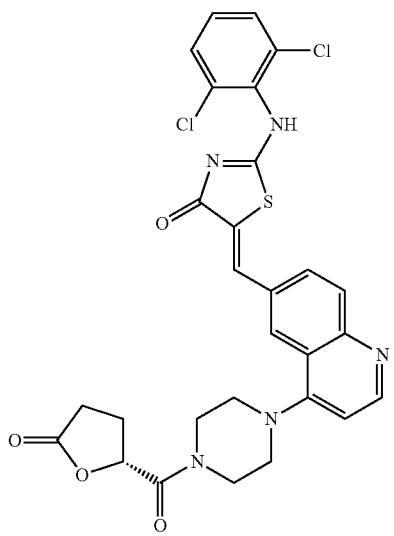

XXIV-1

(R,Z)-2-(2,6-dichlorophenylamino)-5-((4-(4-(5-oxo-tetrahydrofuran-2-carbonyl)piperazin-1-yl)quinolin-6-yl)methylene)thiazol-4(5H)-one In similar fashion, the following compound was prepared when using (R)-5-oxotetrahydrofuran-2-carboxylic acid in step 10e: MS m/z: 597.2 (M+H$^+$).

Example 142

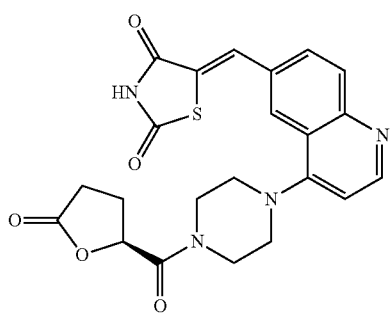

XXII-28

(S,Z)-5-((4-(4-(5-oxotetrahydrofuran-2-carbonyl)piperazin-1-yl)quinolin-6-yl)methylene)thiazolidine-2,4-dione In similar fashion, when using thiazolidine-2,4-dione to couple with tert-butyl 4-(6-formylquinolin-4-yl)piperazine-1-carboxylate in step 10d, followed by step 10e, the title compound can be prepared.

Example 143

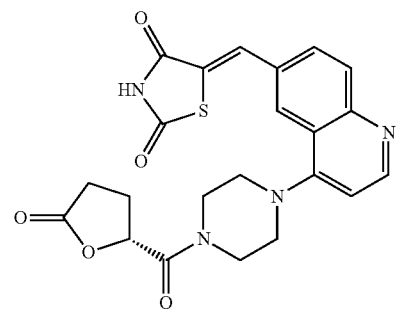

XXII-29

(R,Z)-5-((4-(4-(5-oxotetrahydrofuran-2-carbonyl)piperazin-1-yl)quinolin-6-yl)methylene)thiazolidine-2,4-dione In similar fashion, when using thiazolidine-2,4-dione to couple with tert-butyl 4-(6-formylquinolin-4-yl)piperazine-1-carboxylate in step 10d, followed by step 10e, but using acrylic acid instead, the title compound can be prepared.

Example 144

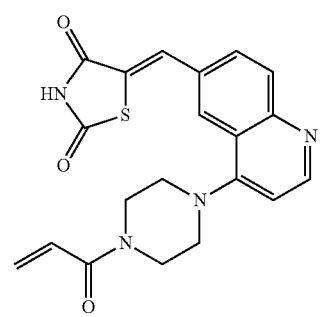

XXIV-3

(Z)-5-((4-(4-acryloylpiperazin-1-yl)quinolin-6-yl)methylene)thiazolidine-2,4-dione

Example 145

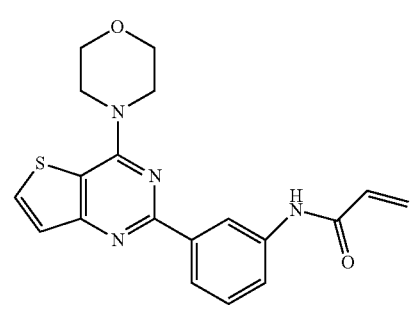

XXII-21

N-(3-(4-morpholinothieno[3,2-d]pyrimidin-2-yl)phenyl)acrylamide

The title compound was prepared according to the steps and intermediates as described below.

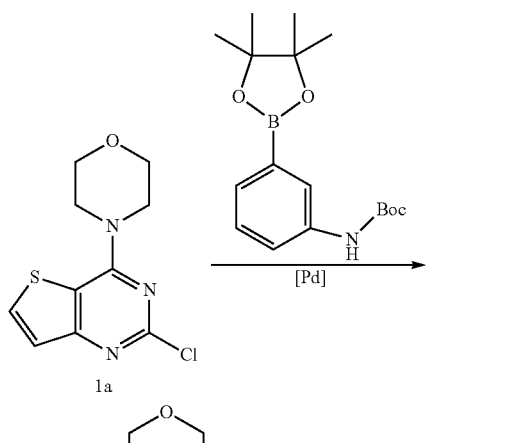

1a

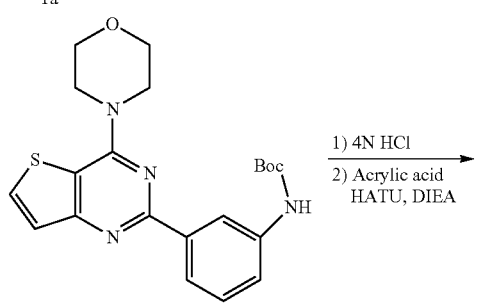

11a

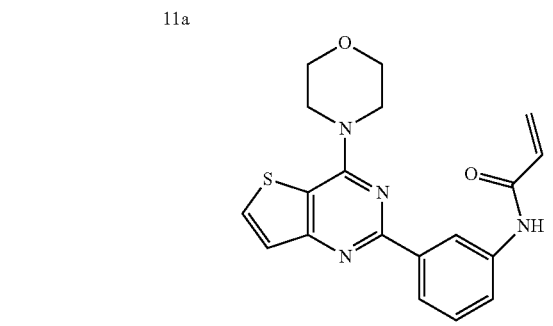

Step 11a: tert-butyl 3-(4-morpholinothieno[3,2-d]pyrimidin-2-yl)phenylcarbamate (Intermediate 11a)

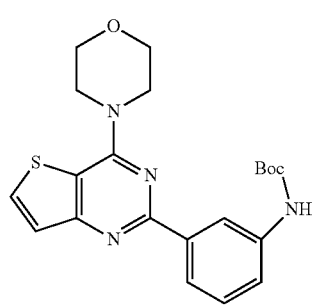 [SMILES: CC(C)(C)OC(=O)Nc1cccc(-c2nc(N3CCOCC3)c3sccc3n2)c1]

Intermediate 11a was prepared by coupling Intermediate 1a and tert-butyl 3-(4,4,5,5-tetramethyl-1,3,2-dioxaborolan-2-yl)phenylcarbamate following the standard Suzuki coupling conditions described in step 3c, Example 3. MS m/z: 413.3 (M+1).

Step 11b: N-(3-(4-morpholinothieno[3,2-d]pyrimidin-2-yl)phenyl)acrylamide

The title compound was prepared by following the procedures described in Example 96, step 1e and 1f. MS m/z: 367.2 (M+H$^+$).

Example 146

XXII-20

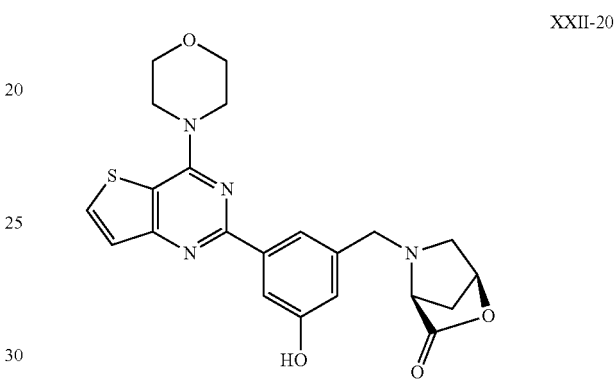

(1S,4S)-5-(3-hydroxy-5-(4-morpholinothieno[3,2-d]pyrimidin-2-yl)benzyl)-2-oxa-5-azabicyclo[2.2.1]heptan-3-one The title compound was prepared according to the steps and intermediates as described below.

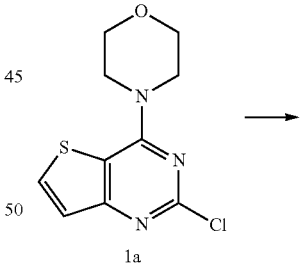

1a

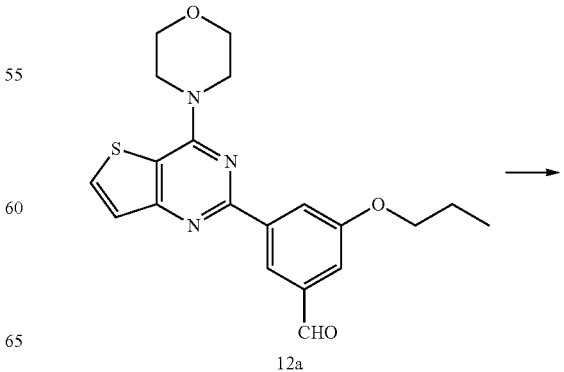

12a

-continued

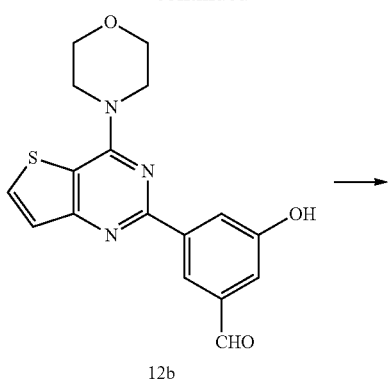

12b

Step 12a: 3-(4-morpholinothieno[3,2-d]pyrimidin-2-yl)-5-propoxybenzaldehyde Intermediate 12a

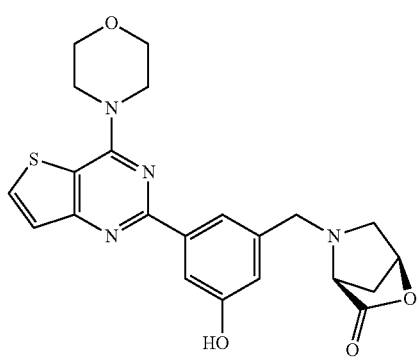

Intermediate 12a was prepared by coupling Intermediate 1a and 3-formyl-5-propoxyphenylboronic acid following the standard Suzuki coupling conditions described in step 3c, Example 3. MS m/z: 384.1 (M+1).

Step 12b: 3-hydroxy-5-(4-morpholinothieno[3,2-d]pyrimidin-2-yl)benzaldehyde (Intermediate 12b)

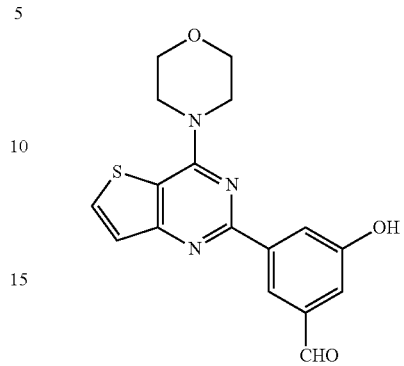

The title compound was prepared by treating intermediate 12a with 2 equivalents BBr3 in dichloromethane at −78° C. to RT for 1 hour. MS m/z: 342.1 (M+H⁺).

Step 12c: (1S,4S)-5-(3-hydroxy-5-(4-morpholinothieno[3,2-d]pyrimidin-2-yl)benzyl)-2-oxa-5-azabicyclo[2.2.1]heptan-3-one The title compound was prepared by treating intermediate 12b with (1S,4S)-2-oxa-5-azabicyclo[2.2.1]heptan-3-one TFA salt (2 equivalents), NaBH3CN (4 equivalent) in acetonitrile/acetic acid (3:1). MS m/z: 439.2 (M+H⁺).

XXII-30

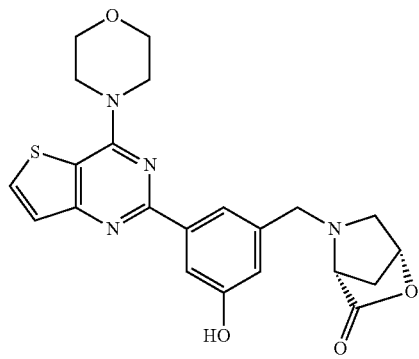

Example 147

(1R,4R)-5-(3-hydroxy-5-(4-morpholinothieno[3,2-d]pyrimidin-2-yl)benzyl)-2-oxa-5-azabicyclo[2.2.1]heptan-3-one In similar fashion, when using (1R,4R)-2-oxa-5-azabicyclo[2.2.1]heptan-3-one TFA salt, the following compound can be prepared:

Example 148

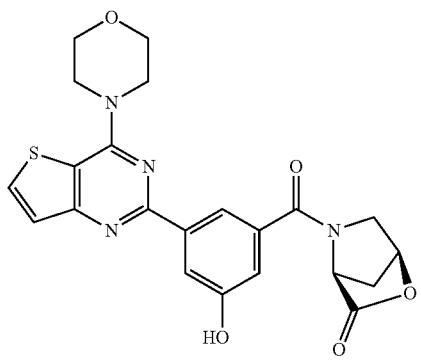

XXII-31

(1S,4S)-5-(3-hydroxy-5-(4-morpholinothieno[3,2-d]pyrimidin-2-yl)benzoyl)-2-oxa-5-azabicyclo[2.2.1]heptan-3-one The title compound can be prepared from compound 12b by a two-step sequence: 1) oxidation to the carboxylic acid by a suitable oxidant, 2) coupling of the resulting acid with an appropriate amine.

Example 149

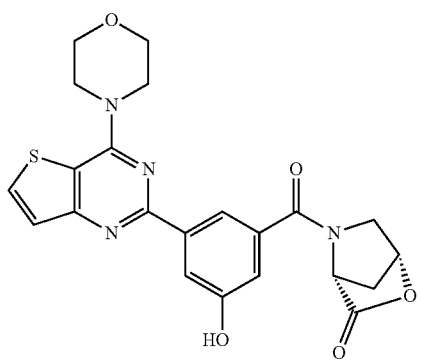

XXII-32

(1R,4R)-5-(3-hydroxy-5-(4-morpholinothieno[3,2-d]pyrimidin-2-yl)benzoyl)-2-oxa-5-azabicyclo[2.2.1]heptan-3-one The title compound can be prepared from compound 12b by a two-step sequence: 1) oxidation to the carboxylic acid by a suitable oxidant, 2) coupling of the resulting acid with an appropriate amine.

Example 150

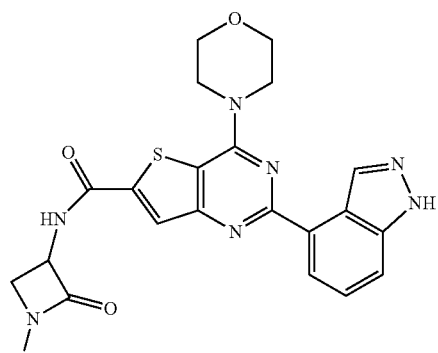

XXII-33

2-(1H-indazol-4-yl)-N-(1-methoxy-2-oxoazetidin-3-yl)-4-morpholinothieno[3,2-d]pyrimidine-6-carboxamide Using the intermediates described in the above examples and the chemistry outlined in the procedures, the title compound can be prepared accordingly.

Example 151

2, 4-difluoro-N-(2-methoxy-5-(4-(4-((1S,4S)-3-oxo-2-oxa-5-azabicyclo[2.2.1]heptane-5-carbonyl)phenyl)quinolin-6-yl)pyridin-3-yl)benzenesulfonamide (XXV-13)

The title compound was prepared through the following intermediate as described below.

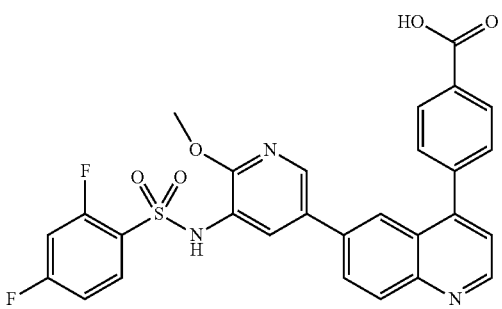 [SMILES: COc1ncc(-c2ccc3nccc(-c4ccc(C(=O)O)cc4)c3c2)cc1NS(=O)(=O)c1ccc(F)cc1F]

4-(6-(5-(2,4-difluorophenylsulfonamido)-6-methoxypyridin-3-yl)quinolin-4-yl)benzoic acid The title acid was prepared by following the similar chemistry as published in patents WO2008144463 and WO20081444464.

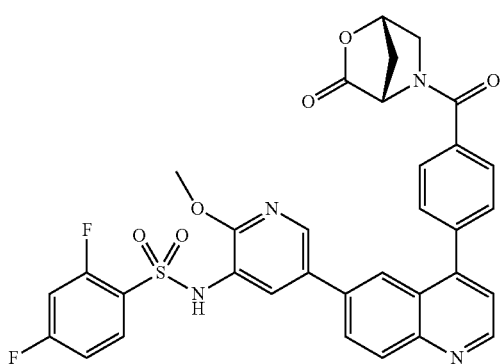

2,4-difluoro-N-(2-methoxy-5-(4-(4-((1S,4S)-3-oxo-2-oxa-5-azabicyclo[2.2.1]heptane-5-carbonyl)phenyl)quinolin-6-yl)pyridin-3-yl)benzenesulfonamide (XXV-13)

The title compound was prepared through standard HATU coupling of the benzoic acid above and (1S,4S)-2-oxa-5-azabicyclo[2.2.1]heptan-3-one.

¹H-NMR (CDCl₃, 500 MHz): δ 8.99 (d, J=4.0 Hz, 1H), 8.27 (d, J=8.5 Hz, 1H), 8.15 (s, 1H), 7.98-7.88 (m, 5H), 7.78-7.75 (m, 1H), 7.66 (d, J=7.5 Hz, 1H), 7.39 (d, J=3.5 Hz, 1H), 7.29-7.25 (m, 1H), 6.91 (d, J=5.5 Hz, 2H), 5.26 (bs, 1H), 4.95-4.91 (m, 1H), 3.96-3.93 (m, 4H), 2.36 (d, J=10 Hz, 1H), 2.17 (d, J=10.5 Hz, 1H), 2.05-2.03 (m, 1H).
MS: m/z=643.1 [M+H]

Example 152

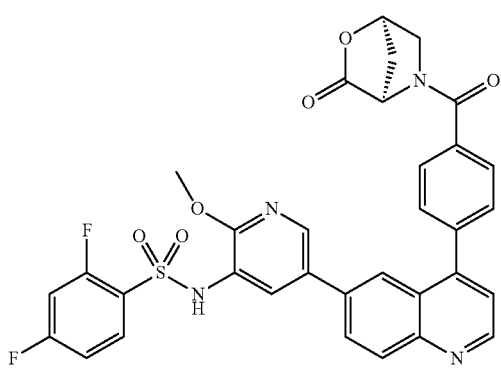

2,4-difluoro-N-(2-methoxy-5-(4-(4-((1R,4R)-3-oxo-2-oxa-5-azabicyclo[2.2.1]heptane-5-carbonyl)phenyl)quinolin-6-yl)pyridin-3-yl)benzenesulfonamide (XXV-15)

The title compound was prepared in the same way as for XXV-13 using enantiomeric amine in the final coupling step.

¹H-NMR (CDCl₃, 500 MHz): δ 8.99 (d, J=4.0 Hz, 1H), 8.27 (d, J=8.5 Hz, 1H), 8.15 (s, 1H), 7.98-7.88 (m, 5H), 7.78-7.75 (m, 1H), 7.66 (d, J=7.5 Hz, 1H), 7.39 (d, J=3.5 Hz, 1H), 7.29-7.25 (m, 1H), 6.91 (d, J=5.5 Hz, 2H), 5.26 (bs, 1H), 4.95-4.91 (m, 1H), 3.96-3.93 (m, 4H), 2.36 (d, J=10 Hz, 1H), 2.17 (d, J=10.5 Hz, 1H), 2.05-2.03 (m, 1H).
MS: m/z 643.1 [M+H].

Example 153

N-(4-(6-(5-(2,4-difluorophenylsulfonamido)-6-methoxypyridin-3-yl)quinolin-4-yl)phenyl) acrylamide (XXV-14)

The title compound was prepared through the following intermediate as described below.

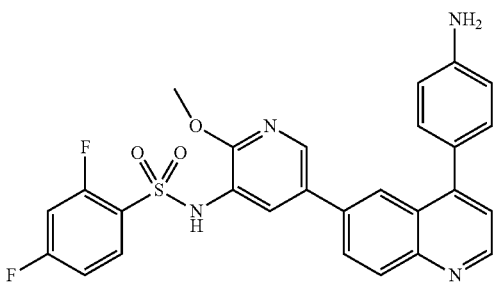 [SMILES: COc1ncc(-c2ccc3nccc(-c4ccc(N)cc4)c3c2)cc1NS(=O)(=O)c1ccc(F)cc1F]

N-(5-(4-(4-aminophenyl)quinolin-6-yl)-2-methoxy-pyridin-3-yl)-2,4-difluorobenzene-sulfonamide The title acid was prepared by following the similar chemistry as published in patents WO2008144463 and WO20081444464.

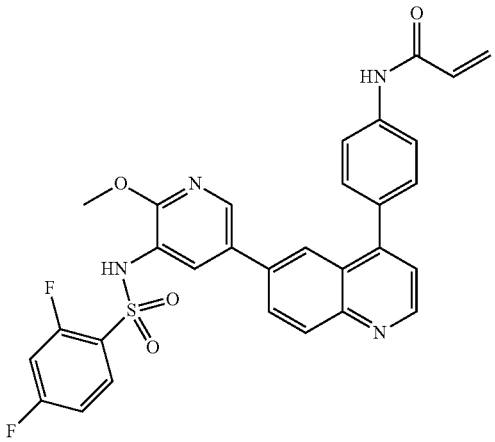

N-(4-(6-(5-(2,4-difluorophenylsulfonamido)-6-methoxypyridin-3-yl)quinolin-4-yl)phenyl) acrylamide The title compound was prepared through the standard HATU coupling of the aniline above and acrylic acid.

¹H-NMR (CDCl₃+CD₃OD, 500 MHz): δ 8.88 (d, J=5.0 Hz, 1H), 8.22 (d, J=9.0 Hz, 1H), 8.11 (d, J=2.0 Hz, 1H), 8.02 (s, 1H), 7.97 (d, J=2.0 Hz, 1H), 7.91-7.88 (m, 3H), 7.78-7.73 (m, 1H), 7.54 (d, J=8.5 Hz, 2H), 7.42 (d, J=4.5 Hz, 1H), 6.95-6.84 (m, 2H), 6.48-6.40 (m, 2H), 5.79 (d, J=9.5 Hz, 1H), 3.93 (s, 3H).
LCMS: 595 [M+Na], 573 [M+H]

Example 154
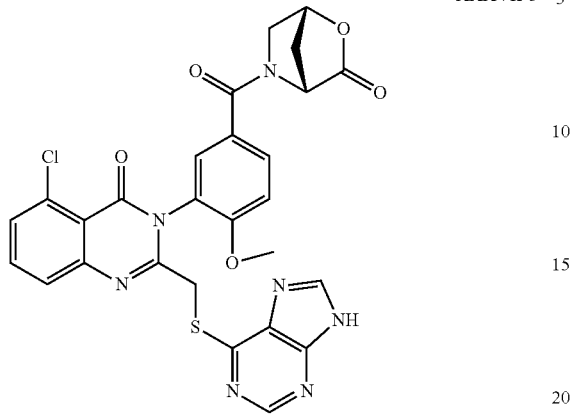
(1R,4R)-5-(3-(2-((9H-purin-6-ylthio)methyl)-5-
chloro-4-oxoquinazolin-3(4H)-yl)-4-methoxyben-
zoyl)-2-oxa-5-azabicyclo[2.2.1]heptan-3-one
(XXXVII-5)
The title compound was prepared according to the steps and intermediates as described below.
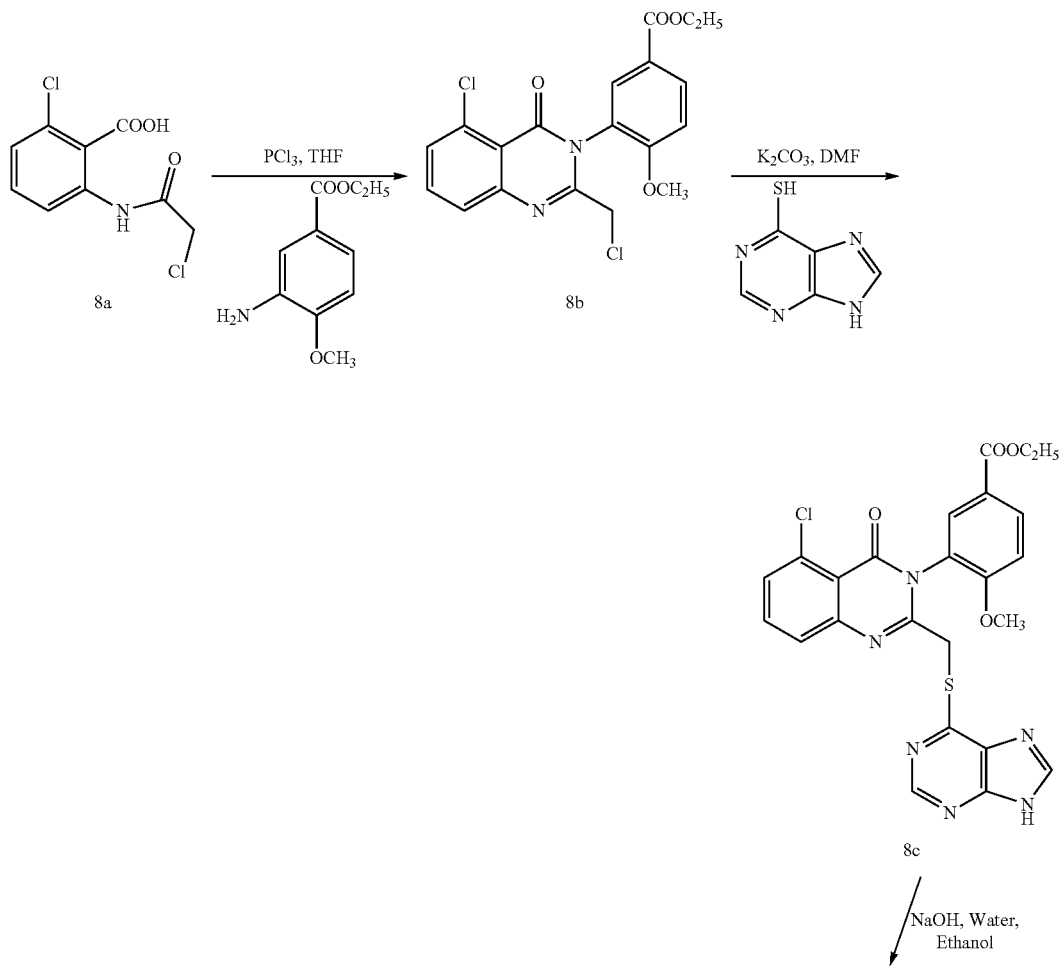

421

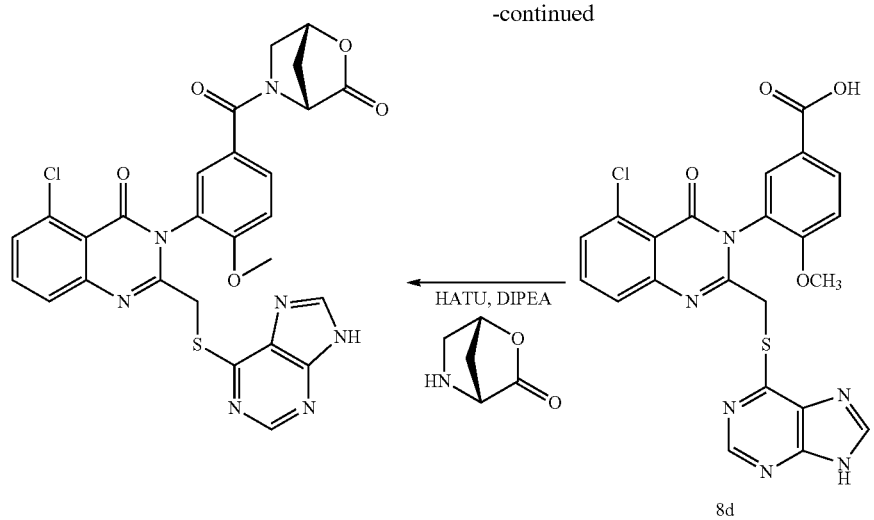

Step 8b: Ethyl 3-(5-chloro-2-(chloromethyl)-4-oxo-quinazolin-3(4H)-yl)-4-methoxybenzoate To a mixture of 2-chloro-6-(2-chloroacetamido)benzoic acid (5.7 g, 22.97 mmol), ethyl 3-amino-4-methoxybenzoate (4.0 g, 20.67 mmol) in THF (24 mL) at 0° C., was added $PCl_3$ (4.7 mL, 34.45 mmol). The reaction mixture was then refluxed at 65° C. for 1-2 h. After completion of reaction, reaction mixture was poured into water and extracted with EtOAc. Organic layer was washed with dilute HCl (2×25 mL) and saturated $NaHCO_3$ (2×25 mL), brine solution and dried over anhydrous $Na_2SO_4$. After filtration and concentration, the crude product was purified by column chromatography using 17% EtOAc in Hexane, giving compound 8b as a white solid (5.4 g, 65% yield).

$^1$H NMR: (DMSO, 400 MHz): δ 1.280 (t, 3H), 3.831 (s, 3H), 4.254 (m, 4H), 7.359-8.145 (m, 6H).

Mass: 407.0 (M+1)

422

Step 8c: ethyl 3-(2-((9H-purin-6-ylthio)methyl)-5-chloro-4-oxoquinazolin-3(4H)-yl)-4-methoxybenzoate

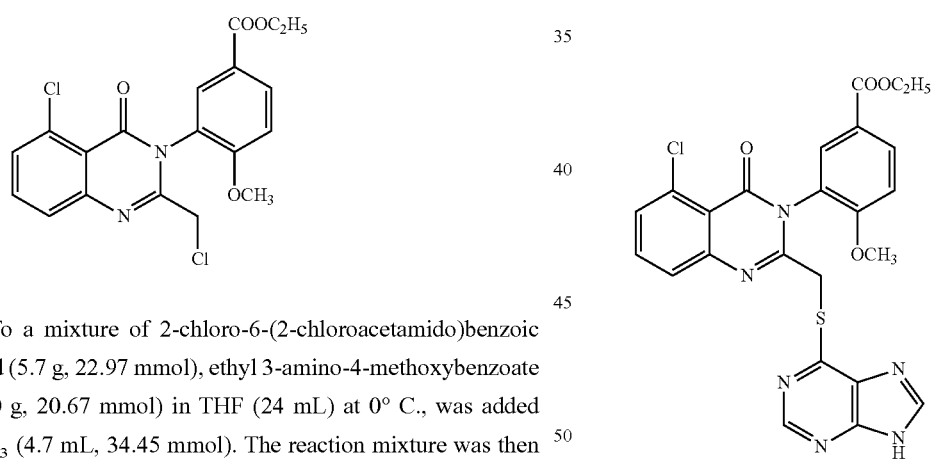

To a solution of 6-mercaptopurine (0.459 g, 2.70 mmol) in DMF (10 mL), was added anhydrous $K_2CO_3$ (0.397 g. 2.94 mmol). After stirring for 15-20 min, compound 8b (1.0 g, 2.45 mmol) was added and the reaction was continued under for 1-1.5 hr. The reaction mixture was then poured in water (150 mL), and the precipitated was filtered out, giving white solid (1.1 g, 86% yield).

$^1$H NMR: (DMSO, 400 MHz): δ 1.233 (t, 3H), 3.801 (s, 3H), 4.182 (m, 2H), 4.227 (q, 2H), 7.143-8.392 (m, 8H).

Mass: 523.0 (M$^+$+1).

Step 8d: 3-(2-((9H-purin-6-ylthio)methyl)-5-chloro-4-oxoquinazolin-3(4H)-yl)-4-methoxybenzoic acid

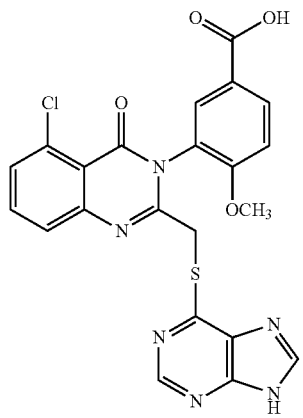 [SMILES: COc1ccc(C(=O)O)cc1-n1c(CSc2ncnc3[nH]cnc23)nc2cccc(Cl)c2c1=O]

Compound 8c (1.4 g, 2.67 mmol) and NaOH (0.214 g, 5.35 mmol) was stirred in a mixed solvent of in ethanol (5 mL) and water (15 mL). Reaction was monitored by TLC/mass periodically, and stopped at ~50% conversion. Reaction mixture was worked up by removing ethanol-water then, water (15 mL) was added and then HCl was added at 0-5° C. up to acidic pH. The white solid was filtered out, giving 560 mg of desired acid (41% yield).
Mass: 495.0 (M+1).

Step 8e: (1R,4R)-5-(3-(2-((9H-purin-6-ylthio)methyl)-5-chloro-4-oxoquinazolin-3(4H)-yl)-4-methoxybenzoyl)-2-oxa-5-azabicyclo[2.2.1]heptan-3-one

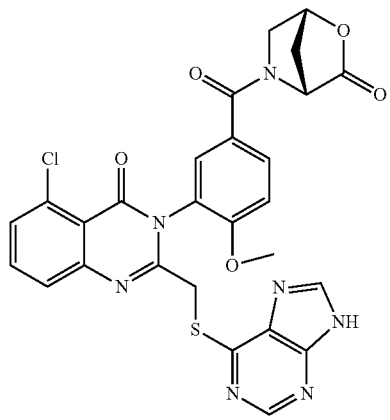 [SMILES: COc1ccc(C(=O)N2C[C@H]3C[C@@H]2C(=O)O3)cc1-n1c(CSc2ncnc3[nH]cnc23)nc2cccc(Cl)c2c1=O]

To a mixture of Compound 8d (0.4 g, 0.81 mmol), (1R,4R)-2-oxa-5-azabicyclo[2.2.1]heptan-3-one (0.179 g, 1.21 mmol), DIPEA (0.628 g, 4.86 mmol) in 5 mL of acetonitrile was HATU (0.456 g, 1.21 mmol). After 10 min, the reaction mixture was concentrated, and purified by prep-HPLC.
¹H NMR: (DMSO, 400 MHz): δ 2.143 (t, 2H), 2.287 (t, 2H), 3.769 (s, 3H), 4.482 (dd, 2H), 5.303 (s, 1H), 7.137-8.480 (m, 8H), 13.508 (s, 1H).
Mass: 590.1 (M+1).

Example 155

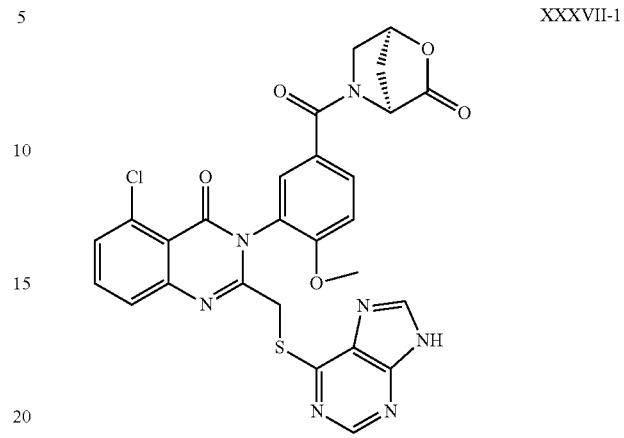

(1S,4S)-5-(3-(2-((9H-purin-6-ylthio)methyl)-5-chloro-4-oxoquinazolin-3(4H)-yl)-4-methoxybenzoyl)-2-oxa-5-azabicyclo[2.2.1]heptan-3-one (XXXVII-1)

The title compound was made in the same way as for using enantiomeric amine in the final step.
¹H NMR: (DMSO, 400 MHz): δ 2.143 (t, 2H), 2.287 (t, 2H), 3.769 (s, 3H), 4.482 (dd, 2H), 5.303 (s, 1H), 7.137-8.480 (m, 8H), 13.508 (s, 1H).
Mass: 590.1 (M+1).

Example 156

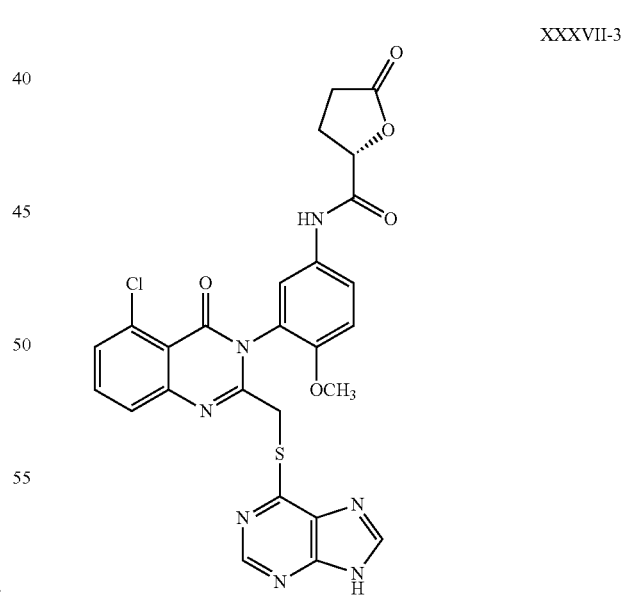

(S)-N-(3-(2-((9H-purin-6-ylthio)methyl)-5-chloro-4-oxoquinazolin-3(4H)-yl)-4-methoxyphenyl)-5-oxo-tetrahydrofuran-2-carboxamide (XXXVII-3)

The title compound was made through the intermediates as described below.

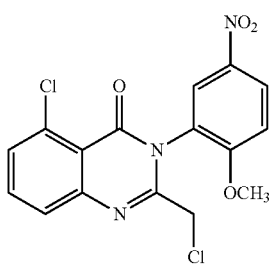 [SMILES: COc1ccc([N+](=O)[O-])cc1-n1c(CCl)nc2cccc(Cl)c2c1=O]

5-chloro-2-(chloromethyl)-3-(2-methoxy-5-nitrophenyl)quinazolin-4(3H)-one

The title intermediate was made in a similar way as describe in step 8b using 2-methoxy-5-nitroaniline as aniline counterpart.

¹H NMR: (DMSO, 400 MHz): δ 3.336 (s, 3H), 4.366 (dd, 2H), 7.460-8.575 (m, 6H).

Mass: 380 (M⁺).

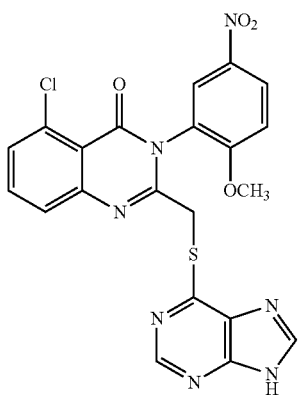 [SMILES: COc1ccc([N+](=O)[O-])cc1-n1c(CSc2ncnc3[nH]cnc23)nc2cccc(Cl)c2c1=O]

2-((9H-purin-6-ylthio)methyl)-5-chloro-3-(2-methoxy-5-nitrophenyl)quinazolin-4(3H)-one The title intermediate was made in the same way as describe in step 8c. Mass: 496 (M+1), 498 (M+2).

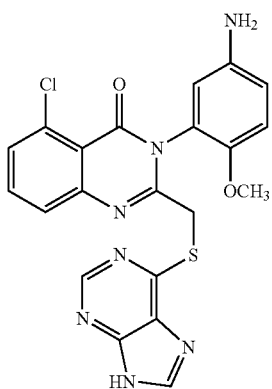 [SMILES: COc1ccc(N)cc1-n1c(CSc2ncnc3[nH]cnc23)nc2cccc(Cl)c2c1=O]

2-((9H-purin-6-ylthio)methyl)-3-(5-amino-2-methoxyphenyl)-5-chloroquinazolin-4(3H)-one The nitro group was reduced by Fe powder in the presence of catalytic amount of HCl, giving the desired aniline as brownish solid.

¹H NMR: (DMSO, 400 MHz): δ 3.596 (s, 3H), 4.420 (dd, 2H), 4.892 (s, 2H), 6.624-8.552 (m, 8H).

Mass: 466 (M+1).

Example 157

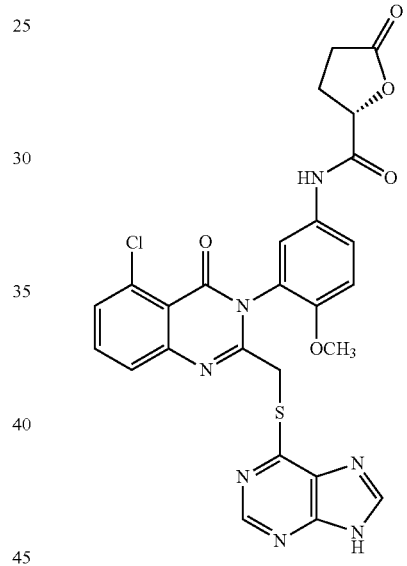

XXXVII-3

(S)-N-(3-(2-((9H-purin-6-ylthio)methyl)-5-chloro-4-oxoquinazolin-3(4H)-yl)-4-methoxyphenyl)-5-oxo-tetrahydrofuran-2-carboxamide (XXXVII-3)

The title compound was made through standard HATU coupling of the aniline above with (R)-5-Oxo-2-tetrahydrofuran carboxylic acid.

¹H NMR: (DMSO, 400 MHz): δ 2.309 (m, 2H), 2.474 (m, 2H), 3.582 (s, 3H), 4.430 (dd, 2H), 4.976 (t, 1H), 7.059-8.425 (m, 8H), 10.100 (s, 1H).

Mass: 578.1 (M+1).

Example 158

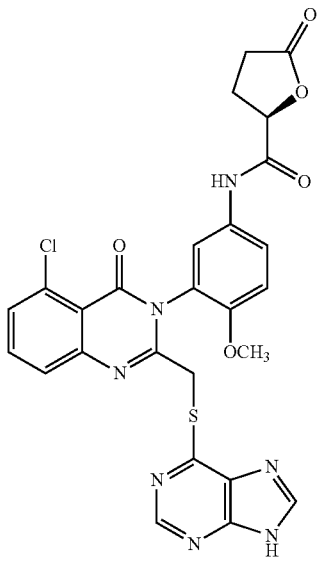

(R)-N-(3-(2-((9H-purin-6-ylthio)methyl)-5-chloro-4-oxoquinazolin-3(4H)-yl)-4-methoxyphenyl)-5-oxo-tetrahydrofuran-2-carboxamide (XXXVII-2)

The title compound was made in the same way as for XXXVII-3 using (S)-5-Oxo-2-tetrahydrofuran carboxylic acid in the final step.

$^1$H NMR: (DMSO, 400 MHz): δ 2.309 (m, 2H), 2.474 (m, 2H), 3.582 (s, 3H), 4.430 (dd, 2H), 4.976 (t, 1H), 7.059-8.425 (m, 8H), 10.100 (s, 1H).
Mass: 578.1 (M+1).

Example 159

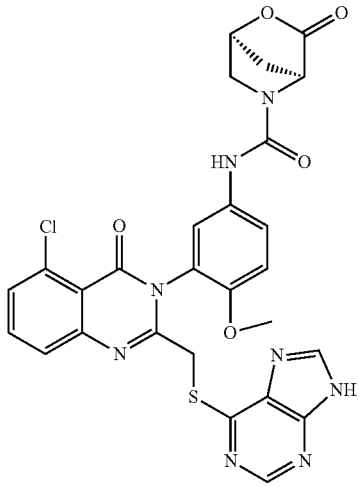

(1S,4S)-N-(3-(2-((9H-purin-6-ylthio)methyl)-5-chloro-4-oxoquinazolin-3(4H)-yl)-4-methoxyphenyl)-3-oxo-2-oxa-5-azabicyclo[2.2.1]heptane-5-carboxamide (XXXVII-4)

The title compound was made using the aniline as for XXXVII-3, triphosgene, (1S,4S)-2-oxa-5-azabicyclo[2.2.1]heptan-3-one in the presence of triethylamine.

$^1$H NMR: (DMSO, 400 MHz): δ 2.044 (t, 2H), 2.219 (t, 2H), 3.678 (s, 3H), 4.492 (dd, 2H), 4.784 (s, 1H), 4.875 (s, 1H), 7.003-8.746 (m, 8H).
Mass: 605.1 (M+1).

Example 160

N-(7-methoxy-8-(4-oxo-4-((1R,4R)-3-oxo-2-oxa-5-azabicyclo[2.2.1]heptan-5-yl)butoxy)-2,3-dihydro-imidazo[1,2-c]quinazolin-5-yl)nicotinamide (XXVII-13)

The title compound was prepared through the following intermediate as described below.

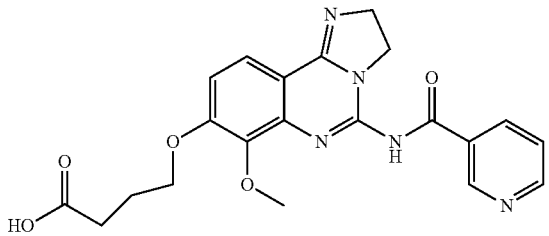 [SMILES: COc1c(OCCCC(=O)O)ccc2c1N=C(NC(=O)c1cccnc1)N1CCN=C21]

4-(7-methoxy-5-(nicotinamido)-2,3-dihydroimidazo[1,2-c]quinazolin-8-yloxy)butanoic acid The title acid was prepared by following the similar chemistry as published in patents WO2009091550.

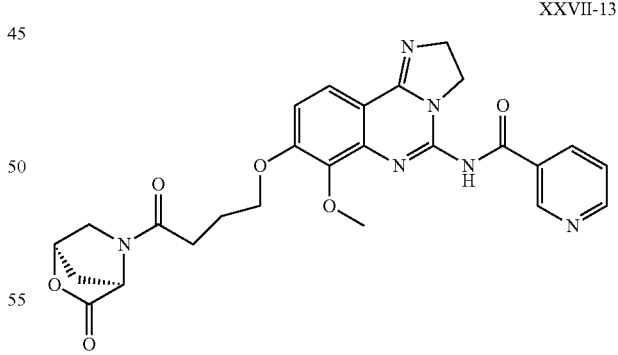

N-(7-methoxy-8-(4-oxo-4-((1R,4R)-3-oxo-2-oxa-5-azabicyclo[2.2.1]heptan-5-yl)butoxy)-2,3-dihydro-imidazo[1,2-c]quinazolin-5-yl)nicotinamide (XXVII-13)

The title compound was prepared by standard HATU coupling of the carboxylic acid above and (1R,4R)-2-oxa-5-azabicyclo[2.2.1]heptan-3-one.

¹H-NMR (CDCl₃, 500 MHz): δ 12.82 (bs, 1H), 9.47 (s, 1H), 8.70 (d, J=4.0 Hz, 1H), 8.46 (d, J=7.5 Hz, 1H), 7.70 (d, J=6.0 Hz, 1H), 7.35-7.31 (m, 1H), 6.81 (d, J=9.5 Hz, 1H), 5.11-5.15 (m, 1H), 4.20-4.17 (m, 5H), 4.04 (s, 3H), 3.70-3.50 (m, 4H), 2.65-2.60 (m, 2H), 2.50-2.45 (m, 2H), 2.22-2.20 (m, 2H).

MS: m/z 519.1 (M⁺+1)

Example 161

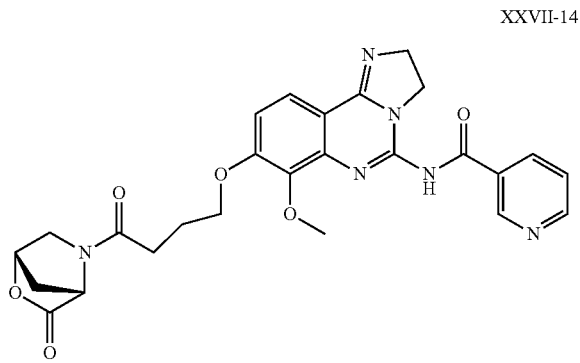 [SMILES: COc1c(OCCCC(=O)N2C[C@@H]3C[C@H]2C(=O)O3)ccc2c1N=C(NC(=O)c1cccnc1)N1CCN=C21]

XXVII-14

N-(7-methoxy-8-(4-oxo-4-((1S,4S)-3-oxo-2-oxa-5-azabicyclo[2.2.1]heptan-5-yl)butoxy)-2,3-dihydro-imidazo[1,2-c]quinazolin-5-yl)nicotinamide (XXVII-14)

The title compound was prepared in the same way as for XXVII-13 using (1R,4R)-2-oxa-5-azabicyclo[2.2.1]heptan-3-one in the final coupling step.

¹H-NMR (CDCl₃, 500 MHz): δ 12.82 (bs, 1H), 9.47 (s, 1H), 8.70 (d, J=4.0 Hz, 1H), 8.46 (d, J=7.5 Hz, 1H), 7.70 (d, J=6.0 Hz, 1H), 7.35-7.31 (m, 1H), 6.81 (d, J=9.5 Hz, 1H), 5.11-5.15 (m, 1H), 4.20-4.17 (m, 5H), 4.04 (s, 3H), 3.70-3.50 (m, 4H), 2.65-2.60 (m, 2H), 2.50-2.45 (m, 2H), 2.22-2.20 (m, 2H).

MS: m/z 519.1 (M+H)

E. PI3K Biological Data

Compounds of the present invention are assayed as inhibitors of PI3 kinases using the following general protocol.

Example 162

HTRF Assay Protocol for Potency Assessment Against the Active Form of p110α/p85α:

The protocol below describes an end-point, competition-binding HTRF assay used to measure inherent potency of test compounds against active p110α/p85α, p110β/p85α, p120γ enzymes. The mechanics of the assay platform are best described by the vendor (Millipore, Billerica, Mass.) on their website at the following URL: http://www.millipore.com/coa/tech1/74jt4z.

Briefly, Stop solution (Stop A, #33-007 and Stop B, #33-009; 3:1 ratio) and Detection Mix (DMC, #33-015 with DMA, #33-011 and DMB, #33-013; 18:1:1 ratio) were prepared as recommended by the manufacturer ~2 hrs prior to use. Additionally, 1× reaction buffer (4× buffer stock #33-003), a 1.4× stock of enzyme from BPS Bioscience (San Diego, Ca) or Millipore (Billerica, Mass.) with di-C8-PIP2 lipid substrate (#33-005), and a 4×ATP solution (#A7699) Sigma/Aldrich (St. Louis, Mo.) were prepared in 1×reaction buffer. 15 µL of enzyme and lipid substrate mix were pre-incubated in a Corning (#3573) 384-well, black, non-treated microtiter plate (Corning, N.Y.) for 30 min at 25° C. with a 0.5 µL volume of 50% DMSO and serially diluted compounds prepared in 50%-75% DMSO. Lipid kinase reactions were started with the addition of 5 µL of ATP solution, mixed for 15 sec on a rotary plate shaker and incubated for 15-30 minutes at 25° C. Next, reactions were stopped with a 5 µL addition of Stop solution followed by a 5 µL volume of Detection Mix. Stopped reactions were equilibrated for 1 and 18 hrs at room temperature and then read in a Synergy4 plate reader from BioTek (Winooski, Vt.) at λex330-80/λem620-35 and λem665-7.5. At the conclusion of each assay, the HTRF ratio from fluorescence emission values for each well was calculated and % Inhibition determined from averaged controls wells. % Inhibition values for each compound re then plotted against inhibitor concentration to estimate IC50 from log [Inhibitor] vs Response, Variable Slope model in GraphPad Prism from GraphPad Software (San Diego, Calif.).

Reagents Used in Optimized Protocol:
[p110α/p85α]=500-750 pM, [ATP]=50 µM, [di-C8-PIP2]=10 µM
(40620; BPS Bioscience or 14-602; Millipore)
Reference Inhibitor IC₅₀s:
LY294002=1.3 µM (published IC50's=0.7-3 µM)
Wortmannin=2.9 nM (published IC50's=1-5 nM)
Reagents Used in Optimized Protocol:
[p110β/p85α]=750 pM-1.25 nM, [ATP]=50 µM, [di-C8-PIP2]=10 µM
(14-603; Millipore)
Reference Inhibitor IC50s:
PIK75=249 nM (published IC50's=343 nM)
AZ-REF=21 nM
Reagents Used in Optimized Protocol:
[p120γ]=1-4 nM, [ATP]=50 µM, [di-C8-PIP2]=10 µM
(40625; BPS Bioscience)
Reference Inhibitor IC50s:
PIK75=55 nM
AZ-REF=14 nM
[ATP] and [PIP₂] were kept static at or below $K_{Mapp}$ for each.

Table 4 shows the activity of selected compounds of this invention in the PI3Kα-HTRF-IC50 nM, PI3KBg-HTRF-IC50 nM, and HCT116-WB Assays. Compounds having an activity designated as "A" provide an IC50≤10 nM; compounds having an activity designated as "B" provide an IC50>10 nM and ≤100 nM; compounds having an activity designated as "C" provide an IC50>100 nM and ≤1000 nM; compounds having an activity designated as "D" provide an IC50>1000 nM and <10,000 nM; and compounds having an activity designated as "E" provide an IC50≤10,000 nM.

TABLE 4

| Compound Designation | Enzyme/Assay | Inhibition Designation |
|---|---|---|
| XXII-1 | PI3Kα | B |
|  | PI3Kγ | C |
| XXII-2 | PI3Kα | B |
|  | PI3Kγ | C |
|  | HCT116-WB | C |
| XXIV-1 | PI3Kα | B |
|  | PI3Kγ | C |
| XXIV-2 | PI3Kα | C |
|  | PI3Kγ | C |
| XXIII-1 | PI3Kα | C |
|  | PI3Kγ | C |

TABLE 4-continued

| Compound Designation | Enzyme/Assay | Inhibition Designation |
|---|---|---|
| XXIII-2 | PI3Kα | C |
|  | PI3Kγ | C |
| XXII-3 | PI3Kα | B |
|  | PI3Kγ | C |
|  | HCT116-WB | C |
| XXIII-3 | PI3Kα | C |
|  | PI3Kγ | C |
| XXIII-4 | PI3Kα | C |
|  | PI3Kγ | C |
| XXIII-5 | PI3Kα | C |
|  | PI3Kγ | C |
| XXII-4 | PI3Kα | B |
|  | PI3Kγ | C |
| XXII-5 | PI3Kα | B |
|  | PI3Kγ | C |
| XXIII-6 | PI3Kα | C |
|  | PI3Kγ | C |
| XXII-6 | PI3Kα | B |
|  | PI3Kγ | C |
|  | HCT116-WB | B |
| XXII-7 | PI3Kα | C |
|  | PI3Kγ | C |
|  | HCT116-WB | B |
| XXIII-7 | PI3Kα | D |
|  | PI3Kγ | D |
| XXII-8 | PI3Kα | C |
|  | PI3Kγ | C |
| XXII-9 | PI3Kα | C |
|  | PI3Kγ | C |
| XXII-10 | PI3Kα | B |
|  | PI3Kγ | C |
|  | HCT116-WB | C |
| XXII-11 | PI3Kα | B |
|  | PI3Kγ | C |
|  | HCT116-WB | B |
| XXIII-8 | PI3Kα | C |
|  | PI3Kγ | C |
|  | HCT116-WB | D |
| XXII-12 | PI3Kα | B |
|  | PI3Kγ | C |
| XXII-13 | PI3Kα | C |
|  | PI3Kγ | C |
| XXII-14 | PI3Kα | B |
| XXII-15 | PI3Kα | B |
|  | PI3Kγ | C |
| XXII-16 | PI3Kα | B |
| XXII-17 | PI3Kα | B |
| XXII-18 | PI3Kα | D |
| XXII-19 | PI3Kα | D |
| XXII-20 | PI3Kα | C |
|  | PI3Kγ | D |
| XXII-21 | PI3Kα | D |
|  | PI3Kγ | D |
| XXII-22 | PI3Kβ | C |
|  | PI3Kγ | C |
| XXII-23 | PI3Kβ | D |
|  | PI3Kγ | C |
| XXII-24 | PI3Kβ | C |
|  | PI3Kγ |  |
| XXII-25 | PI3Kβ | C |
|  | PI3Kγ | B |
| XXII-26 | PI3Kβ | C |
|  | PI3Kγ | C |
| XXII-27 | PI3Kβ | C |
|  | PI3Kγ | C |
| XXII-28 | PI3Kβ | C |
|  | PI3Kγ | C |
| XXII-29 | PI3Kβ | C |
|  | PI3Kγ | C |
| XXII-30 | PI3Kβ | C |
|  | PI3Kγ | B |
| XXII-31 | PI3Kβ | C |
|  | PI3Kγ | C |
| XXII-32 | PI3Kβ | C |
|  | PI3Kγ | C |
| XXII-33 | PI3Kβ | C |
|  | PI3Kγ | C |
| XXXVII-1 | PI3Kβ | C |
| XXXVII-2 | PI3Kβ | C |
| XXXVII-3 | PI3Kβ | C |
| XXXVII-4 | PI3Kβ | C |
| XXXVII-5 | PI3Kβ |  |
| XXV-13 | PI3Kβ | A |
| XXV-14 | PI3Kβ | A |
| XXV-15 | PI3Kβ | A |
| XXVII-13 | PI3Kβ | C |
| XXVII-14 | PI3Kβ | C |

I. Mass Spectrometric Analysis of PI3K Contacted with Compounds of the Invention

Example 163

Intact PI3Kβ was incubated for 3 hr at a 10× fold access of compound to protein. 5 µL aliquots of the samples were diluted with 15 µL of 0.1% TFA prior to micro C4 ZipTipping directly onto the MALDI target using Sinapinic acid as the desorption matrix (10 mg/mL in 0.1% TFA:Acetonitrile 50:50). Spots were then analyzed via MALDI-MS. XXII-10 modified PI3Kβ 100% by 3h. XXII-8, XXII-6, XXIII-4, and XXIII-3 each provided between about 35% to about 55% modification.

Example 164

Figure 22:
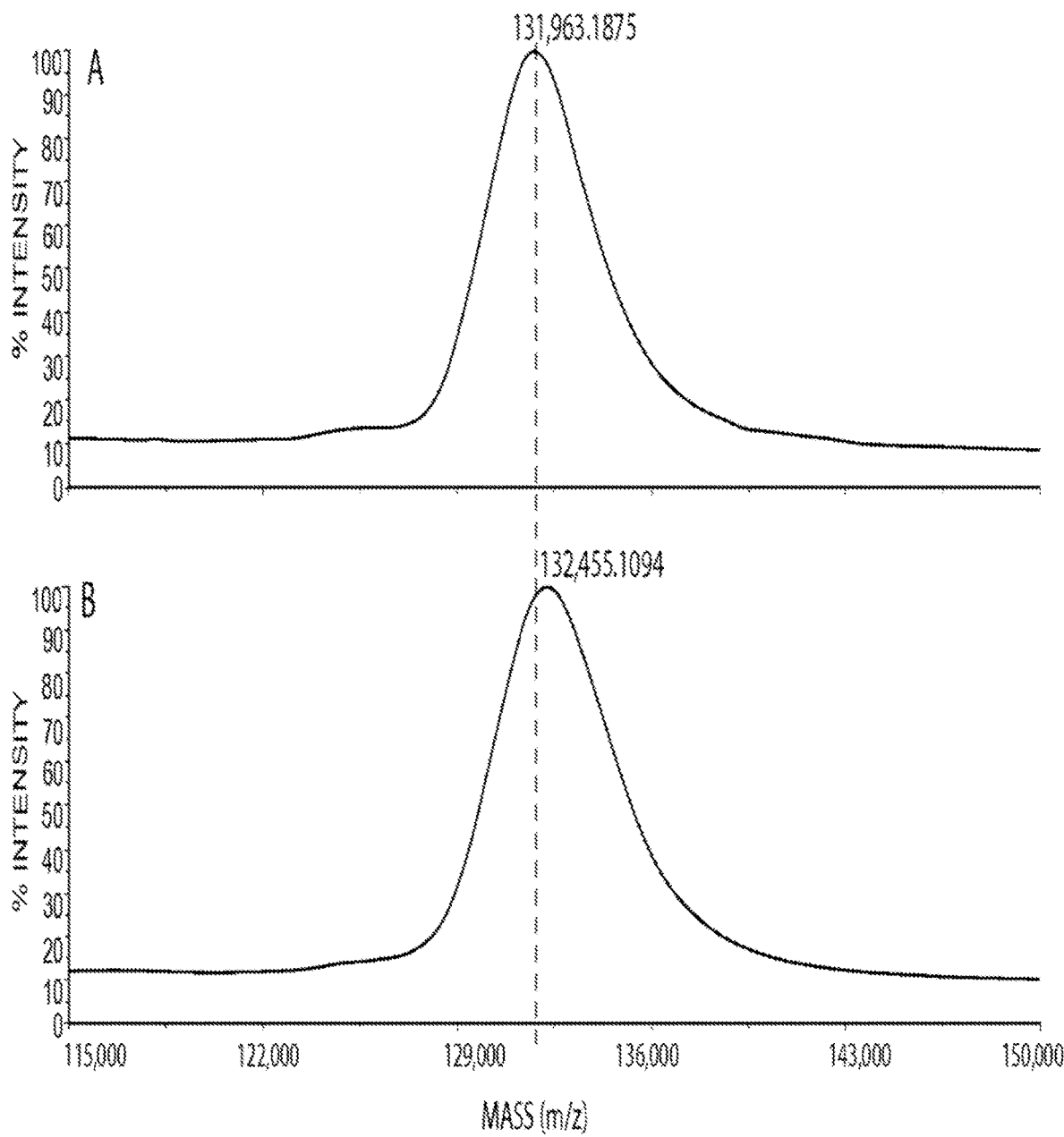
FIG. 22 depicts the mass spectrometric analysis of Compound XXII-33 contacted with PI3Kγ(whole protein).

Intact PI3Kγ was incubated for 1 hr at a 10-fold excess of compound XXII-33 to protein at 37° C. 5 µL aliquots of the samples were diluted with 10 µL of 0.1% TFA prior to micro C4 Ziptipping directly onto the MALDI target plate using sinapinic acid as the desorption matrix (10 mg/mL in 0.1% TFA:Acetonitrile 50:50). The top panel of FIG. 22 shows the mass spectral trace of the intact PI3Kγ protein (m/z=131,963 Da). The bottom panel of FIG. 22 shows the mass spectral trace when PI3Kγ was incubated with compound XXII-33 (mw=550.64). The centroid mass (m/z=132,455 Da) shows a mass shift of 492 Da (90%), indicating complete modification of PI3Kγ by compound XXII-33.

J. PDPK-1 Inhibitors Synthetic Examples

Example 165

Synthetic Scheme for Intermediate A

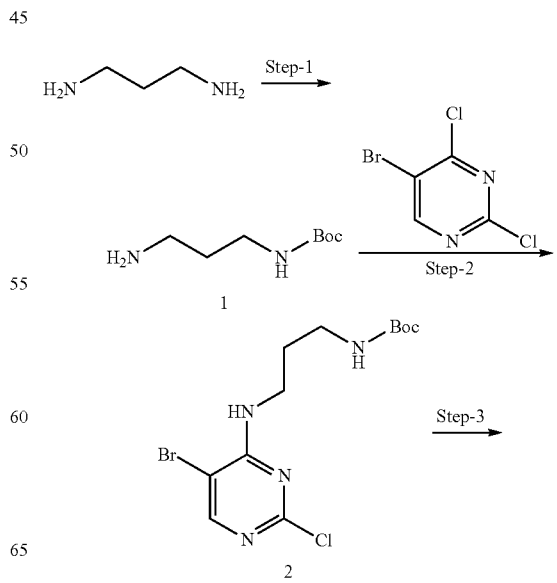

433

-continued

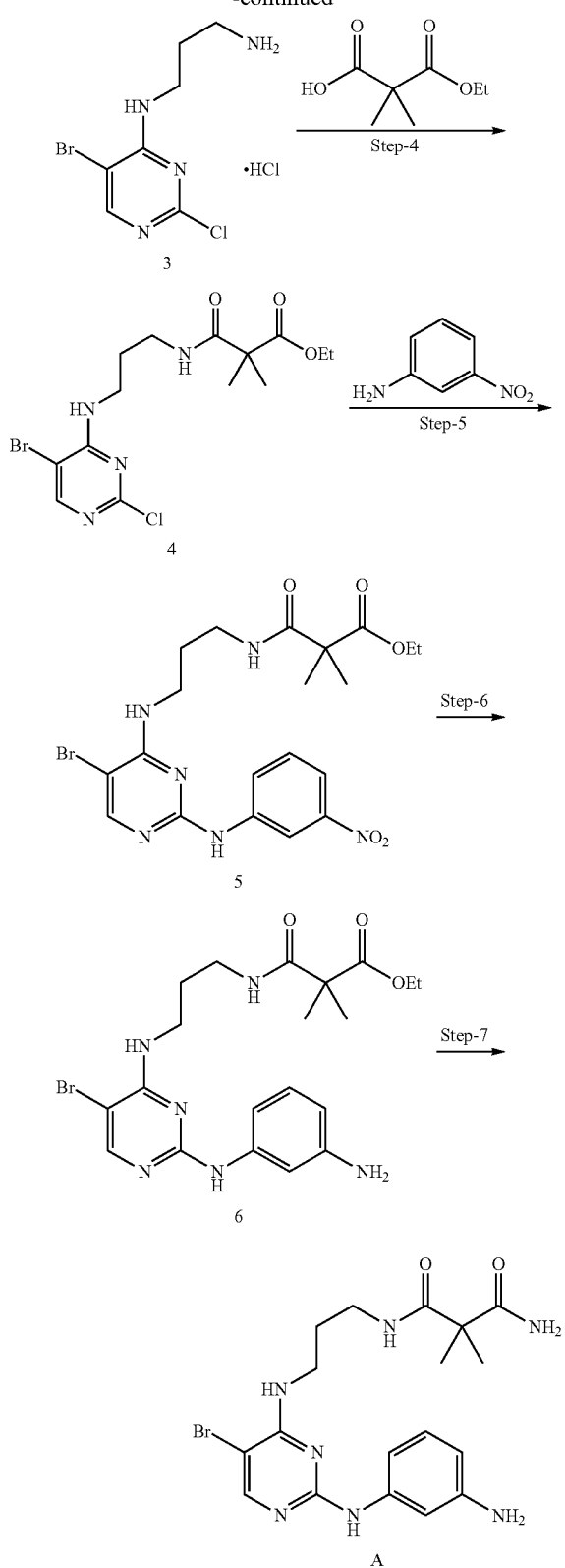

Step-1: Boc-anhydride, CHCl3, 0° C.-RT, 16 h. Step-2: Et3N, CH3CN, 0° C.-RT, 16 h. Step-3: 4M HCl in dioxane, RT, 5 h. Step-4: (i) 3-ethoxy-2,2-dimethyl-3-oxopropanoic acid, Oxalyl chloride, DMF, CH2Cl2, 2 h; (ii) DIPEA, CH3CN, RT, 16 h. Step-5: Ethanol, HCl, 60° C., 16 h. Step-6: Ethyl acetate, SnCl2•2H2O, 90° C., 3 h. Step-7: Ammonia, methanol, 80° C., 4 days.

434

Step-1: Compound 1

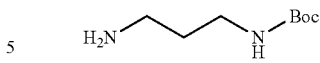

To a stirred solution of propane-1,3-diamine (10 g, 134.9 mmol) in chloroform (250 ml) at 0° C. was added boc-anhydride (6.2 ml, 26.9 mmol) in chloroform (250 ml) dropwise and the reaction mixture was stirred at room temperature overnight. (5 parallel reactions were carried out). Then the reaction mixtures were mixed together, concentrated to ~50% of its total volume and filtered. The filtrate was washed with brine, dried over sodium sulphate and concentrated. The residue was taken in petroleum ether and the undissolved portion was removed by filtration. The filtrate was concentrated to obtain compound 1 (19 g, 80.8%) as colorless liquid.

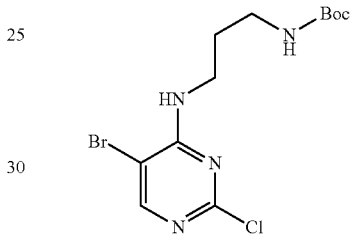

Step-2: Compound 2

To a stirred solution of 1 (19 g, 109 mmol) in acetonitrile (120 mL) at 0° C. was added triethylamine (23 ml, 165 mmol) followed by 5-bromo-2,4-dichloropyrimidine (35 g, 153.5 mmol). Stirring continued at room temperature for 16 h. The reaction mixture was concentrated completely and the residue obtained was diluted with ethyl acetate, washed with water and brine solution, dried over anhydrous Na2SO4, filtered and concentrated. The crude was then purified using column chromatography (SiO2, petroleum ether: ethyl acetate, 9:1) to obtain compound 2 as pale brown solid (26.5 g, 66.5%).

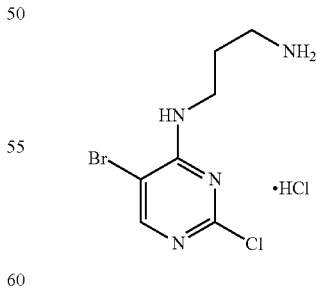

Step-3: Compound 3

A cooled solution of HCl in dioxane (4M, 150 mL) was added to compound 2 (30 g, 82 mmol) and then stirred at room temperature for 5 h. The solid obtained was collected by filtration, washed with petroleum ether and dried (25 g, quantitative).

Step-4: Compound 4

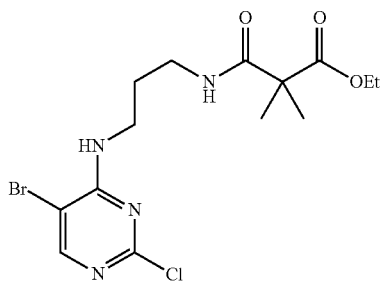 [SMILES: CCOC(=O)C(C)(C)C(=O)NCCCNc1nc(Cl)ncc1Br]

To a stirred solution of 3-ethoxy-2,2-dimethyl-3-oxopropanoic acid (10 g, 62.4 mmol) in dichloromethane (100 ml) at 0° C. was added oxalyl chloride (6.4 g, 75.6 mmol) followed by two drops DMF. The reaction mixture was stirred at room temperature for 2 h and then concentrated under vacuum to obtain brown oil. This was then added dropwise into a solution of 3 (15.5 g, 51.3 mmol) and DIPEA (36 ml, 206.7 mmol) in acetonitrile (100 ml) at 0° C. and stirred at room temperature for 16 h. The reaction mixture was completely concentrated under vacuum to obtain a residue. One more similar batch of reaction was carried out in parallel and both the residues were taken together in ethyl acetate. The ethyl acetate layer was washed with 1.5 N HCl, 10% NaHCO$_3$ solution and brine, dried over anhydrous Na$_2$SO$_4$, filtered and concentrated. The crude was purified using column chromatography (SiO$_2$, 15-20% ethyl acetate in petroleum ether) to yield compound 4 as white solid (25 g, 59.7%).

Step-5: Compound 5

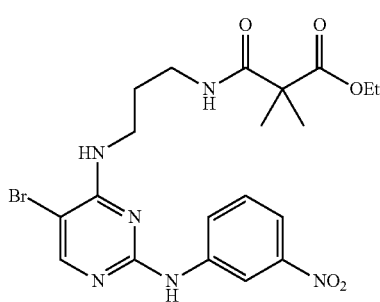 [SMILES: CCOC(=O)C(C)(C)C(=O)NCCCNc1nc(Nc2cccc([N+](=O)[O-])c2)ncc1Br]

To a stirred solution of 4 (10 g, 24.5 mmol) in ethanol (200 mL) were added 3-nitroaniline (4.4 g, 31.85 mmol) and conc. HCl (0.2 ml). The reaction mixture then stirred at 60° C. in a sealed tube for 16 h during which time pale yellow solid separated out. The solid obtained (compound 5) was collected by filtration, washed with petroleum ether and dried (11.7 g, 93.6%).

Step-6: Compound 6

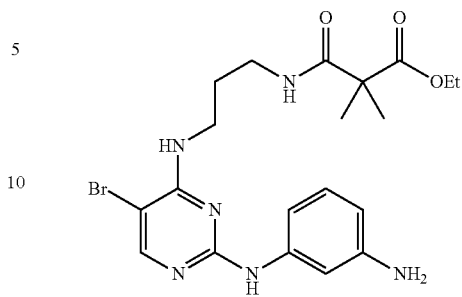

To a stirred solution of 5 (11.7 g, 23 mmol) in ethyl acetate (120 mL) was added stannous chloride (26 g, 115 mmol) in portions. Then the reaction mixture was refluxed for 3 h. It was cooled to r.t., diluted with ethyl acetate and washed with sodium bicarbonate solution. Filtered to remove the insolubles; the filtrate was washed with brine, dried over anhydrous Na$_2$SO$_4$ and concentrated to obtain compound 6 as pale brown viscous oil (9.98 g, 90.6%).

Step-7: Intermediate A

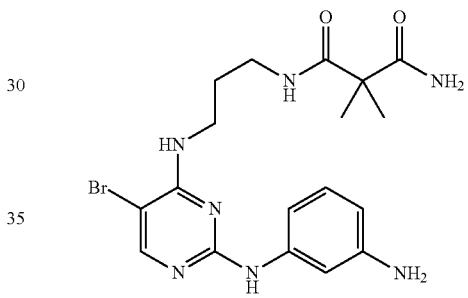

To a solution of 6 (9.98 g, 20.8 mmol) in dry methanol (50 mL) at 0° C. was added saturated methanolic ammonia (50 mL) in a sealed tube. Then the reaction mixture was heated at 80° C. for 4 days. The reaction mixture was concentrated and the crude product obtained was purified by column chromatography (SiO$_2$, 4% methanol in chloroform) to obtain Intermediate A as white solid (6.2 g, 66%). MS m/z: 450.1, 452.0 (M+H$^+$).

Preparation of Intermediate B

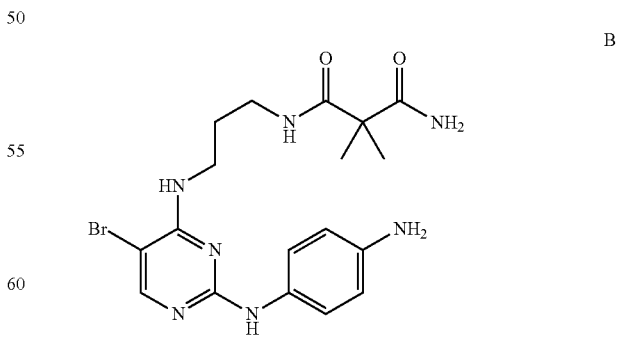

Intermediate B was prepared similarly following the synthetic procedures described for Intermediate A, except using 4-nitroaniline in step 5. MS m/z: 450.1, 452.0 (M+H$^+$).

In similar fashion, Intermediate C and Intermediate D were prepared:

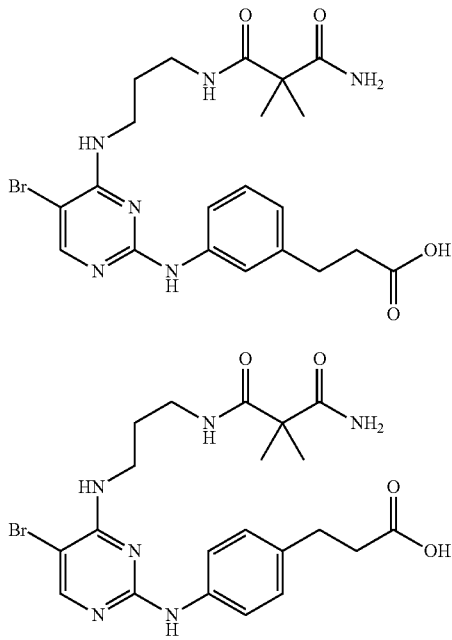

Example 166

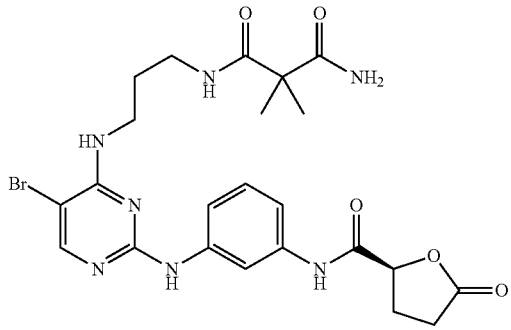

XI-52

To a solution of intermediate A (0.5 g, 1.11 mmol), (S)-5-oxotetrahydrofuran-2-carboxylic acid (0.29 g, 2.23 mmol) and DIPEA (0.3 ml, 1.72 mmol) in dichloromethane (2.5 ml) at 0° C. was added T3P (2-Propanephosphonic acid anhydride, 50% solution in ethyl acetate, 1.8 ml, 2.83 mmol) and the reaction mixture was stirred at room temperature for 16h. The reaction mixture was directly adsorbed on basic alumina and subjected to column chromatography (eluted with dichloromethane). The residue obtained after evaporating the column fractions was treated with sodium bicarbonate solution and extracted with dichloromethane. The organic layer was dried over sodium sulphate and concentrated to obtain pale yellow solid. The product was further washed with diethyl ether and dried under vacuum to obtain the title compound as pale yellow solid (0.13 g, 20.8%).

$^1$H NMR (DMSO-$d_6$): δ=1.28 (s, 6H), 1.65 (m, 2H), 2.22 (m, 1H), 2.54 (m, 3H), 3.11 (m, 2H), 3.41 (m, 2H), 5.06 (m, 1H), 7.08-7.21 (m, 5H), 7.45 (m, 1H), 7.64 (t, J=6 Hz, 1H), 7.99 (s, 1H), 8.03 (s, 1H), 9.34 (s, 1H), 10.18 (s, 1H); LCMS: m/e: 562.0, 564.0 (M+1).

Example 167

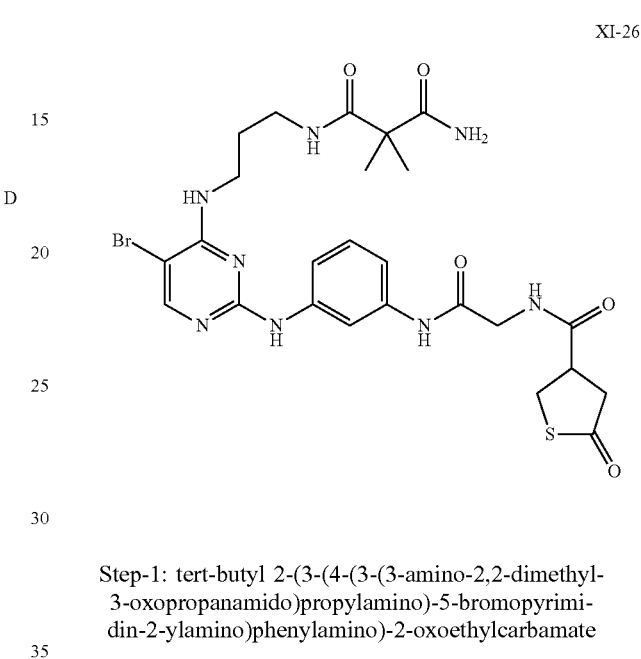

XI-26

Step-1: tert-butyl 2-(3-(4-(3-(3-amino-2,2-dimethyl-3-oxopropanamido)propylamino)-5-bromopyrimidin-2-ylamino)phenylamino)-2-oxoethylcarbamate

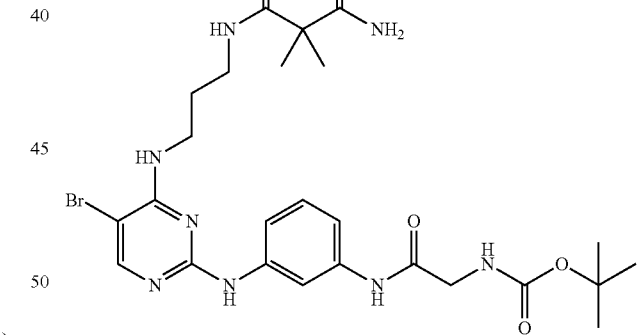

Intermediate A (102 mg, 0.23 mmoL), Boc-glycine (44 mg, 0.25 mmoL) was dissolved in DMF (1 mL). Hydroxybenzotriazole (38 mg, 0.25 mmoL) was added followed by N-ethyl-N$^{1'}$-(3-dimethylaminopropyl)carbodiimide hydrochloride salt (48 mg, 0.25 mmoL) and N-methyl morpholine (75 uL, 0.68 mmoL). Stir at room temperature for 1h, partition with saturated Sodium bicarbonate solution (2 mL) and ethyl acetate (5 mL). The layers were separated and the organic layer was dried over sodium sulfate; filtration and the solvent was removed via rotary evaporation gave a yellow oil 164 mg. LC/MS: RT=2.27 min, m/e 607.0/609.2 (M+1).

Step-2: N1-(3-(2-(3-(2-aminoacetamido)phe-nylamino)-5-bromopyrimidin-4-ylamino)propyl)-2,2-dimethylmalonamide (HCl salt)

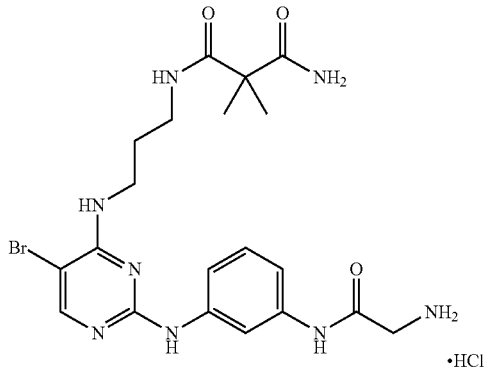 [SMILES: CC(C)(C(N)=O)C(=O)NCCCNc1nc(Nc2cccc(NC(=O)CN)c2)ncc1Br ; Cl]

To a solution of tert-butyl 2-(3-(4-(3-(3-amino-2,2-dimethyl-3-oxopropanamido)propylamino)-5-bromopyrimidin-2-ylamino)phenylamino)-2-oxoethylcarbamate (164 mg, 0.27 mmol) in DCM (5 mL) was added HCl (4N in dioxane 1 mL). Stir overnight at rt; remove solvent via rotary evaporation to give a white solid 170 mg. LC/MS: RT=2.13 min, m/e: 507.1/509.1 (M+1).

Step-3: XI-26

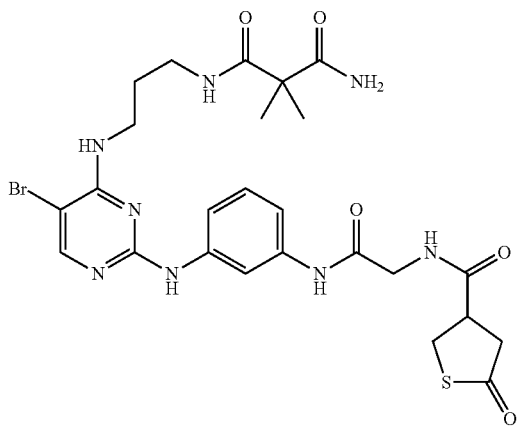 [SMILES: CC(C)(C(N)=O)C(=O)NCCCNc1nc(Nc2cccc(NC(=O)CNC(=O)C3CSC(=O)C3)c2)ncc1Br]

N1-(3-(2-(3-(2-aminoacetamido)phenylamino)-5-bromopyrimidin-4-ylamino)propyl)-2,2-dimethylmalonamide (HCl salt from step 2) (31 mg, 0.06 mmol) was charged in DMF (500 uL). To this was added 5-oxotetrahydrothiophene-3-carboxylic acid (8 mg, 0.06 mmoL), DIPEA (40 uL, 0.23 mmoL), and HATU (22 mg, 0.06 mmoL) and stirred for 30 min at room temperature. The mixture was purified directly using prep HPLC to give a white solid 9 mg as the TFA salt LC/MS: RT=2.02 m/e 635.1/637.0 (M+1).

Example 168

XI-41

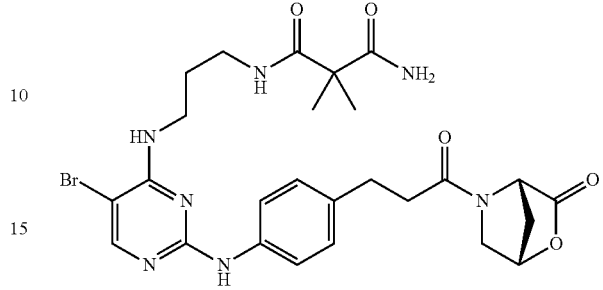

To a solution of intermediate D (125 mg, 0.25 mmol), HATU (0.50 mmol) and DIPEA (excess) in DMF was added (1S,4S)-2-oxa-5-azabicyclo[2.2.1]heptan-3-one (TFA salt, 0.50 mmol) at room temperature for 16h. After work-up, the crude product was obtained as a gummy material (125 mg, LCMS purity ~58%). The title compound was obtained after purification over preparative HPLC (20 mg). LCMS: m/e: 599.6, 601.6 (M−1).

In similar fashion, the compounds in the following table were made according to the procedures described above and from an appropriate intermediate A, B, C, or D.

| Compound Structures | MS (M + 1) | From Intermediate |
|---|---|---|
| XI-21 | 578.1/580.0 | A |
| XI-22 | 635.1/637.0 | A |
| XI-23 | 578.1/580.0 | A |
| XI-24 | 635.1/637.0 | A |
| XI-25 | 626.1/628.0 | A |
| XI-26 | 635.1/637.0 | A |
| XI-27 | 578.1/580.0 | A |
| XI-28 | 617.1/619.0 | A |
| XI-29 | 588.2/590.1 | A |
| XI-30 | 602.1/604.0 | A |
| XI-31 | 561.0/563.1 | A |
| XI-32 | 691.0/693.2 | A |
| XI-33 | 660.2/662.1 | A |
| XI-34 | 649.0/651.0 | A |
| XI-35 | 624.1/626.1 | B |
| XI-36 | 623.6/625.6 (M−1) | A |
| XI-37 | — | A |
| XI-38 | 619.2/621.2 | A |
| XI-39 | 504.1/506.1 | B |
| XI-40 | 602.1/604.1 | D |
| XI-41 | 599.6/601.6 (M−1) | D |
| XI-42 | 562.1/564.1 | B |
| XI-43 | 562.1/564.1 | B |
| XI-44 | 602.1/604.1 | C |
| XI-45 | 602.1/604.1 | C |
| XI-46 | 532.0/534.0 | A |
| XI-47 | 648.1/650.0 | A |
| XI-48 | 645.0/647.0 | A |
| XI-49 | 645.0/647.0 | A |
| XI-50 | 562.0/564.0 | A |
| XI-51 | 547.0/549.0 | A |
| XI-52 | 562.0,564.0 | A |
| XI-53 | 504.2/506.2 | A |
| XI-55 | 603.2/605.2 | A |
| XI-56 | 1202.4/1204.3 | A |
| XI-57 | 716.1/718.0 | A |
| XI-58 | 627.2/629.1 | A |
| XI-59 | 590.0/592.2 | A |

Example 169
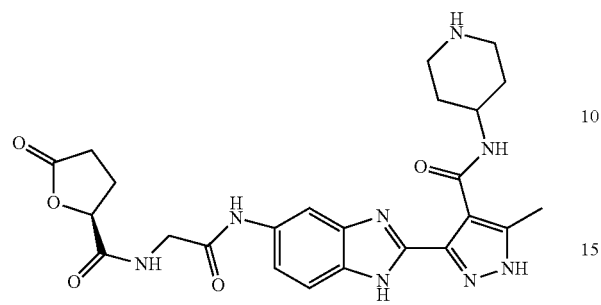
Example 170
Synthetic Scheme for Intermediate E:
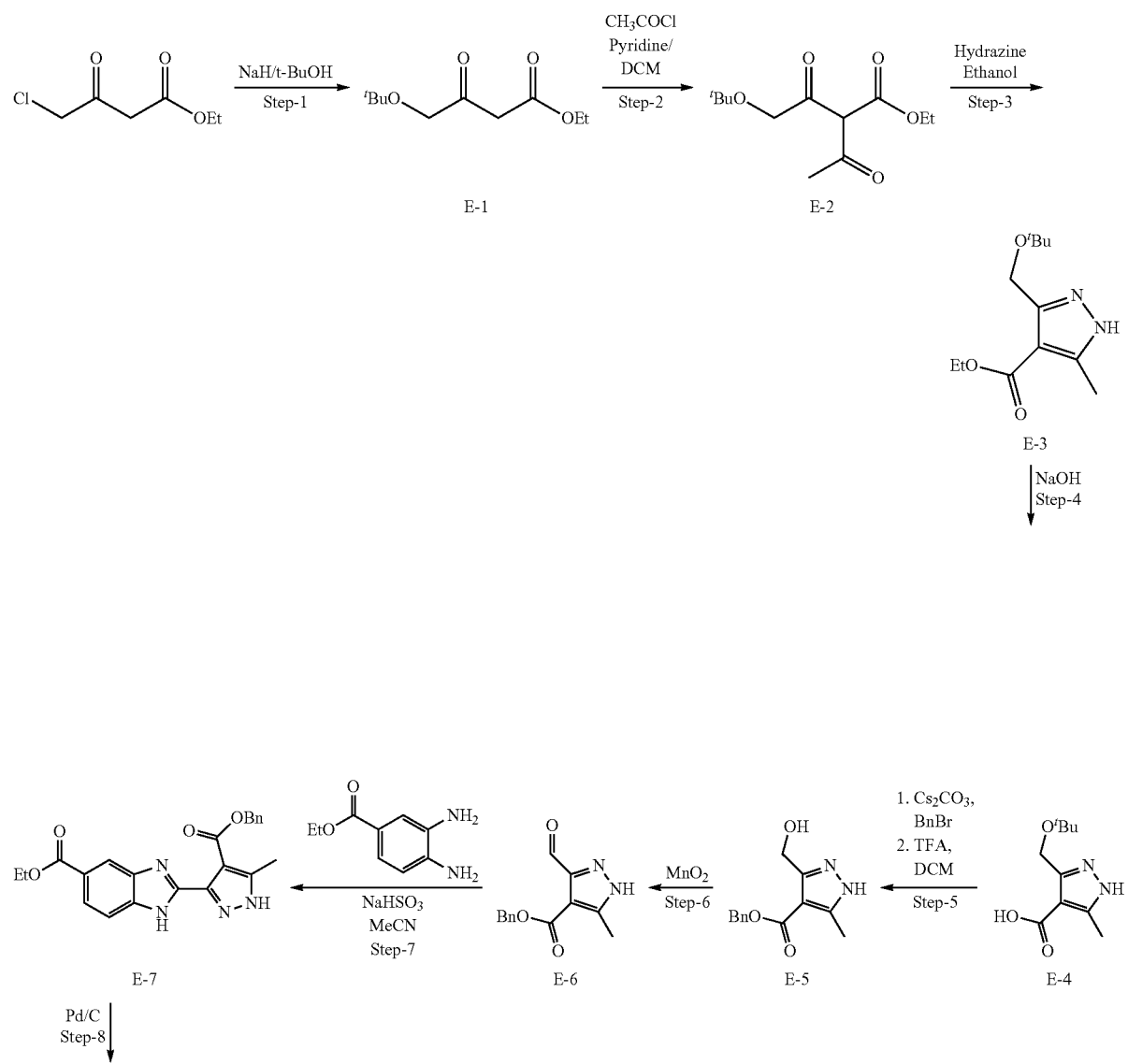

-continued

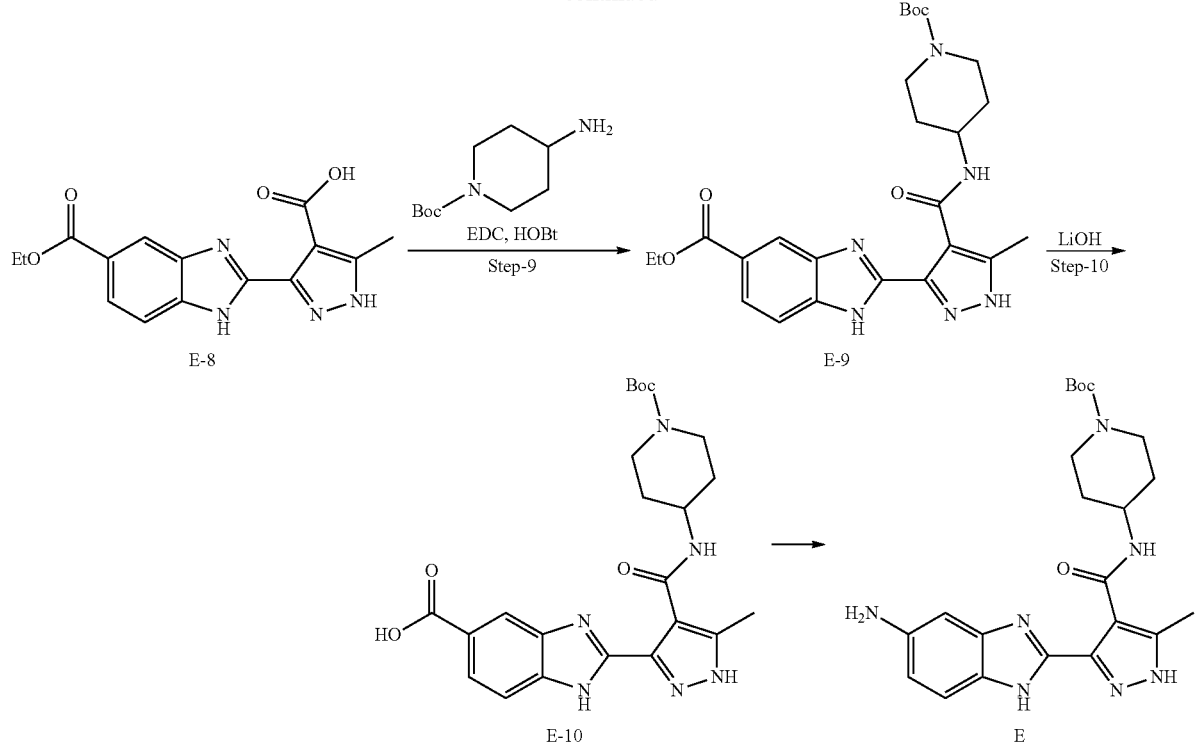

Step-1: Preparation of Ethyl 4-tert-butoxy-3-oxobutanoate (E-1)

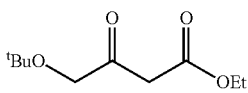

To a suspension of NaH (39 g, 1.61 mmol) in DMF (200 mL) was added Ethyl 4-chloro-3-oxobutanoate (50 g, 0.303 mmol) slowly drop wise at 0° C., followed by t-BuOH (58 mL, 0.607 mmol) and stirred for 14 h at ambient temperature. After completion of the reaction, reaction mixture was acidified up to pH=4 to 5 and diluted with ethyl acetate, washed with water and brine solution, dried over $Na_2SO_4$ and evaporated. The crude compound was purified by column chromatography [silica gel (60-120 mesh), 7% ethyl acetate in hexane] to afford compound E-1 as a yellow oily liquid (27 g, 45.7%). TLC System: 5% Ethyl acetate in hexane, ($R_f$): 0.4. $^1$H NMR (CDCl3): □=1.20 (s, 9H), 1.29 (t, 3H), 3.55 (s, 2H), 4.01 (s, 2H), 4.20 (q, 2H).

Step-2: Preparation of Ethyl 2-acetyl-4-tert-butoxy-3-oxobutanoate (E-2)

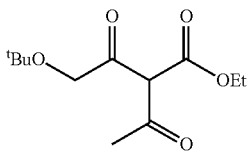

To a solution of Ethyl 4-tert-butoxy-3-oxobutanoate (75 g, 0.37 mmol) in DCM (300 mL) was added pyridine (292 mL, 4.455 mmol) followed by acetyl chloride (30 mL, 0.44 mmol) and $MgCl_2$ (17.5 g, 0.185 mmol) at 0° C. and stirred for 16h at room temperature. The reaction mixture was poured into ethyl acetate, washed with water, dilute HCl and brine solution to afford compound E-2 (40 g, 44%) as a pale yellow liquid. ($R_f$):0.5, TLC System: 10% Ethyl acetate in hexane.

Step-3: Preparation of Ethyl 3-(tert-butoxymethyl)-5-methyl-1H-pyrazole-4-carboxylate (E-3)

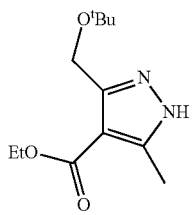

To a solution of Ethyl-2-acetyl-4-tert-butoxy-3-oxobutanoate (26 g, 0.106 mmol) in glacial acetic acid (100 mL) was added hydrazine hydrate (6.1 g, 0.12 mmol) drop wise at 5-10° C. and stirred for 30 min. After completion of the reaction, reaction mixture was neutralized with saturated $NaHCO_3$, extracted with ethyl acetate and washed with $NaHCO_3$, brine solution, dried over $Na_2SO_4$ and evaporated. The crude compound was purified by column chromatography (Silica gel (60-120), 27% ethyl acetate in hexane) to afford compound E-3 (8 g, 32%) as a pale yellow solid. ($R_f$): 0.2, TLC System: 10% Ethyl acetate in hexane. $^1$H NMR (CDCl3): ☐=1.28 (s, 9H), 1.35 (t, 3H), 2.50 (s, 3H), 4.30 (q, 2H), 4.78 (s, 2H), 7.60 (br, 1H).

Step-4: Preparation of 3-(Tert-butoxymethyl)-5-methyl-1H-pyrazole-4-carboxylic acid (E-4)

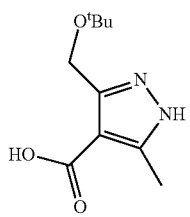

To a solution of Ethyl 3-(tert-butoxymethyl)-5-methyl-1H-pyrazole-4-carboxylate (19 g, 0.07 mmol) in ethanol (130 mL) was added 10% NaoH (31 g, 0.79 mmol) solution and reflux for 16h at 82° C. After completion of the reaction, reaction mixture was acidified, adjusted to pH<1 and filtered the solid to afford compound E-4 (14 g, 87%) as a colorless solid. (R$_f$): 0.5, TLC System: 10% Methanol in chloroform. $^1$H NMR (DMSO-d$_6$): ☐=1.20 (s, 9H), 2.31 (s, 3H), 4.54 (s, 2H), 12.6 (br, 2H).

Step-5: Preparation of Benzyl 3-(hydroxymethyl)-5-methyl-1H-pyrazole-4-carboxylate (E-5)

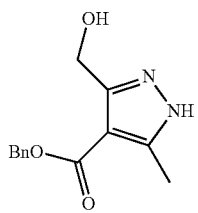 [SMILES: Cc1[nH]nc(CO)c1C(=O)OCc1ccccc1]

To a 3-(Tert-butoxymethyl)-5-methyl-1H-pyrazole-4-carboxylic acid (5 g, 0.0235 mmol) in methanol (30 mL) was added Cs$_2$CO$_3$ (7.66 g, 0.23 mmol) and stirred for 1h at ambient temperature, then methanol was removed completely and to this DMF (25 mL) was added followed by benzyl bromide (4.03 g, 0.023 mmol) under N$_2$ atmosphere and stirred for 4h at room temperature. After completion of the reaction, reaction mixture was diluted with ethyl acetate, washed with water, 1N HCl, NaHCO$_3$ and brine solution, dried over Na$_2$SO$_4$ and evaporated under reduced pressure. The crude compound was purified by column chromatography (silica gel (60-120), 3% Methanol in chloroform). The obtained crude compound was treated with TFA at ambient temperature for 24h. Then the reaction mixture was concentrated and triturated with pentane to afford compound E-5 (1.8 g, 37%) as a colorless solid. (R$_f$): 0.6, TLC System: 10% Methanol in chloroform.

Step-6: Preparation of Benzyl 3-formyl-5-methyl-1H-pyrazole-4-carboxylate (E-6)

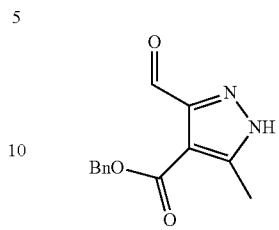

To a stirred solution of Benzyl3-(hydroxymethyl)-5-methyl-1H-pyrazole-4-carboxylate (8.5 g, 0.034 mmol) in Dimethoxy ethane (200 mL) was added MnO$_2$ (29.7 g) and heated to 80° C. for 2h. After completion of the reaction, reaction mixture was filtered through celite bed and concentrated. The obtained crude compound was triturated with pentane to afford compound E-6 (7 g, 83%) as a gray solid. (R$_f$): 0.6, TLC System: 40% ethyl acetate in hexane.

Step-7: Preparation of Ethyl 2-(4-(benzyloxycarbonyl)-5-methyl-1H-pyrazol-3-yl)-1H-benzo[d]imidazole-5-carboxylate (E-7)

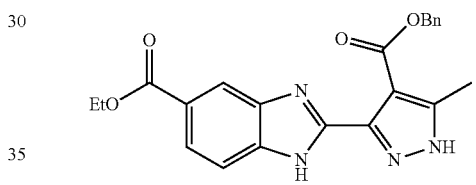

To a stirred solution of Ethyl 3,4-diaminobenzoate (3.8 g, 0.022 mmol) In Acetonitrile (100 mL) was added NaHSO$_4$ (3.61 g, 0.43 mmol) and heated to reflux, then Benzyl 3-formyl-5-methyl-1H-pyrazole-4-carboxylate (7 g, 0.0286 mmol) was added slowly and maintained the same temperature for 3h. After completion of the reaction, reaction mixture was concentrated and diluted with ethyl acetate, washed with water, dried over Na$_2$SO$_4$ and concentrated. The obtained crude compound was triturated with diethyl ether to afford compound E-7 (5.5 g, 43.5%) as a white solid. (R$_f$): 0.7, TLC System: 10% Ethyl acetate in hexane. LCMS: m/e: 405.0 (M+1).

Step-8: Preparation of 3-(5-(Ethoxycarbonyl)-1H-benzo[d]imidazol-2-yl)-5-methyl-1H-pyrazole-4-carboxylic acid (E-8)

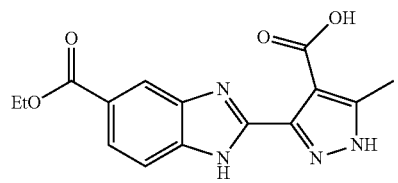 [SMILES: CCOC(=O)c1ccc2[nH]c(-c3n[nH]c(C)c3C(=O)O)nc2c1]

To a solution of Ethyl 2-(4-(benzyloxycarbonyl)-5-methyl-1H-pyrazol-3-yl)-1H-benzo[d]imidazole-5-carboxylate (5.5 g, 13.6 mmol) in THF:MeOH (1:1, 100 mL)

was added 10% Pd/C (1g) and stirred for 16h at 100 psi pressure of hydrogen at rt. After completion of the reaction, reaction mixture was filtered through celite bed and concentrated. The obtained crude compound was purified by triturating with diethyl ether to afford compound E-8 (3 g, 71%) as a brownish solid. ($R_f$): 0.1, TLC System: 10% Methanol in chloroform. LCMS: m/e: 315.0 (M+1).

Step-9: Preparation of Ethyl 2-(4-(1-(tert-butoxycarbonyl)piperidin-4-ylcarbamoyl)-5-methyl-1H-pyrazol-3-yl)-1H-benzo[d]imidazole-5-carboxylate (E-9)

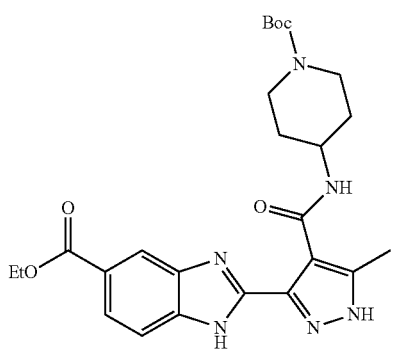 [SMILES: Cc1[nH]nc(-c2nc3cc(C(=O)O)ccc3[nH]2)c1C(=O)NC1CCN(C(=O)OC(C)(C)C)CC1]

To a solution of 3-(5-(Ethoxycarbonyl)-1H-benzo[d]imidazol-2-yl)-5-methyl-1H-pyrazole-4-carboxylicacid (500 mg, 0.00159 mol) in DMF (2 mL) was added tert-butyl 4-aminopiperidine-1-carboxylate (637 mg, 0.00318 mol) followed by EDC.HCl (606 mg, 0.00318 mol), HOBT (434 mg, 0.00138 mol), DIPEA (404 g, 0.00318 mol) and stirred for 2h at room temperature. After completion of the reaction, reaction mixture was poured into water and stirred for 1 hour, the solid precipitated was filtered off and dried over $Na_2SO_4$. The obtained crude compound was purified by column chromatography (silica gel(60-120 mesh), 3% methanol in chloroform) to afford compound E-9 (600 mg, 76%) as white solid. ($R_f$): 0.4, TLC System: 10% Methanol in chloroform. LCMS: m/e: 497.1 (M+1).

Step-10: Preparation of 2-(4-(1-(tert-butoxycarbonyl)piperidin-4-ylcarbamoyl)-5-methyl-1H-pyrazol-3-yl)-1H-benzo[d]imidazole-5-carboxylic acid (E-10)

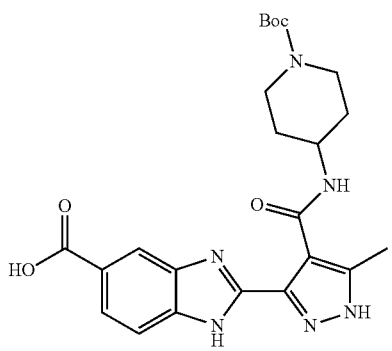

To a solution of Ethyl 2-(4-(1-(tert-butoxycarbonyl)piperidin-4-ylcarbamoyl)-5-methyl-1H-pyrazol-3-yl)-1H-benzo[d]imidazole-5-carboxylate (600 mg, 1.909 mmol) in THF (15 mL) was added NaOH (484 mg, 12.9 mmol) and heated reflux for 16h. After completion of the reaction, reaction mixture was concentrated and diluted with water and acidified with dil HCl to pH=4-5, the solid precipitated was filtered off and dried under vacuum to afford compound E-10 (480 mg, 42.5%) as a white solid. ($R_f$): 0.2, TLC System: 10% Methanol in chloroform with $NH_3$. LCMS: m/e: 469.1 (M+1).

Step-11: Preparation of Tert-butyl 4-(5-methyl-3-(5-methyl-1H-benzo[d]imidazol-2-yl)-1H-pyrazole-4-carboxamido)piperidine-1-carboxylate (E)

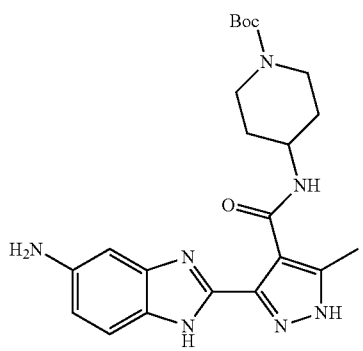 [SMILES: Cc1[nH]nc(-c2nc3cc(N)ccc3[nH]2)c1C(=O)NC1CCN(C(=O)OC(C)(C)C)CC1]

To a solution of 2-(4-(1-(tert-butoxycarbonyl)piperidin-4-ylcarbamoyl)-5-methyl-1H-pyrazol-3-yl)-1H-benzo[d]imidazole-5-carboxylic acid (450 mg, 0.9615 mol) in toluene (8 mL) was added DPPA (0.318 g, 1.44 mmol) followed by DIPEA (183 mg, 1.44 mmol) and stirred for 2h at ambient temperature, then benzyl alcohol was added and heated to reflux for 16h. After completion of the reaction, reaction mixture was concentrated. The obtained crude compound was purified by column chromatography (silica gel (60-120 mesh), 3% methanol in chloroform with $NH_3$) to afford the cbz-protected compound E (270 mg, 49%) as an off white solid. ($R_f$): 0.4, TLC System: 10% Methanol in chloroform with NH3. LCMS: m/e: 574.1 (M+1).

The above compound was added to a mixture of THF: MeOH (1:1, 20 mL) followed by 10% Pd/C (27 mg) and stirred for 16h at 100 PSI pressure of hydrogen. After completion of the reaction, reaction mixture was filtered through celite bed and concentrated. The obtained crude compound was triturated with diethyl ether to afford compound E (130 mg, 63%) as a black solid. ($R_f$): 0.1, TLC System: 10% Methanol in chloroform with $NH_3$. LCMS: m/e: 440.1 (M+1).

Example 171

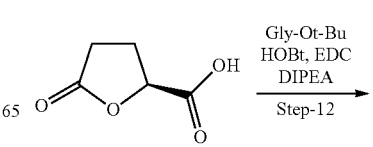

-continued

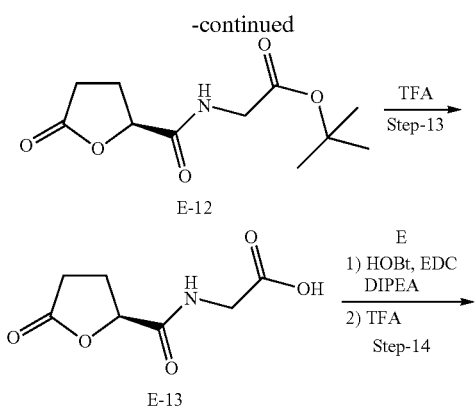

E-12

E-13

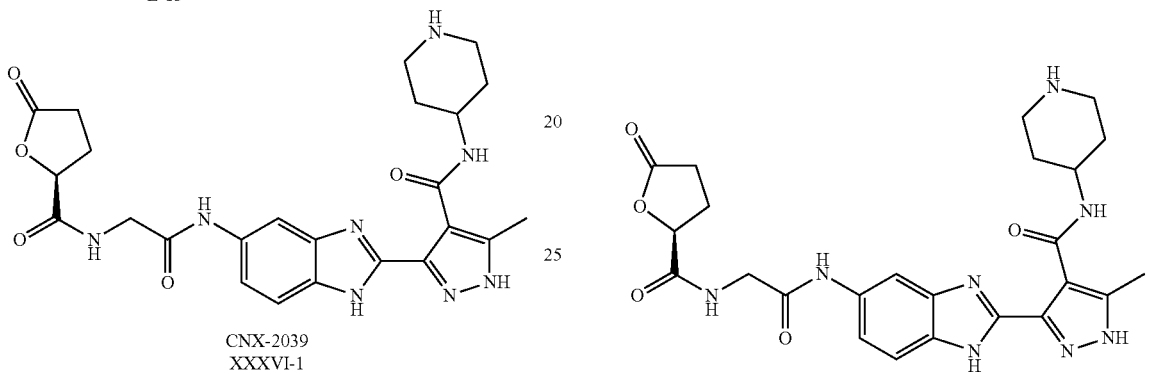

CNX-2039
XXXVI-1

Step-12: Preparation of (S)-tert-butyl 2-(5-oxotetrahydrofuran-2-carboxamido)acetate (E-12)

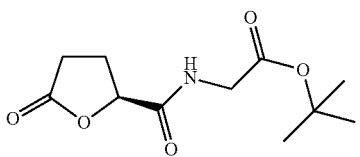 [SMILES: CC(C)(C)OC(=O)CNC(=O)[C@@H]1CCC(=O)O1]

To a solution of (S)-5-Oxotetrahydrofuran-2-carboxylic acid (300 mg, 00230 mol) in DMF (4 ml) was added HATU (2.622 g, 0.0069 mol), DIPEA (584 mg, 0.0046 mol), followed by Glycine tert butyl ester (578 mg, 0.0034 mol) and stirred for 20 min at ambient temperature. After completion of the reaction, reaction mixture was poured into water, extracted with ethyl acetate, dried and concentrated to afford compound E-12 (120 mg, 21%) as a pale yellow liquid. (R$_f$): 0.8, System: 10% acetone in chloroform. LCMS: m/e: 242.1 (M−1).

Step-13: Preparation of (S)-2-(5-oxotetrahydrofuran-2-carboxamido)acetic acid (E-13)

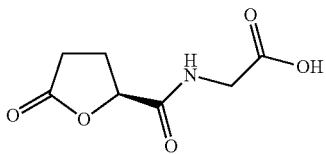 [SMILES: O=C(O)CNC(=O)[C@@H]1CCC(=O)O1]

To a solution of (S)-Tert-butyl 2-(5-oxotetrahydrofuran-2-carboxamido)acetate (120 mg, 0.493 mmol) was treated with TFA (7eq) in DCM (5 ml) for 3h at ambient temperature. After completion of the reaction, DCM was evaporated along with excess of TFA. The obtained crude compound was purified by triturating with diethyl ether to afford compound E-13 (107 mg, 90%) as a pale yellow liquid. (R$_f$): 0.1, TLC System: 10% acetone in chloroform. LCMS: m/e: 186.1 (M−1).

Step-14: Preparation of (S)-5-methyl-3-(5-(2-(5-oxotetrahydrofuran-2-carboxamido)acetamido)-1H-benzo[d]imidazol-2-yl)-N-(piperidin-4-yl)-1H-pyrazole-4-carboxamide (XXXVI-1)

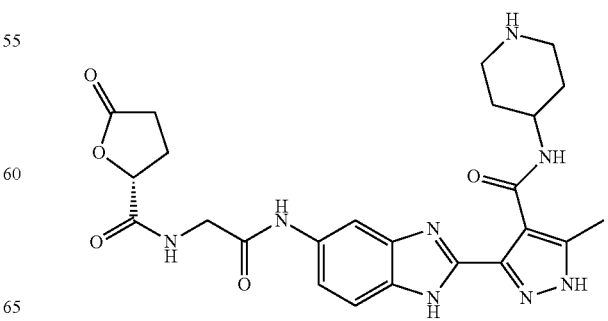

To a solution of (S)-2-(5-oxotetrahydrofuran-2-carboxamido)acetic acid (30 mg, 0.16 mmol) in DMF (2 ml) was added tert-butyl 4-(3-(5-amino-1H-benzo[d]imidazol-2-yl)-5-methyl-1H-pyrazole-4-carboxamido)piperidine-1-carboxylate (70 mg, 0.11 mmol) followed by EDC.HCl (44 mg, 0.23 mmol), HOBt (31 mg, 0.23 mmol) and DIPEA (30 mg, 0.23 mmol), then stirred for 3h at ambient temperature. After completion of the reaction, reaction mixture was poured into water; solid precipitated was filtered off and dried under vacuum. The crude compound was purified by preparative HPLC to afford the Boc-title compound as a solid. The solid was treated with triflouro acetic acid in DCM at RT for 2h to remove the Boc group. The reaction solution was concentrated and the residue was triturated with diethyl ether to afford the title compound as a solid (40 mg, HPLC purity: 93%). LCMS: m/e: 509.0 (M+1).

Example 172

In similar fashion, starting from intermediate E, the following compound was prepared:

(R)-5-methyl-3-(5-(2-(5-oxotetrahydrofuran-2-carboxamido)acetamido)-1H-benzo[d]imidazol-2-yl)-N-(piperidin-4-yl)-1H-pyrazole-4-carboxamide 5.0 mg, HPLC purity: 95%. LCMS: m/e: 509.1 (M+1).

C. PDPK-1 Biological Data

Example 173

Briefly, a 10× stock of PDPK1 enzyme from Invitrogen (P3001) or BPS (40080) or SignalChem (P14-10H), 1.13× ATP (AS001A) and ST28-Sox peptide substrate (KNZ1281C) were prepared in 1× kinase reaction buffer consisting of 20 mM Tris, pH 7.5, 5 mM MgCl2, 1 mM EGTA, 5 mM β-glycerophosphate, 5% glycerol (10× stock, KB002A) and 0.2 mM DTT (DS001A). 5 µL of enzyme were pre-incubated in a Corning (#3574) 384-well, white, non-binding surface microtiter plate (Corning, N.Y.) for 30 min at 25° C. with a 0.5 µL volume of 50% DMSO and serially diluted compounds prepared in 50% DMSO. Kinase reactions were started with the addition of 45 λL of the ST28-Sox peptide substrate and monitored every 71 seconds for 30-60 minutes at λex360/λem485 in a Synergy4 plate reader from BioTek (Winooski, Vt.). At the conclusion of each assay, progress curves from each well were examined for linear reaction kinetics and fit statistics ($R^2$, 95% confidence interval, absolute sum of squares). Post-lag velocity (+10 minutes to 20+ minutes) from each reaction was estimated from the slope of a plot of relative fluorescence units vs time (minutes) and normalized to the no enzyme and no inhibitor control groups for % Inhibition. The resulting inhibition values were then plotted against inhibitor concentration to estimate IC50 from log [Inhibitor] vs Response, Variable Slope model in GraphPad Prism from GraphPad Software (San Diego, Calif.).

[Reagent] used in provisional protocol(s): Invitrogen—[PDPK1]=5-10 nM, [ATP]=5 µM and [ST28-Sox]=5 µM or 10 µM (ATP KMapp=4-6 µM); BPS—[PDPK1]=10-15 nM, [ATP]=5 µM and [ST28-Sox]=10 µM (ATP KMapp=3-5 µM); SignalChem—[PDPK1]=5-10 nM, [ATP]=5 µM and [ST28-Sox]=5 µM or 10 µM (ATP KMapp ND)

Table 6 shows the activity of selected compounds in the PDK1-OMNIA Assays. Compounds having an activity designated as "A" provide an IC50≤10 nM; compounds having an activity designated as "B" provide an IC50>10 nM and ≤100 nM; compounds having an activity designated as "C" provide an IC50>100 nM and ≤1000 nM; compounds having an activity designated as "D" provide an IC50>1000 nM and <10,000 nM; and compounds having an activity designated as "E" provide an IC50≤10,000 nM.

TABLE 6

| Compound Designation | Enzyme/Assay | Inhibition/Modification Designation |
|---|---|---|
| XI-21 | PDK1-OMNIA | A |
| XI-22 | PDK1-OMNIA | A |
| XI-23 | PDK1-OMNIA | B |
| XI-24 | PDK1-OMNIA | B |
| XXXVI-1 | PDK1-OMNIA | |
| XXXVI-2 | PDK1-OMNIA | |
| XI-25 | PDK1-OMNIA | A |
| XI-26 | PDK1-OMNIA | B |
| XI-27 | PDK1-OMNIA | A |
| XI-28 | PDK1-OMNIA | |
| XI-29 | PDK1-OMNIA | B |
| XI-30 | PDK1-OMNIA | B |
| XI-31 | PDK1-OMNIA | B |

TABLE 6-continued

| Compound Designation | Enzyme/Assay | Inhibition/Modification Designation |
|---|---|---|
| XI-32 | PDK1-OMNIA | C |
| XI-33 | PDK1-OMNIA | B |
| XI-56 | PDK1-OMNIA | C |
| Vernalis Reversible | PDK1-OMNIA | B |
| XI-34 | PDK1-OMNIA | B |
| XI-35 | PDK1-OMNIA | |
| XI-36 | PDK1-OMNIA | B |
| XI-37 | PDK1-OMNIA | B |
| XI-38 | PDK1-OMNIA | B |
| XI-39 | PDK1-OMNIA | B |
| XI-40 | PDK1-OMNIA | A |
| XI-41 | PDK1-OMNIA | A |
| XI-42 | PDK1-OMNIA | B |
| XI-43 | PDK1-OMNIA | C |
| XI-44 | PDK1-OMNIA | B |
| XI-45 | PDK1-OMNIA | B |
| XI-46 | PDK1-OMNIA | B |
| XI-47 | PDK1-OMNIA | A |
| XI-48 | PDK1-OMNIA | A |
| XI-49 | PDK1-OMNIA | A |
| XI-50 | PDK1-OMNIA | B |
| XI-51 | PDK1-OMNIA | |
| XI-52 | PDK1-OMNIA | B |
| XI-53 | PDK1-OMNIA | |
| XI-55 | PDK1-OMNIA | A |

K. MASS SPECTROMETRIC Analysis of PDPK-1 Contacted with Compounds of the Invention Example 174

Figure 12:
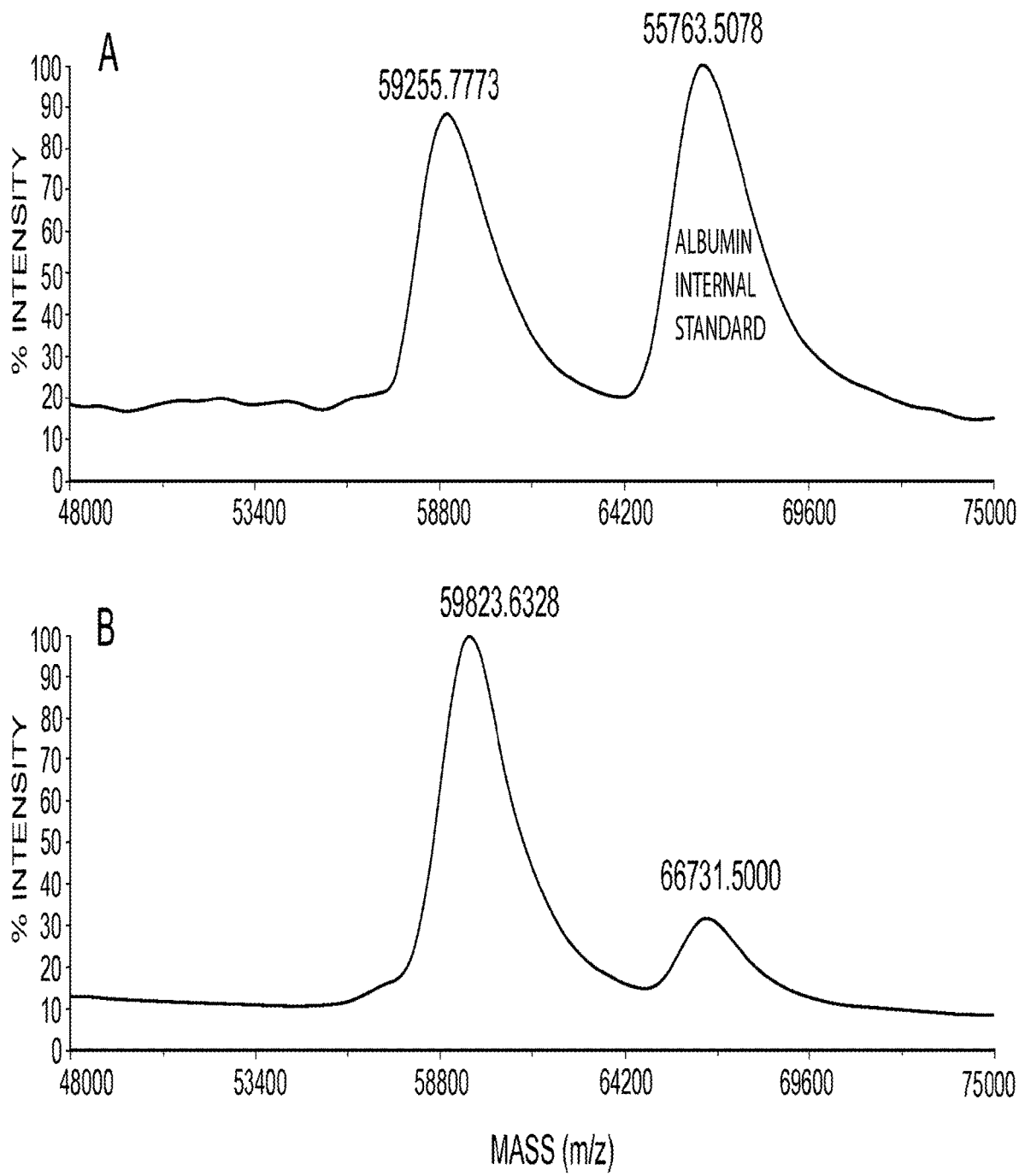
FIG. 12 depicts the mass spectrometric analysis of Compound XI-27 contacted with PDPK-1 (whole protein).

Intact PDPK1 was incubated for 3 hr at a 10-fold excess of compound XI-27 to protein. 3 µL aliquots of the samples were diluted with 10 µL of 0.1% TFA prior to micro C4 Ziptipping directly onto the MALDI target plate using sinapinic acid as the desorption matrix (10 mg/mL in 0.1% TFA:Acetonitrile 50:50). The top panel of FIG. 12 shows mass spectrometric trace of the intact PDPK-1 protein (m/z 59,255 Da). The bottom panel of FIG. 12 shows mass spectrometric trace of PDPK-1 incubated with XI-27 (mw=578.5) for 3 hr (m/z of 59,823), which shows a mass shift of 568 Da, with no m/z of 59255 Da, which indicates complete modification of PDPK1 by XI-27 within 3h.

Figure 13:
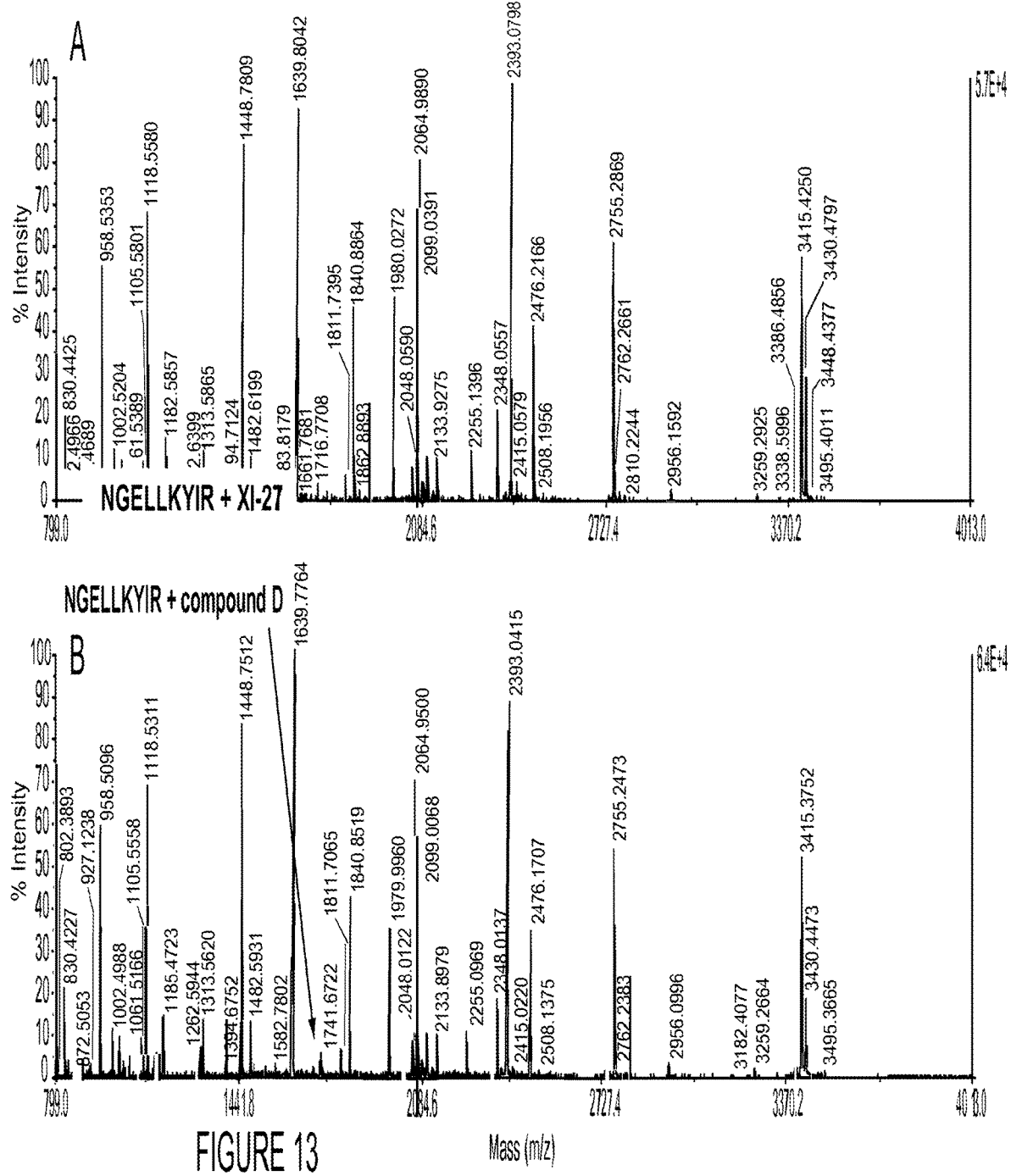
FIG. 13 depicts the mass spectrometric analysis of the trypsin digestion of PDPK-1 (whole protein) contacted with Compound XI-27 identifying the peptide $^{164}$NGELLKYIR$^{172}$ (SEQ ID NO:1).

Compound XI-27 modifies the peptide $^{164}$NGELLKYIR$^{172}$ (SEQ ID NO: 1) on PDPK1, as confirmed by peptide MS analysis after trypsin digestion in solution. Intact PDPK1 (Millipore, 14-452) was incubated for 3 hr at a 10-fold excess of compound D to protein. Following the reaction, approximately 5 µgs of protein was subjected to a standard trypsin solution digestion by reducing the protein with DTT, alkylating thiols with iodoacetamide, adding trypsin (1:20, protease: protein), and incubation at 37° C. for 1.5 hr. After digestion, the peptides were purified using C18 ziptips, spotted on the MALDI target plate with alpha cyano 4-hydroxycinnamic acid as the desorption matrix (10 mg/mL in 0.1% TFA: acetonitrile 50:50), and analyzed in reflectron mode. The top panel of FIG. 13 shows the trypsin digest profile for the control PDPK1 digest. Panel B shows the trypsin digest profile for PDPK1 treated with compound XI-27 prior to digestion. The arrows in FIG. 13 are pointing to a peak at 1,741 Da that corresponds to the mass of 164NGELLKYIR172 (SEQ ID NO: 1) (1,106 Da), compound XI-27 (mw 578.50), and an iodoacetamide (+57) that alkylates the compound at the thiol. The peptide was selected for MSMS analysis to confirm the exact amino acid being modified.

Figure 14:
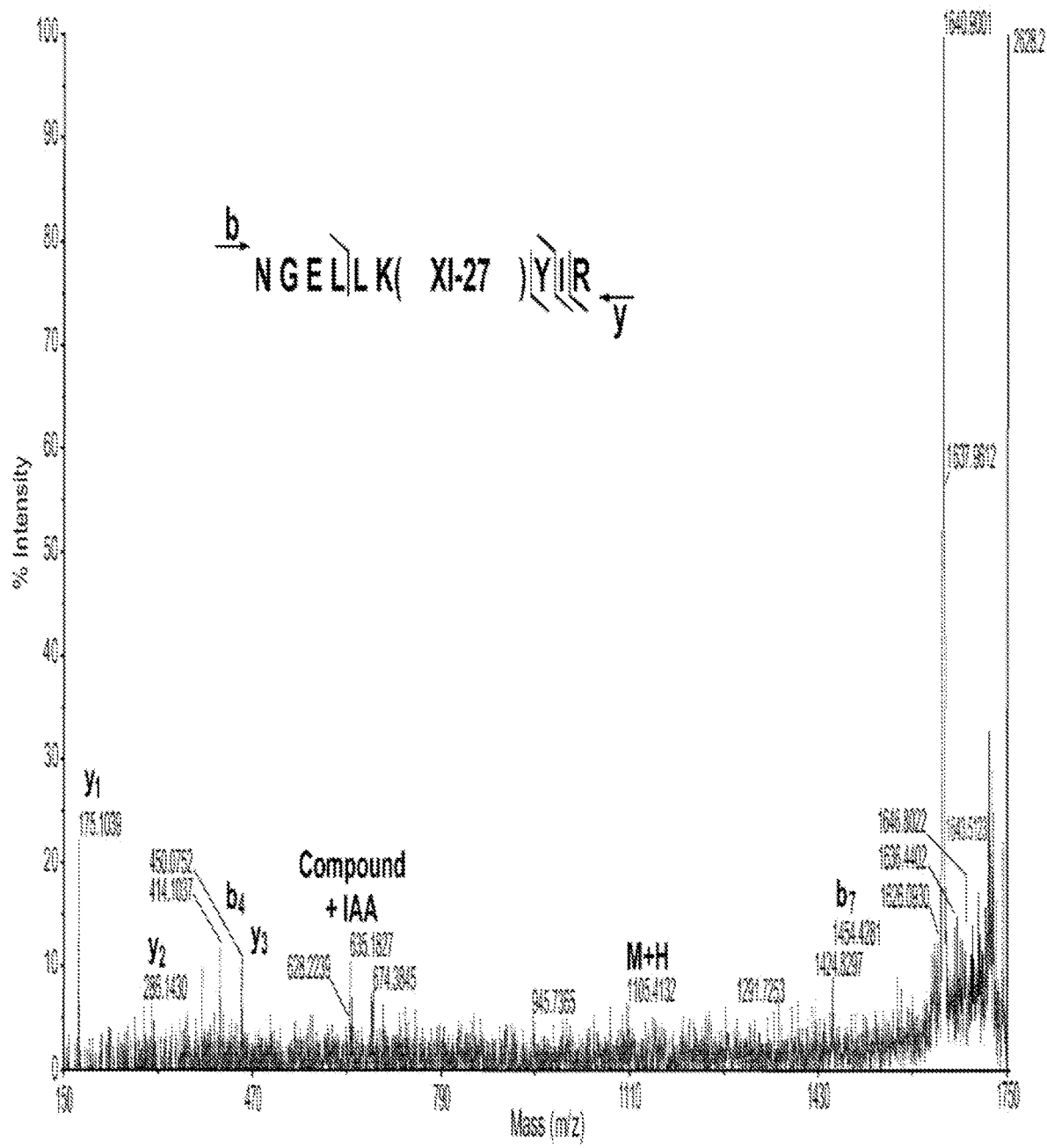
FIG. 14 depicts the MSMS analysis of the peptide $^{164}$NGELLKYIR$^{172}$ (SEQ ID NO:1) modified by XI-27 from the digest depicted in FIG. 13 and identifying K169 as the lysine modified by XI-27.

Compound XI-27 modifies K169 on PDPK1, as confirmed by MSMS analysis. The peptide of interest, 1,741 Da, was selected for MSMS analysis from the compound XI-27 treated PDPK1 trypsin digest. FIG. 14 shows the MSMS spectrum of the peptide 164NGELLKYIR172 (SEQ ID NO: 1) modified by compound XI-27. The alignment of b and y ions confirms that K169 is the amino acid modified by compound XI-27.

Example 175

Figure 15:
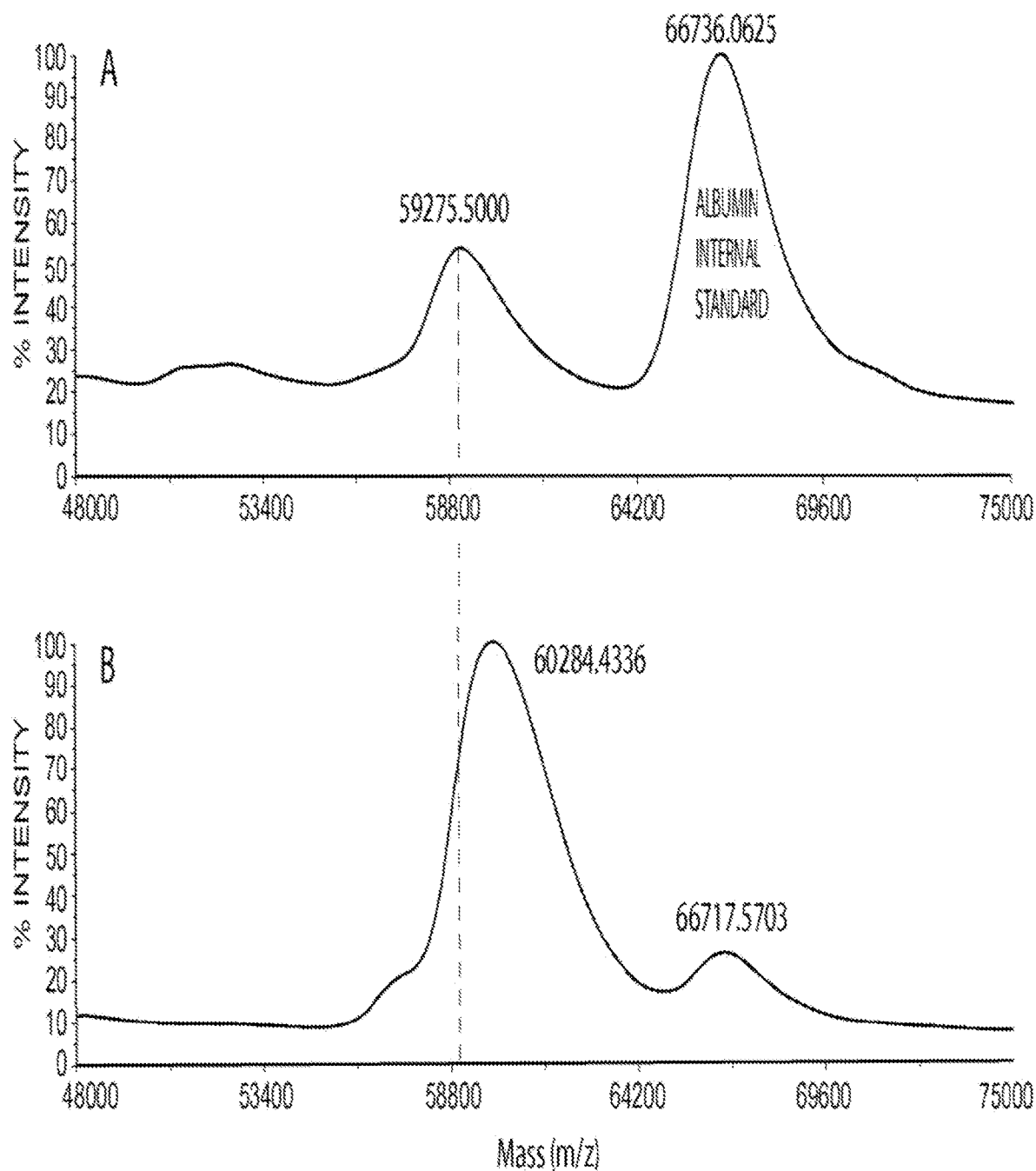
FIG. 15 depicts the mass spectrometric analysis of Compound XI-21 contacted with PDPK-1 (whole protein).

Intact PDPK1 was incubated for 3 hr at a 10-fold excess of compound XI-21 to protein. 3 μL aliquots of the samples were diluted with 10 μL of 0.1% TFA prior to micro C4 Ziptipping directly onto the MALDI target plate using sinapinic acid as the desorption matrix (10 mg/mL in 0.1% TFA:Acetonitrile 50:50). The top panel of FIG. 15 shows the mass spec trace of the intact PDPK1 protein (m/z 59,275 Da). The bottom panel FIG. 15 shows the mass spec trace when PDPK1 was incubated with compound XI-21 (mw=578.50). The centroid mass (m/z=60,284 Da) shows a mass shift of 1,009 Da (175%), indicating complete multiple modification of PDPK1 by compound XI-21.

Figure 16:
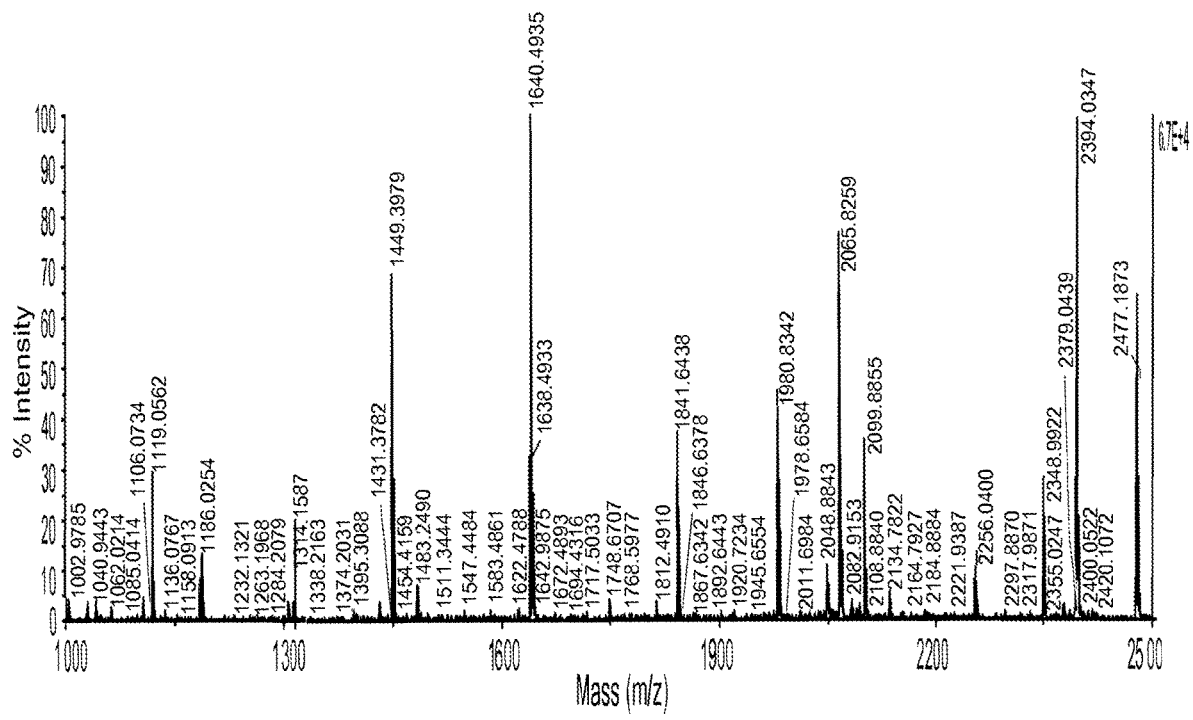
FIG. 16 depicts the mass spectrometric analysis of the trypsin digestion of PDPK-1 (whole protein) contacted with Compound XI-21 identifying three peptides $^{164}$NGELLKYIR$^{172}$ (SEQ ID NO:1), $^{173}$KIGSFDETCTR$^{183}$ (SEQ ID NO:2), and $^{84}$FGKILGEGSFSTVVLAR$^{100}$ (SEQ ID NO:3).
Figure 16:
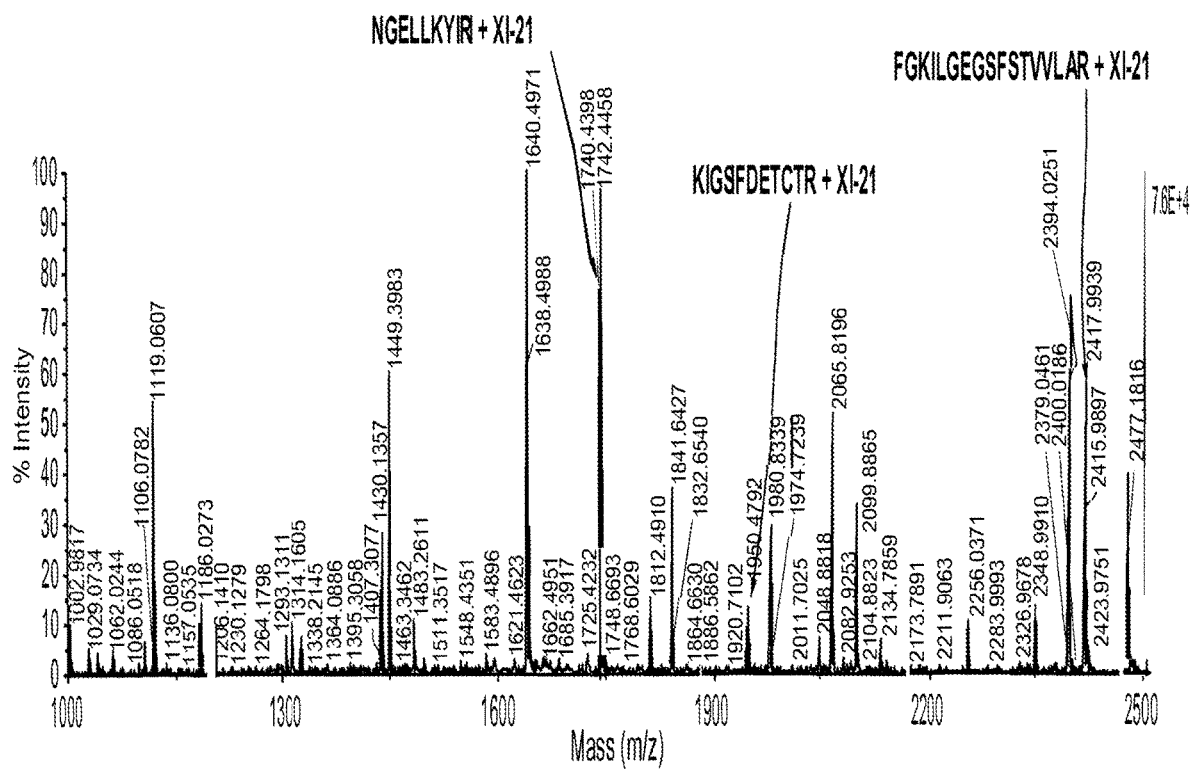

Compound XI-21 modifies three peptides, $^{164}$NGELLKYIR$^{172}$ (SEQ ID NO: 1), $^{173}$KIGSFDETC(IAA)TR$^{183}$ (SEQ ID NO: 182), $^{84}$FGKILGEGSFSTVVLAR$^{100}$ (SEQ ID NO: 3) on PDPK1, as confirmed by peptide MS analysis after trypsin digestion in solution. Intact PDPK1 (Millipore, 14-452) was incubated for 3 hr at a 10-fold excess of compound XI-21 to protein. Following the reaction, approximately 5 μgs of protein was subjected to a standard trypsin solution digestion by reducing the protein with DTT, alkylating thiols with iodoacetamide, adding trypsin (1:20, protease: protein), and incubation at 37° C. for 1.5 hr. After digestion, the peptides were purified using C18 ziptips, spotted on the MALDI target plate with alpha cyano 4-hydroxycinnamic acid as the desorption matrix (10 mg/mL in 0.1% TFA: acetonitrile 50:50), and analyzed in reflectron mode. The top panel of FIG. 16 shows the trypsin digest profile for the control PDPK1 digest. The bottom panel of FIG. 16 shows the trypsin digest profile for PDPK1 treated with compound XI-21 prior to digestion. The arrows in the top panel of FIG. 16 are pointing to a peak at 1,740 Da that corresponds to the mass of $^{164}$NGELLKYIR$^{172}$ (SEQ ID NO: 1) (1,106 Da) and compound XI-21 (mw 578.50), a peak at 1,950 Da that corresponds to the mass of $^{173}$KIGSFDETC(IAA)TR$^{183}$ (SEQ ID NO: 182) (1,313 Da) and compound XI-21 with 2 iodoacetamides, and a peak at 2,417 Da corresponding to the mass of $^{84}$FGKILGEGSFSTVVLAR$^{100}$ (SEQ ID NO: 3) (1,780 Da) with compound XI-21 and iodacetamide. All three peptides were selected for MSMS analysis to confirm the exact amino acid being modified.

Figure 17:
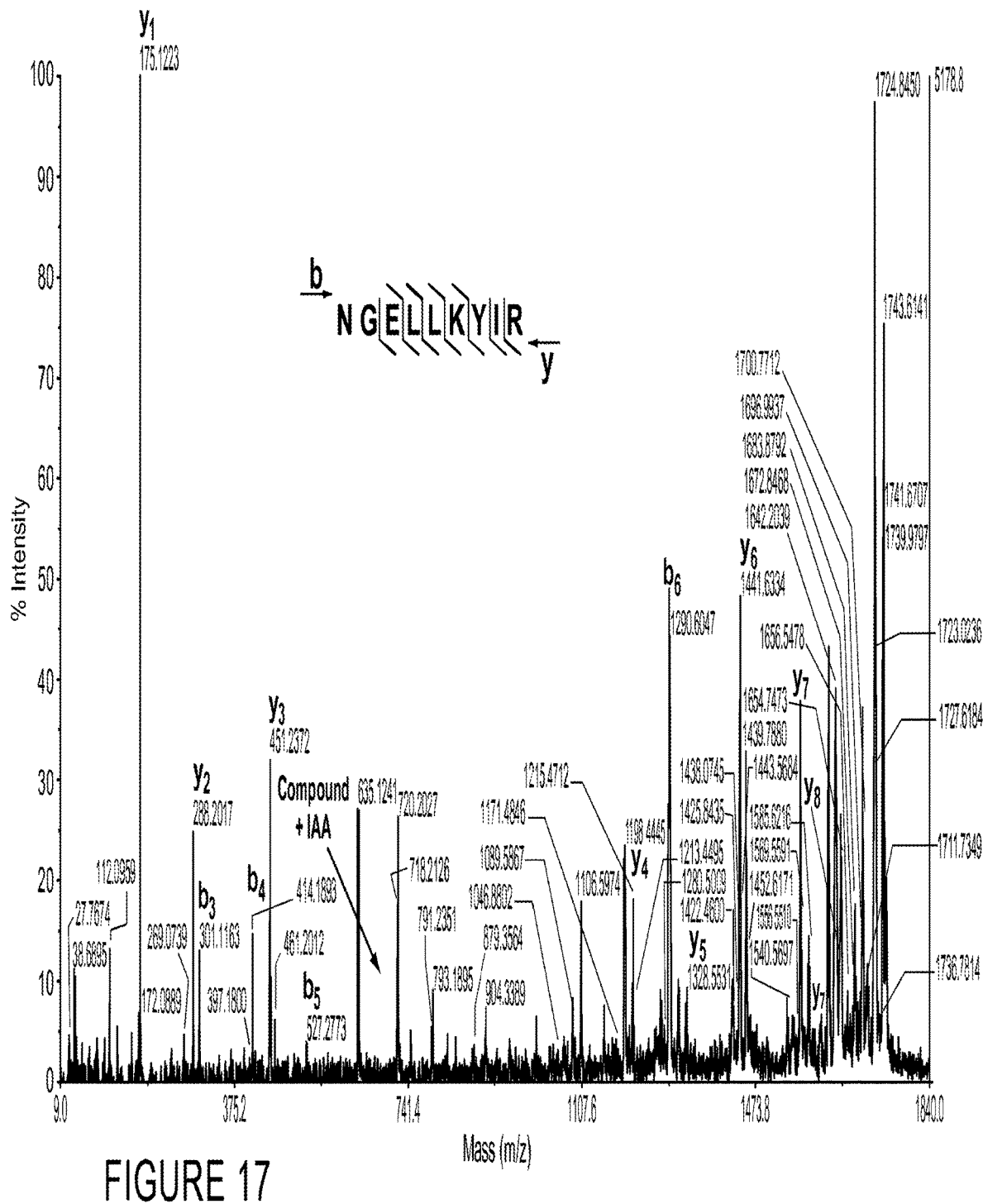
FIG. 17 depicts the MSMS analysis of the peptide $^{164}$NGELLKYIR$^{172}$ (SEQ ID NO:1) from the digest depicted in FIG. 16 and identifying K169 as the lysine modified by XI-21.

Compound XI-21 modifies K169 on PDPK1, as confirmed by MSMS analysis. The peptide of interest, 1,740 Da, was selected for MSMS analysis from the compound XI-21 treated PDPK1 trypsin digest. FIG. 17 shows the MSMS spectrum of the peptide $^{164}$NGELLKYIR$^{172}$ (SEQ ID NO: 1) modified by compound XI-21. The alignment of b and y ions confirms that K169 is the amino acid modified by compound XI-21.

Figure 18:
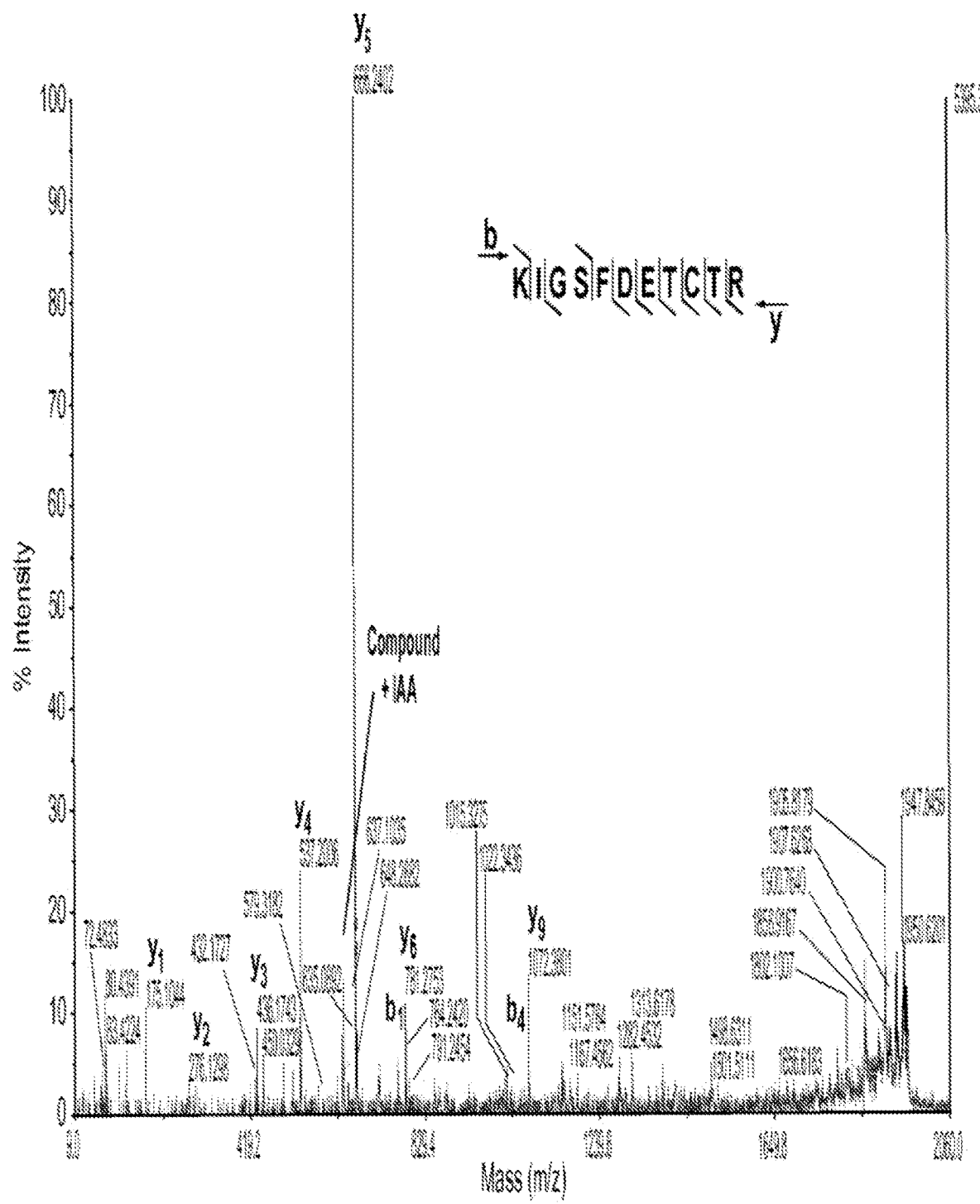
FIG. 18 depicts the MSMS analysis of the peptide $^{173}$KIGSFDETCTR$^{183}$ (SEQ ID NO:2) from the digest depicted in FIG. 16 and identifying K173 as the lysine modified by XI-21.

Compound XI-21 modifies K173 on PDPK1, as confirmed by MSMS analysis. The peptide of interest, 1,950 Da, was selected for MSMS analysis from the compound B treated PDPK1 trypsin digest. FIG. 18 shows the MSMS spectrum of the peptide $^{173}$KIGSFDETCTR$^{183}$ (SEQ ID NO: 2) modified by compound XI-21. The alignment of b and y ions confirms that K173 is the amino acid modified by compound XI-21.

Figure 19:
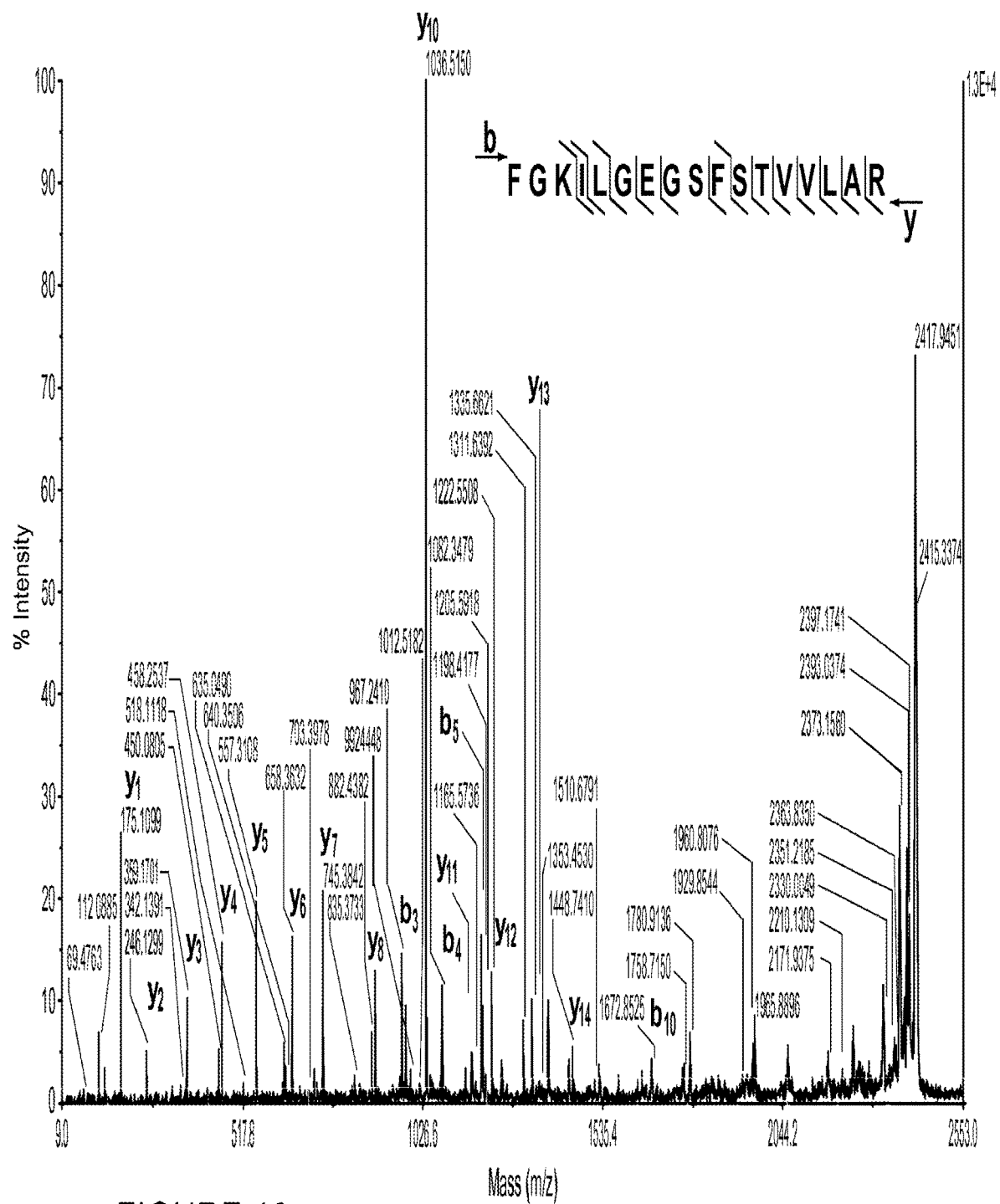
FIG. 19 depicts the MSMS analysis of the peptide $^{84}$FGKILGEGSFSTVVLAR$^{100}$ (SEQ ID NO:3) from the digest depicted in FIG. 16 and identifying K86 as the lysine modified by XI-21.
Figure 20:
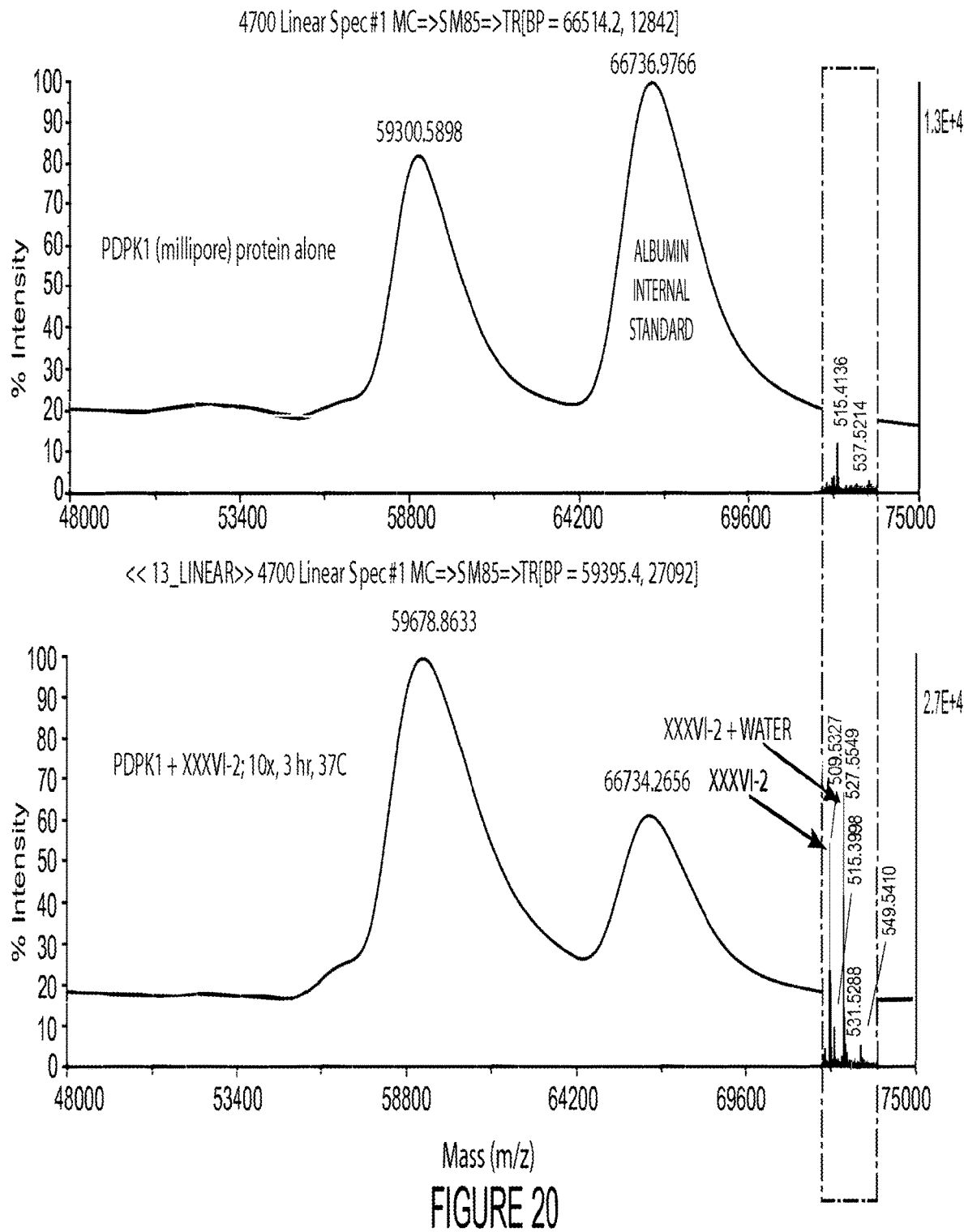
FIG. 20 depicts the mass spectrometric analysis of Compound XXXVI-2 contacted with PDPK-1 (whole protein).
Figure 21:
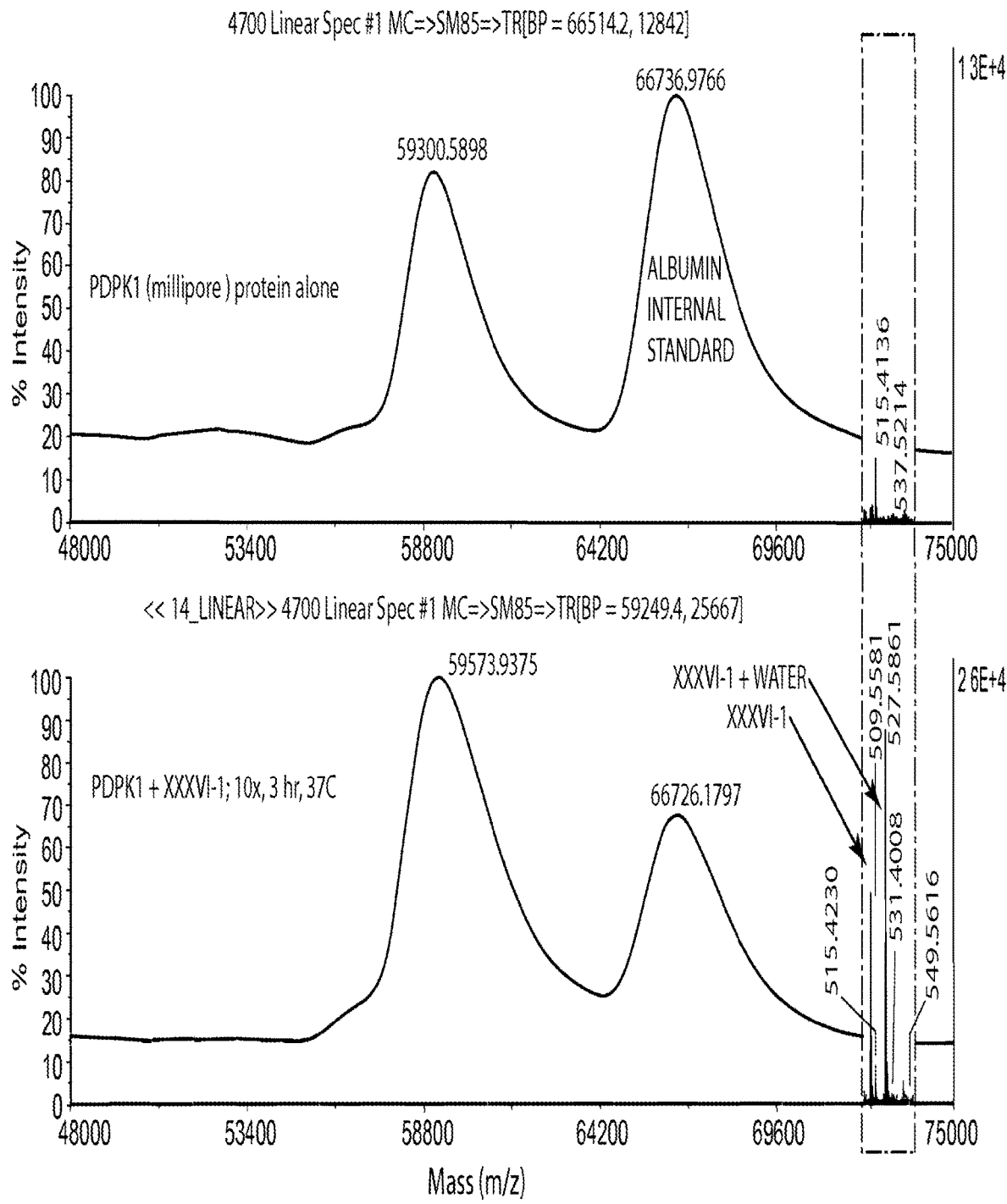
FIG. 21 depicts the mass spectrometric analysis of Compound XXXVI-1 contacted with PDPK-1 (whole protein).

Compound XI-21 modifies K86 on PDPK1, as confirmed by MSMS analysis. The peptide of interest, 2,417 Da, was selected for MSMS analysis from the compound B treated PDPK1 trypsin digest. FIG. 19 shows the MSMS spectrum of the peptide $^{84}$FGKILGEGSFSTVVLAR$^{100}$ (SEQ ID NO: 3) modified by compound XI-21. The alignment of b and y ions confirms that K86 is the amino acid modified by compound XI-21.

Other examples of PDPK1 inhibitors disclosed herein demonstrate covalent modification of PDPK1 similar to the mass shift and digestion results described above. For example, Table 7 lists non-limiting examples of compounds that modify PDPK1 whole protein, the number of modifications per protein and the lysines modified within the protein. Compounds XI-27, XI-26, XI-22, and XI-21 each have a thiolactone warhead, yet demonstrate different modification profiles on the protein. Also, the lysine modified in PDPK-1 by XI-27, XI-26, XI-22, and XI-21 are not the same for each compound. Without wishing to be bound to any particular theory, the position of the warhead, as presented by the scaffold and tether to the lysines in the binding site, effects different results on the modification of the different lysines in the binding site of PDPK-1.

TABLE 7

| Compound | Structure | Number of Modifications on Whole Protein | Lys 86 | Lys 169 | Lys 173 |
|---|---|---|---|---|---|
| XI-49 | 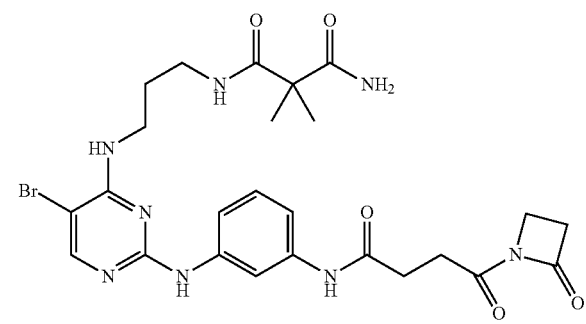 [SMILES: CC(C)(C(N)=O)C(=O)NCCCNc1nc(Nc2cccc(NC(=O)CCC(=O)N3CCC3=O)c2)ncc1Br] | 1 | | | X |

TABLE 7-continued
| Compound | Structure | Number of Modifications on Whole Protein | Lys 86 | Lys 169 | Lys 173 |
|---|---|---|---|---|---|
| XI-53 | 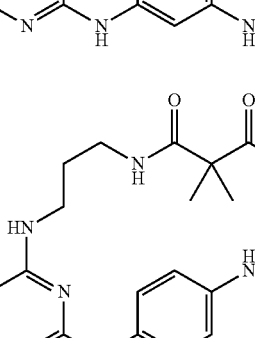 | 1 | <u>X</u> | X | |
| XI-39 | 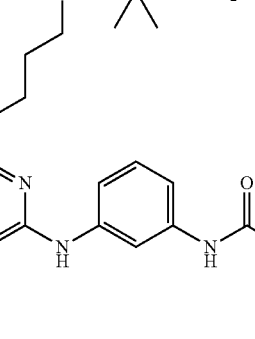 | 1 | <u>X</u> | X | |
| XI-27 | 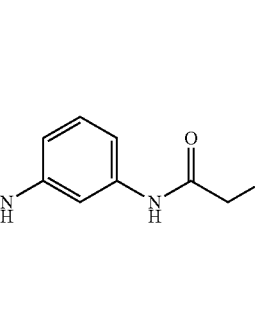 | 1 | | X | |
| XI-26 | 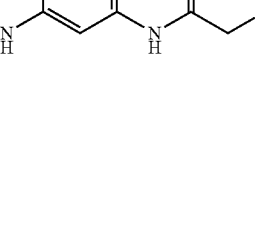 | 1 | | X | X |

TABLE 7-continued

| Compound | Structure | Number of Modifications on Whole Protein | Lys 86 | Lys 169 | Lys 173 |
|---|---|---|---|---|---|
| XI-22 | 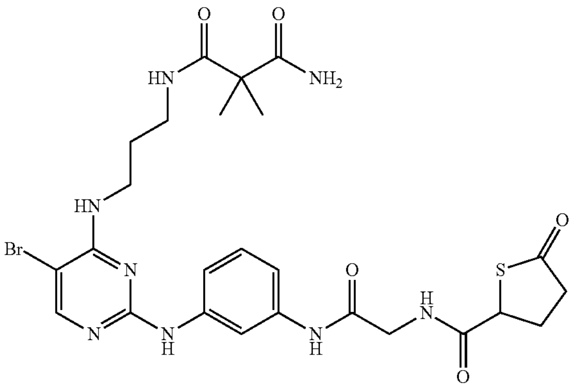 [SMILES: CC(C)(C(N)=O)C(=O)NCCCNc1nc(Nc2cccc(NC(=O)CNC(=O)C3CCC(=O)S3)c2)ncc1Br] | 2 | X | X | X |
| XI-21 | 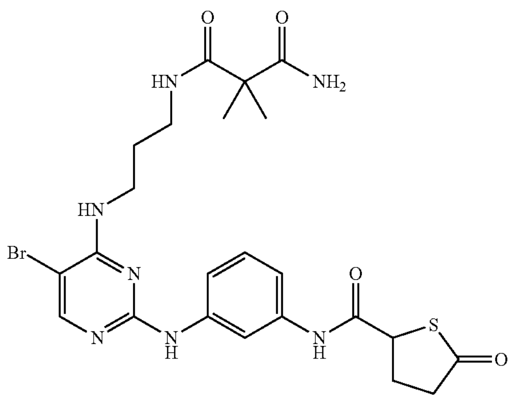 [SMILES: CC(C)(C(N)=O)C(=O)NCCCNc1nc(Nc2cccc(NC(=O)C3CCC(=O)S3)c2)ncc1Br] | 2 | X | X | X |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A protein-modifier-ligand conjugate of the Formula XIII,

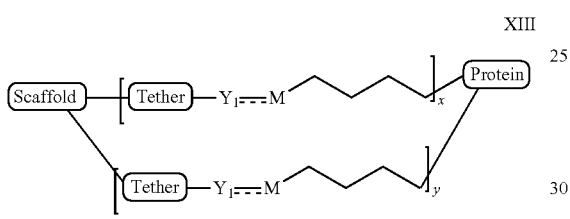

XIII wherein

Scaffold is an inhibitor of Protein,

Protein is X linked Inhibitor of Apoptosis Protein (XIAP); wherein Protein contains the lysine residue in, or in proximity to, the substrate-binding site or cofactor-binding site of Protein, and wherein a portion of the lysine residue is depicted in Formula XIII; and Tether is a bond, a bivalent $C_1$-$C_{15}$ saturated or unsaturated, straight, branched, or cyclic hydrocarbon moiety, an aryl moiety, or a heteroaryl moiety; wherein, optionally, one or more methylene units of the hydrocarbon chain are independently replaced by —$NR_1$—, —O—, —C(O)—, —S—, —SO—, —$SO_2$—, —C(=S)—, or —C(=$NR_1$)—; and one or more methine groups of the $C_1$-$C_{15}$ alkyl, when present, can be independently replaced by

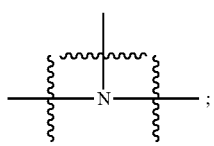

x is 0 or 1;
y is 1;
$R_1$ is hydrogen or $C_1$-$C_8$alkyl; and
$Y_1$ is a moiety of Formula XV-a, XV-b, or XV-d,

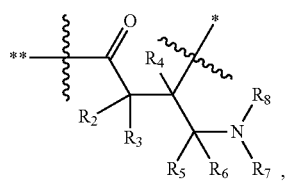

XV-a

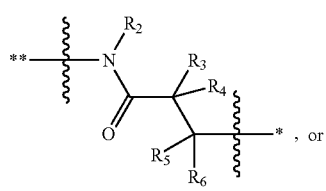

XV-b

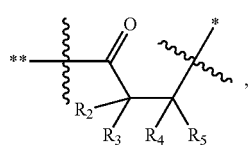

XV-d wherein each $R_2$, $R_3$, $R_4$, $R_5$, $R_6$, $R_7$, and $R_8$ is independently hydrogen or $C_1$-$C_6$ alkyl;

optionally when proper any two of $R_2$, $R_3$, $R_4$, $R_5$, $R_6$, $R_7$, and $R_8$ can be linked together to form a 3- to 8-membered carbocyclic or heterocyclic ring;

one or more methylene groups of the $C_1$-$C_6$ alkyl can be replaced by —$NR_1$—, —O—, —C(O)—, —S—, —SO—, —$SO_2$—, or —C(=S)—; one or more methine groups of the $C_1$-$C_6$ alkyl, when present, can be independently replaced by

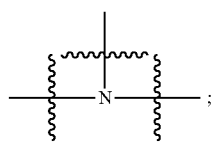

and

M is connected to the position labeled as "*";

Tether is connected to the position of Yi labeled as "**";

---- is a single bond;

M is —NH—, the nitrogen atom of M being a nitrogen from the side chain primary amine group of the lysine residue of Protein, and wherein M(CH$_2$)$_4$-Protein is selected from the group consisting of K297-XIAP and K299-XIAP.

2. The conjugate of claim 1, wherein the conjugate of Formula XIII is a conjugate of Formula XIII':

XIII'

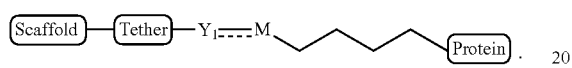

3. The conjugate of claim 2, wherein Scaffold is a radical resulting from the removal of one or more hydrogens of a compound of Formula VII, VIII, IX-a, or IX-b:

VII

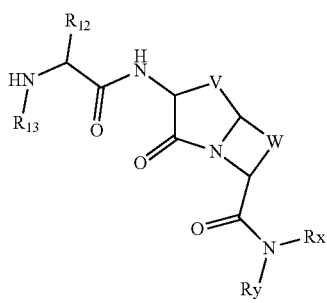

wherein

V and W are each independently —(CR$_{14}$R$_{15}$)$_q$X$_3$(CR$_{16}$R$_{17}$)$_r$—;

q and r are each independently 0, 1, 2, 3, or 4;

X$_3$ is —CR$_{18}$R$_{19}$— or —NR$_{20}$—;

R$_x$, R$_y$, R$_{12}$, R$_{13}$, R$_{14}$, R$_{15}$, R$_{16}$, R$_{17}$, R$_{18}$, R$_{19}$, and R$_{20}$ are each independently hydrogen or C$_1$-C$_6$ alkyl; wherein one or more methylene groups of the C$_1$-C$_6$ alkyl can be replaced by —NR$_1$—, —O—, —C(O)—, —S—, —SO—, —SO$_2$—, —C(=S)—, optionally substituted aryl or heteroaryl groups; one or more methine groups of the C$_1$-C$_6$ alkyl, when present, can be independently replaced by

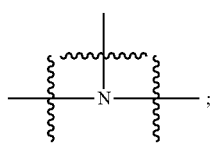 [SMILES: *N(*)*]

and

R$_1$ is hydrogen or C$_1$-C$_8$ alkyl;

VIII

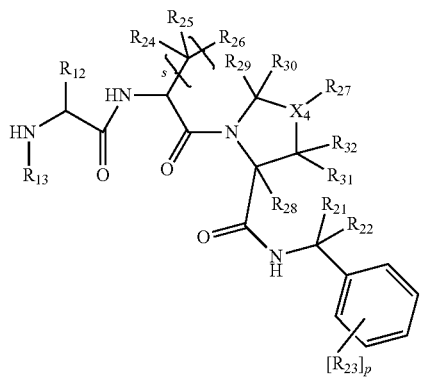

wherein

X$_4$ is —CR$_{33}$— or —N—;

p and s are each independently 0, 1, 2, 3, or 4;

R$_{12}$, R$_{13}$, R$_{21}$, R$_{22}$, R$_{24}$, R$_{25}$, R$_{26}$, R$_{27}$, R$_{28}$, R$_{29}$, R$_{30}$, R$_{31}$, R$_{32}$, and R$_{33}$ are each independently hydrogen or C$_1$-C$_6$ alkyl;

R$_{23}$ is hydrogen, C$_1$-C$_6$ alkyl, halogen, amino, or nitro; wherein one or more methylene groups of C$_1$-C$_6$ alkyl can be optionally replaced by —NR$_1$—, —O—, —C(O)—, —S—, —SO—, —SO$_2$—, or —C(=S)—; one or more methine groups of the C$_1$-C$_6$ alkyl, when present, can be independently replaced by

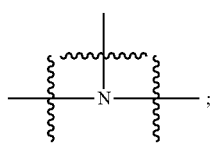 [SMILES: *N(*)*]

R$_1$ is hydrogen or C$_1$-C$_8$ alkyl; and optionally R$_{21}$ and R$_{23}$ taken together can form a 4- to 8-membered carbocyclic or heterocyclic ring;

IX-a

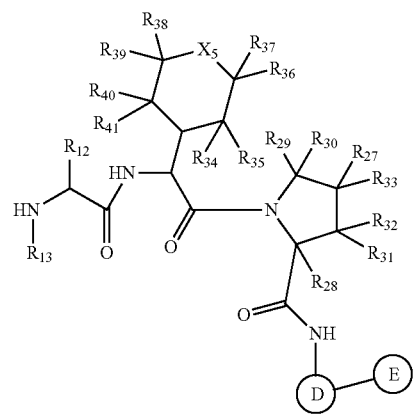

513

-continued

IX-b

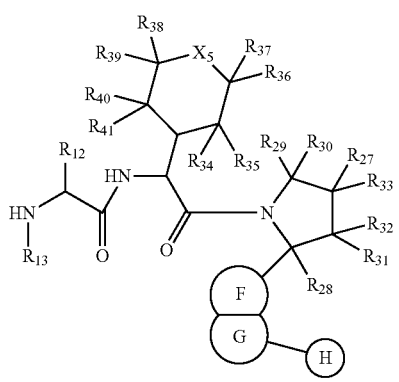

wherein
X₅ is —O—, —CR₄₂R₄₃— or —NR₄₂—;
R₁₂, R₁₃, R₂₇, R₂₈, R₂₉, R₃₀, R₃₁, R₃₂, R₃₃, R₃₄, R₃₅, R₃₆, R₃₇, R₃₈, R₃₉, R₄₀, R₄₁, R₄₂, and R₄₃ are each independently hydrogen or $C_1$-$C_6$ alkyl; wherein one or more methylene groups of $C_1$-$C_6$ alkyl can be optionally replaced by —NR₁—, —O—, —C(O)—, —S—, —SO—, —SO₂—, or —C(=S)—; one or more methine groups of the $C_1$-$C_6$ alkyl, when present, can be independently replaced by

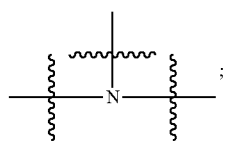

$R_1$ is hydrogen or $C_1$-$C_8$ alkyl; and
D, E, F, G, and H are each independently optionally substituted aryl or heteroaryl;
wherein F and G are fused together to form a bicyclic optionally substituted aryl or heteroaryl.

4. The conjugate of claim 2, wherein the bivalent moiety of Formula XV-a, XV-b, or XV-d is a bivalent moiety of Formula XV-h, XV-i, or XV-1;

XV-h

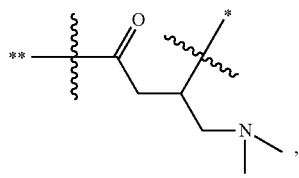

XV-i

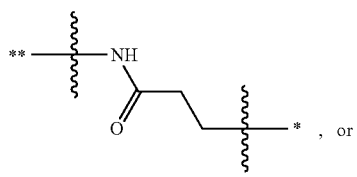
, or

XV-l

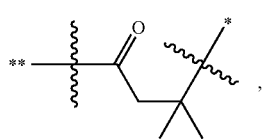
,

514

-continued

XV-p

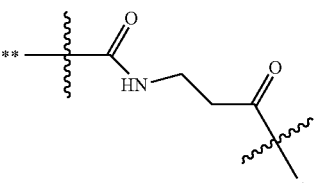

XV-q

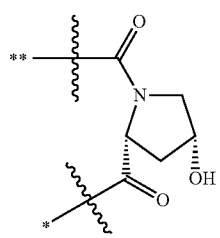

XV-r

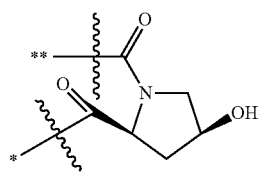

XV-s

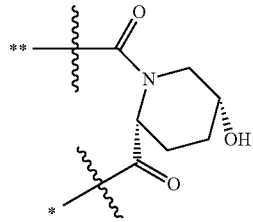

XV-t

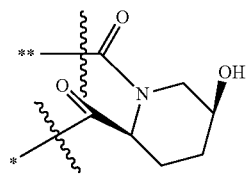

wherein
M is connected to the position of $Y_1$ labeled as "*"; and
Tether is connected to the position of $Y_1$ labeled as "**".

5. The conjugate of claim 2, wherein $Y_1$ is a moiety of Formula XV-a:

XV-a

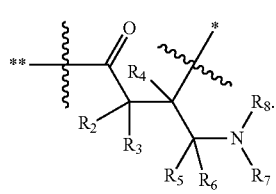

6. The conjugate of claim 2, wherein $Y_1$ is a moiety of Formula XV-b:
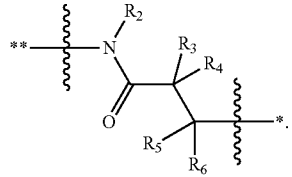
XV-b
7. The conjugate of claim 2, wherein $Y_1$ is a moiety of Formula XV-d:
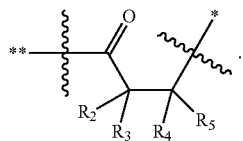
XV-d
* * * * *

```
                        SEQUENCE LISTING

<160> NUMBER OF SEQ ID NOS: 182

<210> SEQ ID NO 1
<211> LENGTH: 9
<212> TYPE: PRT
<213> ORGANISM: Homo sapiens

<400> SEQUENCE: 1

Asn Gly Glu Leu Leu Lys Tyr Ile Arg
1               5

<210> SEQ ID NO 2
<211> LENGTH: 11
<212> TYPE: PRT
<213> ORGANISM: Homo sapiens

<400> SEQUENCE: 2

Lys Ile Gly Ser Phe Asp Glu Thr Cys Thr Arg
```

```
1               5                  10
```

<210> SEQ ID NO 3
<211> LENGTH: 17
<212> TYPE: PRT
<213> ORGANISM: Homo sapiens

<400> SEQUENCE: 3

```
Phe Gly Lys Ile Leu Gly Glu Gly Ser Phe Ser Thr Val Val Leu Ala
1               5                   10                  15

Arg
```

<210> SEQ ID NO 4
<211> LENGTH: 7
<212> TYPE: PRT
<213> ORGANISM: Homo sapiens

<400> SEQUENCE: 4

```
Leu Gly Glu Lys Val Ser Gln
1               5
```

<210> SEQ ID NO 5
<211> LENGTH: 7
<212> TYPE: PRT
<213> ORGANISM: Homo sapiens

<400> SEQUENCE: 5

```
Pro Leu His Lys Ala Leu Gln
1               5
```

<210> SEQ ID NO 6
<211> LENGTH: 7
<212> TYPE: PRT
<213> ORGANISM: Homo sapiens

<400> SEQUENCE: 6

```
Gly Trp Asn Lys Ile Leu Val
1               5
```

<210> SEQ ID NO 7
<211> LENGTH: 7
<212> TYPE: PRT
<213> ORGANISM: Homo sapiens

<400> SEQUENCE: 7

```
Ser Val Gln Lys Glu Val Glu
1               5
```

<210> SEQ ID NO 8
<211> LENGTH: 7
<212> TYPE: PRT
<213> ORGANISM: Homo sapiens

<400> SEQUENCE: 8

```
Glu Val Glu Lys Asn Leu Lys
1               5
```

<210> SEQ ID NO 9
<211> LENGTH: 7
<212> TYPE: PRT
<213> ORGANISM: Homo sapiens

<400> SEQUENCE: 9

```
Val Met Glu Lys Glu Phe Glu
```

```
1               5

<210> SEQ ID NO 10
<211> LENGTH: 7
<212> TYPE: PRT
<213> ORGANISM: Homo sapiens

<400> SEQUENCE: 10

Phe Val Lys Lys Phe Glu Pro
1               5

<210> SEQ ID NO 11
<211> LENGTH: 7
<212> TYPE: PRT
<213> ORGANISM: Homo sapiens

<400> SEQUENCE: 11

Thr Trp Gly Lys Val Val Ser
1               5

<210> SEQ ID NO 12
<211> LENGTH: 7
<212> TYPE: PRT
<213> ORGANISM: Homo sapiens

<400> SEQUENCE: 12

Glu Ala Leu Lys Gly Gly Asn
1               5

<210> SEQ ID NO 13
<211> LENGTH: 7
<212> TYPE: PRT
<213> ORGANISM: Homo sapiens

<400> SEQUENCE: 13

His Phe Thr Lys Leu Glu Ile
1               5

<210> SEQ ID NO 14
<211> LENGTH: 7
<212> TYPE: PRT
<213> ORGANISM: Homo sapiens

<400> SEQUENCE: 14

Ala Ser Ile Lys Ala Val Thr
1               5

<210> SEQ ID NO 15
<211> LENGTH: 7
<212> TYPE: PRT
<213> ORGANISM: Homo sapiens

<400> SEQUENCE: 15

Leu Gly His Lys Pro Met Val
1               5

<210> SEQ ID NO 16
<211> LENGTH: 7
<212> TYPE: PRT
<213> ORGANISM: Homo sapiens

<400> SEQUENCE: 16

Asn Phe His Lys Leu Asn Val
1               5
```

<210> SEQ ID NO 17
<211> LENGTH: 7
<212> TYPE: PRT
<213> ORGANISM: Homo sapiens

<400> SEQUENCE: 17

Glu Ala Leu Lys Gly Gly Ser
1               5

<210> SEQ ID NO 18
<211> LENGTH: 7
<212> TYPE: PRT
<213> ORGANISM: Homo sapiens

<400> SEQUENCE: 18

His Phe Asp Lys Val Glu Ile
1               5

<210> SEQ ID NO 19
<211> LENGTH: 7
<212> TYPE: PRT
<213> ORGANISM: Homo sapiens

<400> SEQUENCE: 19

Arg Asn Thr Lys Arg Gly Ser
1               5

<210> SEQ ID NO 20
<211> LENGTH: 7
<212> TYPE: PRT
<213> ORGANISM: Homo sapiens

<400> SEQUENCE: 20

Arg Asn Ser Lys Asp Gly Ser
1               5

<210> SEQ ID NO 21
<211> LENGTH: 7
<212> TYPE: PRT
<213> ORGANISM: Homo sapiens

<400> SEQUENCE: 21

Asp Phe Cys Lys Asp Pro Ser
1               5

<210> SEQ ID NO 22
<211> LENGTH: 7
<212> TYPE: PRT
<213> ORGANISM: Homo sapiens

<400> SEQUENCE: 22

Lys Val Pro Lys Leu His Ser
1               5

<210> SEQ ID NO 23
<211> LENGTH: 7
<212> TYPE: PRT
<213> ORGANISM: Homo sapiens

<400> SEQUENCE: 23

Val Ser Asn Lys Asp Asp Lys
1               5

<210> SEQ ID NO 24

```
<211> LENGTH: 7
<212> TYPE: PRT
<213> ORGANISM: Homo sapiens

<400> SEQUENCE: 24

Lys Asp Asp Lys Lys Asn Met
1               5

<210> SEQ ID NO 25
<211> LENGTH: 7
<212> TYPE: PRT
<213> ORGANISM: Homo sapiens

<400> SEQUENCE: 25

Asp Asp Lys Lys Asn Met Gly
1               5

<210> SEQ ID NO 26
<211> LENGTH: 7
<212> TYPE: PRT
<213> ORGANISM: Homo sapiens

<400> SEQUENCE: 26

Arg Asp Pro Lys Ser Gly Ser
1               5

<210> SEQ ID NO 27
<211> LENGTH: 7
<212> TYPE: PRT
<213> ORGANISM: Homo sapiens

<400> SEQUENCE: 27

Val Ser Val Lys Gly Ile Tyr
1               5

<210> SEQ ID NO 28
<211> LENGTH: 7
<212> TYPE: PRT
<213> ORGANISM: Homo sapiens

<400> SEQUENCE: 28

Thr Ser Leu Lys Asp Arg Gln
1               5

<210> SEQ ID NO 29
<211> LENGTH: 7
<212> TYPE: PRT
<213> ORGANISM: Homo sapiens

<400> SEQUENCE: 29

Gly Phe Leu Lys Gly Glu Asp
1               5

<210> SEQ ID NO 30
<211> LENGTH: 7
<212> TYPE: PRT
<213> ORGANISM: Homo sapiens

<400> SEQUENCE: 30

Glu His Pro Lys Leu Lys Ala
1               5

<210> SEQ ID NO 31
<211> LENGTH: 7
<212> TYPE: PRT
```

```
<213> ORGANISM: Homo sapiens

<400> SEQUENCE: 31

Pro Lys Leu Lys Ala Pro Leu
1               5

<210> SEQ ID NO 32
<211> LENGTH: 7
<212> TYPE: PRT
<213> ORGANISM: Homo sapiens

<400> SEQUENCE: 32

Met Cys Arg Lys Arg Asn Asp
1               5

<210> SEQ ID NO 33
<211> LENGTH: 7
<212> TYPE: PRT
<213> ORGANISM: Homo sapiens

<400> SEQUENCE: 33

Ile Phe Met Lys Phe Leu Lys
1               5

<210> SEQ ID NO 34
<211> LENGTH: 7
<212> TYPE: PRT
<213> ORGANISM: Homo sapiens

<400> SEQUENCE: 34

Asp Cys Asp Lys Met Asp Lys
1               5

<210> SEQ ID NO 35
<211> LENGTH: 7
<212> TYPE: PRT
<213> ORGANISM: Homo sapiens

<400> SEQUENCE: 35

Lys Met Asp Lys Ala Cys Met
1               5

<210> SEQ ID NO 36
<211> LENGTH: 7
<212> TYPE: PRT
<213> ORGANISM: Homo sapiens

<400> SEQUENCE: 36

Glu Lys Ala Lys Val Tyr Ile
1               5

<210> SEQ ID NO 37
<211> LENGTH: 7
<212> TYPE: PRT
<213> ORGANISM: Homo sapiens

<400> SEQUENCE: 37

Thr Pro Asp Lys Val Asn His
1               5

<210> SEQ ID NO 38
<211> LENGTH: 7
<212> TYPE: PRT
<213> ORGANISM: Homo sapiens
```

```
<400> SEQUENCE: 38

Ile Asn Met Lys Pro Leu Gln
1               5

<210> SEQ ID NO 39
<211> LENGTH: 7
<212> TYPE: PRT
<213> ORGANISM: Hepatitis C virus genotype 1b

<400> SEQUENCE: 39

Gly Ser Gly Lys Ser Thr Lys
1               5

<210> SEQ ID NO 40
<211> LENGTH: 7
<212> TYPE: PRT
<213> ORGANISM: Hepatitis C virus genotype 1b

<400> SEQUENCE: 40

Arg Gly Tyr Lys Gly Val Trp
1               5

<210> SEQ ID NO 41
<211> LENGTH: 7
<212> TYPE: PRT
<213> ORGANISM: Hepatitis C virus genotype 1b

<400> SEQUENCE: 41

Ile Met Ala Lys Asn Glu Val
1               5

<210> SEQ ID NO 42
<211> LENGTH: 7
<212> TYPE: PRT
<213> ORGANISM: Homo sapiens

<400> SEQUENCE: 42

His Pro Met Lys Pro His Arg
1               5

<210> SEQ ID NO 43
<211> LENGTH: 7
<212> TYPE: PRT
<213> ORGANISM: Homo sapiens

<400> SEQUENCE: 43

Gly Tyr Gln Lys Arg Thr Ala
1               5

<210> SEQ ID NO 44
<211> LENGTH: 7
<212> TYPE: PRT
<213> ORGANISM: Homo sapiens

<400> SEQUENCE: 44

His Pro Met Lys Pro His Arg
1               5

<210> SEQ ID NO 45
<211> LENGTH: 7
<212> TYPE: PRT
<213> ORGANISM: Homo sapiens

<400> SEQUENCE: 45
```

His Pro Met Lys Pro His Arg
1               5

<210> SEQ ID NO 46
<211> LENGTH: 7
<212> TYPE: PRT
<213> ORGANISM: Homo sapiens

<400> SEQUENCE: 46

Gly Asp Pro Lys Gly Glu Met
1               5

<210> SEQ ID NO 47
<211> LENGTH: 7
<212> TYPE: PRT
<213> ORGANISM: Homo sapiens

<400> SEQUENCE: 47

Ser Leu Ala Lys Ile Pro Lys
1               5

<210> SEQ ID NO 48
<211> LENGTH: 7
<212> TYPE: PRT
<213> ORGANISM: Homo sapiens

<400> SEQUENCE: 48

Asp Ala Ala Lys Ser Gln Ala
1               5

<210> SEQ ID NO 49
<211> LENGTH: 7
<212> TYPE: PRT
<213> ORGANISM: Homo sapiens

<400> SEQUENCE: 49

Phe Asp Ala Lys Arg Leu Ile
1               5

<210> SEQ ID NO 50
<211> LENGTH: 7
<212> TYPE: PRT
<213> ORGANISM: Homo sapiens

<400> SEQUENCE: 50

Glu Arg Ala Lys Arg Thr Leu
1               5

<210> SEQ ID NO 51
<211> LENGTH: 7
<212> TYPE: PRT
<213> ORGANISM: Homo sapiens

<400> SEQUENCE: 51

Asp Ala Ala Lys Asn Gln Val
1               5

<210> SEQ ID NO 52
<211> LENGTH: 7
<212> TYPE: PRT
<213> ORGANISM: Homo sapiens

<400> SEQUENCE: 52

Phe Asp Ala Lys Arg Leu Ile
1               5

<210> SEQ ID NO 53
<211> LENGTH: 7
<212> TYPE: PRT
<213> ORGANISM: Homo sapiens

<400> SEQUENCE: 53

Glu Arg Ala Lys Arg Thr Leu
1               5

<210> SEQ ID NO 54
<211> LENGTH: 7
<212> TYPE: PRT
<213> ORGANISM: Homo sapiens

<400> SEQUENCE: 54

Ala Leu Asp Lys Ile Arg Tyr
1               5

<210> SEQ ID NO 55
<211> LENGTH: 7
<212> TYPE: PRT
<213> ORGANISM: Homo sapiens

<400> SEQUENCE: 55

Ala Leu Asp Lys Ile Arg Tyr
1               5

<210> SEQ ID NO 56
<211> LENGTH: 7
<212> TYPE: PRT
<213> ORGANISM: Homo sapiens

<400> SEQUENCE: 56

Phe Thr Gly Lys Gln Asp Thr
1               5

<210> SEQ ID NO 57
<211> LENGTH: 7
<212> TYPE: PRT
<213> ORGANISM: Homo sapiens

<400> SEQUENCE: 57

Glu His Ala Lys Trp Phe Pro
1               5

<210> SEQ ID NO 58
<211> LENGTH: 7
<212> TYPE: PRT
<213> ORGANISM: Homo sapiens

<400> SEQUENCE: 58

Asp Asp Val Lys Cys Phe Cys
1               5

<210> SEQ ID NO 59
<211> LENGTH: 7
<212> TYPE: PRT
<213> ORGANISM: Homo sapiens

<400> SEQUENCE: 59

Asp Asp Val Lys Cys Phe Cys
1               5

```
<210> SEQ ID NO 60
<211> LENGTH: 7
<212> TYPE: PRT
<213> ORGANISM: Homo sapiens

<400> SEQUENCE: 60

Glu Gly Asp Lys Val Lys Cys
1               5

<210> SEQ ID NO 61
<211> LENGTH: 7
<212> TYPE: PRT
<213> ORGANISM: Homo sapiens

<400> SEQUENCE: 61

Asp Lys Cys Lys Cys Phe His
1               5

<210> SEQ ID NO 62
<211> LENGTH: 7
<212> TYPE: PRT
<213> ORGANISM: Homo sapiens

<400> SEQUENCE: 62

Thr Asp Trp Lys Pro Ser Glu
1               5

<210> SEQ ID NO 63
<211> LENGTH: 7
<212> TYPE: PRT
<213> ORGANISM: Homo sapiens

<400> SEQUENCE: 63

Phe Cys Phe Lys Glu Leu Glu
1               5

<210> SEQ ID NO 64
<211> LENGTH: 7
<212> TYPE: PRT
<213> ORGANISM: Homo sapiens

<400> SEQUENCE: 64

Glu Lys His Lys Lys Ser Ser
1               5

<210> SEQ ID NO 65
<211> LENGTH: 7
<212> TYPE: PRT
<213> ORGANISM: Homo sapiens

<400> SEQUENCE: 65

His Gln Asp Lys Val Arg Cys
1               5

<210> SEQ ID NO 66
<211> LENGTH: 7
<212> TYPE: PRT
<213> ORGANISM: Homo sapiens

<400> SEQUENCE: 66

Gln Ser Trp Lys Arg Gly Asp
1               5

<210> SEQ ID NO 67
<211> LENGTH: 7
```

```
<212> TYPE: PRT
<213> ORGANISM: Homo sapiens

<400> SEQUENCE: 67

Glu His Ala Lys Trp Pro Phe
1               5

<210> SEQ ID NO 68
<211> LENGTH: 7
<212> TYPE: PRT
<213> ORGANISM: Homo sapiens

<400> SEQUENCE: 68

Gln Glu Asp Lys Val Gln Cys
1               5

<210> SEQ ID NO 69
<211> LENGTH: 7
<212> TYPE: PRT
<213> ORGANISM: Homo sapiens

<400> SEQUENCE: 69

Ala Asn Trp Lys Pro Lys Glu
1               5

<210> SEQ ID NO 70
<211> LENGTH: 7
<212> TYPE: PRT
<213> ORGANISM: Homo sapiens

<400> SEQUENCE: 70

Gln His Ala Lys Trp Tyr Pro
1               5

<210> SEQ ID NO 71
<211> LENGTH: 7
<212> TYPE: PRT
<213> ORGANISM: Homo sapiens

<400> SEQUENCE: 71

Val Ala Val Lys Met Leu Asn
1               5

<210> SEQ ID NO 72
<211> LENGTH: 7
<212> TYPE: PRT
<213> ORGANISM: Homo sapiens

<400> SEQUENCE: 72

Ile Met Ser Lys Thr Leu Gly
1               5

<210> SEQ ID NO 73
<211> LENGTH: 7
<212> TYPE: PRT
<213> ORGANISM: Homo sapiens

<400> SEQUENCE: 73

Thr Cys Lys Lys Val Ala Ile
1               5

<210> SEQ ID NO 74
<211> LENGTH: 7
<212> TYPE: PRT
<213> ORGANISM: Homo sapiens
```

```
<400> SEQUENCE: 74

Val Ala Ile Lys Ile Ser Lys
1               5

<210> SEQ ID NO 75
<211> LENGTH: 7
<212> TYPE: PRT
<213> ORGANISM: Homo sapiens

<400> SEQUENCE: 75

Arg Asp Leu Lys Pro Glu Asn
1               5

<210> SEQ ID NO 76
<211> LENGTH: 7
<212> TYPE: PRT
<213> ORGANISM: Homo sapiens

<400> SEQUENCE: 76

Lys Lys Ile Lys Val Leu Gly
1               5

<210> SEQ ID NO 77
<211> LENGTH: 7
<212> TYPE: PRT
<213> ORGANISM: Homo sapiens

<400> SEQUENCE: 77

Thr Val Tyr Lys Gly Leu Trp
1               5

<210> SEQ ID NO 78
<211> LENGTH: 7
<212> TYPE: PRT
<213> ORGANISM: Homo sapiens

<400> SEQUENCE: 78

Val Ala Ile Lys Glu Leu Arg
1               5

<210> SEQ ID NO 79
<211> LENGTH: 7
<212> TYPE: PRT
<213> ORGANISM: Homo sapiens

<400> SEQUENCE: 79

Cys Ala Val Lys Ser Leu Asn
1               5

<210> SEQ ID NO 80
<211> LENGTH: 7
<212> TYPE: PRT
<213> ORGANISM: Homo sapiens

<400> SEQUENCE: 80

Pro Tyr Met Lys His Gly Asp
1               5

<210> SEQ ID NO 81
<211> LENGTH: 7
<212> TYPE: PRT
<213> ORGANISM: Homo sapiens

<400> SEQUENCE: 81
```

```
Lys Phe Gly Lys Ile Leu Gly
1               5

<210> SEQ ID NO 82
<211> LENGTH: 7
<212> TYPE: PRT
<213> ORGANISM: Homo sapiens

<400> SEQUENCE: 82

Ser Tyr Ala Lys Asn Gly Glu
1               5

<210> SEQ ID NO 83
<211> LENGTH: 7
<212> TYPE: PRT
<213> ORGANISM: Homo sapiens

<400> SEQUENCE: 83

Glu Leu Leu Lys Tyr Ile Arg
1               5

<210> SEQ ID NO 84
<211> LENGTH: 7
<212> TYPE: PRT
<213> ORGANISM: Homo sapiens

<400> SEQUENCE: 84

Tyr Ile Arg Lys Ile Gly Ser
1               5

<210> SEQ ID NO 85
<211> LENGTH: 7
<212> TYPE: PRT
<213> ORGANISM: Homo sapiens

<400> SEQUENCE: 85

Arg Asp Leu Lys Pro Glu Asn
1               5

<210> SEQ ID NO 86
<211> LENGTH: 7
<212> TYPE: PRT
<213> ORGANISM: Homo sapiens

<400> SEQUENCE: 86

Arg Asp Ile Lys Asp Glu Asn
1               5

<210> SEQ ID NO 87
<211> LENGTH: 7
<212> TYPE: PRT
<213> ORGANISM: Homo sapiens

<400> SEQUENCE: 87

Val Ala Val Lys Met Leu Lys
1               5

<210> SEQ ID NO 88
<211> LENGTH: 7
<212> TYPE: PRT
<213> ORGANISM: Homo sapiens

<400> SEQUENCE: 88

Tyr Ala Ser Lys Gly Asn Leu
```

```
<210> SEQ ID NO 89
<211> LENGTH: 7
<212> TYPE: PRT
<213> ORGANISM: Homo sapiens

<400> SEQUENCE: 89

Val Ala Val Lys Met Leu Lys
1               5

<210> SEQ ID NO 90
<211> LENGTH: 7
<212> TYPE: PRT
<213> ORGANISM: Homo sapiens

<400> SEQUENCE: 90

Tyr Ala Ser Lys Gly Asn Leu
1               5

<210> SEQ ID NO 91
<211> LENGTH: 7
<212> TYPE: PRT
<213> ORGANISM: Homo sapiens

<400> SEQUENCE: 91

Tyr Ala Ala Lys Gly Asn Leu
1               5

<210> SEQ ID NO 92
<211> LENGTH: 7
<212> TYPE: PRT
<213> ORGANISM: Homo sapiens

<400> SEQUENCE: 92

Val Ala Val Lys Met Leu Lys
1               5

<210> SEQ ID NO 93
<211> LENGTH: 7
<212> TYPE: PRT
<213> ORGANISM: Homo sapiens

<400> SEQUENCE: 93

Val Ala Val Lys Met Leu Lys
1               5

<210> SEQ ID NO 94
<211> LENGTH: 7
<212> TYPE: PRT
<213> ORGANISM: Homo sapiens

<400> SEQUENCE: 94

Cys Ala Ala Lys Gly Asn Leu
1               5

<210> SEQ ID NO 95
<211> LENGTH: 7
<212> TYPE: PRT
<213> ORGANISM: Homo sapiens

<400> SEQUENCE: 95

Thr Val Tyr Lys Gly Lys Trp
1               5
```

```
<210> SEQ ID NO 96
<211> LENGTH: 7
<212> TYPE: PRT
<213> ORGANISM: Homo sapiens

<400> SEQUENCE: 96

Thr Val Tyr Lys Gly Lys Trp
1               5

<210> SEQ ID NO 97
<211> LENGTH: 7
<212> TYPE: PRT
<213> ORGANISM: Homo sapiens

<400> SEQUENCE: 97

Val Ala Val Lys Ile Leu Lys
1               5

<210> SEQ ID NO 98
<211> LENGTH: 7
<212> TYPE: PRT
<213> ORGANISM: Homo sapiens

<400> SEQUENCE: 98

Ser Leu Tyr Lys His Leu His
1               5

<210> SEQ ID NO 99
<211> LENGTH: 7
<212> TYPE: PRT
<213> ORGANISM: Homo sapiens

<400> SEQUENCE: 99

Leu Glu Asp Lys Glu Leu Gly
1               5

<210> SEQ ID NO 100
<211> LENGTH: 7
<212> TYPE: PRT
<213> ORGANISM: Homo sapiens

<400> SEQUENCE: 100

Thr Val Lys Lys Gly Tyr Tyr
1               5

<210> SEQ ID NO 101
<211> LENGTH: 7
<212> TYPE: PRT
<213> ORGANISM: Homo sapiens

<400> SEQUENCE: 101

Pro Leu Asn Lys Tyr Leu Gln
1               5

<210> SEQ ID NO 102
<211> LENGTH: 7
<212> TYPE: PRT
<213> ORGANISM: Homo sapiens

<400> SEQUENCE: 102

Tyr Thr Met Lys Glu Val Leu
1               5

<210> SEQ ID NO 103
```

```
<211> LENGTH: 7
<212> TYPE: PRT
<213> ORGANISM: Homo sapiens

<400> SEQUENCE: 103

Phe Ser Val Lys Glu His Arg
1               5

<210> SEQ ID NO 104
<211> LENGTH: 7
<212> TYPE: PRT
<213> ORGANISM: Homo sapiens

<400> SEQUENCE: 104

Phe Thr Val Lys Glu Val Met
1               5

<210> SEQ ID NO 105
<211> LENGTH: 7
<212> TYPE: PRT
<213> ORGANISM: Homo sapiens

<400> SEQUENCE: 105

Phe Ser Val Lys Asp Pro Ser
1               5

<210> SEQ ID NO 106
<211> LENGTH: 7
<212> TYPE: PRT
<213> ORGANISM: Homo sapiens

<400> SEQUENCE: 106

Lys Thr His Lys Leu Gln Asp
1               5

<210> SEQ ID NO 107
<211> LENGTH: 7
<212> TYPE: PRT
<213> ORGANISM: Homo sapiens

<400> SEQUENCE: 107

Ile Pro Met Lys Leu Ala Gly
1               5

<210> SEQ ID NO 108
<211> LENGTH: 7
<212> TYPE: PRT
<213> ORGANISM: Homo sapiens

<400> SEQUENCE: 108

Ser His Asp Lys Glu Tyr Ile
1               5

<210> SEQ ID NO 109
<211> LENGTH: 7
<212> TYPE: PRT
<213> ORGANISM: Homo sapiens

<400> SEQUENCE: 109

Ser Asp Pro Lys Ala Val Met
1               5

<210> SEQ ID NO 110
<211> LENGTH: 7
<212> TYPE: PRT
```

<213> ORGANISM: Homo sapiens

<400> SEQUENCE: 110

Pro Thr Tyr Lys Tyr Val Asp
1               5

<210> SEQ ID NO 111
<211> LENGTH: 7
<212> TYPE: PRT
<213> ORGANISM: Homo sapiens

<400> SEQUENCE: 111

Ala Phe Lys Lys Ala Phe Lys
1               5

<210> SEQ ID NO 112
<211> LENGTH: 7
<212> TYPE: PRT
<213> ORGANISM: Homo sapiens

<400> SEQUENCE: 112

Tyr Thr Gly Lys Ser His Phe
1               5

<210> SEQ ID NO 113
<211> LENGTH: 7
<212> TYPE: PRT
<213> ORGANISM: Homo sapiens

<400> SEQUENCE: 113

Ala Ile Arg Lys Ala Phe Arg
1               5

<210> SEQ ID NO 114
<211> LENGTH: 7
<212> TYPE: PRT
<213> ORGANISM: Homo sapiens

<400> SEQUENCE: 114

Tyr Gln Trp Lys Asp Val Asp
1               5

<210> SEQ ID NO 115
<211> LENGTH: 7
<212> TYPE: PRT
<213> ORGANISM: Homo sapiens

<400> SEQUENCE: 115

Tyr Lys Tyr Lys Asn Pro Tyr
1               5

<210> SEQ ID NO 116
<211> LENGTH: 7
<212> TYPE: PRT
<213> ORGANISM: Homo sapiens

<400> SEQUENCE: 116

Tyr Ser Met Lys Cys Lys Asn
1               5

<210> SEQ ID NO 117
<211> LENGTH: 7
<212> TYPE: PRT
<213> ORGANISM: Homo sapiens

<400> SEQUENCE: 117

Ser Trp Ala Lys Lys Ile Pro
1               5

<210> SEQ ID NO 118
<211> LENGTH: 7
<212> TYPE: PRT
<213> ORGANISM: Homo sapiens

<400> SEQUENCE: 118

Met Ala Glu Lys Thr Leu Val
1               5

<210> SEQ ID NO 119
<211> LENGTH: 7
<212> TYPE: PRT
<213> ORGANISM: Homo sapiens

<400> SEQUENCE: 119

Met Glu Pro Lys Phe Asp Phe
1               5

<210> SEQ ID NO 120
<211> LENGTH: 7
<212> TYPE: PRT
<213> ORGANISM: Homo sapiens

<400> SEQUENCE: 120

Gln Leu Pro Lys Ile Leu Ala
1               5

<210> SEQ ID NO 121
<211> LENGTH: 7
<212> TYPE: PRT
<213> ORGANISM: Homo sapiens

<400> SEQUENCE: 121

Ser Ser Ala Lys Arg Pro Leu
1               5

<210> SEQ ID NO 122
<211> LENGTH: 7
<212> TYPE: PRT
<213> ORGANISM: Homo sapiens

<400> SEQUENCE: 122

Ile Ile Phe Lys Asn Gly Asp
1               5

<210> SEQ ID NO 123
<211> LENGTH: 7
<212> TYPE: PRT
<213> ORGANISM: Homo sapiens

<400> SEQUENCE: 123

Glu Lys Cys Lys Tyr Met Asp
1               5

<210> SEQ ID NO 124
<211> LENGTH: 7
<212> TYPE: PRT
<213> ORGANISM: Homo sapiens

<400> SEQUENCE: 124

Val Ile Phe Lys Asn Gly Asp
1               5

<210> SEQ ID NO 125
<211> LENGTH: 7
<212> TYPE: PRT
<213> ORGANISM: Homo sapiens

<400> SEQUENCE: 125

Glu Lys Cys Lys Val Met Ala
1               5

<210> SEQ ID NO 126
<211> LENGTH: 7
<212> TYPE: PRT
<213> ORGANISM: Homo sapiens

<400> SEQUENCE: 126

Met Ala Ser Lys Lys Lys Pro
1               5

<210> SEQ ID NO 127
<211> LENGTH: 7
<212> TYPE: PRT
<213> ORGANISM: Homo sapiens

<400> SEQUENCE: 127

Ile Ile Phe Lys His Gly Asp
1               5

<210> SEQ ID NO 128
<211> LENGTH: 7
<212> TYPE: PRT
<213> ORGANISM: Homo sapiens

<400> SEQUENCE: 128

Glu Ile Val Lys Asp Ala Thr
1               5

<210> SEQ ID NO 129
<211> LENGTH: 7
<212> TYPE: PRT
<213> ORGANISM: Homo sapiens

<400> SEQUENCE: 129

Thr Ile Ala Lys Ile Gln Gln
1               5

<210> SEQ ID NO 130
<211> LENGTH: 7
<212> TYPE: PRT
<213> ORGANISM: Homo sapiens

<400> SEQUENCE: 130

Asp Asp Glu Lys Gln Leu Met
1               5

<210> SEQ ID NO 131
<211> LENGTH: 7
<212> TYPE: PRT
<213> ORGANISM: Homo sapiens

<400> SEQUENCE: 131

Asn Arg Asn Lys Cys Ala Glu
1               5

```
<210> SEQ ID NO 132
<211> LENGTH: 7
<212> TYPE: PRT
<213> ORGANISM: Homo sapiens

<400> SEQUENCE: 132

Gly Ser Leu Lys Cys Ala Gln
1               5

<210> SEQ ID NO 133
<211> LENGTH: 7
<212> TYPE: PRT
<213> ORGANISM: Homo sapiens

<400> SEQUENCE: 133

Gln Glu Cys Lys Leu Leu Tyr
1               5

<210> SEQ ID NO 134
<211> LENGTH: 7
<212> TYPE: PRT
<213> ORGANISM: Homo sapiens

<400> SEQUENCE: 134

Asn Arg Tyr Lys Asn Ile Leu
1               5

<210> SEQ ID NO 135
<211> LENGTH: 7
<212> TYPE: PRT
<213> ORGANISM: Homo sapiens

<400> SEQUENCE: 135

Glu Arg Gly Lys Ser Lys Cys
1               5

<210> SEQ ID NO 136
<211> LENGTH: 7
<212> TYPE: PRT
<213> ORGANISM: Homo sapiens

<400> SEQUENCE: 136

Gly Lys Ser Lys Cys Val Lys
1               5

<210> SEQ ID NO 137
<211> LENGTH: 7
<212> TYPE: PRT
<213> ORGANISM: Homo sapiens

<400> SEQUENCE: 137

Gln Glu Leu Lys Pro Leu Asp
1               5

<210> SEQ ID NO 138
<211> LENGTH: 7
<212> TYPE: PRT
<213> ORGANISM: Homo sapiens

<400> SEQUENCE: 138

Asn Arg Tyr Lys Asn Ile Leu
1               5
```

```
<210> SEQ ID NO 139
<211> LENGTH: 7
<212> TYPE: PRT
<213> ORGANISM: Homo sapiens

<400> SEQUENCE: 139

Glu Gly Glu Lys Ile Lys Cys
1               5

<210> SEQ ID NO 140
<211> LENGTH: 7
<212> TYPE: PRT
<213> ORGANISM: Homo sapiens

<400> SEQUENCE: 140

Glu Lys Ile Lys Cys Gln Arg
1               5

<210> SEQ ID NO 141
<211> LENGTH: 7
<212> TYPE: PRT
<213> ORGANISM: Homo sapiens

<400> SEQUENCE: 141

Gly Arg Thr Lys Ser His Arg
1               5

<210> SEQ ID NO 142
<211> LENGTH: 7
<212> TYPE: PRT
<213> ORGANISM: Homo sapiens

<400> SEQUENCE: 142

Gln Ile Pro Lys Lys Lys Ala
1               5

<210> SEQ ID NO 143
<211> LENGTH: 7
<212> TYPE: PRT
<213> ORGANISM: Homo sapiens

<400> SEQUENCE: 143

Ile Pro Lys Lys Lys Ala Asn
1               5

<210> SEQ ID NO 144
<211> LENGTH: 7
<212> TYPE: PRT
<213> ORGANISM: Homo sapiens

<400> SEQUENCE: 144

Ala Ala Trp Lys Ala Asp Gly
1               5

<210> SEQ ID NO 145
<211> LENGTH: 7
<212> TYPE: PRT
<213> ORGANISM: Homo sapiens

<400> SEQUENCE: 145

Asn Arg Tyr Lys Asp Val Leu
1               5

<210> SEQ ID NO 146
<211> LENGTH: 7
```

```
<212> TYPE: PRT
<213> ORGANISM: Homo sapiens

<400> SEQUENCE: 146

Arg Val Ala Lys Phe Pro Glu
1               5

<210> SEQ ID NO 147
<211> LENGTH: 7
<212> TYPE: PRT
<213> ORGANISM: Homo sapiens

<400> SEQUENCE: 147

Leu Lys Leu Lys Arg Gln Ser
1               5

<210> SEQ ID NO 148
<211> LENGTH: 7
<212> TYPE: PRT
<213> ORGANISM: Homo sapiens

<400> SEQUENCE: 148

Thr Lys Tyr Lys Ala Asp Lys
1               5

<210> SEQ ID NO 149
<211> LENGTH: 7
<212> TYPE: PRT
<213> ORGANISM: Homo sapiens

<400> SEQUENCE: 149

Glu Met Gly Lys Lys Lys Cys
1               5

<210> SEQ ID NO 150
<211> LENGTH: 7
<212> TYPE: PRT
<213> ORGANISM: Homo sapiens

<400> SEQUENCE: 150

Gly Lys Lys Lys Cys Glu Arg
1               5

<210> SEQ ID NO 151
<211> LENGTH: 7
<212> TYPE: PRT
<213> ORGANISM: Homo sapiens

<400> SEQUENCE: 151

Leu Tyr Arg Lys Lys Pro Gly
1               5

<210> SEQ ID NO 152
<211> LENGTH: 7
<212> TYPE: PRT
<213> ORGANISM: Homo sapiens

<400> SEQUENCE: 152

Thr Phe Ala Lys Leu Pro Gln
1               5

<210> SEQ ID NO 153
<211> LENGTH: 7
<212> TYPE: PRT
<213> ORGANISM: Homo sapiens
```

```
<400> SEQUENCE: 153

Asn Arg Tyr Lys Asp Val Leu
1               5

<210> SEQ ID NO 154
<211> LENGTH: 7
<212> TYPE: PRT
<213> ORGANISM: Homo sapiens

<400> SEQUENCE: 154

Gly Arg Thr Lys Cys His Gln
1               5

<210> SEQ ID NO 155
<211> LENGTH: 7
<212> TYPE: PRT
<213> ORGANISM: Homo sapiens

<400> SEQUENCE: 155

Leu Tyr Arg Lys Lys Pro Gly
1               5

<210> SEQ ID NO 156
<211> LENGTH: 7
<212> TYPE: PRT
<213> ORGANISM: Homo sapiens

<400> SEQUENCE: 156

Gly Arg Val Lys Cys His Gln
1               5

<210> SEQ ID NO 157
<211> LENGTH: 7
<212> TYPE: PRT
<213> ORGANISM: Homo sapiens

<400> SEQUENCE: 157

Asn Arg Tyr Lys Thr Ile Leu
1               5

<210> SEQ ID NO 158
<211> LENGTH: 7
<212> TYPE: PRT
<213> ORGANISM: Homo sapiens

<400> SEQUENCE: 158

Met Asn Glu Lys Cys Thr Glu
1               5

<210> SEQ ID NO 159
<211> LENGTH: 7
<212> TYPE: PRT
<213> ORGANISM: Homo sapiens

<400> SEQUENCE: 159

Asn Arg Tyr Lys Asn Ile Leu
1               5

<210> SEQ ID NO 160
<211> LENGTH: 7
<212> TYPE: PRT
<213> ORGANISM: Homo sapiens

<400> SEQUENCE: 160
```

```
Asp Arg Tyr Lys Thr Ile Leu
1               5

<210> SEQ ID NO 161
<211> LENGTH: 7
<212> TYPE: PRT
<213> ORGANISM: Homo sapiens

<400> SEQUENCE: 161

Gly Arg Arg Lys Cys Gly Gln
1               5

<210> SEQ ID NO 162
<211> LENGTH: 7
<212> TYPE: PRT
<213> ORGANISM: Homo sapiens

<400> SEQUENCE: 162

Gly Arg Val Lys Cys Asp His
1               5

<210> SEQ ID NO 163
<211> LENGTH: 7
<212> TYPE: PRT
<213> ORGANISM: Homo sapiens

<400> SEQUENCE: 163

Leu Met Val Lys Val Leu Asp
1               5

<210> SEQ ID NO 164
<211> LENGTH: 7
<212> TYPE: PRT
<213> ORGANISM: Homo sapiens

<400> SEQUENCE: 164

Met Val Ser Lys Ser Ala Asn
1               5

<210> SEQ ID NO 165
<211> LENGTH: 7
<212> TYPE: PRT
<213> ORGANISM: Homo sapiens

<400> SEQUENCE: 165

Glu Asn Ser Lys Ser Ala Gly
1               5

<210> SEQ ID NO 166
<211> LENGTH: 7
<212> TYPE: PRT
<213> ORGANISM: Homo sapiens

<400> SEQUENCE: 166

Asp Gly His Lys Ala Val Phe
1               5

<210> SEQ ID NO 167
<211> LENGTH: 7
<212> TYPE: PRT
<213> ORGANISM: Homo sapiens

<400> SEQUENCE: 167

His Tyr Ser Lys Ser Asp Thr
```

```
<210> SEQ ID NO 168
<211> LENGTH: 7
<212> TYPE: PRT
<213> ORGANISM: Homo sapiens

<400> SEQUENCE: 168

Ser Tyr Gly Lys Gly Thr Tyr
1               5

<210> SEQ ID NO 169
<211> LENGTH: 7
<212> TYPE: PRT
<213> ORGANISM: Homo sapiens

<400> SEQUENCE: 169

Tyr Ser Ala Lys Asp Thr Tyr
1               5

<210> SEQ ID NO 170
<211> LENGTH: 7
<212> TYPE: PRT
<213> ORGANISM: Homo sapiens

<400> SEQUENCE: 170

Arg Ser Pro Lys Leu Phe Val
1               5

<210> SEQ ID NO 171
<211> LENGTH: 7
<212> TYPE: PRT
<213> ORGANISM: Homo sapiens

<400> SEQUENCE: 171

Asn Ser Ser Lys Ser Asn Gln
1               5

<210> SEQ ID NO 172
<211> LENGTH: 7
<212> TYPE: PRT
<213> ORGANISM: Homo sapiens

<400> SEQUENCE: 172

Ser Thr Ile Lys Met Ala His
1               5

<210> SEQ ID NO 173
<211> LENGTH: 7
<212> TYPE: PRT
<213> ORGANISM: Human immunodeficiency virus type 1 group M subtype B

<400> SEQUENCE: 173

Trp Lys Pro Lys Met Ile Gly
1               5

<210> SEQ ID NO 174
<211> LENGTH: 13
<212> TYPE: PRT
<213> ORGANISM: Homo sapiens

<400> SEQUENCE: 174

Ala Gly Phe Tyr Ala Leu Gly Glu Gly Asp Lys Val Lys
1               5                   10
```

-continued

<210> SEQ ID NO 175
<211> LENGTH: 11
<212> TYPE: PRT
<213> ORGANISM: Homo sapiens

<400> SEQUENCE: 175

Ala Leu Gly Glu Gly Asp Lys Val Lys Cys Phe
1               5                   10

<210> SEQ ID NO 176
<211> LENGTH: 72
<212> TYPE: DNA
<213> ORGANISM: Artificial Sequence
<220> FEATURE:
<223> OTHER INFORMATION: oligonucleotide primer

<400> SEQUENCE: 176
taataagcta gcaccatgga ctacaaagat gatgacgata aaggagcgcc tattacggcc        60
tactcccaac ag                                                            72

<210> SEQ ID NO 177
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 177
ttattatcta gactagcact cttccatctc atcgaactcc cggtaaag                     48

<210> SEQ ID NO 178
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 178
atctttcggg ctgccgtgag cacccgaggg gttgcgaag                               39

<210> SEQ ID NO 179
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 179
cttcgcaacc cctcgggtgc tcacggcagc ccgaaagat                               39

<210> SEQ ID NO 180
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 180
gtctcctact tgaggggctc ttcgggcggt                                         30

<210> SEQ ID NO 181
<211> LENGTH: 30
<212> TYPE: DNA
<213> ORGANISM: Artificial Sequence
<220> FEATURE:

```
<223> OTHER INFORMATION: oligonucleotide primer

<400> SEQUENCE: 181
accgcccgaa gagcccctca agtaggagac                                        30

<210> SEQ ID NO 182
<211> LENGTH: 14
<212> TYPE: PRT
<213> ORGANISM: Homo sapiens

<400> SEQUENCE: 182

Lys Ile Gly Ser Phe Asp Glu Thr Cys Ile Ala Ala Thr Arg
1               5                   10
```